United States Patent
Wang et al.

(10) Patent No.: US 11,293,018 B2
(45) Date of Patent: Apr. 5, 2022

(54) MANIPULATION OF NUCLEAR ARCHITECTURE

(71) Applicants: THE BOARD OF TRUSTEES OF THE LELAND STANFORD JUNIOR UNIVERSITY, Stanford, CA (US); SYSTEM BIOSCIENCES, INC., Palo Alto, CA (US)

(72) Inventors: Kevin Chun-Kai Wang, Stanford, CA (US); Stefanie Morgan, Palo Alto, CA (US); Fangting Wu, San Jose, CA (US); Chiao-Chain Huang, Los Altos, CA (US)

(73) Assignees: THE BOARD OF TRUSTEES OF THE LELAND STANFORD JUNIOR UNIVERSITY, Stanford, CA (US); SYSTEM BIOSCIENCES INC., Palo Alto, CA (US)

(*) Notice: Subject to any disclaimer, the term of this patent is extended or adjusted under 35 U.S.C. 154(b) by 792 days.

(21) Appl. No.: 16/004,162

(22) Filed: Jun. 8, 2018

(65) Prior Publication Data
US 2018/0355344 A1 Dec. 13, 2018

Related U.S. Application Data

(60) Provisional application No. 62/517,339, filed on Jun. 9, 2017.

(51) Int. Cl.
| | |
|---|---|
| *C12N 15/10* | (2006.01) |
| *C12N 15/11* | (2006.01) |
| *C12N 9/22* | (2006.01) |
| *C07K 14/415* | (2006.01) |
| *C07K 14/47* | (2006.01) |
| *C12N 9/96* | (2006.01) |
| *C12N 15/82* | (2006.01) |
| *C12N 15/63* | (2006.01) |

(52) U.S. Cl.
CPC .......... *C12N 15/102* (2013.01); *C07K 14/415* (2013.01); *C07K 14/4703* (2013.01); *C12N 9/22* (2013.01); *C12N 9/96* (2013.01); *C12N 15/11* (2013.01); *C12N 15/63* (2013.01); *C12N 15/8213* (2013.01); *C12N 2310/20* (2017.05)

(58) Field of Classification Search
None
See application file for complete search history.

(56) References Cited

U.S. PATENT DOCUMENTS 9,315,806 B2 4/2016 Lu et al.

FOREIGN PATENT DOCUMENTS

WO WO 2016/098078 A2 6/2016

OTHER PUBLICATIONS

Ameres, S., L. et al., Inducible DNA-Loop Formation Blocks Transcriptional Activation By An SV40 Enhancer, The EMBO Journal, vol. 24, pp. 358-367, 2005.
Church, G. et al., Cas9 As A Versatile Tool For Engineering Biology, Nature Methods, vol. 10, No. 10, pp. 957-963, 2013.
Dekker, J. et al., Exploring The Three-Dimensional Organization Of Genomes: Interpreting Chromatin Interaction Data, Nature Rev Genet, vol. 14, pp. 390-403, 2013.
Dekker, J. et al., The Hierarchy Of The 3d Genome, Molecular Cell, vol. 49, No. 5, pp. 773-782, 2013.
Deng, W. et al. Controlling Long-Range Genomic Interactions At A Native Locus By Targeted Tethering Of A Looping Factor, Cell, vol. 149, pp. 1233-1244, 2012.
Deng, W. et al., Reactivation Of Developmentally Silenced Globin Genes By Forced Chromatin Looping, Cell, vol. 158, pp. 849-860, 2014.
Dixon, J. et al., Chromatin Architecture Reorganization During Stem Cell Differentiation, Nature, vol. 518, pp. 331-336, 2015.
Drier, Y. et al., An Oncogenic MYB Feedback Loop Drives Alternate Cell Fates In Adenoid Cystic Carcinoma, Nature Genetics, vol. 48, pp. 265-272, 2016.
Kim, A. et al., Chromatin Loop Formation In The B-Globin Locus And Its Role In Globin Gene Transcription, Molecules and Cells, vol. 34, pp. 1-5, 2012.
Krivega, I. et al., Chromatin Looping As A Target For Altering Erythroid Gene Expression, Annals of the New York Academy of Science, vol. 1368, No. 1, pp. 31-39, 2016.
Liang, F.-S. et al., Engineering The ABA Plant Stress Pathway For Regulation Of Induced Proximity, Science Signaling, vol. 4, 2011.
Lupianez, D., G. et al., Disruptions Of Topological Chromatin Domains Cause Pathogenic Rewiring Of Gene-Enhancer Interactions, Cell, vol. 161, pp. 1012-1025, 2015.
Matharu, N. et al., Minor Loops In Major Folds: Enhancer-Promoter Looping, Chromatin Restructuring, And Their Association With Transcriptional Regulation And Disease. PLOS Genetics, vol. 11, No. 12, e1005640, 2015.
Mehra, P. et al., Long-Range Transcriptional Control Of The Il2 Gene By An Intergenic Enhancer, Molecular and Cellular Biology, vol. 35, No. 22, pp. 3880-3891, 2015.
Mokry, M. et al., Integrated Genome-Wide Analysis Of Transcription Factor Occupancy, RNA Polymerase II Binding And Steady State RNA Levels Identify Differentially Regulated Functional Gene Classes, Nucleic Acids Research, vol. 40, No. 1, pp. 148-158, 2012 (Published Online Sep. 13, 2011).

(Continued)

*Primary Examiner* — Suzanne M Noakes
(74) *Attorney, Agent, or Firm* — Knobbe, Martens, Olson & Bear LLP

(57) ABSTRACT

Chromatin looping is key to gene regulation, yet no broadly applicable methods to selectively modify chromatin loops have been described. Disclosed herein is an engineered method for chromatin loop reorganization using CRISPR-dCas9 (CLOuD9) to selectively and reversibly establish chromatin loops. Disclosed herein is the power of this technology to selectively modulate gene expression at targeted loci.

23 Claims, 50 Drawing Sheets

Specification includes a Sequence Listing.

(56) References Cited

OTHER PUBLICATIONS

Montavon, T. et al., A Regulatory Archipelago Conuols Hox Genes Transcription In Digits, Cell, vol. 147, pp. 1132-1145, 2011.

Nishimasu, H. et al., Crystal Structure Of Cas9 In Complex With Guide RNA and Target DNA, Cell, vol. 156, No. 5, pp. 935-949, 2014.

Nishimasu, H. et al., Crystal Structure Of *Staphylococcus aureus* Cas9, Cell, vol. 162, No. 5, pp. 1113-1126, 2015.

Petrascheck, M. et al., DNA Looping Induced By A Transcriptional Enhancer In Vivo, Nucleic Acids Research, vol. 33, No. 12, pp. 3743-3750, 2005.

Pomerantz, M. et al., The 8q24 Cancer Risk Variant rs6983267 Shows Long-Range Interaction With MYC In Colorectal Cancer, Nature Genetics, vol. 41, No. 8, pp. 882-884, 2009.

Ryan, R., J., H. et al., Detection Of Enhancer-Associated Rearrangements Reveals Mechanisms Of Oncogene Dysregulation In B-Cell Lymphoma, Cancer Discovery, vol. 5, No. 10, pp. 1058-1071, 2015.

Stadhouders, R. et al., Transcription Regulation By Distal Enhancers, Transcription, vol. 3, No. 4, pp. 181-186, 2012.

Theunissen, T., W. et al., Systematic Identification Of Culture Conditions For Induction And Maintenance Of Naive Human Pluripotency, Cell Stem Cell, vol. 15, pp. 471-487, 2014.

Van Steensel, B. et al., Genomics Tools For Unraveling Chromosome Architecture. Nature Biotechnology, vol. 28, No. 10, pp. 1089-1095, 2010.

Williams, L. et al., Table of Contents of Remington's The Science and Practice of Pharmacy, 21st Ed, 2005.

Zhang, H. et al. Inkrachromosomal Looping Is Required For Activation Of Endogenous Pluripotency Genes During Reprogramming, Cell Stem Cell, vol. 13, pp. 30-35, 2013.

Hao, Q. et al., The Molecular Basis of ABA-Independent Inhibition of PP2Cs by a Subclass of PYL Proteins, Molecular Cell, vol. 42, pp. 662-672, 2011.

Nakagawa, M. et al., Mechanism of high-affinity abscisic acid binding to PYL9/RCAR1, Genes to Cells, vol. 19, pp. 386-404, 2014.

Wang, J. et al., Phase separation of OCT4 controls TAD reorganization to promote cell fate transitions, Cell Stem Cell, vo. 28, pp. 1-16, 2021.

FIG. 19C

| 72 hour Dimerized | 7 Day Dimerized |
|---|---|
| *S. pyogenes* dCas9 | HNRNPD |
| *S. aureus* dCas9 | HNRNPM1 |
| DDX3Y | DDX3Y |
| DDX17 | DDX5 |
| HNRNPK | DDX17 |
| DDX5 | DHX9 |
| DDX21 | HNRPC |
| HNRNPC | DDX39B |
| YBX1 | DDX6 |
| HNRNPU | DDX1 |

MANIPULATION OF NUCLEAR ARCHITECTURE

CROSS-REFERENCE TO RELATED APPLICATIONS

This application claims the benefit of U.S. Provisional Application 62/517,339, filed on Jun. 9, 2017, which is hereby incorporated by reference in its entirety.

ELECTRONIC SEQUENCE LISTING

The present application is being filed along with an electronic Sequence Listing as an ASCII text file via EFS-Web. The electronic Sequence Listing is provided as a file entitled STFRD3021ASEQLIST.txt, created and last saved on Jun. 8, 2018, which is 12,240 bytes in size. The information in the electronic Sequence Listing is incorporated herein by reference in its entirety.

BACKGROUND

Field

The present disclosure is generally related to manipulation of nuclear architecture. Some embodiments are related to manipulation of nuclear architecture through CRISPR-mediated chromosomal looping. Some embodiments are related to manipulation of nuclear architecture through CRISPR dCas9-mediated chromosomal looping.

Description of the Related Art

There is growing appreciation that genome organization and the folding of chromatin within the nucleus are key determinants of gene expression programs[1,2]. Further, it has long been postulated that chromosomal contacts created by the three-dimensional (3D) organization of chromatin are critical in the regulation of gene expression[3].

SUMMARY

In some embodiments, a system for juxtaposing a first chromosomal locus and a second chromosomal locus is provided. In some embodiments, the system comprises a first nucleic acid construct encoding a first fusion protein and a first guide RNA, wherein the first fusion protein comprises a dCas9 from a first species, a first dimerization protein, and a first tag, and a second nucleic acid construct encoding a second fusion protein and a second guide RNA, wherein the second fusion protein comprises a dCas9 from a second species, a second dimerization protein, and a second tag. In some embodiments of the system, the first fusion protein is directed to the first chromosomal locus by the first guide RNA, and the second fusion protein is directed to the second chromosomal locus by the second guide RNA. In some embodiments of the system, the first fusion protein and the second fusion protein are configured to dimerize, thereby juxtaposing the first chromosomal locus and the second chromosomal locus.

In some embodiments of the system, the first nucleic acid construct and the second nucleic acid construct are DNA-based. In some embodiments of the system, the first nucleic acid construct and the second nucleic acid construct are RNA-based. In some embodiments of the system, the first guide RNA and the second guide RNA are about 5 to about 100 nucleotides. In some embodiments of the system, the first species and second species are selected from the group consisting of *S. pyogenes, S. aureus, N. meningitides, S. thermophiles, T. denticola, S. pasteurianus, N. cinerea, C. lari, P. lavamentivorans, C. diphtheria*, and any bacterial species utilizing the CRISPR-Cas9 bacterial adaptive immune system. In some embodiments of the system, the first fusion protein and the second fusion protein are configured to dimerize via a reversible chemical induced proximity system. In some embodiments of the system, the reversible chemical induced proximity system comprises the first dimerization protein and second dimerization protein, wherein the first dimerization protein and the second dimerization protein are configured to be brought into proximity in the presence of a dimerizing agent, thereby allowing the first fusion protein and the second fusion protein to dimerize. In some embodiments of the system, the first dimerization protein and the second dimerization protein are selected from the group consisting of plant ABA signaling pathway, gibberellin-induced dimerization system, rapalog-induced dimerization system, RNA-mediated protein recruitment dimerization system, and derivatives thereof. In some embodiments of the system, the first dimerization protein is ABI1 and the second dimerization protein is PYL1 of the plant ABA signaling pathway. In some embodiments of the system, the first dimerization protein is PYL1 and the second dimerization protein is ABI1 of the plant ABA signaling pathway. In some embodiments of the system, the dimerizing agent is ABA.

In some embodiments, a method to alter an expression of at least one gene at a first chromosomal locus by juxtaposing the first chromosomal locus and a second chromosomal locus is provided. In some embodiments, the method comprises providing a first nucleic acid construct encoding a first fusion protein and a first guide RNA, wherein the first fusion protein comprises a dCas9 from a first species, a first dimerization protein, and a first tag; and providing a second nucleic acid construct encoding a second fusion protein and a second guide RNA, wherein the second fusion protein comprises a dCas9 from a second species, a second dimerization protein, and a second tag. In some embodiments, of the method, the first fusion protein is directed to the first chromosomal locus by the first guide RNA, and the second fusion protein is directed to the second chromosomal locus by the second guide RNA. In some embodiments, of the method, the first fusion protein and the second fusion protein dimerize to juxtapose the first chromosomal locus and the second chromosomal locus, thereby altering an expression of at least one gene at a first chromosomal locus. In some embodiments, of the method, the expression of at least one gene at the second chromosomal locus is altered by juxtaposing the first chromosomal locus and the second chromosomal locus. In some embodiments, of the method, the second chromosomal locus comprises one or more regulatory elements that alter the expression of the at least one gene at the first chromosomal locus. In some embodiments, of the method, the first chromosomal locus comprises one or more regulatory elements that alter the expression of the at least one gene at the second chromosomal locus. In some embodiments, of the method, the first species and second species are selected from the group consisting of *S. pyogenes, S. aureus, N. meningitides, S. thermophiles, T. denticola, S. pasteurianus, N. cinerea, C. lari, P. lavamentivorans, C. diphtheria*, and any bacterial species utilizing the CRISPR-Cas9 bacterial adaptive immune system. In some embodiments, of the method, the first fusion protein and the second fusion protein dimerize via a reversible chemical induced proximity system. In some embodiments, of the method, the reversible chemical induced proximity system comprises the first dimerization protein and second dimerization protein, wherein the first dimerization protein and the second dimerization protein are brought into proximity in the presence of a dimerizing agent, thereby allowing the first fusion protein and the second fusion protein to dimerize. In some embodiments, of the method, the first dimerization protein and the second dimerization protein are selected from the group consisting of plant ABA signaling pathway, gibberellin-induced dimerization system, rapalog-induced dimerization system, RNA-mediated protein recruitment dimerization system, and derivatives thereof. In some embodiments, of the method, the first dimerization protein is ABI1 and the second dimerization protein is PYL1 of the plant ABA signaling pathway. In some embodiments, of the method, the first dimerization protein is ABI1 and the second dimerization protein is PYL1 of the plant ABA signaling pathway. In some embodiments, of the method, the dimerizing agent is ABA.

In some embodiments, a system for juxtaposing a first chromosomal locus and a second chromosomal locus is provided. In some embodiments, the system comprises a first fusion protein and a first guide RNA, wherein the first fusion protein comprises a dCas9 from a first species, a first dimerization protein, and a first tag; and a second fusion protein and a second guide RNA, wherein the second fusion protein comprises a dCas9 from a second species, a second dimerization protein, and a second tag. In some embodiments of the system, the first fusion protein is directed to the first chromosomal locus by the first guide RNA, and the second fusion protein is directed to the second chromosomal locus by the second guide RNA. In some embodiments of the system, the first fusion protein and the second fusion protein are configured to dimerize, thereby juxtaposing the first chromosomal locus and the second chromosomal locus.

BRIEF DESCRIPTION OF THE DRAWINGS

FIG. 1I shows a schematic of long-range looping interactions at the globin locus in K562 cells.

FIG. 19C shows MS/ChIP data of dimerized CLOuD9 cells.

DETAILED DESCRIPTION

Figure 1:
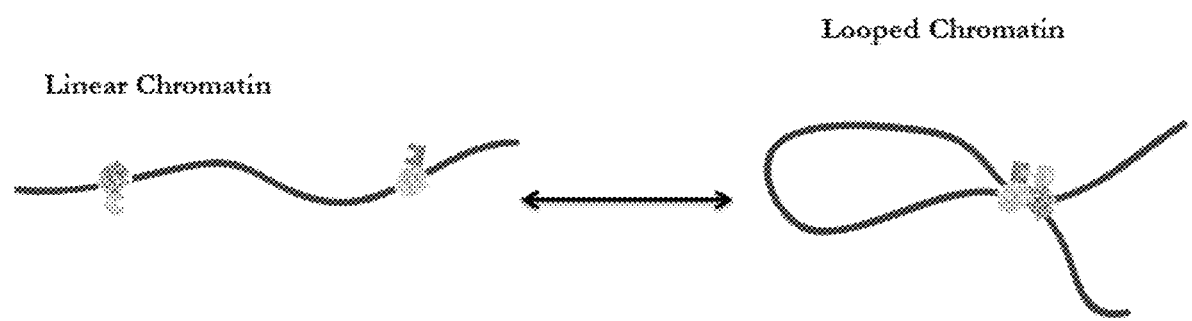
FIG. 1 shows a schematic of an embodiment of CLOuD9 design strategy.

In recent years it is being increasingly appreciated that the DNA within the nucleus has a distinct organizational structure, on the nucleosomal scale (about 1 kb-about 10 kb), supranucelosomal scale (about 100 kb-about 10,000 kb), and nuclear scale (about 100,000 kb), and that this structure is important to regulation of gene expression (Gibcus & Dekker 2013 Mol Cell 49(5):773-82). There is growing appreciation that genome organization and the folding of chromatin within the nucleus are key determinants of gene expression programs[1,2]. Chromatin is organized into a distinct 3-dimensional structure within the nucleus. Further, it has long been postulated that chromosomal contacts created by the three-dimensional (3D) organization of chromatin are critical in the regulation of gene expression[3].

This has been most thoroughly demonstrated at the human β-globin gene locus, where a locus control region (LCR) regulates the expression of the distant β-like globin genes through formation of a long-range chromatin loop[4]. Interestingly, while numerous long-range looping interactions have been identified with the advent of genomic technologies[5,6], precisely how chromatin loops and the dynamic genome architecture contribute to the regulation of gene expression to affect cellular functions is not fully understood. Furthermore, whether chromatin looping is a cause or a consequence of gene activity remains unknown.

A significant challenge to obtaining a comprehensive understanding of the functional organization and formation of chromatin loops has been the availability of tools to study them. Although multiple groups have forcibly looped distant regulatory elements to influence gene expression[7-10], the described methodologies often involve either gross alterations of the linear DNA sequence or are technically challenging and demand significant prior knowledge of the loop-mediating factors.

Chromosomal conformation capture (3C)-based technologies have provided insight into the static spatial organization of the genome. 3C-based technologies have given us an appreciation for how important specific chromatin contacts can be to regulation of cellular programs and to regulation of specific gene expression. However, the limitation of these technologies is that they only provide a snapshot of the conformation of the chromatin at any given point in time. Dynamic long-range chromatin contacts regulate gene expression in a number of contexts, for example, immunity, cancer and pluripotency (Dixon et al. 2015, Nature 518: 331-336; Mehra & Wells 2015, Mol Cell Biol 25(22); Deng et al. 2012, Cell 149(6); Zhang et al. 2013, Cell Stem Cell 13(1); Pomerantz et al. 2009 Nat Genet 41).

Current technological limitations that inhibit the study of chromatin architecture include, but are not limited to, the inability to manipulate chromatin structure without modifying the underlying DNA sequence. This limits the extent to which novel biological findings from 3C and associated technologies can be validated or understood, and prevents a thorough understanding of the role of chromatin architecture in regulating gene expression and coordinating biological processes. Further limitations include the irreversible nature of any current manipulations to the chromatin structure, as well as the vast knowledge of a genomic region required for its manipulation.

While previous work with the β-globin locus has demonstrated that gene expression requires the pre-existing establishment of the proper chromosomal architecture[10], how chromatin dynamics specifically impact transcription apparatus and overall genome folding are central issues to resolve. Although there is growing appreciation for the interplay between looping and gene function, the mechanisms by which long-range chromosomal contacts are established or maintained with regulatory elements such as enhancers and promoters, among other types of contacts, to bring about functional changes in gene expression remain unclear.

The clustered regularly interspaced short palindromic repeats (CRISPR)-Cas9 system and its nuclease deficient derivatives (CRISPR-dCas9) (Nishimasu et al. 2014, Cell 156(5): 935-949; Church, G. M. 2013. Nat Methods 10(10): 957-63) offer an approachable alternative for manipulating chromatin architecture. CRISPR-based technology offers a number of advantages including, but not limited to, allowing greater flexibility of targeting regions without the need for an extensive amount of knowledge about the proteins and specific transcription factors involved in the region, and is easily utilized. In some embodiments, manipulation of nuclear architecture through CRISPR-mediated chromosomal looping is provided. In some embodiments, CRISPR technology is utilized to manipulate chromatin structure. In some embodiments, CRISPR technology is utilized to manipulate chromatin structure using nuclease deficient Cas9 (dCas9). In some embodiments, this approach offers a number of advantages including, but not limited to, allowing greater flexibility of targeting regions without the need for an extensive amount of knowledge about the proteins and specific transcription factors involved in the region, and the ease of use of the CRISPR-based technology.

In some embodiments, through targeted modification of the existing nuclease deficient CRISPR-CRISPR associated protein 9 (CRISPR-dCas9) system components, a powerful tool for targeted, reversible chromatin loop re-organization using nuclease-deficient Cas9 (CLOuD9) is provided. The "CLOuD9 tool" described herein is interchangeably referred to herein as "CLOuD9 system," "CLOuD9 method," "CLOuD9 technology," "CLOuD9 design," and "CLOuD9."

In some embodiments, the CLOuD9 design strategy (FIG. 1) comprises a series of directed modifications of dCas9 from S. aureus and S. pyogenes to combine them with ABI1/PYL1 heterodimerization domains to make them inducibly dimerizeable. In some embodiments, the CLOuD9 design strategy comprises dCas9 constructs that are directed to genomically distant regions of the DNA and that are reversibly brought into proximity and released back to their endogenous states as required. As used herein, the definition of "dimerization," "dimerize," "dimerizable," "dimerizing," or "dimerized" is not limited to dimers but also encompasses trimers, oligomers and/or multimers. In some embodiments, dimerization may by related to signaling. Thus, a dimerization protein may be analogous to a signaling protein.

In some embodiments, CLOuD9 is applicable as a genome repair and restructuring application. Chromatin looping is key to gene regulation, yet no broadly applicable methods to selectively modify chromatin loops have been described. In some embodiments, an engineered CRISPR-dCas9 based method for chromatin loop reorganization (CLOuD9) to selectively and reversibly establish chromatin loops is provided. In some embodiments, this technology can be utilized to selectively modulate gene expression at targeted loci.

Prior to development of this technology, no method for the targeted, selective, reversible modification of chromatin structure in the absence of manipulation of the underlying target DNA region was known to exist. There is currently no easily utilized method to bring two chromatin regions into proximity to study the downstream effects on cellular behavior. By taking advantage of the basic principles of CRISPR technology, the novel technology disclosed herein can be easily applied in any laboratory to manipulate chromatin structure.

Thus, in some embodiments, systems and methods based on CLOuD9 for juxtaposing a first chromosomal locus and a second chromosomal locus are provided. In some embodiments, the systems and methods comprise a first construct and a second construct for juxtaposing a first chromosomal locus and a second chromosomal locus. In some embodiments of the systems and methods, the first construct comprises a first guide RNA encoding sequence, a first dCas9 coding sequence from a first species, a first dimerization protein coding sequence linked to the first dCas9 coding sequence via a first spacer, a first tag coding sequence linked to the first dimerization protein coding sequence via a second spacer. In some embodiments of the systems and methods, the first guide RNA encoding sequence encodes a first guide RNA. In some embodiments of the systems and methods, the first dCas9 coding sequence, the first dimerization protein coding sequence, and the first tag coding sequence encode a first fusion protein. In some embodiments of the systems and methods, the second construct comprises a second guide RNA encoding sequence, a second dCas9 coding sequence from a second, a second dimerization protein coding sequence linked to the second dCas9 coding sequence via a third spacer, a second tag coding sequence linked to the second dimerization protein coding sequence via a fourth spacer. In some embodiments of the systems and methods, the the second guide RNA encoding sequence encodes a second guide RNA. In some embodiments of the systems and methods, the second dCas9 coding sequence, the second dimerization protein coding sequence, and the second tag coding sequence encode a second fusion protein. In some embodiments of the systems and methods, the first fusion protein is directed to the first chromosomal locus by the first guide RNA and the second fusion protein is directed to the second chromosomal locus by the second guide RNA.

In some embodiments, a system for juxtaposing a first chromosomal locus and a second chromosomal locus is provided. In some embodiments, the system comprises a first construct comprising a first guide RNA encoding sequence, a first dCas9 coding sequence from a first species, a first dimerization protein coding sequence linked to the first dCas9 coding sequence via a first spacer, a first tag coding sequence linked to the first dimerization protein coding sequence via a second spacer, wherein the first guide RNA encoding sequence encodes a first guide RNA, and wherein the first dCas9 coding sequence, the first dimerization protein coding sequence, and the first tag coding sequence encode a first fusion protein, a second construct comprising a second guide RNA encoding sequence, a second dCas9 coding sequence from a second species, a second dimerization protein coding sequence linked to the second dCas9 coding sequence via a third spacer, a second tag coding sequence linked to the second dimerization protein coding sequence via a fourth spacer, wherein the second guide RNA encoding sequence encodes a second guide RNA, and wherein the second dCas9 coding sequence, the second dimerization protein coding sequence, and the second tag coding sequence encode a second fusion protein, wherein the first fusion protein is directed to the first chromosomal locus by the first guide RNA and the second fusion protein is directed to the second chromosomal locus by the second guide RNA, wherein the first fusion protein and the second fusion protein are configured to dimerize via a reversible chemical induced proximity system in the presence of a dimerizing agent, thereby juxtaposing the first chromosomal locus and the second chromosomal locus.

In some embodiments of the system, the first construct and the second construct are DNA-based. In some embodiments of the system, the first construct and the second construct are RNA-based. In some embodiments of the system, the first guide RNA and the second guide RNA are about 5 to about 100 nucleotides. In some embodiments of the system, the first species and second species are selected from the group consisting of *S. pyogenes, S. aureus, N. meningitides, S. thermophiles, T. denticola, S. pasteurianus, N. cinerea, C. lari, P. lavamentivorans, C. diphtheria*, and any bacterial species utilizing the CRISPR-Cas9 bacterial adaptive immune system.

In some embodiments of the system, the reversible chemical induced proximity system comprises the first dimerization protein and second dimerization protein, wherein the first dimerization protein and the second dimerization protein are configured to be brought into proximity in the presence of the dimerizing agent, thereby allowing the first fusion protein and the second fusion protein to dimerize.

In some embodiments of the system, the first dimerization protein and the second dimerization protein are selected from the group consisting of plant ABA signaling pathway, gibberellin-induced dimerization system, rapalog-induced dimerization system, RNA-mediated protein recruitment dimerization system, and derivatives thereof. In some embodiments of the system, the first dimerization protein is ABI1 and the second dimerization protein is PYL1 of the plant ABA signaling pathway. In some embodiments of the system, the dimerizing agent is ABA.

In some embodiments, a method to alter an expression of at least one gene at a first chromosomal locus by juxtaposing the first chromosomal locus and a second chromosomal locus is provided. In some embodiments, the method comprises providing a first construct comprising a first guide RNA encoding sequence, a first dCas9 coding sequence, a first dimerization protein coding sequence linked to the first dCas9 coding sequence via a first spacer, a first tag coding sequence linked to the first dimerization protein coding sequence via a second spacer, wherein the first guide RNA encoding sequence encodes a first guide RNA, and wherein the first dCas9 coding sequence, the first dimerization protein coding sequence, and the first tag coding sequence encode a first fusion protein, providing a second construct comprising a second guide RNA encoding sequence, a second dCas9 coding sequence, a second dimerization protein coding sequence linked to the second dCas9 coding sequence via a third spacer, a second tag coding sequence linked to the second dimerization protein coding sequence via a fourth spacer, wherein the second guide RNA encoding sequence encodes a second guide RNA, and wherein the second dCas9 coding sequence, the second dimerization protein coding sequence, and the second tag coding sequence encode a second fusion protein, wherein the first fusion protein is directed to the first chromosomal locus by the first guide RNA and the second fusion protein is directed to the second chromosomal locus by the second guide RNA, wherein the first fusion protein and the second fusion protein are configured to dimerize via a reversible chemical induced proximity system in the presence of a dimerizing agent, thereby juxtaposing the first chromosomal locus and the second chromosomal locus, The second chromosomal locus may comprise one or more regulatory elements that alter the expression of the at least one gene at the first chromosomal locus. In some embodiments of the method, the expression of at least one gene at the second chromosomal locus is altered by juxtaposing the first chromosomal locus and the second chromosomal locus. In some embodiments of the method, the first chromosomal locus comprises one or more regulatory elements that alter the expression of the at least one gene at the second chromosomal locus.

In some embodiments of the method, the first species and second species are selected from the group consisting of S. pyogenes, S. aureus, N. meningitides, S. thermophiles, T. denticola, S. pasteurianus, N. cinerea, C. lari, P. lavamentivorans, C. diphtheria, and any bacterial species utilizing the CRISPR-Cas9 bacterial adaptive immune system.

In some embodiments of the method, the reversible chemical induced proximity system comprises the first dimerization protein and second dimerization protein, wherein the first dimerization protein and the second dimerization protein are configured to be brought into proximity in the presence of the dimerizing agent, thereby allowing the first fusion protein and the second fusion protein to dimerize.

In some embodiments of the method, the first dimerization protein and the second dimerization protein are selected from the group consisting of plant ABA signaling pathway, gibberellin-induced dimerization system, rapalog-induced dimerization system, RNA-mediated protein recruitment dimerization system, and derivatives thereof. In some embodiments of the method, the first dimerization protein is ABI1 and the second dimerization protein is PYL1 of the plant ABA signaling pathway. In some embodiments of the method, the dimerizing agent is ABA.

In some embodiments, CLOuD9 is a broadly applicable method that enables the forced juxtaposition of any two genomic loci. In some embodiments, modification of loop structure can reversibly alter gene expression. In some embodiments, through use of this technology, evidence of a possible mechanism for the formation of stable de novo chromatin loops observed in development and cancer alike is provided. In some embodiments, a novel design based on the combination of the dCas9s with ABI1/PYL1 heterodimerization domains is provided.

Figure 1A:
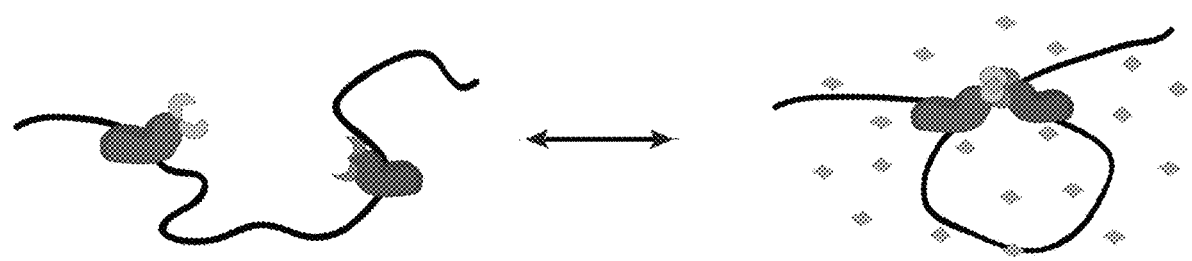
FIG. 1A shows a schematic of CLOuD9 induced reversible β-globin promoter-LCR looping.

In some embodiments, CLOuD9 technology consists of dCas9 proteins linked to a unique, reversible chemical induced proximity (CIP) system that utilizes the plant phytohormone S-(+)-abscisic acid (ABA) and modified components of the plant ABA signaling pathway (ABI1 and PYL1)[11] (FIG. 1A). Each of the dCas9 components are directed to a target locus using standard CRISPR guide RNAs (gRNAs), and juxtaposition of the two chromosomal loci is induced with addition of ABA which facilitates reversible association of the CIP proteins (dimerization)[11]. In some embodiments, the size of the guide RNA can be from approximately 5 to approximately 35 nucleotides. In some embodiments, the size of the guide RNA can be about 30 to about 65 nucleotides. In some embodiments, the size of the guide RNA can be about 60 to about 100 nucleotides.

[0078] In some embodiments of the systems and methods, the first fusion protein and the second fusion protein are configured to dimerize via a reversible chemical induced proximity system in the presence of a dimerizing agent. In some embodiments of the systems and methods, the first fusion protein and the second fusion protein are configured to dimerize via a reversible chemical induced proximity system in the presence of a dimerizing agent thereby juxtaposing the first chromosomal locus and the second chromosomal locus. In some embodiments, addition of abscisic acid (ABA, green) brings two complementary CLOuD9 constructs (CLOuD9 Streptococcus pyogenes (CSP), CLOuD9 Staphylococcus aureus (CSA), red and blue, respectively) into proximity, remodeling chromatin structure. Removal of ABA restores the endogenous chromatin conformation (FIG. 1A). In some embodiments, addition of abscisic acid (ABA, green) brings two complementary CLOuD9 constructs (CLOuD9 Streptococcus pyogenes (CSP), CLOuD9 Staphylococcus aureus (CSA), red and blue, respectively) into proximity, remodeling chromatin structure. Removal of ABA restores the endogenous chromatin conformation (FIG. 1A). Other sources of dCas9 include, without limitations, S. pyogenes, S. aureus, N. meningitides, S. thermophiles, T. denticola, S. pasteurianus, N. cinerea, C. lari, P. lavamentivorans, C. diphtheria, and any bacterial species utilizing the CRISPR-Cas9 bacterial adaptive immune system.

As used herein, the term "construct" or "vector" refers to a polynucleotide construct. Constructs can be DNA- or RNA-based vectors. DNA-based vectors can be non-viral, and include molecules such as plasmids, minicircles, closed linear DNA, doggybones, linear DNA, single-stranded DNA, cosmids, phage, phagemids, phasmid, etc. DNA-based vectors can also be viral, and include adeno-associated virus, lentivirus, adenovirus, etc. RNA-based vectors include, without limitations, linear or circular forms of RNA with or without nucleotide modifications. Nucleotide modifications are designed to increase such properties as half-life, decrease immunogenicity, increase level of translation, etc. In some embodiments, vectors are capable of autonomous replication in a prokaryote such as E. coli. In some embodiments, a vector may be stably integrated into the genome. In some embodiments, a vector remains separate from the genome, either in the cytoplasm or the nucleus. In some embodiments, a vector comprises one or more of a targeting sequence, an antibiotic resistance gene, regulatory elements for regulating gene expression. Constructs can also include, without limitations, lentiviral vectors, adenoviral vectors, adeno-associated viral (AAV) vectors, and/or retroviral vectors. A suitable vector can be selected depending on a number of factors, for example, the cell type to be genetically engineered, construct to be expressed, patient characteristics, disease indication, etc. In some embodiments, vector is further modified and/or optimized for a particular use or set of uses. Recombinant adeno-associated viruses (AAVs) are capable of expressing one or more proteins of interest in an appropriate environment, for example, in a cell, a tissue, an organ, or a subject transfected with the recombinant AAVs in vivo, ex vivo, or in vitro. In some embodiments of the systems and methods, the first construct and the second construct are nucleic acids/polynucleotides. In some embodiments of the systems and methods, the first construct and the second construct are DNA-based. In some embodiments of the systems and methods, the first construct is DNA-based and the second construct is RNA-based. In some embodiments of the systems and methods, the first construct is RNA-based and the second construct is DNA-based. In some embodiments of the systems and methods, the first construct and the second construct are RNA-based.

As used herein, "associated virus (AAV) vector" refers to a virus that is widely used for generating viral vectors for therapeutic interventions such as gene therapy as well as for gene expression.

In some embodiments, constructs can further comprise one or more regulatory elements. Non-limiting examples of prokaryotic regulatory elements include promoters, operators and ribosome binding sites. Non-limiting examples of eukaryotic regulatory elements include, without limitation, transcriptional and translational control sequences, such as promoters, terminators, enhancers, insulators, splicing signals, polyadenylation signals, terminators, protein degradation signals, internal ribosome-entry element (IRES), spacers such as 2A self-cleaving peptide sequences and 2A-like sequences (e.g., porcine teschovirus-1 2A (P2A), thosea asigna virus 2A (T2A), equine rhinitis A virus 2A (E2A), cytoplasmic polyhedrosis virus (BmCPV 2A), and flacherie virus (BmIFV 2A) of *B. mori*), etc., that provide for and/or regulate expression of a coding sequence and/or production of an encoded polypeptide in a host cell.

In some embodiments of the systems and methods, the size of the first guide RNA and the second guide RNA ranges from about 5 to about 100 nucleotides. In some embodiments of the systems and methods, the size of the first guide RNA and the second guide RNA ranges from about 5 to about 200 nucleotides. In some embodiments of the systems and methods, the size of the first guide RNA and the second guide RNA is about 5, 10, 15, 20, 25, 30, 35, 40, 45, 50, 55, 60, 65, 70, 75, 80, 85, 90, 95, 100, 125, 150, 175, or 200 nucleotides, or a value within a range deifned by any two of the aforementioned values.

In some embodiments of the systems and methods, the species of the first Cas9 coding sequence is selected from the group consisting of *S. pyogenes, S. aureus, N. meningitides, S. thermophiles, T. denticola, S. pasteurianus, N. cinerea, C. lari, P. lavamentivorans*, and *C. diphtheria*. In some embodiments of the systems and methods, the species of the first Cas9 coding sequence is from any bacterial species utilizing the CRISPR-Cas9 bacterial adaptive immune system. In some embodiments of the systems and methods, the species of the second Cas9 coding sequence is selected from the group consisting of *S. pyogenes, S. aureus, N. meningitides, S. thermophiles, T. denticola, S. pasteurianus, N. cinerea, C. lari, P. lavamentivorans*, and *C. diphtheria*. In some embodiments of the systems and methods, the species of the second Cas9 coding sequence is from any bacterial species utilizing the CRISPR-Cas9 bacterial adaptive immune system. In some embodiments of the systems and methods, the species of the first Cas9 coding sequence and the species of the second Cas9 coding sequence are different. In some embodiments of the systems and methods, the species of the first Cas9 coding sequence and the species of the second Cas9 coding sequence are different.

Proteins expressed in cells can include one or more tags for purification, solubilization, detection, etc. Non-limiting examples include AviTag, Calmodulin-tag, polyglutamate tag, E-tag, FLAG-tag, HA-tag, His-tag, Myc-tag, NE-tag, S-tag, SBP-tag, Softag 1, Softag 3, Strep-tag, TC tag, V5 tag, VSV-tag, Xpress tag, Isopeptag, SpyTag, SnoopTag, BCCP (Biotin Carboxyl Carrier Protein), Glutathione-S-transferase-tag, Green fluorescent protein-tag, other fluorescent protein tags, HaloTag, Maltose binding protein-tag, Nus-tag, Thioredoxin-tag, Fc-tag, Designed Intrinsically Disordered tags containing disorder promoting amino acids (e.g., P, E, S, T, A, Q, G), Ty tag, etc.

In some embodiments of the systems and methods, the reversible chemical induced proximity comprises a first dimerization protein and a second dimerization protein. In some embodiments of the systems, the first dimerization protein and the second dimerization protein are configured to be brought into proximity in the presence of a dimerizing agent. In some embodiments of the systems, the first dimerization protein and the second dimerization protein are configured to juxtapositioned in the presence of a dimerizing agent. In some embodiments of the methods, the first dimerization protein and the second dimerization protein are brought into proximity in the presence of a dimerizing agent. In some embodiments of the methods, the first dimerization protein and the second dimerization protein are juxtapositioned in the presence of a dimerizing agent. In some embodiments of the systems, the first dimerization protein and the second dimerization protein are configured to juxtapositioned in the presence of a dimerizing agent allowing the first fusion protein and the second fusion protein to dimerize. In some embodiments of the methods, the first dimerization protein and the second dimerization protein are juxtapositioned in the presence of a dimerizing agent allowing the first fusion protein and the second fusion protein to dimerize.

In some embodiments of the systems and methods, the first dimerization protein is selected from the group consisting of plant ABA signaling pathway, gibberellin-induced dimerization system, rapalog-induced dimerization system, RNA-mediated protein recruitment dimerization system, and derivatives thereof. In some embodiments of the systems and methods, the second dimerization protein is selected from the group consisting of plant ABA signaling pathway, gibberellin-induced dimerization system, rapalog-induced dimerization system, RNA-mediated protein recruitment dimerization system, and derivatives thereof. In some embodiments of the systems and methods, the first dimerization protein and the second dimerization protein are different. In some embodiments of the systems and methods, the first dimerization protein and the second dimerization protein are the same.

In some embodiments of the systems and methods, the first dimerization protein is ABI1 and the second dimerization protein is PYL1 of the plant ABA signaling pathway. In some embodiments of the systems and methods, the first dimerization protein is PYL1 and the second dimerization protein is ABI1 of the plant ABA signaling pathway. In some embodiments of the systems and methods, the dimerizing agent is ABA.

Without being bound by any theory, components of the plant stress response pathway were chosen because the pathway relies on a substance (ABA) naturally found in plant-based diets at low levels. Thus, there is minimal and/or no concern related to toxicity with respect to CLOuD9 system. In comparison, some other systems have prohibitively high toxicity, and therefore, have severely adverse effects on cells (e.g., an FKBP-based system described in WO 2016/098078 A2, which is hereby incorporated by reference in its entirety). Thus, the CLOuD9 technology is superior in that there is minimal and/or no impact on overall cell health. For example, in some embodiments, CLOuD9 technology did not have any notable harmful impacts on cell proliferation. In some embodiments, the use of other similar minimally toxic/non-toxic reversibly dimerizeable protein systems is also contemplated.

Several additional embodiments of CLOuD9 are contemplated. For example, some embodiments allow for greater numbers of loci to be targeted simultaneously, or some embodiments allow for greater specificity or flexibility of targeting as necessary. In some embodiments, alternate species of dCas9 can be utilized, or additional dimerization proteins can be utilized, for example, utilizing gibberellin induced OP system and its derivatives in conjunction with any of the dCas9 proteins, RNAs in conjunction with the dCas9s to facilitate specific dimerization, or minimally toxic/non-toxic alternative of the FKBP system. In some embodiments, combinations of other derivations of this technology that allow for multiple regions to be dimerized simultaneously (i.e., that allow for multiple loci to simultaneously contacted and multimerized) are contemplated and within the scope of this disclosure.

Multiple species of dCas9 that have recently been characterized (Nishimasu et al. 2014, Cell 156(5): 935-949; Nishimasu et al. 2015, Cell 162(5):1113-1126). In some embodiments, CLOuD9 takes advantage of multiple species of dCas9, which is a critical element for the design of the CLOuD9 technology.

In some embodiments, dCas9 from both S. aureus (CSA) and S. pyogenes (CSP) was used, tethering one half of the dimerization construct to the C terminus of each of the dCas9 proteins (FIG. 1B) and ensuring 100% functional juxtaposition of the two target genomic regions. Thus, dCas9 from both S. aureus (CSA) and S. pyogenes (CSP) were used, tethering one half of the dimerization construct to the C terminus of each of the dCas9 protein and ensuring 100% functional juxtaposition of the two target genomic regions.

Figure 1B:
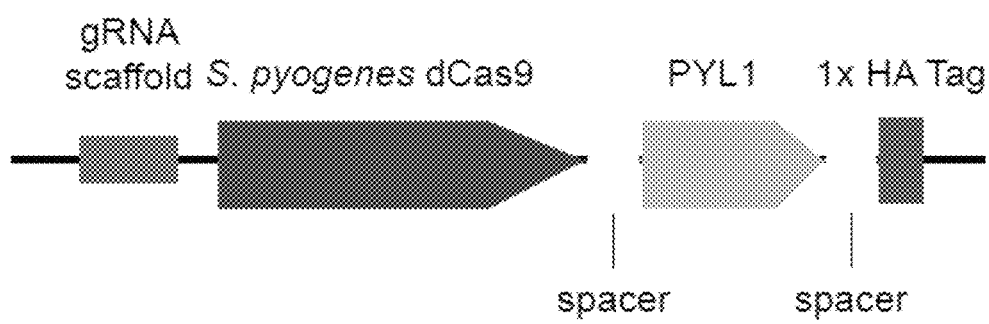
FIG. 1B shows a schematic of an embodiment of CLOuD9 constructs combining CRISPR-dCas9 technology from S. aureus and S. pyogenes with reversibly dimerizeable PYL1 and ABI1 domains.
Figure 1B:
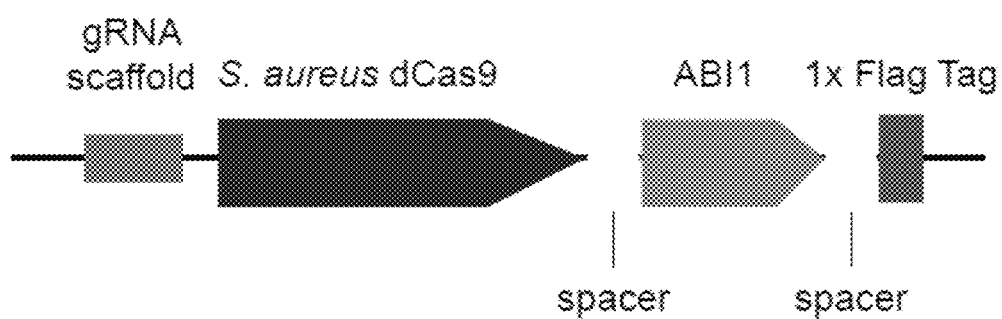

Without being bound by any theory, in principle, this simple CLOuD9 system offers the ease and flexibility of reversible chromosomal manipulation between any two genomic regions targetable by CRISPR gRNAs. In some embodiments, CLOuD9 constructs combined CRISPR-dCas9 technology from S. aureus and S. pyogenes with reversibly dimerizeable PYL1 and ABI1 domains (FIG. 1B). HA or Flag tags were utilized in the constructs for Western, IP, and/or CHIP experiments (FIG. 1B). In some embodiments, other dimerizable protein pairs and their derivatives are also contemplated. Non-limiting examples include the gibberellin induced dimerization system, rapalog induced dimerization system, RNA-mediated protein recruitment dimerization system, and derivatives thereof.

In some embodiments of the methods, an expression of at least one gene at a first chromosomal locus is altered by juxtaposing the first chromosomal locus and a second chromosomal locus. In some embodiments of the methods, an expression of at least one gene at a second chromosomal locus is altered by juxtaposing the first chromosomal locus and a second chromosomal locus. In some embodiments of the methods, an expression of at least one gene at both a first chromosomal locus and a second chromosomal locus is altered by juxtaposing the first chromosomal locus and a second chromosomal locus. In some embodiments of the methods, an expression of at least one gene at a first chromosomal locus is altered by juxtaposing the first chromosomal locus and one or more regulatory elements at a second chromosomal locus that alter the expression of the at least one gene at the first chromosomal locus. In some embodiments of the methods, an expression of at least one gene at a second chromosomal locus is altered by juxtaposing the second chromosomal locus and one or more regulatory elements at a first chromosomal locus that alter the expression of the at least one gene at the second chromosomal locus. In some embodiments of the methods, the first chromosomal locus and the second chromosomal locus are on the same chromosome. In some embodiments of the methods, the first chromosomal locus and the second chromosomal locus are on different chromosomes.

In some embodiments, the at least one gene whose expression altered encodes for a regulatory protein. Non-limiting examples of regulatory proteins include proteins that regulate transcription, translation, DNA synthesis, DNA repair, cellular structure, metabolism, and other cellular processes. Thus, in some embodiments, the at least one gene can affect the expression of one or more other genes. Therefore, in some embodiments, an expression of 1 to about 10,000 genes is altered. In some embodiments, an expression of 1, 10, 25, 50, 75, 100, 250, 500, 750, 1000, 2500, 5000, 7500, 10,000, 12,500, or 15,000 genes is altered, or a number within a range defined by any two of the aforementioned values. In some embodiments, an expression of more than 15,000 genes is altered. In some embodiments, an alteration of expression is an upregulation of expression. In some embodiments, an upregulation of expression is an increase in expression of a gene at the RNA level, protein level or both as compared to a basal, reference, or control level. In some embodiments, the increase in expression ranges from about 1.5 fold to about 1500 fold. In some embodiments, the increase in expression ranges from about 2 fold to about 2000 fold. In some embodiments, the increase in expression is about 1.1, 1.2, 1.3, 1.4, 1.5, 2, 10, 25, 50, 75, 100, 150, 200, 250, 500, 750, 1000, 1500, 2000, 2500, 3000, 3500, 4000, 4500, or 5000 fold, or a value within a range defined by any two of the aforementioned values. In some embodiments, upregulation can be an increase in the number of copies of a gene.

In some embodiments, an alteration of expression is a downregulation of expression. In some embodiments, a downregulation of expression is a decrease in expression of a gene at the RNA level, protein level or both as compared to a basal, reference, or control level. In some embodiments, the decrease in expression ranges from about 1.5 fold to about 1500 fold. In some embodiments, the decrease in expression ranges from about 2 fold to about 2000 fold. In some embodiments, the decrease in expression is about 1.1, 1.2, 1.3, 1.4, 1.5, 2, 10, 25, 50, 75, 100, 150, 200, 250, 500, 750, 1000, 1500, 2000, 2500, 3000, 3500, 4000, 4500, or 5000 fold, or a value within a range defined by any two of the aforementioned values. In some embodiments, downregulation can be a decrease in the number of copies of a gene.

In some embodiments, the cells are of human origin. In some embodiments, the cells are of non-human origin. In some embodiments, the cells are a fusion of human and non-human origin. In some embodiments, the cells are primary cells. In some embodiments, the cells are cells lines. In some embodiments, the cells are immortalized cells lines. Non-limiting examples of cell lines are provided at the URL accessible on the World Wide Web at en.wikipedia.org/wiki/Cell_culture, which is hereby incorporated by reference in its entirety).

In some embodiments, the systems and methods herein are adaptable and applicable to other model organisms such as plants, fungi, yeast, drosohpila, xenopus, insects, model fish (e.g. zebra fish), mice, rats, guinea pigs, model worms, parasites (e.g, Plasmodium spp., Babesia spp., Toxoplama spp., etc.), an the like.

In some embodiments, a system for juxtaposing a first chromosomal locus and a second chromosomal locus is provided. In some embodiments, the system comprises a first fusion protein and a first guide RNA, wherein the first fusion protein comprises a dCas9 from a first species, a first dimerization protein, and a first tag; and a second fusion protein and a second guide RNA, wherein the second fusion protein comprises a dCas9 from a second species, a second dimerization protein, and a second tag. In some embodiments of the system, the first fusion protein is directed to the first chromosomal locus by the first guide RNA. In some embodiments of the system, the second fusion protein is directed to the second chromosomal locus by the second guide RNA. In some embodiments of the system, the first fusion protein and the second fusion protein are configured to dimerize. In some embodiments of the system, the first fusion protein and the second fusion protein are configured to dimerize and juxtapose the first chromosomal locus and the second chromosomal locus.

In some embodiments, the fusion proteins and guide RNAs are delivered to cells encapsulated in liposomes, nanoparticles, micelles, etc. In some embodiments, the proteins are delivered to cells encapsulated in liposomes, nanoparticles, micelles, etc., whereas the guide RNAs are provided as a nucleic acid construct. In some embodiments, the fusion proteins are associated with cell-penetrating peptides. In some embodiments, the guide RNAs are associated with cell-penetrating peptides. In some embodiments, the fusion proteins and/or guide RNAs are associated with cell-penetrating peptides covalently. In some embodiments, the fusion proteins and/or guide RNAs are associated with cell-penetrating peptides non-covalently. with Deliver gRNA and protein. Cell penetrating peptides facilitate cellular uptake of macromolecules such as proteins and nucleic acids (See, en.wikipedia.org/wiki/Cell-penetrating_peptide, which is hereby incorporated by reference in its entirety).

Figure 1C:
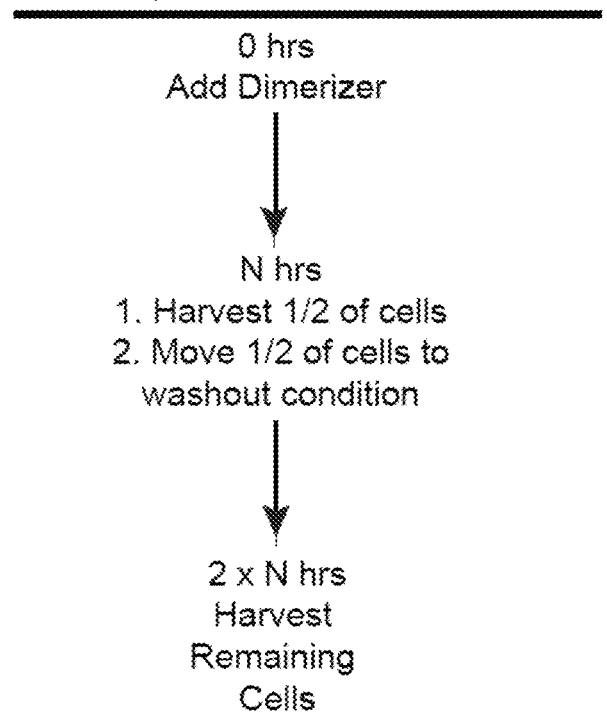
FIG. 1C shows a schematic of an embodiment of timeline of CLOuD9 dimerization experiments disclosed herein.
Figure 1D:
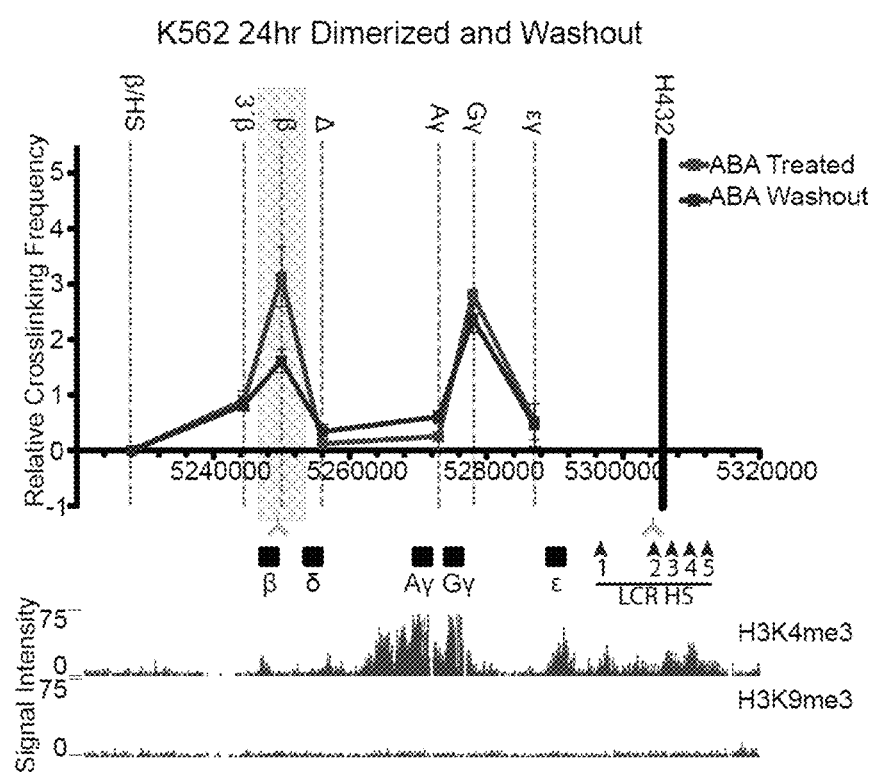
FIG. 1D shows an embodiment of 3C assay measuring β-globin locus-wide crosslinking frequencies in K562 cells.
Figure 1E:
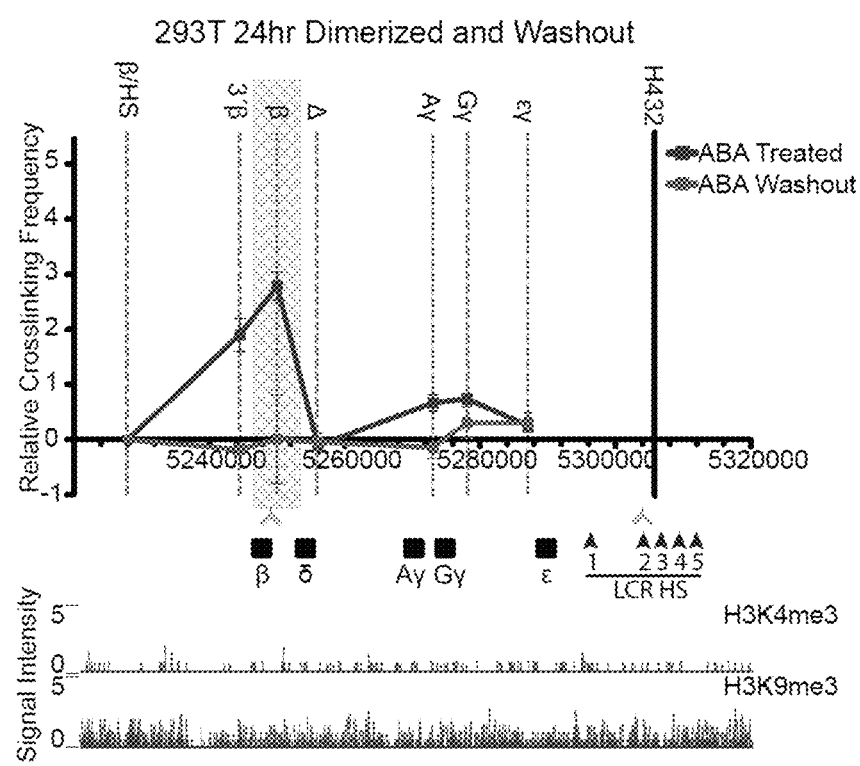
FIG. 1E shows reversible changes in chromatin structure in HEK 293T cells.
Figure 1F:
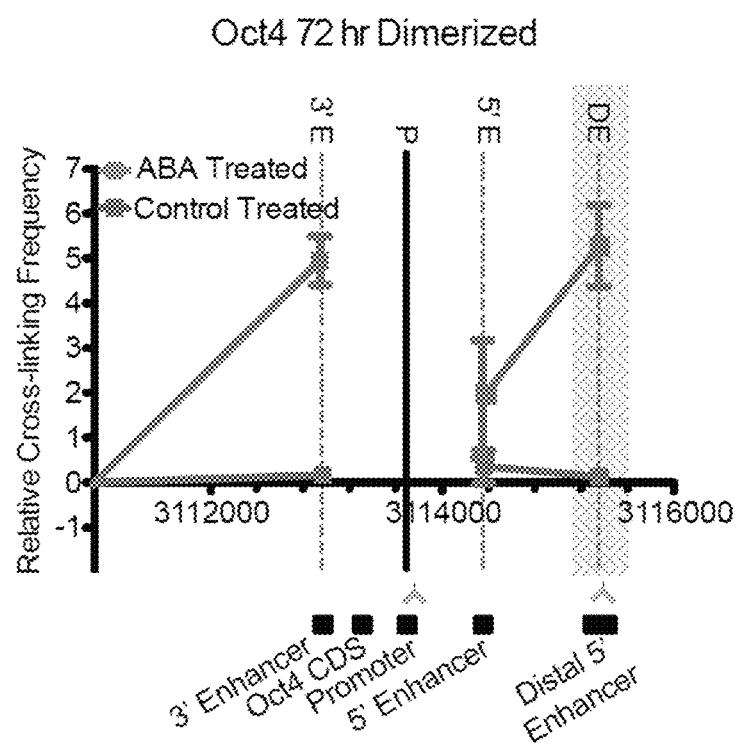
FIG. 1F shows an embodiment of 3C assay measuring Oct4 locus-wide crosslinking frequencies in 293T cells.

The utility of CLOuD9 on the human globin locus was first tested, given the well-characterized, dynamic chromosomal rearrangements that regulate globin gene expression during development (for review see[1]). Long-range looping interactions at the globin locus are well studied and ideal for testing the CLOuD9 system (FIG. 1H). The beta globin locus is a very well-studied example of malleable long-range loop interactions, and had recently been utilized by others for similar manipulations. Thus, in some embodiments, the CLOuD9 system was tested on the beta globin locus. In healthy adult cells, the endogenous contact in this region is between the locus control region (LCR; a strong enhancer) and the beta globin promoter (FIG. 1H). In contrast, K562 cells endogenously express gamma globin (FIG. 1I).

As the K562 human erythroleukemia cell line has been exhaustively characterized to aberrantly express the fetal γ-globin gene at high levels, rather than the β-globin gene traditionally seen in adult human erythroid lineage cells, K562 cells were investigated to determine whether β-globin gene expression in these cells could be re-established. CLOuD9 constructs were targeted to the promoter of the β-globin locus (CSA) and the HS2 region of the LCR (CSP) (FIG. 1J). Cells with CLOuD9 targeting either two separate β-globin promoter or two separate HS2 regions were used as controls. ABA was then added for varying durations to induce dimerization. The timeline of an embodiment of a CLOuD9 dimerization experiment is shown in FIG. 1C.

Figure 1G:
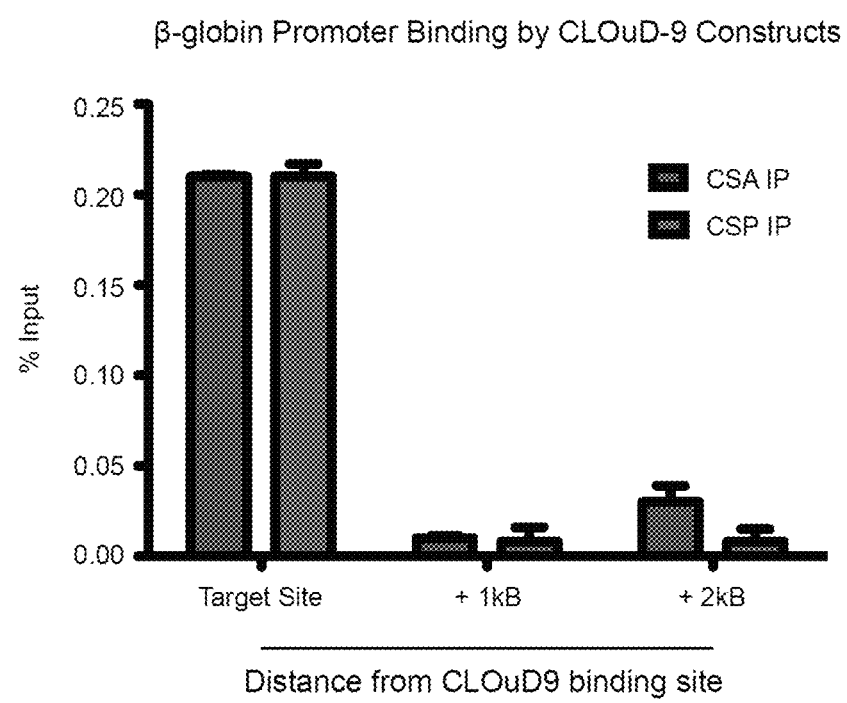
FIG. 1G shows localization of CLOuD9 constructs to their intended target regions.
Figure 1H:
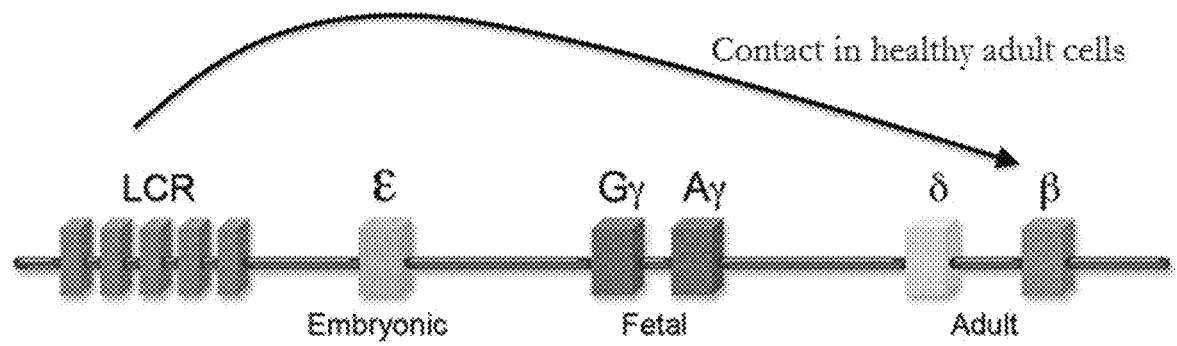
FIG. 1H shows a schematic of long-range looping interactions at the globin locus in healthy adult cells.
Figure 1J:
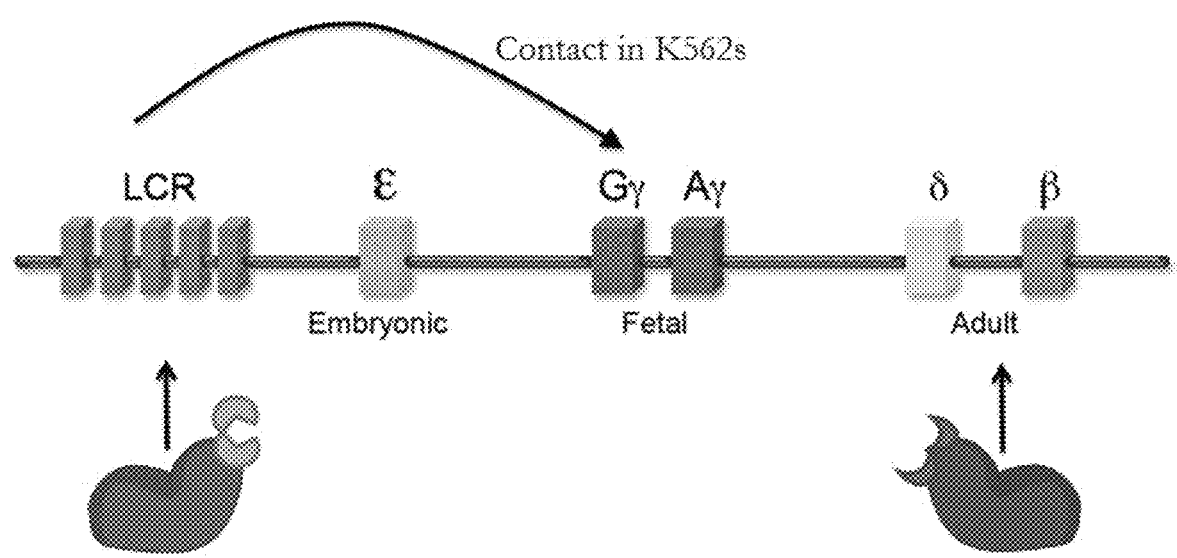
FIG. 1J shows a schematic of CLOuD9 design strategy for forcible long-range looping interactions at the globin locus in K562 cells.

The correct localization and targeting of each CRISPR-dCas9 component was first confirmed by ChIP-qPCR (FIG. 1G). Chromatin immunoprecipitation and quantitative PCR of CLOuD9 constructs demonstrates correct localization to their intended genomic loci. Additionally, to verify that CSA and CSP were indeed dimerizing upon addition of the ligand, co-immunoprecipitations were performed both in the presence and absence of ABA, as well as after ligand washout (FIG. 2G). Co-immunoprecipitations demonstrating association of the dCas9 proteins following 72 hours of ABA treatment is reversed following subsequent 72 hours of ligand washout (FIG. 2G).

Figure 18:
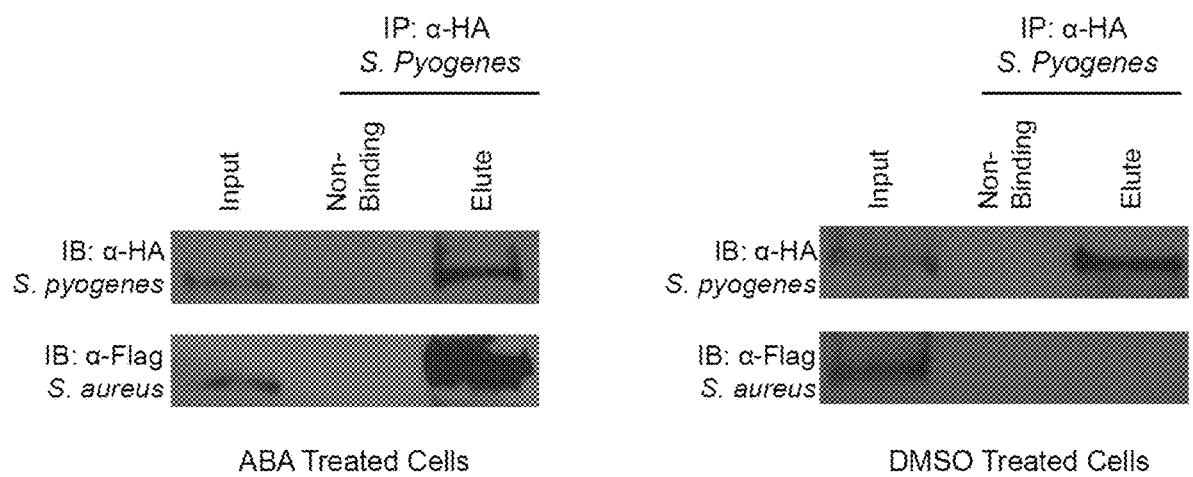
FIG. 18 shows CLOuD9 dimerizers associate in response to ABA treatment.

FIG. 18 shows CLOuD9 dimerizers associate in response to ABA treatment. To verify that CSA and CSP were indeed dimerizing upon addition of the ligand, co-immunoprecipitations were performed both in the presence and absence of ABA, as well as after ligand washout (FIG. 18). As expected, addition of the ligand induced clear dimerization of CSA and CSP, and this effect was reversible upon ligand removal. Co-immunoprecipitations demonstrated association of the dCas9 proteins following immunoprecipitation with anti-HA antibody in the presence of ABA only.

Without being limited by any particular theory, as expected, addition of the ligand induced clear dimerization of CSA and CSP, and this effect was reversible upon ligand removal. Next, it was tested whether forced dimerization induced a conformational change in the chromatin that was specific to the targeted sites. Indeed, as early as 24 hours after the addition of ABA, an increase in the frequency of β-globin/LCR contacts was observed through chromosome conformation capture (3C) in cells containing both dimerization partners, but not in any of the controls (FIG. 1D, FIG. 3G and FIG. 4G).

FIG. 1D shows an embodiment of 3C assay measuring β-globin locus-wide crosslinking frequencies in K562 cells after 24 hours of treatment with ABA (red) and subsequent washout (blue) showing reversibility of induced β-globin/LCR contacts (highlighted in grey). Orange arrowheads indicate specific CLOuD9 construct target regions. The EcoRI fragment containing hypersensitivity sites 1-4 of the LCR (black bar) was used as the anchor region. Its cross-linking frequency with other indicated EcoRI fragments (names on the top of the graph) were assessed. The human β-globin genes and LCR hypersensitivity sites are depicted on the bottom of the graph with chromosomal position coordinates. Data from ChIP-seq of H3K4me3 and H3K9me3 demonstrate that this region is euchromatic in K562 cells.

Figure 4G:
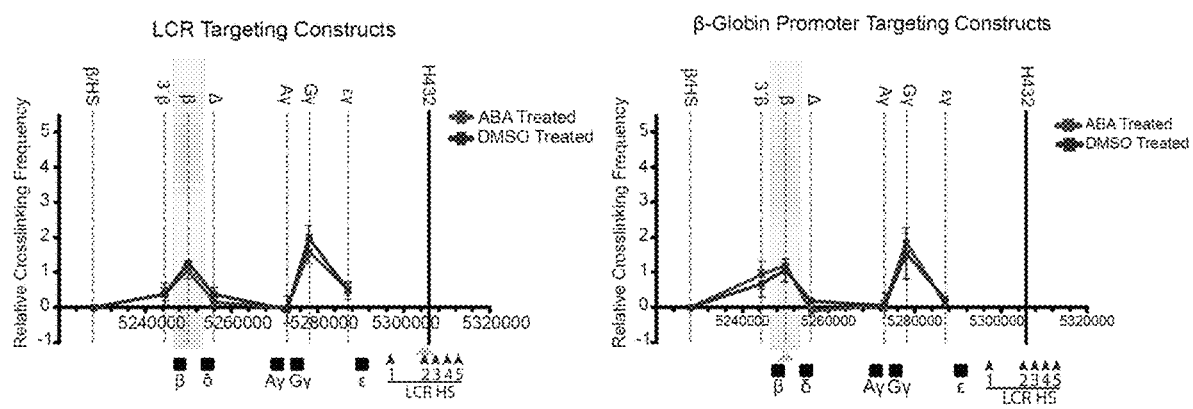
FIG. 4G shows control CLOuD9 transduced cells show no alterations in chromatin looping.
Figure 5:
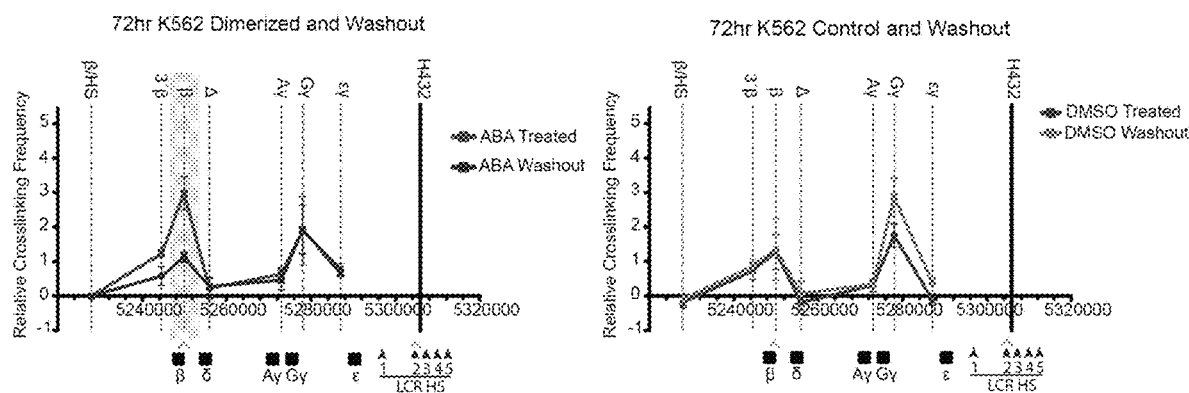
FIG. 5 shows CLOuD9 chromatin looping remains reversible after 72 hours of dimerization.
Figure 6:
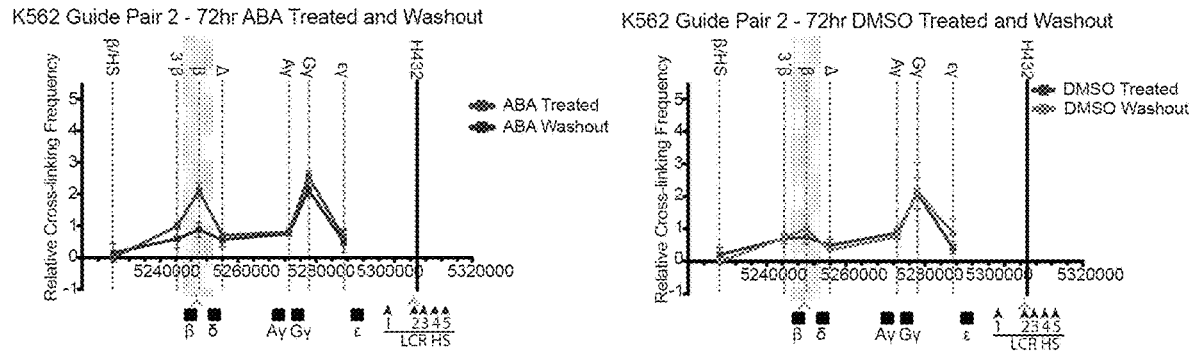
FIG. 6 shows CLOuD9 induced β-globin/LCR looping is not impacted by globin target site.

Consistent with previous reports, it was observed that induction of an LCR/β-globin contact did not destroy the endogenous LCR/globin contact—rather, the new LCR/β-globin contact appears in addition to the endogenous connection[10]. This effect was sustained throughout 72 hours of dimerization regardless of the precise region within the LCR and β-globin promoter that was targeted (FIG. 5 and FIG. 6). Importantly, the chromatin loop modification induced by CLOuD9 was reversible, as 3C performed after ligand washout (in as little as 24 hours) resulted in restoration of the LCR chromosomal configuration to its endogenous state (FIG. 1D, FIG. 3G, FIG. 4G, FIG. 5 and FIG. 6).

Figure 3A:
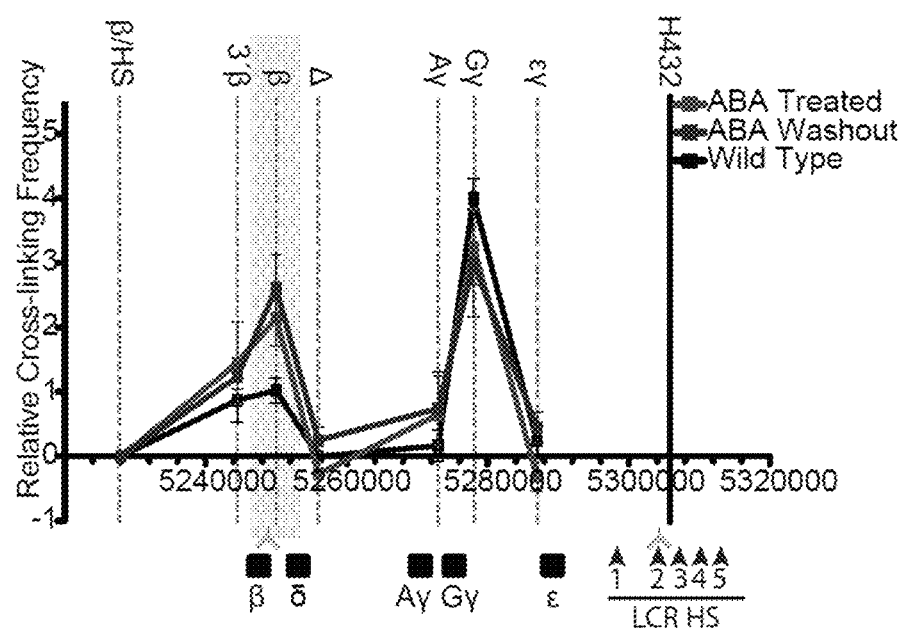
FIG. 3A shows CLOuD9 induced chromatin looping following long-term dimerization in K562 cells.
Figure 3B:
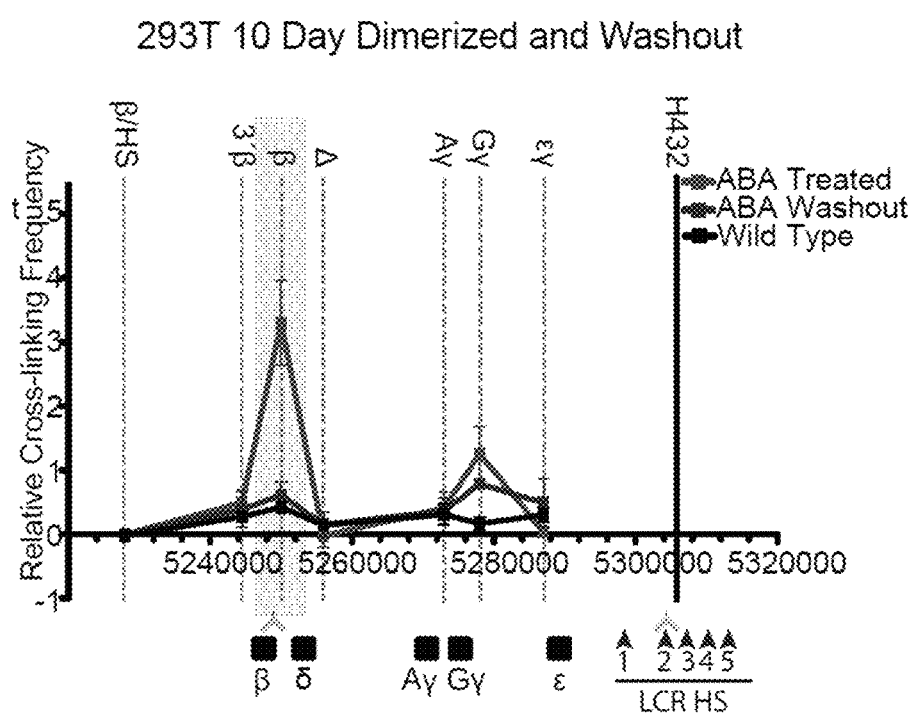
FIG. 3B shows CLOuD9 induced chromatin looping following long-term dimerization in 293T cells.
Figure 3C:
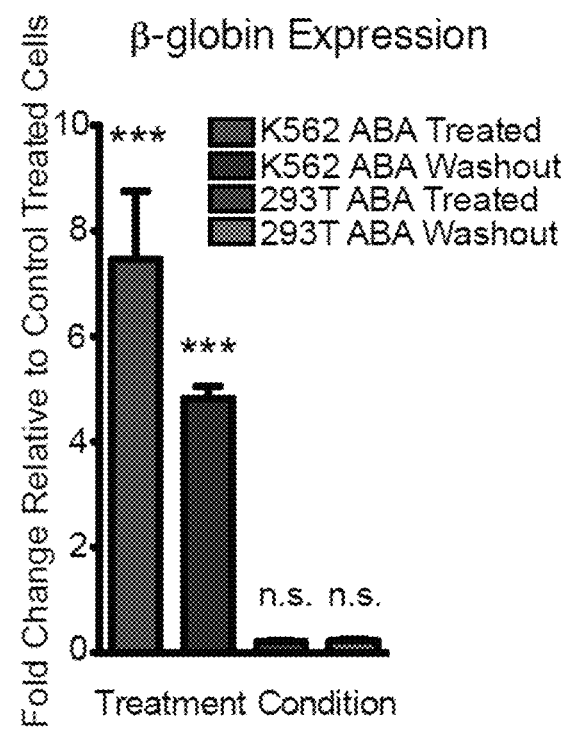
FIG. 3C shows loop stabilization in K562 cells.
Figure 3D:
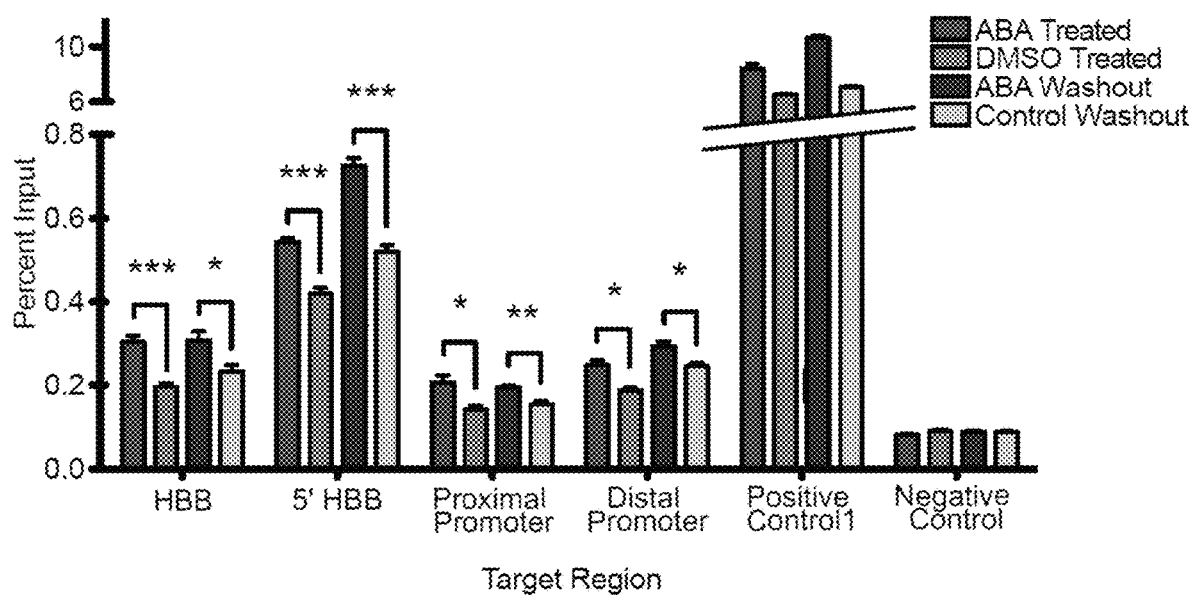
FIG. 3D shows ChIP-qPCR data for in H3K4me3 marks over the β-globin locus in K562 cells.
Figure 3E:
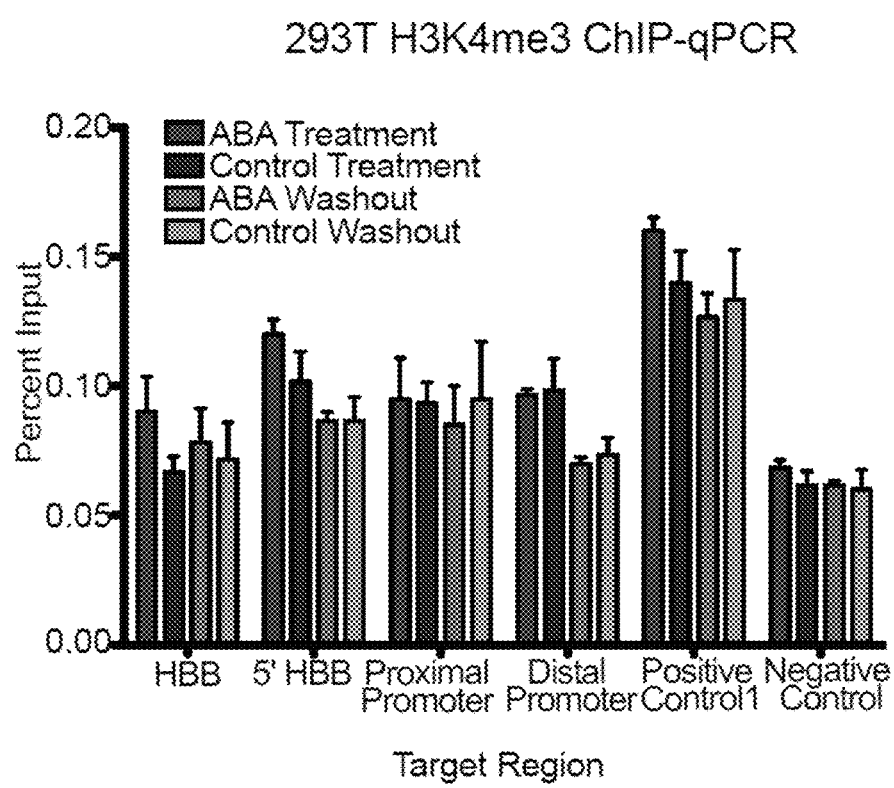
FIG. 3E shows ChIP-qPCR data for in H3K4me3 marks over the β-globin locus in 293T cells.
Figure 3F:
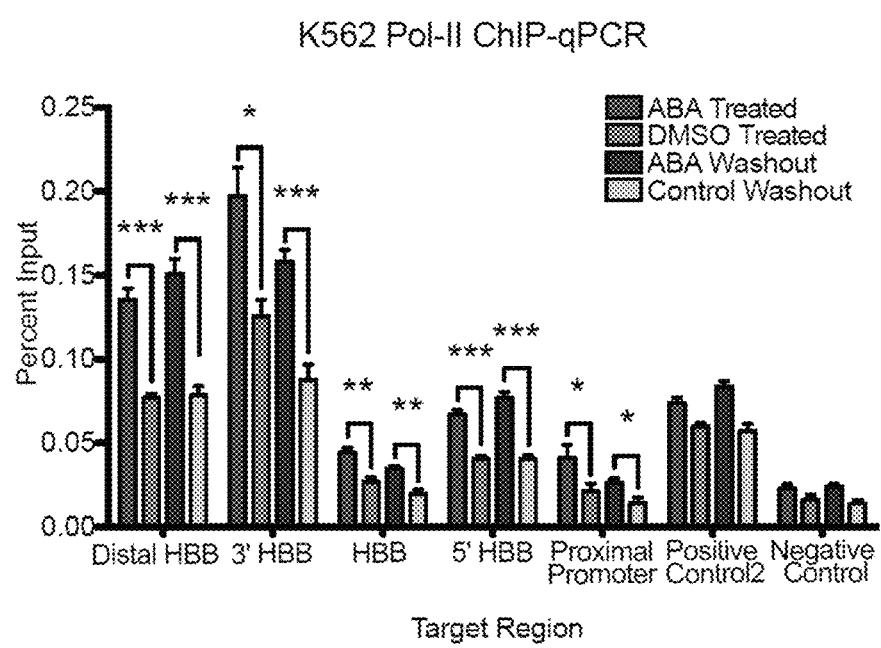
FIG. 3F shows data related to RNA Pol-II occupancy of the β-globin locus.
Figure 3G:
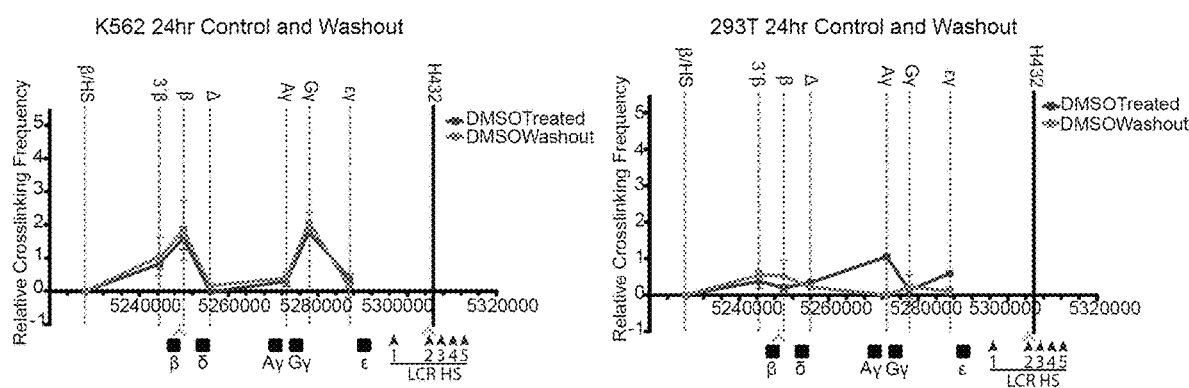
FIG. 3G shows control treatment induces no changes in chromatin contacts.

FIG. 3G shows control treatment induces no changes in chromatin contacts. Treatment with DMSO, a control agent, for 24 hours induces no changes in the endogenous chromatin conformation by 3C in either K562 cells or HEK 293T cells. 3C values were normalized to tubulin, and interaction frequencies between the anchor fragment and the fragment encompassing the β/HS fragment were set to zero. Error bars indicate SD. n=3.

FIG. 4G shows control CLOuD9 transduced cells show no alterations in chromatin looping. Directing two CLOuD9 constructs to either the LCR or the β-globin promoter induces no significant changes in chromatin structure by 3C following ABA treatment relative to control treatment. 3C values were normalized to tubulin, and interaction frequencies between the anchor fragment and the fragment encompassing the β/HS fragment were set to zero. Error bars indicate SD. n=3.

FIG. 5 shows CLOuD9 chromatin looping remains reversible after 72 hours of dimerization. 3C assay in K562 cells demonstrates reversibility of CLOuD9 induced β-globin/LCR contacts after 72 hours of ABA treatment. 3C values were normalized to tubulin, and interaction frequencies between the anchor fragment and the fragment encompassing the β/HS fragment were set to zero. Error bars indicate SD. n=3.

FIG. 6 shows CLOuD9 induced β-globin/LCR looping is not impacted by globin target site. Directing CSA and CSP constructs to alternate regions of the LCR or the (3-globin promoter results in similar reversible changes in loop induction by 3C following 72 hours of ABA treatment. 3C values were normalized to tubulin, and interaction frequencies between the anchor fragment and the fragment encompassing the β/HS fragment were set to zero. Error bars indicate SD. n=3.

As the globin locus in K562 cells is a large span of euchromatin and thus may be more amenable to manipulation (FIG. 1D), it was tested whether loop formation would be possible in regions of heterochromatin. Accordingly, CLOuD9 constructs targeting the LCR and β-globin loci were introduced into HEK 293T cells, where the globin genes are not expressed and are heterochromatic (FIG. 1E). As observed in K562 cells, addition of ABA for 24 hours resulted in an increase in the frequency of β-globin/LCR contacts as measured by 3C (FIG. 1E and FIG. 3G).

FIG. 1E shows similar reversible changes in chromatin structure in HEK 293T cells, despite evidence from H3K4me3 and H3K9me3 ChIP-seq data that the globin region is heterochromatic in this cell type. This illustrates the robustness of CLOuD9 in its ability to operate in multiple cellular environments, regardless of endogenous chromatin state, accessibility, or conformation.

As CLOuD9 is designed to be broadly applicable, it was tested whether CLOuD9 could induce alterations in chromatin conformation at additional loci. CLOuD9 was targeted to the Oct4 promoter and distal 5' enhancer in 293T cells where no endogenous contacts have been reported and Oct4 is not expressed at detectable levels. These regions were chosen as targets due to evidence that contact of the distal 5' enhancer with the promoter of Oct4 drives expression of this gene in embryonic stem cells[12]. Similar to observations at the β-globin locus, addition of ABA to CLOuD9-enabled cells resulted in induction of a contact between the Oct4 distal 5' enhancer and promoter that was not present in control cells (FIG. 1F).

Interestingly, induction of this contact also recruited a 3' enhancer to the Oct4 promoter, consistent with previous reports that the 3' enhancer is juxtaposed to the Oct4 promoter/5' distal enhancer complex during endogenous gene activation[13].

FIG. 1F shows an embodiment of 3C assay measuring Oct4 locus-wide crosslinking frequencies in 293T cells after 72 hours of treatment with ABA (red) showing induced Oct4/distal enhancer contacts (highlighted in grey). Orange arrowheads indicate specific CLOuD9 construct target regions. The MboI fragment containing the Oct4 promoter (black bar) was used as the anchor region. Its crosslinking frequency with other indicated MboI fragments (names on the top of the graph) were assessed. The human Oct4 regions are depicted on the bottom of the graph with chromosomal position coordinates. All of the 3C results were obtained from at least three independent experiments. 3C values were normalized to tubulin. For β-globin, interaction frequencies between the anchor fragment and the fragment encompassing the β/HS fragment were set to zero. For Oct4, interaction frequencies between the anchor fragment and a negative control fragment outside of the Oct4 interacting region were set to zero. Error bars indicate SD. n=3.

Whether CLOuD9 induced chromatin conformation changes altered gene expression was investigated. As the LCR contact with the globin gene loci and the distal 5' enhancer contact with the Oct4 promoter have been shown to be critical for transcription[1, 13], it was reasoned that forcible loop induction would promote strong gene expression in both contexts. Indeed, reverse transcription quantitative PCR (qRT-PCR) analyses demonstrated that for both loci, addition of ABA resulted in marked increases in gene expression compared to controls (FIG. 2A and FIG. 2B).

Figure 2A:
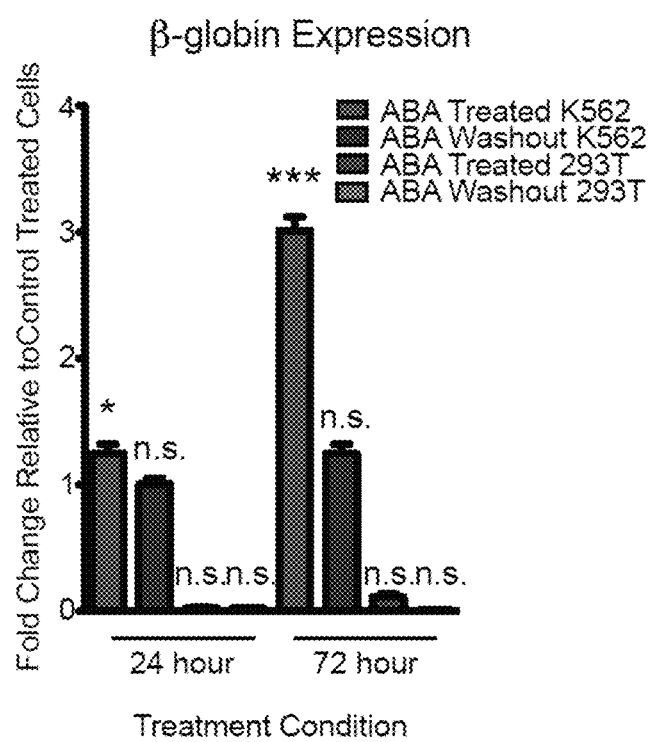
FIG. 2A shows CLOuD9 induces context specific alterations in gene expression and chromatin state.

FIG. 2A shows CLOuD9 induced chromatin looping at the β-globin locus results in reversible induction of β-globin expression in K562 cells but not in 293T cells. Significance given relative to control treated cells. *p<0.05, t=3.418, df=5; ***p<0.0001, t=10.42 df=5; n.s. non-significant. Error bars indicate SD. n=3.

Figure 2B:
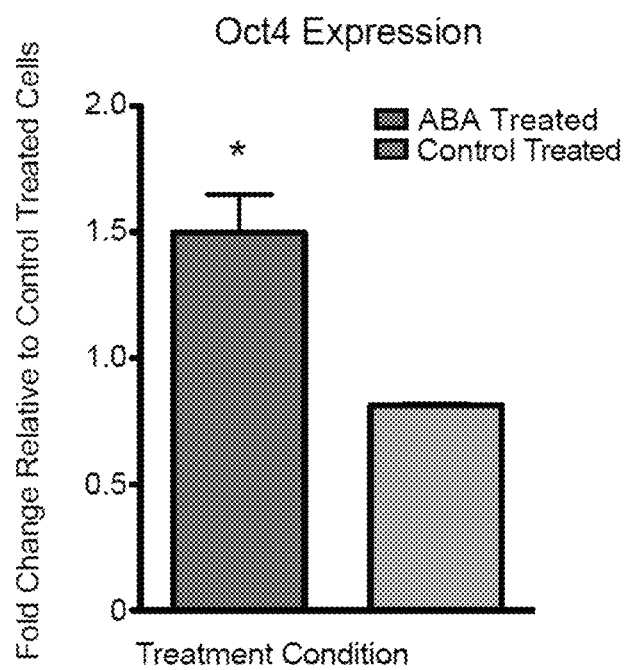
FIG. 2B shows induction of Oct4 expression was observed in 293T cells.

FIG. 2B shows induction of Oct4 expression was observed in 293T cells following CLOuD9 induced looping at the same locus. Significance given relative to control treated cells. *p<0.05, t=4.562, df=2. Error bars indicate SD.

Interestingly, while Oct4 levels were increased in 293T cells in response to dimerization at that locus, induction of a new LCR and β-globin contact in 293T cells and K562 cells significantly altered β-globin expression only in K562 cells (FIG. 2A). Addition of ABA for as little as 24 hours drove significant changes in β-globin expression, and robust increases were observed following 72 hours of ABA-induced dimerization (FIG. 2A). This effect was seen in ligand treated cells containing dimerization partners directed to both the LCR and β-globin promoter simultaneously regardless of position (FIG. 7), but was not observed in controls (FIG. 8).

Figure 7:
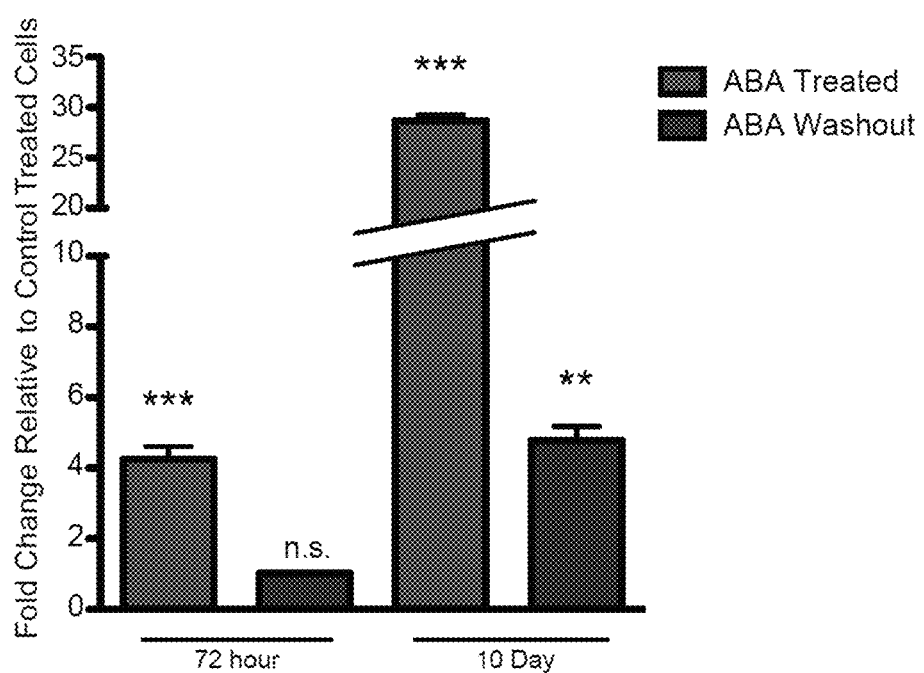
FIG. 7 shows CLOuD9 induced alterations in gene expression are sustained regardless of globin target site.

FIG. 7 shows CLOuD9 induced alterations in gene expression are sustained regardless of globin target site. Directing CSA and CSP constructs to alternate regions of the β-globin promoter and LCR has no impact on induction of gene expression following 72 hours of dimerization. However, while some impact on the strength of gene expression following long-term (10 day) dimerization was observed, high levels of β-globin relative to control treated cells were sustained following subsequent ligand washout for 10 additional days. Significance given relative to control treated cells. p<0.001, t=10.25, df=5; *p<0.0001, left to right t=8.697, df=6, t=40.31, df=7; n.s. non-significant. All error bars indicate SD.

Figure 8:
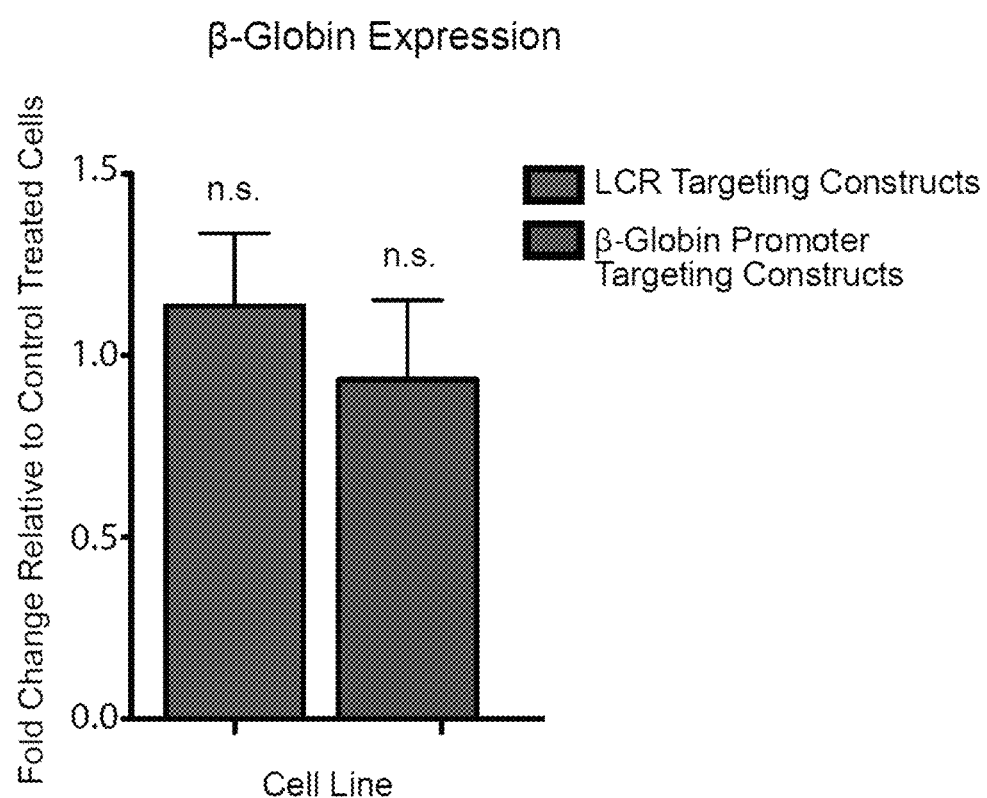
FIG. 8 shows control CLOuD9 transduced cells show no alterations in β-globin expression.

FIG. 8 shows control CLOuD9 transduced cells show no alterations in β-globin expression. Directing two CLOuD9 constructs to either the LCR or the β-globin promoter induces no significant changes in β-globin expression following ABA treatment relative to control treatment. Significance given relative to control treated cells. n.s. non-significant.

Critically, endogenous levels of β-globin were restored upon ABA removal, regardless of whether initial dimerization was for 24 hours or 72 hours (FIG. 2A and FIG. 7). In support of these observations, ChIP-qPCR of K562 cells and 293T cells showed increases in H3K4me3 along the β-globin gene only in K562 cells following dimerization, with baseline levels being restored following ligand washout (FIG. 2C-FIG. 2E).

Figure 19A:
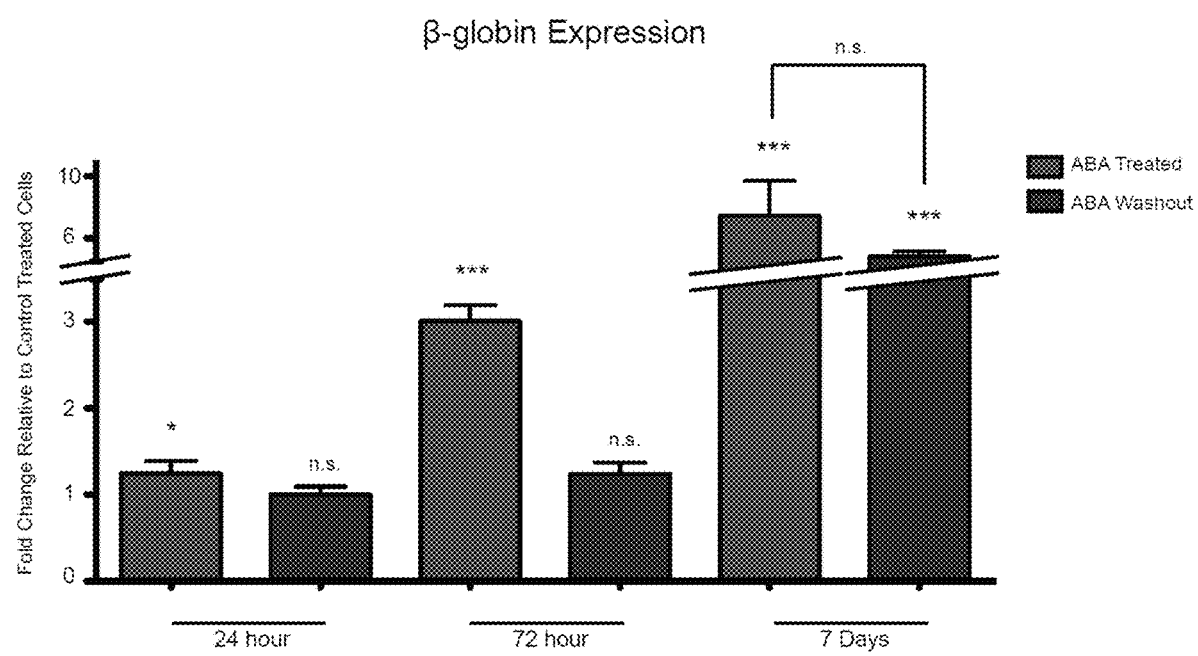
FIG. 19A shows results of CLOuD9 induced chromatin looping.

FIG. 19A shows CLOuD9 establishes stable chromatin loops that sustain robust gene expression following long-term dimerization. CLOuD9 induced chromatin looping results in reversible expression of β-globin up to 72 hours of dimerization. β-globin expression becomes persistent after 7 days of dimerization, even when ABA is removed for up to a week. *p<0.02, t=3.418, df=5; ***p<0.0001, at 72 hours t=10.42 df=5; at 7 days t=5.963, df=5; n.s. non-significant. Error bars indicate SD. n=3.

Reverse transcription quantitative PCR (qRT-PCR) analyses demonstrated that when a new contact between the LCR and β-globin is created upon addition of ABA for 24 hours, a small but notable increase in β-globin gene expression was also observed compared to controls (FIG. 19A). This effect was increased significantly with 72 hours of ABA-induced dimerization (FIG. 19A). Critically, we observed restoration of endogenous levels of β-globin expression upon ABA removal after both 24 hours and 72 hours of ligand treatment (FIG. 19A). In addition, no β-globin transcript was detectable by qPCR when the same chromosomal looping was created in HEK 293Ts, pointing to the importance of appropriate cellular context with regard to functional consequences of loci juxtaposition. Although a slight but non-significant reduction in gene expression was observed following 7 days of washout, a markedly elevated level of gene expression persisted (FIG. 19A).

Figure 2C:
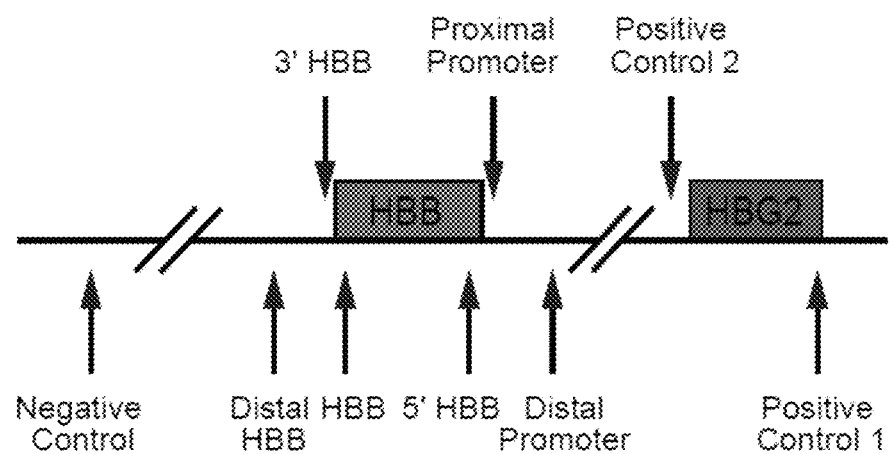
FIG. 2C shows a schematic of chromatin immunoprecipitation (ChIP)-quantitative PCR (qPCR) primer locations along the β-globin gene body.
Figure 2D:
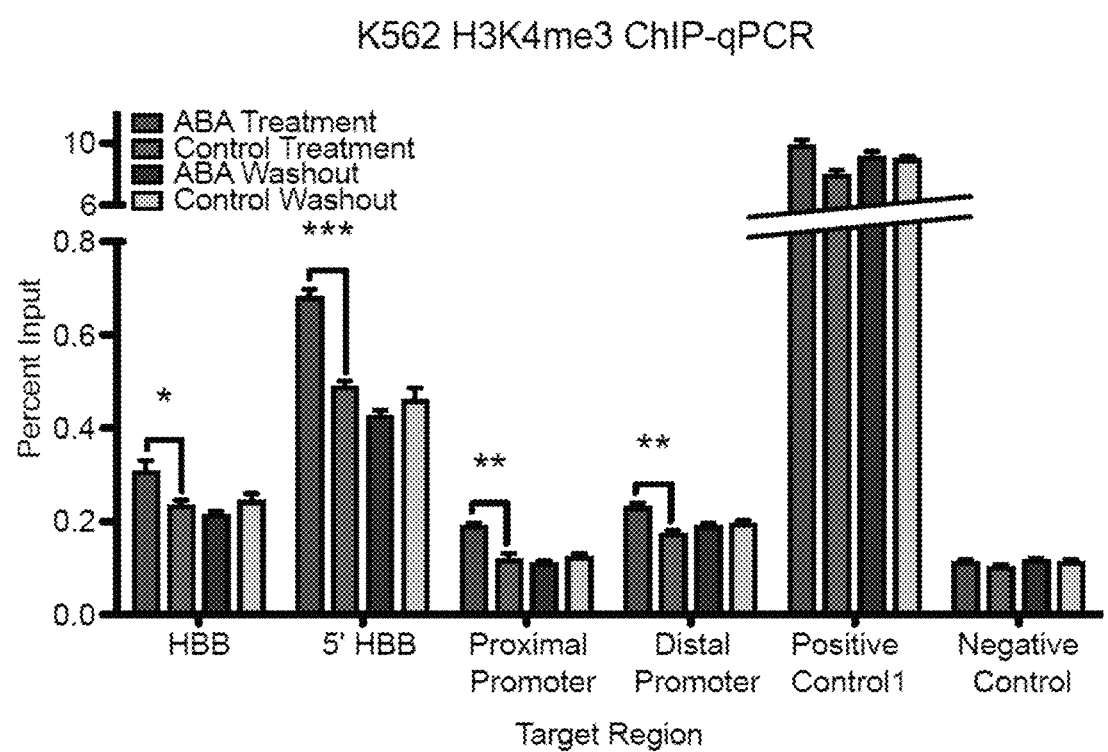
FIG. 2D shows ChIP-qPCR data of alterations in H3K4me3 at the β-globin locus in K562 cells.
Figure 2E:
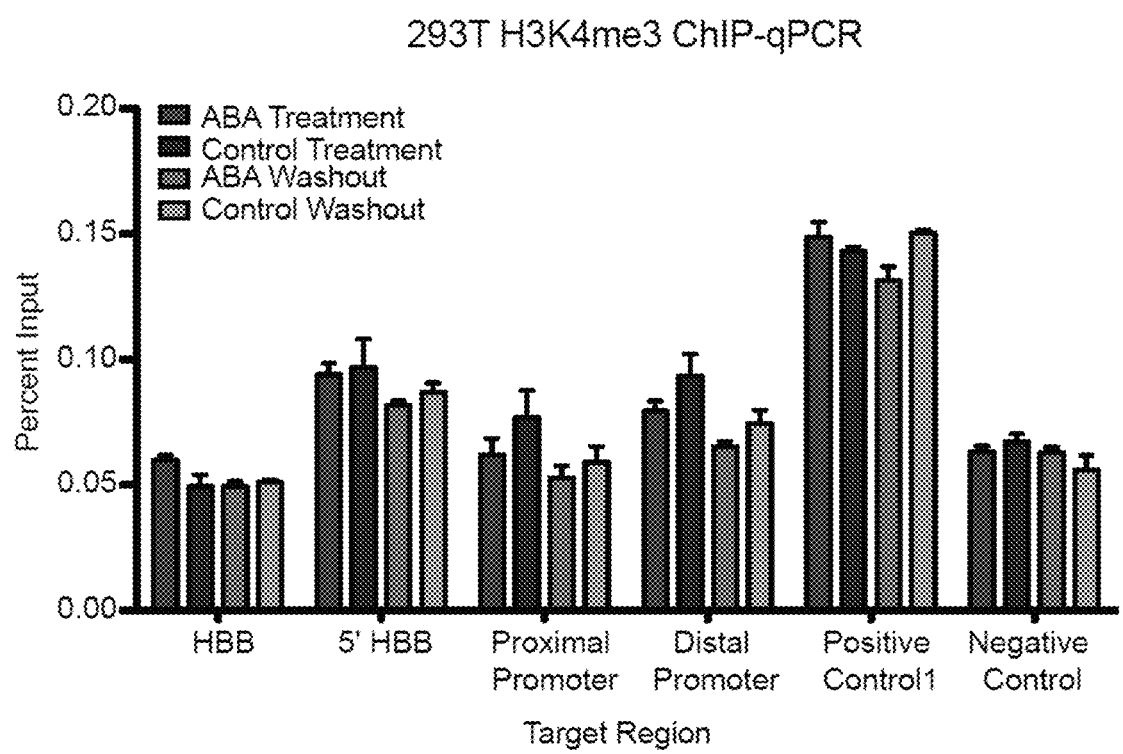
FIG. 2E shows ChIP-qPCR data of alterations in H3K4me3 at the β-globin locus in 293T cells.

FIG. 2C shows induction of Oct4 expression was observed in 293T cells. FIG. 2D and FIG. 2E show ChIP-qPCR data demonstrating reversible alterations in H3K4me3 at the (3-globin locus in K562 cells but not in 293T cells following CLOuD9 induced looping. *p<0.05, p<0.001, *p<0.0001. Error bars indicate SD.

Figure 2F:
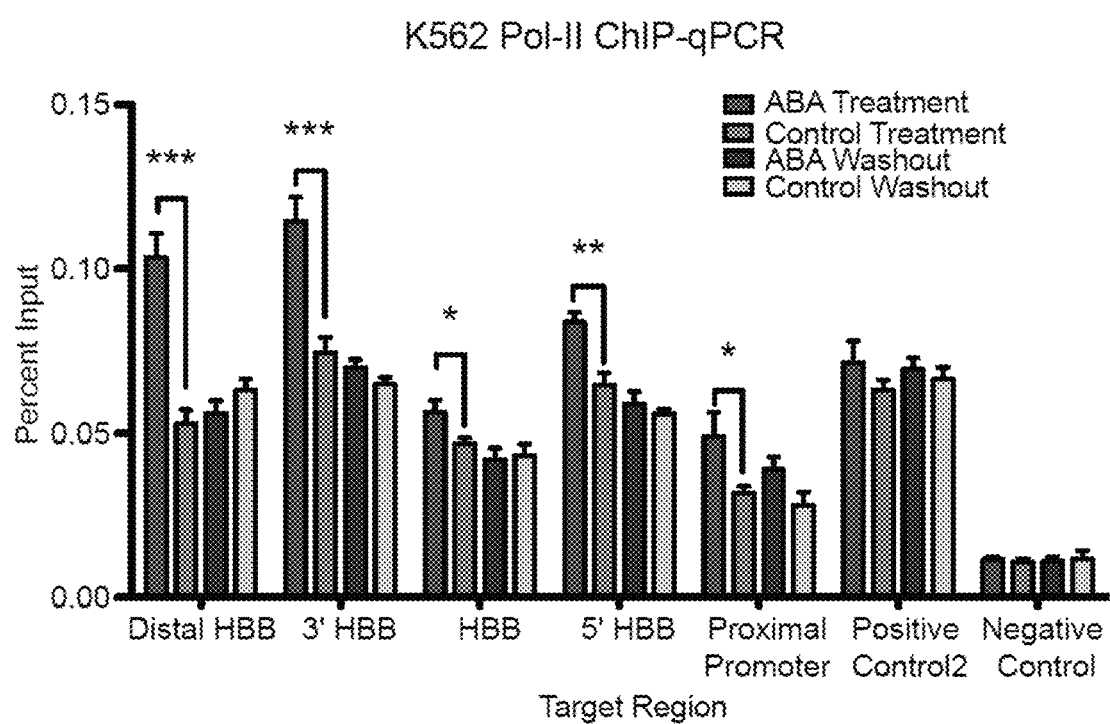
FIG. 2F shows CLOuD9 mediated alterations in β-globin transcription in K562 cells.
Figure 2G:
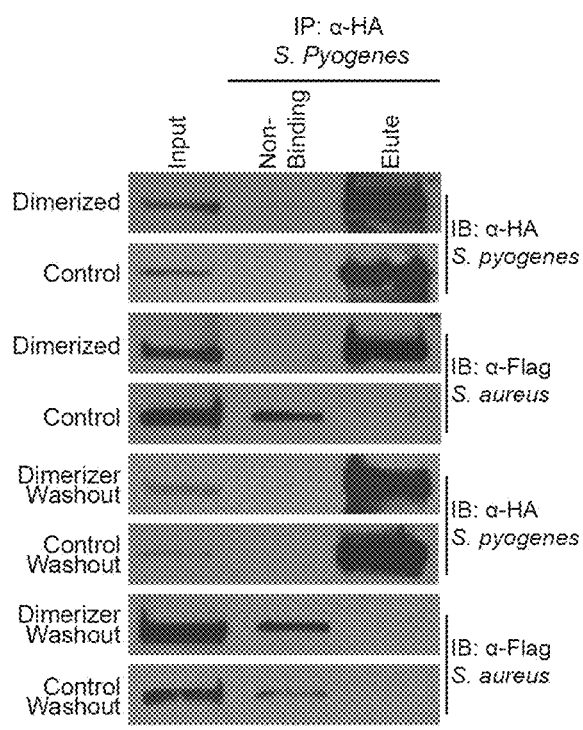
FIG. 2G shows CLOuD9 constructs reversibly associate in response to ABA treatment.

Furthermore, increased RNA Pol-II occupancy of the β-globin gene locus following dimerization corroborated the increased transcription of β-globin in K562 cells, an event that was also reversible after ligand removal[14] (FIG. 2F).

FIG. 2F shows CLOuD9 mediated alterations in β-globin transcription in K562 cells correspond with increases in RNA Pol-II occupancy across the entirety of the β-globin gene body. *p<0.05, p<0.001, *p<0.0001. Error bars indicate SD.

Taken together, these results highlight the importance of appropriate cellular context in driving functional consequences of loci juxtaposition.

Having established that CLOuD9 can reversibly manipulate chromatin contacts and induce corresponding alterations in gene expression, the impacts of long-term induced chromosomal looping was investigated next. Following 10 days of ABA-induced dimerization, both K562 and 293T CLOuD9 transduced cells demonstrated increased β-globin/LCR contacts relative to controls, as observed previously (FIG. 3A, FIG. 3B, FIG. 9 and FIG. 10).

FIG. 3A and FIG. 3B CLOuD9 establishes stable chromatin loops that sustain robust gene expression following long-term dimerization. 3C assay demonstrates that in K562 cells (FIG. 3A) but not 293T cells (FIG. 3B), CLOuD9 induced chromatin looping becomes irreversible after 10 days of ABA treatment, even when ABA is removed for up to 10 additional days. All 3C results were obtained from at least three independent experiments. 3C values were normalized to tubulin, and interaction frequencies between the anchor fragment and the fragment encompassing the β/HS fragment were set to zero. Error bars indicate SD. n=3.

Figure 19B:
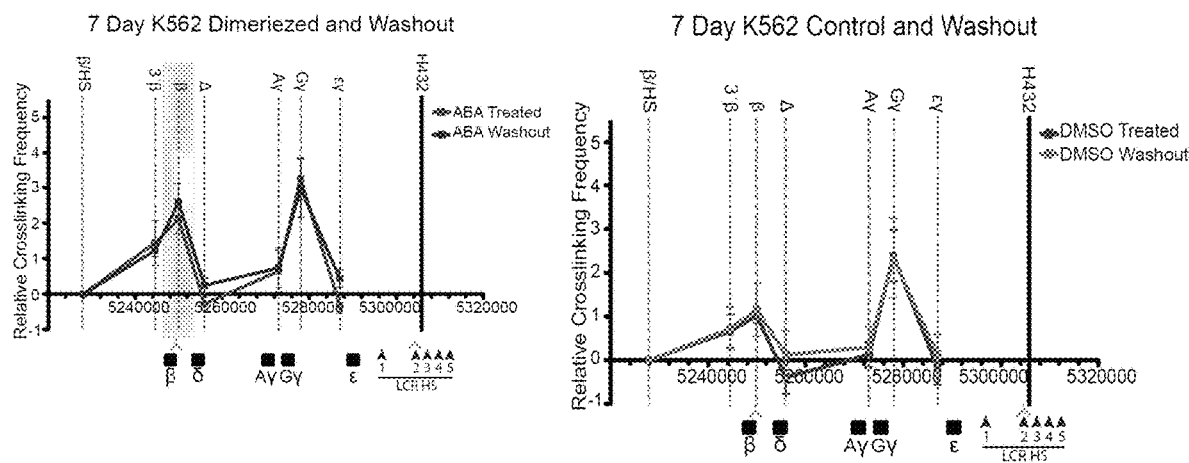
FIG. 19B shows data for 3C assay data K562 cells and control.

FIG. 19B shows 3C assay in K562s demonstrates the irreversibility of CLOuD9 induced chromatin contacts after 7 days of ABA treatment. FIG. 19B also shows 7 days of control treatment induces no change in endogenous chromatin contacts. Treatment with a control agent for 7 days induces no change in endogenous chromatin conformation in K562 cells.

Having established that CLOuD9 can reversibly manipulate chromatin contacts and induce corresponding alterations in gene expression, the impacts of long-term induced chromosomal looping was investigated. Following 1 week of ABA-induced dimerization, CLOuD9 transduced cells demonstrated increased β-globin/LCR contacts relative to controls, as observed previously (FIG. 19B). Remarkably, removal of ABA in these cells no longer resulted in the reversal of chromatin contacts (FIG. 19B).

Figure 9:
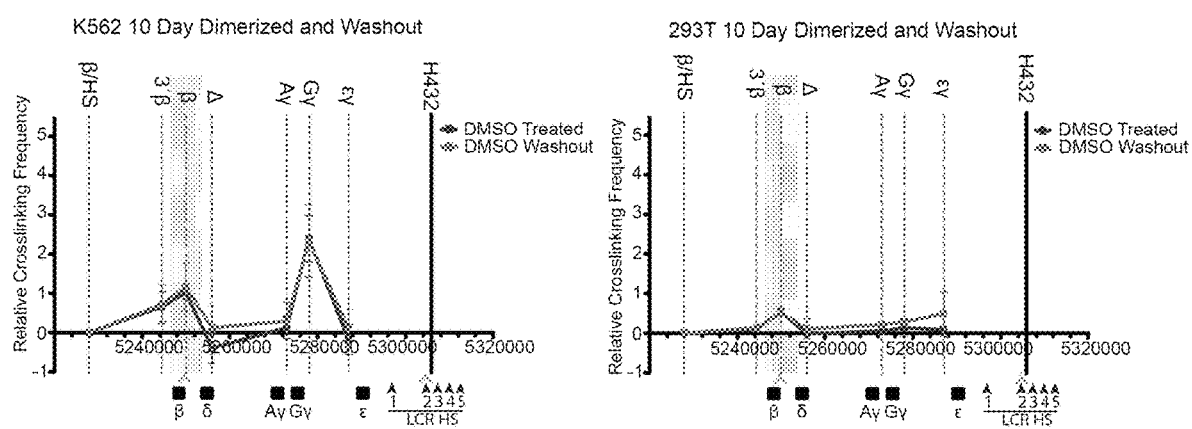
FIG. 9 shows long-term control treatment induces no changes in chromatin contacts.

FIG. 9 shows long-term control treatment induces no changes in chromatin contacts. Treatment with DMSO, a control agent, for 10 days induces no change in endogenous chromatin conformation by 3C in either K562 cells or HEK 293T cells. 3C values were normalized to tubulin, and interaction frequencies between the anchor fragment and the fragment encompassing the β/HS fragment were set to zero. Error bars indicate SD. n=3.

Figure 10:
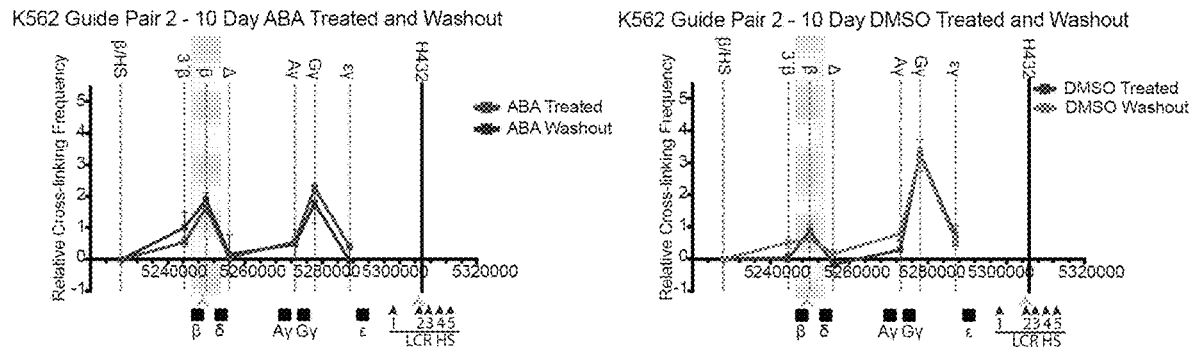
FIG. 10 shows long-term CLOuD9 induced β-globin/LCR looping is not impacted by globin target site.
Figure 11:
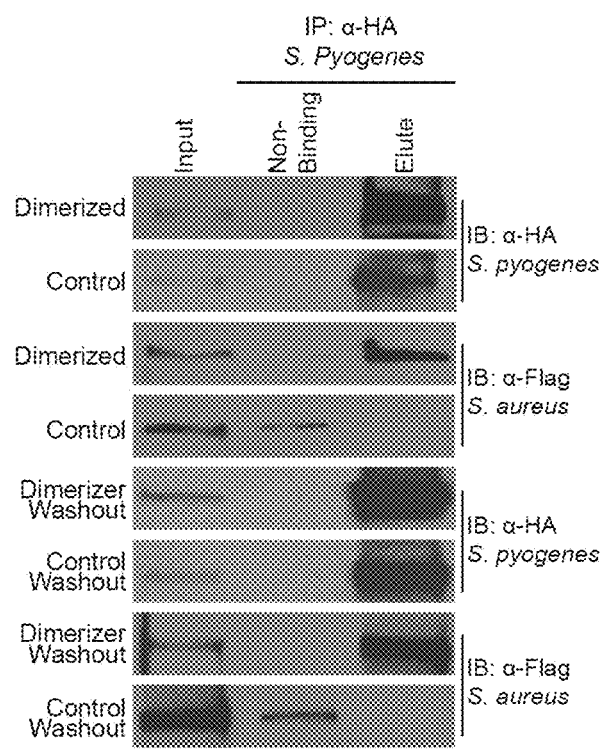

FIG. 10 shows long-term CLOuD9 induced β-globin/LCR looping is not impacted by globin target site. Directing CSA and CSP constructs to alternate regions of the LCR or the β-globin promoter results in similarly sustained loop induction as demonstrated by 3C following 10 days of ABA treatment and 10 days of subsequent ligand washout. 3C values were normalized to tubulin, and interaction frequencies between the anchor fragment and the fragment encompassing the β/HS fragment were set to zero. Error bars indicate SD. n=3.

As discovered previously, increased β-globin expression as a result of dimerization was only observed in K562 cells (FIG. 3C).

FIG. 3C shows loop stabilization in K562 cells results in persistent expression of β-globin, even following 10 days of ABA washout. No changes in β-globin expression are observed in 293T cells. Significance given relative to control treated cells. ***p<0.0001, t=5.963, df=5; n.s. non-significant.

Further, the location of the CLOuD9 construct within the β-globin promoter region had notable impacts on the strength of β-globin expression at this extended timepoint (FIG. 7). Remarkably, regardless of construct location, removal of ABA in K562 cells, but not 293T cells, no longer resulted in the reversal of chromatin contacts (FIG. 3A, FIG. 3B and FIG. 9-FIG. 11).

Figure 11:
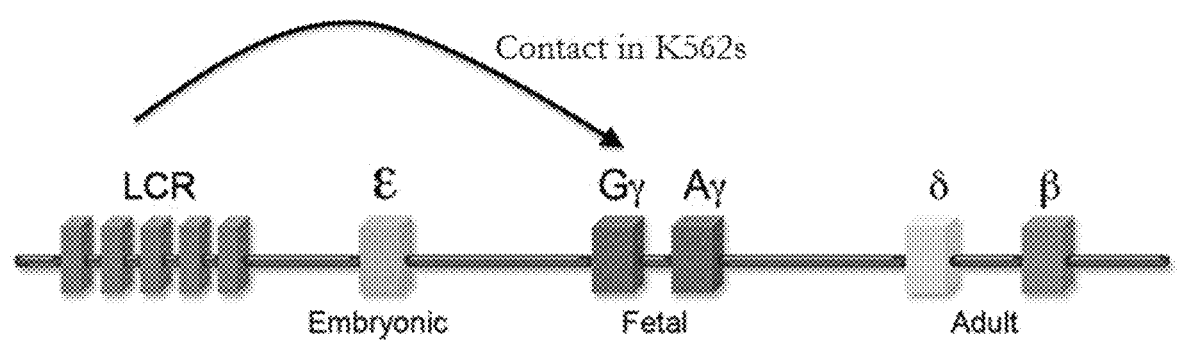
FIG. 11 shows CLOuD9 constructs irreversibly associate in response to long-term ABA treatment.

FIG. 11 shows CLOuD9 constructs irreversibly associate in response to long-term ABA treatment. Co-immunoprecipitations demonstrating irreversible association of the CSA and CSP dCas9 proteins following 10 days of ABA treatment and 10 subsequent days of ligand washout.

Although a slight reduction in gene expression was observed following 10 days of ligand washout, a markedly elevated level of gene expression persisted (FIG. 3C). Consistent with these observations, ChIP-qPCR demonstrated significant increases in H3K4me3 relative to controls along the β-globin gene in K562 cells but not 293T cells (FIG. 3D and FIG. 3E).

FIG. 3D shows ChIP-qPCR data showing increases in H3K4me3 marks over the β-globin locus in response to CLOuD9 induced looping are sustained following 10 days of ligand washout in K562 cells. *p<0.05, p<0.001, *p<0.0001. FIG. 3E shows data showing no significant alterations in H3K4me3 signals following long-term dimerization were observed by ChIP-qPCR in 293T cells.

In addition, a significant increase in RNA Pol-II occupancy (relative to controls) along the same gene region was sustained following ligand washout in K562 cells as measured by ChIP-qPCR (FIG. 3F), suggesting stabilization of the induced chromatin contact driving sustained gene expression. FIG. 3F shows increased RNA Pol-II occupancy of the β-globin locus following long-term loop induction was maintained in K562 cells following 10 days of ligand washout. *p<0.05, p<0.001, *p<0.0001. All error bars indicate SD.

Figure 4A:
FIG. 4A shows mass spectrometry (MS)/ChIP data of dimerized CLOuD9 cells.

In order to determine the mechanisms underlying preservation of the chromatin conformation with long-term induced dimerization, mass spectrometry analysis was performed following chromatin immunoprecipitation (MS/ChIP) on CLOuD9 cells dimerized for 72 hours and 10 days. As shown in FIG. 4A, after 72 hours of induced looping, the CLOuD9 associated dCas9 proteins, a small number of RNA helicases, and members of the heterogeneous nuclear ribonucleoprotein machinery are preferentially enriched in the dimerized samples.

FIG. 4A shows RNA helicases DDX5 and DDX17 stabilize long-term chromatin loops as seen from MS/ChIP of dimerized CLOuD9 cells after 72 hour and 10 day treatments demonstrate differential enrichment of novel proteins at the induced looping loci after 10 days.

However, longer duration chromatin loop formation was accompanied by recruitment of similar RNA helicases and heterogeneous nuclear ribonucleoprotein to the contact region, that remained at the site of induced contact even after 10 subsequent days of ligand washout (FIG. 4A, and Table 1-Table 8), implying a functional role for these proteins in maintaining the early stages of de novo chromatin contacts. Notably absent from the MS analyses are the traditional regulators of chromatin architecture, CCCTC-binding factor (CTCF) and cohesin (FIG. 4A, FIG. 4B, FIG. 12, and Table 1-Table 8), suggesting a possible novel regulatory mechanism of RNA helicases in stabilizing genome topology.

Table 1-Table 8 show data for peptide identification by MS for each sample, treatment condition, and treatment duration.

In some embodiments, the number of peptide sequence hits in the MS analysis for a protein can range from about 1 to about 25. In some embodiments, the number of peptide sequence hits in the MS analysis for a protein can range from about 1 to about 50. In some embodiments, the number of peptide sequence hits in the MS analysis for a protein can range from about 1 to about 75. In some embodiments, the number of peptide sequence hits in the MS analysis for a protein can range from about 1 to about 100. In some embodiments, the number of peptide sequence hits in the MS analysis for a protein can range from about 1 to about 125. In some embodiments, the number of peptide sequence hits in the MS analysis for a protein can range from about 1 to about 150. In some embodiments, the number of peptide sequence hits in the MS analysis for a protein can range from about 1 to about 175. In some embodiments, the number of peptide sequence hits in the MS analysis for a protein can range from about 1 to about 200. In some embodiments, the number of peptide sequence hits in the MS analysis for a protein can range from about 1 to about 225. In some embodiments, the number of peptide sequence hits in the MS analysis for a protein can range from about 1 to about 250. In some embodiments, the number of peptide sequence hits in the MS analysis for a protein can range from about 1 to about 275. In some embodiments, the number of peptide sequence hits in the MS analysis for a protein can range from about 1 to about 300. In some embodiments, the number of peptide sequence hits in the MS analysis for a protein can range from about 1 to about 325. In some embodiments, the number of peptide sequence hits in the MS analysis for a protein can range from about 1 to about 350. In some embodiments, the number of peptide sequence hits in the MS analysis for a protein can range from about 1 to about 375.

For example, the number of peptide sequence hits in the MS analysis for Histone H2A was about 25 in the 72 hr dimerized samples (Table 1), the number of peptide sequence hits in the MS analysis for epididymis luminal protein was about 50 in the 72 hr dimerized samples (Table 1), the number of peptide sequence hits in the MS analysis for tubulin beta chain was about 100 in the 10 day dimerized samples (Table 4), and the number of peptide sequence hits in the MS analysis for Cas9 was about 300 in the 10 day dimerized samples (Table 4). In some embodiments, the number of peptide sequence hits in the MS analysis for a protein can range from about 1 to about 1000.

In some embodiments, the number of peptide sequences identified in the MS analysis can range from about 100 to about 500. In some embodiments, the number of peptide sequences identified in the MS analysis can range from about 500 to about 1000. In some embodiments, the number of peptide sequences identified in the MS analysis can range from about 1000 to about 5,000. In some embodiments, the number of peptide sequences identified in the MS analysis can range from about 5,000 to about 10,000. For example, the number of peptide sequences identified in the MS analysis for the 72 hr dimerized samples was about 650 to about 925, and the number of peptide sequences identified in the MS analysis for the 10 day dimerized samples was about 950 to about 1050.

In some embodiments, multiple replicates of peptide identification by MS was performed for each sample, treatment condition, and treatment duration. For example, peptide identifications for 72 hr dimerized sample and 72 hr control sample were performed in three replicates, peptide identifications for 10 day dimerized sample and 10 day control sample were performed in four replicates. In some embodiments, the number of replicates can range from about 2 to about 20.

Table 1 Shows Data for Peptide Identification by MS for 72 hr Dimerized Sample 1. 14-3-3 protein zeta/delta (cDNA, FLJ79516, highly similar to 14-3-3 protein zeta/delta)
2. 2-oxoisovalerate dehydrogenase subunit beta, mitochondrial (EC 1.2.4.4) (Branched-chain alpha-keto acid dehydrogenase E1 component beta chain) (BCKDE1B) (BCKDH E1-beta)
3. 40S ribosomal protein S10
4. 40S ribosomal protein S13 (Fragment)
5. 40S ribosomal protein S14
6. 40S ribosomal protein S2
7. 40S ribosomal protein S20
8. 40S ribosomal protein S25
9. 40S ribosomal protein S26
10. 40S ribosomal protein S3
11. 40S ribosomal protein S5 [Cleaved into: 40S ribosomal protein S5, N-terminally processed]

-continued 12. 40S ribosomal protein S6
13. 40S ribosomal protein S8
14. 40S ribosomal protein SA
15. 5'-AMP-activated protein kinase catalytic subunit alpha-2 (AMPK subunit alpha-2) (EC 2.7.11.1) (Acetyl-CoA carboxylase kinase) (ACACA kinase) (EC 2.7.11.27) (Hydroxymethylglutaryl-CoA reductase kinase) (HMGCR kinase) (EC 2.7.11.31)
16. 60S ribosomal protein L10a (CSA-19) (Neural precursor cell expressed developmentally down-regulated protein 6) (NEDD-6)
17. 60S ribosomal protein L11 (CLL-associated antigen KW-12)
18. 60S ribosomal protein L12
19. 60S ribosomal protein L13a (23 kDa highly basic protein)
20. 60S ribosomal protein L14
21. 60S ribosomal protein L18a
22. 60S ribosomal protein L21
23. 60S ribosomal protein L22 (EBER-associated protein) (EAP) (Epstein-Barr virus small RNA-associated protein) (Heparin-binding protein HBp15)
24. 60S ribosomal protein L23 (60S ribosomal protein L17)
25. 60S ribosomal protein L27
26. 60S ribosomal protein L27a
27. 60S ribosomal protein L35
28. 60S ribosomal protein L4
29. 60S ribosomal protein L6 (Neoplasm-related protein C140) (Tax-responsive enhancer element-binding protein 107) (TaxREB107)
30. 60S ribosomal protein L7
31. 60S ribosomal protein L7-like 1
32. 60S ribosomal protein L7a (PLA-X polypeptide) (Surfeit locus protein 3)
33. 60S ribosomal protein L8
34. Actin-binding LIM protein 2 (Fragment)
35. Actin, alpha skeletal muscle
36. ADP/ATP translocase 2 (ADP, ATP carrier protein 2) (ADP, ATP carrier protein, fibroblast isoform) (Adenine nucleotide translocator 2) (ANT 2) (Solute carrier family 25 member 5) [Cleaved into: ADP/ATP translocase 2, N-terminally processed]
37. Alkyldihydroxyacetonephosphate synthase, peroxisomal
38. Alpha-1B-glycoprotein (Alpha-1-B glycoprotein)
39. Alpha-enolase (EC 4.2.1.11) (2-phospho-D-glycerate hydro-lyase) (C-myc promoter-binding protein) (Enolase 1) (MBP-1) (MPB-1) (Non-neural enolase) (NNE) (Phosphopyruvate hydratase) (Plasminogen-binding protein)
40. Alpha-protein kinase 1 (cDNA FLJ39927 fis, clone SPLEN2021194, highly similar to Homo sapiens alpha-kinase 1 (ALPK1), mRNA)
41. Annexin A1 (Annexin I) (Annexin-1) (Calpactin II) (Calpactin-2) (Chromobindin-9) (Lipocortin I) (Phospholipase A2 inhibitory protein) (p35)
42. Annexin A2 (Annexin II) (Annexin-2) (Calpactin I heavy chain) (Calpactin-1 heavy chain) (Chromobindin-8) (Lipocortin II) (Placental anticoagulant protein IV) (PAP-IV) (Protein I) (p36)
43. Arginase-1 (EC 3.5.3.1) (Liver-type arginase) (Type I arginase)
44. ATP synthase subunit alpha, mitochondrial
45. ATP-dependent RNA helicase A
46. ATP-dependent RNA helicase DDX1 (DEAD (Asp-Glu-Ala-Asp) box polypeptide 1, isoform CRA_d) (DEAD box polypeptide 1) (cDNA, FLJ94573, Homo sapiens DEAD (Asp-Glu-Ala-Asp) box polypeptide 1 (DDX1), mRNA)
47. ATP-dependent RNA helicase DDX18
48. ATP-dependent RNA helicase DDX3X (EC 3.6.4.13) (DEAD box protein 3, X-chromosomal) (DEAD box, X isoform) (Helicase-like protein 2) (HLP2)
49. ATP-dependent RNA helicase DDX50
50. BAH and coiled-coil domain-containing protein 1 (Bromo adjacent homology domain-containing protein 2) (BAH domain-containing protein 2)
51. Bleomycin hydrolase
52. Brain-specific angiogenesis inhibitor 1-associated protein 2 (BAI-associated protein 2) (BAI1-associated protein 2) (Protein BAP2) (Fas ligand-associated factor 3) (FLAF3) (Insulin receptor substrate p53/p58) (IRS-58) (IRSp53/58) (Insulin receptor substrate protein of 53 kDa) (IRSp53) (Insulin receptor substrate p53)
53. BRCA2 and CDKN1A-interacting protein (P21- and CDK-associated protein 1) (Protein TOK-1)
54. Breast cancer anti-estrogen resistance protein 1 (CRK-associated substrate) (Cas scaffolding protein family member 1) (p130cas)
55. C-type lysozyme (Lysozyme) (EC 3.2.1.17) (Lysozyme (Renal amyloidosis), isoform CRA_a) (Lysozyme F1) (cDNA, FLJ92040, Homo sapiens lysozyme (renal amyloidosis) (LYZ), mRNA)
56. Calmodulin-like protein 5 (Calmodulin-like skin protein)
57. Calnexin (IP90) (Major histocompatibility complex class I antigen-binding protein p88) (p90)
58. Carbamoyl-phosphate synthase [ammonia], mitochondrial (Fragment)
59. Cas scaffolding protein family member 4 (HEF-like protein) (HEF1-EFS-p130Cas-like protein) (HEPL)
60. Caspase 14, apoptosis-related cysteine peptidase (Caspase-14) (cDNA, FLJ94644, Homo sapiens caspase 14, apoptosis-related cysteine protease(CASP14), mRNA)
61. Cathepsin D (EC 3.4.23.5) [Cleaved into: Cathepsin D light chain; Cathepsin D heavy chain]
62. Cation-independent mannose-6-phosphate receptor (CI Man-6-P receptor) (CI-MPR) (M6PR) (300 kDa mannose 6-phosphate receptor) (MPR 300) (Insulin-like growth factor 2 receptor) (Insulin-like growth factor II receptor) (IGF-II receptor) (M6P/IGF2 receptor) (M6P/IGF2R) (CD antigen CD222)
63. CCAAT/enhancer-binding protein zeta
64. cDNA FLJ44468 fis, clone UTERU2026025, moderately similar to SPLICING FACTOR, ARGININE/SERINE-RICH 2
65. cDNA FLJ51138, highly similar to Arfaptin-2
66. cDNA FLJ51275
67. cDNA FLJ51535, highly similar to Phosphatidylethanolamine-binding protein 1
68. cDNA FLJ52536, highly similar to Tubulin beta-4 chain
69. cDNA FLJ52842, highly similar to Actin, cytoplasmic 1
70. cDNA FLJ53341, highly similar to Tubulin beta-4 chain
71. cDNA FLJ54020, highly similar to Heterogeneous nuclear ribonucleoprotein U
72. cDNA FLJ54552, highly similar to Heterogeneous nuclear ribonucleoprotein K
73. cDNA FLJ55805, highly similar to Keratin, type II cytoskeletal 4
74. cDNA FLJ56548, highly similar to Elongation factor 2
75. cDNA FLJ57726, highly similar to Heterogeneous nuclear ribonucleoprotein H3

-continued 76. cDNA FLJ59335, highly similar to Transmembrane glycoprotein NMB
77. cDNA FLJ59790, highly similar to Origin recognition complex subunit 3
78. cDNA FLJ59973, highly similar to Elongation factor 1-gamma
79. cDNA FLJ60675, highly similar to ATP-dependent RNA helicase DDX3X (EC 3.6.1.—)
80. cDNA FLJ61500, highly similar to NNP-1 protein
81. Cellular tumor antigen p53
82. Centrosome-associated protein CEP250 (250 kDa centrosomal protein) (Cep250) (Centrosomal Nek2-associated protein 1) (C-Nap1) (Centrosomal protein 2)
83. Cleavage stimulation factor subunit 3
84. Coiled-coil domain-containing 129
85. Collagen alpha-1(XIX) chain (Collagen alpha-1(Y) chain)
86. Copper homeostasis protein cutC homolog (Fragment)
87. Corneodesmosin
88. Cornifin-A (19 kDa pancornulin) (SPRK) (Small proline-rich protein IA) (SPR-IA)
89. Cornifin-B
90. Creatine kinase U-type, mitochondrial (EC 2.7.3.2) (Acidic-type mitochondrial creatine kinase) (Mia-CK) (Ubiquitous mitochondrial creatine kinase) (U-MtCK)
91. CRISPR-associated endonuclease Cas9 (EC 3.1.—.—) (SaCas9)
92. CRISPR-associated endonuclease Cas9/Csn1 (EC 3.1.—.—) (SpCas9) (SpyCas9)
93. Cyclic AMP-dependent transcription factor ATF-7 (cAMP-dependent transcription factor ATF-7) (Activating transcription factor 7) (Transcription factor ATF-A)
94. Cyclin-dependent kinase 1 (Fragment)
95. Cystatin-A (Cystatin-AS) (Stefin-A) [Cleaved into: Cystatin-A, N-terminally processed]
96. Cystatin-B (CPI-B) (Liver thiol proteinase inhibitor) (Stefin-B)
97. Cystatin-M (Cystatin-6) (Cystatin-E)
98. Cystatin-S (Cystatin-4) (Cystatin-SA-III) (Salivary acidic protein 1)
99. Cystatin-SN (Cystain-SA-I) (Cystatin-1) (Salivary cystatin-SA-1)
100. Dedicator of cytokinesis protein 4
101. Deleted in malignant brain tumors 1 protein (Glycoprotein 340) (Gp-340) (Hensin) (Salivary agglutinin) (SAG) (Surfactant pulmonary-associated D-binding protein)
102. Desmin
103. Desmocollin-1 (Cadherin family member 1) (Desmosomal glycoprotein 2/3) (DG2/DG3)
104. Desmocollin-3 (Cadherin family member 3) (Desmocollin-4) (HT-CP)
105. Desmoglein-1 (Cadherin family member 4) (Desmosomal glycoprotein 1) (DG1) (DGI) (Pemphigus foliaceus antigen)
106. Desmoplakin (DP) (250/210 kDa paraneoplastic pemphigus antigen)
107. Dipeptidyl peptidase 2
108. DNA polymerase
109. Doublecortin domain-containing protein 1
110. Dynein heavy chain 8, axonemal (Axonemal beta dynein heavy chain 8) (Ciliary dynein heavy chain 8)
111. Dystonin
112. E3 ubiquitin/ISG15 ligase TRIM25 (EC 6.3.2.n3) (Estrogen-responsive finger protein) (RING finger protein 147) (RING-type E3 ubiquitin transferase) (EC 2.3.2.27) (Tripartite motif-containing protein 25) (Ubiquitin/ISG15-conjugating enzyme TRIM25) (Zinc finger protein 147)
113. EBNA1 binding protein 2 (EBNA1 binding protein 2 variant) (EBNA1 binding protein 2, isoform CRA_a) (EBNA1BP2 protein)
114. Echinoderm microtubule-associated protein-like 5 (EMAP-5)
115. EF-hand calcium-binding domain-containing protein 2
116. ELAV-like protein 1 (Hu-antigen R) (HuR)
117. Elongation factor 1-alpha 1 (EF-1-alpha-1) (Elongation factor Tu) (EF-Tu) (Eukaryotic elongation factor 1 A-1) (eEF1A-1) (Leukocyte receptor cluster member 7)
118. Elongation factor 2
119. Elongation factor 2 (EF-2)
120. Endogenous retrovirus group S71 member 1 Env polyprotein (Envelope polyprotein) (HERV-T Env protein) (HERV-T_19q13.11 provirus ancestral Env polyprotein) [Includes: Surface protein (SU); Transmembrane protein (TM)]
121. Envoplakin (210 kDa cornified envelope precursor protein) (210 kDa paraneoplastic pemphigus antigen) (p210)
122. Epididymis luminal protein 112 (Ribosomal protein S27a, isoform CRA_c) (cDNA, FLJ96793, *Homo sapiens* ribosomal protein S27a (RPS27A), mRNA)
123. Epididymis luminal protein 4 (Epididymis secretory protein Li 3) (Epididymis secretory protein Li 93) (Tyrosine 3-monooxygenase/tryptophan 5-monooxygenase activation protein zeta polypeptide) (Tyrosine 3-monooxygenase/tryptophan 5-monooxygenase activation protein, zeta polypeptide, isoform CRA_a)
124. Epiplakin
125. Eukaryotic initiation factor 4A-I (eIF-4A-I) (eIF4A-I) (EC 3.6.4.13) (ATP-dependent RNA helicase eIF4A-1)
126. Eukaryotic initiation factor 4A-II
127. Eukaryotic initiation factor 4A-III (eIF-4A-III) (eIF4A-III) (EC 3.6.4.13) (ATP-dependent RNA helicase DDX48) (ATP-dependent RNA helicase eIF4A-3) (DEAD box protein 48) (Eukaryotic initiation factor 4A-like NUK-34) (Eukaryotic translation initiation factor 4A isoform 3) (Nuclear matrix protein 265) (NMP 265) (hNMP 265) [Cleaved into: Eukaryotic initiation factor 4A-III, N-terminally processed]
128. F-box only protein 50 (NCC receptor protein 1 homolog) (NCCRP-1) (Non-specific cytotoxic cell receptor protein 1 homolog)
129. Far upstream element-binding protein 3 (FUSE-binding protein 3)
130. Fibroblast growth factor 14 (FGF-14) (Fibroblast growth factor homologous factor 4) (FHF-4)
131. Filaggrin
132. Filaggrin-2 (FLG-2) (Intermediate filament-associated and psoriasis-susceptibility protein) (Ifapsoriasin)
133. Filamin-B (FLN-B) (ABP-278) (ABP-280 homolog) (Actin-binding-like protein) (Beta-filamin) (Filamin homolog 1) (Fh1) (Filamin-3) (Thyroid autoantigen) (Truncated actin-binding protein) (Truncated ABP)
134. Fragile X mental retardation syndrome-related protein 1 (cDNA FLJ58644, highly similar to Fragile X mental retardation syndrome-related protein 1)
135. Fructose-bisphosphate aldolase A (EC 4.1.2.13) (Lung cancer antigen NY-LU-1) (Muscle-type aldolase)
136. Fused in sarcoma
137. G protein-coupled receptor 146 (HCG1747714, isoform CRA_a) (cDNA, FLJ93668, *Homo sapiens* G protein-coupled receptor 146 (GPR146), mRNA)

-continued

138. Galectin-7 (Gal-7) (HKL-14) (PI7) (p53-induced gene 1 protein)
139. Glyceraldehyde-3-phosphate dehydrogenase (GAPDH) (EC 1.2.1.12) (Peptidyl-cysteine S-nitrosylase GAPDH) (EC 2.6.99.—)
140. GTP-binding nuclear protein Ran (Androgen receptor-associated protein 24) (GTPase Ran) (Ras-like protein TC4) (Ras-related nuclear protein)
141. Guanine nucleotide-binding protein-like 3 (E2-induced gene 3 protein) (Novel nucleolar protein 47) (NNP47) (Nucleolar GTP-binding protein 3) (Nucleostemin)
142. Heat shock protein beta-1 (HspB1) (28 kDa heat shock protein) (Estrogen-regulated 24 kDa protein) (Heat shock 27 kDa protein) (HSP 27) (Stress-responsive protein 27) (SRP27)
143. Heat shock protein HSP 90-alpha (Heat shock 86 kDa) (HSP 86) (HSP86) (Lipopolysaccharide-associated protein 2) (LAP-2) (LPS-associated protein 2) (Renal carcinoma antigen NY-REN-38)
144. Heat shock protein HSP 90-beta
145. Heat shock protein HSP 90-beta (HSP 90) (Heat shock 84 kDa) (HSP 84) (HSP84)
146. Hemoglobin subunit zeta (HBAZ) (Hemoglobin zeta chain) (Zeta-globin)
147. Hemoglobin, gamma A
148. Heterogeneous nuclear ribonucleoprotein F (hnRNP F) (Nucleolin-like protein mcs94-1) [Cleaved into: Heterogeneous nuclear ribonucleoprotein F, N-terminally processed]
149. Heterogeneous nuclear ribonucleoprotein M (hnRNP M)
150. Heterogeneous nuclear ribonucleoprotein Q (hnRNP Q) (Glycine- and tyrosine-rich RNA-binding protein) (GRY-RBP) (NS1-associated protein 1) (Synaptotagmin-binding cytoplasmic RNA-interacting protein)
151. Heterogeneous nuclear ribonucleoproteins A2/B1 (hnRNP A2/B1)
152. Heterogeneous nuclear ribonucleoproteins C1/C2 (hnRNP C1/C2)
153. Histone 1, H1e (Histone H1e)
154. Histone H2A
155. Histone H2B
156. Histone H3
157. Histone H4
158. HLA-B associated transcript 1
159. Hornerin
160. HSPB1-associated protein 1 (27 kDa heat shock protein-associated protein 1) (Protein associated with small stress protein 1)
161. ibonucleoside-diphosphate reductase
162. Ig alpha-1 chain C region
163. Ig gamma-1 chain C region
164. Ig kappa chain C region
165. Ig kappa chain V-II region Cum
166. Ig lambda-7 chain C region
167. Immunoglobulin heavy variable 3-33 (Ig heavy chain V-III region HIL) (Ig heavy chain V-III region KOL)
168. Immunoglobulin lambda-like polypeptide 5 (G lambda-1) (Germline immunoglobulin lambda 1)
169. Inosine-5'-monophosphate dehydrogenase 1 (IMP dehydrogenase 1) (IMPDH 1) (EC 1.1.1.205) (IMPDH-I)
170. Insulin receptor (IR) (EC 2.7.10.1) (CD antigen CD220) [Cleaved into: Insulin receptor subunit alpha; Insulin receptor subunit beta]
171. Insulin-like growth factor 2 mRNA-binding protein 1 (IGF2 mRNA-binding protein 1) (IMP-1) (IMP1) (Coding region determinant-binding protein) (CRD-BP) (IGF-II mRNA-binding protein 1) (VICKZ family member 1) (Zipcode-binding protein 1) (ZBP-1)
172. Insulin-like growth factor 2 mRNA-binding protein 2 (IGF2 mRNA-binding protein 2) (IMP-2) (Hepatocellular carcinoma autoantigen p62) (IGF-II mRNA-binding protein 2) (VICKZ family member 2)
173. Insulin-like growth factor 2 mRNA-binding protein 3 (IGF2 mRNA-binding protein 3) (IMP-3) (IGF-II mRNA-binding protein 3) (KH domain-containing protein overexpressed in cancer) (hKOC) (VICKZ family member 3)
174. Intraflagellar transport protein 172 homolog
175. Involucrin
176. Iodotyrosine deiodinase 1 (IYD-1) (EC 1.21.1.1) (Iodotyrosine dehalogenase 1)
177. Junction plakoglobin (Catenin gamma) (Desmoplakin III) (Desmoplakin-3)
178. Kelch-like protein 1
179. Kelch-like protein 11
180. Keratin, type I cuticular Ha2 (Hair keratin, type I Ha2) (Keratin-32) (K32)
181. Keratin, type I cuticular Ha3-I (Hair keratin, type I Ha3-I) (Keratin-33A) (K33A)
182. Keratin, type I cytoskeletal 10 (Cytokeratin-10) (CK-10) (Keratin-10) (K10)
183. Keratin, type I cytoskeletal 13 (Cytokeratin-13) (CK-13) (Keratin-13) (K13)
184. Keratin, type I cytoskeletal 14 (Cytokeratin-14) (CK-14) (Keratin-14) (K14)
185. Keratin, type I cytoskeletal 16 (Cytokeratin-16) (CK-16) (Keratin-16) (K16)
186. Keratin, type I cytoskeletal 17
187. Keratin, type I cytoskeletal 17 (39.1) (Cytokeratin-17) (CK-17) (Keratin-17) (K17)
188. Keratin, type I cytoskeletal 9 (Cytokeratin-9) (CK-9) (Keratin-9) (K9)
189. Keratin, type II cytoskeletal 1 (67 kDa cytokeratin) (Cytokeratin-1) (CK-1) (Hair alpha protein) (Keratin-1) (K1) (Type-II keratin Kb1)
190. Keratin, type II cytoskeletal 2 epidermal (Cytokeratin-2e) (CK-2e) (Epithelial keratin-2e) (Keratin-2 epidermis) (Keratin-2e) (K2e) (Type-II keratin Kb2)
191. Keratin, type II cytoskeletal 2 oral (Cytokeratin-2P) (CK-2P) (K2P) (Keratin-76) (K76) (Type-II keratin Kb9)
192. Keratin, type II cytoskeletal 3 (65 kDa cytokeratin) (Cytokeratin-3) (CK-3) (Keratin-3) (K3) (Type-II keratin Kb3)
193. Keratin, type II cytoskeletal 5 (58 kDa cytokeratin) (Cytokeratin-5) (CK-5) (Keratin-5) (K5) (Type-II keratin Kb5)
194. Keratin, type II cytoskeletal 6A (Cytokeratin-6A) (CK-6A) (Cytokeratin-6D) (CK-6D) (Keratin-6A) (K6A) (Type-II keratin Kb6) (allergen Hom s 5)
195. Keratin, type II cytoskeletal 6B (Cytokeratin-6B) (CK-6B) (Keratin-6B) (K6B) (Type-II keratin Kb10)
196. Keratin, type II cytoskeletal 6C
197. Keratin, type II cytoskeletal 78 (Cytokeratin-78) (CK-78) (Keratin-5b) (Keratin-78) (K78) (Type-II keratin Kb40)
198. KIAA0415 gene product
199. Kinase suppressor of Ras 2
200. Kinesin-like protein
201. Kinesin-like protein KIF18A (Marrow stromal KIF18A) (MS-KIF18A)
202. Kinesin-like protein KIF26B
203. L-lactate dehydrogenase B chain (LDH-B) (EC 1.1.1.27) (LDH heart subunit) (LDH-H) (Renal carcinoma antigen NY-REN-46)

204. Lactotransferrin (Lactoferrin) (EC 3.4.21.—) (Growth-inhibiting protein 12) (Talalactoferrin) [Cleaved into: Lactoferricin-H (Lfcin-H); Kaliocin-1; Lactoferroxin-A; Lactoferroxin-B; Lactoferroxin-C]
205. Leucine-rich repeat-containing protein 74A (Leucine-rich repeat-containing protein 74)
206. Leukocyte immunoglobulin-like receptor subfamily A member 4 (CD85 antigen-like family member G) (Immunoglobulin-like transcript 7) (ILT-7) (CD antigen CD85g)
207. Lipocalin-1 (Tear lipocalin) (Tlc) (Tear prealbumin) (TP) (Von Ebner gland protein) (VEG protein)
208. Loricrin
209. Matrin-3
210. Melanoma-associated antigen D4 (MAGE-D4 antigen) (MAGE-E1 antigen)
211. Methyltransferase-like protein 7B (EC 2.1.1.—)
212. Microcephalin
213. Mitogen-activated protein kinase kinase kinase kinase 1 (EC 2.7.11.1) (Hematopoietic progenitor kinase) (MAPK/ERK kinase kinase kinase 1) (MEK kinase kinase 1) (MEKKK 1)
214. MKI67 FHA domain-interacting nucleolar phosphoprotein (Fragment)
215. Moesin (Membrane-organizing extension spike protein)
216. Mov10, Moloney leukemia virus 10, homolog (Mouse), isoform CRA_a (Putative helicase MOV-10)
217. Multidrug resistance-associated protein 1
218. Myb-binding protein 1A
219. Myosin-9 (Cellular myosin heavy chain, type A) (Myosin heavy chain 9) (Myosin heavy chain, non-muscle IIa) (Non-muscle myosin heavy chain A) (NMMHC-A) (Non-muscle myosin heavy chain IIa) (NMMHC II-a) (NMMHC-IIA)
220. NADH dehydrogenase [ubiquinone] 1 beta subcomplex subunit 11, mitochondrial (Complex I-ESSS) (CI-ESSS) (NADH-ubiquinone oxidoreductase ESSS subunit) (Neuronal protein 17.3) (Np17.3) (p17.3)
221. NADH dehydrogenase [ubiquinone] iron-sulfur protein 2, mitochondrial (EC 1.6.5.3) (EC 1.6.99.3) (Complex I-49 kD) (CI-49 kD) (NADH-ubiquinone oxidoreductase 49 kDa subunit)
222. Nebulin
223. Neuroblast differentiation-associated protein AHNAK (Desmoyokin)
224. Neurocan core protein (Chondroitin sulfate proteoglycan 3)
225. Nipped-B-like protein (Delangin) (SCC2 homolog)
226. NOP56 ribonucleoprotein homolog (yeast)
227. Nuclear valosin-containing protein-like (NVLp) (Nuclear VCP-like protein)
228. Nuclease-sensitive element-binding protein 1
229. Nucleolar GTP-binding protein 1
230. Nucleolar RNA helicase 2 (EC 3.6.4.13) (DEAD box protein 21) (Gu-alpha) (Nucleolar RNA helicase Gu) (Nucleolar RNA helicase II) (RH II/Gu)
231. Nucleolar transcription factor 1
232. Nucleolin
233. Nucleolin (Protein C23)
234. Nucleophosmin (Fragment)
235. Nucleophosmin (NPM) (Nucleolar phosphoprotein B23) (Nucleolar protein NO38) (Numatrin)
236. Nucleosome-remodeling factor subunit BPTF (Fragment)
237. PAI-1 mRNA-binding protein variant (cDNA, FLJ92551, Homo sapiens PAI-1 mRNA-binding protein (PAI-RBP1), mRNA)
238. Peptidyl-prolyl cis-trans isomerase A (PPIase A) (EC 5.2.1.8) (Cyclophilin A) (Cyclosporin A-binding protein) (Rotamase A) [Cleaved into: Peptidyl-prolyl cis-trans isomerase A, N-terminally processed]
239. Periplakin (190 kDa paraneoplastic pemphigus antigen) (195 kDa cornified envelope precursor protein)
240. Peroxiredoxin 2, isoform CRA_a (Peroxiredoxin-2)
241. Peroxiredoxin-1 (EC 1.11.1.15) (Natural killer cell-enhancing factor A) (NKEF-A) (Proliferation-associated gene protein) (PAG) (Thioredoxin peroxidase 2) (Thioredoxin-dependent peroxide reductase 2)
242. Peroxiredoxin-5, mitochondrial (EC 1.11.1.15) (Alu corepressor 1) (Antioxidant enzyme B166) (AOEB166) (Liver tissue 2D-page spot 71B) (PLP) (Peroxiredoxin V) (Prx-V) (Peroxisomal antioxidant enzyme) (TPx type VI) (Thioredoxin peroxidase PMP20) (Thioredoxin reductase)
243. Peroxiredoxin-6 (EC 1.11.1.15) (1-Cys peroxiredoxin) (1-Cys PRX) (24 kDa protein) (Acidic calcium-independent phospholipase A2) (aiPLA2) (EC 3.1.1.—) (Antioxidant protein 2) (Liver 2D page spot 40) (Non-selenium glutathione peroxidase) (NSGPx) (EC 1.11.1.9) (Red blood cells page spot 12)
244. Pescadillo homolog
245. Phosphoglycerate kinase 1 (EC 2.7.2.3) (Cell migration-inducing gene 10 protein) (Primer recognition protein 2) (PRP 2)
246. Phosphoglycerate mutase 1
247. Plakophilin-1 (Band 6 protein) (B6P)
248. Plakophilin-3
249. Poly [ADP-ribose] polymerase 1 (PARP-1) (EC 2.4.2.30) (ADP-ribosyltransferase diphtheria toxin-like 1) (ARTD1) (NAD(+) ADP-ribosyltransferase 1) (ADPRT 1) (Poly[ADP-ribose] synthase 1)
250. Poly(rC)-binding protein 1 (Alpha-CP1) (Heterogeneous nuclear ribonucleoprotein E1) (hnRNP E1) (Nucleic acid-binding protein SUB2.3)
251. Poly(rC)-binding protein 2 (Alpha-CP2) (Heterogeneous nuclear ribonucleoprotein E2) (hnRNP E2)
252. Polyadenylate-binding protein (PABP)
253. Polyadenylate-binding protein 1 (Fragment)
254. Polyadenylate-binding protein 4 (PABP-4) (Poly(A)-binding protein 4) (Activated-platelet protein 1) (APP-1) (Inducible poly(A)-binding protein) (iPABP)
255. Polymeric immunoglobulin receptor (PIgR) (Poly-Ig receptor) (Hepatocellular carcinoma-associated protein TB6) [Cleaved into: Secretory component]
256. pre-rRNA processing protein FTSJ3 (EC 2.1.1.—) (2'-O-ribose RNA methyltransferase SPB1 homolog) (Protein ftsJ homolog 3) (Putative rRNA methyltransferase 3)
257. Prelamin-A/C [Cleaved into: Lamin-A/C (70 kDa lamin) (Renal carcinoma antigen NY-REN-32)]
258. Probable 28S rRNA (cytosine(4447)-C(5))-methyltransferase (EC 2.1.1.—) (Nucleolar protein 1) (Nucleolar protein 2 homolog) (Proliferating-cell nucleolar antigen p120) (Proliferation-associated nucleolar protein p120)
259. Probable ATP-dependent RNA helicase DDX17
260. Probable ATP-dependent RNA helicase DDX27 (EC 3.6.4.13) (DEAD box protein 27)
261. Probable ATP-dependent RNA helicase DDX5 (EC 3.6.4.13) (DEAD box protein 5) (RNA helicase p68)
262. Probable ATP-dependent RNA helicase DDX6 (EC 3.6.4.13) (ATP-dependent RNA helicase p54) (DEAD box protein 6) (Oncogene RCK)

-continued

263. Probable ubiquitin carboxyl-terminal hydrolase FAF-X
264. Profilin-1 (Epididymis tissue protein Li 184a) (Profilin I)
265. Prolactin-inducible protein (Gross cystic disease fluid protein 15) (GCDFP-15) (Prolactin-induced protein) (Secretory actin-binding protein) (SABP) (gp17)
266. Protein canopy homolog 3 (CTG repeat protein 4a) (Expanded repeat-domain protein CAG/CTG 5) (Protein associated with TLR4) (Trinucleotide repeat-containing gene 5 protein)
267. Protein cordon-bleu
268. Protein jagged-2 (Jagged2) (hJ2)
269. Protein mago nashi homolog 2
270. Protein NDRG1 (Differentiation-related gene 1 protein) (DRG-1) (N-myc downstream-regulated gene 1 protein) (Nickel-specific induction protein Cap43) (Reducing agents and tunicamycin-responsive protein) (RTP) (Rit42)
271. Protein PRRC2A
272. Protein RRP5 homolog (NF-kappa-B-binding protein) (NFBP) (Programmed cell death protein 11)
273. Protein S100-A11 (Calgizzarin) (Metastatic lymph node gene 70 protein) (MLN 70) (Protein S100-C) (S100 calcium-binding protein A11) [Cleaved into: Protein S100-A11, N-terminally processed]
274. Protein S100-A14 (S100 calcium-binding protein A14) (S114)
275. Protein S100-A16 (Aging-associated gene 13 protein) (Protein S100-F) (S100 calcium-binding protein A16)
276. Protein S100-A8 (Calgranulin-A) (Calprotectin L1L subunit) (Cystic fibrosis antigen) (CFAG) (Leukocyte L1 complex light chain) (Migration inhibitory factor-related protein 8) (MRP-8) (p8) (S100 calcium-binding protein A8) (Urinary stone protein band A) [Cleaved into: Protein S100-A8, N-terminally processed]
277. Protein S100-A9 (Calgranulin-B) (Calprotectin L1H subunit) (Leukocyte L1 complex heavy chain) (Migration inhibitory factor-related protein 14) (MRP-14) (p14) (S100 calcium-binding protein A9)
278. Protein Shroom3 (Shroom-related protein) (hShrmL)
279. Protein sprouty homolog 1 (Fragment)
280. Protein-glutamine gamma-glutamyltransferase E (EC 2.3.2.13) (Transglutaminase E) (TG(E)) (TGE) (TGase E) (Transglutaminase-3) (TGase-3) [Cleaved into: Protein-glutamine gamma-glutamyltransferase E 50 kDa catalytic chain; Protein-glutamine gamma-glutamyltransferase E 27 kDa non-catalytic chain]
281. Protein-glutamine gamma-glutamyltransferase E 50 kDa catalytic chain
282. Protein-glutamine gamma-glutamyltransferase K (EC 2.3.2.13) (Epidermal TGase) (Transglutaminase K) (TG(K)) (TGK) (TGase K) (Transglutaminase-1) (TGase-1)
283. Putative annexin A2-like protein (Annexin A2 pseudogene 2) (Lipocortin II pseudogene)
284. Putative tubulin beta chain-like protein
285. Putative uncharacterized protein encoded by ERICH1-AS1 (ERICH1 antisense RNA 1) (ERICH1 antisense gene protein 1) (Putative DAP-2 like protein)
286. Putative uncharacterized protein ENSP00000334305
287. Putative uncharacterized protein ENSP00000382790
288. Putative uncharacterized protein ENSP00000383309
289. Putative uncharacterized protein FLJ13197
290. Pyruvate kinase
291. Radixin
292. Ras GTPase-activating protein nGAP
293. Regulator of nonsense transcripts 1 (EC 3.6.4.—) (ATP-dependent helicase RENT1) (Nonsense mRNA reducing factor 1) (NORF1) (Up-frameshift suppressor 1 homolog) (hUpf1)
294. Replication protein A 70 kDa DNA-binding subunit (RP-A p70) (Replication factor A protein 1) (RF-A protein 1) (Single-stranded DNA-binding protein) [Cleaved into: Replication protein A 70 kDa DNA-binding subunit, N-terminally processed]
295. Reticulon-4-interacting protein 1, mitochondrial (NOGO-interacting mitochondrial protein)
296. Rho GTPase-activating protein 20 (Rho-type GTPase-activating protein 20)
297. Rho-related GTP-binding protein RhoV (CDC42-like GTPase 2) (GTP-binding protein-like 2) (Rho GTPase-like protein ARHV) (Wnt-1 responsive Cdc42 homolog 2) (WRCH-2)
298. Ribosomal protein L15
299. Ribosome biogenesis regulatory protein homolog
300. RIMS-binding protein 2 (RIM-BP2)
301. RNA-binding motif protein, X chromosome (Glycoprotein p43) (Heterogeneous nuclear ribonucleoprotein G) (hnRNP G) [Cleaved into: RNA-binding motif protein, X chromosome, N-terminally processed]
302. RNA-binding protein 14 (Paraspeckle protein 2) (PSP2) (RNA-binding motif protein 14) (RRM-containing coactivator activator/modulator) (Synaptotagmin-interacting protein) (SYT-interacting protein)
303. RNA-binding protein 28 (Fragment)
304. RNA-binding protein 28 (RNA-binding motif protein 28)
305. RNA-binding protein NOB1 (Phosphorylation regulatory protein HP-10) (Protein ART-4)
306. Scaffold attachment factor B1 (SAF-B) (SAF-B1) (HSP27 estrogen response element-TATA box-binding protein) (HSP27 ERE-TATA-binding protein)
307. Schlafen family member 5
308. Sciellin
309. Selenium-binding protein 1 (56 kDa selenium-binding protein) (SBP56) (SP56)
310. Serine/arginine-rich splicing factor 10 (40 kDa SR-repressor protein) (SRrp40) (FUS-interacting serine-arginine-rich protein 1) (Splicing factor SRp38) (Splicing factor, arginine/serine-rich 13A) (TLS-associated protein with Ser-Arg repeats) (TASR) (TLS-associated protein with SR repeats) (TLS-associated serine-arginine protein) (TLS-associated SR protein)
311. Serine/threonine-protein kinase tousled-like 1 (EC 2.7.11.1) (PKU-beta) (Tousled-like kinase 1)
312. Serpin B3 (Protein T4-A) (Squamous cell carcinoma antigen 1) (SCCA-1)
313. SH2 domain-containing adapter protein E
314. Skin-specific protein 32
315. Small proline-rich protein 2A (SPR-2A) (2-1)
316. Small proline-rich protein 2D (SPR-2D) (Small proline-rich protein II) (SPR-II)
317. Small proline-rich protein 2E (SPR-2E) (Small proline-rich protein II) (SPR-II)
318. Small proline-rich protein 3 (Fragment)
319. Sodium-independent sulfate anion transporter (Solute carrier family 26 member 11)
320. Sodium/hydrogen exchanger 11 (Na(+)/H(+) exchanger 11) (NHE-11) (Solute carrier family 9 member 11) (Solute carrier family 9 member C2)
321. Spatacsin (Colorectal carcinoma-associated protein) (Spastic paraplegia 11 protein)

-continued

322. Splicing factor arginine/serine-rich 3 (Splicing factor, arginine/serine-rich 3, isoform CRA_d) (cDNA, FLJ92926, *Homo sapiens* splicing factor, arginine/serine-rich 3 (SFRS3), mRNA)
323. Splicing factor U2AF 65 kDa subunit (U2 auxiliary factor 65 kDa subunit) (hU2AF(65)) (hU2AF65) (U2 snRNP auxiliary factor large subunit)
324. Splicing factor, proline- and glutamine-rich (100 kDa DNA-pairing protein) (hPOMp100) (DNA-binding p52/p100 complex, 100 kDa subunit) (Polypyrimidine tract-binding protein-associated-splicing factor) (PSF) (PTB-associated-splicing factor)
325. STAGA complex 65 subunit gamma (Adenocarcinoma antigen ART1) (SPTF-associated factor 65 gamma) (STAF65gamma) (Suppressor of Ty 7-like)
326. Stress-induced-phosphoprotein 1
327. Suprabasin
328. Surfeit locus protein 6
329. TBCC domain-containing protein 1
330. Titin (EC 2.7.11.1) (Connectin) (Rhabdomyosarcoma antigen MU-RMS-40.14)
331. Trafficking protein particle complex subunit 10 (Epilepsy holoprosencephaly candidate 1 protein) (EHOC-1) (Protein GT334) (Trafficking protein particle complex subunit TMEM1) (Transport protein particle subunit TMEM1) (TRAPP subunit TMEM1)
332. Transcription factor SOX-9
333. Transcription termination factor 4, mitochondrial (cDNA FLJ54914, highly similar to *Homo sapiens* MTERF domain containing 2 (MTERFD2), mRNA)
334. Transgelin-2 (Epididymis tissue protein Li 7e) (SM22-alpha homolog)
335. Transitional endoplasmic reticulum ATPase (TER ATPase) (EC 3.6.4.6) (15S Mg(2+)-ATPase p97 subunit) (Valosin-containing protein) (VCP)
336. Triosephosphate isomerase (TIM) (EC 5.3.1.1) (Triose-phosphate isomerase)
337. tRNA:m(4)X modification enzyme TRM13 homolog
338. Trypsin-1
339. Trypsin-3 (EC 3.4.21.4) (Brain trypsinogen) (Mesotrypsinogen) (Serine protease 3) (Serine protease 4) (Trypsin III) (Trypsin IV)
340. Tubulin alpha-1B chain (Alpha-tubulin ubiquitous) (Tubulin K-alpha-1) (Tubulin alpha-ubiquitous chain) [Cleaved into: Detyrosinated tubulin alpha-1B chain]
341. Tubulin alpha-1C chain
342. Tubulin alpha-4A chain (Alpha-tubulin 1) (Testis-specific alpha-tubulin) (Tubulin H2-alpha) (Tubulin alpha-1 chain)
343. Tubulin beta chain
344. Tubulin beta chain (Tubulin beta-5 chain)
345. TYMS opposite strand protein
346. Uncharacterized protein
347. Uncharacterized protein
348. Uncharacterized protein (cDNA FLJ57652, highly similar to Ephrin-A3)
349. Unhealthy ribosome biogenesis protein 2 homolog
350. UPF0631 protein C17orf108
351. Vacuolar fusion protein MON1 homolog B
352. VIP peptides [Cleaved into: Intestinal peptide PHV-42 (Peptide histidine valine 42); Intestinal peptide PHM-27 (Peptide histidine methioninamide 27); Vasoactive intestinal peptide (VIP) (Vasoactive intestinal polypeptide)]
353. Xyloside xylosyltransferase 1 (EC 2.4.2.n3) (UDP-xylose:alpha-xyloside alpha-1,3-xylosyltransferase)
354. Zinc finger and BTB domain-containing protein 32 (FANCC-interacting protein) (Fanconi anemia zinc finger protein) (Testis zinc finger protein) (Zinc finger protein 538)
355. ZNF584 protein (Fragment)
356. Zymogen granule protein 16 homolog B Table 2 Shows Data for Peptide Identification by MS for 72 hr Control Sample 1. 60S ribosomal protein L4
2. 60S ribosomal protein L8
3. Actin, alpha skeletal muscle
4. Alpha-enolase (EC 4.2.1.11) (2-phospho-D-glycerate hydro-lyase) (C-myc promoter-binding protein) (Enolase 1) (MBP-1) (MPB-1) (Non-neural enolase) (NNE) (Phosphopyruvate hydratase) (Plasminogen-binding protein)
5. Beta-casein
6. Bleomycin hydrolase
7. Breast cancer anti-estrogen resistance protein 1 (CRK-associated substrate) (Cas scaffolding protein family member 1) (p130cas)
8. C-type lysozyme (Lysozyme) (EC 3.2.1.17) (Lysozyme (Renal amyloidosis), isoform CRA_a) (Lysozyme F1) (cDNA, FLJ92040, *Homo sapiens* lysozyme (renal amyloidosis) (LYZ), mRNA)
9. Calmodulin-like protein 5 (Calmodulin-like skin protein)
10. Cas scaffolding protein family member 4 (HEF-like protein) (HEF1-EFS-p130Cas-like protein) (HEPL)
11. Caspase 14, apoptosis-related cysteine peptidase (Caspase-14) (cDNA, FLJ94644, *Homo sapiens* caspase 14, apoptosis-related cysteine protease(CASP14), mRNA)
12. Catalase (EC 1.11.1.6)
13. Cathepsin D (EC 3.4.23.5) [Cleaved into: Cathepsin D light chain; Cathepsin D heavy chain]
14. Cation-independent mannose-6-phosphate receptor (CI Man-6-P receptor) (CI-MPR) (M6PR) (300 kDa mannose 6-phosphate receptor) (MPR 300) (Insulin-like growth factor 2 receptor) (Insulin-like growth factor II receptor) (IGF-II receptor) (M6P/IGF2 receptor) (M6P/IGF2R) (CD antigen CD222)
15. cDNA FLJ50994, moderately similar to 60S ribosomal protein L4
16. cDNA FLJ52243, highly similar to Heat-shock protein beta-1
17. cDNA FLJ52842, highly similar to Actin, cytoplasmic 1
18. cDNA FLJ54020, highly similar to Heterogeneous nuclear ribonucleoprotein U
19. cDNA FLJ57507, highly similar to Ran-specific GTPase-activating protein
20. cDNA FLJ59335, highly similar to Transmembrane glycoprotein NMB
21. cDNA FLJ60461, highly similar to Peroxiredoxin-2 (EC 1.11.1.15)
22. Cleavage stimulation factor subunit 3

-continued

23. Coiled-coil domain-containing 129
24. Collagen alpha-1(III) chain
25. Corneodesmosin
26. CRISPR-associated endonuclease Cas9/Csn1 (EC 3.1.—.—) (SpCas9) (SpyCas9)
27. Cystatin-A (Cystatin-AS) (Stefin-A) [Cleaved into: Cystatin-A, N-terminally processed]
28. Cystatin-M (Cystatin-6) (Cystatin-E)
29. Deleted in esophageal cancer 1 (Candidate tumor suppressor CTS9)
30. Desmin
31. Desmocollin-1 (Cadherin family member 1) (Desmosomal glycoprotein 2/3) (DG2/DG3)
32. Desmocollin-3 (Cadherin family member 3) (Desmocollin-4) (HT-CP)
33. Desmoglein-1 (Cadherin family member 4) (Desmosomal glycoprotein 1) (DG1) (DGI) (Pemphigus foliaceus antigen)
34. Desmoplakin (DP) (250/210 kDa paraneoplastic pemphigus antigen)
35. DNA ligase 3 (EC 6.5.1.1) (DNA ligase III) (Polydeoxyribonucleotide synthase [ATP] 3)
36. Echinoderm microtubule-associated protein-like 5 (EMAP-5)
37. Elongation factor 1-alpha 1 (EF-1-alpha-1) (Elongation factor Tu) (EF-Tu) (Eukaryotic elongation factor 1 A-1) (eEF1A-1) (Leukocyte receptor cluster member 7)
38. Elongation factor 2
39. Epididymis luminal protein 112 (Ribosomal protein S27a, isoform CRA_c) (cDNA, FLJ96793, *Homo sapiens* ribosomal protein S27a (RPS27A), mRNA)
40. Epididymis secretory protein Li 103 (Heat shock 70 kDa protein 1A) (Heat shock 70 kDa protein 1B) (cDNA FLJ75127, highly similar to *Homo sapiens* heat shock 70 kDa protein 1A, mRNA)
41. Epiplakin
42. Eukaryotic initiation factor 4A-II
43. F-box only protein 50 (NCC receptor protein 1 homolog) (NCCRP-1) (Non-specific cytotoxic cell receptor protein 1 homolog)
44. Filaggrin
45. Filaggrin-2 (FLG-2) (Intermediate filament-associated and psoriasis-susceptibility protein) (Ifapsoriasin)
46. Fructose-bisphosphate aldolase
47. Glyceraldehyde-3-phosphate dehydrogenase
48. Glyceraldehyde-3-phosphate dehydrogenase (GAPDH) (EC 1.2.1.12) (Peptidyl-cysteine S-nitrosylase GAPDH) (EC 2.6.99.—)
49. Heat shock protein beta-1 (HspB1) (28 kDa heat shock protein) (Estrogen-regulated 24 kDa protein) (Heat shock 27 kDa protein) (HSP 27) (Stress-responsive protein 27) (SRP27)
50. Heat shock protein HSP 90-alpha (Heat shock 86 kDa) (HSP 86) (HSP86) (Lipopolysaccharide-associated protein 2) (LAP-2) (LPS-associated protein 2) (Renal carcinoma antigen NY-REN-38)
51. Heat shock protein HSP 90-beta (HSP 90) (Heat shock 84 kDa) (HSP 84) (HSP84)
52. Hemoglobin subunit zeta (HBAZ) (Hemoglobin zeta chain) (Zeta-globin)
53. Heterogeneous nuclear ribonucleoprotein H
54. Heterogeneous nuclear ribonucleoproteins A2/B1 (hnRNP A2/B1)
55. Heterogeneous nuclear ribonucleoproteins C1/C2 (hnRNP C1/C2)
56. Histone 1, H1e (Histone H1e)
57. Histone H2A
58. Histone H2B
59. Histone H3
60. Ig alpha-1 chain C region
61. Ig gamma-1 chain C region
62. Ig kappa chain V-II region Cum
63. Ig lambda-7 chain C region
64. Insulin receptor (IR) (EC 2.7.10.1) (CD antigen CD220) [Cleaved into: Insulin receptor subunit alpha; Insulin receptor subunit beta]
65. Interleukin-37 (FIL1 zeta) (IL-1X) (Interleukin-1 family member 7) (IL-1F7) (Interleukin-1 homolog 4) (IL-1H) (IL-1H4) (Interleukin-1 zeta) (IL-1 zeta) (Interleukin-1-related protein) (IL-1RP1) (Interleukin-23) (IL-37)
66. Iodotyrosine deiodinase 1 (IYD-1) (EC 1.21.1.1) (Iodotyrosine dehalogenase 1)
67. Junction plakoglobin (Catenin gamma) (Desmoplakin III) (Desmoplakin-3)
68. Kelch-like protein 36
69. Keratin, type I cytoskeletal 10 (Cytokeratin-10) (CK-10) (Keratin-10) (K10)
70. Keratin, type I cytoskeletal 13
71. Keratin, type I cytoskeletal 14 (Cytokeratin-14) (CK-14) (Keratin-14) (K14)
72. Keratin, type I cytoskeletal 16 (Cytokeratin-16) (CK-16) (Keratin-16) (K16)
73. Keratin, type I cytoskeletal 17
74. Keratin, type I cytoskeletal 9 (Cytokeratin-9) (CK-9) (Keratin-9) (K9)
75. Keratin, type II cytoskeletal 1 (67 kDa cytokeratin) (Cytokeratin-1) (CK-1) (Hair alpha protein) (Keratin-1) (K1) (Type-II keratin Kb1)
76. Keratin, type II cytoskeletal 1b (Cytokeratin-1B) (CK-1B) (Keratin-77) (K77) (Type-II keratin Kb39)
77. Keratin, type II cytoskeletal 2 epidermal (Cytokeratin-2e) (CK-2e) (Epithelial keratin-2e) (Keratin-2 epidermis) (Keratin-2e) (K2e) (Type-II keratin Kb2)
78. Keratin, type II cytoskeletal 5 (58 kDa cytokeratin) (Cytokeratin-5) (CK-5) (Keratin-5) (K5) (Type-II keratin Kb5)
79. Keratin, type II cytoskeletal 6A
80. Keratin, type II cytoskeletal 6A (Cytokeratin-6A) (CK-6A) (Cytokeratin-6D) (CK-6D) (Keratin-6A) (K6A) (Type-II keratin Kb6) (allergen Hom s 5)
81. Keratin, type II cytoskeletal 6B
82. Keratin, type II cytoskeletal 6B (Cytokeratin-6B) (CK-6B) (Keratin-6B) (K6B) (Type-II keratin Kb10)
83. Keratin, type II cytoskeletal 6C
84. Keratin, type II cytoskeletal 78 (Cytokeratin-78) (CK-78) (Keratin-5b) (Keratin-78) (K78) (Type-II keratin Kb40)
85. Keratinocyte proline-rich protein (hKPRP)
86. Kinase suppressor of Ras 2
87. L-lactate dehydrogenase B chain (LDH-B) (EC 1.1.1.27) (LDH heart subunit) (LDH-H) (Renal carcinoma antigen NY-REN-46)
88. Lipocalin-1 (Tear lipocalin) (Tlc) (Tear prealbumin) (TP) (Von Ebner gland protein) (VEG protein)
89. Loricrin
90. Microcephalin
91. NADH dehydrogenase [ubiquinone] iron-sulfur protein 2, mitochondrial (EC 1.6.5.3) (EC 1.6.99.3) (Complex I-49 kD) (CI-49 kD) (NADH-ubiquinone oxidoreductase 49 kDa subunit)

-continued

92. NADH dehydrogenase [ubiquinone] iron-sulfur protein 3, mitochondrial (EC 1.6.5.3) (EC 1.6.99.3) (Complex I-30 kD) (CI-30 kD) (NADH-ubiquinone oxidoreductase 30 kDa subunit)
93. Nuclear receptor coactivator 2
94. Peptidyl-prolyl cis-trans isomerase A (PPIase A) (EC 5.2.1.8) (Cyclophilin A) (Cyclosporin A-binding protein) (Rotamase A) [Cleaved into: Peptidyl-prolyl cis-trans isomerase A, N-terminally processed]
95. Peroxiredoxin-1 (EC 1.11.1.15) (Natural killer cell-enhancing factor A) (NKEF-A) (Proliferation-associated gene protein) (PAG) (Thioredoxin peroxidase 2) (Thioredoxin-dependent peroxide reductase 2)
96. Peroxiredoxin-6 (EC 1.11.1.15) (1-Cys peroxiredoxin) (1-Cys PRX) (24 kDa protein) (Acidic calcium-independent phospholipase A2) (aiPLA2) (EC 3.1.1.—) (Antioxidant protein 2) (Liver 2D page spot 40) (Non-selenium glutathione peroxidase) (NSGPx) (EC 1.11.1.9) (Red blood cells page spot 12)
97. Peroxisomal trans-2-enoyl-CoA reductase (TERP) (EC 1.3.1.38) (2,4-dienoyl-CoA reductase-related protein) (DCR-RP) (HPDHase) (Short chain dehydrogenase/reductase family 29C member 1) (pVI-ARL)
98. Phosphoglycerate kinase 1 (EC 2.7.2.3) (Cell migration-inducing gene 10 protein) (Primer recognition protein 2) (PRP 2)
99. Plakophilin-1 (Band 6 protein) (B6P)
100. POTE ankyrin domain family member F (ANKRD26-like family C member 1B) (Chimeric POTE-actin protein)
101. Probable ATP-dependent RNA helicase DDX17
102. Probable ATP-dependent RNA helicase DDX5 (EC 3.6.4.13) (DEAD box protein 5) (RNA helicase p68)
103. Prostatic acid phosphatase (Fragment)
104. Protein deglycase DJ-1 (DJ-1) (EC 3.1.2.—) (EC 3.5.1.—) (Oncogene DJ1) (Parkinson disease protein 7)
105. Protein S100-A7 (Psoriasin) (S100 calcium-binding protein A7)
106. Protein Shroom3 (Shroom-related protein) (hShrmL)
107. Protein-glutamine gamma-glutamyltransferase E (EC 2.3.2.13) (Transglutaminase E) (TG(E)) (TGE) (TGase E) (Transglutaminase-3) (TGase-3) [Cleaved into: Protein-glutamine gamma-glutamyltransferase E 50 kDa catalytic chain; Protein-glutamine gamma-glutamyltransferase E 27 kDa non-catalytic chain]
108. Protein-glutamine gamma-glutamyltransferase E 50 kDa catalytic chain
109. Protein-glutamine gamma-glutamyltransferase K (EC 2.3.2.13) (Epidermal TGase) (Transglutaminase K) (TG(K)) (TGK) (TGase K) (Transglutaminase-1) (TGase-1)
110. Protocadherin-15 (Fragment)
111. Putative uncharacterized protein encoded by ERICH1-AS1 (ERICH1 antisense RNA 1) (ERICH1 antisense gene protein 1) (Putative DAP-2 like protein)
112. Pyruvate kinase
113. Radical S-adenosyl methionine domain-containing protein
114. Radixin
115. Rap guanine nucleotide exchange factor 6 (PDZ domain-containing guanine nucleotide exchange factor 2) (PDZ-GEF2) (RA-GEF-2)
116. Rho GTPase-activating protein 20 (Rho-type GTPase-activating protein 20)
117. Schlafen family member 5
118. Serum albumin
119. Skin-specific protein 32
120. Sodium/hydrogen exchanger 11 (Na(+)/H(+) exchanger 11) (NHE-11) (Solute carrier family 9 member 11) (Solute carrier family 9 member C2)
121. Speedy protein E1 (Williams-Beuren syndrome chromosomal region 19 protein)
122. T-cell receptor-associated transmembrane adapter 1
123. Tesmin (Metallothionein-like 5, testis-specific) (Testis-specific metallothionein-like protein)
124. Tetratricopeptide repeat protein 21A
125. Transmembrane channel-like protein 8 (Epidermodysplasia verruciformis protein 2)
126. tRNA:m(4)X modification enzyme TRM13 homolog
127. Trypsin-2 (EC 3.4.21.4) (Anionic trypsinogen) (Serine protease 2) (Trypsin II)
128. Trypsin-3 (EC 3.4.21.4) (Brain trypsinogen) (Mesotrypsinogen) (Serine protease 3) (Serine protease 4) (Trypsin III) (Trypsin IV)
129. Tubulin alpha-1B chain (Alpha-tubulin ubiquitous) (Tubulin K-alpha-1) (Tubulin alpha-ubiquitous chain) [Cleaved into: Detyrosinated tubulin alpha-1B chain]
130. Tubulin beta chain (Tubulin beta-5 chain)
131. Uncharacterized protein
132. Uncharacterized protein
133. UPF0631 protein C17orf108

Table 3 Shows Data for Peptide Identification by MS for 72 hr Dimerized Washout Sample 1. 14-3-3 protein sigma (Epithelial cell marker protein 1) (Stratifin)
2. 40S ribosomal protein S14
3. 40S ribosomal protein SA
4. 60S ribosomal protein L6 (Neoplasm-related protein C140) (Tax-responsive enhancer element-binding protein 107) (TaxREB107)
5. 60S ribosomal protein L7
6. 60S ribosomal protein L8
7. A disintegrin and metalloproteinase with thrombospondin motifs 14 (ADAM-TS 14) (ADAM-TS14) (ADAMTS-14) (EC 3.4.24.—)
8. Acyl-coenzyme A thioesterase 13 (Acyl-CoA thioesterase 13) (EC 3.1.2.—) (Thioesterase superfamily member 2) [Cleaved into: Acyl-coenzyme A thioesterase 13, N-terminally processed]
9. Adhesion G protein-coupled receptor B2
10. Adrenocorticotropic hormone receptor (ACTH receptor) (ACTH-R) (Adrenocorticotropin receptor) (Melanocortin receptor 2) (MC2-R)
11. Alpha-enolase (EC 4.2.1.11) (2-phospho-D-glycerate hydro-lyase) (C-myc promoter-binding protein) (Enolase 1) (MBP-1) (MPB-1) (Non-neural enolase) (NNE) (Phosphopyruvate hydratase) (Plasminogen-binding protein)
12. Alpha-N-acetyl-neuraminyl-2,3-beta-galactosyl-1,3-N-acetyl-galactosaminide alpha-2,6-sialyltransferase (Fragment)
13. Annexin A2 (Annexin II) (Annexin-2) (Calpactin I heavy chain) (Calpactin-1 heavy chain) (Chromobindin-8) (Lipocortin II) (Placental anticoagulant protein IV) (PAP-IV) (Protein I) (p36)

14. Apolipoprotein A-I (Apo-AI) (ApoA-I) (Apolipoprotein A1) [Cleaved into: Proapolipoprotein A-I (ProapoA-I); Truncated apolipoprotein A-I (Apolipoprotein A-I(1-242))]
15. Arachidonate 12-lipoxygenase, 12R-type (12R-LOX) (12R-lipoxygenase) (EC 1.13.11.—) (Epidermis-type lipoxygenase 12)
16. Arginase-1 (EC 3.5.3.1) (Liver-type arginase) (Type I arginase)
17. ATP synthase subunit beta, mitochondrial (EC 3.6.3.14)
18. Bleomycin hydrolase
19. Breast cancer anti-estrogen resistance protein 1 (CRK-associated substrate) (Cas scaffolding protein family member 1) (p130cas)
20. Calmodulin 1 (Phosphorylase kinase, delta), isoform CRA_a (Calmodulin 3 (Phosphorylase kinase, delta), isoform CRA_b) (Epididymis secretory protein Li 72) (cDNA FLJ61744, highly similar to Calmodulin)
21. Calmodulin-like protein 3 (CaM-like protein) (CLP) (Calmodulin-related protein NB-1)
22. Calmodulin-like protein 5 (Calmodulin-like skin protein)
23. Calnexin (IP90) (Major histocompatibility complex class I antigen-binding protein p88) (p90)
24. Carboxypeptidase D (EC 3.4.17.22) (Metallocarboxypeptidase D) (gp180)
25. Cas scaffolding protein family member 4 (HEF-like protein) (HEF1-EFS-p130Cas-like protein) (HEPL)
26. Caspase 14, apoptosis-related cysteine peptidase (Caspase-14) (cDNA, FLJ94644, *Homo sapiens* caspase 14, apoptosis-related cysteine protease(CASP14), mRNA)
27. Catalase (EC 1.11.1.6)
28. Cation-independent mannose-6-phosphate receptor (CI Man-6-P receptor) (CI-MPR) (M6PR) (300 kDa mannose 6-phosphate receptor) (MPR 300) (Insulin-like growth factor 2 receptor) (Insulin-like growth factor II receptor) (IGF-II receptor) (M6P/IGF2 receptor) (M6P/IGF2R) (CD antigen CD222)
29. cDNA FLJ44468 fis, clone UTERU2026025, moderately similar to SPLICING FACTOR, ARGININE/SERINE-RICH 2
30. cDNA FLJ50994, moderately similar to 60S ribosomal protein L4
31. cDNA FLJ52243, highly similar to Heat-shock protein beta-1
32. cDNA FLJ52842, highly similar to Actin, cytoplasmic 1
33. cDNA FLJ54020, highly similar to Heterogeneous nuclear ribonucleoprotein U
34. cDNA FLJ54552, highly similar to Heterogeneous nuclear ribonucleoprotein K
35. cDNA FLJ55372, highly similar to FH1/FH2 domain-containing protein
36. cDNA FLJ55805, highly similar to Keratin, type II cytoskeletal 4
37. cDNA FLJ56548, highly similar to Elongation factor 2
38. cDNA FLJ57507, highly similar to Ran-specific GTPase-activating protein
39. cDNA FLJ57660, highly similar to *Homo sapiens* zinc finger, CW type with PWWP domain 1 (ZCWPW1), mRNA
40. cDNA FLJ60461, highly similar to Peroxiredoxin-2 (EC 1.11.1.15)
41. Centromere-associated protein E (Fragment)
42. Charged multivesicular body protein 7 (Chromatin-modifying protein 7)
43. Chloride intracellular channel protein 1 (Chloride channel ABP) (Nuclear chloride ion channel 27) (NCC27) (Regulatory nuclear chloride ion channel protein) (hRNCC)
44. Cleavage stimulation factor subunit 3
45. Collagen alpha-1(VII) chain (Long-chain collagen) (LC collagen)
46. Collagen alpha-2(I) chain
47. Connector enhancer of kinase suppressor of ras 2 (Connector enhancer of KSR 2) (CNK homolog protein 2) (CNK2)
48. Copine-6 (Copine VI) (Neuronal-copine) (N-copine)
49. Copper homeostasis protein cutC homolog (Fragment)
50. Corneodesmosin
51. CRISPR-associated endonuclease Cas9 (EC 3.1.—.—) (SaCas9)
52. CRISPR-associated endonuclease Cas9/Csn1 (EC 3.1.—.—) (SpCas9) (SpyCas9)
53. Cyclic nucleotide-gated cation channel beta-1 (Cyclic nucleotide-gated cation channel 4) (CNG channel 4) (CNG-4) (CNG4) (Cyclic nucleotide-gated cation channel gamma) (Cyclic nucleotide-gated cation channel modulatory subunit) (Cyclic nucleotide-gated channel beta-1) (CNG channel beta-1) (Glutamic acid-rich protein) (GARP)
54. Cystatin-A (Cystatin-AS) (Stefin-A) [Cleaved into: Cystatin-A, N-terminally processed]
55. Cystatin-SN (Cystain-SA-I) (Cystatin-1) (Salivary cystatin-SA-1)
56. DENN domain-containing protein 5B (Rab6IP1-like protein)
57. Dermcidin (EC 3.4.—.—) (Preproteolysin) [Cleaved into: Survival-promoting peptide; DCD-1]
58. Desmocollin-1 (Cadherin family member 1) (Desmosomal glycoprotein 2/3) (DG2/DG3)
59. Desmocollin-3 (Cadherin family member 3) (Desmocollin-4) (HT-CP)
60. Desmoglein-1 (Cadherin family member 4) (Desmosomal glycoprotein 1) (DG1) (DGI) (Pemphigus foliaceus antigen)
61. Desmoplakin (DP) (250/210 kDa paraneoplastic pemphigus antigen)
62. Disintegrin and metalloproteinase domain-containing protein 29 (ADAM 29) (Cancer/testis antigen 73) (CT73)
63. DNA topoisomerase 1 (EC 5.99.1.2) (DNA topoisomerase I)
64. Dynein heavy chain 12, axonemal
65. E3 ubiquitin-protein ligase FANCL
66. E3 ubiquitin-protein ligase Itchy homolog (Itch) (EC 2.3.2.26) (Atrophin-1-interacting protein 4) (AIP4) (HECT-type E3 ubiquitin transferase Itchy homolog) (NFE2-associated polypeptide 1) (NAPP1)
67. E3 ubiquitin-protein ligase RNF133 (EC 6.3.2.—) (RING finger protein 133)
68. Elongation factor 1-alpha 1 (EF-1-alpha-1) (Elongation factor Tu) (EF-Tu) (Eukaryotic elongation factor 1 A-1) (eEF1A-1) (Leukocyte receptor cluster member 7)
69. Epididymis luminal protein 112 (Ribosomal protein S27a, isoform CRA_c) (cDNA, FLJ96793, *Homo sapiens* ribosomal protein S27a (RPS27A), mRNA)
70. Epiplakin
71. Eukaryotic initiation factor 4A-III (eIF-4A-III) (eIF4A-III) (EC 3.6.4.13) (ATP-dependent RNA helicase DDX48) (ATP-dependent RNA helicase eIF4A-3) (DEAD box protein 48) (Eukaryotic initiation factor 4A-like NUK-34) (Eukaryotic translation initiation factor 4A isoform 3) (Nuclear matrix protein 265) (NMP 265) (hNMP 265) [Cleaved into: Eukaryotic initiation factor 4A-III, N-terminally processed]
72. Eukaryotic translation initiation factor 5B (eIF-5B) (EC 3.6.5.3) (Translation initiation factor IF-2)
73. Extracellular matrix protein 1 (Secretory component p85)
74. Fanconi-associated nuclease 1 (EC 3.1.21.—) (EC 3.1.4.1) (FANCD2/FANCI-associated nuclease 1) (hFAN1) (Myotubularin-related protein 15)
75. Fatty acid binding protein 5 (Psoriasis-associated)
76. Fibronectin type III domain-containing protein 1 (Activation-associated cDNA protein) (Expressed in synovial lining protein)
77. Filaggrin 78. Filaggrin-2 (FLG-2) (Intermediate filament-associated and psoriasis-susceptibility protein) (Ifapsoriasin)
79. Fructose-bisphosphate aldolase
80. Fructose-bisphosphate aldolase A (EC 4.1.2.13) (Lung cancer antigen NY-LU-1) (Muscle-type aldolase)
81. Gamma-glutamylcyclotransferase
82. Gamma-tubulin complex component 3 (GCP-3) (hGCP3) (Gamma-ring complex protein 104 kDa) (h104p) (hGrip104) (Spindle pole body protein Spc98 homolog) (hSpc98)
83. Glutathione S-transferase P
84. Glycogen debranching enzyme (Glycogen debrancher) [Includes: 4-alpha-glucanotransferase (EC 2.4.1.25) (Oligo-1,4-1,4-glucantransferase); Amylo-alpha-1,6-glucosidase (Amylo-1,6-glucosidase) (EC 3.2.1.33) (Dextrin 6-alpha-D-glucosidase)]
85. Heat shock protein beta-1 (HspB1) (28 kDa heat shock protein) (Estrogen-regulated 24 kDa protein) (Heat shock 27 kDa protein) (HSP 27) (Stress-responsive protein 27) (SRP27)
86. Heat shock protein HSP 90-alpha (Heat shock 86 kDa) (HSP 86) (HSP86) (Lipopolysaccharide-associated protein 2) (LAP-2) (LPS-associated protein 2) (Renal carcinoma antigen NY-REN-38)
87. Heat shock protein HSP 90-beta (HSP 90) (Heat shock 84 kDa) (HSP 84) (HSP84)
88. Heat shock protein, alpha-crystallin-related, B6
89. Heme oxygenase 2 (HO-2) (EC 1.14.14.18)
90. Hepatitis A virus cellular receptor 2
91. Heterogeneous nuclear ribonucleoprotein F (hnRNP F) (Nucleolin-like protein mcs94-1) [Cleaved into: Heterogeneous nuclear ribonucleoprotein F, N-terminally processed]
92. Heterogeneous nuclear ribonucleoprotein M (hnRNP M)
93. Heterogeneous nuclear ribonucleoproteins A2/B1 (hnRNP A2/B1)
94. Heterogeneous nuclear ribonucleoproteins C1/C2 (hnRNP C1/C2)
95. Histone 1, H1e (Histone H1e)
96. Histone H2A
97. Histone H2B
98. Histone H4
99. Hornerin
100. Ig alpha-1 chain C region
101. Ig gamma-1 chain C region
102. Inosine-5'-monophosphate dehydrogenase 1 (IMP dehydrogenase 1) (IMPD 1) (IMPDH 1) (EC 1.1.1.205) (IMPDH-I)
103. Insulin receptor (IR) (EC 2.7.10.1) (CD antigen CD220) [Cleaved into: Insulin receptor subunit alpha; Insulin receptor subunit beta]
104. Iodotyrosine deiodinase 1 (IYD-1) (EC 1.21.1.1) (Iodotyrosine dehalogenase 1)
105. Junction plakoglobin (Catenin gamma) (Desmoplakin III) (Desmoplakin-3)
106. Kelch-like protein 34
107. Keratin-associated protein 13-1 (High sulfur keratin-associated protein 13.1)
108. Keratin-associated protein 13-2
109. Keratin-associated protein 16-1
110. Keratin-associated protein 2-2 (High sulfur keratin-associated protein 2.2) (Keratin-associated protein 2.2)
111. Keratin-associated protein 3-1 (High sulfur keratin-associated protein 3.1) (Keratin-associated protein 3.1)
112. Keratin-associated protein 3-2 (High sulfur keratin-associated protein 3.2) (Keratin-associated protein 3.2)
113. Keratin-associated protein 3-3 (High sulfur keratin-associated protein 3.3) (Keratin-associated protein 3.3)
114. Keratin-associated protein 6-1
115. Keratin, type I cuticular Ha1 (Hair keratin, type I Ha1) (Keratin-31) (K31)
116. Keratin, type I cuticular Ha2 (Hair keratin, type I Ha2) (Keratin-32) (K32)
117. Keratin, type I cuticular Ha3-I (Hair keratin, type I Ha3-I) (Keratin-33A) (K33A)
118. Keratin, type I cuticular Ha3-II (Hair keratin, type I Ha3-II) (Keratin-33B) (K33B)
119. Keratin, type I cuticular Ha5
120. Keratin, type I cuticular Ha6 (Hair keratin, type I Ha6) (Keratin-36) (K36)
121. Keratin, type I cuticular Ha8 (Hair keratin, type I Ha8) (Keratin-38) (K38)
122. Keratin, type I cytoskeletal 10 (Cytokeratin-10) (CK-10) (Keratin-10) (K10)
123. Keratin, type I cytoskeletal 13 (Cytokeratin-13) (CK-13) (Keratin-13) (K13)
124. Keratin, type I cytoskeletal 14 (Cytokeratin-14) (CK-14) (Keratin-14) (K14)
125. Keratin, type I cytoskeletal 16 (Cytokeratin-16) (CK-16) (Keratin-16) (K16)
126. Keratin, type I cytoskeletal 17
127. Keratin, type I cytoskeletal 17 (39.1) (Cytokeratin-17) (CK-17) (Keratin-17) (K17)
128. Keratin, type I cytoskeletal 19 (Cytokeratin-19) (CK-19) (Keratin-19) (K19)
129. Keratin, type I cytoskeletal 25 (Cytokeratin-25) (CK-25) (Keratin-25) (K25) (Keratin-25A) (K25A) (Type I inner root sheath-specific keratin-K25irs1)
130. Keratin, type I cytoskeletal 39 (Cytokeratin-39) (CK-39) (Keratin-39) (K39) (Type I hair keratin Ka35)
131. Keratin, type I cytoskeletal 9 (Cytokeratin-9) (CK-9) (Keratin-9) (K9)
132. Keratin, type II cuticular Hb2 (Keratin-82) (K82) (Type II hair keratin Hb2) (Type-II keratin Kb22)
133. Keratin, type II cuticular Hb3 (Hair keratin K2.10) (Keratin-83) (K83) (Type II hair keratin Hb3) (Type-II keratin Kb23)
134. Keratin, type II cuticular Hb4 (Keratin-84) (K84) (Type II hair keratin Hb4) (Type-II keratin Kb24)
135. Keratin, type II cuticular Hb5 (Hair keratin K2.12) (Keratin-85) (K85) (Type II hair keratin Hb5) (Type-II keratin Kb25)
136. Keratin, type II cuticular Hb6 (Hair keratin K2.11) (Keratin-86) (K86) (Type II hair keratin Hb6) (Type-II keratin Kb26)
137. Keratin, type II cytoskeletal 1 (67 kDa cytokeratin) (Cytokeratin-1) (CK-1) (Hair alpha protein) (Keratin-1) (K1) (Type-II keratin Kb1)
138. Keratin, type II cytoskeletal 1b (Cytokeratin-1B) (CK-1B) (Keratin-77) (K77) (Type-II keratin Kb39)
139. Keratin, type II cytoskeletal 2 epidermal (Cytokeratin-2e) (CK-2e) (Epithelial keratin-2e) (Keratin-2 epidermis) (Keratin-2e) (K2e) (Type-II keratin Kb2)
140. Keratin, type II cytoskeletal 3 (65 kDa cytokeratin) (Cytokeratin-3) (CK-3) (Keratin-3) (K3) (Type-II keratin Kb3)
141. Keratin, type II cytoskeletal 5 (58 kDa cytokeratin) (Cytokeratin-5) (CK-5) (Keratin-5) (K5) (Type-II keratin Kb5)
142. Keratin, type II cytoskeletal 6A (Cytokeratin-6A) (CK-6A) (Cytokeratin-6D) (CK-6D) (Keratin-6A) (K6A) (Type-II keratin Kb6) (allergen Hom s 5)
143. Keratin, type II cytoskeletal 6B (Cytokeratin-6B) (CK-6B) (Keratin-6B) (K6B) (Type-II keratin Kb10)
144. Keratin, type II cytoskeletal 6C
145. Keratin, type II cytoskeletal 73 (Cytokeratin-73) (CK-73) (Keratin-73) (K73) (Type II inner root sheath-specific keratin-K6irs3) (Type-II keratin Kb36)
146. Keratin, type II cytoskeletal 78 (Cytokeratin-78) (CK-78) (Keratin-5b) (Keratin-78) (K78) (Type-II keratin Kb40)

147. Keratin, type II cytoskeletal 8 (Cytokeratin-8) (CK-8) (Keratin-8) (K8) (Type-II keratin Kb8)
148. Keratin, type II cytoskeletal 80 (Cytokeratin-80) (CK-80) (Keratin-80) (K80) (Type-II keratin Kb20)
149. Keratinocyte proline-rich protein (hKPRP)
150. Lactotransferrin (Lactoferrin) (EC 3.4.21.—) (Growth-inhibiting protein 12) (Talalactoferrin) [Cleaved into: Lactoferricin-H (Lfcin-H); Kaliocin-1; Lactoferroxin-A; Lactoferroxin-B; Lactoferroxin-C]
151. Ligand-dependent nuclear receptor-interacting factor 1 (Receptor-interacting factor 1)
152. Lipocalin-1 (Tear lipocalin) (Tlc) (Tear prealbumin) (TP) (Von Ebner gland protein) (VEG protein)
153. Mammaglobin-B (Lacryglobin) (Lipophilin-C) (Mammaglobin-2) (Secretoglobin family 2A member 1)
154. Melanoma-associated antigen D4 (MAGE-D4 antigen) (MAGE-E1 antigen)
155. Membrane-associated transporter protein
156. Monofunctional C1-tetrahydrofolate synthase, mitochondrial (Fragment)
157. Mothers against decapentaplegic homolog 6 (MAD homolog 6) (Mothers against DPP homolog 6) (SMAD family member 6) (SMAD 6) (Smad6) (hSMAD6)
158. NADH dehydrogenase [ubiquinone] iron-sulfur protein 2, mitochondrial (EC 1.6.5.3) (EC 1.6.99.3) (Complex I-49 kD) (CI-49 kD) (NADH-ubiquinone oxidoreductase 49 kDa subunit)
159. Neuroblast differentiation-associated protein AHNAK (Desmoyokin)
160. Neuromedin-U receptor 1 (NMU-R1) (G-protein coupled receptor 66) (G-protein coupled receptor FM-3)
161. Nitric oxide-associated protein 1
162. Non-POU domain-containing octamer-binding protein (Fragment)
163. Nuclear factor erythroid 2-related factor 3
164. Nuclease-sensitive element-binding protein 1
165. Nucleophosmin (NPM) (Nucleolar phosphoprotein B23) (Nucleolar protein NO 38) (Numatrin)
166. Oral cancer overexpressed 1
167. Peroxiredoxin-1 (EC 1.11.1.15) (Natural killer cell-enhancing factor A) (NKEF-A) (Proliferation-associated gene protein) (PAG) (Thioredoxin peroxidase 2) (Thioredoxin-dependent peroxide reductase 2)
168. Peroxiredoxin-6 (EC 1.11.1.15) (1-Cys peroxiredoxin) (1-Cys PRX) (24 kDa protein) (Acidic calcium-independent phospholipase A2) (aiPLA2) (EC 3.1.1.—) (Antioxidant protein 2) (Liver 2D page spot 40) (Non-selenium glutathione peroxidase) (NSGPx) (EC 1.11.1.9) (Red blood cells page spot 12)
169. Phosphoglycerate kinase 1 (EC 2.7.2.3) (Cell migration-inducing gene 10 protein) (Primer recognition protein 2) (PRP 2)
170. Phosphotriesterase-related protein (EC 3.1.—.—) (Parathion hydrolase-related protein) (hPHRP)
171. Plakophilin-1 (Band 6 protein) (B6P)
172. PML-RARA regulated adaptor molecule 1, isoform CRA_b
173. POTE ankyrin domain family member F (ANKRD26-like family C member 1B) (Chimeric POTE-actin protein)
174. PRAME family member 8
175. Probable ATP-dependent RNA helicase DDX17
176. Probable ATP-dependent RNA helicase DDX5 (EC 3.6.4.13) (DEAD box protein 5) (RNA helicase p68)
177. Probable cation-transporting ATPase 13A2 (EC 3.6.3.—)
178. Probable E3 ubiquitin-protein ligase DTX2
179. Prolactin-inducible protein (Gross cystic disease fluid protein 15) (GCDFP-15) (Prolactin-induced protein) (Secretory actin-binding protein) (SABP) (gp17)
180. Proteasome subunit alpha type-3 (EC 3.4.25.1) (Macropain subunit C8) (Multicatalytic endopeptidase complex subunit C8) (Proteasome component C8)
181. Protein CREG1 (Cellular repressor of E1A-stimulated genes 1)
182. Protein deglycase DJ-1 (DJ-1) (EC 3.1.2.—) (EC 3.5.1.—) (Oncogene DJ1) (Parkinson disease protein 7)
183. Protein FAM156A/FAM156B
184. Protein phosphatase 1 regulatory subunit 15B
185. Protein S100-A14 (S100 calcium-binding protein A14) (S114)
186. Protein S100-A3 (Protein S-100E) (S100 calcium-binding protein A3)
187. Protein S100-A7 (Psoriasin) (S100 calcium-binding protein A7)
188. Protein Shroom3 (Shroom-related protein) (hShrmL)
189. Protein SMG5
190. Protein-glutamine gamma-glutamyltransferase E (EC 2.3.2.13) (Transglutaminase E) (TG(E)) (TGE) (TGase E) (Transglutaminase-3) (TGase-3) [Cleaved into: Protein-glutamine gamma-glutamyltransferase E 50 kDa catalytic chain; Protein-glutamine gamma-glutamyltransferase E 27 kDa non-catalytic chain]
191. Protein-glutamine gamma-glutamyltransferase E 50 kDa catalytic chain
192. Protein-glutamine gamma-glutamyltransferase K (EC 2.3.2.13) (Epidermal TGase) (Transglutaminase K) (TG(K)) (TGK) (TGase K) (Transglutaminase-1) (TGase-1)
193. Protocadherin-16 (Cadherin-19) (Cadherin-25) (Fibroblast cadherin-1) (Protein dachsous homolog 1)
194. Putative uncharacterized protein C14orf144
195. Pyruvate kinase
196. Radixin
197. Ras-specific guanine nucleotide-releasing factor 2
198. Receptor protein-tyrosine kinase (EC 2.7.10.1)
199. Rho guanine nucleotide exchange factor 7
200. RNA exonuclease 1 homolog (EC 3.1.—.—) (Elongin-A-binding protein 1) (EloA-BP1) (Transcription elongation factor B polypeptide 3-binding protein 1)
201. Sarcolemmal membrane-associated protein (Sarcolemmal-associated protein)
202. Selenium-binding protein 1 (56 kDa selenium-binding protein) (SBP56) (SP56)
203. Sentrin-specific protease 5 (EC 3.4.22.68) (Sentrin/SUMO-specific protease SENP5)
204. Serine/threonine-protein kinase PAK 1 (cDNA FLJ30666 fis, clone FCBBF1000627, highly similar to Serine/threonine-protein kinase PAK1 (EC 2.7.11.1))
205. Serpin B12
206. Skin-specific protein 32
207. Small proline-rich protein 2E (SPR-2E) (Small proline-rich protein II) (SPR-II)
208. Spectrin repeat containing, nuclear envelope 1
209. Speedy protein E1 (Williams-Beuren syndrome chromosomal region 19 protein)
210. Striated muscle preferentially-expressed protein kinase
211. T-complex protein 1 subunit beta
212. Thioredoxin (Trx) (ATL-derived factor) (ADF) (Surface-associated sulphydryl protein) (SASP)

-continued

213. THO complex subunit 4
214. Transforming protein RhoA
215. Trypsin-1
216. Trypsin-2 (EC 3.4.21.4) (Anionic trypsinogen) (Serine protease 2) (Trypsin II)
217. Tubulin alpha-1C chain
218. Tubulin beta chain (Tubulin beta-5 chain)
219. Tyrosine-protein kinase Fer
220. Uncharacterized protein
221. Uncharacterized protein C17orf96
222. Uncharacterized protein C9orf114
223. Uncharacterized protein C9orf172
224. UPF0631 protein C17orf108
225. V-set and immunoglobulin domain-containing protein 8
226. Vacuolar protein sorting-associated protein 51 homolog
227. Zinc finger protein 830 (Coiled-coil domain-containing protein 16)
228. Zinc-alpha-2-glycoprotein Table 4 Shows Data for Peptide Identification by MS for 72 hr Control Washout Sample 1. HLA-B associated transcript 1
2. Deleted in malignant brain tumors 1 protein (Glycoprotein 340) (Gp-340) (Hensin) (Salivary agglutinin) (SAG) (Surfactant pulmonary-associated D-binding protein)
3. Epididymis luminal protein 112 (Ribosomal protein S27a, isoform CRA_c) (cDNA, FLJ96793, *Homo sapiens* ribosomal protein S27a (RPS27A), mRNA)
4. Keratin, type II cytoskeletal 2 epidermal (Cytokeratin-2e) (CK-2e) (Epithelial keratin-2e) (Keratin-2 epidermis) (Keratin-2e) (K2e) (Type-II keratin Kb2)
5. cDNA FLJ52842, highly similar to Actin, cytoplasmic 1
6. Tubulin beta chain (Tubulin beta-5 chain)
7. Histone H2A
8. Keratin, type I cytoskeletal 10 (Cytokeratin-10) (CK-10) (Keratin-10) (K10)
9. Uncharacterized protein
10. Epiplakin
11. Tubulin alpha-1A chain (Alpha-tubulin 3) (Tubulin B-alpha-1) (Tubulin alpha-3 chain) [Cleaved into: Detyrosinated tubulin alpha-1A chain]
12. Myosin heavy chain 11 smooth muscle isoform
13. Histone H2B
14. 14-3-3 protein zeta/delta (cDNA, FLJ79516, highly similar to 14-3-3 protein zeta/delta)
15. L-lactate dehydrogenase (EC 1.1.1.27) (Fragment)
16. Alpha-enolase (EC 4.2.1.11) (2-phospho-D-glycerate hydro-lyase) (C-myc promoter-binding protein) (Enolase 1) (MBP-1) (MPB-1) (Non-neural enolase) (NNE) (Phosphopyruvate hydratase) (Plasminogen-binding protein)
17. Serine/threonine-protein phosphatase 2B catalytic subunit alpha isoform (EC 3.1.3.16) (CAM-PRP catalytic subunit) (Calmodulin-dependent calcineurin A subunit alpha isoform)
18. Keratin, type I cytoskeletal 16 (Cytokeratin-16) (CK-16) (Keratin-16) (K16)
19. Keratin, type I cytoskeletal 9 (Cytokeratin-9) (CK-9) (Keratin-9) (K9)
20. Copine-6 (Copine VI) (Neuronal-copine) (N-copine)
21. Small proline-rich protein 2E (SPR-2E) (Small proline-rich protein II) (SPR-II)
22. Keratin, type II cytoskeletal 3 (65 kDa cytokeratin) (Cytokeratin-3) (CK-3) (Keratin-3) (K3) (Type-II keratin Kb3)
23. Keratin, type II cytoskeletal 1 (67 kDa cytokeratin) (Cytokeratin-1) (CK-1) (Hair alpha protein) (Keratin-1) (K1) (Type-II keratin Kb1)
24. Breast cancer anti-estrogen resistance protein 1 (CRK-associated substrate) (Cas scaffolding protein family member 1) (p130cas)
25. Inosine-5'-monophosphate dehydrogenase 1 (IMP dehydrogenase 1) (IMPD 1) (IMPDH 1) (EC 1.1.1.205) (IMPDH-I)
26. Prelamin-A/C [Cleaved into: Lamin-A/C (70 kDa lamin) (Renal carcinoma antigen NY-REN-32)]
27. Keratin, type I cytoskeletal 13 (Cytokeratin-13) (CK-13) (Keratin-13) (K13)
28. Tropomyosin alpha-3 chain (Gamma-tropomyosin) (Tropomyosin-3) (Tropomyosin-5) (hTM5)
29. Keratin, type I cuticular Ha5
30. cDNA FLJ57964, highly similar to Heterogeneous nuclear ribonucleoprotein H'
31. Hemoglobin, epsilon 1
32. Actin, alpha 2, smooth muscle, aorta (Actin, alpha 2, smooth muscle, aorta, isoform CRA_a)
33. Polyadenylate-binding protein (PABP)
34. Keratin, type II cytoskeletal 6A (Cytokeratin-6A) (CK-6A) (Cytokeratin-6D) (CK-6D) (Keratin-6A) (K6A) (Type-II keratin Kb6) (allergen Hom s 5)
35. Probable ATP-dependent RNA helicase DDX17
36. cDNA FLJ54552, highly similar to Heterogeneous nuclear ribonucleoprotein K
37. Histone 1, H1e (Histone H1e)
38. cDNA FLJ57507, highly similar to Ran-specific GTPase-activating protein
39. Epididymis secretory protein Li 103 (Heat shock 70 kDa protein 1A) (Heat shock 70 kDa protein 1B) (cDNA FLJ75127, highly similar to *Homo sapiens* heat shock 70 kDa protein 1A, mRNA)
40. Serine/arginine-rich splicing factor 10 (40 kDa SR-repressor protein) (SRrp40) (FUS-interacting serine-arginine-rich protein 1) (Splicing factor SRp38) (Splicing factor, arginine/serine-rich 13A) (TLS-associated protein with Ser-Arg repeats) (TASR) (TLS-associated protein with SR repeats) (TLS-associated serine-arginine protein) (TLS-associated SR protein)
41. Radixin
42. Nuclear pore complex protein Nup214
43. Poly(rC)-binding protein 2 (Alpha-CP2) (Heterogeneous nuclear ribonucleoprotein E2) (hnRNP E2)
44. cDNA FLJ44468 fis, clone UTERU2026025, moderately similar to SPLICING FACTOR, ARGININE/SERINE-RICH 2
45. Keratin, type I cytoskeletal 17

46. Phosphoglycerate kinase 1 (EC 2.7.2.3) (Cell migration-inducing gene 10 protein) (Primer recognition protein 2) (PRP 2)
47. Pyruvate kinase PKM (EC 2.7.1.40) (Cytosolic thyroid hormone-binding protein) (CTHBP) (Opa-interacting protein 3) (OIP-3) (Pyruvate kinase 2/3) (Pyruvate kinase muscle isozyme) (Thyroid hormone-binding protein 1) (THBP1) (Tumor M2-PK) (p58)
48. Heat shock protein HSP 90-beta (HSP 90) (Heat shock 84 kDa) (HSP 84) (HSP84)
49. Lactotransferrin (Lactoferrin) (EC 3.4.21.—) (Growth-inhibiting protein 12) (Talalactoferrin) [Cleaved into: Lactoferricin-H (Lfcin-H); Kaliocin-1; Lactoferroxin-A; Lactoferroxin-B; Lactoferroxin-C]
50. Eukaryotic translation initiation factor 5A (eIF-5A) (Fragment)
51. Heat shock 70 kDa protein 1-like (Heat shock 70 kDa protein 1L) (Heat shock 70 kDa protein 1-Hom) (HSP70-Hom)
52. Tubulin beta-4B chain (Tubulin beta-2 chain) (Tubulin beta-2C chain)
53. Ig lambda-7 chain C region
54. 60S ribosomal protein L8
55. Heat shock cognate 71 kDa protein (Heat shock 70 kDa protein 8) (Lipopolysaccharide-associated protein 1) (LAP-1) (LPS-associated protein 1)
56. Splicing factor, proline- and glutamine-rich (100 kDa DNA-pairing protein) (hPOMp100) (DNA-binding p52/p100 complex, 100 kDa subunit) (Polypyrimidine tract-binding protein-associated-splicing factor) (PSF) (PTB-associated-splicing factor)
57. Elongation factor 1-alpha 1 (EF-1-alpha-1) (Elongation factor Tu) (EF-Tu) (Eukaryotic elongation factor 1 A-1) (eEF1A-1) (Leukocyte receptor cluster member 7)
58. Vimentin (Vimentin variant 3)
59. Hemoglobin, gamma A
60. Protein mago nashi homolog 2
61. Heterogeneous nuclear ribonucleoprotein A3, isoform CRA_a (cDNA FLJ52659, highly similar to Heterogeneous nuclear ribonucleoprotein A3) (cDNA, FLJ79333, highly similar to Heterogeneous nuclear ribonucleoprotein A3)
62. Junction plakoglobin (Catenin gamma) (Desmoplakin III) (Desmoplakin-3)
63. Heterogeneous nuclear ribonucleoproteins C1/C2 (hnRNP C1/C2)
64. Nuclear factor of activated T-cells, cytoplasmic 2 (NF-ATc2) (NFATc2) (NFAT pre-existing subunit) (NF-ATp) (T-cell transcription factor NFAT1)
65. Eukaryotic initiation factor 4A-II
66. T-complex protein 1 subunit gamma (TCP-1-gamma) (CCT-gamma) (hTRiC5)
67. Trypsin-3 (Fragment)
68. Acidic leucine-rich nuclear phosphoprotein 32 family member A
69. cDNA FLJ50692, highly similar to RAD51-associated protein 1 (cDNA, FLJ79266, highly similar to RAD51-associated protein 1)
70. Keratin, type I cytoskeletal 14 (Cytokeratin-14) (CK-14) (Keratin-14) (K14)
71. Keratin, type I cytoskeletal 17 (39.1) (Cytokeratin-17) (CK-17) (Keratin-17) (K17)
72. cDNA FLJ59335, highly similar to Transmembrane glycoprotein NMB
73. Histone-lysine N-methyltransferase NSD2 (EC 2.1.1.43) (Multiple myeloma SET domain-containing protein) (MMSET) (Nuclear SET domain-containing protein 2) (NSD2) (Protein trithorax-5) (Wolf-Hirschhorn syndrome candidate 1 protein) (WHSC1)
74. Elongation factor 2 (EF-2)
75. Glutathione S-transferase omega-1 (GSTO-1) (EC 2.5.1.18) (Glutathione S-transferase omega 1-1) (GSTO 1-1) (Glutathione-dependent dehydroascorbate reductase) (EC 1.8.5.1) (Monomethylarsonic acid reductase) (MMA(V) reductase) (EC 1.20.4.2) (S-(Phenacyl)glutathione reductase) (SPG-R)
76. 60S ribosomal protein L7a (PLA-X polypeptide) (Surfeit locus protein 3)
77. Calmodulin 1 (Phosphorylase kinase, delta), isoform CRA_a (Calmodulin 3 (Phosphorylase kinase, delta), isoform CRA_b) (Epididymis secretory protein Li 72) (cDNA FLJ61744, highly similar to Calmodulin)
78. Pyruvate kinase
79. Glyceraldehyde-3-phosphate dehydrogenase (GAPDH) (EC 1.2.1.12) (Peptidyl-cysteine S-nitrosylase GAPDH) (EC 2.6.99.—)
80. RNA-binding motif protein, X chromosome (Glycoprotein p43) (Heterogeneous nuclear ribonucleoprotein G) (hnRNP G) [Cleaved into: RNA-binding motif protein, X chromosome, N-terminally processed]
81. Annexin A2 (Annexin II) (Annexin-2) (Calpactin I heavy chain) (Calpactin-1 heavy chain) (Chromobindin-8) (Lipocortin II) (Placental anticoagulant protein IV) (PAP-IV) (Protein I) (p36)
82. Myosin-6 (Myosin heavy chain 6) (Myosin heavy chain, cardiac muscle alpha isoform) (MyHC-alpha)
83. Peptidyl-prolyl cis-trans isomerase A (PPIase A) (EC 5.2.1.8) (Cyclophilin A) (Cyclosporin A-binding protein) (Rotamase A) [Cleaved into: Peptidyl-prolyl cis-trans isomerase A, N-terminally processed]
84. Spectrin beta chain, erythrocytic (Beta-I spectrin)
85. Elongation factor 1-gamma (EF-1-gamma) (eEF-1B gamma)
86. Heterogeneous nuclear ribonucleoprotein A1 (hnRNP A1) (Helix-destabilizing protein) (Single-strand RNA-binding protein) (hnRNP core protein A1) [Cleaved into: Heterogeneous nuclear ribonucleoprotein A1, N-terminally processed]
87. Trypsin-1
88. Ig kappa chain V-III region SIE
89. cDNA FLJ54020, highly similar to Heterogeneous nuclear ribonucleoprotein U
90. Melanoma-associated antigen D4 (MAGE-D4 antigen) (MAGE-E1 antigen)
91. Dermcidin (EC 3.4.—.—) (Preproteolysin) [Cleaved into: Survival-promoting peptide; DCD-1]
92. Nucleophosmin (NPM) (Nucleolar phosphoprotein B23) (Nucleolar protein NO38) (Numatrin)
93. Eukaryotic translation initiation factor 5A-1 (eIF-5A-1) (eIF-5A1) (Eukaryotic initiation factor 5A isoform 1) (eIF-5A) (Rev-binding factor) (eIF-4D)
94. Extracellular matrix protein 1 (Secretory component p85)
95. Keratin, type II cytoskeletal 80 (Cytokeratin-80) (CK-80) (Keratin-80) (K80) (Type-II keratin Kb20)
96. Golgin subfamily B member 1 (372 kDa Golgi complex-associated protein) (GCP372) (Giantin) (Macrogolgin)
97. cDNA FLJ55805, highly similar to Keratin, type II cytoskeletal 4
98. Desmocollin-1 (Cadherin family member 1) (Desmosomal glycoprotein 2/3) (DG2/DG3)
99. 40S ribosomal protein SA
100. Cornifin-B
101. Peroxiredoxin 2, isoform CRA_a (Peroxiredoxin-2)
102. CD70 antigen (CD27 ligand) (CD27-L) (Tumor necrosis factor ligand superfamily member 7) (CD antigen CD70)
103. Keratin, type I cytoskeletal 19 (Cytokeratin-19) (CK-19) (Keratin-19) (K19)
104. Uncharacterized protein C9orf114
105. Serpin B4 (Fragment)
106. Peroxiredoxin-1 (EC 1.11.1.15) (Natural killer cell-enhancing factor A) (NKEF-A) (Proliferation-associated gene protein) (PAG) (Thioredoxin peroxidase 2) (Thioredoxin-dependent peroxide reductase 2)
107. Nascent polypeptide-associated complex subunit alpha (NAC-alpha) (Alpha-NAC) (allergen Hom s 2)

108. Corneodesmosin
109. Arginase-1 (EC 3.5.3.1) (Liver-type arginase) (Type I arginase)
110. Myeloperoxidase (MPO) (EC 1.11.2.2) [Cleaved into: Myeloperoxidase; 89 kDa myeloperoxidase; 84 kDa myeloperoxidase; Myeloperoxidase light chain; Myeloperoxidase heavy chain]
111. cDNA FLJ52243, highly similar to Heat-shock protein beta-1
112. NADH dehydrogenase [ubiquinone] iron-sulfur protein 3, mitochondrial (EC 1.6.5.3) (EC 1.6.99.3) (Complex I-30 kD) (CI-30 kD) (NADH-ubiquinone oxidoreductase 30 kDa subunit)
113. Ubiquitin-conjugating enzyme E2 L3 (EC 2.3.2.23) (E2 ubiquitin-conjugating enzyme L3) (L-UBC) (UbcH7) (Ubiquitin carrier protein L3) (Ubiquitin-conjugating enzyme E2-F1) (Ubiquitin-protein ligase L3)
114. Fermitin family homolog 3 (Fragment)
115. cDNA FLJ50994, moderately similar to 60S ribosomal protein L4
116. Tubulin alpha-1B chain (Alpha-tubulin ubiquitous) (Tubulin K-alpha-1) (Tubulin alpha-ubiquitous chain) [Cleaved into: Detyrosinated tubulin alpha-1B chain]
117. Glyceraldehyde-3-phosphate dehydrogenase
118. Ig gamma-1 chain C region
119. Protocadherin Fat 4 (hFat4) (Cadherin family member 14) (FAT tumor suppressor homolog 4) (Fat-like cadherin protein FAT-J)
120. Ig lambda-2 chain C regions
121. Desmoplakin (DP) (250/210 kDa paraneoplastic pemphigus antigen)
122. Keratin, type II cytoskeletal 5 (58 kDa cytokeratin) (Cytokeratin-5) (CK-5) (Keratin-5) (K5) (Type-II keratin Kb5)
123. Mineralocorticoid receptor (Mineralocorticoid receptor 3) (Nuclear receptor subfamily 3, group C, member 2 variant 4)
124. Plakophilin-1 (Band 6 protein) (B6P)
125. Caspase 14, apoptosis-related cysteine peptidase (Caspase-14) (cDNA, FLJ94644, *Homo sapiens* caspase 14, apoptosis-related cysteine protease(CASP14), mRNA)
126. Keratin, type II cytoskeletal 6B (Cytokeratin-6B) (CK-6B) (Keratin-6B) (K6B) (Type-II keratin Kb10)
127. OTU domain-containing protein 4 (EC 3.4.19.12) (HIV-1-induced protein HIN-1)
128. Proteasome subunit alpha type-3 (EC 3.4.25.1) (Macropain subunit C8) (Multicatalytic endopeptidase complex subunit C8) (Proteasome component C8)
129. Heat shock protein 75 kDa, mitochondrial (HSP 75) (TNFR-associated protein 1) (Tumor necrosis factor type 1 receptor-associated protein) (TRAP-1)
130. Programmed cell death 6-interacting protein (PDCD6-interacting protein) (ALG-2-interacting protein 1) (ALG-2-interacting protein X) (Hp95)
131. Kinase suppressor of Ras 2
132. THO complex subunit 4
133. Rho-related GTP-binding protein RhoG
134. Heterogeneous nuclear ribonucleoproteins A2/B1 (hnRNP A2/B1)
135. Keratin, type II cytoskeletal 1b (Cytokeratin-1B) (CK-1B) (Keratin-77) (K77) (Type-II keratin Kb39)
136. Ig alpha-1 chain C region
137. Cytoplasmic dynein 2 heavy chain 1 (Cytoplasmic dynein 2 heavy chain) (Dynein cytoplasmic heavy chain 2) (Dynein heavy chain 11) (hDHC11) (Dynein heavy chain isotype 1B)
138. Desmocollin-3 (Cadherin family member 3) (Desmocollin-4) (HT-CP)
139. Histone H4
140. Keratin, type II cytoskeletal 78 (Cytokeratin-78) (CK-78) (Keratin-5b) (Keratin-78) (K78) (Type-II keratin Kb40)
141. DC-STAMP domain-containing protein 2
142. Serpin B12
143. Insulin receptor (IR) (EC 2.7.10.1) (CD antigen CD220) [Cleaved into: Insulin receptor subunit alpha; Insulin receptor subunit beta]
144. Nucleolar RNA helicase 2 (EC 3.6.4.13) (DEAD box protein 21) (Gu-alpha) (Nucleolar RNA helicase Gu) (Nucleolar RNA helicase II) (RH II/Gu)
145. T-complex protein 1 subunit delta (TCP-1-delta) (CCT-delta) (Stimulator of TAR RNA-binding)
146. Neuroblastoma-amplified sequence (Neuroblastoma-amplified gene protein)
147. Voltage-dependent R-type calcium channel subunit alpha-1E (Brain calcium channel II) (BII) (Calcium channel, L type, alpha-1 polypeptide, isoform 6) (Voltage-gated calcium channel subunit alpha Cav2.3)
148. Cas scaffolding protein family member 4 (HEF-like protein) (HEF1-EFS-p130Cas-like protein) (HEPL)
149. Malate dehydrogenase, mitochondrial (EC 1.1.1.37)
150. Lipocalin-1 (Tear lipocalin) (Tlc) (Tear prealbumin) (TP) (Von Ebner gland protein) (VEG protein)
151. C-type lysozyme (Lysozyme) (EC 3.2.1.17) (Lysozyme (Renal amyloidosis), isoform CRA_a) (Lysozyme F1) (cDNA, FLJ92040, *Homo sapiens* lysozyme (renal amyloidosis) (LYZ), mRNA)
152. Immunoglobulin heavy variable 3-13 (Ig heavy chain V-III region BRO)
153. Superoxide dismutase 1, soluble
154. Chloride intracellular channel protein 1 (Chloride channel ABP) (Nuclear chloride ion channel 27) (NCC27) (Regulatory nuclear chloride ion channel protein) (hRNCC)
155. WD repeat domain phosphoinositide-interacting protein 2 (WIPI-2) (WIPI49-like protein 2)
156. Inorganic pyrophosphatase (EC 3.6.1.1) (Pyrophosphate phospho-hydrolase) (PPase)
157. Cystatin-A (Cystatin-AS) (Stefin-A) [Cleaved into: Cystatin-A, N-terminally processed]
158. Heat shock protein HSP 90-alpha (Heat shock 86 kDa) (HSP 86) (HSP86) (Lipopolysaccharide-associated protein 2) (LAP-2) (LPS-associated protein 2) (Renal carcinoma antigen NY-REN-38)
159. T-complex protein 1 subunit zeta (TCP-1-zeta) (Acute morphine dependence-related protein 2) (CCT-zeta-1) (HTR3) (Tcp20)
160. ATP-dependent RNA helicase A
161. Probable ATP-dependent RNA helicase DDX5 (EC 3.6.4.13) (DEAD box protein 5) (RNA helicase p68)
162. Protein phosphatase 1, regulatory subunit 15A
163. FB19 protein (Protein phosphatase 1, regulatory (Inhibitor) subunit 10) (Protein phosphatase 1, regulatory subunit 10) (Testis tissue sperm-binding protein Li 67n)
164. Stress-induced-phosphoprotein 1 (STI1) (Hsc70/Hsp90-organizing protein) (Hop) (Renal carcinoma antigen NY-REN-11) (Transformation-sensitive protein IEF SSP 3521)
165. Bleomycin hydrolase
166. Heterogeneous nuclear ribonucleoprotein M (hnRNP M)
167. Transcription factor Spi-B
168. Creatine kinase B-type
169. T-complex protein 1 subunit beta
170. Serine/threonine-protein kinase PRP4 homolog -continued 171. Transgelin-2 (Epididymis tissue protein Li 7e) (SM22-alpha homolog)
172. Lysine-specific demethylase 2A (EC 1.14.11.27) (CXXC-type zinc finger protein 8) (F-box and leucine-rich repeat protein 11) (F-box protein FBL7) (F-box protein Lilina) (F-box/LRR-repeat protein 11) (JmjC domain-containing histone demethylation protein 1A) ([Histone-H3]-lysine-36 demethylase 1A)
173. Hornerin
174. Frizzled-3 (Fz-3) (hFz3)
175. Keratinocyte proline-rich protein (hKPRP)
176. Desmoglein-1 (Cadherin family member 4) (Desmosomal glycoprotein 1) (DG1) (DGI) (Pemphigus foliaceus antigen)
177. Peptidyl-prolyl cis-trans isomerase A
178. CRISPR-associated endonuclease Cas9/Csn1 (EC 3.1.—.—) (SpCas9) (SpyCas9)
179. Condensin complex subunit 3 (Chromosome-associated protein G) (Condensin subunit CAP-G) (hCAP-G) (Melanoma antigen NY-MEL-3) (Non-SMC condensin I complex subunit G) (XCAP-G homolog)
180. Fructose-bisphosphate aldolase A (EC 4.1.2.13) (Lung cancer antigen NY-LU-1) (Muscle-type aldolase)
181. Cleavage stimulation factor subunit 3
182. Putative uncharacterized protein LOC152225
183. Filaggrin
184. Prolactin-inducible protein (Gross cystic disease fluid protein 15) (GCDFP-15) (Prolactin-induced protein) (Secretory actin-binding protein) (SABP) (gp17)
185. Protein MAK16 homolog (NNP78) (Protein RBM13)
186. Protein deglycase DJ-1 (DJ-1) (EC 3.1.2.—) (EC 3.5.1.—) (Oncogene DJ1) (Parkinson disease protein 7)
187. 60S ribosomal protein L6 (Neoplasm-related protein C140) (Tax-responsive enhancer element-binding protein 107) (TaxREB107)
188. Complement component C8 alpha chain (Complement component 8 subunit alpha)
189. Histone H1.5 (Histone H1a) (Histone H1b) (Histone H1s-3)
190. Eukaryotic initiation factor 4A-III (eIF-4A-III) (eIF4A-III) (EC 3.6.4.13) (ATP-dependent RNA helicase DDX48) (ATP-dependent RNA helicase eIF4A-3) (DEAD box protein 48) (Eukaryotic initiation factor 4A-like NUK-34) (Eukaryotic translation initiation factor 4A isoform 3) (Nuclear matrix protein 265) (NMP 265) (hNMP 265) [Cleaved into: Eukaryotic initiation factor 4A-III, N-terminally processed]
191. Survival of motor neuron-related-splicing factor 30 (30 kDa splicing factor SMNrp) (SMN-related protein) (Survival motor neuron domain-containing protein 1)
192. 40S ribosomal protein S5 [Cleaved into: 40S ribosomal protein S5, N-terminally processed]
193. Catalase (EC 1.11.1.6)
194. Beta-1,3-galactosyl-O-glycosyl-glycoprotein beta-1,6-N-acetylglucosaminyltransferase 4 (EC 2.4.1.102) (Core 2-branching enzyme 3) (Core2-GlcNAc-transferase 3) (C2GnT3)
195. 60S ribosomal protein L35a (Cell growth-inhibiting gene 33 protein)
196. Secretoglobin family 1D member 2 (Lipophilin-B)
197. Protein-glutamine gamma-glutamyltransferase K (EC 2.3.2.13) (Epidermal TGase) (Transglutaminase K) (TG(K)) (TGK) (TGase K) (Transglutaminase-1) (TGase-1)
198. Src-like-adapter (Fragment)
199. Polymeric immunoglobulin receptor (PIgR) (Poly-Ig receptor) (Hepatocellular carcinoma-associated protein TB6) [Cleaved into: Secretory component]
200. Cation-independent mannose-6-phosphate receptor (CI Man-6-P receptor) (CI-MPR) (M6PR) (300 kDa mannose 6-phosphate receptor) (MPR 300) (Insulin-like growth factor 2 receptor) (Insulin-like growth factor II receptor) (IGF-II receptor) (M6P/IGF2 receptor) (M6P/IGF2R) (CD antigen CD222)
201. Protocadherin-16 (Cadherin-19) (Cadherin-25) (Fibroblast cadherin-1) (Protein dachsous homolog 1)
202. Arachidonate 12-lipoxygenase, 12R-type (12R-LOX) (12R-lipoxygenase) (EC 1.13.11.—) (Epidermis-type lipoxygenase 12)
203. Skin-specific protein 32
204. 60S ribosomal protein L7
205. Prostasin (EC 3.4.21.—) (Channel-activating protease 1) (CAP1) (Serine protease 8) [Cleaved into: Prostasin light chain; Prostasin heavy chain]
206. T-complex protein 1 subunit theta (TCP-1-theta) (CCT-theta) (Renal carcinoma antigen NY-REN-15)
207. 60S ribosomal protein L12
208. Eukaryotic translation initiation factor 5B (eIF-5B) (EC 3.6.5.3) (Translation initiation factor IF-2)
209. Cathepsin D (EC 3.4.23.5) [Cleaved into: Cathepsin D light chain; Cathepsin D heavy chain]
210. Hemoglobin subunit zeta (HBAZ) (Hemoglobin zeta chain) (Zeta-globin)
211. Protein S100-A8 (Calgranulin-A) (Calprotectin L1L subunit) (Cystic fibrosis antigen) (CFAG) (Leukocyte L1 complex light chain) (Migration inhibitory factor-related protein 8) (MRP-8) (p8) (S100 calcium-binding protein A8) (Urinary stone protein band A) [Cleaved into: Protein S100-A8, N-terminally processed]
212. Mucin-like protein 1 (Protein BS106) (Small breast epithelial mucin)
213. Signal peptidase complex subunit 2
214. Iodotyrosine deiodinase 1 (IYD-1) (EC 1.21.1.1) (Iodotyrosine dehalogenase 1)
215. Ferric-chelate reductase 1 (EC 1.—.—.—) (Stromal cell-derived receptor 2) (SDR-2)
216. Protein-glutamine gamma-glutamyltransferase E (EC 2.3.2.13) (Transglutaminase E) (TG(E)) (TGE) (TGase E) (Transglutaminase-3) (TGase-3) [Cleaved into: Protein-glutamine gamma-glutamyltransferase E 50 kDa catalytic chain; Protein-glutamine gamma-glutamyltransferase E 27 kDa non-catalytic chain]
217. NADH dehydrogenase [ubiquinone] iron-sulfur protein 2, mitochondrial (EC 1.6.5.3) (EC 1.6.99.3) (Complex I-49 kD) (CI-49 kD) (NADH-ubiquinone oxidoreductase 49 kDa subunit)
218. Enhancer of rudimentary homolog
219. Uncharacterized protein C7orf72
220. BPI fold-containing family B member 1 (Long palate, lung and nasal epithelium carcinoma-associated protein 1) (Von Ebner minor salivary gland protein) (VEMSGP)
221. Putative insulin-like growth factor 2 antisense gene protein (IGF2 antisense RNA 1) (IGF2 antisense gene protein 1) (PEG8/IGF2AS protein) (Putative insulin-like growth factor 2 antisense gene protein 1) (IGF2-AS1)
222. Conserved oligomeric Golgi complex subunit 7 (COG complex subunit 7) (Component of oligomeric Golgi complex 7)
223. Mammaglobin-B (Lacryglobin) (Lipophilin-C) (Mammaglobin-2) (Secretoglobin family 2A member 1)
224. Uncharacterized protein C17orf96
225. Ras association domain-containing protein 2
226. Heat shock protein beta-1 (HspB1) (28 kDa heat shock protein) (Estrogen-regulated 24 kDa protein) (Heat shock 27 kDa protein) (HSP 27) (Stress-responsive protein 27) (SRP27)
227. Kelch-like protein 1

-continued

228. ATP synthase subunit beta, mitochondrial (EC 3.6.3.14)
229. Protein S100-A7 (Psoriasin) (S100 calcium-binding protein A7)
230. 40S ribosomal protein S13
231. Calmodulin-like protein 5 (Calmodulin-like skin protein)
232. Peroxiredoxin-6 (EC 1.11.1.15) (1-Cys peroxiredoxin) (1-Cys PRX) (24 kDa protein) (Acidic calcium-independent phospholipase A2) (aiPLA2) (EC 3.1.1.—) (Antioxidant protein 2) (Liver 2D page spot 40) (Non-selenium glutathione peroxidase) (NSGPx) (EC 1.11.1.9) (Red blood cells page spot 12)
233. Immunoglobulin heavy variable 3-33 (Ig heavy chain V-III region HIL) (Ig heavy chain V-III region KOL)
234. Eukaryotic translation initiation factor 6 (eIF-6) (B(2)GCN homolog) (B4 integrin interactor) (CAB) (p27(BBP))
235. Proteasome subunit alpha type-4 (EC 3.4.25.1) (Macropain subunit C9) (Multicatalytic endopeptidase complex subunit C9) (Proteasome component C9) (Proteasome subunit L)
236. Eosinophil cationic protein (ECP) (EC 3.1.27.—) (Ribonuclease 3) (RNase 3)
237. Latent-transforming growth factor beta-binding protein 2 (LTBP-2)
238. Cystatin-SN (Cystain-SA-I) (Cystatin-1) (Salivary cystatin-SA-1)
239. 60S ribosomal protein L18
240. Probable ATP-dependent RNA helicase DDX6 (EC 3.6.4.13) (ATP-dependent RNA helicase p54) (DEAD box protein 6) (Oncogene RCK)
241. Filaggrin-2 (FLG-2) (Intermediate filament-associated and psoriasis-susceptibility protein) (Ifapsoriasin)
242. Protein S100-A14 (S100 calcium-binding protein A14) (S114)
243. Kelch-like protein 11

20

Table 5 Shows Data for Peptide Identification by MS for 10 Day Dimerized Sample

1. CRISPR-associated endonuclease Cas9/Csn1 (EC 3.1.—.—) (SpCas9) (SpyCas9)
2. >sp|A6NKO7|IF2BL_HUMAN Eukaryotic translation initiation factor 2 subunit 2-like protein OS = Homo sapiens PE = 1 SV = 1
3. >sp|J7RUA5|CAS9_STAAU CRISPR-associated endonuclease Cas9 OS = Staphylococcus aureus GN = cas9 PE = 1 SV = 1
4. >sp|O00151|PDLI1_HUMAN PDZ and LIM domain protein 1 OS = Homo sapiens GN = PDLIM1 PE = 1 SV = 4
5. >sp|O00231|PSD11_HUMAN 26S proteasome non-ATPase regulatory subunit 11 OS = Homo sapiens GN = PSMD11 PE = 1 SV = 3
6. >sp|O00299|CLIC1_HUMAN Chloride intracellular channel protein 1 OS = Homo sapiens GN = CLIC1 PE = 1 SV = 4
7. >sp|O00410|IPO5_HUMAN Importin-5 OS = Homo sapiens GN = IPO5 PE = 1 SV = 4
8. >sp|O00422|SAP18_HUMAN Histone deacetylase complex subunit SAP18 OS = Homo sapiens GN = SAP18 PE = 1 SV = 1
9. >sp|O00425|IF2B3_HUMAN Insulin-like growth factor 2 mRNA-binding protein 3 OS = Homo sapiens GN = IGF2BP3 PE = 1 SV = 2
10. >sp|O00571|DDX3X_HUMAN ATP-dependent RNA helicase DDX3X OS = Homo sapiens GN = DDX3X PE = 1 SV = 3
11. >sp|O00712|NFIB_HUMAN Nuclear factor 1 B-type OS = Homo sapiens GN = NFIB PE = 1 SV = 2
12. >sp|O15446|RPA34_HUMAN DNA-directed RNA polymerase I subunit RPA34 OS = Homo sapiens GN = CD3EAP PE = 1 SV = 1
13. >sp|O43242|PSMD3_HUMAN 26S proteasome non-ATPase regulatory subunit 3 OS = Homo sapiens GN = PSMD3 PE = 1 SV = 2
14. >sp|O43684|BUB3_HUMAN Mitotic checkpoint protein BUB3 OS = Homo sapiens GN = BUB3 PE = 1 SV = 1
15. >sp|O60506|HNRPQ_HUMAN Heterogeneous nuclear ribonucleoprotein Q OS = Homo sapiens GN = SYNCRIP PE = 1 SV = 2
16. >sp|O60841|IF2P_HUMAN Eukaryotic translation initiation factor 5B OS = Homo sapiens GN = EIF5B PE = 1 SV = 4
17. >sp|O60869|EDF1_HUMAN Endothelial differentiation-related factor 1 OS = Homo sapiens GN = EDF1 PE = 1 SV = 1
18. >sp|O60884|DNJA2_HUMAN DnaJ homolog subfamily A member 2 OS = Homo sapiens GN = DNAJA2 PE = 1 SV = 1
19. >sp|O75306|NDUS2_HUMAN NADH dehydrogenase [ubiquinone] iron-sulfur protein 2, mitochondrial OS = Homo sapiens GN = NDUFS2 PE = 1 SV = 2
20. >sp|O75390|CISY_HUMAN Citrate synthase, mitochondrial OS = Homo sapiens GN = CS PE = 1 SV = 2
21. >sp|O75494|SRS10_HUMAN Serine/arginine-rich splicing factor 10 OS = Homo sapiens GN = SRSF10 PE = 1 SV = 1
22. >sp|O75533|SF3B1_HUMAN Splicing factor 3B subunit 1 OS = Homo sapiens GN = SF3B1 PE = 1 SV = 3
23. >sp|O76094|SRP72_HUMAN Signal recognition particle 72 kDa protein OS = Homo sapiens GN = SRP72 PE = 1 SV = 3
24. >sp|O94826|TOM70_HUMAN Mitochondrial import receptor subunit TOM70 OS = Homo sapiens GN = TOMM70A PE = 1 SV = 1
25. >sp|O95373|IPO7_HUMAN Importin-7 OS = Homo sapiens GN = IPO7 PE = 1 SV = 1
26. >sp|O95816|BAG2_HUMAN BAG family molecular chaperone regulator 2 OS = Homo sapiens GN = BAG2 PE = 1 SV = 1
27. >sp|P01857|IGHG1_HUMAN Ig gamma-1 chain C region OS = Homo sapiens GN = IGHG1 PE = 1 SV = 1
28. >sp|P02008|HBAZ_HUMAN Hemoglobin subunit zeta OS = Homo sapiens GN = HBZ PE = 1 SV = 2
29. >sp|P02533|K1C14_HUMAN Keratin, type I cytoskeletal 14 OS = Homo sapiens GN = KRT14 PE = 1 SV = 4
30. >sp|P02538|K2C6A_HUMAN Keratin, type II cytoskeletal 6A OS = Homo sapiens GN = KRT6A PE = 1 SV = 3
31. >sp|P02545|LMNA_HUMAN Prelamin-A/C OS = Homo sapiens GN = LMNA PE = 1 SV = 1
32. >sp|P04075|ALDOA_HUMAN Fructose-bisphosphate aldolase A OS = Homo sapiens GN = ALDOA PE = 1 SV = 2
33. >sp|P04083|ANXA1_HUMAN Annexin A1 OS = Homo sapiens GN = ANXA1 PE = 1 SV = 2
34. >sp|P04183|KITH_HUMAN Thymidine kinase, cytosolic OS = Homo sapiens GN = TK1 PE = 1 SV = 2
35. >sp|P04264|K2C1_HUMAN Keratin, type II cytoskeletal 1 OS = Homo sapiens GN = KRT1 PE = 1 SV = 6
36. >sp|P05141|ADT2_HUMAN ADP/ATP translocase 2 OS = Homo sapiens GN = SLC25A5 PE = 1 SV = 7
37. >sp|P05387|RLA2_HUMAN 60S acidic ribosomal protein P2 OS = Homo sapiens GN = RPLP2 PE = 1 SV = 1
38. >sp|P05388|RLA0_HUMAN 60S acidic ribosomal protein P0 OS = Homo sapiens GN = RPLP0 PE = 1 SV = 1
39. >sp|P06576|ATPB_HUMAN ATP synthase subunit beta, mitochondrial OS = Homo sapiens GN = ATP5B PE = 1 SV = 3
40. >sp|P06703|S10A6_HUMAN Protein S100-A6 OS = Homo sapiens GN = S100A6 PE = 1 SV = 1
41. >sp|P06733|ENOA_HUMAN Alpha-enolase OS = Homo sapiens GN = ENO1 PE = 1 SV = 2
42. >sp|P06748|NPM_HUMAN Nucleophosmin OS = Homo sapiens GN = NPM1 PE = 1 SV = 2
43. >sp|P06753-2|TPM3_HUMAN Isoform 2 of Tropomyosin alpha-3 chain OS = Homo sapiens GN = TPM3
44. >sp|P06899|H2B1J_HUMAN Histone H2B type 1-J OS = Homo sapiens GN = HIST1H2BJ PE = 1 SV = 3
45. >sp|P07355|ANXA2_HUMAN Annexin A2 OS = Homo sapiens GN = ANXA2 PE = 1 SV = 2
46. >sp|P07737|PROF1_HUMAN Profilin-1 OS = Homo sapiens GN = PFN1 PE = 1 SV = 2
47. >sp|P07900|HS90A_HUMAN Heat shock protein HSP 90-alpha OS = Homo sapiens GN = HSP90AA1 PE = 1 SV = 5
48. >sp|P07910|HNRPC_HUMAN Heterogeneous nuclear ribonucleoproteins C1/C2 OS = Homo sapiens GN = HNRNPC PE = 1 SV = 4
49. >sp|P08238|HS90B_HUMAN Heat shock protein HSP 90-beta OS = Homo sapiens GN = HSP90AB1 PE = 1 SV = 4
50. >sp|P08579|RU2B_HUMAN U2 small nuclear ribonucleoprotein B" OS = Homo sapiens GN = SNRPB2 PE = 1 SV = 1
51. >sp|P08621|RU17_HUMAN U1 small nuclear ribonucleoprotein 70 kDa OS = Homo sapiens GN = SNRNP70 PE = 1 SV = 2

-continued

| | |
|---|---|
| 52. | >sp\|P08670\|VIME_HUMAN Vimentin OS = *Homo sapiens* GN = VIM PE = 1 SV = 4 |
| 53. | >sp\|P08779\|K1C16_HUMAN Keratin, type I cytoskeletal 16 OS = *Homo sapiens* GN = KRT16 PE = 1 SV = 4 |
| 54. | >sp\|P09651\|ROA1_HUMAN Heterogeneous nuclear ribonucleoprotein A1 OS = *Homo sapiens* GN = HNRNPA1 PE = 1 SV = 5 |
| 55. | >sp\|P09874\|PARP1_HUMAN Poly [ADP-ribose] polymerase 1 OS = *Homo sapiens* GN = PARP1 PE = 1 SV = 4 |
| 56. | >sp\|P10515\|ODP2_HUMAN Dihydrolipoyllysine-residue acetyltransferase component of pyruvate dehydrogenase complex, mitochondrial OS = *Homo sapiens* GN = DLAT PE = 1 SV = 3 |
| 57. | >sp\|P10768\|ESTD_HUMAN S-formylglutathione hydrolase OS = *Homo sapiens* GN = ESD PE = 1 SV = 2 |
| 58. | >sp\|P10809\|CH60_HUMAN 60 kDa heat shock protein, mitochondrial OS = *Homo sapiens* GN = HSPD1 PE = 1 SV = 2 |
| 59. | >sp\|P11387\|TOP1_HUMAN DNA topoisomerase 1 OS = *Homo sapiens* GN = TOP1 PE = 1 SV = 2 |
| 60. | >sp\|P12004\|PCNA_HUMAN Proliferating cell nuclear antigen OS = *Homo sapiens* GN = PCNA PE = 1 SV = 1 |
| 61. | >sp\|P12268\|IMDH2_HUMAN Inosine-5'-monophosphate dehydrogenase 2 OS = *Homo sapiens* GN = IMPDH2 PE = 1 SV = 2 |
| 62. | >sp\|P12277\|KCRB_HUMAN Creatine kinase B-type OS = *Homo sapiens* GN = CKB PE = 1 SV = 1 |
| 63. | >sp\|P13010\|XRCC5_HUMAN X-ray repair cross-complementing protein 5 OS = *Homo sapiens* GN = XRCC5 PE = 1 SV = 3 |
| 64. | >sp\|P13639\|EF2_HUMAN Elongation factor 2 OS = *Homo sapiens* GN = EEF2 PE = 1 SV = 4 |
| 65. | >sp\|P13645\|K1C10_HUMAN Keratin, type I cytoskeletal 10 OS = *Homo sapiens* GN = KRT10 PE = 1 SV = 6 |
| 66. | >sp\|P13647\|K2C5_HUMAN Keratin, type II cytoskeletal 5 OS = *Homo sapiens* GN = KRT5 PE = 1 SV = 3 |
| 67. | >sp\|P14625\|ENPL_HUMAN Endoplasmin OS = *Homo sapiens* GN = HSP90B1 PE = 1 SV = 1 |
| 68. | >sp\|P14866\|HNRPL_HUMAN Heterogeneous nuclear ribonucleoprotein L OS = *Homo sapiens* GN = HNRNPL PE = 1 SV = 2 |
| 69. | >sp\|P14868\|SYDC_HUMAN Aspartyl-tRNA synthetase, cytoplasmic OS = *Homo sapiens* GN = DARS PE = 1 SV = 2 |
| 70. | >sp\|P14923\|PLAK_HUMAN Junction plakoglobin OS = *Homo sapiens* GN = JUP PE = 1 SV = 3 |
| 71. | >sp\|P15880\|RS2_HUMAN 40S ribosomal protein S2 OS = *Homo sapiens* GN = RPS2 PE = 1 SV = 2 |
| 72. | >sp\|P15924\|DESP_HUMAN Desmoplakin OS = *Homo sapiens* GN = DSP PE = 1 SV = 3 |
| 73. | >sp\|P16401\|H15_HUMAN Histone H1.5 OS = *Homo sapiens* GN = HIST1H1B PE = 1 SV = 3 |
| 74. | >sp\|P16402\|H13_HUMAN Histone H1.3 OS = *Homo sapiens* GN = HIST1H1D PE = 1 SV = 2 |
| 75. | >sp\|P16949\|STMN1_HUMAN Stathmin OS = *Homo sapiens* GN = STMN1 PE = 1 SV = 3 |
| 76. | >sp\|P16989\|DBPA_HUMAN DNA-binding protein A OS = *Homo sapiens* GN = CSDA PE = 1 SV = 4 |
| 77. | >sp\|P17066\|HSP76_HUMAN Heat shock 70 kDa protein 6 OS = *Homo sapiens* GN = HSPA6 PE = 1 SV = 2 |
| 78. | >sp\|P18124\|RL7_HUMAN 60S ribosomal protein L7 OS = *Homo sapiens* GN = RPL7 PE = 1 SV = 1 |
| 79. | >sp\|P18206\|VINC_HUMAN Vinculin OS = *Homo sapiens* GN = VCL PE = 1 SV = 4 |
| 80. | >sp\|P18621\|RL17_HUMAN 60S ribosomal protein L17 OS = *Homo sapiens* GN = RPL17 PE = 1 SV = 3 |
| 81. | >sp\|P19338\|NUCL_HUMAN Nucleolin OS = *Homo sapiens* GN = NCL PE = 1 SV = 3 |
| 82. | >sp\|P20073\|ANXA7_HUMAN Annexin A7 OS = *Homo sapiens* GN = ANXA7 PE = 1 SV = 3 |
| 83. | >sp\|P20671\|H2A1D_HUMAN Histone H2A type 1-D OS = *Homo sapiens* GN = HIST1H2AD PE = 1 SV = 2 |
| 84. | >sp\|P20700\|LMNB1_HUMAN Lamin-B1 OS = *Homo sapiens* GN = LMNB1 PE = 1 SV = 2 |
| 85. | >sp\|P22626\|ROA2_HUMAN Heterogeneous nuclear ribonucleoproteins A2/B1 OS = *Homo sapiens* GN = HNRNPA2B1 PE = 1 SV = 2 |
| 86. | >sp\|P23246\|SFPQ_HUMAN Splicing factor, proline- and glutamine-rich OS = *Homo sapiens* GN = SFPQ PE = 1 SV = 2 |
| 87. | >sp\|P23284\|PPIB_HUMAN Peptidyl-prolyl cis-trans isomerase B OS = *Homo sapiens* GN = PPIB PE = 1 SV = 2 |
| 88. | >sp\|P23381\|SYWC_HUMAN Tryptophanyl-tRNA synthetase, cytoplasmic OS = *Homo sapiens* GN = WARS PE = 1 SV = 2 |
| 89. | >sp\|P24534\|EF1B_HUMAN Elongation factor 1-beta OS = *Homo sapiens* GN = EEF1B2 PE = 1 SV = 3 |
| 90. | >sp\|P24539\|AT5F1_HUMAN ATP synthase subunit b, mitochondrial OS = *Homo sapiens* GN = ATP5F1 PE = 1 SV = 2 |
| 91. | >sp\|P25398\|RS12_HUMAN 40S ribosomal protein S12 OS = *Homo sapiens* GN = RPS12 PE = 1 SV = 3 |
| 92. | >sp\|P25705\|ATPA_HUMAN ATP synthase subunit alpha, mitochondrial OS = *Homo sapiens* GN = ATP5A1 PE = 1 SV = 1 |
| 93. | >sp\|P25788\|PSA3_HUMAN Proteasome subunit alpha type-3 OS = *Homo sapiens* GN = PSMA3 PE = 1 SV = 2 |
| 94. | >sp\|P25789\|PSA4_HUMAN Proteasome subunit alpha type-4 OS = *Homo sapiens* GN = PSMA4 PE = 1 SV = 1 |
| 95. | >sp\|P26038\|MOES_HUMAN Moesin OS = *Homo sapiens* GN = MSN PE = 1 SV = 3 |
| 96. | >sp\|P26196\|DDX6_HUMAN Probable ATP-dependent RNA helicase DDX6 OS = *Homo sapiens* GN = DDX6 PE = 1 SV = 2 |
| 97. | >sp\|P26368\|U2AF2_HUMAN Splicing factor U2AF 65 kDa subunit OS = *Homo sapiens* GN = U2AF2 PE = 1 SV = 4 |
| 98. | >sp\|P26583\|HMGB2_HUMAN High mobility group protein B2 OS = *Homo sapiens* GN = HMGB2 PE = 1 SV = 2 |
| 99. | >sp\|P28066\|PSA5_HUMAN Proteasome subunit alpha type-5 OS = *Homo sapiens* GN = PSMA5 PE = 1 SV = 3 |
| 100. | >sp\|P30041\|PRDX6_HUMAN Peroxiredoxin-6 OS = *Homo sapiens* GN = PRDX6 PE = 1 SV = 3 |
| 101. | >sp\|P30043\|BLVRB_HUMAN Flavin reductase OS = *Homo sapiens* GN = BLVRB PE = 1 SV = 3 |
| 102. | >sp\|P30050\|RL12_HUMAN 60S ribosomal protein L12 OS = *Homo sapiens* GN = RPL12 PE = 1 SV = 1 |
| 103. | >sp\|P30101\|PDIA3_HUMAN Protein disulfide-isomerase A3 OS = *Homo sapiens* GN = PDIA3 PE = 1 SV = 4 |
| 104. | >sp\|P30419\|NMT1_HUMAN Glycylpeptide N-tetradecanoyltransferase 1 OS = *Homo sapiens* GN = NMT1 PE = 1 SV = 2 |
| 105. | >sp\|P31689\|DNJA1_HUMAN DnaJ homolog subfamily A member 1 OS = *Homo sapiens* GN = DNAJA1 PE = 1 SV = 2 |
| 106. | >sp\|P31930\|QCR1_HUMAN Cytochrome b-c1 complex subunit 1, mitochondrial OS = *Homo sapiens* GN = UQCRC1 PE = 1 SV = 3 |
| 107. | >sp\|P31946\|1433B_HUMAN 14-3-3 protein beta/alpha OS = *Homo sapiens* GN = YWHAB PE = 1 SV = 3 |
| 108. | >sp\|P31947\|1433S_HUMAN 14-3-3 protein sigma OS = *Homo sapiens* GN = SFN PE = 1 SV = 1 |
| 109. | >sp\|P31948\|STIP1_HUMAN Stress-induced-phosphoprotein 1 OS = *Homo sapiens* GN = STIP1 PE = 1 SV = 1 |
| 110. | >sp\|P32119\|PRDX2_HUMAN Peroxiredoxin-2 OS = *Homo sapiens* GN = PRDX2 PE = 1 SV = 5 |
| 111. | >sp\|P33991\|MCM4_HUMAN DNA replication licensing factor MCM4 OS = *Homo sapiens* GN = MCM4 PE = 1 SV = 5 |
| 112. | >sp\|P33993\|MCM7_HUMAN DNA replication licensing factor MCM7 OS = *Homo sapiens* GN = MCM7 PE = 1 SV = 4 |
| 113. | >sp\|P34932\|HSP74_HUMAN Heat shock 70 kDa protein 4 OS = *Homo sapiens* GN = HSPA4 PE = 1 SV = 4 |
| 114. | >sp\|P35268\|RL22_HUMAN 60S ribosomal protein L22 OS = *Homo sapiens* GN = RPL22 PE = 1 SV = 2 |
| 115. | >sp\|P35527\|K1C9_HUMAN Keratin, type I cytoskeletal 9 OS = *Homo sapiens* GN = KRT9 PE = 1 SV = 3 |
| 116. | >sp\|P35908\|K22E_HUMAN Keratin, type II cytoskeletal 2 epidermal OS = *Homo sapiens* GN = KRT2 PE = 1 SV = 2 |
| 117. | >sp\|P35998\|PRS7_HUMAN 26S protease regulatory subunit 7 OS = *Homo sapiens* GN = PSMC2 PE = 1 SV = 3 |
| 118. | >sp\|P37108\|SRP14_HUMAN Signal recognition particle 14 kDa protein OS = *Homo sapiens* GN = SRP14 PE = 1 SV = 2 |
| 119. | >sp\|P38159\|HNRPG_HUMAN Heterogeneous nuclear ribonucleoprotein G OS = *Homo sapiens* GN = RBMX PE = 1 SV = 3 |
| 120. | >sp\|P38646\|GRP75_HUMAN Stress-70 protein, mitochondrial OS = *Homo sapiens* GN = HSPA9 PE = 1 SV = 2 |
| 121. | >sp\|P38919\|IF4A3_HUMAN Eukaryotic initiation factor 4A-III OS = *Homo sapiens* GN = EIF4A3 PE = 1 SV = 4 |
| 122. | >sp\|P40227\|TCPZ_HUMAN T-complex protein 1 subunit zeta OS = *Homo sapiens* GN = CCT6A PE = 1 SV = 3 |
| 123. | >sp\|P40429\|RL13A_HUMAN 60S ribosomal protein L13a OS = *Homo sapiens* GN = RPL13A PE = 1 SV = 2 |
| 124. | >sp\|P41250\|SYG_HUMAN Glycyl-tRNA synthetase OS = *Homo sapiens* GN = GARS PE = 1 SV = 3 |
| 125. | >sp\|P42166\|LAP2A_HUMAN Lamina-associated polypeptide 2, isoform alpha OS = *Homo sapiens* GN = TMPO PE = 1 SV = 2 |
| 126. | >sp\|P42677\|RS27_HUMAN 40S ribosomal protein S27 OS = *Homo sapiens* GN = RPS27 PE = 1 SV = 3 |
| 127. | >sp\|P42766\|RL35_HUMAN 60S ribosomal protein L35 OS = *Homo sapiens* GN = RPL35 PE = 1 SV = 2 |
| 128. | >sp\|P45880\|VDAC2_HUMAN Voltage-dependent anion-selective channel protein 2 OS = *Homo sapiens* GN = VDAC2 PE = 1 SV = 2 |
| 129. | >sp\|P46778\|RL21_HUMAN 60S ribosomal protein L21 OS = *Homo sapiens* GN = RPL21 PE = 1 SV = 2 |

-continued

| | |
|---|---|
| 130. | >sp|P46782|RS5_HUMAN 40S ribosomal protein S5 OS = *Homo sapiens* GN = RPS5 PE = 1 SV = 4 |
| 131. | >sp|P46783|RS10_HUMAN 40S ribosomal protein S10 OS = *Homo sapiens* GN = RPS10 PE = 1 SV = 1 |
| 132. | >sp|P47914|RL29_HUMAN 60S ribosomal protein L29 OS = *Homo sapiens* GN = RPL29 PE = 1 SV = 2 |
| 133. | >sp|P49207|RL34_HUMAN 60S ribosomal protein L34 OS = *Homo sapiens* GN = RPL34 PE = 1 SV = 3 |
| 134. | >sp|P49327|FAS_HUMAN Fatty acid synthase OS = *Homo sapiens* GN = FASN PE = 1 SV = 3 |
| 135. | >sp|P49411|EFTU_HUMAN Elongation factor Tu, mitochondrial OS = *Homo sapiens* GN = TUFM PE = 1 SV = 2 |
| 136. | >sp|P50990|TCPQ_HUMAN T-complex protein 1 subunit theta OS = *Homo sapiens* GN = CCT8 PE = 1 SV = 4 |
| 137. | >sp|P51858|HDGF_HUMAN Hepatoma-derived growth factor OS = *Homo sapiens* GN = HDGF PE = 1 SV = 1 |
| 138. | >sp|P52272|HNRPM_HUMAN Heterogeneous nuclear ribonucleoprotein M OS = *Homo sapiens* GN = HNRNPM PE = 1 SV = 3 |
| 139. | >sp|P52597|HNRPF_HUMAN Heterogeneous nuclear ribonucleoprotein F OS = *Homo sapiens* GN = HNRNPF PE = 1 SV = 3 |
| 140. | >sp|P54136|SYRC_HUMAN Arginyl-tRNA synthetase, cytoplasmic OS = *Homo sapiens* GN = RARS PE = 1 SV = 2 |
| 141. | >sp|P54577|SYYC_HUMAN Tyrosyl-tRNA synthetase, cytoplasmic OS = *Homo sapiens* GN = YARS PE = 1 SV = 4 |
| 142. | >sp|P55060|XPO2_HUMAN Exportin-2 OS = *Homo sapiens* GN = CSE1L PE = 1 SV = 3 |
| 143. | >sp|P55072|TERA_HUMAN Transitional endoplasmic reticulum ATPase OS = *Homo sapiens* GN = VCP PE = 1 SV = 4 |
| 144. | >sp|P56182|RRP1_HUMAN Ribosomal RNA processing protein 1 homolog A OS = *Homo sapiens* GN = RRP1 PE = 1 SV = 1 |
| 145. | >sp|P56381|ATP5E_HUMAN ATP synthase subunit epsilon, mitochondrial OS = *Homo sapiens* GN = ATP5E PE = 1 SV = 2 |
| 146. | >sp|P58546|MTPN_HUMAN Myotrophin OS = *Homo sapiens* GN = MTPN PE = 1 SV = 2 |
| 147. | >sp|P60228|EIF3E_HUMAN Eukaryotic translation initiation factor 3 subunit E OS = *Homo sapiens* GN = EIF3E PE = 1 SV = 1 |
| 148. | >sp|P60842|IF4A1_HUMAN Eukaryotic initiation factor 4A-I OS = *Homo sapiens* GN = EIF4A1 PE = 1 SV = 1 |
| 149. | >sp|P60891|PRPS1_HUMAN Ribose-phosphate pyrophosphokinase 1 OS = *Homo sapiens* GN = PRPS1 PE = 1 SV = 2 |
| 150. | >sp|P60900|PSA6_HUMAN Proteasome subunit alpha type-6 OS = *Homo sapiens* GN = PSMA6 PE = 1 SV = 1 |
| 151. | >sp|P61247|RS3A_HUMAN 40S ribosomal protein S3a OS = *Homo sapiens* GN = RPS3A PE = 1 SV = 2 |
| 152. | >sp|P61353|RL27_HUMAN 60S ribosomal protein L27 OS = *Homo sapiens* GN = RPL27 PE = 1 SV = 2 |
| 153. | >sp|P61981|1433G_HUMAN 14-3-3 protein gamma OS = *Homo sapiens* GN = YWHAG PE = 1 SV = 2 |
| 154. | >sp|P62191|PRS4_HUMAN 26S protease regulatory subunit 4 OS = *Homo sapiens* GN = PSMC1 PE = 1 SV = 1 |
| 155. | >sp|P62241|RS8_HUMAN 40S ribosomal protein S8 OS = *Homo sapiens* GN = RPS8 PE = 1 SV = 2 |
| 156. | >sp|P62249|RS16_HUMAN 40S ribosomal protein S16 OS = *Homo sapiens* GN = RPS16 PE = 1 SV = 2 |
| 157. | >sp|P62258|1433E_HUMAN 14-3-3 protein epsilon OS = *Homo sapiens* GN = YWHAE PE = 1 SV = 1 |
| 158. | >sp|P62263|RS14_HUMAN 40S ribosomal protein S14 OS = *Homo sapiens* GN = RPS14 PE = 1 SV = 3 |
| 159. | >sp|P62269|RS18_HUMAN 40S ribosomal protein S18 OS = *Homo sapiens* GN = RPS18 PE = 1 SV = 3 |
| 160. | >sp|P62280|RS11_HUMAN 40S ribosomal protein S11 OS = *Homo sapiens* GN = RPS11 PE = 1 SV = 3 |
| 161. | >sp|P62314|SMD1_HUMAN Small nuclear ribonucleoprotein Sm D1 OS = *Homo sapiens* GN = SNRPD1 PE = 1 SV = 1 |
| 162. | >sp|P62316|SMD2_HUMAN Small nuclear ribonucleoprotein Sm D2 OS = *Homo sapiens* GN = SNRPD2 PE = 1 SV = 1 |
| 163. | >sp|P62424|RL7A_HUMAN 60S ribosomal protein L7a OS = *Homo sapiens* GN = RPL7A PE = 1 SV = 2 |
| 164. | >sp|P62829|RL23_HUMAN 60S ribosomal protein L23 OS = *Homo sapiens* GN = RPL23 PE = 1 SV = 1 |
| 165. | >sp|P62841|RS15_HUMAN 40S ribosomal protein S15 OS = *Homo sapiens* GN = RPS15 PE = 1 SV = 2 |
| 166. | >sp|P62851|RS25_HUMAN 40S ribosomal protein S25 OS = *Homo sapiens* GN = RPS25 PE = 1 SV = 1 |
| 167. | >sp|P62854|RS26_HUMAN 40S ribosomal protein S26 OS = *Homo sapiens* GN = RPS26 PE = 1 SV = 3 |
| 168. | >sp|P62888|RL30_HUMAN 60S ribosomal protein L30 OS = *Homo sapiens* GN = RPL30 PE = 1 SV = 2 |
| 169. | >sp|P62899|RL31_HUMAN 60S ribosomal protein L31 OS = *Homo sapiens* GN = RPL31 PE = 1 SV = 1 |
| 170. | >sp|P62906|RL10A_HUMAN 60S ribosomal protein L10a OS = *Homo sapiens* GN = RPL10A PE = 1 SV = 2 |
| 171. | >sp|P62913|RL11_HUMAN 60S ribosomal protein L11 OS = *Homo sapiens* GN = RPL11 PE = 1 SV = 2 |
| 172. | >sp|P63167|DYL1_HUMAN Dynein light chain 1, cytoplasmic OS = *Homo sapiens* GN = DYNLL1 PE = 1 SV = 1 |
| 173. | >sp|P63220|RS21_HUMAN 40S ribosomal protein S21 OS = *Homo sapiens* GN = RPS21 PE = 1 SV = 1 |
| 174. | >sp|P63241|IF5A1_HUMAN Eukaryotic translation initiation factor 5A-1 OS = *Homo sapiens* GN = EIF5A PE = 1 SV = 2 |
| 175. | >sp|P67809|YBOX1_HUMAN Nuclease-sensitive element-binding protein 1 OS = *Homo sapiens* GN = YBX1 PE = 1 SV = 3 |
| 176. | >sp|P68036|UB2L3_HUMAN Ubiquitin-conjugating enzyme E2 L3 OS = *Homo sapiens* GN = UBE2L3 PE = 1 SV = 1 |
| 177. | >sp|P68104|EF1A1_HUMAN Elongation factor 1-alpha 1 OS = *Homo sapiens* GN = EEF1A1 PE = 1 SV = 1 |
| 178. | >sp|P68371|TBB2C_HUMAN Tubulin beta-2C chain OS = *Homo sapiens* GN = TUBB2C PE = 1 SV = 1 |
| 179. | >sp|P68431|H31_HUMAN Histone H3.1 OS = *Homo sapiens* GN = HIST1H3A PE = 1 SV = 2 |
| 180. | >sp|P78371|TCPB_HUMAN T-complex protein 1 subunit beta OS = *Homo sapiens* GN = CCT2 PE = 1 SV = 4 |
| 181. | >sp|P84090|ERH_HUMAN Enhancer of rudimentary homolog OS = *Homo sapiens* GN = ERH PE = 1 SV = 1 |
| 182. | >sp|P84098|RL19_HUMAN 60S ribosomal protein L19 OS = *Homo sapiens* GN = RPL19 PE = 1 SV = 1 |
| 183. | >sp|P98179|RBM3_HUMAN Putative RNA-binding protein 3 OS = *Homo sapiens* GN = RBM3 PE = 1 SV = 1 |
| 184. | >sp|Q00610|CLH1_HUMAN Clathrin heavy chain 1 OS = *Homo sapiens* GN = CLTC PE = 1 SV = 5 |
| 185. | >sp|Q00839|HNRPU_HUMAN Heterogeneous nuclear ribonucleoprotein U OS = *Homo sapiens* GN = HNRNPU PE = 1 SV = 6 |
| 186. | >sp|Q01130|SRSF2_HUMAN Serine/arginine-rich splicing factor 2 OS = *Homo sapiens* GN = SRSF2 PE = 1 SV = 4 |
| 187. | >sp|Q02413|DSG1_HUMAN Desmoglein-1 OS = *Homo sapiens* GN = DSG1 PE = 1 SV = 2 |
| 188. | >sp|Q02543|RL18A_HUMAN 60S ribosomal protein L18a OS = *Homo sapiens* GN = RPL18A PE = 1 SV = 2 |
| 189. | >sp|Q02790|FKBP4_HUMAN Peptidyl-prolyl cis-trans isomerase FKBP4 OS = *Homo sapiens* GN = FKBP4 PE = 1 SV = 3 |
| 190. | >sp|Q02878|RL6_HUMAN 60S ribosomal protein L6 OS = *Homo sapiens* GN = RPL6 PE = 1 SV = 3 |
| 191. | >sp|Q04695|K1C17_HUMAN Keratin, type I cytoskeletal 17 OS = *Homo sapiens* GN = KRT17 PE = 1 SV = 2 |
| 192. | >sp|Q04917|1433F_HUMAN 14-3-3 protein eta OS = *Homo sapiens* GN = YWHAH PE = 1 SV = 4 |
| 193. | >sp|Q06830|PRDX1_HUMAN Peroxiredoxin-1 OS = *Homo sapiens* GN = PRDX1 PE = 1 SV = 1 |
| 194. | >sp|Q07955|SRSF1_HUMAN Serine/arginine-rich splicing factor 1 OS = *Homo sapiens* GN = SRSF1 PE = 1 SV = 2 |
| 195. | >sp|Q08211|DHX9_HUMAN ATP-dependent RNA helicase A OS = *Homo sapiens* GN = DHX9 PE = 1 SV = 4 |
| 196. | >sp|Q12904|AIMP1_HUMAN Aminoacyl tRNA synthase complex-interacting multifunctional protein 1 OS = *Homo sapiens* GN = AIMP1 PE = 1 SV = 2 |
| 197. | >sp|Q12906|ILF3_HUMAN Interleukin enhancer-binding factor 3 OS = *Homo sapiens* GN = ILF3 PE = 1 SV = 3 |
| 198. | >sp|Q13151|ROA0_HUMAN Heterogeneous nuclear ribonucleoprotein A0 OS = *Homo sapiens* GN = HNRNPA0 PE = 1 SV = 1 |
| 199. | >sp|Q13247|SRSF6_HUMAN Serine/arginine-rich splicing factor 6 OS = *Homo sapiens* GN = SRSF6 PE = 1 SV = 2 |
| 200. | >sp|Q13263|TIF1B_HUMAN Transcription intermediary factor 1-beta OS = *Homo sapiens* GN = TRIM28 PE = 1 SV = 5 |
| 201. | >sp|Q13838|DX39B_HUMAN Spliceosome RNA helicase DDX39B OS = *Homo sapiens* GN = DDX39B PE = 1 SV = 1 |
| 202. | >sp|Q14209|E2F2_HUMAN Transcription factor E2F2 OS = *Homo sapiens* GN = E2F2 PE = 1 SV = 1 |
| 203. | >sp|Q14247|SRC8_HUMAN Src substrate cortactin OS = *Homo sapiens* GN = CTTN PE = 1 SV = 2 |
| 204. | >sp|Q14974|IMB1_HUMAN Importin subunit beta-1 OS = *Homo sapiens* GN = KPNB1 PE = 1 SV = 2 |
| 205. | >sp|Q14978|NOLC1_HUMAN Nucleolar and coiled-body phosphoprotein 1 OS = *Homo sapiens* GN = NOLC1 PE = 1 SV = 2 |
| 206. | >sp|Q15056|IF4H_HUMAN Eukaryotic translation initiation factor 4H OS = *Homo sapiens* GN = EIF4H PE = 1 SV = 5 |
| 207. | >sp|Q15181|IPYR_HUMAN Inorganic pyrophosphatase OS = *Homo sapiens* GN = PPA1 PE = 1 SV = 2 |

| | |
|---|---|
| 208. | >sp|Q15233|NONO_HUMAN Non-POU domain-containing octamer-binding protein OS = *Homo sapiens* GN = NONO PE = 1 SV = 4 |
| 209. | >sp|Q15365|PCBP1_HUMAN Poly(rC)-binding protein 1 OS = *Homo sapiens* GN = PCBP1 PE = 1 SV = 2 |
| 210. | >sp|Q16658|FSCN1_HUMAN Fascin OS = *Homo sapiens* GN = FSCN1 PE = 1 SV = 3 |
| 211. | >sp|Q1KMD3|HNRL2_HUMAN Heterogeneous nuclear ribonucleoprotein U-like protein 2 OS = *Homo sapiens* GN = HNRNPUL2 PE = 1 SV = 1 |
| 212. | >sp|Q5D862|FILA2_HUMAN Filaggrin-2 OS = *Homo sapiens* GN = FLG2 PE = 1 SV = 1 |
| 213. | >sp|Q5U651|RAIN_HUMAN Ras-interacting protein 1 OS = *Homo sapiens* GN = RASIP1 PE = 1 SV = 1 |
| 214. | >sp|Q69YZ2|T200B_HUMAN Transmembrane protein 200B OS = *Homo sapiens* GN = TMEM200B PE = 2 SV = 1 |
| 215. | >sp|Q6P2E9|EDC4_HUMAN Enhancer of mRNA-decapping protein 4 OS = *Homo sapiens* GN = EDC4 PE = 1 SV = 1 |
| 216. | >sp|Q6P2Q9|PRP8_HUMAN Pre-mRNA-processing-splicing factor 8 OS = *Homo sapiens* GN = PRPF8 PE = 1 SV = 2 |
| 217. | >sp|Q6PKG0|LARP1_HUMAN La-related protein 1 OS = *Homo sapiens* GN = LARP1 PE = 1 SV = 2 |
| 218. | >sp|Q86UX7|URP2_HUMAN Fermitin family homolog 3 OS = *Homo sapiens* GN = FERMT3 PE = 1 SV = 1 |
| 219. | >sp|Q86YZ3|HORN_HUMAN Hornerin OS = *Homo sapiens* GN = HRNR PE = 1 SV = 1 |
| 220. | >sp|Q8N9V7|CCO77_HUMAN Uncharacterized protein C3orf77 OS = *Homo sapiens* GN = C3orf77 PE = 2 SV = 3 |
| 221. | >sp|Q8TF72|SHRM3_HUMAN Protein Shroom3 OS = *Homo sapiens* GN = SHROOM3 PE = 1 SV = 2 |
| 222. | >sp|Q92841|DDX17_HUMAN Probable ATP-dependent RNA helicase DDX17 OS = *Homo sapiens* GN = DDX17 PE = 1 SV = 1 |
| 223. | >sp|Q92945|FUBP2_HUMAN Far upstream element-binding protein 2 OS = *Homo sapiens* GN = KHSRP PE = 1 SV = 4 |
| 224. | >sp|Q96AG4|LRC59_HUMAN Leucine-rich repeat-containing protein 59 OS = *Homo sapiens* GN = LRRC59 PE = 1 SV = 1 |
| 225. | >sp|Q96CT7|CC124_HUMAN Coiled-coil domain-containing protein 124 OS = *Homo sapiens* GN = CCDC124 PE = 1 SV = 1 |
| 226. | >sp|Q96MK3|FA20A_HUMAN Protein FAM20A OS = *Homo sapiens* GN = FAM20A PE = 2 SV = 4 |
| 227. | >sp|Q96PK6|RBM14_HUMAN RNA-binding protein 14 OS = *Homo sapiens* GN = RBM14 PE = 1 SV = 2 |
| 228. | >sp|Q99832|TCPH_HUMAN T-complex protein 1 subunit eta OS = *Homo sapiens* GN = CCT7 PE = 1 SV = 2 |
| 229. | >sp|Q99ZW2|CAS9_STRP1 CRISPR-associated endonuclease Cas9/Csn1 OS = *Streptococcus pyogenes* serotype M1 GN = cas9 PE = 1 SV = 1 |
| 230. | >sp|Q9BXL5|HEMGN_HUMAN Hemogen OS = *Homo sapiens* GN = HEMGN PE = 1 SV = 1 |
| 231. | >sp|Q9BXP5|SRRT_HUMAN Serrate RNA effector molecule homolog OS = *Homo sapiens* GN = SRRT PE = 1 SV = 1 |
| 232. | >sp|Q9H307|PININ_HUMAN Pinin OS = *Homo sapiens* GN = PNN PE = 1 SV = 4 |
| 233. | >sp|Q9NQ75|CASS4_HUMAN Cas scaffolding protein family member 4 OS = *Homo sapiens* GN = CASS4 PE = 1 SV = 2 |
| 234. | >sp|Q9NR30|DDX21_HUMAN Nucleolar RNA helicase 2 OS = *Homo sapiens* GN = DDX21 PE = 1 SV = 5 |
| 235. | >sp|Q9NX58|LYAR_HUMAN Cell growth-regulating nucleolar protein OS = *Homo sapiens* GN = LYAR PE = 1 SV = 2 |
| 236. | >sp|Q9NZI8|IF2B1_HUMAN Insulin-like growth factor 2 mRNA-binding protein 1 OS = *Homo sapiens* GN = IGF2BP1 PE = 1 SV = 2 |
| 237. | >sp|Q9P0L0|VAPA_HUMAN Vesicle-associated membrane protein-associated protein A OS = *Homo sapiens* GN = VAPA PE = 1 SV = 3 |
| 238. | >sp|Q9UBQ0|VPS29_HUMAN Vacuolar protein sorting-associated protein 29 OS = *Homo sapiens* GN = VPS29 PE = 1 SV = 1 |
| 239. | >sp|Q9UII2|ATIF1_HUMAN ATPase inhibitor, mitochondrial OS = *Homo sapiens* GN = ATPIF1 PE = 1 SV = 1 |
| 240. | >sp|Q9ULC4|MCTS1_HUMAN Malignant T cell-amplified sequence 1 OS = *Homo sapiens* GN = MCTS1 PE = 1 SV = 1 |
| 241. | >sp|Q9UMS4|PRP19_HUMAN Pre-mRNA-processing factor 19 OS = *Homo sapiens* GN = PRPF19 PE = 1 SV = 1 |
| 242. | >sp|Q9UQ80|PA2G4_HUMAN Proliferation-associated protein 2G4 OS = *Homo sapiens* GN = PA2G4 PE = 1 SV = 3 |
| 243. | >sp|Q9Y230|RUVB2_HUMAN RuvB-like 2 OS = *Homo sapiens* GN = RUVBL2 PE = 1 SV = 3 |
| 244. | >sp|Q9Y266|NUDC_HUMAN Nuclear migration protein nudC OS = *Homo sapiens* GN = NUDC PE = 1 SV = 1 |
| 245. | >sp|Q9Y490|TLN1_HUMAN Talin-1 OS = *Homo sapiens* GN = TLN1 PE = 1 SV = 3 |
| 246. | >sp|Q9Y4G6|TLN2_HUMAN Talin-2 OS = *Homo sapiens* GN = TLN2 PE = 1 SV = 4 |
| 247. | >sp|Q9Y5B9|SP16H_HUMAN FACT complex subunit SPT16 OS = *Homo sapiens* GN = SUPT16H PE = 1 SV = 1 |
| 248. | >sp|Q9Y5S9|RBM8A_HUMAN RNA-binding protein 8A OS = *Homo sapiens* GN = RBM8A PE = 1 SV = 1 |
| 249. | >tr|A0AV56|A0AV56_HUMAN SAFB protein OS = *Homo sapiens* GN = SAFB PE = 2 SV = 1 |
| 250. | >tr|A0MNP2|A0MNP2_HUMAN CDW11/WDR57 OS = *Homo sapiens* GN = WDR57 PE = 2 SV = 1 |
| 251. | >tr|A2A3R6|A2A3R6_HUMAN 40S ribosomal protein S6 OS = *Homo sapiens* GN = RPS6 PE = 2 SV = 1 |
| 252. | >tr|A2AB48|A2AB48_HUMAN HLA-B associated transcript 3 (Fragment) OS = *Homo sapiens* GN = BAT3 PE = 4 SV = 1 |
| 253. | >tr|A2BF54|A2BF54_HUMAN HLA-B associated transcript 1 (Fragment) OS = *Homo sapiens* GN = BAT1 PE = 4 SV = 1 |
| 254. | >tr|A2BF75|A2BF75_HUMAN ATP-binding cassette sub-family F (GCN20) member 1 OS = *Homo sapiens* GN = ABCF1 PE = 2 SV = 1 |
| 255. | >tr|A2RUM7|A2RUM7_HUMAN Ribosomal protein L5 OS = *Homo sapiens* GN = RPL5 PE = 2 SV = 1 |
| 256. | >tr|A3KPC7|A3KPC7_HUMAN Histone H2A OS = *Homo sapiens* GN = HIST1H2AH PE = 2 SV = 1 |
| 257. | >tr|A3R0T8|A3R0T8_HUMAN Histone 1, H1e OS = *Homo sapiens* GN = HIST1H1E PE = 2 SV = 1 |
| 258. | >tr|A3RJH1|A3RJH1_HUMAN ATP-dependent RNA helicase DDX1 OS = *Homo sapiens* GN = DDX1 PE = 2 SV = 1 |
| 259. | >tr|A4D177|A4D177_HUMAN Chromobox homolog 3 (HP1 gamma homolog *Drosophila*) OS = *Homo sapiens* GN = CBX3 PE = 4 SV = 1 |
| 260. | >tr|A4D1U3|A4D1U3_HUMAN Single-stranded DNA binding protein 1 OS = *Homo sapiens* GN = SSBP1 PE = 2 SV = 1 |
| 261. | >tr|A4K467|A4K467_HUMAN Actinin alpha4 isoform OS = *Homo sapiens* GN = ACTN4 PE = 2 SV = 1 |
| 262. | >tr|A5JHP3|A5JHP3_HUMAN Dermcidin isoform 2 OS = *Homo sapiens* GN = DCD PE = 2 SV = 1 |
| 263. | >tr|A6NBZ8|A6NBZ8_HUMAN Uncharacterized protein OS = *Homo sapiens* GN = ALB PE = 4 SV = 2 |
| 264. | >tr|A6NC17|A6NC17_HUMAN Uncharacterized protein OS = *Homo sapiens* GN = MARS PE = 4 SV = 3 |
| 265. | >tr|A6NDY9|A6NDY9_HUMAN Filamin A OS = *Homo sapiens* GN = FLNA PE = 2 SV = 4 |
| 266. | >tr|A6NE05|A6NE05_HUMAN Uncharacterized protein OS = *Homo sapiens* GN = RPL26 PE = 3 SV = 1 |
| 267. | >tr|A6NE09|A6NE09_HUMAN Uncharacterized protein OS = *Homo sapiens* PE = 3 SV = 1 |
| 268. | >tr|A6NE14|A6NE14_HUMAN Uncharacterized protein OS = *Homo sapiens* GN = CCT3 PE = 2 SV = 1 |
| 269. | >tr|A6NFM2|A6NFM2_HUMAN Pyrroline-5-carboxylate reductase OS = *Homo sapiens* GN = PYCR1 PE = 3 SV = 1 |
| 270. | >tr|A6NGV1|A6NGV1_HUMAN Uncharacterized protein OS = *Homo sapiens* GN = SET PE = 2 SV = 2 |
| 271. | >tr|A6NJA2|A6NJA2_HUMAN Ubiquitin carboxyl-terminal hydrolase OS = *Homo sapiens* GN = USP14 PE = 3 SV = 1 |
| 272. | >tr|A6NJH9|A6NJH9_HUMAN Uncharacterized protein OS = *Homo sapiens* GN = EIF1AY PE = 4 SV = 1 |
| 273. | >tr|A6NKB1|A6NKB1_HUMAN Uncharacterized protein OS = *Homo sapiens* GN = TTN PE = 4 SV = 4 |
| 274. | >tr|A6NNE8|A6NNE8_HUMAN Uncharacterized protein OS = *Homo sapiens* GN = SRSF7 PE = 4 SV = 3 |
| 275. | >tr|A7MAP1|A7MAP1_HUMAN Coronin-1C_i3 protein OS = *Homo sapiens* GN = CORO1C PE = 2 SV = 1 |
| 276. | >tr|A8K0N0|A8K0N0_HUMAN Signal recognition particle 9 kDa protein OS = *Homo sapiens* GN = SRP9 PE = 3 SV = 1 |
| 277. | >tr|A8K1R6|A8K1R6_HUMAN cDNA FLJ77026, highly similar to *Homo sapiens* ataxin 2-like (ATXN2L), transcript variant E, mRNA OS = *Homo sapiens* PE = 2 SV = 1 |
| 278. | >tr|A8K220|A8K220_HUMAN Peptidyl-prolyl cis-trans isomerase OS = *Homo sapiens* GN = PPIA PE = 1 SV = 1 |
| 279. | >tr|A8K2Y9|A8K2Y9_HUMAN 6-phosphogluconate dehydrogenase, decarboxylating OS = *Homo sapiens* GN = PGD PE = 2 SV = 1 |
| 280. | >tr|A8K3Z8|A8K3Z8_HUMAN RAN, member RAS oncogene family, isoform CRA_b OS = *Homo sapiens* GN = RAN PE = 1 SV = 1 |
| 281. | >tr|A8K401|A8K401_HUMAN Prohibitin, isoform CRA_a OS = *Homo sapiens* GN = PHB PE = 2 SV = 1 |
| 282. | >tr|A8K4C8|A8K4C8_HUMAN 60S ribosomal protein L13 OS = *Homo sapiens* GN = RPL13 PE = 2 SV = 1 |
| 283. | >tr|A8K4I2|A8K4I2_HUMAN Histone 1, H1c OS = *Homo sapiens* GN = HIST1H1C PE = 2 SV = 1 |

| | |
|---|---|
| 284. | >tr\|A8K4W6\|A8K4W6_HUMAN Phosphoglycerate kinase OS = *Homo sapiens* GN = PGK1 PE = 2 SV = 1 |
| 285. | >tr\|A8K5I0\|A8K5I0_HUMAN Heat shock 70 kDa protein 1A OS = *Homo sapiens* GN = HSPA1A PE = 2 SV = 1 |
| 286. | >tr\|A8K7B7\|A8K7B7_HUMAN Protein phosphatase 2 (Formerly 2A), regulatory subunit A (PR 65), alpha isoform OS = *Homo sapiens* GN = PPP2R1A PE = 2 SV = 1 |
| 287. | >tr\|A8K7X6\|A8K7X6_HUMAN Poly(RC) binding protein 2, isoform CRA_b OS = *Homo sapiens* GN = PCBP2 PE = 2 SV = 1 |
| 288. | >tr\|A8K9B1\|A8K9B1_HUMAN Sialophorin (GpL115, leukosialin, CD43), isoform CRA_a OS = *Homo sapiens* GN = SPN PE = 2 SV = 1 |
| 289. | >tr\|A8MTA5\|A8MTA5_HUMAN Uncharacterized protein OS = *Homo sapiens* GN = SEC13 PE = 4 SV = 1 |
| 290. | >tr\|A8MTG3\|A8MTG3_HUMAN Uncharacterized protein OS = *Homo sapiens* GN = ZNF207 PE = 4 SV = 1 |
| 291. | >tr\|A8MU27\|A8MU27_HUMAN Uncharacterized protein OS = *Homo sapiens* GN = SUMO3 PE = 4 SV = 1 |
| 292. | >tr\|A8MUB1\|A8MUB1_HUMAN Tubulin, alpha 1 (Testis specific), isoform CRA_a OS = *Homo sapiens* GN = TUBA4A PE = 2 SV = 1 |
| 293. | >tr\|A8MUF7\|A8MUF7_HUMAN Uncharacterized protein OS = *Homo sapiens* GN = HBE1 PE = 3 SV = 1 |
| 294. | >tr\|A8MUS3\|A8MUS3_HUMAN Ribosomal protein L23a, isoform CRA_a OS = *Homo sapiens* GN = RPL23A PE = 3 SV = 1 |
| 295. | >tr\|A8MUT5\|A8MUT5_HUMAN Uncharacterized protein OS = *Homo sapiens* GN = DKC1 PE = 4 SV = 1 |
| 296. | >tr\|A8MV89\|A8MV89_HUMAN Uncharacterized protein OS = *Homo sapiens* GN = SPECC1 PE = 4 SV = 1 |
| 297. | >tr\|A8MVA9\|A8MVA9_HUMAN Uncharacterized protein OS = *Homo sapiens* GN = WDR1 PE = 4 SV = 2 |
| 298. | >tr\|A8MW50\|A8MW50_HUMAN L-lactate dehydrogenase OS = *Homo sapiens* GN = LDHB PE = 3 SV = 1 |
| 299. | >tr\|A8MWD3\|A8MWD3_HUMAN Uncharacterized protein OS = *Homo sapiens* GN = EIF3D PE = 2 SV = 2 |
| 300. | >tr\|A8MX94\|A8MX94_HUMAN Uncharacterized protein OS = *Homo sapiens* GN = GSTP1 PE = 4 SV = 1 |
| 301. | >tr\|A8MX97\|A8MX97_HUMAN Uncharacterized protein OS = *Homo sapiens* GN = PICALM PE = 4 SV = 1 |
| 302. | >tr\|A8MXP9\|A8MXP9_HUMAN Uncharacterized protein OS = *Homo sapiens* GN = MATR3 PE = 4 SV = 1 |
| 303. | >tr\|A8MYV2\|A8MYV2_HUMAN LUC7-like (*S. cerevisiae*) OS = *Homo sapiens* GN = LUC7L PE = 4 SV = 1 |
| 304. | >tr\|A9C4C1\|A9C4C1_HUMAN Ribosomal protein S9 OS = *Homo sapiens* GN = RPS9 PE = 3 SV = 1 |
| 305. | >tr\|B0LPF3\|B0LPF3_HUMAN Growth factor receptor-bound protein 2 OS = *Homo sapiens* GN = GRB2 PE = 2 SV = 1 |
| 306. | >tr\|B0QY89\|B0QY89_HUMAN Eukaryotic translation initiation factor 3, subunit E interacting protein OS = *Homo sapiens* GN = EIF3EIP PE = 4 SV = 1 |
| 307. | >tr\|B0QYK0\|B0QYK0_HUMAN Ewing sarcoma breakpoint region 1 OS = *Homo sapiens* GN = EWSR1 PE = 4 SV = 1 |
| 308. | >tr\|B0QYT4\|B0QYT4_HUMAN Ran GTPase activating protein 1 (Fragment) OS = *Homo sapiens* GN = RANGAP1 PE = 4 SV = 1 |
| 309. | >tr\|B0V043\|B0V043_HUMAN Valyl-tRNA synthetase OS = *Homo sapiens* GN = VARS PE = 3 SV = 1 |
| 310. | >tr\|B0ZBD0\|B0ZBD0_HUMAN 40S ribosomal protein S19 OS = *Homo sapiens* GN = RPS19 PE = 2 SV = 1 |
| 311. | >tr\|B1AH89\|B1AH89_HUMAN Tubulin tyrosine ligase-like family, member 12 OS = *Homo sapiens* GN = TTLL12 PE = 4 SV = 1 |
| 312. | >tr\|B1AHC7\|B1AHC7_HUMAN X-ray repair complementing defective repair in Chinese hamster cells 6 (Ku autoantigen, 70 kDa) OS = *Homo sapiens* GN = XRCC6 PE = 4 SV = 1 |
| 313. | >tr\|B1ALW1\|B1ALW1_HUMAN Thioredoxin OS = *Homo sapiens* GN = TXN PE = 4 SV = 1 |
| 314. | >tr\|B1ALY5\|B1ALY5_HUMAN ROD1 regulator of differentiation 1 (*S. pombe*) OS = *Homo sapiens* GN = ROD1 PE = 2 SV = 1 |
| 315. | >tr\|B1Q2N1\|B1Q2N1_HUMAN DEAD (Asp-Glu-Ala-Asp) box polypeptide 39 transcript variant OS = *Homo sapiens* GN = DDX39 PE = 2 SV = 1 |
| 316. | >tr\|B2R491\|B2R491_HUMAN Ribosomal protein S4, X-linked, isoform CRA_c OS = *Homo sapiens* GN = RPS4X PE = 2 SV = 1 |
| 317. | >tr\|B2R4P8\|B2R4P8_HUMAN HCG2016482, isoform CRA_b OS = *Homo sapiens* GN = hCG_2016482 PE = 2 SV = 1 |
| 318. | >tr\|B2R4P9\|B2R4P9_HUMAN Histone H3 OS = *Homo sapiens* GN = H3F3A PE = 2 SV = 1 |
| 319. | >tr\|B2R4R0\|B2R4R0_HUMAN Histone H4 OS = *Homo sapiens* GN = HIST1H4J PE = 3 SV = 1 |
| 320. | >tr\|B2R4R9\|B2R4R9_HUMAN HCG26477 OS = *Homo sapiens* GN = RPS28 PE = 4 SV = 1 |
| 321. | >tr\|B2R4S9\|B2R4S9_HUMAN Histone H2B OS = *Homo sapiens* GN = HIST1H2BC PE = 2 SV = 1 |
| 322. | >tr\|B2R4W8\|B2R4W8_HUMAN HCG1994130, isoform CRA_a OS = *Homo sapiens* GN = hCG_1994130 PE = 2 SV = 1 |
| 323. | >tr\|B2R6F3\|B2R6F3_HUMAN Splicing factor arginine/serine-rich 3 OS = *Homo sapiens* GN = SFRS3 PE = 2 SV = 1 |
| 324. | >tr\|B2RDW1\|B2RDW1_HUMAN Ribosomal protein S27a, isoform CRA_c OS = *Homo sapiens* GN = RPS27A PE = 2 SV = 1 |
| 325. | >tr\|B2REA7\|B2REA7_HUMAN Ribosomal protein L36a OS = *Homo sapiens* GN = RPL36A PE = 3 SV = 1 |
| 326. | >tr\|B2RP62\|B2RP62_HUMAN HCG2027369, isoform CRA_a OS = *Homo sapiens* GN = KIF21B PE = 2 SV = 1 |
| 327. | >tr\|B3KPZ8\|B3KPZ8_HUMAN cDNA FLJ32530 fis, clone SMINT2000185, highly similar to TRANSKETOLASE (EC 2.2.1.1) OS = *Homo sapiens* PE = 2 SV = 1 |
| 328. | >tr\|B3KS98\|B3KS98_HUMAN Eukaryotic translation initiation factor 3, subunit 3 gamma, 40 kDa, isoform CRA_b OS = *Homo sapiens* GN = EIF3S3 PE = 2 SV = 1 |
| 329. | >tr\|B3KSH1\|B3KSH1_HUMAN HCG1784554, isoform CRA_a OS = *Homo sapiens* GN = hCG_1784554 PE = 2 SV = 1 |
| 330. | >tr\|B3KTE3\|B3KTE3_HUMAN cDNA FLJ38125 fis, clone D6OST2000127, moderately similar to RAS-RELATED PROTEIN RAB-8B OS = *Homo sapiens* PE = 4 SV = 1 |
| 331. | >tr\|B3KVR1\|B3KVR1_HUMAN cDNA FLJ41124 fis, clone BRACE2014850, highly similar to Small nuclear ribonucleoprotein-associated protein N OS = *Homo sapiens* PE = 2 SV = 1 |
| 332. | >tr\|B4DDB6\|B4DDB6_HUMAN Heterogeneous nuclear ribonucleoprotein A3, isoform CRA_a OS = *Homo sapiens* GN = HNRPA3 PE = 2 SV = 1 |
| 333. | >tr\|B4DEP9\|B4DEP9_HUMAN cDNA FLJ57954, highly similar to 60S ribosomal protein L28 OS = *Homo sapiens* PE = 2 SV = 1 |
| 334. | >tr\|B4DF96\|B4DF96_HUMAN cDNA FLJ57962, highly similar to *Homo sapiens* eukaryotic translation initiation factor (eIF) 2A (eIF2A), mRNA OS = *Homo sapiens* PE = 2 SV = 1 |
| 335. | >tr\|B4DGP8\|B4DGP8_HUMAN cDNA FLJ55574, highly similar to Calnexin OS = *Homo sapiens* PE = 2 SV = 1 |
| 336. | >tr\|B4DGT6\|B4DGT6_HUMAN cDNA FLJ56692, highly similar to Asparaginyl-tRNA synthetase, cytoplasmic (EC 6.1.1.22) OS = *Homo sapiens* PE = 2 SV = 1 |
| 337. | >tr\|B4DH61\|B4DH61_HUMAN cDNA FLJ60521, highly similar to Protein kinase-like protein C9orf96 OS = *Homo sapiens* PE = 2 SV = 1 |
| 338. | >tr\|B4DIN1\|B4DIN1_HUMAN cDNA FLJ60566, highly similar to Clathrin light chain A OS = *Homo sapiens* PE = 2 SV = 1 |
| 339. | >tr\|B4DIW5\|B4DIW5_HUMAN cDNA FLJ55515, highly similar to Breast cancer anti-estrogen resistanceprotein 1 OS = *Homo sapiens* PE = 2 SV = 1 |
| 340. | >tr\|B4DJ10\|B4DJ10_HUMAN cDNA FLJ58533, highly similar to Leucyl-tRNA synthetase, cytoplasmic (EC 6.1.1.4) OS = *Homo sapiens* PE = 2 SV = 1 |
| 341. | >tr\|B4DK30\|B4DK30_HUMAN cDNA FLJ59627, highly similar to 116 kDa U5 small nuclear ribonucleoprotein component OS = *Homo sapiens* PE = 2 SV = 1 |
| 342. | >tr\|B4DKQ2\|B4DKQ2_HUMAN L-lactate dehydrogenase OS = *Homo sapiens* PE = 2 SV = 1 |
| 343. | >tr\|B4DL87\|B4DL87_HUMAN Uncharacterized protein OS = *Homo sapiens* GN = HSPB1 PE = 2 SV = 1 |
| 344. | >tr\|B4DLP4\|B4DLP4_HUMAN Ribosomal protein L15 OS = *Homo sapiens* PE = 2 SV = 1 |
| 345. | >tr\|B4DM12\|B4DM12_HUMAN cDNA FLJ51242, moderately similar to Eukaryotic translation initiation factor 2 subunit 1 OS = *Homo sapiens* PE = 2 SV = 1 |
| 346. | >tr\|B4DMK0\|B4DMK0_HUMAN cDNA FLJ61134, highly similar to Ras-related protein Rab-11B OS = *Homo sapiens* PE = 2 SV = 1 |
| 347. | >tr\|B4DP17\|B4DP17_HUMAN cDNA FLJ61146, highly similar to Cellular nucleic acid-binding protein OS = *Homo sapiens* PE = 2 SV = 1 |

-continued

348. >tr|B4DP75|B4DP75_HUMAN cDNA FLJ56579, highly similar to Prohibitin-2 OS = *Homo sapiens* PE = 2 SV = 1
349. >tr|B4DR70|B4DR70_HUMAN cDNA FLJ58049, highly similar to RNA-binding protein FUS OS = *Homo sapiens* PE = 2 SV = 1
350. >tr|B4DT30|B4DT30_HUMAN cDNA FLJ57496, moderately similar to Tubulin-specific chaperone A OS = *Homo sapiens* PE = 2 SV = 1
351. >tr|B4DT31|B4DT31_HUMAN Uncharacterized protein OS = *Homo sapiens* GN = FUBP1 PE = 2 SV = 1
352. >tr|B4DTG2|B4DTG2_HUMAN cDNA FLJ56389, highly similar to Elongation factor 1-gamma OS = *Homo sapiens* PE = 2 SV = 1
353. >tr|B4DU42|B4DU42_HUMAN cDNA FLJ56153, highly similar to *Homo sapiens* transforming growth factor beta regulator 4 (TBRG4), transcript variant 1, mRNA OS = *Homo sapiens* PE = 2 SV = 1
354. >tr|B4DUI3|B4DUI3_HUMAN cDNA FLJ57599, moderately similar to Eukaryotic translation initiation factor 3 subunit 1 OS = *Homo sapiens* PE = 2 SV = 1
355. >tr|B4DUQ1|B4DUQ1_HUMAN cDNA FLJ54552, highly similar to Heterogeneous nuclear ribonucleoprotein K OS = *Homo sapiens* PE = 2 SV = 1
356. >tr|B4DV82|B4DV82_HUMAN cDNA FLJ58629, highly similar to Poly (ADP-ribose) polymerase 2 (EC 2.4.2.30) OS = *Homo sapiens* PE = 2 SV = 1
357. >tr|B4DVB8|B4DVB8_HUMAN cDNA FLJ60076, highly similar to ELAV-like protein 1 OS = *Homo sapiens* PE = 2 SV = 1
358. >tr|B4DW28|B4DW28_HUMAN cDNA FLJ58953, highly similar to 40S ribosomal protein S20 OS = *Homo sapiens* PE = 2 SV = 1
359. >tr|B4DWW4|B4DWW4_HUMAN MCM3 minichromosome maintenance deficient 3 (*S. cerevisiae*), isoform CRA_b OS = *Homo sapiens* GN = MCM3 PE = 2 SV = 1
360. >tr|B4DXZ6|B4DXZ6_HUMAN cDNA FLJ58644, highly similar to Fragile X mental retardation syndrome-related protein 1 OS = *Homo sapiens* PE = 2 SV = 1
361. >tr|B4DYD8|B4DYD8_HUMAN cDNA FLJ52362, highly similar to T-complex protein 1 subunit epsilon OS = *Homo sapiens* PE = 2 SV = 1
362. >tr|B4DZF2|B4DZF2_HUMAN cDNA FLJ59571, highly similar to Eukaryotic translation initiation factor 4gamma 2 OS = *Homo sapiens* PE = 2 SV = 1
363. >tr|B4DZM8|B4DZM8_HUMAN cDNA FLJ52877, highly similar to 26S proteasome non-ATPase regulatory subunit 5 OS = *Homo sapiens* PE = 2 SV = 1
364. >tr|B4DZP5|B4DZP5_HUMAN Uncharacterized protein OS = *Homo sapiens* GN = DDB1 PE = 2 SV = 1
365. >tr|B4E335|B4E335_HUMAN cDNA FLJ52842, highly similar to Actin, cytoplasmic 1 OS = *Homo sapiens* PE = 2 SV = 1
366. >tr|B5MCP9|B5MCP9_HUMAN Uncharacterized protein OS = *Homo sapiens* GN = RPS7 PE = 4 SV = 1
367. >tr|B5MD38|B5MD38_HUMAN Uncharacterized protein OS = *Homo sapiens* GN = HADHB PE = 3 SV = 1
368. >tr|B7Z4N6|B7Z4N6_HUMAN Stathmin OS = *Homo sapiens* GN = STMN2 PE = 2 SV = 1
369. >tr|B8ZZ38|B8ZZ38_HUMAN Uncharacterized protein OS = *Homo sapiens* GN = LRPPRC PE = 4 SV = 1
370. >tr|B8ZZL8|B8ZZL8_HUMAN Heat shock 10 kDa protein 1 (Chaperonin 10), isoform CRA_b OS = *Homo sapiens* GN = HSPE1 PE = 3 SV = 1
371. >tr|B8ZZQ7|B8ZZQ7_HUMAN Uncharacterized protein OS = *Homo sapiens* GN = IMMT PE = 4 SV = 2
372. >tr|C9J0E4|C9J0E4_HUMAN Uncharacterized protein OS = *Homo sapiens* GN = CSTA PE = 4 SV = 1
373. >tr|C9J4Z3|C9J4Z3_HUMAN Ribosomal protein L37a, isoform CRA_c OS = *Homo sapiens* GN = RPL37A PE = 4 SV = 1
374. >tr|C9J5P2|C9J5P2_HUMAN DNA topoisomerase 2 OS = *Homo sapiens* GN = TOP2A PE = 3 SV = 1
375. >tr|C9J7T6|C9J7T6_HUMAN Uncharacterized protein OS = *Homo sapiens* GN = RPL10 PE = 4 SV = 1
376. >tr|C9JBL2|C9JBL2_HUMAN Uncharacterized protein OS = *Homo sapiens* GN = RPL32 PE = 4 SV = 1
377. >tr|C9JLK0|C9JLK0_HUMAN Uncharacterized protein OS = *Homo sapiens* GN = ATIC PE = 4 SV = 1
378. >tr|C9JNW5|C9JNW5_HUMAN Ribosomal protein L24, isoform CRA_e OS = *Homo sapiens* GN = RPL24 PE = 4 SV = 1
379. >tr|C9JTK6|C9JTK6_HUMAN Uncharacterized protein OS = *Homo sapiens* GN = OLA1 PE = 4 SV = 1
380. >tr|C9JW69|C9JW69_HUMAN Uncharacterized protein OS = *Homo sapiens* GN = RCC1 PE = 4 SV = 1
381. >tr|C9JXG8|C9JXG8_HUMAN Uncharacterized protein OS = *Homo sapiens* GN = RANBP1 PE = 4 SV = 2
382. >tr|C9K025|C9K025_HUMAN Uncharacterized protein OS = *Homo sapiens* GN = RPL35A PE = 4 SV = 1
383. >tr|D0PNI1|D0PNI1_HUMAN Tyrosine 3-monooxygenase/tryptophan 5-monooxygenase activation protein zeta polypeptide OS = *Homo sapiens* GN = YWHAZ PE = 3 SV = 1
384. >tr|D1MGQ2|D1MGQ2_HUMAN Alpha-2 globin chain OS = *Homo sapiens* GN = HBA2 PE = 3 SV = 1
385. >tr|D2K8Q1|D2K8Q1_HUMAN AAA domain containing 3A protein OS = *Homo sapiens* GN = ATAD3A PE = 2 SV = 1
386. >tr|D3DUS9|D3DUS9_HUMAN Triosephosphate isomerase OS = *Homo sapiens* GN = TPI1 PE = 3 SV = 1
387. >tr|D6RAF8|D6RAF8_HUMAN Uncharacterized protein OS = *Homo sapiens* GN = HNRNPD PE = 4 SV = 1
388. >tr|D6RDG3|D6RDG3_HUMAN Uncharacterized protein OS = *Homo sapiens* GN = BTF3 PE = 4 SV = 1
389. >tr|D6RF62|D6RF62_HUMAN Phosphoribosylaminoimidazole carboxylase, phosphoribosylaminoimidazole succinocarboxamide synthetase, isoform CRA_b OS = *Homo sapiens* GN = PAICS PE = 4 SV = 1
390. >tr|D6RHZ4|D6RHZ4_HUMAN Uncharacterized protein OS = *Homo sapiens* PE = 4 SV = 1
391. >tr|D9YZU8|D9YZU8_HUMAN Hemoglobin, gamma A OS = *Homo sapiens* GN = HBG1 PE = 3 SV = 1
392. >tr|E5RFP6|E5RFP6_HUMAN Uncharacterized protein OS = *Homo sapiens* GN = VDAC3 PE = 4 SV = 1
393. >tr|E5RGD9|E5RGD9_HUMAN Uncharacterized protein OS = *Homo sapiens* GN = TCEB1 PE = 4 SV = 1
394. >tr|E7EME9|E7EME9_HUMAN Uncharacterized protein OS = *Homo sapiens* GN = EIF3B PE = 3 SV = 1
395. >tr|E7EMI4|E7EMI4_HUMAN Uncharacterized protein OS = *Homo sapiens* GN = SART3 PE = 4 SV = 1
396. >tr|E7EMN0|E7EMN0_HUMAN Uncharacterized protein OS = *Homo sapiens* GN = EPRS PE = 3 SV = 1
397. >tr|E7EMU2|E7EMU2_HUMAN Uncharacterized protein OS = *Homo sapiens* GN = HMGA1 PE = 4 SV = 1
398. >tr|E7ENH9|E7ENH9_HUMAN Uncharacterized protein OS = *Homo sapiens* GN = ACLY PE = 4 SV = 2
399. >tr|E7ENJ6|E7ENJ6_HUMAN Uncharacterized protein OS = *Homo sapiens* GN = AP1M1 PE = 4 SV = 1
400. >tr|E7EPB3|E7EPB3_HUMAN Uncharacterized protein OS = *Homo sapiens* GN = RPL14 PE = 4 SV = 1
401. >tr|E7EQD1|E7EQD1_HUMAN Uncharacterized protein OS = *Homo sapiens* GN = TRA2B PE = 4 SV = 1
402. >tr|E7EQR4|E7EQR4_HUMAN Uncharacterized protein OS = *Homo sapiens* GN = EZR PE = 4 SV = 2
403. >tr|E7EQV3|E7EQV3_HUMAN Uncharacterized protein OS = *Homo sapiens* GN = PABPC1 PE = 4 SV = 1
404. >tr|E7EQZ3|E7EQZ3_HUMAN Uncharacterized protein OS = *Homo sapiens* GN = GSPT1 PE = 4 SV = 1
405. >tr|E7ERA3|E7ERA3_HUMAN Uncharacterized protein OS = *Homo sapiens* GN = FN1 PE = 4 SV = 1
406. >tr|E7ERE4|E7ERE4_HUMAN Uncharacterized protein OS = *Homo sapiens* GN = HNRNPR PE = 4 SV = 1
407. >tr|E7ERF2|E7ERF2_HUMAN Uncharacterized protein OS = *Homo sapiens* GN = TCP1 PE = 4 SV = 1
408. >tr|E7ERL0|E7ERL0_HUMAN Uncharacterized protein OS = *Homo sapiens* GN = NME1 PE = 3 SV = 1
409. >tr|E7ERS3|E7ERS3_HUMAN Uncharacterized protein OS = *Homo sapiens* GN = ZC3H18 PE = 4 SV = 1
410. >tr|E7ESL4|E7ESL4_HUMAN Uncharacterized protein OS = *Homo sapiens* GN = LTN1 PE = 4 SV = 1
411. >tr|E7ESM6|E7ESM6_HUMAN Uncharacterized protein OS = *Homo sapiens* GN = SND1 PE = 4 SV = 2
412. >tr|E7ET98|E7ET98_HUMAN Uncharacterized protein OS = *Homo sapiens* GN = KHDRBS1 PE = 4 SV = 2
413. >tr|E7ETK6|E7ETK6_HUMAN Uncharacterized protein OS = *Homo sapiens* GN = SRP68 PE = 4 SV = 1
414. >tr|E7ETK8|E7ETK8_HUMAN Uncharacterized protein OS = *Homo sapiens* GN = AARS PE = 3 SV = 1
415. >tr|E7ETL9|E7ETL9_HUMAN Uncharacterized protein OS = *Homo sapiens* GN = DDX5 PE = 3 SV = 1

| | |
|---|---|
| 416. | >tr\|E7EU23\|E7EU23_HUMAN Uncharacterized protein OS = *Homo sapiens* GN = GDI2 PE = 4 SV = 1 |
| 417. | >tr\|E7EUT4\|E7EUT4_HUMAN Glyceraldehyde-3-phosphate dehydrogenase OS = *Homo sapiens* GN = GAPDH PE = 3 SV = 1 |
| 418. | >tr\|E7EUY0\|E7EUY0_HUMAN Uncharacterized protein OS = *Homo sapiens* GN = PRKDC PE = 4 SV = 1 |
| 419. | >tr\|E7EVA0\|E7EVA0_HUMAN Microtubule-associated protein OS = *Homo sapiens* GN = MAP4 PE = 4 SV = 1 |
| 420. | >tr\|E7EW92\|E7EW92_HUMAN Ribosomal protein L18 OS = *Homo sapiens* GN = RPL18 PE = 3 SV = 2 |
| 421. | >tr\|E7EWF1\|E7EWF1_HUMAN Uncharacterized protein OS = *Homo sapiens* GN = RPL4 PE = 4 SV = 1 |
| 422. | >tr\|E7EWQ9\|E7EWQ9_HUMAN Uncharacterized protein OS = *Homo sapiens* GN = UTP14A PE = 4 SV = 1 |
| 423. | >tr\|E9KL30\|E9KL30_HUMAN Proteasome subunit beta type OS = *Homo sapiens* PE = 2 SV = 1 |
| 424. | >tr\|E9KL35\|E9KL35_HUMAN Epididymis tissue sperm binding protein Li 3a OS = *Homo sapiens* PE = 2 SV = 1 |
| 425. | >tr\|E9KL39\|E9KL39_HUMAN Epididymis tissue sperm binding protein Li 7e OS = *Homo sapiens* PE = 2 SV = 1 |
| 426. | >tr\|E9KL44\|E9KL44_HUMAN Epididymis tissue sperm binding protein Li 14m OS = *Homo sapiens* PE = 2 SV = 1 |
| 427. | >tr\|E9PAN3\|E9PAN3_HUMAN Protein-L-isoaspartate O-methyltransferase OS = *Homo sapiens* GN = PCMT1 PE = 3 SV = 1 |
| 428. | >tr\|E9PBQ9\|E9PBQ9_HUMAN Uncharacterized protein OS = *Homo sapiens* GN = EEF1D PE = 3 SV = 1 |
| 429. | >tr\|E9PCY7\|E9PCY7_HUMAN Uncharacterized protein OS = *Homo sapiens* GN = HNRNPH1 PE = 4 SV = 1 |
| 430. | >tr\|E9PD78\|E9PD78_HUMAN Ribonucleoside-diphosphate reductase OS = *Homo sapiens* GN = RRM1 PE = 3 SV = 2 |
| 431. | >tr\|E9PDB2\|E9PDB2_HUMAN Uncharacterized protein OS = *Homo sapiens* GN = MDH2 PE = 4 SV = 1 |
| 432. | >tr\|E9PDF3\|E9PDF3_HUMAN Uncharacterized protein OS = *Homo sapiens* GN = RALY PE = 4 SV = 1 |
| 433. | >tr\|E9PDV8\|E9PDV8_HUMAN Glucose-6-phosphate 1-dehydrogenase OS = *Homo sapiens* GN = G6PD PE = 3 SV = 1 |
| 434. | >tr\|E9PE52\|E9PE52_HUMAN Uncharacterized protein OS = *Homo sapiens* GN = RSL1D1 PE = 4 SV = 1 |
| 435. | >tr\|E9PEK6\|E9PEK6_HUMAN Uncharacterized protein OS = *Homo sapiens* GN = CAPRIN1 PE = 4 SV = 2 |
| 436. | >tr\|E9PFF0\|E9PFF0_HUMAN Uncharacterized protein OS = *Homo sapiens* GN = HMGB1 PE = 4 SV = 1 |
| 437. | >tr\|E9PFH8\|E9PFH8_HUMAN Uncharacterized protein OS = *Homo sapiens* GN = SSB PE = 4 SV = 1 |
| 438. | >tr\|E9PFN5\|E9PFN5_HUMAN Uncharacterized protein OS = *Homo sapiens* GN = GSTK1 PE = 4 SV = 1 |
| 439. | >tr\|E9PFU1\|E9PFU1_HUMAN Uncharacterized protein OS = *Homo sapiens* GN = PDCD6IP PE = 4 SV = 1 |
| 440. | >tr\|E9PGZ0\|E9PGZ0_HUMAN Uncharacterized protein OS = *Homo sapiens* GN = CSDE1 PE = 4 SV = 1 |
| 441. | >tr\|E9PIZ3\|E9PIZ3_HUMAN Uncharacterized protein OS = *Homo sapiens* GN = RPL8 PE = 4 SV = 1 |
| 442. | >tr\|E9PJ81\|E9PJ81_HUMAN Uncharacterized protein OS = *Homo sapiens* GN = UBXN1 PE = 4 SV = 1 |
| 443. | >tr\|E9PJA7\|E9PJA7_HUMAN Uncharacterized protein OS = *Homo sapiens* GN = BCLAF1 PE = 4 SV = 1 |
| 444. | >tr\|E9PJD9\|E9PJD9_HUMAN Uncharacterized protein OS = *Homo sapiens* GN = RPL27A PE = 3 SV = 1 |
| 445. | >tr\|E9PK25\|E9PK25_HUMAN Uncharacterized protein OS = *Homo sapiens* GN = CFL1 PE = 4 SV = 1 |
| 446. | >tr\|E9PKD5\|E9PKD5_HUMAN Uncharacterized protein OS = *Homo sapiens* GN = PSMC3 PE = 3 SV = 1 |
| 447. | >tr\|E9PKE3\|E9PKE3_HUMAN Uncharacterized protein OS = *Homo sapiens* GN = HSPA8 PE = 3 SV = 1 |
| 448. | >tr\|E9PL09\|E9PL09_HUMAN Uncharacterized protein OS = *Homo sapiens* GN = RPS3 PE = 3 SV = 1 |
| 449. | >tr\|F2Z393\|F2Z393_HUMAN Uncharacterized protein OS = *Homo sapiens* GN = TALDO1 PE = 4 SV = 1 |
| 450. | >tr\|F2Z3A5\|F2Z3A5_HUMAN Uncharacterized protein OS = *Homo sapiens* GN = RPL3 PE = 4 SV = 1 |
| 451. | >tr\|F2Z3H3\|F2Z3H3_HUMAN Uncharacterized protein OS = *Homo sapiens* GN = ANP32A PE = 4 SV = 2 |
| 452. | >tr\|F5GWQ7\|F5GWQ7_HUMAN Uncharacterized protein OS = *Homo sapiens* GN = TAF15 PE = 4 SV = 1 |
| 453. | >tr\|F5GX11\|F5GX11_HUMAN Uncharacterized protein OS = *Homo sapiens* GN = PSMA1 PE = 4 SV = 1 |
| 454. | >tr\|F5GZ16\|F5GZ16_HUMAN Uncharacterized protein OS = *Homo sapiens* GN = PSMD2 PE = 4 SV = 1 |
| 455. | >tr\|F5H0F5\|F5H0F5_HUMAN Uncharacterized protein OS = *Homo sapiens* GN = ZC3H15 PE = 4 SV = 1 |
| 456. | >tr\|F5H131\|F5H131_HUMAN Uncharacterized protein OS = *Homo sapiens* GN = NUP214 PE = 4 SV = 1 |
| 457. | >tr\|F5H2F4\|F5H2F4_HUMAN Uncharacterized protein OS = *Homo sapiens* GN = MTHFD1 PE = 4 SV = 1 |
| 458. | >tr\|F5H335\|F5H335_HUMAN Uncharacterized protein OS = *Homo sapiens* GN = EIF3A PE = 4 SV = 1 |
| 459. | >tr\|F5H3J2\|F5H3J2_HUMAN Uncharacterized protein OS = *Homo sapiens* GN = NASP PE = 4 SV = 1 |
| 460. | >tr\|F5H3U9\|F5H3U9_HUMAN Uncharacterized protein OS = *Homo sapiens* GN = MAGOHB PE = 4 SV = 1 |
| 461. | >tr\|F5H4D6\|F5H4D6_HUMAN Uncharacterized protein OS = *Homo sapiens* GN = G3BP1 PE = 4 SV = 1 |
| 462. | >tr\|F5H568\|F5H568_HUMAN Uncharacterized protein OS = *Homo sapiens* PE = 4 SV = 1 |
| 463. | >tr\|F5H5W3\|F5H5W3_HUMAN Uncharacterized protein OS = *Homo sapiens* GN = CCT4 PE = 4 SV = 1 |
| 464. | >tr\|F5H6K0\|F5H6K0_HUMAN Uncharacterized protein OS = *Homo sapiens* GN = DHX15 PE = 4 SV = 1 |
| 465. | >tr\|F5H737\|F5H737_HUMAN Uncharacterized protein OS = *Homo sapiens* GN = AHCY PE = 4 SV = 1 |
| 466. | >tr\|F5H7E2\|F5H7E2_HUMAN Uncharacterized protein OS = *Homo sapiens* GN = SKIV2L2 PE = 4 SV = 1 |
| 467. | >tr\|F5H897\|F5H897_HUMAN Uncharacterized protein OS = *Homo sapiens* GN = TRAP1 PE = 4 SV = 1 |
| 468. | >tr\|Q4VC03\|Q4VC03_HUMAN PABPC4 protein OS = *Homo sapiens* GN = PABPC4 PE = 2 SV = 1 |
| 469. | >tr\|Q5TEC6\|Q5TEC6_HUMAN Histone H3 OS = *Homo sapiens* GN = HIST2H3PS2 PE = 3 SV = 1 |
| 470. | >tr\|Q5VU21\|Q5VU21_HUMAN PAI-1 mRNA-binding protein variant OS = *Homo sapiens* GN = SERBP1 PE = 2 SV = 1 |
| 471. | >tr\|Q5VXN0\|Q5VXN0_HUMAN Brix domain containing 1 (Fragment) OS = *Homo sapiens* GN = BXDC1 PE = 2 SV = 1 |
| 472. | >tr\|Q5VY93\|Q5VY93_HUMAN Rho/rac guanine nucleotide exchange factor (GEF) 2 OS = *Homo sapiens* GN = ARHGEF2 PE = 2 SV = 1 |
| 473. | >tr\|Q659C6\|Q659C6_HUMAN Putative uncharacterized protein DKFZp434G0310 (Fragment) OS = *Homo sapiens* GN = DKFZp434G0310 PE = 2 SV = 1 |
| 474. | >tr\|Q9H8T8\|Q9H8T8_HUMAN cDNA FLJ13235 fis, clone OVARC1000304, highly similar to PROTEIN MOV-10 OS = *Homo sapiens* PE = 2 SV = 1 |
| 475. | 10 kDa heat shock protein, mitochondrial (Heat shock 10 kDa protein 1 (Chaperonin 10), isoform CRA_b) |
| 476. | 14-3-3 protein beta/alpha (Protein 1054) (Protein kinase C inhibitor protein 1) (KCIP-1) [Cleaved into: 14-3-3 protein beta/alpha, N-terminally processed] |
| 477. | 14-3-3 protein epsilon (14-3-3E) |
| 478. | 14-3-3 protein eta (Protein AS1) |
| 479. | 14-3-3 protein gamma (Protein kinase C inhibitor protein 1) (KCIP-1) [Cleaved into: 14-3-3 protein gamma, N-terminally processed] |
| 480. | 14-3-3 protein theta (Fragment) |
| 481. | 26S protease regulatory subunit 10B (26S proteasome AAA-ATPase subunit RPT4) (Proteasome 26S subunit ATPase 6) (Proteasome subunit p42) |
| 482. | 26S protease regulatory subunit 4 (P26s4) (26S proteasome AAA-ATPase subunit RPT2) (Proteasome 26S subunit ATPase 1) |
| 483. | 26S protease regulatory subunit 6A |
| 484. | 26S protease regulatory subunit 7 (26S proteasome AAA-ATPase subunit RPT1) (Proteasome 26S subunit ATPase 2) (Protein MSS1) |
| 485. | 26S protease regulatory subunit 8 (26S proteasome AAA-ATPase subunit RPT6) (Proteasome 26S subunit ATPase 5) (Proteasome subunit p45) (Thyroid hormone receptor-interacting protein 1) (TRIP1) (p45/SUG) |
| 486. | 26S proteasome non-ATPase regulatory subunit 1 (26S proteasome regulatory subunit RPN2) (26S proteasome regulatory subunit S1) (26S proteasome subunit p112) |

-continued

| | |
|---|---|
| 487. | 26S proteasome non-ATPase regulatory subunit 11 (26S proteasome regulatory subunit RPN6) (26S proteasome regulatory subunit S9) (26S proteasome regulatory subunit p44.5) |
| 488. | 26S proteasome non-ATPase regulatory subunit 14 (EC 3.4.19.—) (26S proteasome regulatory subunit RPN11) (26S proteasome-associated PAD1 homolog 1) |
| 489. | 26S proteasome non-ATPase regulatory subunit 3 |
| 490. | 26S proteasome non-ATPase regulatory subunit 7 (26S proteasome regulatory subunit RPN8) (26S proteasome regulatory subunit S12) (Mov34 protein homolog) (Proteasome subunit p40) |
| 491. | 28S ribosomal protein S11, mitochondrial (MRP-S11) (S11mt) (Mitochondrial small ribosomal subunit protein uS11m) (Cervical cancer proto-oncogene 2 protein) (HCC-2) |
| 492. | 28S ribosomal protein S16, mitochondrial |
| 493. | 28S ribosomal protein S7, mitochondrial (MRP-S7) (S7mt) (Mitochondrial small ribosomal subunit protein uS7m) (bMRP-27a) (bMRP27a) |
| 494. | 3'(2'),5'-bisphosphate nucleotidase 1 |
| 495. | 39S ribosomal protein L14, mitochondrial (L14mt) (MRP-L14) (39S ribosomal protein L32, mitochondrial) (L32mt) (MRP-L32) (Mitochondrial large ribosomal subunit protein uL14m) |
| 496. | 39S ribosomal protein L15, mitochondrial (L15mt) (MRP-L15) (Mitochondrial large ribosomal subunit protein uL15m) |
| 497. | 39S ribosomal protein L17, mitochondrial (Fragment) |
| 498. | 39S ribosomal protein L19, mitochondrial (L19mt) (MRP-L19) (39S ribosomal protein L15, mitochondrial) (L15mt) (MRP-L15) (Mitochondrial large ribosomal subunit protein bL19m) |
| 499. | 39S ribosomal protein L39, mitochondrial (Fragment) |
| 500. | 39S ribosomal protein L43, mitochondrial |
| 501. | 39S ribosomal protein L45, mitochondrial (L45mt) (MRP-L45) (Mitochondrial large ribosomal subunit protein mL45) |
| 502. | 40S ribosomal protein S10 (Small ribosomal subunit protein eS10) |
| 503. | 40S ribosomal protein S11 (Small ribosomal subunit protein uS17) |
| 504. | 40S ribosomal protein S12 (Small ribosomal subunit protein eS12) |
| 505. | 40S ribosomal protein S13 (Small ribosomal subunit protein uS15) |
| 506. | 40S ribosomal protein S14 (Small ribosomal subunit protein uS11) |
| 507. | 40S ribosomal protein S15 (RIG protein) (Small ribosomal subunit protein uS19) |
| 508. | 40S ribosomal protein S16 (Small ribosomal subunit protein uS9) |
| 509. | 40S ribosomal protein S17 (Small ribosomal subunit protein eS17) |
| 510. | 40S ribosomal protein S18 (Ke-3) (Ke3) (Small ribosomal subunit protein uS13) |
| 511. | 40S ribosomal protein S19 (Ribosomal protein S19, isoform CRA_a) (cDNA, FLJ92047, Homo sapiens ribosomal protein S19 (RPS19), mRNA) |
| 512. | 40S ribosomal protein S2 (40S ribosomal protein S4) (Protein LLRep3) (Small ribosomal subunit protein uS5) |
| 513. | 40S ribosomal protein S21 (Small ribosomal subunit protein eS21) |
| 514. | 40S ribosomal protein S25 (Small ribosomal subunit protein eS25) |
| 515. | 40S ribosomal protein S26 (Small ribosomal subunit protein eS26) |
| 516. | 40S ribosomal protein S27 (Metallopan-stimulin 1) (MPS-1) (Small ribosomal subunit protein eS27) |
| 517. | 40S ribosomal protein S27-like (Small ribosomal subunit protein eS27-like) |
| 518. | 40S ribosomal protein S29 (Small ribosomal subunit protein uS14) |
| 519. | 40S ribosomal protein S3 |
| 520. | 40S ribosomal protein S3 (EC 4.2.99.18) (Small ribosomal subunit protein uS3) |
| 521. | 40S ribosomal protein S30 |
| 522. | 40S ribosomal protein S3a (Small ribosomal subunit protein eS1) (v-fos transformation effector protein) (Fte-1) |
| 523. | 40S ribosomal protein S4 |
| 524. | 40S ribosomal protein S5 (Small ribosomal subunit protein uS7) [Cleaved into: 40S ribosomal protein S5, N-terminally processed] |
| 525. | 40S ribosomal protein S6 |
| 526. | 40S ribosomal protein S7 |
| 527. | 40S ribosomal protein S7 (Small ribosomal subunit protein eS7) |
| 528. | 40S ribosomal protein S8 (Small ribosomal subunit protein eS8) |
| 529. | 40S ribosomal protein SA (Fragment) |
| 530. | 55 kDa erythrocyte membrane protein (p55) (Membrane protein, palmitoylated 1) |
| 531. | 60 kDa heat shock protein, mitochondrial (EC 3.6.4.9) (60 kDa chaperonin) (Chaperonin 60) (CPN60) (Heat shock protein 60) (HSP-60) (Hsp60) (HuCHA60) (Mitochondrial matrix protein P1) (P60 lymphocyte protein) |
| 532. | 60 kDa SS-A/Ro ribonucleoprotein (60 kDa Ro protein) (60 kDa ribonucleoprotein Ro) (RoRNP) (Ro 60 kDa autoantigen) (Sjoegren syndrome antigen A2) (Sjoegren syndrome type A antigen) (SS-A) (TROVE domain family member 2) |
| 533. | 60S acidic ribosomal protein P0 (60S ribosomal protein L10E) (Large ribosomal subunit protein uL10) |
| 534. | 60S acidic ribosomal protein P2 (Large ribosomal subunit protein P2) (Renal carcinoma antigen NY-REN-44) |
| 535. | 60S ribosomal export protein NMD3 |
| 536. | 60S ribosomal protein L10 (Laminin receptor homolog) (Large ribosomal subunit protein uL16) (Protein QM) (Tumor suppressor QM) |
| 537. | 60S ribosomal protein L10a (CSA-19) (Large ribosomal subunit protein uL1) (Neural precursor cell expressed developmentally down-regulated protein 6) (NEDD-6) |
| 538. | 60S ribosomal protein L11 (CLL-associated antigen KW-12) (Large ribosomal subunit protein uL5) |
| 539. | 60S ribosomal protein L12 (Large ribosomal subunit protein uL11) |
| 540. | 60S ribosomal protein L13 |
| 541. | 60S ribosomal protein L13a (23 kDa highly basic protein) (Large ribosomal subunit protein uL13) |
| 542. | 60S ribosomal protein L14 |
| 543. | 60S ribosomal protein L15 (Large ribosomal subunit protein eL15) |
| 544. | 60S ribosomal protein L17 (60S ribosomal protein L23) (Large ribosomal subunit protein uL22) (PD-1) |
| 545. | 60S ribosomal protein L18 (Large ribosomal subunit protein eL18) |
| 546. | 60S ribosomal protein L18a (Large ribosomal subunit protein eL20) |
| 547. | 60S ribosomal protein L19 (Large ribosomal subunit protein eL19) |
| 548. | 60S ribosomal protein L21 (Large ribosomal subunit protein eL21) |
| 549. | 60S ribosomal protein L22 (EBER-associated protein) (EAP) (Epstein-Barr virus small RNA-associated protein) (Heparin-binding protein HBp15) (Large ribosomal subunit protein eL22) |
| 550. | 60S ribosomal protein L23 (60S ribosomal protein L17) (Large ribosomal subunit protein uL14) |
| 551. | 60S ribosomal protein L23a (Ribosomal protein L23a, isoform CRA_a) |
| 552. | 60S ribosomal protein L24 (60S ribosomal protein L30) (Large ribosomal subunit protein eL24) |

| | |
|---|---|
| 553. | 60S ribosomal protein L24 (Ribosomal protein L24, isoform CRA_e) |
| 554. | 60S ribosomal protein L26 (Large ribosomal subunit protein uL24) |
| 555. | 60S ribosomal protein L27 (Large ribosomal subunit protein eL27) |
| 556. | 60S ribosomal protein L27a |
| 557. | 60S ribosomal protein L27a (Large ribosomal subunit protein uL15) |
| 558. | 60S ribosomal protein L29 (Cell surface heparin-binding protein HIP) (Large ribosomal subunit protein eL29) |
| 559. | 60S ribosomal protein L3 (HIV-1 TAR RNA-binding protein B) (TARBP-B) (Large ribosomal subunit protein uL3) |
| 560. | 60S ribosomal protein L30 (Fragment) |
| 561. | 60S ribosomal protein L31 (cDNA FLJ57527, highly similar to 60S ribosomal protein L31) |
| 562. | 60S ribosomal protein L31 (Large ribosomal subunit protein eL31) |
| 563. | 60S ribosomal protein L34 (Large ribosomal subunit protein eL34) |
| 564. | 60S ribosomal protein L35 |
| 565. | 60S ribosomal protein L35 (Large ribosomal subunit protein uL29) |
| 566. | 60S ribosomal protein L35a (Cell growth-inhibiting gene 33 protein) (Large ribosomal subunit protein eL33) |
| 567. | 60S ribosomal protein L36 (Large ribosomal subunit protein eL36) |
| 568. | 60S ribosomal protein L36a (60S ribosomal protein L44) (Cell growth-inhibiting gene 15 protein) (Cell migration-inducing gene 6 protein) (Large ribosomal subunit protein eL42) |
| 569. | 60S ribosomal protein L37 (G1.16) (Large ribosomal subunit protein eL37) |
| 570. | 60S ribosomal protein L37a (Large ribosomal subunit protein eL43) |
| 571. | 60S ribosomal protein L38 (Large ribosomal subunit protein eL38) |
| 572. | 60S ribosomal protein L39 (Large ribosomal subunit protein eL39) |
| 573. | 60S ribosomal protein L4 (60S ribosomal protein L1) (Large ribosomal subunit protein uL4) |
| 574. | 60S ribosomal protein L6 (Large ribosomal subunit protein eL6) (Neoplasm-related protein C140) (Tax-responsive enhancer element-binding protein 107) (TaxREB107) |
| 575. | 60S ribosomal protein L7 (Large ribosomal subunit protein uL30) |
| 576. | 60S ribosomal protein L7-like 1 (Large ribosomal subunit protein uL30-like 1) |
| 577. | 60S ribosomal protein L7a (Large ribosomal subunit protein eL8) (PLA-X polypeptide) (Surfeit locus protein 3) |
| 578. | 60S ribosomal protein L8 (Large ribosomal subunit protein uL2) |
| 579. | 60S ribosomal protein L9 (Fragment) |
| 580. | 60S ribosomal protein L9 (Large ribosomal subunit protein uL6) |
| 581. | 60S ribosome subunit biogenesis protein NIP7 homolog (KD93) |
| 582. | 78 kDa glucose-regulated protein (GRP-78) (Endoplasmic reticulum lumenal Ca(2+)-binding protein grp78) (Heat shock 70 kDa protein 5) (Immunoglobulin heavy chain-binding protein) (BiP) |
| 583. | Acetyl-CoA acetyltransferase, cytosolic (EC 2.3.1.9) (Acetyl-CoA transferase-like protein) (Cytosolic acetoacetyl-CoA thiolase) |
| 584. | Acetyl-CoA acetyltransferase, mitochondrial (EC 2.3.1.9) (Acetoacetyl-CoA thiolase) (T2) |
| 585. | Acetyl-Coenzyme A carboxylase alpha (HCG30204, isoform CRA_b) |
| 586. | Acetyltransferase component of pyruvate dehydrogenase complex (EC 2.3.1.12) |
| 587. | Acidic leucine-rich nuclear phosphoprotein 32 family member B (Acidic protein rich in leucines) (Putative HLA-DR-associated protein 1-2) (PHAPI2) (Silver-stainable protein SSP29) |
| 588. | Acidic leucine-rich nuclear phosphoprotein 32 family member E (Fragment) |
| 589. | Aconitate hydratase, mitochondrial |
| 590. | Actin related protein 2/3 complex, subunit 1B, 41 kDa (Actin related protein 2/3 complex, subunit 1B, 41 kDa, isoform CRA_a) (cDNA, FLJ95695, *Homo sapiens* actin related protein 2/3 complex, subunit 1B, 41 kDa(ARPC1B), mRNA) |
| 591. | Actin-like protein 6A (53 kDa BRG1-associated factor A) (Actin-related protein Baf53a) (ArpNbeta) (BRG1-associated factor 53A) (BAF53A) (INO80 complex subunit K) |
| 592. | Actin-related protein 2/3 complex subunit 5 (Arp2/3 complex 16 kDa subunit) (p16-ARC) |
| 593. | Actin, alpha 2, smooth muscle, aorta (Actin, alpha 2, smooth muscle, aorta, isoform CRA_a) |
| 594. | Actin, cytoplasmic 1 (Beta-actin) [Cleaved into: Actin, cytoplasmic 1, N-terminally processed] |
| 595. | Activated RNA polymerase II transcriptional coactivator p15 (Positive cofactor 4) (PC4) (SUB1 homolog) (p14) |
| 596. | Adenine phosphoribosyltransferase (APRT) (EC 2.4.2.7) |
| 597. | Adenosylhomocysteinase (AdoHcyase) (EC 3.3.1.1) (S-adenosyl-L-homocysteine hydrolase) |
| 598. | Adenylate kinase 2, mitochondrial (AK 2) (EC 2.7.4.3) (ATP-AMP transphosphorylase 2) (ATP:AMP phosphotransferase) (Adenylate monophosphate kinase) [Cleaved into: Adenylate kinase 2, mitochondrial, N-terminally processed] |
| 599. | Adenylosuccinate lyase (ADSL) (ASL) (EC 4.3.2.2) (Adenylosuccinase) (ASase) |
| 600. | Adenylosuccinate synthetase isozyme 2 (AMPSase 2) (AdSS 2) (EC 6.3.4.4) (Adenylosuccinate synthetase, acidic isozyme) (Adenylosuccinate synthetase, liver isozyme) (L-type adenylosuccinate synthetase) (IMP--aspartate ligase 2) |
| 601. | ADP-ribosylation factor 5 (ADP-ribosylation factor 5, isoform CRA_a) (cDNA, FLJ92389, *Homo sapiens* ADP-ribosylation factor 5 (ARF5), mRNA) |
| 602. | ADP-sugar pyrophosphatase |
| 603. | ADP/ATP translocase 2 (ADP, ATP carrier protein 2) (ADP, ATP carrier protein, fibroblast isoform) (Adenine nucleotide translocator 2) (ANT 2) (Solute carrier family 25 member 5) [Cleaved into: ADP/ATP translocase 2, N-terminally processed] |
| 604. | Alanine--tRNA ligase, cytoplasmic (EC 6.1.1.7) (Alanyl-tRNA synthetase) (AlaRS) (Renal carcinoma antigen NY-REN-42) |
| 605. | Alcohol dehydrogenase class-3 (EC 1.1.1.1) (Alcohol dehydrogenase 5) (Alcohol dehydrogenase class chi chain) (Alcohol dehydrogenase class-III) (Glutathione-dependent formaldehyde dehydrogenase) (FALDH) (FDH) (GSH-FDH) (EC 1.1.1.—) (S-(hydroxymethyl)glutathione dehydrogenase) (EC 1.1.1.284) |
| 606. | Aldo-keto reductase family 1 member C1 (EC 1.1.1.—) (20-alpha-hydroxysteroid dehydrogenase) (20-alpha-HSD) (EC 1.1.1.149) (Chlordecone reductase homolog HAKRC) (Dihydrodiol dehydrogenase 1/2) (DD1/DD2) (High-affinity hepatic bile acid-binding protein) (HBAB) (Indanol dehydrogenase) (EC 1.1.1.112) (Trans-1,2-dihydrobenzene-1,2-diol dehydrogenase) (EC 1.3.1.20) |
| 607. | Aldo-keto reductase family 1 member C2 (cDNA FLJ52680, highly similar to Aldo-keto reductase family 1 member C2 (EC 1.—.—.—)) |
| 608. | Alpha-2 globin chain (Delta globin) (HCG1745306, isoform CRA_b) |
| 609. | Alpha-2-HS-glycoprotein |
| 610. | Alpha-actinin-1 (Alpha-actinin cytoskeletal isoform) (F-actin cross-linking protein) (Non-muscle alpha-actinin-1) |
| 611. | Alpha-actinin-4 (Non-muscle alpha-actinin 4) |
| 612. | Alpha-enolase (EC 4.2.1.11) (2-phospho-D-glycerate hydro-lyase) (C-myc promoter-binding protein) (Enolase 1) (MBP-1) (MPB-1) (Non-neural enolase) (NNE) (Phosphopyruvate hydratase) (Plasminogen-binding protein) |
| 613. | Amidophosphoribosyltransferase (ATase) (EC 2.4.2.14) (Glutamine phosphoribosylpyrophosphate amidotransferase) |
| 614. | Aminoacyl tRNA synthase complex-interacting multifunctional protein 1 (Multisynthase complex auxiliary component p43) [Cleaved into: Endothelial monocyte-activating polypeptide 2 (EMAP-2) (Endothelial monocyte-activating polypeptide II) (EMAP-II) (Small inducible cytokine subfamily E member 1)] |

-continued

| | |
|---|---|
| 615. | Aminoacyl tRNA synthase complex-interacting multifunctional protein 2 (Multisynthase complex auxiliary component p38) (Protein JTV-1) |
| 616. | Anamorsin (Cytokine-induced apoptosis inhibitor 1) (Fe—S cluster assembly protein DRE2 homolog) |
| 617. | Anaphase-promoting complex subunit 7 (APC7) (Cyclosome subunit 7) |
| 618. | Ankyrin repeat domain-containing protein 20A4 |
| 619. | Annexin A1 (Annexin I) (Annexin-1) (Calpactin II) (Calpactin-2) (Chromobindin-9) (Lipocortin I) (Phospholipase A2 inhibitory protein) (p35) |
| 620. | Annexin A2 (Annexin II) (Annexin-2) (Calpactin I heavy chain) (Calpactin-1 heavy chain) (Chromobindin-8) (Lipocortin II) (Placental anticoagulant protein IV) (PAP-IV) (Protein I) (p36) |
| 621. | Annexin A7 (Annexin VII) (Annexin-7) (Synexin) |
| 622. | AP-2 complex subunit alpha-1 (100 kDa coated vesicle protein A) (Adaptor protein complex AP-2 subunit alpha-1) (Adaptor-related protein complex 2 subunit alpha-1) (Alpha-adaptin A) (Alpha1-adaptin) (Clathrin assembly protein complex 2 alpha-A large chain) (Plasma membrane adaptor HA2/AP2 adaptin alpha A subunit) |
| 623. | AP-2 complex subunit beta (AP105B) (Adaptor protein complex AP-2 subunit beta) (Adaptor-related protein complex 2 subunit beta) (Beta-2-adaptin) (Beta-adaptin) (Clathrin assembly protein complex 2 beta large chain) (Plasma membrane adaptor HA2/AP2 adaptin beta subunit) |
| 624. | AP-2 complex subunit mu |
| 625. | Apolipoprotein B mRNA editing enzyme, catalytic polypeptide-like 3C variant (Fragment) |
| 626. | Apolipoprotein D (Fragment) |
| 627. | Apoptosis-inducing factor 1, mitochondrial (EC 1.1.1.—) (Programmed cell death protein 8) |
| 628. | Apoptotic chromatin condensation inducer in the nucleus |
| 629. | Arachidonate 12-lipoxygenase, 12R-type (12R-LOX) (12R-lipoxygenase) (EC 1.13.11.—) (Epidermis-type lipoxygenase 12) |
| 630. | Arginase-1 (EC 3.5.3.1) (Liver-type arginase) (Type I arginase) |
| 631. | Arginine--tRNA ligase, cytoplasmic (EC 6.1.1.19) (Arginyl-tRNA synthetase) (ArgRS) |
| 632. | Asparagine--tRNA ligase, cytoplasmic (EC 6.1.1.22) (Asparaginyl-tRNA synthetase) (AsnRS) |
| 633. | Aspartate aminotransferase, cytoplasmic (cAspAT) (EC 2.6.1.1) (EC 2.6.1.3) (Cysteine aminotransferase, cytoplasmic) (Cysteine transaminase, cytoplasmic) (cCAT) (Glutamate oxaloacetate transaminase 1) (Transaminase A) |
| 634. | Aspartate--tRNA ligase, cytoplasmic (EC 6.1.1.12) (Aspartyl-tRNA synthetase) (AspRS) (Cell proliferation-inducing gene 40 protein) |
| 635. | ATP synthase F(0) complex subunit B1, mitochondrial (ATP synthase proton-transporting mitochondrial F(0) complex subunit B1) (ATP synthase subunit b) (ATPase subunit b) |
| 636. | ATP synthase subunit alpha, mitochondrial |
| 637. | ATP synthase subunit beta, mitochondrial (EC 3.6.3.14) |
| 638. | ATP synthase subunit d, mitochondrial |
| 639. | ATP synthase subunit gamma, mitochondrial (F-ATPase gamma subunit) |
| 640. | ATP synthase subunit 0, mitochondrial (Oligomycin sensitivity conferral protein) (OSCP) |
| 641. | ATP-binding cassette sub-family E member 1 |
| 642. | ATP-binding cassette sub-family E member 1 (2'-5'-oligoadenylate-binding protein) (HuHP68) (RNase L inhibitor) (Ribonuclease 4 inhibitor) (RNS4I) |
| 643. | ATP-dependent 6-phosphofructokinase, platelet type (ATP-PFK) (PFK-P) (EC 2.7.1.11) (6-phosphofructokinase type C) (Phosphofructo-1-kinase isozyme C) (PFK-C) (Phosphohexokinase) |
| 644. | ATP-dependent RNA helicase A (RHA) (EC 3.6.4.13) (DEAH box protein 9) (Leukophysin) (LKP) (Nuclear DNA helicase II) (NDHII) |
| 645. | ATP-dependent RNA helicase DDX1 (DEAD (Asp-Glu-Ala-Asp) box polypeptide 1, isoform CRA_d) (DEAD box polypeptide 1) (cDNA, FLJ94573, *Homo sapiens* DEAD (Asp-Glu-Ala-Asp) box polypeptide 1 (DDX1), mRNA) |
| 646. | ATP-dependent RNA helicase DDX18 (EC 3.6.4.13) (DEAD box protein 18) (Myc-regulated DEAD box protein) (MrDb) |
| 647. | ATP-dependent RNA helicase DDX19A (EC 3.6.4.13) (DDX19-like protein) (DEAD box protein 19A) |
| 648. | ATP-dependent RNA helicase DDX39A (EC 3.6.4.13) (DEAD box protein 39) (Nuclear RNA helicase URH49) |
| 649. | ATP-dependent RNA helicase DDX3X (EC 3.6.4.13) (DEAD box protein 3, X-chromosomal) (DEAD box, X isoform) (Helicase-like protein 2) (HLP2) |
| 650. | ATP-dependent RNA helicase DDX54 (EC 3.6.4.13) (ATP-dependent RNA helicase DP97) (DEAD box RNA helicase 97 kDa) (DEAD box protein 54) |
| 651. | BAG family molecular chaperone regulator 2 (BAG-2) (Bcl-2-associated athanogene 2) |
| 652. | Barrier-to-autointegration factor (Breakpoint cluster region protein 1) [Cleaved into: Barrier-to-autointegration factor, N-terminally processed] |
| 653. | Bcl-2-associated transcription factor 1 |
| 654. | Bifunctional coenzyme A synthase (CoA synthase) (NBP) (POV-2) [Includes: Phosphopantetheine adenylyltransferase (EC 2.7.7.3) (Dephospho-CoA pyrophosphorylase) (Pantetheine-phosphate adenylyltransferase) (PPAT); Dephospho-CoA kinase (DPCK) (EC 2.7.1.24) (Dephosphocoenzyme A kinase) (DPCOAK)] |
| 655. | Bifunctional glutamate/proline--tRNA ligase (Bifunctional aminoacyl-tRNA synthetase) (Cell proliferation-inducing gene 32 protein) (Glutamatyl-prolyl-tRNA synthetase) [Includes: Glutamate--tRNA ligase (EC 6.1.1.17) (Glutamyl-tRNA synthetase) (GluRS); Proline--tRNA ligase (EC 6.1.1.15) (Prolyl-tRNA synthetase)] |
| 656. | Bifunctional purine biosynthesis protein PURH [Cleaved into: Bifunctional purine biosynthesis protein PURH, N-terminally processed] [Includes: Phosphoribosylaminoimidazolecarboxamide formyltransferase (EC 2.1.2.3) (5-aminoimidazole-4-carboxamide ribonucleotide formyltransferase) (AICAR transformylase); IMP cyclohydrolase (EC 3.5.4.10) (ATIC) (IMP synthase) (Inosinicase)] |
| 657. | Biliverdin reductase A (BVR A) (EC 1.3.1.24) (Biliverdin-IX alpha-reductase) |
| 658. | BolA-like protein 2 |
| 659. | Bystin |
| 660. | C-1-tetrahydrofolate synthase, cytoplasmic |
| 661. | C-terminal-binding protein 1 (Fragment) |
| 662. | C-type lysozyme (Lysozyme) (EC 3.2.1.17) (Lysozyme (Renal amyloidosis), isoform CRA_a) (Lysozyme F1) (cDNA, FLJ92040, *Homo sapiens* lysozyme (renal amyloidosis) (LYZ), mRNA) |
| 663. | CAD protein [Includes: Glutamine-dependent carbamoyl-phosphate synthase (EC 6.3.5.5); Aspartate carbamoyltransferase (EC 2.1.3.2); Dihydroorotase (EC 3.5.2.3)] |
| 664. | Calcium homeostasis endoplasmic reticulum protein (ERPROT 213-21) (SR-related CTD-associated factor 6) |
| 665. | Calmodulin 1 (Phosphorylase kinase, delta), isoform CRA_a (Calmodulin 3 (Phosphorylase kinase, delta), isoform CRA_b) (Epididymis secretory protein Li 72) (cDNA FLJ61744, highly similar to Calmodulin) |
| 666. | Calmodulin-like protein 5 (Calmodulin-like skin protein) |
| 667. | Calpain-1 catalytic subunit (Fragment) |
| 668. | Calreticulin (CRP55) (Calregulin) (Endoplasmic reticulum resident protein 60) (ERp60) (HACBP) (grp60) |

-continued 669. cAMP-dependent protein kinase type II-alpha regulatory subunit
670. cAMP-specific 3',5'-cyclic phosphodiesterase 4D (EC 3.1.4.53) (DPDE3) (PDE43)
671. Carboxymethylenebutenolidase homolog (EC 3.1.—.—)
672. Carboxypeptidase A4 (Carboxypeptidase A4, isoform CRA_a) (cDNA FLJ75086, highly similar to Homo sapiens carboxypeptidase A4, mRNA)
673. Cas scaffolding protein family member 4 (HEF-like protein) (HEF1-EFS-p130Cas-like protein) (HEPL)
674. Caspase 14, apoptosis-related cysteine peptidase (Caspase-14) (cDNA, FLJ94644, Homo sapiens caspase 14, apoptosis-related cysteine protease(CASP14), mRNA)
675. Catalase (EC 1.11.1.6)
676. Catechol O-methyltransferase (EC 2.1.1.6)
677. Cathepsin D (EC 3.4.23.5) [Cleaved into: Cathepsin D light chain; Cathepsin D heavy chain]
678. CD2-associated protein (Adapter protein CMS) (Cas ligand with multiple SH3 domains)
679. cDNA FLJ38868 fis, clone MESAN2013211, highly similar to Protein FAM98A
680. cDNA FLJ44468 fis, clone UTERU2026025, moderately similar to SPLICING FACTOR, ARGININE/SERINE-RICH 2
681. cDNA FLJ50653, highly similar to Rattus norvegicus CUG triplet repeat, RNA binding protein 2 (Cugbp2), mRNA (cDNA FLJ52051, highly similar to Rattus norvegicus CUG triplet repeat, RNA binding protein 2 (Cugbp2), mRNA)
682. cDNA FLJ51512, highly similar to Periodic tryptophan protein 1 homolog
683. cDNA FLJ52068, highly similar to Microtubule-associated protein RP/EB family member 1
684. cDNA FLJ52137, moderately similar to Glioma tumor suppressor candidate region gene 2 protein
685. cDNA FLJ52243, highly similar to Heat-shock protein beta-1
686. cDNA FLJ52842, highly similar to Actin, cytoplasmic 1
687. cDNA FLJ53122, highly similar to ATP-dependent RNA helicase DDX3Y (EC 3.6.1.—)
688. cDNA FLJ53425, highly similar to Far upstream element-binding protein 1
689. cDNA FLJ54020, highly similar to Heterogeneous nuclear ribonucleoprotein U
690. cDNA FLJ54552, highly similar to Heterogeneous nuclear ribonucleoprotein K
691. cDNA FLJ57690, highly similar to WD repeat protein 74
692. cDNA FLJ58049, highly similar to RNA-binding protein FUS
693. cDNA FLJ58065, highly similar to LIM and SH3 domain protein 1
694. cDNA FLJ59402, highly similar to Eukaryotic translation initiation factor 4B
695. cDNA FLJ60461, highly similar to Peroxiredoxin-2 (EC 1.11.1.15)
696. CDW11/WDR57 (WD repeat domain 57 (U5 snRNP specific), isoform CRA_a) (cDNA FLJ90035 fis, clone HEMBA1001878, highly similar to WD repeat protein 57)
697. CDW3/SMU1 (Smu-1 suppressor of mec-8 and unc-52 homolog (C. elegans), isoform CRA_a)
698. Cell cycle and apoptosis regulator protein 2 (Cell division cycle and apoptosis regulator protein 2) (DBIRD complex subunit KIAA1967) (Deleted in breast cancer gene 1 protein) (DBC-1) (DBC.1) (NET35) (p30 DBC)
699. Cell growth-regulating nucleolar protein
700. Chloride intracellular channel protein 1 (Chloride channel ABP) (Nuclear chloride ion channel 27) (NCC27) (Regulatory nuclear chloride ion channel protein) (hRNCC)
701. Chromatin target of PRMT1 protein
702. Chromobox homolog 3 (HP1 gamma homolog Drosophila) (Chromobox homolog 3 (HP1 gamma homolog Drosophila), isoform CRA_a) (Coiled-coil domain containing 32, isoform CRA_c)
703. Chromodomain-helicase-DNA-binding protein 4
704. Citrate synthase, mitochondrial (EC 2.3.3.1) (Citrate (Si)-synthase)
705. Clathrin heavy chain 1 (Clathrin heavy chain on chromosome 17) (CLH-17)
706. CLE7 (Chromosome 14 open reading frame 166, isoform CRA_a) (Lcrp369) (cDNA, FLJ92278)
707. Cleavage and polyadenylation specificity factor subunit 5 (Cleavage and polyadenylation specificity factor 25 kDa subunit) (CFIm25) (CPSF 25 kDa subunit) (Nucleoside diphosphate-linked moiety X motif 21) (Nudix motif 21) (Pre-mRNA cleavage factor Im 25 kDa subunit)
708. Cleavage and polyadenylation-specificity factor subunit 7 (Fragment)
709. Coatomer subunit alpha (Alpha-coat protein) (Alpha-COP) (HEP-COP) (HEPCOP) [Cleaved into: Xenin (Xenopsin-related peptide); Proxenin]
710. Coatomer subunit beta (Beta-coat protein) (Beta-COP)
711. Coatomer subunit delta
712. Coatomer subunit gamma-1 (Gamma-1-coat protein) (Gamma-1-COP)
713. Coatomer subunit zeta-1 (Zeta-1-coat protein) (Zeta-1 COP)
714. Cofilin-1
715. Coiled-coil domain-containing protein 124
716. Coiled-coil domain-containing protein 86 (Cytokine-induced protein with coiled-coil domain)
717. COMM domain-containing protein 8
718. Complex III assembly factor LYRM7 (LYR motif-containing protein 7)
719. Condensin complex subunit 3 (Chromosome-associated protein G) (Condensin subunit CAP-G) (hCAP-G) (Melanoma antigen NY-MEL-3) (Non-SMC condensin I complex subunit G) (XCAP-G homolog)
720. COP9 signalosome complex subunit 2 (SGN2) (Signalosome subunit 2) (Alien homolog) (JAB1-containing signalosome subunit 2) (Thyroid receptor-interacting protein 15) (TR-interacting protein 15) (TRIP-15)
721. Copine-3 (Copine III)
722. Core histone macro-H2A.1 (Histone macroH2A1) (mH2A1) (Histone H2A.y) (H2A/y) (Medulloblastoma antigen MU-MB-50.205)
723. Corneodesmosin
724. Cornifin-B (14.9 kDa pancornulin) (Small proline-rich protein IB) (SPR-IB)
725. Coronin-1B (Coronin-2)
726. Creatine kinase B-type (EC 2.7.3.2) (B-CK) (Creatine kinase B chain)
727. CRISPR-associated endonuclease Cas9 (EC 3.1.—.—) (SaCas9)
728. Crk-like protein
729. CUGBP Elav-like family member 1 (CELF-1) (50 kDa nuclear polyadenylated RNA-binding protein) (Bruno-like protein 2) (CUG triplet repeat RNA-binding protein 1) (CUG-BP1) (CUG-BP- and ETR-3-like factor 1) (Deadenylation factor CUG-BP) (Embryo deadenylation element-binding protein homolog) (EDEN-BP homolog) (RNA-binding protein BRUNOL-2)
730. Cullin-5 (CUL-5) (Vasopressin-activated calcium-mobilizing receptor 1) (VACM-1)
731. Cullin-associated NEDD8-dissociated protein 1 (Cullin-associated and neddylation-dissociated protein 1) (TBP-interacting protein of 120 kDa A) (TBP-interacting protein 120A) (p120 CAND1)

732. Cyclin-dependent kinase 1 (CDK1) (EC 2.7.11.22) (EC 2.7.11.23) (Cell division control protein 2 homolog) (Cell division protein kinase 1) (p34 protein kinase)
733. Cyclin-dependent kinase 1 (Fragment)
734. Cyclin-dependent kinase 2
735. Cystatin-A
736. Cystatin-B (CPI-B) (Liver thiol proteinase inhibitor) (Stefin-B)
737. Cysteine and histidine-rich domain-containing protein 1 (CHORD domain-containing protein 1) (CHORD-containing protein 1) (CHP-1) (Protein morgana)
738. Cysteinyl-tRNA synthetase, isoform CRA_b (cDNA FLJ38994 fis, clone NT2RI2009259, highly similar to Cysteinyl-tRNA synthetase (EC 6.1.1.16))
739. Cytochrome b-c1 complex subunit 1, mitochondrial (Complex III subunit 1) (Core protein I) (Ubiquinol-cytochrome-c reductase complex core protein 1)
740. Cytochrome b-c1 complex subunit 2, mitochondrial (Complex III subunit 2) (Core protein II) (Ubiquinol-cytochrome-c reductase complex core protein 2)
741. Cytochrome b-c1 complex subunit 7 (cDNA FLJ52271, moderately similar to Ubiquinol-cytochrome c reductase complex 14 kDa protein (EC 1.10.2.2))
742. Cytochrome c (Fragment)
743. Cytochrome c oxidase subunit 2 (Cytochrome c oxidase polypeptide II)
744. Cytochrome c oxidase subunit 5B, mitochondrial (Cytochrome c oxidase polypeptide Vb)
745. Cytochrome c1, heme protein, mitochondrial (Complex III subunit 4) (Complex III subunit IV) (Cytochrome b-c1 complex subunit 4) (Ubiquinol-cytochrome-c reductase complex cytochrome c1 subunit) (Cytochrome c-1)
746. Cytoplasmic dynein 1 heavy chain 1 (Cytoplasmic dynein heavy chain 1) (Dynein heavy chain, cytosolic)
747. Cytoskeleton-associated protein 5 (Colonic and hepatic tumor overexpressed gene protein) (Ch-TOG)
748. Cytosol aminopeptidase (EC 3.4.11.1) (Leucine aminopeptidase 3) (LAP-3) (Leucyl aminopeptidase) (Peptidase S) (Proline aminopeptidase) (EC 3.4.11.5) (Prolyl aminopeptidase)
749. DAZ-associated protein 1 (Deleted in azoospermia-associated protein 1)
750. Delta-1-pyrroline-5-carboxylate synthase (P5CS) (Aldehyde dehydrogenase family 18 member A1) [Includes: Glutamate 5-kinase (GK) (EC 2.7.2.11) (Gamma-glutamyl kinase); Gamma-glutamyl phosphate reductase (GPR) (EC 1.2.1.41) (Glutamate-5-semialdehyde dehydrogenase) (Glutamyl-gamma-semialdehyde dehydrogenase)]
751. Desmocollin-1 (Cadherin family member 1) (Desmosomal glycoprotein 2/3) (DG2/DG3)
752. Desmocollin-3 (Cadherin family member 3) (Desmocollin-4) (HT-CP)
753. Desmoglein-1 (Cadherin family member 4) (Desmosomal glycoprotein 1) (DG1) (DGI) (Pemphigus foliaceus antigen)
754. Desmoplakin (DP) (250/210 kDa paraneoplastic pemphigus antigen)
755. Diablo homolog mitochondrial (Fragment)
756. Dihydrofolate reductase (EC 1.5.1.3) (cDNA, FLJ93028, *Homo sapiens* dihydrofolate reductase (DHFR), mRNA)
757. DNA helicase (EC 3.6.4.12)
758. DNA mismatch repair protein Msh6 (hMSH6) (G/T mismatch-binding protein) (GTBP) (GTMBP) (MutS protein homolog 6) (MutS-alpha 160 kDa subunit) (p160)
759. DNA repair protein RAD50 (hRAD50) (EC 3.6.—.—)
760. DNA replication licensing factor MCM6 (EC 3.6.4.12) (p105MCM)
761. DNA replication licensing factor MCM7 (EC 3.6.4.12) (CDC47 homolog) (P1.1-MCM3)
762. DNA topoisomerase (EC 5.99.1.2)
763. DNA topoisomerase 1 (EC 5.99.1.2) (DNA topoisomerase I)
764. DNA-(apurinic or apyrimidinic site) lyase (EC 3.1.—.—) (EC 4.2.99.18) (APEX nuclease) (APEN) (Apurinic-apyrimidinic endonuclease 1) (AP endonuclease 1) (APE-1) (REF-1) (Redox factor-1) [Cleaved into: DNA-(apurinic or apyrimidinic site) lyase, mitochondrial]
765. DNA-directed RNA polymerase subunit beta (EC 2.7.7.6)
766. DNA-directed RNA polymerases I and III subunit RPAC1
767. DnaJ homolog subfamily A member 1 (DnaJ protein homolog 2) (HSDJ) (Heat shock 40 kDa protein 4) (Heat shock protein J2) (HSJ-2) (Human DnaJ protein 2) (hDj-2)
768. DnaJ homolog subfamily B member 1 (DnaJ protein homolog 1) (Heat shock 40 kDa protein 1) (HSP40) (Heat shock protein 40) (Human DnaJ protein 1) (hDj-1)
769. DnaJ homolog subfamily C member 2 (M-phase phosphoprotein 11) (Zuotin-related factor 1) [Cleaved into: DnaJ homolog subfamily C member 2, N-terminally processed]
770. DnaJ homolog subfamily C member 8 (Splicing protein spf31)
771. Dolichyl-diphosphooligosaccharide--protein glycosyltransferase 48 kDa subunit (DDOST 48 kDa subunit) (Oligosaccharyl transferase 48 kDa subunit) (EC 2.4.99.18)
772. Dolichyl-diphosphooligosaccharide--protein glycosyltransferase subunit 1 (EC 2.4.99.18) (Dolichyl-diphosphooligosaccharide--protein glycosyltransferase 67 kDa subunit) (Ribophorin I) (RPN-I) (Ribophorin-1)
773. Dolichyl-diphosphooligosaccharide--protein glycosyltransferase subunit 2 (EC 2.4.99.18) (Dolichyl-diphosphooligosaccharide--protein glycosyltransferase 63 kDa subunit) (RIBIIR) (Ribophorin II) (RPN-II) (Ribophorin-2)
774. Double-stranded RNA-binding protein Staufen homolog 2 (Fragment)
775. Doublesex- and mab-3-related transcription factor A1
776. Dynactin 2 (P50), isoform CRA_b (cDNA FLJ31120 fis, clone IMR322000730, highly similar to Dynactin subunit 2) (cDNA FLJ77785)
777. Dynamin 1-like, isoform CRA_f
778. Dynein light chain 1, cytoplasmic (8 kDa dynein light chain) (DLC8) (Dynein light chain LC8-type 1) (Protein inhibitor of neuronal nitric oxide synthase) (PIN)
779. E3 SUMO-protein ligase RanBP2 (EC 6.3.2.—) (358 kDa nucleoporin) (Nuclear pore complex protein Nup358) (Nucleoporin Nup358) (Ran-binding protein 2) (RanBP2) (p270)
780. E3 ubiquitin-protein ligase CHIP (EC 2.3.2.27) (Antigen NY-CO-7) (CLL-associated antigen KW-8) (Carboxy terminus of Hsp70-interacting protein) (RING-type E3 ubiquitin transferase CHIP) (STIP1 homology and U box-containing protein 1)
781. E3 ubiquitin-protein ligase RBBP6 (EC 2.3.2.27) (Proliferation potential-related protein) (Protein P2P-R) (RING-type E3 ubiquitin transferase RBBP6) (Retinoblastoma-binding Q protein 1) (RBQ-1) (Retinoblastoma-binding protein 6) (p53-associated cellular protein of testis)
782. E3 ubiquitin-protein ligase UBR4 (EC 2.3.2.27) (600 kDa retinoblastoma protein-associated factor) (N-recognin-4) (RING-type E3 ubiquitin transferase UBR4) (Retinoblastoma-associated factor of 600 kDa) (RBAF600) (p600) (Zinc finger UBR1-type protein 1)
783. EBNA1 binding protein 2 (EBNA1 binding protein 2 variant) (EBNA1 binding protein 2, isoform CRA_a) (EBNA1BP2 protein)
784. EH-domain containing 1, isoform CRA_b (cDNA FLJ40523 fis, clone TESTI2046872, highly similar to EH-domain-containing protein 1) (cDNA, FLJ92624, highly similar to *Homo sapiens* EH-domain containing 1 (EHD1), mRNA)

-continued 785. eIF-2-alpha kinase activator GCN1 (GCN1 eIF-2-alpha kinase activator homolog) (GCN1-like protein 1) (General control of amino-acid synthesis 1-like protein 1) (Translational activator GCN1) (HsGCN1)
786. Electron transfer flavoprotein subunit alpha, mitochondrial (Alpha-ETF)
787. Electron transfer flavoprotein subunit beta (Beta-ETF)
788. Elongation factor 1-alpha 1 (EF-1-alpha-1) (Elongation factor Tu) (EF-Tu) (Eukaryotic elongation factor 1 A-1) (eEF1A-1) (Leukocyte receptor cluster member 7)
789. Elongation factor 1-beta (EF-1-beta)
790. Elongation factor 1-delta
791. Elongation factor 1-delta (Fragment)
792. Elongation factor 2 (EF-2)
793. Elongation factor G, mitochondrial
794. Elongation factor Tu, mitochondrial (EF-Tu) (P43)
795. Emerin
796. Endoplasmic reticulum resident protein 29 (ERp29) (Endoplasmic reticulum resident protein 28) (ERp28) (Endoplasmic reticulum resident protein 31) (ERp31)
797. Endoplasmin (94 kDa glucose-regulated protein) (GRP-94) (Heat shock protein 90 kDa beta member 1) (Tumor rejection antigen 1) (gp96 homolog)
798. Endothelial differentiation-related factor 1 (EDF-1) (Multiprotein-bridging factor 1) (MBF1)
799. Enhancer of mRNA-decapping protein 4 (Autoantigen Ge-1) (Autoantigen RCD-8) (Human enhancer of decapping large subunit) (Hedls)
800. Enhancer of rudimentary homolog
801. Enoyl-CoA delta isomerase 1, mitochondrial (EC 5.3.3.8) (3,2-trans-enoyl-CoA isomerase) (Delta(3),Delta(2)-enoyl-CoA isomerase) (D3,D2-enoyl-CoA isomerase) (Dodecenoyl-CoA isomerase)
802. Epidermal growth factor receptor substrate 15
803. Epidermal growth factor receptor substrate 15-like 1 (Eps15-related protein) (Eps15R)
804. Epididymis luminal protein 112 (Ribosomal protein S27a, isoform CRA_c) (cDNA, FLJ96793, Homo sapiens ribosomal protein S27a (RPS27A), mRNA)
805. Epididymis luminal protein 4 (Epididymis secretory protein Li 3) (Epididymis secretory protein Li 93) (Tyrosine 3-monooxygenase/tryptophan 5-monooxygenase activation protein zeta polypeptide) (Tyrosine 3-monooxygenase/tryptophan 5-monooxygenase activation protein, zeta polypeptide, isoform CRA_a)
806. Epididymis secretory protein Li 103 (Heat shock 70 kDa protein 1A) (Heat shock 70 kDa protein 1B) (cDNA FLJ75127, highly similar to Homo sapiens heat shock 70 kDa protein 1A, mRNA)
807. Epididymis tissue sperm binding protein Li 18mP (Glutamate dehydrogenase 1, isoform CRA_d)
808. ER membrane protein complex subunit 1
809. ES1 protein homolog mitochondrial (Protein GT335) (Protein KNP-I)
810. Eukaryotic initiation factor 4A-I (eIF-4A-I) (eIF4A-I) (EC 3.6.4.13) (ATP-dependent RNA helicase eIF4A-1)
811. Eukaryotic initiation factor 4A-III (eIF-4A-III) (eIF4A-III) (EC 3.6.4.13) (ATP-dependent RNA helicase DDX48) (ATP-dependent RNA helicase eIF4A-3) (DEAD box protein 48) (Eukaryotic initiation factor 4A-like NUK-34) (Eukaryotic translation initiation factor 4A isoform 3) (Nuclear matrix protein 265) (NMP 265) (hNMP 265) [Cleaved into: Eukaryotic initiation factor 4A-III, N-terminally processed]
812. Eukaryotic peptide chain release factor subunit 1 (cDNA FLJ56175, highly similar to Eukaryotic peptide chain release factor subunit1)
813. Eukaryotic translation elongation factor 1 epsilon-1 (Aminoacyl tRNA synthetase complex-interacting multifunctional protein 3) (Elongation factor p18) (Multisynthase complex auxiliary component p18)
814. Eukaryotic translation initiation factor 1A, X-chromosomal (eIF-1A X isoform) (Eukaryotic translation initiation factor 4C) (eIF-4C)
815. Eukaryotic translation initiation factor 2 subunit 1 (Eukaryotic translation initiation factor 2 subunit alpha) (eIF-2-alpha) (eIF-2A) (eIF-2 alpha)
816. Eukaryotic translation initiation factor 2 subunit 3 (Eukaryotic translation initiation factor 2 subunit gamma X) (eIF-2-gamma X) (eIF-2gX)
817. Eukaryotic translation initiation factor 3 subunit A (eIF3a) (Eukaryotic translation initiation factor 3 subunit 10) (eIF-3-theta) (eIF3 p167) (eIF3 p180) (eIF3 p185)
818. Eukaryotic translation initiation factor 3 subunit C (eIF3c) (Eukaryotic translation initiation factor 3 subunit 8) (eIF3 p110)
819. Eukaryotic translation initiation factor 3 subunit E (eIF3e) (Eukaryotic translation initiation factor 3 subunit 6) (Viral integration site protein INT-6 homolog) (eIF-3 p48)
820. Eukaryotic translation initiation factor 3 subunit F (eIF3f) (Eukaryotic translation initiation factor 3 subunit 5) (eIF-3-epsilon) (eIF3 p47)
821. Eukaryotic translation initiation factor 3 subunit G (eIF3g) (Eukaryotic translation initiation factor 3 RNA-binding subunit) (eIF-3 RNA-binding subunit) (Eukaryotic translation initiation factor 3 subunit 4) (eIF-3-delta) (eIF3 p42) (eIF3 p44)
822. Eukaryotic translation initiation factor 3 subunit H (eIF3h) (Eukaryotic translation initiation factor 3 subunit 3) (eIF-3 gamma) (eIF3 p40 subunit)
823. Eukaryotic translation initiation factor 3 subunit I (eIF3i) (Eukaryotic translation initiation factor 3 subunit 2) (TGF-beta receptor-interacting protein 1) (TRIP-1) (eIF-3-beta) (eIF3 p36)
824. Eukaryotic translation initiation factor 3 subunit K (eIF3k) (Eukaryotic translation initiation factor 3 subunit 12) (Muscle-specific gene M9 protein) (PLAC-24) (eIF-3 p25) (eIF-3 p28)
825. Eukaryotic translation initiation factor 3 subunit L (eIF3l) (Eukaryotic translation initiation factor 3 subunit 6-interacting protein) (Eukaryotic translation initiation factor 3 subunit E-interacting protein)
826. Eukaryotic translation initiation factor 4H (eIF-4H) (Williams-Beuren syndrome chromosomal region 1 protein)
827. Eukaryotic translation initiation factor 5 (eIF-5)
828. Eukaryotic translation initiation factor 5A (eIF-5A) (Fragment)
829. Eukaryotic translation initiation factor 5A-1 (eIF-5A-1) (eIF-5A1) (Eukaryotic initiation factor 5A isoform 1) (eIF-5A) (Rev-binding factor) (eIF-4D)
830. Eukaryotic translation initiation factor 5B (eIF-5B) (EC 3.6.5.3) (Translation initiation factor IF-2)
831. Eukaryotic translation initiation factor 6 (eIF-6) (B(2)GCN homolog) (B4 integrin interactor) (CAB) (p27(BBP))
832. Eukaryotic translation initiation factor 6 (Fragment)
833. Exosome complex component CSL4
834. Exosome complex component RRP40 (Exosome component 3) (Ribosomal RNA-processing protein 40) (p10)
835. Exosome complex component RRP41
836. Exosome complex component RRP45 (Exosome component 9, isoform CRA_f)

-continued

837. Exosome complex component RRP46 (Chronic myelogenous leukemia tumor antigen 28) (Exosome component 5) (Ribosomal RNA-processing protein 46) (p12B)
838. Exosome complex exonuclease RRP44 (EC 3.1.13.—) (EC 3.1.26.—) (Protein DIS3 homolog) (Ribosomal RNA-processing protein 44)
839. Exportin-1 (Exp1) (Chromosome region maintenance 1 protein homolog)
840. Exportin-2 (Exp2) (Cellular apoptosis susceptibility protein) (Chromosome segregation 1-like protein) (Importin-alpha re-exporter)
841. Extracellular glycoprotein lacritin
842. Extracellular matrix protein 1 (Secretory component p85)
843. Ezrin
844. Ezrin (Cytovillin) (Villin-2) (p81)
845. F-actin-capping protein subunit alpha-1 (Cap Z alpha-1)
846. F-box only protein 50 (NCC receptor protein 1 homolog) (NCCRP-1) (Non-specific cytotoxic cell receptor protein 1 homolog)
847. FACT complex subunit SSRP1 (Chromatin-specific transcription elongation factor 80 kDa subunit) (Facilitates chromatin transcription complex 80 kDa subunit) (FACT 80 kDa subunit) (FACTp80) (Facilitates chromatin transcription complex subunit SSRP1) (Recombination signal sequence recognition protein 1) (Structure-specific recognition protein 1) (hSSRP1) (T160)
848. Far upstream element-binding protein 2 (FUSE-binding protein 2) (KH type-splicing regulatory protein) (KSRP) (p75)
849. FARSLA protein (Phenylalanine-tRNA synthetase-like, alpha subunit, isoform CRA_b) (cDNA FLJ34774 fis, clone NT2NE2003309, highly similar to Phenylalanyl-tRNA synthetase alpha chain (EC 6.1.1.20))
850. Fascin (55 kDa actin-bundling protein) (Singed-like protein) (p55)
851. Fatty acid binding protein 5 (Psoriasis-associated)
852. Fatty acid synthase (EC 2.3.1.85) [Includes: [Acyl-carrier-protein] S-acetyltransferase (EC 2.3.1.38); [Acyl-carrier-protein] S-malonyltransferase (EC 2.3.1.39); 3-oxoacyl-[acyl-carrier-protein] synthase (EC 2.3.1.41); 3-oxoacyl-[acyl-carrier-protein] reductase (EC 1.1.1.100); 3-hydroxyacyl-[acyl-carrier-protein] dehydratase (EC 4.2.1.59); Enoyl-[acyl-carrier-protein] reductase (EC 1.3.1.39); Oleoyl-[acyl-carrier-protein] hydrolase (EC 3.1.2.14)]
853. Fermitin family homolog 3 (Kindlin-3) (MIG2-like protein) (Unc-112-related protein 2)
854. Ferric-chelate reductase 1 (EC 1.—.—.—) (Stromal cell-derived receptor 2) (SDR-2)
855. Ferrochelatase, mitochondrial (EC 4.99.1.1) (Heme synthase) (Protoheme ferro-lyase)
856. Filaggrin
857. Filaggrin-2 (FLG-2) (Intermediate filament-associated and psoriasis-susceptibility protein) (Ifapsoriasin)
858. Filamin A
859. Filamin-C (FLN-C) (FLNc) (ABP-280-like protein) (ABP-L) (Actin-binding-like protein) (Filamin-2) (Gamma-filamin)
860. Flap endonuclease 1 (FEN-1) (EC 3.1.—.—) (DNase IV) (Flap structure-specific endonuclease 1) (Maturation factor 1) (MF1) (hFEN-1)
861. Flavin reductase (NADPH) (FR) (EC 1.5.1.30) (Biliverdin reductase B) (BVR-B) (EC 1.3.1.24) (Biliverdin-IX beta-reductase) (Green heme-binding protein) (GHBP) (NADPH-dependent diaphorase) (NADPH-flavin reductase) (FLR)
862. Flotillin-1
863. Fragile X mental retardation syndrome-related protein 1 (cDNA FLJ58644, highly similar to Fragile X mental retardation syndrome-related protein 1)
864. Fructose-bisphosphate aldolase A (EC 4.1.2.13) (Lung cancer antigen NY-LU-1) (Muscle-type aldolase)
865. G2/mitotic-specific cyclin-B1
866. Galectin-1 (Gal-1) (14 kDa laminin-binding protein) (HLBP14) (14 kDa lectin) (Beta-galactoside-binding lectin L-14-I) (Galaptin) (HBL) (HPL) (Lactose-binding lectin 1) (Lectin galactoside-binding soluble 1) (Putative MAPK-activating protein PM12) (S-Lac lectin 1)
867. Galectin-7 (Gal-7) (HKL-14) (PI7) (p53-induced gene 1 protein)
868. Gamma-glutamyl hydrolase (EC 3.4.19.9) (Conjugase) (GH) (Gamma-Glu-X carboxypeptidase)
869. Gamma-glutamylcyclotransferase
870. Gamma-taxilin (Environmental lipopolysaccharide-responding gene protein) (Factor inhibiting ATF4-mediated transcription) (FIAT) (Lipopolysaccharide-specific response protein 5)
871. Gasdermin-A (Gasdermin-1)
872. Gem-associated protein 4 (Gemin-4) (Component of gems 4) (p97)
873. General transcription factor II-I (GTFII-I) (TFII-I) (Bruton tyrosine kinase-associated protein 135) (BAP-135) (BTK-associated protein 135) (SRF-Phox1-interacting protein) (SPIN) (Williams-Beuren syndrome chromosomal region 6 protein)
874. Globin B2 (Hemoglobin, gamma G)
875. Globin B3 (Hemoglobin, epsilon 1)
876. Glutamine--fructose-6-phosphate aminotransferase [isomerizing] 1 (EC 2.6.1.16) (D-fructose-6-phosphate amidotransferase 1) (Glutamine:fructose-6-phosphate amidotransferase 1) (GFAT1) (GFAT1) (Hexosephosphate aminotransferase 1)
877. Glutamine--tRNA ligase (EC 6.1.1.18) (Glutaminyl-tRNA synthetase) (GlnRS)
878. Glutaredoxin-3 (PKC-interacting cousin of thioredoxin) (PICOT) (PKC-theta-interacting protein) (PKCq-interacting protein) (Thioredoxin-like protein 2)
879. Glutathione reductase, mitochondrial (GR) (GRase) (EC 1.8.1.7)
880. Glutathione S-transferase omega-1 (GSTO-1) (EC 2.5.1.18) (Glutathione S-transferase omega 1-1) (GSTO 1-1) (Glutathione-dependent dehydroascorbate reductase) (EC 1.8.5.1) (Monomethylarsonic acid reductase) (MMA(V) reductase) (EC 1.20.4.2) (S-(Phenacyl)glutathione reductase) (SPG-R)
881. Glutathione S-transferase P
882. Glutathione S-transferase P (EC 2.5.1.18) (GST class-pi) (GSTP1-1)
883. Glyceraldehyde-3-phosphate dehydrogenase (GAPDH) (EC 1.2.1.12) (Peptidyl-cysteine S-nitrosylase GAPDH) (EC 2.6.99.—)
884. Glycine--tRNA ligase (EC 3.6.1.17) (EC 6.1.1.14) (Diadenosine tetraphosphate synthetase) (AP-4-A synthetase) (Glycyl-tRNA synthetase) (GlyRS)
885. Glycogen debranching enzyme (Glycogen debrancher) [Includes: 4-alpha-glucanotransferase (EC 2.4.1.25) (Oligo-1,4-1,4-glucantransferase); Amylo-alpha-1,6-glucosidase (Amylo-1,6-glucosidase) (EC 3.2.1.33) (Dextrin 6-alpha-D-glucosidase)]
886. Guanine nucleotide-binding protein G(s) subunit alpha isoforms short (Fragment)
887. Guanine nucleotide-binding protein-like 3 (E2-induced gene 3 protein) (Novel nucleolar protein 47) (NNP47) (Nucleolar GTP-binding protein 3) (Nucleostemin)
888. H/ACA ribonucleoprotein complex subunit 1 (Nucleolar protein family A member 1) (snoRNP protein GAR1)
889. H/ACA ribonucleoprotein complex subunit 3 (Nucleolar protein 10) (Nucleolar protein family A member 3) (snoRNP protein NOP10)
890. HCG1994130, isoform CRA_a (cDNA FLJ30359 fis, clone BRACE2007760, highly similar to 40S RIBOSOMAL PROTEIN S15A) (cDNA, FLJ92249, Homo sapiens ribosomal protein S15a (RPS15A), mRNA)
891. HCG2005638, isoform CRA_c (cDNA FLJ53073, highly similar to Spliceosome RNA helicase Bat1 (EC 3.6.1.—))
892. HCG2033702, isoform CRA_a (Suppressor of SWI4 1 homolog)

-continued

893. HCG26477 (Ribosomal protein S28, isoform CRA_a) (cDNA, FLJ92192, *Homo sapiens* ribosomal protein S28 (RPS28), mRNA)
894. HCTP4 (TPX2, microtubule-associated, homolog (*Xenopus laevis*), isoform CRA_b) (cDNA, FLJ92922)
895. Heat shock 70 kDa protein 4 (HSP70RY) (Heat shock 70-related protein APG-2)
896. Heat shock 70 kDa protein 6 (Heat shock 70 kDa protein B')
897. Heat shock cognate 71 kDa protein (Heat shock 70 kDa protein 8) (Lipopolysaccharide-associated protein 1) (LAP-1) (LPS-associated protein 1)
898. Heat shock protein beta-1 (HspB1) (28 kDa heat shock protein) (Estrogen-regulated 24 kDa protein) (Heat shock 27 kDa protein) (HSP 27) (Stress-responsive protein 27) (SRP27)
899. Heat shock protein HSP 90-alpha (Heat shock 86 kDa) (HSP 86) (HSP86) (Lipopolysaccharide-associated protein 2) (LAP-2) (LPS-associated protein 2) (Renal carcinoma antigen NY-REN-38)
900. Heat shock protein HSP 90-beta (HSP 90) (Heat shock 84 kDa) (HSP 84) (HSP84)
901. Hemogen (Erythroid differentiation-associated gene protein) (EDAG-1) (Hemopoietic gene protein) (Negative differentiation regulator protein)
902. Hemoglobin subunit gamma-1 (Gamma-1-globin) (Hb F Agamma) (Hemoglobin gamma-1 chain) (Hemoglobin gamma-A chain)
903. Hemoglobin subunit zeta (HBAZ) (Hemoglobin zeta chain) (Zeta-globin)
904. Heterochromatin protein 1-binding protein 3 (Fragment)
905. Heterogeneous nuclear ribonucleoprotein A/B
906. Heterogeneous nuclear ribonucleoprotein A0 (hnRNP A0)
907. Heterogeneous nuclear ribonucleoprotein A1 (hnRNP A1) (Helix-destabilizing protein) (Single-strand RNA-binding protein) (hnRNP core protein A1) [Cleaved into: Heterogeneous nuclear ribonucleoprotein A1, N-terminally processed]
908. Heterogeneous nuclear ribonucleoprotein A3 (hnRNP A3)
909. Heterogeneous nuclear ribonucleoprotein A3, isoform CRA_a (cDNA FLJ52659, highly similar to Heterogeneous nuclear ribonucleoprotein A3) (cDNA, FLJ79333, highly similar to Heterogeneous nuclear ribonucleoprotein A3)
910. Heterogeneous nuclear ribonucleoprotein D-like (hnRNP D-like) (hnRNP DL) (AU-rich element RNA-binding factor) (JKT41-binding protein) (Protein laAUF1)
911. Heterogeneous nuclear ribonucleoprotein F (hnRNP F) (Nucleolin-like protein mcs94-1) [Cleaved into: Heterogeneous nuclear ribonucleoprotein F, N-terminally processed]
912. Heterogeneous nuclear ribonucleoprotein H
913. Heterogeneous nuclear ribonucleoprotein H (hnRNP H) [Cleaved into: Heterogeneous nuclear ribonucleoprotein H, N-terminally processed]
914. Heterogeneous nuclear ribonucleoprotein H2 (hnRNP H2) (FTP-3) (Heterogeneous nuclear ribonucleoprotein H') (hnRNP H') [Cleaved into: Heterogeneous nuclear ribonucleoprotein H2, N-terminally processed]
915. Heterogeneous nuclear ribonucleoprotein H3 (hnRNP H3) (Heterogeneous nuclear ribonucleoprotein 2H9) (hnRNP 2H9)
916. Heterogeneous nuclear ribonucleoprotein K (hnRNP K) (Transformation up-regulated nuclear protein) (TUNP)
917. Heterogeneous nuclear ribonucleoprotein L (hnRNP L)
918. Heterogeneous nuclear ribonucleoprotein M (hnRNP M)
919. Heterogeneous nuclear ribonucleoprotein Q (hnRNP Q) (Glycine- and tyrosine-rich RNA-binding protein) (GRY-RBP) (NS1-associated protein 1) (Synaptotagmin-binding cytoplasmic RNA-interacting protein)
920. Heterogeneous nuclear ribonucleoprotein U (hnRNP U) (Scaffold attachment factor A) (SAF-A) (p120) (pp120)
921. Heterogeneous nuclear ribonucleoprotein U-like protein 1 (Adenovirus early region 1B-associated protein 5) (E1B-55 kDa-associated protein 5) (E1B-AP5)
922. Heterogeneous nuclear ribonucleoprotein U-like protein 2 (Scaffold-attachment factor A2) (SAF-A2)
923. Heterogeneous nuclear ribonucleoproteins A2/B1 (hnRNP A2/B1)
924. Heterogeneous nuclear ribonucleoproteins C1/C2 (hnRNP C1/C2)
925. High mobility group nucleosome-binding domain-containing protein 3 (Thyroid receptor-interacting protein 7) (TR-interacting protein 7) (TRIP-7)
926. High mobility group protein B1 (High mobility group protein 1) (HMG-1)
927. High mobility group protein B2 (Fragment)
928. High mobility group protein B3 (Fragment)
929. Histidine triad nucleotide-binding protein 1 (EC 3.—.—.—) (Adenosine 5'-monophosphoramidase) (Protein kinase C inhibitor 1) (Protein kinase C-interacting protein 1) (PKCI-1)
930. Histone 1, H1e (Histone H1e)
931. Histone acetyltransferase type B catalytic subunit (EC 2.3.1.48) (Histone acetyltransferase 1)
932. Histone H1.5 (Histone H1a) (Histone H1b) (Histone H1s-3)
933. Histone H1x
934. Histone H2A
935. Histone H2A type 1-C (Histone H2A/1)
936. Histone H2A type 2-B
937. Histone H2A.Z (H2A/z)
938. Histone H2B
939. Histone H2B type 1-J (Histone H2B.1) (Histone H2B.r) (H2B/r)
940. Histone H2B type 1-K (H2B K) (HIRA-interacting protein 1)
941. Histone H2B type 1-L (Histone H2B.c) (H2B/c)
942. Histone H2B type 1-O (Histone H2B.2) (Histone H2B.n) (H2B/n)
943. Histone H3
944. Histone H3.1 (Histone H3/a) (Histone H3/b) (Histone H3/c) (Histone H3/d) (Histone H3/f) (Histone H3/h) (Histone H3/i) (Histone H3/j) (Histone H3/k) (Histone H3/l)
945. Histone H4
946. Histone-arginine methyltransferase CARM1 (EC 2.1.1.319) (Coactivator-associated arginine methyltransferase 1) (Protein arginine N-methyltransferase 4)
947. Histone-binding protein RBBP4 (Chromatin assembly factor 1 subunit C) (CAF-1 subunit C) (Chromatin assembly factor I p48 subunit) (CAF-I 48 kDa subunit) (CAF-p48) (Nucleosome-remodeling factor subunit RBAP48) (Retinoblastoma-binding protein 4) (RBBP-4) (Retinoblastoma-binding protein p48)
948. Histone-binding protein RBBP7
949. Hornerin
950. Host cell factor 1
951. Hsp90 co-chaperone Cdc37 (Hsp90 chaperone protein kinase-targeting subunit) (p50Cdc37) [Cleaved into: Hsp90 co-chaperone Cdc37, N-terminally processed]
952. Hydroxyacyl-coenzyme A dehydrogenase, mitochondrial -continued 953. Hypermethylated in cancer 2 protein (Hic-2) (HIC1-related gene on chromosome 22 protein) (Hic-3) (Zinc finger and BTB domain-containing protein 30)
954. Immunoglobulin heavy constant alpha 1 (Ig alpha-1 chain C region) (Ig alpha-1 chain C region BUR) (Ig alpha-1 chain C region TRO)
955. Immunoglobulin heavy constant gamma 1 (Ig gamma-1 chain C region) (Ig gamma-1 chain C region EU) (Ig gamma-1 chain C region KOL) (Ig gamma-1 chain C region NIE)
956. Importin subunit alpha-1 (Karyopherin subunit alpha-2) (RAG cohort protein 1) (SRP1-alpha)
957. Importin subunit alpha-4 (Importin alpha Q2) (Qip2) (Karyopherin subunit alpha-3) (SRP1-gamma)
958. Importin subunit beta-1 (Importin-90) (Karyopherin subunit beta-1) (Nuclear factor p97) (Pore targeting complex 97 kDa subunit) (PTAC97)
959. Importin-5 (Imp5) (Importin subunit beta-3) (Karyopherin beta-3) (Ran-binding protein 5) (RanBP5)
960. Importin-7 (Imp7) (Ran-binding protein 7) (RanBP7)
961. Inorganic pyrophosphatase (EC 3.6.1.1) (Pyrophosphate phospho-hydrolase) (PPase)
962. Inosine-5'-monophosphate dehydrogenase 2 (IMP dehydrogenase 2) (IMPD 2) (IMPDH 2) (EC 1.1.1.205) (IMPDH-II)
963. Insulin-like growth factor 2 mRNA-binding protein 1 (IGF2 mRNA-binding protein 1) (IMP-1) (IMP1) (Coding region determinant-binding protein) (CRD-BP) (IGF-II mRNA-binding protein 1) (VICKZ family member 1) (Zipcode-binding protein 1) (ZBP-1)
964. Insulin-like growth factor 2 mRNA-binding protein 2 (IGF2 mRNA-binding protein 2) (IMP-2) (Hepatocellular carcinoma autoantigen p62) (IGF-II mRNA-binding protein 2) (VICKZ family member 2)
965. Insulin-like growth factor 2 mRNA-binding protein 3 (IGF2 mRNA-binding protein 3) (IMP-3) (IGF-II mRNA-binding protein 3) (KH domain-containing protein overexpressed in cancer) (hKOC) (VICKZ family member 3)
966. Integrin-linked kinase-associated serine/threonine phosphatase 2C (Fragment)
967. Interleukin enhancer-binding factor 2 (Nuclear factor of activated T-cells 45 kDa)
968. Interleukin enhancer-binding factor 3 (Double-stranded RNA-binding protein 76) (DRBP76) (M-phase phosphoprotein 4) (MPP4) (Nuclear factor associated with dsRNA) (NFAR) (Nuclear factor of activated T-cells 90 kDa) (NF-AT-90) (Translational control protein 80) (TCP80)
969. Intron-binding protein aquarius (Intron-binding protein of 160 kDa) (IBP160)
970. Isocitrate dehydrogenase [NADP], mitochondrial (IDH) (EC 1.1.1.42) (ICD-M) (IDP) (NADP(+)-specific ICDH) (Oxalosuccinate decarboxylase)
971. Isoleucine--tRNA ligase, cytoplasmic (EC 6.1.1.5) (Isoleucyl-tRNA synthetase) (IRS) (IleRS)
972. Isoleucine--tRNA ligase, mitochondrial (EC 6.1.1.5) (Isoleucyl-tRNA synthetase) (IleRS)
973. Junction plakoglobin (Catenin gamma) (Desmoplakin III) (Desmoplakin-3)
974. Katanin p60 ATPase-containing subunit A-like 2 (Katanin p60 subunit A-like 2) (EC 3.6.4.3) (p60 katanin-like 2)
975. Keratin, type I cytoskeletal 10 (Cytokeratin-10) (CK-10) (Keratin-10) (K10)
976. Keratin, type I cytoskeletal 14 (Cytokeratin-14) (CK-14) (Keratin-14) (K14)
977. Keratin, type I cytoskeletal 17
978. Keratin, type I cytoskeletal 18 (Cell proliferation-inducing gene 46 protein) (Cytokeratin-18) (CK-18) (Keratin-18) (K18)
979. Keratin, type I cytoskeletal 9 (Cytokeratin-9) (CK-9) (Keratin-9) (K9)
980. Keratin, type II cytoskeletal 1 (67 kDa cytokeratin) (Cytokeratin-1) (CK-1) (Hair alpha protein) (Keratin-1) (K1) (Type-II keratin Kb1)
981. Keratin, type II cytoskeletal 2 epidermal (Cytokeratin-2e) (CK-2e) (Epithelial keratin-2e) (Keratin-2 epidermis) (Keratin-2e) (K2e) (Type-II keratin Kb2)
982. Keratin, type II cytoskeletal 5 (58 kDa cytokeratin) (Cytokeratin-5) (CK-5) (Keratin-5) (K5) (Type-II keratin Kb5)
983. Keratin, type II cytoskeletal 8 (Cytokeratin-8) (CK-8) (Keratin-8) (K8) (Type-II keratin Kb8)
984. KH domain-containing, RNA-binding, signal transduction-associated protein 1 (GAP-associated tyrosine phosphoprotein p62) (Src-associated in mitosis 68 kDa protein) (Sam68) (p21 Ras GTPase-activating protein-associated p62) (p68)
985. Kinesin-1 heavy chain (Conventional kinesin heavy chain) (Ubiquitous kinesin heavy chain) (UKHC)
986. Kinesin-like protein
987. Kinesin-like protein KIF2C (Kinesin-like protein 6) (Mitotic centromere-associated kinesin) (MCAK)
988. Kinetochore protein Spc25 (hSpc25)
989. L-lactate dehydrogenase A chain (LDH-A) (EC 1.1.1.27) (Cell proliferation-inducing gene 19 protein) (LDH muscle subunit) (LDH-M) (Renal carcinoma antigen NY-REN-59)
990. L-lactate dehydrogenase B chain (LDH-B) (EC 1.1.1.27) (LDH heart subunit) (LDH-H) (Renal carcinoma antigen NY-REN-46)
991. La-related protein 1 (Fragment)
992. La-related protein 1 (La ribonucleoprotein domain family member 1)
993. La-related protein 4 (La ribonucleoprotein domain family member 4)
994. Lactoylglutathione lyase (EC 4.4.1.5) (Aldoketomutase) (Glyoxalase I) (Glx I) (Ketone-aldehyde mutase) (Methylglyoxalase) (S-D-lactoylglutathione methylglyoxal lyase)
995. Lamin-B1
996. Lamin-B2
997. Lamina-associated polypeptide 2, isoform alpha (Thymopoietin isoform alpha) (TP alpha) (Thymopoietin-related peptide isoform alpha) (TPRP isoform alpha) [Cleaved into: Thymopoietin (TP) (Splenin); Thymopentin (TP5)]
998. Lamina-associated polypeptide 2, isoforms beta/gamma (Thymopoietin, isoforms beta/gamma) (TP beta/gamma) (Thymopoietin-related peptide isoforms beta/gamma) (TPRP isoforms beta/gamma) [Cleaved into: Thymopoietin (TP) (Splenin); Thymopentin (TP5)]
999. Leucine-rich PPR-motif containing (Mitochondrial leucine-rich PPR motif-containing protein)
1000. Leucine-rich repeat-containing protein 47
1001. Leucine-rich repeat-containing protein 59 (Ribosome-binding protein p34) (p34)
1002. Leukocyte elastase inhibitor (LEI) (Monocyte/neutrophil elastase inhibitor) (EI) (M/NEI) (Peptidase inhibitor 2) (PI-2) (Serpin B1)
1003. LIM and SH3 domain protein 1 (Fragment)
1004. Lipocalin-1 (Tear lipocalin) (Tlc) (Tear prealbumin) (TP) (Von Ebner gland protein) (VEG protein)
1005. Loricrin
1006. Lysine--tRNA ligase (EC 6.1.1.6) (Lysyl-tRNA synthetase) (LysRS)
1007. Lysine-specific histone demethylase 1A (EC 1.—.—.—) (BRAF35-HDAC complex protein BHC110) (Flavin-containing amine oxidase domain-containing protein 2)
1008. Macrophage migration inhibitory factor (MIF) (EC 5.3.2.1) (Glycosylation-inhibiting factor) (GIF) (L-dopachrome isomerase) (L-dopachrome tautomerase) (EC 5.3.3.12) (Phenylpyruvate tautomerase)
1009. Malate dehydrogenase (EC 1.1.1.37) (Fragment)
1010. Malate dehydrogenase, mitochondrial (EC 1.1.1.37)
1011. Malignant T-cell-amplified sequence 1 (MCT-1) (Multiple copies T-cell malignancies)
1012. Matrin-3

1013. Metastasis-associated protein MTA2 (Metastasis-associated 1-like 1) (MTA1-L1 protein) (p53 target protein in deacetylase complex)
1014. Methionine adenosyltransferase 2 subunit beta (Methionine adenosyltransferase II beta) (MAT II beta) (Putative dTDP-4-keto-6-deoxy-D-glucose 4-reductase)
1015. Methionine aminopeptidase 2 (MAP 2) (MetAP 2) (EC 3.4.11.18) (Initiation factor 2-associated 67 kDa glycoprotein) (p67) (p67eIF2) (Peptidase M)
1016. Methionine--tRNA ligase, cytoplasmic (EC 6.1.1.10) (Methionyl-tRNA synthetase) (MetRS)
1017. Methylcytosine dioxygenase TET3 (EC 1.14.11.n2)
1018. MICOS complex subunit
1019. MICOS complex subunit MIC60 (Mitofilin)
1020. Microtubule-associated protein
1021. Mitochondrial carrier homolog 2 (Fragment)
1022. Mitochondrial import inner membrane translocase subunit TIM50
1023. Mitochondrial import receptor subunit TOM70 (Mitochondrial precursor proteins import receptor) (Translocase of outer membrane 70 kDa subunit) (Translocase of outer mitochondrial membrane protein 70)
1024. Mitochondrial Rho GTPase 2 (MIRO-2) (hMiro-2) (EC 3.6.5.—) (Ras homolog gene family member T2)
1025. Mitochondrial transcription factor A (Transcription factor A, mitochondrial, isoform CRA_c)
1026. Mitochondrial-processing peptidase subunit alpha (EC 3.4.24.64) (Alpha-MPP) (P-55)
1027. Mitogen-activated protein kinase 1 (MAP kinase 1) (MAPK 1) (EC 2.7.11.24) (ERT1) (Extracellular signal-regulated kinase 2) (ERK-2) (MAP kinase isoform p42) (p42-MAPK) (Mitogen-activated protein kinase 2) (MAP kinase 2) (MAPK 2)
1028. Mitogen-activated protein kinase kinase kinase 1 (EC 2.7.11.25) (MAPK/ERK kinase kinase 1) (MEK kinase 1) (MEKK 1)
1029. Mitotic checkpoint protein BUB3
1030. MKI67 FHA domain-interacting nucleolar phosphoprotein (Nucleolar phosphoprotein Nopp34) (Nucleolar protein interacting with the FHA domain of pKI-67) (hNIFK)
1031. Moesin (Membrane-organizing extension spike protein)
1032. Mov10, Moloney leukemia virus 10, homolog (Mouse), isoform CRA_a (Putative helicase MOV-10)
1033. mRNA turnover protein 4 homolog (Ribosome assembly factor MRTO4)
1034. Mucin-16 (MUC-16) (Ovarian cancer-related tumor marker CA125) (CA-125) (Ovarian carcinoma antigen CA125)
1035. Multifunctional methyltransferase subunit TRM112-like protein
1036. Multifunctional protein ADE2 [Includes: Phosphoribosylaminoimidazole-succinocarboxamide synthase (EC 6.3.2.6) (SAICAR synthetase); Phosphoribosylaminoimidazole carboxylase (EC 4.1.1.21) (AIR carboxylase) (AIRC)]
1037. Muscleblind-like 2 (*Drosophila*), isoform CRA_a (cDNA FLJ76890, highly similar to *Homo sapiens* muscleblind-like 2 (*Drosophila*) (MBNL2), transcript variant 3, mRNA) (cDNA, FLJ79493, highly similar to *Homo sapiens* muscleblind-like 2 (*Drosophila*) (MBNL2), transcript variant 3, mRNA)
1038. Myb-binding protein 1A
1039. Myosin light chain 4 (Myosin light chain 1, embryonic muscle/atrial isoform) (Myosin light chain alkali GT-1 isoform)
1040. Myosin-10 (Cellular myosin heavy chain, type B) (Myosin heavy chain 10) (Myosin heavy chain, non-muscle IIb) (Non-muscle myosin heavy chain B) (NMMHC-B) (Non-muscle myosin heavy chain IIb) (NMMHC II-b) (NMMHC-IIB)
1041. Myosin-9 (Cellular myosin heavy chain, type A) (Myosin heavy chain 9) (Myosin heavy chain, non-muscle IIa) (Non-muscle myosin heavy chain A) (NMMHC-A) (Non-muscle myosin heavy chain IIa) (NMMHC II-a) (NMMHC-IIA)
1042. Myotrophin (Protein V-1)
1043. N-alpha-acetyltransferase 15, NatA auxiliary subunit (Gastric cancer antigen Ga19) (N-terminal acetyltransferase) (NMDA receptor-regulated protein 1) (Protein tubedown-1) (Tbdn100)
1044. NAD(P) transhydrogenase, mitochondrial
1045. NAD(P)H dehydrogenase [quinone] 1 (cDNA FLJ50573, highly similar to *Homo sapiens* NAD(P)H dehydrogenase, quinone 1 (NQO1), transcript variant 3, mRNA)
1046. NADH dehydrogenase (Ubiquinone) 1 beta subcomplex, 10, 22 kDa, isoform CRA_b (cDNA FLJ78612, highly similar to *Homo sapiens* NADH dehydrogenase (ubiquinone) 1 beta subcomplex, 10, 22 kDa (NDUFB10), mRNA) (cDNA, FLJ92003, *Homo sapiens* NADH dehydrogenase (ubiquinone) 1 beta subcomplex, 10, 22 kDa (NDUFB10), mRNA)
1047. NADH dehydrogenase [ubiquinone] 1 alpha subcomplex assembly factor 3
1048. NADH dehydrogenase [ubiquinone] 1 alpha subcomplex subunit 5 (Complex I subunit B13) (Complex I-13kD-B) (CI-13kD-B) (NADH-ubiquinone oxidoreductase 13 kDa-B subunit)
1049. NADH dehydrogenase [ubiquinone] iron-sulfur protein 2, mitochondrial (EC 1.6.5.3) (EC 1.6.99.3) (Complex I-49 kD) (CI-49 kD) (NADH-ubiquinone oxidoreductase 49 kDa subunit)
1050. NADH dehydrogenase [ubiquinone] iron-sulfur protein 3, mitochondrial (EC 1.6.5.3) (EC 1.6.99.3) (Complex I-30 kD) (CI-30 kD) (NADH-ubiquinone oxidoreductase 30 kDa subunit)
1051. Nascent polypeptide-associated complex subunit alpha, muscle-specific form (Alpha-NAC, muscle-specific form) (skNAC)
1052. NEDD8-conjugating enzyme Ubc12 (EC 6.3.2.—) (NEDD8 carrier protein) (NEDD8 protein ligase) (Ubiquitin-conjugating enzyme E2 M)
1053. NEDD8-MDP1 readthrough (Fragment)
1054. Neuroguidin (Centromere accumulated nuclear protein 1) (CANu1) (EIF4E-binding protein)
1055. Neutral amino acid transporter B(0) (ATB(0)) (Baboon M7 virus receptor) (RD114/simian type D retrovirus receptor) (Sodium-dependent neutral amino acid transporter type 2) (Solute carrier family 1 member 5)
1056. NF-kappaB repressing factor (NF-kappaB repressing factor, isoform CRA_b)
1057. NHP2-like protein 1
1058. Non-histone chromosomal protein HMG-14
1059. Non-histone chromosomal protein HMG-17 (High mobility group nucleosome-binding domain-containing protein 2)
1060. Non-POU domain-containing octamer-binding protein (NonO protein) (54 kDa nuclear RNA- and DNA-binding protein) (55 kDa nuclear protein) (DNA-binding p52/p100 complex, 52 kDa subunit) (NMT55) (p54(nrb)) (p54nrb)
1061. Nuclear autoantigenic sperm protein (NASP)
1062. Nuclear cap-binding protein subunit 1 (80 kDa nuclear cap-binding protein) (CBP80) (NCBP 80 kDa subunit)
1063. Nuclear migration protein nudC (Nuclear distribution protein C homolog)
1064. Nuclear mitotic apparatus protein 1 (NuMA protein) (Nuclear matrix protein-22) (NMP-22) (SP-H antigen)
1065. Nuclear pore complex protein Nup214 (214 kDa nucleoporin) (Nucleoporin Nup214) (Protein CAN)
1066. Nuclear pore complex protein Nup88 (88 kDa nucleoporin) (Nucleoporin Nup88)
1067. Nuclear pore complex protein Nup93 (93 kDa nucleoporin) (Nucleoporin Nup93)
1068. Nuclear pore membrane glycoprotein 210 (Nuclear pore protein gp210) (Nuclear envelope pore membrane protein POM 210) (POM210) (Nucleoporin Nup210) (Pore membrane protein of 210 kDa)

-continued

1069. Nuclease-sensitive element-binding protein 1 (CCAAT-binding transcription factor I subunit A) (CBF-A) (DNA-binding protein B) (DBPB) (Enhancer factor I subunit A) (EFI-A) (Y-box transcription factor) (Y-box-binding protein 1) (YB-1)
1070. Nucleolar and coiled-body phosphoprotein 1 (140 kDa nucleolar phosphoprotein) (Nopp140) (Hepatitis C virus NS5A-transactivated protein 13) (HCV NS5A-transactivated protein 13) (Nucleolar 130 kDa protein) (Nucleolar phosphoprotein p130)
1071. Nucleolar complex protein 2 homolog (Protein NOC2 homolog) (NOC2-like protein) (Novel INHAT repressor)
1072. Nucleolar complex protein 4 homolog (Fragment)
1073. Nucleolar GTP-binding protein 1
1074. Nucleolar GTP-binding protein 2 (Autoantigen NGP-1)
1075. Nucleolar protein 56 (Nucleolar protein 5A)
1076. Nucleolar protein 58 (Nucleolar protein 5)
1077. Nucleolar protein 7 (Nucleolar protein of 27 kDa)
1078. Nucleolar RNA helicase 2 (EC 3.6.4.13) (DEAD box protein 21) (Gu-alpha) (Nucleolar RNA helicase Gu) (Nucleolar RNA helicase II) (RH II/Gu)
1079. Nucleolar transcription factor 1
1080. Nucleolin (Protein C23)
1081. Nucleophosmin (NPM) (Nucleolar phosphoprotein B23) (Nucleolar protein NO38) (Numatrin)
1082. Nucleoplasmin-3
1083. Nucleoporin Nup43 (Nup107-160 subcomplex subunit Nup43) (p42)
1084. Nucleoporin SEH1 (Nup107-160 subcomplex subunit SEH1) (SEC13-like protein)
1085. Nucleoprotein TPR (Megator) (NPC-associated intranuclear protein) (Translocated promoter region protein)
1086. Nucleoside diphosphate kinase A
1087. Nucleoside diphosphate kinase A (NDK A) (NDP kinase A) (EC 2.7.4.6) (Granzyme A-activated DNase) (GAAD) (Metastasis inhibition factor nm23) (NM23-H1) (Tumor metastatic process-associated protein)
1088. Olfactory receptor 11A1 (Hs6M1-18) (Olfactory receptor 11A2) (Olfactory receptor OR6-30)
1089. Ornithine aminotransferase, mitochondrial (EC 2.6.1.13) (Ornithine delta-aminotransferase) (Ornithine--oxo-acid aminotransferase) [Cleaved into: Ornithine aminotransferase, hepatic form; Ornithine aminotransferase, renal form]
1090. OTU domain-containing protein 6B (EC 3.4.19.12) (DUBA-5)
1091. p21-activated protein kinase-interacting protein 1 (PAK/PLC-interacting protein 1) (hPIP1) (PAK1-interacting protein 1) (WD repeat-containing protein 84)
1092. p53 apoptosis effector related to PMP-22 (Keratinocyte-associated protein 1) (KCP-1) (P53-induced protein PIGPC1) (Transmembrane protein THW)
1093. PAI-1 mRNA-binding protein variant (cDNA, FLJ92551, Homo sapiens PAI-1 mRNA-binding protein (PAI-RBP1), mRNA)
1094. PC4 and SFRS1-interacting protein (CLL-associated antigen KW-7) (Dense fine speckles 70 kDa protein) (DFS 70) (Lens epithelium-derived growth factor) (Transcriptional coactivator p75/p52)
1095. PDZ and LIM domain protein 1 (C-terminal LIM domain protein 1) (Elfin) (LIM domain protein CLP-36)
1096. Peptidyl-prolyl cis-trans isomerase B (PPIase B) (EC 5.2.1.8) (CYP-S1) (Cyclophilin B) (Rotamase B) (S-cyclophilin) (SCYLP)
1097. Peptidyl-prolyl cis-trans isomerase F, mitochondrial (PPIase F) (EC 5.2.1.8) (Cyclophilin D) (CyP-D) (CypD) (Cyclophilin F) (Mitochondrial cyclophilin) (CyP-M) (Rotamase F)
1098. Peptidyl-prolyl cis-trans isomerase FKBP3 (PPIase FKBP3) (EC 5.2.1.8) (25 kDa FK506-binding protein) (25 kDa FKBP) (FKBP-25) (FK506-binding protein 3) (FKBP-3) (Immunophilin FKBP25) (Rapamycin-selective 25 kDa immunophilin) (Rotamase)
1099. Peptidyl-prolyl cis-trans isomerase FKBP4 (PPIase FKBP4) (EC 5.2.1.8) (51 kDa FK506-binding protein) (FKBP51) (52 kDa FK506-binding protein) (52 kDa FKBP) (FKBP-52) (59 kDa immunophilin) (p59) (FK506-binding protein 4) (FKBP-4) (FKBP59) (HSP-binding immunophilin) (HBI) (Immunophilin FKBP52) (Rotamase) [Cleaved into: Peptidyl-prolyl cis-trans isomerase FKBP4, N-terminally processed]
1100. Peptidyl-prolyl cis-trans isomerase FKBP8 (PPIase FKBP8) (EC 5.2.1.8) (38 kDa FK506-binding protein) (38 kDa FKBP) (FKBP-38) (hFKBP38) (FK506-binding protein 8) (FKBP-8) (FKBPR38) (Rotamase)
1101. Peptidyl-prolyl cis-trans isomerase G
1102. Peptidyl-prolyl cis-trans isomerase-like 1 (PPIase) (EC 5.2.1.8) (Rotamase PPIL1)
1103. Peptidyl-tRNA hydrolase 2, mitochondrial (PTH 2) (EC 3.1.1.29) (Bcl-2 inhibitor of transcription 1)
1104. Perilipin-3 (47 kDa mannose 6-phosphate receptor-binding protein) (47 kDa MPR-binding protein) (Cargo selection protein TIP47) (Mannose-6-phosphate receptor-binding protein 1) (Placental protein 17) (PP17)
1105. Periodic tryptophan protein 1 homolog (Keratinocyte protein IEF SSP 9502)
1106. Peroxiredoxin-1 (EC 1.11.1.15) (Natural killer cell-enhancing factor A) (NKEF-A) (Proliferation-associated gene protein) (PAG) (Thioredoxin peroxidase 2) (Thioredoxin-dependent peroxide reductase 2)
1107. Peroxiredoxin-4 (EC 1.11.1.15) (Antioxidant enzyme AOE372) (AOE37-2) (Peroxiredoxin IV) (Prx-IV) (Thioredoxin peroxidase AO372) (Thioredoxin-dependent peroxide reductase A0372)
1108. Peroxiredoxin-6 (EC 1.11.1.15) (1-Cys peroxiredoxin) (1-Cys PRX) (24 kDa protein) (Acidic calcium-independent phospholipase A2) (aiPLA2) (EC 3.1.1.—) (Antioxidant protein 2) (Liver 2D page spot 40) (Non-selenium glutathione peroxidase) (NSGPx) (EC 1.11.1.9) (Red blood cells page spot 12)
1109. Peroxisomal multifunctional enzyme type 2 (MFE-2) (17-beta-hydroxysteroid dehydrogenase 4) (17-beta-HSD 4) (D-bifunctional protein) (DBP) (Multifunctional protein 2) (MPF-2) (Short chain dehydrogenase/reductase family 8C member 1) [Cleaved into: (3R)-hydroxyacyl-CoA dehydrogenase (EC 1.1.1.n12); Enoyl-CoA hydratase 2 (EC 4.2.1.107) (EC 4.2.1.119) (3-alpha,7-alpha,12-alpha-trihydroxy-5-beta-cholest-24-enoyl-CoA hydratase)]
1110. Pescadillo homolog
1111. PHD finger-like domain-containing protein 5A (PHD finger-like domain protein 5A) (Splicing factor 3B-associated 14 kDa protein) (SF3b14b)
1112. Phenylalanine--tRNA ligase beta subunit (EC 6.1.1.20) (Phenylalanyl-tRNA synthetase beta subunit) (PheRS)
1113. Phosphate carrier protein, mitochondrial (Phosphate transport protein) (PTP) (Solute carrier family 25 member 3)
1114. Phosphatidylinositide phosphatase SAC1
1115. Pinin (140 kDa nuclear and cell adhesion-related phosphoprotein) (Desmosome-associated protein) (Domain-rich serine protein) (DRS protein) (DRSP) (Melanoma metastasis clone A protein) (Nuclear protein SDK3) (SR-like protein)
1116. Plakophilin-1 (Band 6 protein) (B6P)
1117. Platelet-activating factor acetylhydrolase IB subunit alpha (Lissencephaly-1 protein) (LIS-1) (PAF acetylhydrolase 45 kDa subunit) (PAF-AH 45 kDa subunit) (PAF-AH alpha) (PAFAH alpha)
1118. Platelet-activating factor acetylhydrolase IB subunit gamma (EC 3.1.1.47) (PAF acetylhydrolase 29 kDa subunit) (PAF-AH 29 kDa subunit) (PAF-AH subunit gamma) (PAFAH subunit gamma)
1119. Plectin (PCN) (PLTN) (Hemidesmosomal protein 1) (HD1) (Plectin-1)
1120. Poly [ADP-ribose] polymerase 1 (PARP-1) (EC 2.4.2.30) (ADP-ribosyltransferase diphtheria toxin-like 1) (ARTD1) (NAD(+) ADP-ribosyltransferase 1) (ADPRT 1) (Poly[ADP-ribose] synthase 1)

-continued

1121. Poly(rC)-binding protein 1 (Alpha-CP1) (Heterogeneous nuclear ribonucleoprotein E1) (hnRNP E1) (Nucleic acid-binding protein SUB2.3)
1122. Polyadenylate-binding protein (PABP)
1123. Polyadenylate-binding protein 1 (PABP-1) (Poly(A)-binding protein 1)
1124. Polyadenylate-binding protein 2 (PABP-2) (Poly(A)-binding protein 2) (Nuclear poly(A)-binding protein 1) (Poly(A)-binding protein II) (PABII) (Polyadenylate-binding nuclear protein 1)
1125. Polypyrimidine tract-binding protein 1 (PTB) (57 kDa RNA-binding protein PPTB-1) (Heterogeneous nuclear ribonucleoprotein I) (hnRNP I)
1126. Polyribonucleotide nucleotidyltransferase 1, mitochondrial (EC 2.7.7.8) (3'-5' RNA exonuclease OLD35) (PNPase old-35) (Polynucleotide phosphorylase 1) (PNPase 1) (Polynucleotide phosphorylase-like protein)
1127. Porphobilinogen deaminase
1128. Pre-mRNA-processing factor 19 (EC 2.3.2.27) (Nuclear matrix protein 200) (PRP19/PSO4 homolog) (hPso4) (RING-type E3 ubiquitin transferase PRP19) (Senescence evasion factor)
1129. Pre-mRNA-processing factor 6 (Androgen receptor N-terminal domain-trans activating protein 1) (ANT-1) (PRP6 homolog) (U5 snRNP-associated 102 kDa protein) (U5-102 kDa protein)
1130. Pre-mRNA-processing-splicing factor 8 (220 kDa U5 snRNP-specific protein) (PRP8 homolog) (Splicing factor Prp 8) (p220)
1131. pre-rRNA processing protein FTSJ3 (EC 2.1.1.—) (2'-O-ribose RNA methyltransferase SPB1 homolog) (Protein ftsJ homolog 3) (Putative rRNA methyltransferase 3)
1132. Pre-rRNA-processing protein TSR1 homolog
1133. Prefoldin subunit 2 (cDNA, FLJ96845, *Homo sapiens* prefoldin 2 (PFDN2), mRNA)
1134. Prefoldin subunit 6 (Protein Ke2)
1135. Prelamin-A/C [Cleaved into: Lamin-A/C (70 kDa lamin) (Renal carcinoma antigen NY-REN-32)]
1136. Probable 28S rRNA (cytosine(4447)-C(5))-methyltransferase (EC 2.1.1.—) (Nucleolar protein 1) (Nucleolar protein 2 homolog) (Proliferating-cell nucleolar antigen p120) (Proliferation-associated nucleolar protein p120)
1137. Probable ATP-dependent RNA helicase DDX17 (EC 3.6.4.13) (DEAD box protein 17) (DEAD box protein p72) (DEAD box protein p82) (RNA-dependent helicase p72)
1138. Probable ATP-dependent RNA helicase DDX27 (EC 3.6.4.13) (DEAD box protein 27)
1139. Probable ATP-dependent RNA helicase DDX46 (EC 3.6.4.13) (DEAD box protein 46) (PRP5 homolog)
1140. Probable ATP-dependent RNA helicase DDX5 (EC 3.6.4.13) (DEAD box protein 5) (RNA helicase p68)
1141. Probable ATP-dependent RNA helicase DDX6 (EC 3.6.4.13) (ATP-dependent RNA helicase p54) (DEAD box protein 6) (Oncogene RCK)
1142. Profilin-1 (Epididymis tissue protein Li 184a) (Profilin I)
1143. Programmed cell death protein 10 (Fragment)
1144. Programmed cell death protein 6 (Apoptosis-linked gene 2 protein homolog) (ALG-2)
1145. Programmed cell death protein 6 (Apoptosis-linked gene 2 protein) (Probable calcium-binding protein ALG-2)
1146. Prohibitin-2
1147. Prohibitin, isoform CRA_a (cDNA FLJ78511, highly similar to *Homo sapiens* prohibitin (PHB), mRNA) (cDNA, FLJ93035, *Homo sapiens* prohibitin (PHB), mRNA)
1148. Prolactin-inducible protein (Gross cystic disease fluid protein 15) (GCDFP-15) (Prolactin-induced protein) (Secretory actin-binding protein) (SABP) (gp17)
1149. Proliferating cell nuclear antigen (PCNA) (Cyclin)
1150. Proliferation-associated protein 2G4 (Cell cycle protein p38-2G4 homolog) (hG4-1) (ErbB3-binding protein 1)
1151. Prostaglandin E synthase 3 (EC 5.3.99.3) (Cytosolic prostaglandin E2 synthase) (cPGES) (Hsp90 co-chaperone) (Progesterone receptor complex p23) (Telomerase-binding protein p23)
1152. Proteasome (Prosome, macropain) 26S subunit, ATPase, 4, isoform CRA_b (cDNA FLJ78505, highly similar to *Homo sapiens* proteasome (prosome, macropain) 26S subunit, ATPase, 4 (PSMC4), transcript variant 1, mRNA) (cDNA, FLJ93682, *Homo sapiens* proteasome (prosome, macropain) 26S subunit, ATPase, 4(PSMC4), transcript variant 1, mRNA)
1153. Proteasome assembly chaperone 1 (PAC-1) (Chromosome 21 leucine-rich protein) (C21-LRP) (Down syndrome critical region protein 2)
1154. Proteasome subunit alpha type-1 (EC 3.4.25.1) (30 kDa prosomal protein) (PROS-30) (Macropain subunit C2) (Multicatalytic endopeptidase complex subunit C2) (Proteasome component C2) (Proteasome nu chain)
1155. Proteasome subunit alpha type-2 (EC 3.4.25.1) (Macropain subunit C3) (Multicatalytic endopeptidase complex subunit C3) (Proteasome component C3)
1156. Proteasome subunit alpha type-3 (EC 3.4.25.1) (Macropain subunit C8) (Multicatalytic endopeptidase complex subunit C8) (Proteasome component C8)
1157. Proteasome subunit alpha type-4 (EC 3.4.25.1) (Macropain subunit C9) (Multicatalytic endopeptidase complex subunit C9) (Proteasome component C9) (Proteasome subunit L)
1158. Proteasome subunit alpha type-5 (EC 3.4.25.1) (Macropain zeta chain) (Multicatalytic endopeptidase complex zeta chain) (Proteasome zeta chain)
1159. Proteasome subunit alpha type-6 (EC 3.4.25.1) (27 kDa prosomal protein) (PROS-27) (p27K) (Macropain iota chain) (Multicatalytic endopeptidase complex iota chain) (Proteasome iota chain)
1160. Proteasome subunit alpha type-7 (EC 3.4.25.1) (Proteasome subunit RC6-1) (Proteasome subunit XAPC7)
1161. Proteasome subunit alpha type-7-like
1162. Proteasome subunit beta type-1 (EC 3.4.25.1) (Macropain subunit C5) (Multicatalytic endopeptidase complex subunit C5) (Proteasome component C5) (Proteasome gamma chain)
1163. Proteasome subunit beta type-2 (EC 3.4.25.1) (Macropain subunit C7-I) (Multicatalytic endopeptidase complex subunit C7-I) (Proteasome component C7-I)
1164. Proteasome subunit beta type-3 (EC 3.4.25.1) (Proteasome chain 13) (Proteasome component C10-II) (Proteasome theta chain)
1165. Proteasome subunit beta type-4 (EC 3.4.25.1) (26 kDa prosomal protein) (HsBPROS26) (PROS-26) (Macropain beta chain) (Multicatalytic endopeptidase complex beta chain) (Proteasome beta chain) (Proteasome chain 3) (HsN3)
1166. Proteasome subunit beta type-5 (EC 3.4.25.1) (Macropain epsilon chain) (Multicatalytic endopeptidase complex epsilon chain) (Proteasome chain 6) (Proteasome epsilon chain) (Proteasome subunit MB1) (Proteasome subunit X)
1167. Proteasome subunit beta type-6 (EC 3.4.25.1) (Macropain delta chain) (Multicatalytic endopeptidase complex delta chain) (Proteasome delta chain) (Proteasome subunit Y)
1168. Proteasome-associated protein ECM29 homolog (Ecm29)
1169. Protein arginine N-methyltransferase 1
1170. Protein CutA
1171. Protein DEK
1172. Protein DEK (cDNA FLJ53031, highly similar to Protein DEK)

-continued

1173. Protein disulfide-isomerase A3 (EC 5.3.4.1) (58 kDa glucose-regulated protein) (58 kDa microsomal protein) (p58) (Disulfide isomerase ER-60) (Endoplasmic reticulum resident protein 57) (ER protein 57) (ERp57) (Endoplasmic reticulum resident protein 60) (ER protein 60) (ERp60)
1174. Protein DJ-1 (DJ-1) (Oncogene DJ1) (Parkinson disease protein 7) (Parkinsonism-associated deglycase) (Protein deglycase DJ-1) (EC 3.1.2.—) (EC 3.5.1.124)
1175. Protein ERGIC-53 (ER-Golgi intermediate compartment 53 kDa protein) (Gp58) (Intracellular mannose-specific lectin MR60) (Lectin mannose-binding 1)
1176. Protein kinase C beta type (PKC-B) (PKC-beta) (EC 2.7.11.13)
1177. Protein LTV1 homolog
1178. Protein LYRIC
1179. Protein mago nashi homolog 2
1180. Protein phosphatase 1F (EC 3.1.3.16) (Ca(2+)/calmodulin-dependent protein kinase phosphatase) (CaM-kinase phosphatase) (CaMKPase) (Partner of PIX 2) (Protein fem-2 homolog) (hFem-2)
1181. Protein phosphatase 2 (Formerly 2A), regulatory subunit A (PR 65), alpha isoform (Testicular secretory protein Li 1) (cDNA FLJ78455, highly similar to Homo sapiens protein phosphatase 2 (formerly 2A), regulatory subunit A (PR 65), alpha isoform (PPP2R1A), mRNA) (cDNA, FLJ96799, Homo sapiens protein phosphatase 2 (formerly 2A), regulatory subunit A (PR 65), alpha isoform (PPP2R1A), mRNA)
1182. Protein POF1B (Premature ovarian failure protein 1B)
1183. Protein RCC2 (RCC1-like protein TD-60) (Telophase disk protein of 60 kDa)
1184. Protein S100-A14 (S100 calcium-binding protein A14) (S114)
1185. Protein S100-A16 (Aging-associated gene 13 protein) (Protein S100-F) (S100 calcium-binding protein A16)
1186. Protein S100-A7 (Psoriasin) (S100 calcium-binding protein A7)
1187. Protein S100-A8 (Calgranulin-A) (Calprotectin L1L subunit) (Cystic fibrosis antigen) (CFAG) (Leukocyte L1 complex light chain) (Migration inhibitory factor-related protein 8) (MRP-8) (p8) (S100 calcium-binding protein A8) (Urinary stone protein band A) [Cleaved into: Protein S100-A8, N-terminally processed]
1188. Protein S100-A9 (Calgranulin-B) (Calprotectin L1H subunit) (Leukocyte L1 complex heavy chain) (Migration inhibitory factor-related protein 14) (MRP-14) (p14) (S100 calcium-binding protein A9)
1189. Protein Shroom3 (Shroom-related protein) (hShrmL)
1190. Protein SREK1IP1 (SFRS12-interacting protein 1) (SREK1-interacting protein 1) (Splicing regulatory protein of 18 kDa) (p18SRP)
1191. Protein strawberry notch homolog 1 (Monocyte protein 3) (MOP-3)
1192. Protein transport protein Sec23B (SEC23-related protein B)
1193. Protein-glutamine gamma-glutamyltransferase E (EC 2.3.2.13) (Transglutaminase E) (TG(E)) (TGE) (TGase E) (Transglutaminase-3) (TGase-3) [Cleaved into: Protein-glutamine gamma-glutamyltransferase E 50 kDa catalytic chain; Protein-glutamine gamma-glutamyltransferase E 27 kDa non-catalytic chain]
1194. Protein-glutamine gamma-glutamyltransferase K (EC 2.3.2.13) (Epidermal TGase) (Transglutaminase K) (TG(K)) (TGK) (TGase K) (Transglutaminase-1) (TGase-1)
1195. Pumilio homolog 3 (HBV X-transactivated gene 5 protein) (HBV XAg-transactivated protein 5) (Minor histocompatibility antigen HA-8) (HLA-HA8)
1196. Puromycin-sensitive aminopeptidase
1197. Putative heat shock protein HSP 90-beta 2 (Heat shock protein 90-beta b) (Heat shock protein 90Bb)
1198. Putative helicase MOV-10 (EC 3.6.4.13) (Armitage homolog) (Moloney leukemia virus 10 protein)
1199. Putative RNA-binding protein Luc7-like 2
1200. Putative RRN3-like protein RRN3P2 (RNA polymerase I transcription factor homolog pseudogene 2)
1201. Pyrroline-5-carboxylate reductase 2 (P5C reductase 2) (P5CR 2) (EC 1.5.1.2)
1202. Pyruvate kinase PKM (EC 2.7.1.40) (Cytosolic thyroid hormone-binding protein) (CTHBP) (Opa-interacting protein 3) (OIP-3) (Pyruvate kinase 2/3) (Pyruvate kinase muscle isozyme) (Thyroid hormone-binding protein 1) (THBP1) (Tumor M2-PK) (p58)
1203. Ragulator complex protein LAMTOR1
1204. Ran GTPase-activating protein 1 (RanGAP1)
1205. Ran-specific GTPase-activating protein (Ran-binding protein 1) (RanBP1)
1206. RAP1A, member of RAS oncogene family (Ras-related protein Rap-1A) (cDNA FLJ75985, highly similar to Homo sapiens RAP1A, member of RAS oncogene family (RAP1A), transcript variant 2, mRNA)
1207. Ras GTPase-activating protein-binding protein 1 (G3BP-1) (EC 3.6.4.12) (EC 3.6.4.13) (ATP-dependent DNA helicase VIII) (hDH VIII) (GAP SH3 domain-binding protein 1)
1208. Ras GTPase-activating-like protein IQGAP1 (p195)
1209. Ras-related C3 botulinum toxin substrate 1 (Rho family, small GTP binding protein Rac1) (Ras-related C3 botulinum toxin substrate 1 (Rho family, small GTP binding protein Rac1), isoform CRA_e) (cDNA FLJ77333, highly similar to Homo sapiens ras-related C3 botulinum toxin substrate 1 (rho family, small GTP binding protein Rac1) (RAC1), transcript variant Rac1b, mRNA)
1210. Ras-related protein Rab-10
1211. Ras-related protein Rab-35 (Fragment)
1212. Ras-related protein Rab-5C (L1880) (RAB5L)
1213. Receptor of-activated protein C kinase 1
1214. Regulator of nonsense transcripts 1 (EC 3.6.4.—) (ATP-dependent helicase RENT1) (Nonsense mRNA reducing factor 1) (NORF1) (Up-frameshift suppressor 1 homolog) (hUpf1)
1215. Replication factor C subunit 2 (Activator 1 40 kDa subunit) (A1 40 kDa subunit) (Activator 1 subunit 2) (Replication factor C 40 kDa subunit) (RF-C 40 kDa subunit) (RFC40)
1216. Replication protein A3, 14 kDa (Replication protein A3, 14 kDa, isoform CRA_b) (cDNA, FLJ92105, Homo sapiens replication protein A3, 14 kDa (RPA3), mRNA)
1217. Rho GTPase-activating protein 29 (PTPL1-associated RhoGAP protein 1) (Rho-type GTPase-activating protein 29)
1218. Rho guanine nucleotide exchange factor 2
1219. Rho-related GTP-binding protein RhoC (Fragment)
1220. Rho-related GTP-binding protein RhoG
1221. Ribonuclease inhibitor (Placental ribonuclease inhibitor) (Placental RNase inhibitor) (Ribonuclease/angiogenin inhibitor 1) (RAI)
1222. Ribonucleoprotein PTB-binding 1
1223. Ribose-phosphate pyrophosphokinase 2 (EC 2.7.6.1) (PPRibP) (Phosphoribosyl pyrophosphate synthase II) (PRS-II)
1224. Ribosomal biogenesis protein LAS1L (Protein LAS1 homolog)
1225. Ribosomal L1 domain-containing protein 1 (CATX-11) (Cellular senescence-inhibited gene protein) (Protein PBK1)
1226. Ribosomal protein L15 (Fragment)
1227. Ribosomal protein L5 (Ribosomal protein L5, isoform CRA_c) (cDNA, FLJ95579, Homo sapiens ribosomal protein L5 (RPL5), mRNA)

1228. Ribosomal protein S23, isoform CRA_a (cDNA FLJ77921, highly similar to *Homo sapiens* ribosomal protein S23 (RPS23), mRNA) (cDNA, FLJ92033, *Homo sapiens* ribosomal protein S23 (RPS23), mRNA)
1229. Ribosomal RNA processing protein 1 homolog A (Novel nuclear protein 1) (NNP-1) (Nucleolar protein Nop52) (RRP1-like protein)
1230. Ribosome biogenesis protein BRX1 homolog (Brix domain-containing protein 2)
1231. Ribosome biogenesis protein NSA2 homolog (Hairy cell leukemia protein 1) (TGF-beta-inducible nuclear protein 1)
1232. Ribosome biogenesis regulatory protein homolog
1233. Ribosome maturation protein SBDS (Shwachman-Bodian-Diamond syndrome protein)
1234. Ribosome production factor 2 homolog (Brix domain-containing protein 1) (Ribosome biogenesis protein RPF2 homolog)
1235. RNA 3'-terminal phosphate cyclase (RNA cyclase) (RNA-3'-phosphate cyclase) (EC 6.5.1.4) (RNA terminal phosphate cyclase domain-containing protein 1) (RTC domain-containing protein 1)
1236. RNA binding protein S1 (RNA binding protein S1, serine-rich domain, isoform CRA_a)
1237. RNA-binding motif protein, X chromosome (Glycoprotein p43) (Heterogeneous nuclear ribonucleoprotein G) (hnRNP G) [Cleaved into: RNA-binding motif protein, X chromosome, N-terminally processed]
1238. RNA-binding protein 12 (RNA-binding motif protein 12) (SH3/WW domain anchor protein in the nucleus) (SWAN)
1239. RNA-binding protein 14 (Paraspeckle protein 2) (PSP2) (RNA-binding motif protein 14) (RRM-containing coactivator activator/modulator) (Synaptotagmin-interacting protein) (SYT-interacting protein)
1240. RNA-binding protein 25 (Arg/Glu/Asp-rich protein of 120 kDa) (RED120) (Protein S164) (RNA-binding motif protein 25) (RNA-binding region-containing protein 7)
1241. RNA-binding protein 25 (Fragment)
1242. RNA-binding protein 28 (RNA-binding motif protein 28)
1243. RNA-binding protein 3 (RNA-binding motif protein 3) (RNPL)
1244. RNA-binding protein 34 (Fragment)
1245. RNA-binding protein 34 (RNA-binding motif protein 34)
1246. RNA-binding protein 4 (Fragment)
1247. RNA-binding protein 8A (Binder of OVCA1-1) (BOV-1) (RNA-binding motif protein 8A) (RNA-binding protein Y14) (Ribonucleoprotein RBM8A)
1248. RNA-binding protein EWS
1249. RNA-binding protein NOB1 (Phosphorylation regulatory protein HP-10) (Protein ART-4)
1250. RNA-binding protein PNO1
1251. RNA-binding protein Raly (Fragment)
1252. Rootletin (Fragment)
1253. rRNA 2'-O-methyltransferase fibrillarin (EC 2.1.1.—) (34 kDa nucleolar scleroderma antigen) (Histone-glutamine methyltransferase)
1254. rRNA/tRNA 2'-O-methyltransferase fibrillarin-like protein 1 (EC 2.1.1.—) (Protein-glutamine methyltransferase)
1255. RRP15-like protein (Ribosomal RNA-processing protein 15)
1256. RuvB-like 1 (EC 3.6.4.12) (49 kDa TATA box-binding protein-interacting protein) (49 kDa TBP-interacting protein) (54 kDa erythrocyte cytosolic protein) (ECP-54) (INO80 complex subunit H) (Nuclear matrix protein 238) (NMP 238) (Pontin 52) (TIP49a) (TIP60-associated protein 54-alpha) (TAP54-alpha)
1257. RuvB-like 2 (EC 3.6.4.12) (48 kDa TATA box-binding protein-interacting protein) (48 kDa TBP-interacting protein) (51 kDa erythrocyte cytosolic protein) (ECP-51) (INO80 complex subunit J) (Repressing pontin 52) (Reptin 52) (TIP49b) (TIP60-associated protein 54-beta) (TAP54-beta)
1258. S-adenosylmethionine synthase isoform type-2 (AdoMet synthase 2) (EC 2.5.1.6) (Methionine adenosyltransferase 2) (MAT 2) (Methionine adenosyltransferase II) (MAT-II)
1259. S-formylglutathione hydrolase (FGH) (EC 3.1.2.12) (Esterase D) (Methylumbelliferyl-acetate deacetylase) (EC 3.1.1.56)
1260. SAP domain-containing ribonucleoprotein (Cytokine-induced protein of 29 kDa) (Nuclear protein Hcc-1) (Proliferation-associated cytokine-inducible protein CIP29)
1261. Sarcoplasmic/endoplasmic reticulum calcium ATPase 2 (SERCA2) (SR Ca(2+)-ATPase 2) (EC 3.6.3.8) (Calcium pump 2) (Calcium-transporting ATPase sarcoplasmic reticulum type, slow twitch skeletal muscle isoform) (Endoplasmic reticulum class 1/2 Ca(2+) ATPase)
1262. Septin-11
1263. Septin-2
1264. Septin-7
1265. Septin-9 (MLL septin-like fusion protein MSF-A) (MLL septin-like fusion protein) (Ovarian/Breast septin) (Ov/Br septin) (Septin D1)
1266. Serine--tRNA ligase, cytoplasmic (EC 6.1.1.11) (Seryl-tRNA synthetase) (SerRS) (Seryl-tRNA(Ser/Sec) synthetase)
1267. Serine/arginine repetitive matrix protein 1
1268. Serine/arginine repetitive matrix protein 2 (300 kDa nuclear matrix antigen) (Serine/arginine-rich splicing factor-related nuclear matrix protein of 300 kDa) (SR-related nuclear matrix protein of 300 kDa) (Ser/Arg-related nuclear matrix protein of 300 kDa) (Splicing coactivator subunit SRm300) (Tax-responsive enhancer element-binding protein 803) (TaxREB803)
1269. Serine/arginine-rich splicing factor 1 (Alternative-splicing factor 1) (ASF-1) (Splicing factor, arginine/serine-rich 1) (pre-mRNA-splicing factor SF2, P33 subunit)
1270. Serine/arginine-rich splicing factor 10 (40 kDa SR-repressor protein) (SRrp40) (FUS-interacting serine-arginine-rich protein 1) (Splicing factor SRp38) (Splicing factor, arginine/serine-rich 13A) (TLS-associated protein with Ser-Arg repeats) (TASR) (TLS-associated protein with SR repeats) (TLS-associated serine-arginine protein) (TLS-associated SR protein)
1271. Serine/arginine-rich splicing factor 11 (Arginine-rich 54 kDa nuclear protein) (p54) (Splicing factor, arginine/serine-rich 11)
1272. Serine/arginine-rich splicing factor 2 (Protein PR264) (Splicing component, 35 kDa) (Splicing factor SC35) (SC-35) (Splicing factor, arginine/serine-rich 2)
1273. Serine/arginine-rich splicing factor 5 (Delayed-early protein HRS) (Pre-mRNA-splicing factor SRP40) (Splicing factor, arginine/serine-rich 5)
1274. Serine/arginine-rich splicing factor 6 (Pre-mRNA-splicing factor SRP55) (Splicing factor, arginine/serine-rich 6)
1275. Serine/arginine-rich splicing factor 9 (Pre-mRNA-splicing factor SRp30C) (Splicing factor, arginine/serine-rich 9)
1276. Serine/threonine-protein kinase PAK 2 (EC 2.7.11.1) (Gamma-PAK) (PAK65) (S6/H4 kinase) (p21-activated kinase 2) (PAK-2) (p58) [Cleaved into: PAK-2p27 (p27); PAK-2p34 (p34) (C-t-PAK2)]
1277. Serine/threonine-protein kinase VRK1 (EC 2.7.11.1) (Vaccinia-related kinase 1)
1278. Serine/threonine-protein phosphatase (EC 3.1.3.16)
1279. Serine/threonine-protein phosphatase 6 catalytic subunit (PP6C) (EC 3.1.3.16) [Cleaved into: Serine/threonine-protein phosphatase 6 catalytic subunit, N-terminally processed]
1280. Serine/threonine-protein phosphatase PP1-alpha catalytic subunit (PP-1A) (EC 3.1.3.16)
1281. Serine/threonine-protein phosphatase PP1-beta catalytic subunit (PP-1B) (PPP1CD) (EC 3.1.3.16) (EC 3.1.3.53)
1282. Serpin B3 (Protein T4-A) (Squamous cell carcinoma antigen 1) (SCCA-1)

-continued

1283. Serpin B6 (Cytoplasmic antiproteinase) (CAP) (Peptidase inhibitor 6) (PI-6) (Placental thrombin inhibitor)
1284. Serpin H1 (47 kDa heat shock protein) (Arsenic-transactivated protein 3) (AsTP3) (Cell proliferation-inducing gene 14 protein) (Collagen-binding protein) (Colligin) (Rheumatoid arthritis-related antigen RA-A47)
1285. Serrate RNA effector molecule homolog (Arsenite-resistance protein 2)
1286. SH2 domain-containing protein 3A (Novel SH2-containing protein 1)
1287. Sialic acid synthase (N-acetylneuraminate synthase) (EC 2.5.1.56) (N-acetylneuraminate-9-phosphate synthase) (EC 2.5.1.57) (N-acetylneuraminic acid phosphate synthase) (N-acetylneuraminic acid synthase)
1288. Signal peptidase complex catalytic subunit SEC11A (EC 3.4.21.89) (Endopeptidase SP18) (Microsomal signal peptidase 18 kDa subunit) (SPase 18 kDa subunit) (SEC11 homolog A) (SEC11-like protein 1) (SPC18)
1289. Signal recognition particle 14 kDa protein (SRP14) (18 kDa Alu RNA-binding protein)
1290. Signal recognition particle 19 kDa protein (SRP19)
1291. Signal recognition particle receptor beta subunit (Signal recognition particle receptor, B subunit, isoform CRA_b)
1292. Signal recognition particle receptor subunit alpha (SR-alpha) (Docking protein alpha) (DP-alpha)
1293. Signal recognition particle subunit SRP72 (SRP72) (Signal recognition particle 72 kDa protein)
1294. Signal transducer and activator of transcription 3 (Acute-phase response factor)
1295. Signal transducer and activator of transcription 5A
1296. Single-stranded DNA-binding protein
1297. Sister chromatid cohesion protein PDS5 homolog A (Cell proliferation-inducing gene 54 protein) (Sister chromatid cohesion protein 112) (SCC-112)
1298. Skin-specific protein 32
1299. Small nuclear ribonucleoprotein E (snRNP-E) (Sm protein E) (Sm-E) (SmE)
1300. Small nuclear ribonucleoprotein F (snRNP-F) (Sm protein F) (Sm-F) (SmF)
1301. Small nuclear ribonucleoprotein Sm D1 (Sm-D1) (Sm-D autoantigen) (snRNP core protein D1)
1302. Small nuclear ribonucleoprotein Sm D2 (Sm-D2) (snRNP core protein D2)
1303. Small proline-rich protein 2E (SPR-2E) (Small proline-rich protein II) (SPR-II)
1304. Small ubiquitin-related modifier 3
1305. SMARCD2 protein (SWI/SNF-related matrix-associated actin-dependent regulator of chromatin subfamily D member 2)
1306. SNW domain-containing protein 1 (Nuclear protein SkiP) (Nuclear receptor coactivator NCoA-62) (Ski-interacting protein)
1307. Sodium/potassium-transporting ATPase subunit beta-3 (Fragment)
1308. Sorbitol dehydrogenase (EC 1.1.1.14) (L-iditol 2-dehydrogenase)
1309. Spectrin beta chain
1310. Spermidine synthase (SPDSY) (EC 2.5.1.16) (Putrescine aminopropyltransferase)
1311. Spermine synthase (SPMSY) (EC 2.5.1.22) (Spermidine aminopropyltransferase)
1312. Spindlin-4
1313. Spliceosome RNA helicase DDX39B (EC 3.6.4.13) (56 kDa U2AF65-associated protein) (ATP-dependent RNA helicase p47) (DEAD box protein UAP56) (HLA-B-associated transcript 1 protein)
1314. Splicing factor 3A subunit 1 (SF3a120) (Spliceosome-associated protein 114) (SAP 114)
1315. Splicing factor 3B subunit 1 (Pre-mRNA-splicing factor SF3b 155 kDa subunit) (SF3b155) (Spliceosome-associated protein 155) (SAP 155)
1316. Splicing factor 3B subunit 2 (Pre-mRNA-splicing factor SF3b 145 kDa subunit) (SF3b145) (SF3b150) (Spliceosome-associated protein 145) (SAP 145)
1317. Splicing factor 3B subunit 3 (Pre-mRNA-splicing factor SF3b 130 kDa subunit) (SF3b130) (STAF130) (Spliceosome-associated protein 130) (SAP 130)
1318. Splicing factor arginine/serine-rich 3 (Splicing factor, arginine/serine-rich 3, isoform CRA_d) (cDNA, FLJ92926, *Homo sapiens* splicing factor, arginine/serine-rich 3 (SFRS3), mRNA)
1319. Splicing factor U2AF 35 kDa subunit (U2 auxiliary factor 35 kDa subunit) (U2 small nuclear RNA auxiliary factor 1) (U2 snRNP auxiliary factor small subunit)
1320. Splicing factor U2AF 65 kDa subunit (U2 auxiliary factor 65 kDa subunit) (hU2AF(65)) (hU2AF65) (U2 snRNP auxiliary factor large subunit)
1321. Splicing factor, proline- and glutamine-rich (100 kDa DNA-pairing protein) (hPOMp100) (DNA-binding p52/p100 complex, 100 kDa subunit) (Polypyrimidine tract-binding protein-associated-splicing factor) (PSF) (PTB-associated-splicing factor)
1322. SRA stem-loop-interacting RNA-binding protein, mitochondrial
1323. SRSF protein kinase 3
1324. Stathmin
1325. Stathmin (Fragment)
1326. Stathmin (Leukemia-associated phosphoprotein p18) (Metablastin) (Oncoprotein 18) (Op18) (Phosphoprotein p19) (pp19) (Prosolin) (Protein Pr22) (pp17)
1327. STE20-like serine/threonine-protein kinase (STE20-like kinase) (hSLK) (EC 2.7.11.1) (CTCL tumor antigen se20-9) (STE20-related serine/threonine-protein kinase) (STE20-related kinase) (Serine/threonine-protein kinase 2)
1328. Stress-70 protein, mitochondrial (75 kDa glucose-regulated protein) (GRP-75) (Heat shock 70 kDa protein 9) (Mortalin) (MOT) (Peptide-binding protein 74) (PBP74)
1329. Stress-induced-phosphoprotein 1 (STI1) (Hsc70/Hsp90-organizing protein) (Hop) (Renal carcinoma antigen NY-REN-11) (Transformation-sensitive protein IEF SSP 3521)
1330. Striatin-3 (Cell cycle autoantigen SG2NA) (S/G2 antigen)
1331. Structural maintenance of chromosomes flexible hinge domain-containing protein 1 (SMC hinge domain-containing protein 1)
1332. Structural maintenance of chromosomes protein
1333. Structural maintenance of chromosomes protein 2 (SMC protein 2) (SMC-2) (Chromosome-associated protein E) (hCAP-E) (XCAP-E homolog)
1334. Structural maintenance of chromosomes protein 6 (Fragment)
1335. Succinate dehydrogenase [ubiquinone] iron-sulfur subunit, mitochondrial (EC 1.3.5.1) (Iron-sulfur subunit of complex II) (Ip)
1336. SUMO-activating enzyme subunit 2 (EC 6.3.2.—) (Anthracycline-associated resistance ARX) (Ubiquitin-like 1-activating enzyme E1B) (Ubiquitin-like modifier-activating enzyme 2)
1337. SUMO-conjugating enzyme (EC 2.3.2.—)
1338. Superkiller viralicidic activity 2-like 2 (EC 3.6.4.13) (ATP-dependent RNA helicase DOB1) (ATP-dependent RNA helicase SKIV2L2) (TRAMP-like complex helicase)
1339. Surfeit locus protein 6
1340. SWI/SNF complex subunit SMARCC1 (BRG1-associated factor 155) (BAF155) (SWI/SNF complex 155 kDa subunit) (SWI/SNF-related matrix-associated actin-dependent regulator of chromatin subfamily C member 1)

-continued

1341. SWI/SNF related, matrix associated, actin dependent regulator of chromatin, subfamily a, member 4 (SWI/SNF related, matrix associated, actin dependent regulator of chromatin, subfamily a, member 4, isoform CRA_a) (cDNA FLJ77531, highly similar to *Homo sapiens* SWI/SNF related, matrix associated, actin dependent regulator of chromatin, subfamily a, member 4 (SMARCA4), mRNA)
1342. Synapse-associated protein 1
1343. Synaptosomal-associated protein 29 (Fragment)
1344. T-complex protein 1 subunit alpha (TCP-1-alpha) (CCT-alpha)
1345. T-complex protein 1 subunit beta (TCP-1-beta) (CCT-beta)
1346. T-complex protein 1 subunit delta (TCP-1-delta) (CCT-delta) (Stimulator of TAR RNA-binding)
1347. T-complex protein 1 subunit epsilon (TCP-1-epsilon) (CCT-epsilon)
1348. T-complex protein 1 subunit eta (TCP-1-eta) (CCT-eta) (HIV-1 Nef-interacting protein) [Cleaved into: T-complex protein 1 subunit eta, N-terminally processed]
1349. T-complex protein 1 subunit theta (TCP-1-theta) (CCT-theta) (Renal carcinoma antigen NY-REN-15)
1350. T-complex protein 1 subunit zeta (TCP-1-zeta) (Acute morphine dependence-related protein 2) (CCT-zeta-1) (HTR3) (Tcp20)
1351. Talin-1
1352. TAR DNA-binding protein 43 (TDP-43)
1353. Thioredoxin domain-containing protein 17 (14 kDa thioredoxin-related protein) (TRP14) (Protein 42-9-9) (Thioredoxin-like protein 5)
1354. Thioredoxin domain-containing protein 9 (Fragment)
1355. THO complex subunit 4
1356. Threonine--tRNA ligase, cytoplasmic (EC 6.1.1.3) (Threonyl-tRNA synthetase) (ThrRS)
1357. THUMP domain-containing protein 3
1358. Thymidine kinase, cytosolic (EC 2.7.1.21)
1359. Thymidylate synthase (TS) (TSase) (EC 2.1.1.45)
1360. Thymocyte nuclear protein 1 (Thymocyte protein Thy28)
1361. Thyroid hormone receptor-associated protein 3 (Thyroid hormone receptor-associated protein complex 150 kDa component) (Trap150)
1362. Thyroid receptor-interacting protein 6 (TR-interacting protein 6) (TRIP-6) (Opa-interacting protein 1) (OIP-1) (Zyxin-related protein 1) (ZRP-1)
1363. Torsin-1A-interacting protein 1 (Lamin-associated protein 1B) (LAP1B)
1364. Transaldolase (EC 2.2.1.2)
1365. Transcription elongation factor A protein 1 (Transcription elongation factor S-II protein 1) (Transcription elongation factor TFIIS.o)
1366. Transcription factor BTF3 (Nascent polypeptide-associated complex subunit beta) (NAC-beta) (RNA polymerase B transcription factor 3)
1367. Transcription intermediary factor 1-beta (TIF1-beta) (E3 SUMO-protein ligase TRIM28) (EC 2.3.2.27) (KRAB-associated protein 1) (KAP-1) (KRAB-interacting protein 1) (KRIP-1) (Nuclear corepressor KAP-1) (RING finger protein 96) (RING-type E3 ubiquitin transferase TIF1-beta) (Tripartite motif-containing protein 28)
1368. Transcriptional activator protein Pur-alpha (Purine-rich single-stranded DNA-binding protein alpha)
1369. Transducin beta-like protein 3 (WD repeat-containing protein SAZD)
1370. Transferrin receptor protein 1 (TR) (TfR) (TfR1) (Trfr) (T9) (p90) (CD antigen CD71) [Cleaved into: Transferrin receptor protein 1, serum form (sTfR)]
1371. Transitional endoplasmic reticulum ATPase (TER ATPase) (EC 3.6.4.6) (15S Mg(2+)-ATPase p97 subunit) (Valosin-containing protein) (VCP)
1372. Translation initiation factor eIF-2B subunit delta
1373. Translationally-controlled tumor protein (Fragment)
1374. Translin
1375. Translocon-associated protein subunit delta (TRAP-delta) (Signal sequence receptor subunit delta) (SSR-delta)
1376. Transportin-1 (Importin beta-2) (Karyopherin beta-2) (M9 region interaction protein) (MIP)
1377. Treacle protein
1378. Tricarboxylate transport protein, mitochondrial (Citrate transport protein) (CTP) (Solute carrier family 25 member 1) (Tricarboxylate carrier protein)
1379. Trifunctional enzyme subunit beta, mitochondrial
1380. Trifunctional purine biosynthetic protein adenosine-3 [Includes: Phosphoribosylamine--glycine ligase (EC 6.3.4.13) (Glycinamide ribonucleotide synthetase) (GARS) (Phosphoribosylglycinamide synthetase); Phosphoribosylformylglycinamidine cyclo-ligase (EC 6.3.3.1) (AIR synthase) (AIRS) (Phosphoribosyl-aminoimidazole synthetase); Phosphoribosylglycinamide formyltransferase (EC 2.1.2.2) (5'-phosphoribosylglycinamide transformylase) (GAR transformylase) (GART)]
1381. tRNA-splicing ligase RtcB homolog (EC 6.5.1.3)
1382. Tropomodulin-1 (Erythrocyte tropomodulin) (E-Tmod)
1383. Tropomyosin alpha-3 chain (Gamma-tropomyosin) (Tropomyosin-3) (Tropomyosin-5) (hTM5)
1384. Trypsin-1
1385. Tryptophan--tRNA ligase, cytoplasmic (EC 6.1.1.2) (Interferon-induced protein 53) (IFP53) (Tryptophanyl-tRNA synthetase) (TrpRS) (hWRS) [Cleaved into: T1-TrpRS; T2-TrpRS]
1386. Tubulin alpha chain
1387. Tubulin alpha-1A chain (Alpha-tubulin 3) (Tubulin B-alpha-1) (Tubulin alpha-3 chain) [Cleaved into: Detyrosinated tubulin alpha-1A chain]
1388. Tubulin alpha-1B chain (Alpha-tubulin ubiquitous) (Tubulin K-alpha-1) (Tubulin alpha-ubiquitous chain) [Cleaved into: Detyrosinated tubulin alpha-1B chain]
1389. Tubulin beta chain (Tubulin beta-5 chain)
1390. Tubulin beta-2A chain (Tubulin beta class IIa)
1391. Tubulin beta-4B chain (Tubulin beta-2 chain) (Tubulin beta-2C chain)
1392. Tubulin beta-8 chain (Tubulin beta 8 class VIII)
1393. Tubulin gamma-1 chain (Gamma-1-tubulin) (Gamma-tubulin complex component 1) (GCP-1)
1394. Tubulin-specific chaperone A
1395. Tumor susceptibility gene 101 protein
1396. Tyrosine--tRNA ligase, cytoplasmic (EC 6.1.1.1) (Tyrosyl-tRNA synthetase) (TyrRS) [Cleaved into: Tyrosine--tRNA ligase, cytoplasmic, N-terminally processed]
1397. Tyrosine-protein kinase (EC 2.7.10.2)

-continued

1398. Tyrosine-protein kinase BAZ1B (EC 2.7.10.2) (Bromodomain adjacent to zinc finger domain protein 1B) (Williams syndrome transcription factor) (Williams-Beuren syndrome chromosomal region 10 protein) (Williams-Beuren syndrome chromosomal region 9 protein) (hWALp2)
1399. Tyrosine-protein kinase BTK (EC 2.7.10.2) (Agammaglobulinemia tyrosine kinase) (ATK) (B-cell progenitor kinase) (BPK) (Bruton tyrosine kinase)
1400. U1 small nuclear ribonucleoprotein 70 kDa (U1 snRNP 70 kDa) (U1-70K) (snRNP70)
1401. U1 small nuclear ribonucleoprotein A (U1 snRNP A) (U1-A) (U1A)
1402. U1 small nuclear ribonucleoprotein C (U1 snRNP C) (U1-C) (U1C)
1403. U2 small nuclear ribonucleoprotein A' (U2 snRNP A')
1404. U2 small nuclear ribonucleoprotein B" (U2 snRNP B")
1405. U2 snRNP-associated SURP motif-containing protein
1406. U5 small nuclear ribonucleoprotein 200 kDa helicase (EC 3.6.4.13) (Activating signal cointegrator 1 complex subunit 3-like 1) (BRR2 homolog) (U5 snRNP-specific 200 kDa protein) (U5-200 KD)
1407. U6 snRNA-associated Sm-like protein LSm4 (Glycine-rich protein) (GRP)
1408. Ubiquilin-4 (Ataxin-1 interacting ubiquitin-like protein) (A1Up) (Ataxin-1 ubiquitin-like-interacting protein A1U) (Connexin43-interacting protein of 75 kDa) (CIP75)
1409. Ubiquitin carboxyl-terminal hydrolase 10 (EC 3.4.19.12) (Deubiquitinating enzyme 10) (Ubiquitin thioesterase 10) (Ubiquitin-specific-processing protease 10)
1410. Ubiquitin carboxyl-terminal hydrolase 14
1411. Ubiquitin carboxyl-terminal hydrolase 7 (EC 3.4.19.12) (Deubiquitinating enzyme 7) (Herpesvirus-associated ubiquitin-specific protease) (Ubiquitin thioesterase 7) (Ubiquitin-specific-processing protease 7)
1412. Ubiquitin thioesterase OTUB1
1413. Ubiquitin-associated domain-containing protein 1 (UBA domain-containing protein 1) (E3 ubiquitin-protein ligase subunit KPC2) (Glialblastoma cell differentiation-related protein 1) (Kip1 ubiquitination-promoting complex protein 2)
1414. Ubiquitin-associated protein 2-like (Protein NICE-4)
1415. Ubiquitin-conjugating enzyme E2 D3
1416. Ubiquitin-conjugating enzyme E2 K (EC 2.3.2.23) (E2 ubiquitin-conjugating enzyme K) (Huntingtin-interacting protein 2) (HIP-2) (Ubiquitin carrier protein) (Ubiquitin-conjugating enzyme E2-25 kDa) (Ubiquitin-conjugating enzyme E2(25K)) (Ubiquitin-conjugating enzyme E2-25K) (Ubiquitin-protein ligase)
1417. Ubiquitin-conjugating enzyme E2 L3 (EC 2.3.2.23) (E2 ubiquitin-conjugating enzyme L3) (L-UBC) (UbcH7) (Ubiquitin carrier protein L3) (Ubiquitin-conjugating enzyme E2-F1) (Ubiquitin-protein ligase L3)
1418. Ubiquitin-conjugating enzyme E2 S (EC 2.3.2.23) (E2 ubiquitin-conjugating enzyme S) (E2-EPF) (Ubiquitin carrier protein S) (Ubiquitin-conjugating enzyme E2-24 kDa) (Ubiquitin-conjugating enzyme E2-EPF5) (Ubiquitin-protein ligase S)
1419. Ubiquitin-like modifier-activating enzyme 1 (EC 6.2.1.45) (Protein A1S9) (Ubiquitin-activating enzyme E1)
1420. Ubiquitin-like modifier-activating enzyme 6 (Ubiquitin-activating enzyme 6) (EC 6.2.1.45) (Monocyte protein 4) (MOP-4) (Ubiquitin-activating enzyme E1-like protein 2) (E1-L2)
1421. UMP-CMP kinase (EC 2.7.4.14) (Deoxycytidylate kinase) (CK) (dCMP kinase) (Nucleoside-diphosphate kinase) (EC 2.7.4.6) (Uridine monophosphate/cytidine monophosphate kinase) (UMP/CMP kinase) (UMP/CMPK)
1422. Uncharacterized protein C9orf78 (Hepatocellular carcinoma-associated antigen 59)
1423. Uncharacterized protein KIAA1614
1424. Uroporphyrinogen decarboxylase (UPD) (URO-D) (EC 4.1.1.37)
1425. V-type proton ATPase catalytic subunit A (V-ATPase subunit A) (EC 3.6.3.14) (V-ATPase 69 kDa subunit) (Vacuolar ATPase isoform VA68) (Vacuolar proton pump subunit alpha)
1426. V-type proton ATPase subunit B, brain isoform (V-ATPase subunit B 2) (Endomembrane proton pump 58 kDa subunit) (HO57) (Vacuolar proton pump subunit B 2)
1427. Vacuolar protein sorting-associated protein 4A (EC 3.6.4.6) (Protein SKD2) (VPS4-1) (hVPS4)
1428. Vasodilator-stimulated phosphoprotein (VASP)
1429. Very-long-chain enoyl-CoA reductase (EC 1.3.1.93) (Synaptic glycoprotein SC2) (Trans-2,3-enoyl-CoA reductase) (TER)
1430. Vesicle-associated membrane protein-associated protein A (VAMP-A) (VAMP-associated protein A) (VAP-A) (33 kDa VAMP-associated protein) (VAP-33)
1431. Vesicle-trafficking protein SEC22b (ER-Golgi SNARE of 24 kDa) (ERS-24) (ERS24) (SEC22 vesicle-trafficking protein homolog B) (SEC22 vesicle-trafficking protein-like 1)
1432. Vimentin
1433. Vinculin (Metavinculin) (MV)
1434. Voltage-dependent anion-selective channel protein 1 (VDAC-1) (hVDAC1) (Outer mitochondrial membrane protein porin 1) (Plasmalemmal porin) (Porin 31HL) (Porin 31HM)
1435. Voltage-dependent anion-selective channel protein 2 (Fragment)
1436. Voltage-dependent anion-selective channel protein 2 (VDAC-2) (hVDAC2) (Outer mitochondrial membrane protein porin 2)
1437. Voltage-dependent anion-selective channel protein 3 (VDAC-3) (hVDAC3) (Outer mitochondrial membrane protein porin 3)
1438. WD repeat-containing protein 5 (BMP2-induced 3-kb gene protein)
1439. WD repeat-containing protein 74 (NOP seven-associated protein 1)
1440. WD repeat-containing protein 82 (Protein TMEM113) (Swd2)
1441. X-ray repair cross-complementing protein 5 (EC 3.6.4.—) (86 kDa subunit of Ku antigen) (ATP-dependent DNA helicase 2 subunit 2) (ATP-dependent DNA helicase II 80 kDa subunit) (CTC box-binding factor 85 kDa subunit) (CTC85) (CTCBF) (DNA repair protein XRCC5) (Ku80) (Ku86) (Lupus Ku autoantigen protein p86) (Nuclear factor IV) (Thyroid-lupus autoantigen) (TLAA) (X-ray repair complementing defective repair in Chinese hamster cells 5 (double-strand-break rejoining))
1442. Y-box-binding protein 3 (Cold shock domain-containing protein A) (DNA-binding protein A) (Single-strand DNA-binding protein NF-GMB)
1443. Zinc finger CCCH-type antiviral protein 1
1444. Zinc finger CCHC domain-containing protein 3
1445. Zinc finger MYM-type protein 3
1446. Zinc finger protein 706
1447. Zinc-alpha-2-glycoprotein (Zn-alpha-2-GP) (Zn-alpha-2-glycoprotein)

Table 6 Shows Data for Peptide Identification by MS for 10 Day Control Sample

1. CRISPR-associated endonuclease Cas9/Csn1 (EC 3.1.-.-) (SpCas9) (SpyCas9)
2. >Reverse >sp|A6NN14|ZN729_HUMAN Zinc finger protein 729 OS = *Homo sapiens* GN = ZNF729 PE = 2 SV = 3
3. >Reverse >sp|P0C5W0|PNM6B_HUMAN Paraneoplastic antigen-like protein 6B OS = *Homo sapiens* GN = PNMA6B PE = 2 SV = 1
4. >Reverse >sp|P20929|NEBU_HUMAN Nebulin OS = *Homo sapiens* GN = NEB PE = 1 SV = 4
5. >Reverse >sp|P49454|CENPF_HUMAN Centromere protein F OS = *Homo sapiens* GN = CENPF PE = 1 SV = 2
6. >Reverse >sp|P98088|MUC5A_HUMAN Mucin-5AC (Fragments) OS = *Homo sapiens* GN = MUC5AC PE = 1 SV = 3
7. >Reverse >sp|Q8IV53|DEN1C_HUMAN DENN domain-containing protein 1C OS = *Homo sapiens* GN = DENND1C PE = 1 SV = 1
8. >Reverse >sp|Q8IWX9|TRML3_HUMAN Trem-like transcript 3 protein OS = *Homo sapiens* GN = TREML3 PE = 2 SV = 2
9. >Reverse >sp|Q96J65|MRP9_HUMAN Multidrug resistance-associated protein 9 OS = *Homo sapiens* GN = ABCC12 PE = 1 SV = 2
10. >Reverse >sp|Q9NPC3|CIP1_HUMAN E3 ubiquitin-protein ligase CCNB1IP1 OS = *Homo sapiens* GN = CCNB1IP1 PE = 1 SV = 1
11. >Reverse >sp|Q9P2M7|CING_HUMAN Cingulin OS = *Homo sapiens* GN = CGN PE = 1 SV = 2
12. >Reverse >sp|Q9ULI2|RIMKB_HUMAN Beta-citryl-glutamate synthase B OS = *Homo sapiens* GN = RIMKLB PE = 2 SV = 2
13. >Reverse >tr|B4DL02|B4DL02_HUMAN cDNA FLJ56101, highly similar to SHC-transforming protein 1 OS = *Homo sapiens* PE = 2 SV = 1
14. >Reverse >tr|B8ZZX6|B8ZZX6_HUMAN STEAP family member 3, isoform CRA_c OS = *Homo sapiens* GN = STEAP3 PE = 4 SV = 1
15. >Reverse >tr|C9JM73|C9JM73_HUMAN Uncharacterized protein OS = *Homo sapiens* GN = GPAT2 PE = 4 SV = 1
16. >Reverse >tr|C9JRL1|C9JRL1_HUMAN Uncharacterized protein OS = *Homo sapiens* GN = STOX1 PE = 4 SV = 1
17. >Reverse >tr|D6RFF6|D6RFF6_HUMAN Uncharacterized protein OS = *Homo sapiens* GN = ACAD10 PE = 4 SV = 1
18. >Reverse >tr|E7EP39|E7EP39_HUMAN Uncharacterized protein OS = *Homo sapiens* GN = CEP110 PE = 4 SV = 1
19. >Reverse >tr|E9PM46|E9PM46_HUMAN Ubiquitin carboxyl-terminal hydrolase OS = *Homo sapiens* GN = USP47 PE = 3 SV = 1
20. >Reverse >tr|F5GYI1|F5GYI1_HUMAN Uncharacterized protein OS = *Homo sapiens* GN = VNN3 PE = 4 SV = 1
21. >Reverse >tr|F5H0C0|F5H0C0_HUMAN Uncharacterized protein OS = *Homo sapiens* PE = 4 SV = 1
22. >sp|A1A4S6|RHG10_HUMAN Rho GTPase-activating protein 10 OS = *Homo sapiens* GN = ARHGAP10 PE = 1 SV = 1
23. >sp|A6NK02|TRI75_HUMAN Tripartite motif-containing protein 75 OS = *Homo sapiens* GN = TRIM75 PE = 2 SV = 2
24. >sp|A6NK07|IF2BL_HUMAN Eukaryotic translation initiation factor 2 subunit 2-like protein OS = *Homo sapiens* PE = 1 SV = 1
25. >sp|A6NMY6|AXA2L_HUMAN Putative annexin A2-like protein OS = *Homo sapiens* GN = ANXA2P2 PE = 5 SV = 2
26. >sp|O00148|DX39A_HUMAN ATP-dependent RNA helicase DDX39A OS = *Homo sapiens* GN = DDX39A PE = 1 SV = 2
27. >sp|O00299|CLIC1_HUMAN Chloride intracellular channel protein 1 OS = *Homo sapiens* GN = CLIC1 PE = 1 SV = 4
28. >sp|O00471|EXOC5_HUMAN Exocyst complex component 5 OS = *Homo sapiens* GN = EXOC5 PE = 1 SV = 1
29. >sp|O00479|HMGN4_HUMAN High mobility group nucleosome-binding domain-containing protein 4 OS = *Homo sapiens* GN = HMGN4 PE = 1 SV = 3
30. >sp|O00712|NFIB_HUMAN Nuclear factor 1 B-type OS = *Homo sapiens* GN = NFIB PE = 1 SV = 2
31. >sp|O14979|HNRDL_HUMAN Heterogeneous nuclear ribonucleoprotein D-like OS = *Homo sapiens* GN = HNRPDL PE = 1 SV = 3
32. >sp|O15446|RPA34_HUMAN DNA-directed RNA polymerase I subunit RPA34 OS = *Homo sapiens* GN = CD3EAP PE = 1 SV = 1
33. >sp|O43150|ASAP2_HUMAN Arf-GAP with SH3 domain, ANK repeat and PH domain-containing protein 2 OS = *Homo sapiens* GN = ASAP2 PE = 1 SV = 3
34. >sp|O43151|TET3_HUMAN Methylcytosine dioxygenase TET3 OS = *Homo sapiens* GN = TET3 PE = 2 SV = 3
35. >sp|O60506|HNRPQ_HUMAN Heterogeneous nuclear ribonucleoprotein Q OS = *Homo sapiens* GN = SYNCRIP PE = 1 SV = 2
36. >sp|O60869|EDF1_HUMAN Endothelial differentiation-related factor 1 OS = *Homo sapiens* GN = EDF1 PE = 1 SV = 1
37. >sp|O75306|NDUS2_HUMAN NADH dehydrogenase [ubiquinone] iron-sulfur protein 2, mitochondrial OS = *Homo sapiens* GN = NDUFS2 PE = 1 SV = 2
38. >sp|O75494|SRS10_HUMAN Serine/arginine-rich splicing factor 10 OS = *Homo sapiens* GN = SRSF10 PE = 1 SV = 1
39. >sp|O75821|EIF3G_HUMAN Eukaryotic translation initiation factor 3 subunit G OS = *Homo sapiens* GN = EIF3G PE = 1 SV = 2
40. >sp|P01857|IGHG1_HUMAN Ig gamma-1 chain C region OS = *Homo sapiens* GN = IGHG1 PE = 1 SV = 1
41. >sp|P02008|HBAZ_HUMAN Hemoglobin subunit zeta OS = *Homo sapiens* GN = HBZ PE = 1 SV = 1
42. >sp|P02533|K1C14_HUMAN Keratin, type I cytoskeletal 14 OS = *Homo sapiens* GN = KRT14 PE = 1 SV = 4
43. >sp|P02538|K2C6A_HUMAN Keratin, type II cytoskeletal 6A OS = *Homo sapiens* GN = KRT6A PE = 1 SV = 3
44. >sp|P04040|CATA_HUMAN Catalase OS = *Homo sapiens* GN = CAT PE = 1 SV = 3
45. >sp|P04075|ALDOA_HUMAN Fructose-bisphosphate aldolase A OS = *Homo sapiens* GN = ALDOA PE = 1 SV = 2
46. >sp|P04083|ANXA1_HUMAN Annexin A1 OS = *Homo sapiens* GN = ANXA1 PE = 1 SV = 2
47. >sp|P04259|K2C6B_HUMAN Keratin, type II cytoskeletal 6B OS = *Homo sapiens* GN = KRT6B PE = 1 SV = 5
48. >sp|P04264|K2C1_HUMAN Keratin, type II cytoskeletal 1 OS = *Homo sapiens* GN = KRT1 PE = 1 SV = 6
49. >sp|P05141|ADT2_HUMAN ADP/ATP translocase 2 OS = *Homo sapiens* GN = SLC25A5 PE = 1 SV = 7
50. >sp|P05387|RLA2_HUMAN 60S acidic ribosomal protein P2 OS = *Homo sapiens* GN = RPLP2 PE = 1 SV = 1
51. >sp|P05388|RLA0_HUMAN 60S acidic ribosomal protein P0 OS = *Homo sapiens* GN = RPLP0 PE = 1 SV = 1
52. >sp|P05783|K1C18_HUMAN Keratin, type I cytoskeletal 18 OS = *Homo sapiens* GN = KRT18 PE = 1 SV = 2
53. >sp|P05787|K2C8_HUMAN Keratin, type II cytoskeletal 8 OS = *Homo sapiens* GN = KRT8 PE = 1 SV = 7
54. >sp|P06727|APOA4_HUMAN Apolipoprotein A-IV OS = *Homo sapiens* GN = APOA4 PE = 1 SV = 3
55. >sp|P06733|ENOA_HUMAN Alpha-enolase OS = *Homo sapiens* GN = ENO1 PE = 1 SV = 2
56. >sp|P06748|NPM_HUMAN Nucleophosmin OS = *Homo sapiens* GN = NPM1 PE = 1 SV = 2
57. >sp|P06753-2|TPM3_HUMAN Isoform 2 of Tropomyosin alpha-3 chain OS = *Homo sapiens* GN = TPM3
58. >sp|P06899|H2B1J_HUMAN Histone H2B type 1-J OS = *Homo sapiens* GN = HIST1H2BJ PE = 1 SV = 3
59. >sp|P07195|LDHB_HUMAN L-lactate dehydrogenase B chain OS = *Homo sapiens* GN = LDHB PE = 1 SV = 2
60. >sp|P07437|TBB5_HUMAN Tubulin beta chain OS = *Homo sapiens* GN = TUBB PE = 1 SV = 2
61. >sp|P07737|PROF1_HUMAN Profilin-1 OS = *Homo sapiens* GN = PFN1 PE = 1 SV = 2
62. >sp|P07900|HS90A_HUMAN Heat shock protein HSP 90-alpha OS = *Homo sapiens* GN = HSP90AA1 PE = 1 SV = 5
63. >sp|P07910|HNRPC_HUMAN Heterogeneous nuclear ribonucleoproteins C1/C2 OS = *Homo sapiens* GN = HNRNPCPE = 1 SV = 4
64. >sp|P08238|HS90B_HUMAN Heat shock protein HSP 90-beta OS = *Homo sapiens* GN = HSP90AB1 PE = 1 SV = 4
65. >sp|P08670|VIME_HUMAN Vimentin OS = *Homo sapiens* GN = VIM PE = 1 SV = 4
66. >sp|P08708|RS17_HUMAN 40S ribosomal protein S17 OS = *Homo sapiens* GN = RPS17 PE = 1 SV = 2
67. >sp|P08779|K1C16_HUMAN Keratin, type I cytoskeletal 16 OS = *Homo sapiens* GN = KRT16 PE = 1 SV = 4
68. >sp|P09012|SNRPA_HUMAN U1 small nuclear ribonucleoprotein A OS = *Homo sapiens* GN = SNRPA PE = 1 SV = 3
69. >sp|P09651|ROA1_HUMAN Heterogeneous nuclear ribonucleoprotein A1 OS = *Homo sapiens* GN = HNRNPA1 PE = 1 SV = 5
70. >sp|P09874|PARP1_HUMAN Poly [ADP-ribose] polymerase 1 OS = *Homo sapiens* GN = PARP1 PE = 1 SV = 4
71. >sp|P0CW18|PRS56_HUMAN Putative serine protease 56 OS = *Homo sapiens* GN = PRSS56 PE = 5 SV = 1
72. >sp|P10606|COX5B_HUMAN Cytochrome c oxidase subunit 5B, mitochondrial OS = *Homo sapiens* GN = COX5B PE = 1 SV = 2
73. >sp|P10809|CH60_HUMAN 60 kDa heat shock protein, mitochondrial OS = *Homo sapiens* GN = HSPD1 PE = 1 SV = 2
74. >sp|P13010|XRCC5_HUMAN X-ray repair cross-complementing protein 5 OS = *Homo sapiens* GN = XRCC5 PE = 1 SV = 3

-continued

75. >sp|P13639|EF2_HUMAN Elongation factor 2 OS = *Homo sapiens* GN = EEF2 PE = 1 SV = 4
76. >sp|P13645|K1C10_HUMAN Keratin, type I cytoskeletal 10 OS = *Homo sapiens* GN = KRT10 PE = 1 SV = 6
77. >sp|P13647|K2C5_HUMAN Keratin, type II cytoskeletal 5 OS = *Homo sapiens* GN = KRT5 PE = 1 SV = 3
78. >sp|P14866|HNRPL_HUMAN Heterogeneous nuclear ribonucleoprotein L OS = *Homo sapiens* GN = HNRNPL PE = 1 SV = 2
79. >sp|P14868|SYDC_HUMAN Aspartyl-tRNA synthetase, cytoplasmic OS = *Homo sapiens* GN = DARS PE = 1 SV = 2
80. >sp|P14923|PLAK_HUMAN Junction plakoglobin OS = *Homo sapiens* GN = JUP PE = 1 SV = 3
81. >sp|P15311|EZRI_HUMAN Ezrin OS = *Homo sapiens* GN = EZR PE = 1 SV = 4
82. >sp|P15880|RS2_HUMAN 40S ribosomal protein S2 OS = *Homo sapiens* GN = RPS2 PE = 1 SV = 2
83. >sp|P15924|DESP_HUMAN Desmoplakin OS = *Homo sapiens* GN = DSP PE = 1 SV = 3
84. >sp|P16104|H2AX_HUMAN Histone H2.a.x OS = *Homo sapiens* GN = H2AFX PE = 1 SV = 2
85. >sp|P16401|H15_HUMAN Histone H1.5 OS = *Homo sapiens* GN = HIST1H1B PE = 1 SV = 3
86. >sp|P16989|DBPA_HUMAN DNA-binding protein A OS = *Homo sapiens* GN = CSDA PE = 1 SV = 4
87. >sp|P17066|HSP76_HUMAN Heat shock 70 kDa protein 6 OS = *Homo sapiens* GN = HSPA6 PE = 1 SV = 2
88. >sp|P17096-2|HMGA1_HUMAN Isoform HMG-Y of High mobility group protein HMG-I/HMG-Y OS = *Homo sapiens* GN = HMGA1
89. >sp|P18077|RL35A_HUMAN 60S ribosomal protein L35a OS = *Homo sapiens* GN = RPL35A PE = 1 SV = 2
90. >sp|P18621|RL17_HUMAN 60S ribosomal protein L17 OS = *Homo sapiens* GN = RPL17 PE = 1 SV = 3
91. >sp|P19338|NUCL_HUMAN Nucleolin OS = *Homo sapiens* GN = NCL PE = 1 SV = 3
92. >sp|P20671|H2A1D_HUMAN Histone H2A type 1-D OS = *Homo sapiens* GN = HIST1H2AD PE = 1 SV = 2
93. >sp|P22087|FBRL_HUMAN rRNA 2'-O-methyltransferase fibrillarin OS = *Homo sapiens* GN = FBL PE = 1 SV = 2
94. >sp|P22102|PUR2_HUMAN Trifunctional purine biosynthetic protein adenosine-3 OS = *Homo sapiens* GN = GART PE = 1 SV = 1
95. >sp|P22392|NDKB_HUMAN Nucleoside diphosphate kinase B OS = *Homo sapiens* GN = NME2 PE = 1 SV = 1
96. >sp|P22626|ROA2_HUMAN Heterogeneous nuclear ribonucleoproteins A2/B1 OS = *Homo sapiens* GN = HNRNPA2B1 PE = 1 SV = 2
97. >sp|P23246|SFPQ_HUMAN Splicing factor, proline- and glutamine-rich OS = *Homo sapiens* GN = SFPQ PE = 1 SV = 2
98. >sp|P23396|RS3_HUMAN 40S ribosomal protein S3 OS = *Homo sapiens* GN = RPS3 PE = 1 SV = 2
99. >sp|P25398|RS12_HUMAN 40S ribosomal protein S12 OS = *Homo sapiens* GN = RPS12 PE = 1 SV = 3
100. >sp|P25705|ATPA_HUMAN ATP synthase subunit alpha, mitochondrial OS = *Homo sapiens* GN = ATP5A1 PE = 1 SV = 1
101. >sp|P26038|MOES_HUMAN Moesin OS = *Homo sapiens* GN = MSN PE = 1 SV = 3
102. >sp|P26599|PTBP1_HUMAN Polypyrimidine tract-binding protein 1 OS = *Homo sapiens* GN = PTBP1 PE = 1 SV = 1
103. >sp|P28066|PSA5_HUMAN Proteasome subunit alpha type-5 OS = *Homo sapiens* GN = PSMA5 PE = 1 SV = 3
104. >sp|P28482|MK01_HUMAN Mitogen-activated protein kinase 1 OS = *Homo sapiens* GN = MAPK1 PE = 1 SV = 3
105. >sp|P30041|PRDX6_HUMAN Peroxiredoxin-6 OS = *Homo sapiens* GN = PRDX6 PE = 1 SV = 3
106. >sp|P30050|RL12_HUMAN 60S ribosomal protein L12 OS = *Homo sapiens* GN = RPL12 PE = 1 SV = 1
107. >sp|P31946|1433B_HUMAN 14-3-3 protein beta/alpha OS = *Homo sapiens* GN = YWHAB PE = 1 SV = 3
108. >sp|P34932|HSP74_HUMAN Heat shock 70 kDa protein 4 OS = *Homo sapiens* GN = HSPA4 PE = 1 SV = 4
109. >sp|P35268|RL22_HUMAN 60S ribosomal protein L22 OS = *Homo sapiens* GN = RPL22 PE = 1 SV = 2
110. >sp|P35527|K1C9_HUMAN Keratin, type I cytoskeletal 9 OS = *Homo sapiens* GN = KRT9 PE = 1 SV = 3
111. >sp|P35908|K22E_HUMAN Keratin, type II cytoskeletal 2 epidermal OS = *Homo sapiens* GN = KRT2 PE = 1 SV = 2
112. >sp|P38159|HNRPG_HUMAN Heterogeneous nuclear ribonucleoprotein G OS = *Homo sapiens* GN = RBMX PE = 1 SV = 3
113. >sp|P38646|GRP75_HUMAN Stress-70 protein, mitochondrial OS = *Homo sapiens* GN = HSPA9 PE = 1 SV = 2
114. >sp|P38919|IF4A3_HUMAN Eukaryotic initiation factor 4A-III OS = *Homo sapiens* GN = EIF4A3 PE = 1 SV = 4
115. >sp|P40429|RL13A_HUMAN 60S ribosomal protein L13a OS = *Homo sapiens* GN = RPL13A PE = 1 SV = 2
116. >sp|P40926|MDHM_HUMAN Malate dehydrogenase, mitochondrial OS = *Homo sapiens* GN = MDH2 PE = 1 SV = 3
117. >sp|P41091|IF2G_HUMAN Eukaryotic translation initiation factor 2 subunit 3 OS = *Homo sapiens* GN = EIF2S3 PE = 1 SV = 3
118. >sp|P42166|LAP2A_HUMAN Lamina-associated polypeptide 2, isoform alpha OS = *Homo sapiens* GN = TMPO PE = 1 SV = 2
119. >sp|P42766|RL35_HUMAN 60S ribosomal protein L35 OS = *Homo sapiens* GN = RPL35 PE = 1 SV = 2
120. >sp|P43487|RANG_HUMAN Ran-specific GTPase-activating protein OS = *Homo sapiens* GN = RANBP1 PE = 1 SV = 1
121. >sp|P45880|VDAC2_HUMAN Voltage-dependent anion-selective channel protein 2 OS = *Homo sapiens* GN = VDAC2 PE = 1 SV = 2
122. >sp|P46778|RL21_HUMAN 60S ribosomal protein L21 OS = *Homo sapiens* GN = RPL21 PE = 1 SV = 2
123. >sp|P46782|RS5_HUMAN 40S ribosomal protein S5 OS = *Homo sapiens* GN = RPS5 PE = 1 SV = 4
124. >sp|P46783|RS10_HUMAN 40S ribosomal protein S10 OS = *Homo sapiens* GN = RPS10 PE = 1 SV = 1
125. >sp|P47914|RL29_HUMAN 60S ribosomal protein L29 OS = *Homo sapiens* GN = RPL29 PE = 1 SV = 2
126. >sp|P49006|MRP_HUMAN MARCKS-related protein OS = *Homo sapiens* GN = MARCKSL1 PE = 1 SV = 2
127. >sp|P49207|RL34_HUMAN 60S ribosomal protein L34 OS = *Homo sapiens* GN = RPL34 PE = 1 SV = 3
128. >sp|P49327|FAS_HUMAN Fatty acid synthase OS = *Homo sapiens* GN = FASN PE = 1 SV = 3
129. >sp|P49411|EFTU_HUMAN Elongation factor Tu, mitochondrial OS = *Homo sapiens* GN = TUFM PE = 1 SV = 2
130. >sp|P49591|SYSC_HUMAN Seryl-tRNA synthetase, cytoplasmic OS = *Homo sapiens* GN = SARS PE = 1 SV = 3
131. >sp|P50990|TCPQ_HUMAN T-complex protein 1 subunit theta OS = *Homo sapiens* GN = CCT8 PE = 1 SV = 4
132. >sp|P50991|TCPD_HUMAN T-complex protein 1 subunit delta OS = *Homo sapiens* GN = CCT4 PE = 1 SV = 4
133. >sp|P51858|HDGF_HUMAN Hepatoma-derived growth factor OS = *Homo sapiens* GN = HDGF PE = 1 SV = 1
134. >sp|P52272|HNRPM_HUMAN Heterogeneous nuclear ribonucleoprotein M OS = *Homo sapiens* GN = HNRNPM PE = 1 SV = 3
135. >sp|P52292|IMA2_HUMAN Importin subunit alpha-2 OS = *Homo sapiens* GN = KPNA2 PE = 1 SV = 1
136. >sp|P52597|HNRPF_HUMAN Heterogeneous nuclear ribonucleoprotein F OS = *Homo sapiens* GN = HNRNPF PE = 1 SV = 3
137. >sp|P55072|TERA_HUMAN Transitional endoplasmic reticulum ATPase OS = *Homo sapiens* GN = VCP PE = 1 SV = 4
138. >sp|P60842|IF4A1_HUMAN Eukaryotic initiation factor 4A-I OS = *Homo sapiens* GN = EIF4A1 PE = 1 SV = 1
139. >sp|P61353|RL27_HUMAN 60S ribosomal protein L27 OS = *Homo sapiens* GN = RPL27 PE = 1 SV = 2
140. >sp|P61927|RL37_HUMAN 60S ribosomal protein L37 OS = *Homo sapiens* GN = RPL37 PE = 1 SV = 2
141. >sp|P61981|1433G_HUMAN 14-3-3 protein gamma OS = *Homo sapiens* GN = YWHAG PE = 1 SV = 2
142. >sp|P62241|RS8_HUMAN 40S ribosomal protein S8 OS = *Homo sapiens* GN = RPS8 PE = 1 SV = 2
143. >sp|P62249|RS16_HUMAN 40S ribosomal protein S16 OS = *Homo sapiens* GN = RPS16 PE = 1 SV = 2
144. >sp|P62263|RS14_HUMAN 40S ribosomal protein S14 OS = *Homo sapiens* GN = RPS14 PE = 1 SV = 3
145. >sp|P62269|RS18_HUMAN 40S ribosomal protein S18 OS = *Homo sapiens* GN = RPS18 PE = 1 SV = 3
146. >sp|P62277|RS13_HUMAN 40S ribosomal protein S13 OS = *Homo sapiens* GN = RPS13 PE = 1 SV = 2
147. >sp|P62280|RS11_HUMAN 40S ribosomal protein S11 OS = *Homo sapiens* GN = RPS11 PE = 1 SV = 3
148. >sp|P62316|SMD2_HUMAN Small nuclear ribonucleoprotein Sm D2 OS = *Homo sapiens* GN = SNRPD2 PE = 1 SV = 1
149. >sp|P62424|RL7A_HUMAN 60S ribosomal protein L7a OS = *Homo sapiens* GN = RPL7A PE = 1 SV = 2
150. >sp|P62829|RL23_HUMAN 60S ribosomal protein L23 OS = *Homo sapiens* GN = RPL23 PE = 1 SV = 1
151. >sp|P62841|RS15_HUMAN 40S ribosomal protein S15 OS = *Homo sapiens* GN = RPS15 PE = 1 SV = 2
152. >sp|P62851|RS25_HUMAN 40S ribosomal protein S25 OS = *Homo sapiens* GN = RPS25 PE = 1 SV = 1
153. >sp|P62854|RS26_HUMAN 40S ribosomal protein S26 OS = *Homo sapiens* GN = RPS26 PE = 1 SV = 3

154. >sp|P62888|RL30_HUMAN 60S ribosomal protein L30 OS = *Homo sapiens* GN = RPL30 PE = 1 SV = 2
155. >sp|P62906|RL10A_HUMAN 60S ribosomal protein L10a OS = *Homo sapiens* GN = RPL10A PE = 1 SV = 2
156. >sp|P62913|RL11_HUMAN 60S ribosomal protein L11 OS = *Homo sapiens* GN = RPL11 PE = 1 SV = 2
157. >sp|P63173|RL38_HUMAN 60S ribosomal protein L38 OS = *Homo sapiens* GN = RPL38 PE = 1 SV = 2
158. >sp|P63220|RS21_HUMAN 40S ribosomal protein S21 OS = *Homo sapiens* GN = RPS21 PE = 1 SV = 1
159. >sp|P68036|UB2L3_HUMAN Ubiquitin-conjugating enzyme E2 L3 OS = *Homo sapiens* GN = UBE2L3 PE = 1 SV = 1
160. >sp|P68104|EF1A1_HUMAN Elongation factor 1-alpha 1 OS = *Homo sapiens* GN = EEF1A1 PE = 1 SV = 1
161. >sp|P68363|TBA1B_HUMAN Tubulin alpha-1B chain OS = *Homo sapiens* GN = TUBA1B PE = 1 SV = 1
162. >sp|P68371|TBB2C_HUMAN Tubulin beta-2C chain OS = *Homo sapiens* GN = TUBB2C PE = 1 SV = 1
163. >sp|P68431|H31_HUMAN Histone H3.1 OS = *Homo sapiens* GN = HIST1H3A PE = 1 SV = 2
164. >sp|P78371|TCPB_HUMAN T-complex protein 1 subunit beta OS = *Homo sapiens* GN = CCT2 PE = 1 SV = 4
165. >sp|P84098|RL19_HUMAN 60S ribosomal protein L19 OS = *Homo sapiens* GN = RPL19 PE = 1 SV = 1
166. >sp|P98174|FGD1_HUMAN FYVE, RhoGEF and PH domain-containing protein 1 OS = *Homo sapiens* GN = FGD1 PE = 1 SV = 2
167. >sp|Q00610|CLH1_HUMAN Clathrin heavy chain 1 OS = *Homo sapiens* GN = CLTC PE = 1 SV = 5
168. >sp|Q00839|HNRPU_HUMAN Heterogeneous nuclear ribonucleoprotein U OS = *Homo sapiens* GN = HNRNPU PE = 1 SV = 6
169. >sp|Q01105-2|SET_HUMAN Isoform 2 of Protein SET OS = *Homo sapiens* GN = SET
170. >sp|Q01130|SRSF2_HUMAN Serine/arginine-rich splicing factor 2 OS = *Homo sapiens* GN = SRSF2 PE = 1 SV = 4
171. >sp|Q02413|DSG1_HUMAN Desmoglein-1 OS = *Homo sapiens* GN = DSG1 PE = 1 SV = 2
172. >sp|Q02543|RL18A_HUMAN 60S ribosomal protein L18a OS = *Homo sapiens* GN = RPL18A PE = 1 SV = 2
173. >sp|Q02878|RL6_HUMAN 60S ribosomal protein L6 OS = *Homo sapiens* GN = RPL6 PE = 1 SV = 3
174. >sp|Q04695|K1C17_HUMAN Keratin, type I cytoskeletal 17 OS = *Homo sapiens* GN = KRT17 PE = 1 SV = 2
175. >sp|Q06830|PRDX1_HUMAN Peroxiredoxin-1 OS = *Homo sapiens* GN = PRDX1 PE = 1 SV = 1
176. >sp|Q07020|RL18_HUMAN 60S ribosomal protein L18 OS = *Homo sapiens* GN = RPL18 PE = 1 SV = 2
177. >sp|Q07955|SRSF1_HUMAN Serine/arginine-rich splicing factor 1 OS = *Homo sapiens* GN = SRSF1 PE = 1 SV = 2
178. >sp|Q08211|DHX9_HUMAN ATP-dependent RNA helicase A OS = *Homo sapiens* GN = DHX9 PE = 1 SV = 4
179. >sp|Q08499-12|PDE4D_HUMAN Isoform 12 of cAMP-specific 3',5'-cyclic phosphodiesterase 4D OS = *Homo sapiens* GN = PDE4D
180. >sp|Q12905|ILF2_HUMAN Interleukin enhancer-binding factor 2 OS = *Homo sapiens* GN = ILF2 PE = 1 SV = 2
181. >sp|Q12906|ILF3_HUMAN Interleukin enhancer-binding factor 3 OS = *Homo sapiens* GN = ILF3 PE = 1 SV = 3
182. >sp|Q13151|ROA0_HUMAN Heterogeneous nuclear ribonucleoprotein A0 OS = *Homo sapiens* GN = HNRNPA0 PE = 1 SV = 1
183. >sp|Q13247|SRSF6_HUMAN Serine/arginine-rich splicing factor 6 OS = *Homo sapiens* GN = SRSF6 PE = 1 SV = 2
184. >sp|Q13263|TIF1B_HUMAN Transcription intermediary factor 1-beta OS = *Homo sapiens* GN = TRIM28 PE = 1 SV = 5
185. >sp|Q13838|DX39B_HUMAN Spliceosome RNA helicase DDX39B OS = *Homo sapiens* GN = DDX39B PE = 1 SV = 1
186. >sp|Q14160|SCRIB_HUMAN Protein scribble homolog OS = *Homo sapiens* GN = SCRIB PE = 1 SV = 4
187. >sp|Q14209|E2F2_HUMAN Transcription factor E2F2 OS = *Homo sapiens* GN = E2F2 PE = 1 SV = 1
188. >sp|Q14566|MCM6_HUMAN DNA replication licensing factor MCM6 OS = *Homo sapiens* GN = MCM6 PE = 1 SV = 1
189. >sp|Q14974|IMB1_HUMAN Importin subunit beta-1 OS = *Homo sapiens* GN = KPNB1 PE = 1 SV = 2
190. >sp|Q15056|IF4H_HUMAN Eukaryotic translation initiation factor 4H OS = *Homo sapiens* GN = EIF4H PE = 1 SV = 5
191. >sp|Q15181|IPYR_HUMAN Inorganic pyrophosphatase OS = *Homo sapiens* GN = PPA1 PE = 1 SV = 2
192. >sp|Q15233|NONO_HUMAN Non-POU domain-containing octamer-binding protein OS = *Homo sapiens* GN = NONO PE = 1 SV = 4
193. >sp|Q15365|PCBP1_HUMAN Poly(rC)-binding protein 1 OS = *Homo sapiens* GN = PCBP1 PE = 1 SV = 2
194. >sp|Q16658|FSCN1_HUMAN Fascin OS = *Homo sapiens* GN = FSCN1 PE = 1 SV = 3
195. >sp|Q16878|CDO1_HUMAN Cysteine dioxygenase type 1 OS = *Homo sapiens* GN = CDO1 PE = 1 SV = 2
196. >sp|Q5D862|FILA2_HUMAN Filaggrin-2 OS = *Homo sapiens* GN = FLG2 PE = 1 SV = 1
197. >sp|Q5T9A4|ATD3B_HUMAN ATPase family AAA domain-containing protein 3B OS = *Homo sapiens* GN = ATAD3B PE = 1 SV = 1
198. >sp|Q6BDS2|URFB1_HUMAN UHRF1-binding protein 1 OS = *Homo sapiens* GN = UHRF1BP1 PE = 1 SV = 1
199. >sp|Q86YZ3|HORN_HUMAN Hornerin OS = *Homo sapiens* GN = HRNR PE = 1 SV = 2
200. >sp|Q8NAT2|TDRD5_HUMAN Tudor domain-containing protein 5 OS = *Homo sapiens* GN = TDRD5 PE = 1 SV = 3
201. >sp|Q8NEV9|IL27A_HUMAN Interleukin-27 subunit alpha OS = *Homo sapiens* GN = IL27 PE = 1 SV = 2
202. >sp|Q8TD08|MK15_HUMAN Mitogen-activated protein kinase 15 OS = *Homo sapiens* GN = MAPK15 PE = 1 SV = 1
203. >sp|Q8TF72|SHRM3_HUMAN Protein Shroom3 OS = *Homo sapiens* GN = SHROOM3 PE = 1 SV = 2
204. >sp|Q92841|DDX17_HUMAN Probable ATP-dependent RNA helicase DDX17 OS = *Homo sapiens* GN = DDX17 PE = 1 SV = 1
205. >sp|Q93077|H2A1C_HUMAN Histone H2A type 1-C OS = *Homo sapiens* GN = HIST1H2AC PE = 1 SV = 3
206. >sp|Q96AG4|LRC59_HUMAN Leucine-rich repeat-containing protein 59 OS = *Homo sapiens* GN = LRRC59 PE = 1 SV = 1
207. >sp|Q96MK3|FA20A_HUMAN Protein FAM20A OS = *Homo sapiens* GN = FAM20A PE = 2 SV = 4
208. >sp|Q96PK6|RBM14_HUMAN RNA-binding protein 14 OS = *Homo sapiens* GN = RBM14 PE = 1 SV = 2
209. >sp|Q99497|PARK7_HUMAN Protein DJ-1 OS = *Homo sapiens* GN = PARK7 PE = 1 SV = 2
210. >sp|Q99ZW2|CAS9_STRP1 CRISPR-associated endonuclease Cas9/Csn1 OS = *Streptococcus pyogenes* serotype M1 GN = cas9 PE = 1 SV = 1
211. >sp|Q9BQ61|CS043_HUMAN Uncharacterized protein C19orf43 OS = *Homo sapiens* GN = C19orf43 PE = 1 SV = 1
212. >sp|Q9BUJ2|HNRL1_HUMAN Heterogeneous nuclear ribonucleoprotein U-like protein 1 OS = *Homo sapiens* GN = HNRNPUL1 PE = 1 SV = 2
213. >sp|Q9NQ75|CASS4_HUMAN Cas scaffolding protein family member 4 OS = *Homo sapiens* GN = CASS4 PE = 1 SV = 2
214. >sp|Q9NR30|DDX21_HUMAN Nucleolar RNA helicase 2 OS = *Homo sapiens* GN = DDX21 PE = 1 SV = 5
215. >sp|Q9NR99|MXRA5_HUMAN Matrix-remodeling-associated protein 5 OS = *Homo sapiens* GN = MXRA5 PE = 2 SV = 3
216. >sp|Q9NZI8|IF2B1_HUMAN Insulin-like growth factor 2 mRNA-binding protein 1 OS = *Homo sapiens* GN = IGF2BP1 PE = 1 SV = 2
217. >sp|Q9P258|RCC2_HUMAN Protein RCC2 OS = *Homo sapiens* GN = RCC2 PE = 1 SV = 2
218. >sp|Q9P2D6|F135A_HUMAN Protein FAM135A OS = *Homo sapiens* GN = FAM135A PE = 1 SV = 2
219. >sp|Q9UQ80|PA2G4_HUMAN Proliferation-associated protein 2G4 OS = *Homo sapiens* GN = PA2G4 PE = 1 SV = 3
220. >sp|Q9Y237|PIN4_HUMAN Peptidyl-prolyl cis-trans isomerase NIMA-interacting 4 OS = *Homo sapiens* GN = PIN4 PE = 1 SV = 1
221. >sp|Q9Y266|NUDC_HUMAN Nuclear migration protein nudC OS = *Homo sapiens* GN = NUDC PE = 1 SV = 1
222. >sp|Q9Y383|LC7L2_HUMAN Putative RNA-binding protein Luc7-like 2 OS = *Homo sapiens* GN = LUC7L2 PE = 1 SV = 2
223. >sp|Q9Y3U8|RL36_HUMAN 60S ribosomal protein L36 OS = *Homo sapiens* GN = RPL36 PE = 1 SV = 3
224. >sp|Q9Y4G6|TLN2_HUMAN Talin-2 OS = *Homo sapiens* GN = TLN2 PE = 1 SV = 4
225. >tr|A0AV56|A0AV56_HUMAN SAFB protein OS = *Homo sapiens* GN = SAFB PE = 2 SV = 1
226. >tr|A1XKG3|A1XKG3_HUMAN Protein kinase CDK5 splicing variant OS = *Homo sapiens* PE = 2 SV = 1
227. >tr|A2A3R6|A2A3R6_HUMAN 40S ribosomal protein S6 OS = *Homo sapiens* GN = RPS6 PE = 2 SV = 1
228. >tr|A2BF75|A2BF75_HUMAN ATP-binding cassette sub-family F (GCN20) member 1 OS = *Homo sapiens* GN = ABCF1 PE = 2 SV = 1
229. >tr|A2RUM7|A2RUM7_HUMAN Ribosomal protein L5 OS = *Homo sapiens* GN = RPL5 PE = 2 SV = 1
230. >tr|A3KPC7|A3KPC7_HUMAN Histone H2A OS = *Homo sapiens* GN = HIST1H2AH PE = 2 SV = 1

-continued

231. >tr|A3R0T8|A3R0T8_HUMAN Histone 1, H1e OS = *Homo sapiens* GN = HIST1H1E PE = 2 SV = 1
232. >tr|A3RJH1|A3RJH1_HUMAN ATP-dependent RNA helicase DDX1 OS = *Homo sapiens* GN = DDX1 PE = 2 SV = 1
233. >tr|A4D177|A4D177_HUMAN Chromobox homolog 3 (HP1 gamma homolog, *Drosophila*) OS = *Homo sapiens* GN = CBX3 PE = 4 SV = 1
234. >tr|A4D1N4|A4D1N4_HUMAN Coiled-coil-helix-coiled-coil-helix domain containing 3 OS = *Homo sapiens* GN = CHCHD3 PE = 4 SV = 1
235. >tr|A4D1T6|A4D1T6_HUMAN AarF domain containing kinase 2 OS = *Homo sapiens* GN = ADCK2 PE = 4 SV = 1
236. >tr|A5JHP3|A5JHP3_HUMAN Dermcidin isoform 2 OS = *Homo sapiens* GN = DCD PE = 2 SV = 1
237. >tr|A6NC17|A6NC17_HUMAN Uncharacterized protein OS = *Homo sapiens* GN = MARS PE = 4 SV = 3
238. >tr|A6NCD2|A6NCD2_HUMAN Uncharacterized protein OS = *Homo sapiens* GN = CCT6A PE = 3 SV = 1
239. >tr|A6NE05|A6NE05_HUMAN Uncharacterized protein OS = *Homo sapiens* GN = RPL26 PE = 3 SV = 1
240. >tr|A6NE09|A6NE09_HUMAN Uncharacterized protein OS = *Homo sapiens* PE = 3 SV = 1
241. >tr|A6NE14|A6NE14_HUMAN Uncharacterized protein OS = *Homo sapiens* GN = CCT3 PE = 2 SV = 1
242. >tr|A6NFM2|A6NFM2_HUMAN Pyrroline-5-carboxylate reductase OS = *Homo sapiens* GN = PYCR1 PE = 3 SV = 1
243. >tr|A6NGV1|A6NGV1_HUMAN Uncharacterized protein OS = *Homo sapiens* GN = SET PE = 2 SV = 2
244. >tr|A6NIT8|A6NIT8_HUMAN Uncharacterized protein OS = *Homo sapiens* GN = HNRNPL PE = 2 SV = 1
245. >tr|A6NJH9|A6NJH9_HUMAN Uncharacterized protein OS = *Homo sapiens* GN = EIF1AY PE = 4 SV = 1
246. >tr|A6NL76|A6NL76_HUMAN Uncharacterized protein OS = *Homo sapiens* GN = ACTA1 PE = 3 SV = 2
247. >tr|A6NNE8|A6NNE8_HUMAN Uncharacterized protein OS = *Homo sapiens* GN = SRSF7 PE = 4 SV = 3
248. >tr|A8K220|A8K220_HUMAN Peptidyl-prolyl cis-trans isomerase OS = *Homo sapiens* GN = PPIA PE = 1 SV = 1
249. >tr|A8K2Y9|A8K2Y9_HUMAN 6-phosphogluconate dehydrogenase, decarboxylating OS = *Homo sapiens* GN = PGD PE = 2 SV = 1
250. >tr|A8K3Z8|A8K3Z8_HUMAN RAN, member RAS oncogene family, isoform CRA_b OS = *Homo sapiens* GN = RAN PE = 1 SV = 1
251. >tr|A8K401|A8K401_HUMAN Prohibitin, isoform CRA_a OS = *Homo sapiens* GN = PHB PE = 2 SV = 1
252. >tr|A8K4C8|A8K4C8_HUMAN 60S ribosomal protein L13 OS = *Homo sapiens* GN = RPL13 PE = 2 SV = 1
253. >tr|A8K4I2|A8K4I2_HUMAN Histone 1, H1c OS = *Homo sapiens* GN = HIST1H1C PE = 2 SV = 1
254. >tr|A8K4W6|A8K4W6_HUMAN Phosphoglycerate kinase OS = *Homo sapiens* GN = PGK1 PE = 2 SV = 1
255. >tr|A8K5I0|A8K5I0_HUMAN Heat shock 70 kDa protein 1A OS = *Homo sapiens* GN = HSPA1A PE = 2 SV = 1
256. >tr|A8MUD9|A8MUD9_HUMAN Uncharacterized protein OS = *Homo sapiens* GN = RPL7 PE = 3 SV = 1
257. >tr|A8MUS3|A8MUS3_HUMAN Ribosomal protein L23a, isoform CRA_a OS = *Homo sapiens* GN = RPL23A PE = 3 SV = 1
258. >tr|A8MV89|A8MV89_HUMAN Uncharacterized protein OS = *Homo sapiens* GN = SPECC1 PE = 4 SV = 1
259. >tr|A8MVA9|A8MVA9_HUMAN Uncharacterized protein OS = *Homo sapiens* GN = WDR1 PE = 4 SV = 2
260. >tr|A8MWD3|A8MWD3_HUMAN Uncharacterized protein OS = *Homo sapiens* GN = EIF3D PE = 2 SV = 2
261. >tr|A8MWI8|A8MWI8_HUMAN Uncharacterized protein OS = *Homo sapiens* GN = CCT7 PE = 2 SV = 1
262. >tr|A8MWN8|A8MWN8_HUMAN Uncharacterized protein OS = *Homo sapiens* GN = DLGAP1 PE = 2 SV = 1
263. >tr|A8MX94|A8MX94_HUMAN Uncharacterized protein OS = *Homo sapiens* GN = GSTP1 PE = 4 SV = 1
264. >tr|A8MXP9|A8MXP9_HUMAN Uncharacterized protein OS = *Homo sapiens* GN = MATR3 PE = 4 SV = 1
265. >tr|A8MXQ4|A8MXQ4_HUMAN L-lactate dehydrogenase OS = *Homo sapiens* GN = LDHA PE = 3 SV = 2
266. >tr|A8MZ73|A8MZ73_HUMAN Ribosomal protein S29 OS = *Homo sapiens* GN = RPS29 PE = 3 SV = 1
267. >tr|A9C4C1|A9C4C1_HUMAN Ribosomal protein S9 OS = *Homo sapiens* GN = RPS9 PE = 3 SV = 1
268. >tr|B0QYK0|B0QYK0_HUMAN Ewing sarcoma breakpoint region 1 OS = *Homo sapiens* GN = EWSR1 PE = 4 SV = 1
269. >tr|B0V043|B0V043_HUMAN Valyl-tRNA synthetase OS = *Homo sapiens* GN = VARS PE = 3 SV = 1
270. >tr|B0ZBD0|B0ZBD0_HUMAN 40S ribosomal protein S19 OS = *Homo sapiens* GN = RPS19 PE = 2 SV = 1
271. >tr|B1AHA9|B1AHA9_HUMAN Minichromosome maintenance complex component 5 (Fragment) OS = *Homo sapiens* GN = MCM5 PE = 4 SV = 1
272. >tr|B1ALM3|B1ALM3_HUMAN Calcium channel, voltage-dependent, L type, alpha 1S subunit OS = *Homo sapiens* GN = CACNA1S PE = 3 SV = 1
273. >tr|B2R491|B2R491_HUMAN Ribosomal protein S4, X-linked, isoform CRA_c OS = *Homo sapiens* GN = RPS4X PE = 2 SV = 1
274. >tr|B2R4P9|B2R4P9_HUMAN Histone H3 OS = *Homo sapiens* GN = H3F3A PE = 2 SV = 1
275. >tr|B2R4R0|B2R4R0_HUMAN Histone H4 OS = *Homo sapiens* GN = HIST1H4J PE = 3 SV = 1
276. >tr|B2R4R9|B2R4R9_HUMAN HCG26477 OS = *Homo sapiens* GN = RPS28 PE = 4 SV = 1
277. >tr|B2R4S9|B2R4S9_HUMAN Histone H2B OS = *Homo sapiens* GN = HIST1H2BC PE = 2 SV = 1
278. >tr|B2R4W8|B2R4W8_HUMAN HCG1994130, isoform CRA_a OS = *Homo sapiens* GN = hCG_1994130 PE = 2 SV = 1
279. >tr|B2RDW1|B2RDW1_HUMAN Ribosomal protein S27a, isoform CRA_c OS = *Homo sapiens* GN = RPS27A PE = 2 SV = 1
280. >tr|B3KPZ8|B3KPZ8_HUMAN cDNA FLJ32530 fis, clone SMINT2000185, highly similar to TRANSKETOLASE (EC 2.2.1.1) OS = *Homo sapiens* PE = 2 SV = 1
281. >tr|B3KT17|B3KT17_HUMAN cDNA FLJ37462 fis, clone BRAWH2011343, highly similar to COLD-INDUCIBLE RNA-BINDING PROTEIN OS = *Homo sapiens* PE = 2 SV = 1
282. >tr|B3KTE3|B3KTE3_HUMAN cDNA FLJ38125 fis, clone D6OST2000127, moderately similar to RAS-RELATED PROTEIN RAB-8B OS = *Homo sapiens* PE = 4 SV = 1
283. >tr|B4DDB6|B4DDB6_HUMAN Heterogeneous nuclear ribonucleoprotein A3, isoform CRA_a OS = *Homo sapiens* GN = HNRPA3 PE = 2 SV = 1
284. >tr|B4DDW7|B4DDW7_HUMAN cDNA FLJ57947, highly similar to L-aminoadipate-semialdehydedehydrogenase-phosphopantetheinyl transferase (EC 2.7.8.-) OS = *Homo sapiens* PE = 2 SV = 1
285. >tr|B4DE78|B4DE78_HUMAN cDNA FLJ52141, highly similar to 14-3-3 protein gamma OS = *Homo sapiens* PE = 2 SV = 1
286. >tr|B4DEA3|B4DEA3_HUMAN cDNA FLJ56531, highly similar to UV excision repair protein RAD23 homolog B OS = *Homo sapiens* PE = 2 SV = 1
287. >tr|B4DEP9|B4DEP9_HUMAN cDNA FLJ57954, highly similar to 60S ribosomal protein L28 OS = *Homo sapiens* PE = 2 SV = 1
288. >tr|B4DF70|B4DF70_HUMAN cDNA FLJ60461, highly similar to Peroxiredoxin-2 (EC 1.11.1.15) OS = *Homo sapiens* PE = 2 SV = 1
289. >tr|B4DIN1|B4DIN1_HUMAN cDNA FLJ60566, highly similar to Clathrin light chain A OS = *Homo sapiens* PE = 2 SV = 1
290. >tr|B4DIW5|B4DIW5_HUMAN cDNA FLJ55515, highly similar to Breast cancer anti-estrogen resistanceprotein 1 OS = *Homo sapiens* PE = 2 SV = 1
291. >tr|B4DJ51|B4DJ51_HUMAN Calmodulin 1 (Phosphorylase kinase, delta), isoform CRA_a OS = *Homo sapiens* GN = CALM1 PE = 2 SV = 1
292. >tr|B4DJP0|B4DJP0_HUMAN cDNAFLJ60601, highly similar to Methylosome protein 50 OS = *Homo sapiens* PE = 4 SV = 1
293. >tr|B4DJP7|B4DJP7_HUMAN cDNA FLJ51872, highly similar to Small nuclear ribonucleoprotein Sm D3 OS = *Homo sapiens* PE = 4 SV = 1
294. >tr|B4DL87|B4DL87_HUMAN Uncharacterized protein OS = *Homo sapiens* GN = HSPB1 PE = 2 SV = 1
295. >tr|B4DLR3|B4DLR3_HUMAN cDNA FLJ54020, highly similar to Heterogeneous nuclear ribonucleoprotein U OS = *Homo sapiens* PE = 2SV = 1
296. >tr|B4DM94|B4DM94_HUMAN cDNA FLJ51502, highly similar to 60S ribosomal protein L18a OS = *Homo sapiens* PE = 2 SV = 1
297. >tr|B4DR70|B4DR70_HUMAN cDNA FLJ58049, highly similar to RNA-binding protein FUS OS = *Homo sapiens* PE = 2 SV = 1

-continued

298. >tr|B4DS13|B4DS13_HUMAN cDNA FLJ59405, highly similar to Eukaryotic translation initiation factor 4B OS = *Homo sapiens* PE = 2 SV = 1
299. >tr|B4DT30|B4DT30_HUMAN cDNA FLJ57496, moderately similar to Tubulin-specific chaperone A OS = *Homo sapiens* PE = 2 SV = 1
300. >tr|B4DTG2|B4DTG2_HUMAN cDNA FLJ56389, highly similar to Elongation factor 1-gamma OS = *Homo sapiens* PE = 2 SV = 1
301. >tr|B4DUQ1|B4DUQ1_HUMAN cDNA FLJ54552, highly similar to Heterogeneous nuclear ribonucleoprotein K OS = *Homo sapiens* PE = 2 SV = 1
302. >tr|B4DVB8|B4DVB8_HUMAN cDNA FLJ60076, highly similar to ELAV-like protein 1 OS = *Homo sapiens* PE = 2 SV = 1
303. >tr|B4DW28|B4DW28_HUMAN cDNA FLJ58953, highly similar to 40S ribosomal protein S20 OS = *Homo sapiens* PE = 2 SV = 1
304. >tr|B4DWW4|B4DWW4_HUMAN MCM3 minichromosome maintenance deficient 3 (*S. cerevisiae*), isoform CRA_b OS = *Homo sapiens* GN = MCM3 PE = 2 SV = 1
305. >tr|B4DX20|B4DX20_HUMAN cDNA FLJ60932, highly similar to T-complex protein 1 subunit zeta-2 OS = *Homo sapiens* PE = 2 SV = 1
306. >tr|B4DYD8|B4DYD8_HUMAN cDNA FLJ52362, highly similar to T-complex protein 1 subunit epsilon OS = *Homo sapiens* PE = 2 SV = 1
307. >tr|B4DZX6|B4DZX6_HUMAN cDNA FLJ54769, moderately similar to Ankyrin repeat and SOCS box protein 3 (ASB-3) OS = *Homo sapiens* PE = 2 SV = 1
308. >tr|B4E335|B4E335_HUMAN cDNA FLJ52842, highly similar to Actin, cytoplasmic 1 OS = *Homo sapiens* PE = 2 SV = 1
309. >tr|B5MCP9|B5MCP9_HUMAN Uncharacterized protein OS = *Homo sapiens* GN = RPS7 PE = 4 SV = 1
310. >tr|B7Z4C8|B7Z4C8_HUMAN Uncharacterized protein OS = *Homo sapiens* GN = RPL31 PE = 2 SV = 1
311. >tr|B7Z4N6|B7Z4N6_HUMAN Stathmin OS = *Homo sapiens* GN = STMN2 PE = 2 SV = 1
312. >tr|B7ZAR1|B7ZAR1_HUMAN cDNA, FLJ79275, highly similar to T-complex protein 1 subunit epsilon OS = *Homo sapiens* PE = 2 SV = 1
313. >tr|B7ZL00|B7ZL00_HUMAN SEC31A protein OS = *Homo sapiens* GN = SEC31A PE = 2 SV = 1
314. >tr|B8ZZ54|B8ZZ54_HUMAN Heat shock 10 kDa protein 1 (Chaperonin 10), isoform CRA_h OS = *Homo sapiens* GN = HSPE1 PE = 3 SV = 1
315. >tr|B8ZZL8|B8ZZL8_HUMAN Heat shock 10 kDa protein 1 (Chaperonin 10), isoform CRA_b OS = *Homo sapiens* GN = HSPE1 PE = 3 SV = 1
316. >tr|C9J1C5|C9J1C5_HUMAN Ribosomal protein S27 OS = *Homo sapiens* GN = RPS27L PE = 3 SV = 1
317. >tr|C9J296|C9J296_HUMAN Uncharacterized protein OS = *Homo sapiens* GN = LAMB1 PE = 4SV = 1
318. >tr|C9J4C3|C9J4C3_HUMAN DNA topoisomerase 2 OS = *Homo sapiens* GN = TOP2A PE = 3 SV = 1
319. >tr|C9J4W5|C9J4W5_HUMAN Uncharacterized protein OS = *Homo sapiens* GN = EIF5A2 PE = 4SV = 1
320. >tr|C9J7T6|C9J7T6_HUMAN Uncharacterized protein OS = *Homo sapiens* GN = RPL10 PE = 4 SV = 1
321. >tr|C9JBL2|C9JBL2_HUMAN Uncharacterized protein OS = *Homo sapiens* GN = RPL32 PE = 4 SV = 1
322. >tr|C9JFR7|C9JFR7_HUMAN Uncharacterized protein OS = *Homo sapiens* GN = CYCS PE = 3 SV = 1
323. >tr|C9JNW5|C9JNW5_HUMAN Ribosomal protein L24, isoform CRA_e OS = *Homo sapiens* GN = RPL24 PE = 4 SV = 1
324. >tr|C9JR29|C9JR29_HUMAN Uncharacterized protein OS = *Homo sapiens* GN = CSMD3 PE = 4 SV = 1
325. >tr|C9JV77|C9JV77_HUMAN Uncharacterized protein OS = *Homo sapiens* GN = AHSG PE = 4 SV = 1
326. >tr|D6R9P3|D6R9P3_HUMAN Uncharacterized protein OS = *Homo sapiens* GN = HNRNPAB PE = 4 SV = 1
327. >tr|D6RAC2|D6RAC2_HUMAN Uncharacterized protein OS = *Homo sapiens* GN = GNB2L1 PE = 4SV = 1
328. >tr|D6RAF8|D6RAF8_HUMAN Uncharacterized protein OS = *Homo sapiens* GN = HNRNPD PE = 4 SV = 1
329. >tr|D6RAQ3|D6RAQ3_HUMAN Uncharacterized protein OS = *Homo sapiens* GN = LMNA PE = 3 SV = 1
330. >tr|D6RAT0|D6RAT0_HUMAN Uncharacterized protein OS = *Homo sapiens* GN = RPS3APE = 3 SV = 1
331. >tr|D6RDG3|D6RDG3_HUMAN Uncharacterized protein OS = *Homo sapiens* GN = BTF3 PE = 4SV = 1
332. >tr|D6RFJ8|D6RFJ8_HUMAN Uncharacterized protein OS = *Homo sapiens* GN = G3BP2 PE = 4SV = 1
333. >tr|D6RG13|D6RG13_HUMAN Uncharacterized protein OS = *Homo sapiens* GN = RPS3A PE = 3 SV = 1
334. >tr|D9YZU8|D9YZU8_HUMAN Hemoglobin, gamma A OS = *Homo sapiens* GN = HBG1 PE = 3 SV = 1
335. >tr|E5RIZ6|E5RIZ6_HUMAN Uncharacterized protein OS = *Homo sapiens* GN = G3BP1 PE = 4 SV = 1
336. >tr|E7DVW5|E7DVW5_HUMAN Fatty acid binding protein 5 (Psoriasis-associated) OS = *Homo sapiens* GN = FABP5 PE = 3 SV = 1
337. >tr|E7EMA7|E7EMA7_HUMAN Uncharacterized protein OS = *Homo sapiens* GN = PDPR PE = 3 SV = 1
338. >tr|E7EMA8|E7EMA8_HUMAN Phosphoglycerate mutase OS = *Homo sapiens* GN = PGAM1 PE = 3 SV = 2
339. >tr|E7EME9|E7EME9_HUMAN Uncharacterized protein OS = *Homo sapiens* GN = EIF3B PE = 3 SV = 1
340. >tr|E7EMJ0|E7EMJ0_HUMAN Uncharacterized protein OS = *Homo sapiens* GN = BCAN PE = 4 SV = 1
341. >tr|E7EMN0|E7EMN0_HUMAN Uncharacterized protein OS = *Homo sapiens* GN = EPRS PE = 3 SV = 1
342. >tr|E7EMU2|E7EMU2_HUMAN Uncharacterized protein OS = *Homo sapiens* GN = HMGA1 PE = 4 SV = 1
343. >tr|E7ENH9|E7ENH9_HUMAN Uncharacterized protein OS = *Homo sapiens* GN = ACLY PE = 4 SV = 2
344. >tr|E7EP12|E7EP12_HUMAN Uncharacterized protein OS = *Homo sapiens* GN = TTLL5 PE = 4 SV = 2
345. >tr|E7EP96|E7EP96_HUMAN Uncharacterized protein OS = *Homo sapiens* GN = KHSRP PE = 4 SV = 1
346. >tr|E7EPB3|E7EPB3_HUMAN Uncharacterized protein OS = *Homo sapiens* GN = RPL14 PE = 4 SV = 1
347. >tr|E7EPK6|E7EPK6_HUMAN Uncharacterized protein OS = *Homo sapiens* GN = RPS24 PE = 4 SV = 1
348. >tr|E7EQ64|E7EQ64_HUMAN Uncharacterized protein OS = *Homo sapiens* GN = PRSS1 PE = 3 SV = 1
349. >tr|E7EQD1|E7EQD1_HUMAN Uncharacterized protein OS = *Homo sapiens* GN = TRA2B PE = 4 SV = 1
350. >tr|E7EQR6|E7EQR6_HUMAN T-complex protein 1 subunit alpha OS = *Homo sapiens* GN = TCP1 PE = 3 SV = 1
351. >tr|E7EQT4|E7EQT4_HUMAN Uncharacterized protein OS = *Homo sapiens* GN = ACIN1 PE = 4 SV = 2
352. >tr|E7EQV3|E7EQV3_HUMAN Uncharacterized protein OS = *Homo sapiens* GN = PABPC1 PE = 4 SV = 1
353. >tr|E7EQV9|E7EQV9_HUMAN Ribosomal protein L15 OS = *Homo sapiens* GN = RPL15 PE = 3 SV = 1
354. >tr|E7ERE4|E7ERE4_HUMAN Uncharacterized protein OS = *Homo sapiens* GN = HNRNPR PE = 4 SV = 1
355. >tr|E7ERL0|E7ERL0_HUMAN Uncharacterized protein OS = *Homo sapiens* GN = NME1 PE = 3 SV = 1
356. >tr|E7ERT8|E7ERT8_HUMAN Uncharacterized protein OS = *Homo sapiens* GN = HOXA1 PE = 4 SV = 1
357. >tr|E7ES34|E7ES34_HUMAN Uncharacterized protein OS = *Homo sapiens* GN = KRT7 PE = 3 SV = 2
358. >tr|E7ESM6|E7ESM6_HUMAN Uncharacterized protein OS = *Homo sapiens* GN = SND1 PE = 4 SV = 2
359. >tr|E7ET98|E7ET98_HUMAN Uncharacterized protein OS = *Homo sapiens* GN = KHDRBS1 PE = 4 SV = 2
360. >tr|E7ETA0|E7ETA0_HUMAN Uncharacterized protein OS = *Homo sapiens* GN = YBX1 PE = 4 SV = 1
361. >tr|E7ETL9|E7ETL9_HUMAN Uncharacterized protein OS = *Homo sapiens* GN = DDX5 PE = 3 SV = 1
362. >tr|E7EU23|E7EU23_HUMAN Uncharacterized protein OS = *Homo sapiens* GN = GDI2 PE = 4 SV = 1
363. >tr|E7EUT4|E7EUT4_HUMAN Glyceraldehyde-3-phosphate dehydrogenase OS = *Homo sapiens* GN = GAPDH PE = 3 SV = 1
364. >tr|E7EUX0|E7EUX0_HUMAN Uncharacterized protein OS = *Homo sapiens* GN = FUS PE = 4 SV = 1
365. >tr|E7EV83|E7EV83_HUMAN Uncharacterized protein OS = *Homo sapiens* GN = ACTN4 PE = 4 SV = 1
366. >tr|E7EW92|E7EW92_HUMAN Ribosomal protein L18 OS = *Homo sapiens* GN = RPL18 PE = 3 SV = 2
367. >tr|E7EWF1|E7EWF1_HUMAN Uncharacterized protein OS = *Homo sapiens* GN = RPL4 PE = 4 SV = 1
368. >tr|E7EX81|E7EX81_HUMAN Uncharacterized protein OS = *Homo sapiens* GN = NCLPE = 4 SV = 1
369. >tr|E9KL35|E9KL35_HUMAN Epididymis tissue sperm binding protein Li 3a OS = *Homo sapiens* PE = 2 SV = 1
370. >tr|E9KL39|E9KL39_HUMAN Epididymis tissue sperm binding protein Li 7e OS = *Homo sapiens* PE = 2 SV = 1

-continued

371. >tr|E9PAQ6|E9PAQ6_HUMAN Uncharacterized protein OS = *Homo sapiens* GN = CCT3 PE = 3 SV = 1
372. >tr|E9PB61|E9PB61_HUMAN Uncharacterized protein OS = *Homo sapiens* GN = THOC4 PE = 4 SV = 1
373. >tr|E9PBF6|E9PBF6_HUMAN Uncharacterized protein OS = *Homo sapiens* GN = LMNB1 PE = 3 SV = 1
374. >tr|E9PBS1|E9PBS1_HUMAN Uncharacterized protein OS = *Homo sapiens* GN = PAICS PE = 4 SV = 1
375. >tr|E9PCY7|E9PCY7_HUMAN Uncharacterized protein OS = *Homo sapiens* GN = HNRNPH1 PE = 4 SV = 1
376. >tr|E9PD35|E9PD35_HUMAN Tyrosine-protein kinase receptor OS = *Homo sapiens* GN = FLT4 PE = 3 SV = 1
377. >tr|E9PDU1|E9PDU1_HUMAN Uncharacterized protein OS = *Homo sapiens* GN = KARS PE = 3 SV = 2
378. >tr|E9PE52|E9PE52_HUMAN Uncharacterized protein OS = *Homo sapiens* GN = RSL1D1 PE = 4 SV = 1
379. >tr|E9PEK6|E9PEK6_HUMAN Uncharacterized protein OS = *Homo sapiens* GN = CAPRIN1 PE = 4 SV = 2
380. >tr|E9PFF0|E9PFF0_HUMAN Uncharacterized protein OS = *Homo sapiens* GN = HMGB1 PE = 4 SV = 1
381. >tr|E9PFH8|E9PFH8_HUMAN Uncharacterized protein OS = *Homo sapiens* GN = SSB PE = 4 SV = 1
382. >tr|E9PH51|E9PH51_HUMAN L-lactate dehydrogenase OS = *Homo sapiens* GN = LDHA PE = 3 SV = 2
383. >tr|E9PI39|E9PI39_HUMAN Uncharacterized protein OS = *Homo sapiens* GN = EEF1D PE = 4 SV = 1
384. >tr|E9PIZ3|E9PIZ3_HUMAN Uncharacterized protein OS = *Homo sapiens* GN = RPL8 PE = 4 SV = 1
385. >tr|E9PK09|E9PK09_HUMAN Uncharacterized protein OS = *Homo sapiens* GN = BCLAF1 PE = 4 SV = 1
386. >tr|E9PK25|E9PK25_HUMAN Uncharacterized protein OS = *Homo sapiens* GN = CFL1 PE = 4 SV = 1
387. >tr|E9PKE3|E9PKE3_HUMAN Uncharacterized protein OS = *Homo sapiens* GN = HSPA8 PE = 3 SV = 1
388. >tr|E9PL09|E9PL09_HUMAN Uncharacterized protein OS = *Homo sapiens* GN = RPS3 PE = 3 SV = 1
389. >tr|E9PRH9|E9PRH9_HUMAN Uncharacterized protein OS = *Homo sapiens* GN = NASP PE = 4 SV = 1
390. >tr|F2Z2A5|F2Z2A5_HUMAN Uncharacterized protein OS = *Homo sapiens* GN = TOP3B PE = 4 SV = 1
391. >tr|F2Z3A5|F2Z3A5_HUMAN Uncharacterized protein OS = *Homo sapiens* GN = RPL3 PE = 4 SV = 1
392. >tr|F2Z3H3|F2Z3H3_HUMAN Uncharacterized protein OS = *Homo sapiens* GN = ANP32A PE = 4 SV = 2
393. >tr|F5GWQ7|F5GWQ7_HUMAN Uncharacterized protein OS = *Homo sapiens* GN = TAF15 PE = 4 SV = 1
394. >tr|F5GX11|F5GX11_HUMAN Uncharacterized protein OS = *Homo sapiens* GN = PSMA1 PE = 4 SV = 1
395. >tr|F5GY37|F5GY37_HUMAN Uncharacterized protein OS = *Homo sapiens* GN = PHB2 PE = 4 SV = 1
396. >tr|F5GY56|F5GY56_HUMAN Uncharacterized protein OS = *Homo sapiens* GN = PRPF19 PE = 4 SV = 1
397. >tr|F5GZ35|F5GZ35_HUMAN Uncharacterized protein OS = *Homo sapiens* GN = SH3PXD2A PE = 4 SV = 1
398. >tr|F5H0T1|F5H0T1_HUMAN Uncharacterized protein OS = *Homo sapiens* GN = STIP1 PE = 4 SV = 1
399. >tr|F5H119|F5H119_HUMAN Uncharacterized protein OS = *Homo sapiens* GN = PDIA3 PE = 4 SV = 1
400. >tr|F5H1E9|F5H1E9_HUMAN Uncharacterized protein OS = *Homo sapiens* GN = MCM2 PE = 4 SV = 1
401. >tr|F5H1H8|F5H1H8_HUMAN Uncharacterized protein OS = *Homo sapiens* GN = SUB1 PE = 4 SV = 1
402. >tr|F5H335|F5H335_HUMAN Uncharacterized protein OS = *Homo sapiens* GN = EIF3A PE = 4 SV = 1
403. >tr|F5H369|F5H369_HUMAN Uncharacterized protein OS = *Homo sapiens* GN = PIK3C2G PE = 4 SV = 1
404. >tr|F5H4D6|F5H4D6_HUMAN Uncharacterized protein OS = *Homo sapiens* GN = G3BP1 PE = 4 SV = 1
405. >tr|F5H568|F5H568_HUMAN Uncharacterized protein OS = *Homo sapiens* PE = 4 SV = 1
406. >tr|F5H5W3|F5H5W3_HUMAN Uncharacterized protein OS = *Homo sapiens* GN = CCT4 PE = 4 SV = 1
407. >tr|F5H6K0|F5H6K0_HUMAN Uncharacterized protein OS = *Homo sapiens* GN = DHX15 PE = 4 SV = 1
408. >tr|F5H737|F5H737_HUMAN Uncharacterized protein OS = *Homo sapiens* GN = AHCY PE = 4 SV = 1
409. >tr|Q5R370|Q5R370_HUMAN Calcyclin binding protein OS = *Homo sapiens* GN = CACYBP PE = 2 SV = 1
410. >tr|Q5TEC6|Q5TEC6_HUMAN Histone H3 OS = *Homo sapiens* GN = HIST2H3PS2 PE = 3 SV = 1
411. >tr|Q5VU21|Q5VU21_HUMAN PAI-1 mRNA-binding protein variant OS = *Homo sapiens* GN = SERBP1 PE = 2 SV = 1
412. >tr|Q5VU66|Q5VU66_HUMAN Tropomyosin 3 OS = *Homo sapiens* GN = TPM3 PE = 2 SV = 1
413. >tr|Q86X94|Q86X94_HUMAN TAF15 RNA polymerase II, TATA box binding protein (TBP)-associated factor, 68 kDa OS = *Homo sapiens* GN = TAF15 PE = 2 SV = 2
414. 10 kDa heat shock protein, mitochondrial (Heat shock 10 kDa protein 1 (Chaperonin 10), isoform CRA_b)
415. 14-3-3 protein beta/alpha (Protein 1054) (Protein kinase C inhibitor protein 1) (KCIP-1) [Cleaved into: 14-3-3 protein beta/alpha, N-terminally processed]
416. 14-3-3 protein epsilon (14-3-3E)
417. 14-3-3 protein eta (Fragment)
418. 14-3-3 protein gamma (Protein kinase C inhibitor protein 1) (KCIP-1) [Cleaved into: 14-3-3 protein gamma, N-terminally processed]
419. 14-3-3 protein sigma (Epithelial cell marker protein 1) (Stratifin)
420. 14-3-3 protein theta (14-3-3 protein T-cell) (14-3-3 protein tau) (Protein HS1)
421. 26S protease regulatory subunit 7 (26S proteasome AAA-ATPase subunit RPT1) (Proteasome 26S subunit ATPase 2) (Protein MSS1)
422. 26S proteasome non-ATPase regulatory subunit 8 (26S proteasome regulatory subunit RPN12) (26S proteasome regulatory subunit S14) (p31)
423. 3'-5'exonuclease TREX2 long form
424. 40S ribosomal protein S10 (Small ribosomal subunit protein eS10)
425. 40S ribosomal protein S11 (Small ribosomal subunit protein uS17)
426. 40S ribosomal protein S12 (Small ribosomal subunit protein eS12)
427. 40S ribosomal protein S13 (Small ribosomal subunit protein uS15)
428. 40S ribosomal protein S14 (Small ribosomal subunit protein uS11)
429. 40S ribosomal protein S15 (RIG protein) (Small ribosomal subunit protein uS19)
430. 40S ribosomal protein S16 (Small ribosomal subunit protein uS9)
431. 40S ribosomal protein S17 (Small ribosomal subunit protein eS17)
432. 40S ribosomal protein S18 (Ke-3) (Ke3) (Small ribosomal subunit protein uS13)
433. 40S ribosomal protein S19 (Ribosomal protein S19, isoform CRA_a) (cDNA, FLJ92047, *Homo sapiens* ribosomal protein S19 (RPS19), mRNA)
434. 40S ribosomal protein S2 (40S ribosomal protein S4) (Protein LLRep3) (Small ribosomal subunit protein uS5)
435. 40S ribosomal protein S21 (Small ribosomal subunit protein eS21)
436. 40S ribosomal protein S25 (Small ribosomal subunit protein eS25)
437. 40S ribosomal protein S26 (Small ribosomal subunit protein eS26)
438. 40S ribosomal protein S27
439. 40S ribosomal protein S27 (Metallopan-stimulin 1) (MPS-1) (Small ribosomal subunit protein eS27)
440. 40S ribosomal protein S27-like (Small ribosomal subunit protein eS27-like)
441. 40S ribosomal protein S3
442. 40S ribosomal protein S3 (EC 4.2.99.18) (Small ribosomal subunit protein uS3)
443. 40S ribosomal protein S30

-continued 444. 40S ribosomal protein S3a (Small ribosomal subunit protein eS1) (v-fos transformation effector protein) (Fte-1)
445. 40S ribosomal protein S4
446. 40S ribosomal protein S5 (Small ribosomal subunit protein uS7) [Cleaved into: 40S ribosomal protein S5, N-terminally processed])
447. 40S ribosomal protein S6
448. 40S ribosomal protein S7
449. 40S ribosomal protein S7 (Small ribosomal subunit protein eS7)
450. 40S ribosomal protein S8 (Small ribosomal subunit protein eS8)
451. 60 kDa heat shock protein, mitochondrial (EC 3.6.4.9) (60 kDa chaperonin) (Chaperonin 60) (CPN60) (Heat shock protein 60) (HSP-60) (Hsp60) (HuCHA60) (Mitochondrial matrix protein P1) (P60 lymphocyte protein)
452. 60S acidic ribosomal protein P0 (60S ribosomal protein L10E) (Large ribosomal subunit protein uL10)
453. 60S acidic ribosomal protein P2 (Large ribosomal subunit protein P2) (Renal carcinoma antigen NY-REN-44)
454. 60S ribosomal protein L10a (CSA-19) (Large ribosomal subunit protein uL1) (Neural precursor cell expressed developmentally down-regulated protein 6) (NEDD-6)
455. 60S ribosomal protein L11 (CLL-associated antigen KW-12) (Large ribosomal subunit protein uL5)
456. 60S ribosomal protein L12 (Large ribosomal subunit protein uL11)
457. 60S ribosomal protein L13
458. 60S ribosomal protein L13a (23 kDa highly basic protein) (Large ribosomal subunit protein uL13)
459. 60S ribosomal protein L14
460. 60S ribosomal protein L17 (60S ribosomal protein L23) (Large ribosomal subunit protein uL22) (PD-1)
461. 60S ribosomal protein L18 (Large ribosomal subunit protein eL18)
462. 60S ribosomal protein L18a (Large ribosomal subunit protein eL20)
463. 60S ribosomal protein L19 (Large ribosomal subunit protein eL19)
464. 60S ribosomal protein L21 (Large ribosomal subunit protein eL21)
465. 60S ribosomal protein L22 (EBER-associated protein) (EAP) (Epstein-Barr virus small RNA-associated protein) (Heparin-binding protein HBp15) (Large ribosomal subunit protein eL22)
466. 60S ribosomal protein L23 (60S ribosomal protein L17) (Large ribosomal subunit protein uL14)
467. 60S ribosomal protein L23a (Ribosomal protein L23a, isoform CRA_a)
468. 60S ribosomal protein L24 (Ribosomal protein L24, isoform CRA_e)
469. 60S ribosomal protein L27 (Large ribosomal subunit protein eL27)
470. 60S ribosomal protein L27a
471. 60S ribosomal protein L29 (Cell surface heparin-binding protein HIP) (Large ribosomal subunit protein eL29)
472. 60S ribosomal protein L3 (HIV-1 TAR RNA-binding protein B) (TARBP-B) (Large ribosomal subunit protein uL3)
473. 60S ribosomal protein L30 (Fragment)
474. 60S ribosomal protein L31 (Large ribosomal subunit protein eL31)
475. 60S ribosomal protein L34 (Large ribosomal subunit protein eL34)
476. 60S ribosomal protein L35 (Large ribosomal subunit protein uL29)
477. 60S ribosomal protein L35a (Cell growth-inhibiting gene 33 protein) (Large ribosomal subunit protein eL33)
478. 60S ribosomal protein L36 (Large ribosomal subunit protein eL36)
479. 60S ribosomal protein L36a (60S ribosomal protein L44) (Cell growth-inhibiting gene 15 protein) (Cell migration-inducing gene 6 protein) (Large ribosomal subunit protein eL42)
480. 60S ribosomal protein L38 (Large ribosomal subunit protein eL38)
481. 60S ribosomal protein L6 (Large ribosomal subunit protein eL6) (Neoplasm-related protein C140) (Tax-responsive enhancer element-binding protein 107) (TaxREB107)
482. 60S ribosomal protein L7 (Large ribosomal subunit protein uL30)
483. 60S ribosomal protein L7a (Large ribosomal subunit protein eL8) (PLA-X polypeptide) (Surfeit locus protein 3)
484. 60S ribosomal protein L8 (Fragment)
485. 60S ribosomal protein L9 (Large ribosomal subunit protein uL6)
486. 78 kDa glucose-regulated protein (GRP-78) (Endoplasmic reticulum lumenal Ca(2+)-binding protein grp78) (Heat shock 70 kDa protein 5) (Immunoglobulin heavy chain-binding protein) (BiP)
487. Actin related protein 2/3 complex, subunit 1B, 41 kDa (Actin related protein 2/3 complex, subunit 1B, 41 kDa, isoform CRA_a) (cDNA, FLJ95695, *Homo sapiens* actin related protein 2/3 complex, subunit 1B, 41 kDa(ARPC1B), mRNA)
488. Actin, alpha cardiac muscle 1 (Alpha-cardiac actin)
489. Activated RNA polymerase II transcriptional coactivator p15 (Positive cofactor 4) (PC4) (SUB1 homolog) (p14)
490. Acyl-protein thioesterase 1 (Fragment)
491. ADP-ribosylation factor 5 (ADP-ribosylation factor 5, isoform CRA_a) (cDNA, FLJ92389, *Homo sapiens* ADP-ribosylation factor 5 (ARF5), mRNA)
492. ADP/ATP translocase 2 (ADP, ATP carrier protein 2) (ADP, ATP carrier protein, fibroblast isoform) (Adenine nucleotide translocator 2) (ANT 2) (Solute carrier family 25 member 5) [Cleaved into: ADP/ATP translocase 2, N-terminally processed]
493. Aldehyde dehydrogenase, dimeric NADP-preferring
494. Aldo-keto reductase family 1 member C3 (EC 1.-.-.-) (17-beta-hydroxysteroid dehydrogenase type 5) (17-beta-HSD 5) (3-alpha-HSD type II, brain) (3-alpha-hydroxysteroid dehydrogenase type 2) (3-alpha-HSD type 2) (EC 1.1.1.357) (Chlordecone reductase homolog HAKRb) (Dihydrodiol dehydrogenase 3) (DD-3) (DD3) (Dihydrodiol dehydrogenase type I) (HA1753) (Indanol dehydrogenase) (EC 1.1.1.112) (Prostaglandin F synthase) (PDFS) (EC 1.1.1.188) (Testosterone 17-beta-dehydrogenase 5) (EC 1.1.1.64) (Trans-1,2-dihydrobenzene-1,2-diol dehydrogenase) (EC 1.3.1.20)
495. Alpha-actinin-4 (Non-muscle alpha-actinin 4)
496. Alpha-enolase (EC 4.2.1.11) (2-phospho-D-glycerate hydro-lyase) (C-myc promoter-binding protein) (Enolase 1) (MBP-1) (MPB-1) (Non-neural enolase) (NNE) (Phosphopyruvate hydratase) (Plasminogen-binding protein)
497. Anamorsin (Cytokine-induced apoptosis inhibitor 1) (Fe—S cluster assembly protein DRE2 homolog)
498. Ankyrin repeat domain-containing protein 20A4
499. Annexin A1 (Annexin I) (Annexin-1) (Calpactin II) (Calpactin-2) (Chromobindin-9) (Lipocortin I) (Phospholipase A2 inhibitory protein) (p35)
500. Annexin A2 (Annexin II) (Annexin-2) (Calpactin I heavy chain) (Calpactin-1 heavy chain) (Chromobindin-8) (Lipocortin II) (Placental anticoagulant protein IV) (PAP-IV) (Protein I) (p36)
501. Annexin A7 (Annexin VII) (Annexin-7) (Synexin)
502. AP-1 complex subunit beta-1 (Fragment)
503. Apoptotic chromatin condensation inducer in the nucleus
504. Arachidonate 12-lipoxygenase, 12R-type (12R-LOX) (12R-lipoxygenase) (EC 1.13.11.-) (Epidermis-type lipoxygenase 12)
505. Arginase-1 (EC 3.5.3.1) (Liver-type arginase) (Type I arginase)
506. Arginine and glutamate-rich protein 1

507. Asparagine-tRNA ligase, cytoplasmic (EC 6.1.1.22) (Asparaginyl-tRNA synthetase) (AsnRS)
508. Aspartate-tRNA ligase, cytoplasmic (EC 6.1.1.12) (Aspartyl-tRNA synthetase) (AspRS) (Cell proliferation-inducing gene 40 protein)
509. Ataxin-2 (Spinocerebellar ataxia type 2 protein) (Trinucleotide repeat-containing gene 13 protein)
510. ATP synthase subunit alpha, mitochondrial
511. ATP synthase subunit beta, mitochondrial (EC 3.6.3.14)
512. ATP synthase subunit delta, mitochondrial (F-ATPase delta subunit)
513. ATP synthase subunit g mitochondrial
514. ATP-binding cassette sub-family E member 1
515. ATP-binding cassette sub-family F member 2 (Fragment)
516. ATP-dependent RNA helicase A (RHA) (EC 3.6.4.13) (DEAH box protein 9) (Leukophysin) (LKP) (Nuclear DNA helicase II) (NDHII)
517. ATP-dependent RNA helicase DDX39A (EC 3.6.4.13) (DEAD box protein 39) (Nuclear RNA helicase URH49)
518. ATP-dependent RNA helicase DDX3X (EC 3.6.4.13) (DEAD box protein 3, X-chromosomal) (DEAD box, X isoform) (Helicase-like protein 2) (HLP2)
519. C-1-tetrahydrofolate synthase, cytoplasmic
520. C-type lysozyme (Lysozyme) (EC 3.2.1.17) (Lysozyme (Renal amyloidosis), isoform CRA_a) (Lysozyme F1) (cDNA, FLJ92040, *Homo sapiens* lysozyme (renal amyloidosis) (LYZ), mRNA)
521. Calmodulin 1 (Phosphorylase kinase, delta), isoform CRA_a (Calmodulin 3 (Phosphorylase kinase, delta), isoform CRA_b) (Epididymis secretory protein Li 72) (cDNA FLJ61744, highly similar to Calmodulin)
522. Calmodulin-like protein 3 (CaM-like protein) (CLP) (Calmodulin-related protein NB-1)
523. Calmodulin-like protein 5 (Calmodulin-like skin protein)
524. Calpain-1 catalytic subunit (Fragment)
525. cAMP-specific 3',5'-cyclic phosphodiesterase 4D (EC 3.1.4.53) (DPDE3) (PDE43)
526. Capping protein (Actin filament) muscle Z-line, beta, isoform CRA_a (F-actin-capping protein subunit beta)
527. Carboxypeptidase A4 (Carboxypeptidase A4, isoform CRA_a) (cDNA FLJ75086, highly similar to *Homo sapiens* carboxypeptidase A4, mRNA)
528. Cas scaffolding protein family member 4 (HEF-like protein) (HEF1-EFS-p130Cas-like protein) (HEPL)
529. Caspase 14, apoptosis-related cysteine peptidase (Caspase-14) (cDNA, FLJ94644, *Homo sapiens* caspase 14, apoptosis-related cysteine protease(CASP14), mRNA)
530. Catalase (EC 1.11.1.6)
531. Cathepsin D (EC 3.4.23.5) (Cleaved into: Cathepsin D light chain; Cathepsin D heavy chain)
532. CDGSH iron-sulfur domain-containing protein 2 (Endoplasmic reticulum intermembrane small protein) (MitoNEET-related 1 protein) (Miner 1) (Nutrient-deprivation autophagy factor-1) (NAF-1)
533. cDNA FLJ44468 fis, clone UTERU2026025, moderately similar to SPLICING FACTOR, ARGININE/SERINE-RICH 2
534. cDNA FLJ51535, highly similar to Phosphatidylethanolamine-binding protein 1
535. cDNA FLJ52068, highly similar to Microtubule-associated protein RP/EB family member 1
536. CDNAFLJ52360, highly similar to Heat-shock protein 105 kDa
537. cDNA FLJ52842, highly similar to Actin, cytoplasmic 1
538. cDNA FLJ53122, highly similar to ATP-dependent RNA helicase DDX3Y (EC 3.6.1.-)
539. cDNA FLJ53160, highly similar to Zyxin
540. cDNAFLJ53425, highly similar to Far upstream element-binding protein 1
541. cDNA FLJ54020, highly similar to Heterogeneous nuclear ribonucleoprotein U
542. cDNA FLJ54552, highly similar to Heterogeneous nuclear ribonucleoprotein K
543. cDNA FLJ58049, highly similar to RNA-binding protein FUS
544. cDNA FLJ59402, highly similar to Eukaryotic translation initiation factor 4B
545. cDNA FLJ60058, highly similar to Myosin light chain 1, slow-twitch muscle A isoform
546. cDNA FLJ60461, highly similar to Peroxiredoxin-2 (EC 1.11.1.15)
547. cDNA FLJ60588, highly similar to Protein arginine N-methyltransferase 1 (EC 2.1.1.-)
548. Cell growth-regulating nucleolar protein
549. Chloride intracellular channel protein 1 (Chloride channel ABP) (Nuclear chloride ion channel 27) (NCC27) (Regulatory nuclear chloride ion channel protein) (hRNCC)
550. Chromatin target of PRMT1 protein (Friend of PRMT1 protein) (Small arginine- and glycine-rich protein) (SRAG)
551. Chromobox homolog 3 (HP1 gamma homolog, *Drosophila*) (Chromobox homolog 3 (HP1 gamma homolog, *Drosophila*), isoform CRA_a) (Coiled-coil domain containing 32, isoform CRA_c)
552. Clathrin heavy chain 1 (Clathrin heavy chain on chromosome 17) (CLH-17)
553. Cleavage and polyadenylation specificity factor subunit 5 (Cleavage and polyadenylation specificity factor 25 kDa subunit) (CFIm25) (CPSF 25 kDa subunit) (Nucleoside diphosphate-linked moiety X motif 21) (Nudix motif 21) (Pre-mRNA cleavage factor Im 25 kDa subunit)
554. Coatomer subunit delta
555. Cofilin-1
556. Cold-inducible RNA-binding protein (A18 hnRNP) (Glycine-rich RNA-binding protein CIRP)
557. Complement component 1 Q subcomponent-binding protein, mitochondrial (ASF/SF2-associated protein p32) (Glycoprotein gC1qBP) (C1qBP) (Hyaluronan-binding protein 1) (Mitochondrial matrix protein p32) (gC1q-R protein) (p33)
558. Copine-3 (Copine III)
559. Core histone macro-H2A.1 (Histone macroH2A1) (mH2A1) (Histone H2A.y) (H2A/y) (Medulloblastoma antigen MU-MB-50.205)
560. Corneodesmosin
561. Cornifin-B (14.9 kDa pancornulin) (Small proline-rich protein IB) (SPR-IB)
562. Creatine kinase U-type, mitochondrial (EC 2.7.3.2) (Acidic-type mitochondrial creatine kinase) (Mia-CK) (Ubiquitous mitochondrial creatine kinase) (U-MtCK)
563. CRISPR-associated endonuclease Cas9 (EC 3.1.-.-) (SaCas9)
564. Cyclin-dependent kinase 1 (Fragment)
565. Cystatin-A (Cystatin-AS) (Stefin-A) [Cleaved into: Cystatin-A, N-terminally processed]
566. Cystatin-M (Cystatin-6) (Cystatin-E)
567. Cytochrome c (Fragment)
568. Cytohesin-4 (Fragment)
569. DAZ-associated protein 1 (Deleted in azoospermia-associated protein 1)
570. Delta globin (Delta-globin chain) (Globin A2) (Hemoglobin delta) (Hemoglobin, delta)
571. Desmocollin-1 (Cadherin family member 1) (Desmosomal glycoprotein 2/3) (DG2/DG3)
572. Desmocollin-3 (Cadherin family member 3) (Desmocollin-4) (HT-CP)
573. Desmoglein-1 (Cadherin family member 4) (Desmosomal glycoprotein 1) (DG1) (DGI) (Pemphigus foliaceus antigen)

-continued

574. Desmoplakin (DP) (250/210 kDa paraneoplastic pemphigus antigen)
575. DNA helicase (EC 3.6.4.12)
576. DNA topoisomerase (EC 5.99.1.2)
577. DNA topoisomerase 1 (EC 5.99.1.2) (DNA topoisomerase I)
578. DNA-directed RNA polymerases I and III subunit RPAC1 (Fragment)
579. DnaJ homolog subfamily A member 1 (DnaJ protein homolog 2) (HSDJ) (Heat shock 40 kDa protein 4) (Heat shock protein J2) (HSJ-2) (Human DnaJ protein 2) (hDj-2)
580. Double-stranded RNA-binding protein Staufen homolog 1 (Fragment)
581. E3 ubiquitin-protein ligase RBBP6 (EC 2.3.2.27) (Proliferation potential-related protein) (Protein P2P-R) (RING-type E3 ubiquitin transferase RBBP6) (Retinoblastoma-binding Q protein 1) (RBQ-1) (Retinoblastoma-binding protein 6) (p53-associated cellular protein of testis)
582. Electron transfer flavoprotein subunit beta (Beta-ETF)
583. Elongation factor 1-alpha 1 (EF-1-alpha-1) (Elongation factor Tu) (EF-Tu) (Eukaryotic elongation factor 1 A-1) (eEF1A-1) (Leukocyte receptor cluster member 7)
584. Elongation factor 1-beta (EF-1-beta)
585. Elongation factor 1-delta (Fragment)
586. Elongation factor 2 (EF-2)
587. Elongation factor Tu, mitochondrial (EF-Tu) (P43)
588. Emerin
589. Endoplasmin (94 kDa glucose-regulated protein) (GRP-94) (Heat shock protein 90 kDa beta member 1) (Tumor rejection antigen 1) (gp96 homolog)
590. Endothelial differentiation-related factor 1 (EDF-1) (Multiprotein-bridging factor 1) (MBF1)
591. Enhancer of rudimentary homolog
592. Epididymis luminal protein 112 (Ribosomal protein S27a, isoform CRA_c) (cDNA, FLJ96793, *Homo sapiens* ribosomal protein S27a (RPS27A), mRNA)
593. Epididymis luminal protein 4 (Epididymis secretory protein Li 3) (Epididymis secretory protein Li 93) (Tyrosine 3-monooxygenase/tryptophan 5-monooxygenase activation protein zeta polypeptide) (Tyrosine 3-monooxygenase/tryptophan 5-monooxygenase activation protein, zeta polypeptide, isoform CRA_a)
594. Epididymis secretory protein Li 103 (Heat shock 70 kDa protein 1A) (Heat shock 70 kDa protein 1B) (cDNA FLJ75127, highly similar to *Homo sapiens* heat shock 70 kDa protein 1A, mRNA)
595. Epididymis secretory sperm binding protein Li 44a (Serpin peptidase inhibitor clade A member 1 isoform 1)
596. Epididymis tissue sperm binding protein Li 3a
597. Epiplakin (450 kDa epidermal antigen)
598. Eukaryotic initiation factor 4A-I (eIF-4A-I) (eIF4A-I) (EC 3.6.4.13) (ATP-dependent RNA helicase eIF4A-1)
599. Eukaryotic initiation factor 4A-II
600. Eukaryotic initiation factor 4A-III (eIF-4A-III) (eIF4A-III) (EC 3.6.4.13) (ATP-dependent RNA helicase DDX48) (ATP-dependent RNA helicase eIF4A-3) (DEAD box protein 48) (Eukaryotic initiation factor 4A-like NUK-34) (Eukaryotic translation initiation factor 4A isoform 3) (Nuclear matrix protein 265) (NMP 265) (hNMP 265) [Cleaved into: Eukaryotic initiation factor 4A-III, N-terminally processed]
601. Eukaryotic peptide chain release factor subunit 1 (cDNA FLJ56175, highly similar to Eukaryotic peptide chain release factor subunit1)
602. Eukaryotic peptide chain release factor subunit 1 (Eukaryotic release factor 1) (eRF1) (Protein Cl1) (TB3-1)
603. Eukaryotic translation initiation factor 1A, Y-chromosomal
604. Eukaryotic translation initiation factor 2 subunit 1 (Eukaryotic translation initiation factor 2 subunit alpha) (eIF-2-alpha) (eIF-2A) (eIF-2 alpha)
605. Eukaryotic translation initiation factor 2 subunit 3 (Eukaryotic translation initiation factor 2 subunit gamma X) (eIF-2-gamma X) (eIF-2gX)
606. Eukaryotic translation initiation factor 3 subunit B (Fragment)
607. Eukaryotic translation initiation factor 3 subunit C-like protein
608. Eukaryotic translation initiation factor 3 subunit E (eIF3e) (Eukaryotic translation initiation factor 3 subunit 6) (eIF-3 p48)
609. Eukaryotic translation initiation factor 3 subunit F (eIF3f) (Eukaryotic translation initiation factor 3 subunit 5) (eIF-3-epsilon) (eIF3 p47)
610. Eukaryotic translation initiation factor 3 subunit G (eIF3g) (Eukaryotic translation initiation factor 3 RNA-binding subunit) (eIF-3 RNA-binding subunit) (Eukaryotic translation initiation factor 3 subunit 4) (eIF-3-delta) (eIF3 p42) (eIF3 p44)
611. Eukaryotic translation initiation factor 3 subunit H (eIF3h) (Eukaryotic translation initiation factor 3 subunit 3) (eIF-3 gamma) (eIF3 p40 subunit)
612. Eukaryotic translation initiation factor 3 subunit I (eIF3i) (Eukaryotic translation initiation factor 3 subunit 2) (TGF-beta receptor-interactingprotein 1) (TRIP-1) (eIF-3-beta) (eIF3 p36)
613. Eukaryotic translation initiation factor 5 (eIF-5)
614. Eukaryotic translation initiation factor 5A-1 (eIF-5A-1) (eIF-5A1) (Eukaryotic initiation factor 5A isoform 1) (eIF-5A) (Rev-binding factor) (eIF-4D)
615. Eukaryotic translation initiation factor 5B (eIF-5B) (EC 3.6.5.3) (Translation initiation factor IF-2)
616. Eukaryotic translation initiation factor 6 (Fragment)
617. Exportin-1 (Exp1) (Chromosome region maintenance 1 protein homolog)
618. Extracellular glycoprotein lacritin
619. Extracellular matrix protein 1 (Secretory component p85)
620. Ezrin (Cytovillin) (Villin-2) (p81)
621. F-actin-capping protein subunit alpha-1 (CapZ alpha-1)
622. F-box only protein 50 (NCC receptor protein 1 homolog) (NCCRP-1) (Non-specific cytotoxic cell receptor protein 1 homolog)
623. Far upstream element-binding protein 2 (FUSE-binding protein 2) (KH type-splicing regulatory protein) (KSRP) (p75)
624. Fascin (55 kDa actin-bundling protein) (Singed-like protein) (p55)
625. Fatty acid binding protein 5 (Psoriasis-associated)
626. Fatty acid synthase (EC 2.3.1.85) (Includes: [Acyl-carrier-protein] S-acetyltransferase (EC 2.3.1.38); [Acyl-carrier-protein] S-malonyltransferase (EC 2.3.1.39); 3-oxoacyl-[acyl-carrier-protein] synthase (EC 2.3.1.41); 3-oxoacyl-[acyl-carrier-protein] reductase (EC 1.1.1.100); 3-hydroxyacyl-[acyl-carrier-protein] dehydratase (EC 4.2.1.59); Enoyl-[acyl-carrier-protein] reductase (EC 1.3.1.39); Oleoyl-[acyl-carrier-protein] hydrolase (EC 3.1.2.14))
627. Fermitin family homolog 3 (Kindlin-3) (MIG2-like protein) (Unc-112-related protein 2)
628. Ferric-chelate reductase 1 (EC 1.-.-.-) (Stromal cell-derived receptor 2) (SDR-2)
629. Filaggrin -continued 630. Filaggrin-2 (FLG-2) (Intermediate filament-associated and psoriasis-susceptibility protein) (Ifapsoriasin)
631. Filamin-C (FLN-C) (FLNc) (ABP-280-like protein) (ABP-L) (Actin-binding-like protein) (Filamin-2) (Gamma-filamin)
632. Flap endonuclease 1 (Fragment)
633. Fragile X mental retardation syndrome-related protein 1 (cDNA FLJ58644, highly similar to Fragile X mental retardation syndrome-related protein 1)
634. Fructose-bisphosphate aldolase A (EC 4.1.2.13) (Lung cancer antigen NY-LU-1) (Muscle-type aldolase)
635. Fructose-bisphosphate aldolase C (EC 4.1.2.13) (Brain-type aldolase)
636. G2/mitotic-specific cyclin-B1 (Fragment)
637. Galectin-7 (Gal-7) (HKL-14) (P17) (p53-inducedgene 1 protein)
638. Gametocyte-specific factor 1 (Protein FAM112B)
639. Gamma-glutamylcyclotransferase
640. Gasdermin-A (Gasdermin-1)
641. Glucose-6-phosphate isomerase (GP1) (EC 5.3.1.9) (Autocrine motility factor) (AMF) (Neuroleukin) (NLK) (Phosphoglucose isomerase) (PGI) (Phosphohexose isomerase) (PHI) (Sperm antigen 36) (SA-36)
642. Glutaredoxin-3 (PKC-interacting cousin of thioredoxin) (PICOT) (PKC-theta-interacting protein) (PKCq-interacting protein) (Thioredoxin-like protein 2)
643. Glutathione S-transferase P
644. Glutathione S-transferase P (EC 2.5.1.18) (GST class-pi) (GSTP1-1)
645. Glyceraldehyde-3-phosphate dehydrogenase (GAPDH) (EC 1.2.1.12) (Peptidyl-cysteine S-nitrosylase GAPDH) (EC 2.6.99.-)
646. Glycine-tRNA ligase (EC 3.6.1.17) (EC 6.1.1.14) (Diadenosine tetraphosphate synthetase) (AP-4-A synthetase) (Glycyl-tRNA synthetase) (GlyRS)
647. Growth factor receptor-bound protein 2 (Growth factor receptor-bound protein 2, isoform CRA_a) (cDNA, FLJ96637, Homo sapiens growth factor receptor-bound protein 2 (GRB2J, mRNA)
648. H/ACA ribonucleoprotein complex subunit 1 (Nucleolar protein family A member 1) (snoRNP protein GAR1)
649. HCG1994130, isoform CRA_a (cDNA FLJ30359 fis, clone BRACE2007760, highly similar to 40S RIBOSOMAL PROTEIN S15A) (cDNA, FLJ92249, Homo sapiens ribosomal protein S15a (RPS15AJ, mRNA)
650. HCG2005638, isoform CRA_c (cDNA FLJ53073, highly similar to Spliceosome RNA helicase Bat1 (EC 3.6.1.-))
651. Heat shock 70 kDa protein 4 (HSP70RY) (Heat shock 70-related protein APG-2)
652. Heat shock 70 kDa protein 6 (Heat shock 70 kDa protein B')
653. Heat shock cognate 71 kDa protein (Fragment)
654. Heat shock cognate 71 kDa protein (Heat shock 70 kDa protein 8) (Lipopolysaccharide-associated protein 1) (LAP-1) (LPS-associated protein 1)
655. Heat shock protein beta-1 (HspB1) (28 kDa heat shock protein) (Estrogen-regulated 24 kDa protein) (Heat shock 27 kDa protein) (HSP 27) (Stress-responsive protein 27) (SRP27)
656. Heat shock protein HSP 90-alpha (Heat shock 86 kDa) (HSP 86) (HSP86) (Lipopolysaccharide-associated protein 2) (LAP-2) (LPS-associated protein 2) (Renal carcinoma antigen NY-REN-38)
657. Heat shock protein HSP 90-beta (HSP 90) (Heat shock 84 kDa) (HSP 84) (HSP84)
658. Hemoglobin subunit zeta (HBAZ) (Hemoglobin zeta chain) (Zeta-globin)
659. Heterogeneous nuclear ribonucleoprotein A/B
660. Heterogeneous nuclear ribonucleoprotein A0 (hnRNP A0)
661. Heterogeneous nuclear ribonucleoprotein A1 (hnRNP A1) (Helix-destabilizing protein) (Single-strand RNA-binding protein) (hnRNP core protein A1) [Cleaved into: Heterogeneous nuclear ribonucleoprotein A1, N-terminally processed]
662. Heterogeneous nuclear ribonucleoprotein A3, isoform CRA_a (cDNA FLJ52659, highly similar to Heterogeneous nuclear ribonucleoprotein A3) (cDNA, FLJ79333, highly similar to Heterogeneous nuclear ribonucleoprotein A3)
663. Heterogeneous nuclear ribonucleoprotein D-like (hnRNP D-like) (hnRNP DL) (AU-rich element RNA-binding factor) (JKT41-binding protein) (Protein laAUF1)
664. Heterogeneous nuclear ribonucleoprotein F (hnRNP F) (Nucleolin-like protein mcs94-1) [Cleaved into: Heterogeneous nuclear ribonucleoprotein F, N-terminally processed]
665. Heterogeneous nuclear ribonucleoprotein H
666. Heterogeneous nuclear ribonucleoprotein H3 (hnRNP H3) (Heterogeneous nuclear ribonucleoprotein 2H9) (hnRNP 2H9)
667. Heterogeneous nuclear ribonucleoprotein L (hnRNP L)
668. Heterogeneous nuclear ribonucleoprotein M (hnRNP M)
669. Heterogeneous nuclear ribonucleoprotein Q (hnRNP Q) (Glycine- and tyrosine-rich RNA-binding protein) (GRY-RBP) (NS1-associated protein 1) (Synaptotagmin-binding cytoplasmic RNA-interacting protein)
670. Heterogeneous nuclear ribonucleoprotein R (hnRNP R)
671. Heterogeneous nuclear ribonucleoprotein U (hnRNP U) (Scaffold attachment factor A) (SAF-A) (p120) (pp120)
672. Heterogeneous nuclear ribonucleoproteins A2/B1 (hnRNP A2/B1)
673. Heterogeneous nuclear ribonucleoproteins C1/C2 (hnRNP C1/C2)
674. High mobility group protein B2 (Fragment)
675. High mobility group protein B3 (Fragment)
676. High mobility group protein HMG-I/HMG-Y (HMG-I(Y)) (High mobility group AT-hook protein 1) (High mobility group protein A1) (High mobility group protein R)
677. Histone 1, H1e (Histone H1e)
678. Histone acetyltransferase type B catalytic subunit (EC 2.3.1.48) (Histone acetyltransferase 1)
679. Histone deacetylase complex subunit SAP18 (18 kDa Sin3-associated polypeptide) (2HOR0202) (Cell growth-inhibiting gene 38 protein) (Sin3-associated polypeptide p18)
680. Histone H1.5 (Histone H1a) (Histone H1b) (Histone H1s-3)
681. Histone H1x
682. Histone H2A
683. Histone H2B
684. Histone H2B type 1-J (Histone H2B.1) (Histone H2B.r) (H2B/r)
685. Histone H3
686. Histone H4
687. Histone-binding protein RBBP4 (Fragment)
688. Hornerin
689. Hsp90 co-chaperone Cdc37 (Hsp90 chaperone protein kinase-targeting subunit) (p50Cdc37) [Cleaved into: Hsp90 co-chaperone Cdc37, N-terminally processed]
690. Immunoglobulin heavy constant alpha 1 (Ig alpha-1 chain C region) (Ig alpha-1 chain C region BUR) (Ig alpha-1 chain C region TRO)

-continued

691. Immunoglobulin heavy constant gamma 1 (Ig gamma-1 chain C region) (Ig gamma-1 chain C region EU) (Ig gamma-1 chain C region KOL) (Ig gamma-1 chain C region NIE)
692. Immunoglobulin kappa constant (Ig kappa chain C region) (Ig kappa chain C region AG) (Ig kappa chain C region CUM) (Ig kappa chain C region EU) (Ig kappa chain C region OU) (Ig kappa chain C region ROY) (Ig kappa chain C region TI)
693. Immunoglobulin lambda-like polypeptide 5 (G lambda-1) (Germline immunoglobulin lambda 1)
694. Importin subunit alpha-1 (Karyopherin subunit alpha-2) (RAG cohort protein 1) (SRP1-alpha)
695. Importin subunit beta-1 (Importin-90) (Karyopherin subunit beta-1) (Nuclear factor p97) (Pore targeting complex 97 kDa subunit) (PTAC97)
696. Importin-7 (Imp7) (Ran-binding protein 7) (RanBP7)
697. Inorganic pyrophosphatase (EC 3.6.1.1) (Pyrophosphate phospho-hydrolase) (PPase)
698. Inosine-5'-monophosphate dehydrogenase 2 (IMP dehydrogenase 2) (IMPD 2) (IMPDH 2) (EC 1.1.1.205) (IMPDH-II)
699. Insulin-like growth factor 2 mRNA-binding protein 1 (IGF2 mRNA-binding protein 1) (IMP-1) (IMP1) (Coding region determinant-binding protein) (CRD-BP) (IGF-II mRNA-binding protein 1) (VICKZ family member 1) (Zipcode-binding protein 1) (ZBP-1)
700. Interleukin enhancer-binding factor 2 (Nuclear factor of activated T-cells 45 kDa)
701. Isoleucine--tRNA ligase, cytoplasmic (EC 6.1.1.5) (Isoleucyl-tRNA synthetase) (IRS) (IleRS)
702. Junction plakoglobin (Catenin gamma) (Desmoplakin III) (Desmoplakin-3)
703. Kallikrein-10 (EC 3.4.21.-) (Normal epithelial cell-specific 1) (Protease serine-like 1)
704. Keratin, type I cytoskeletal 17
705. L-lactate dehydrogenase B chain (LDH-B) (EC 1.1.1.27) (LDH heart subunit) (LDH-H) (Renal carcinoma antigen NY-REN-46)
706. La-related protein 1 (La ribonucleoprotein domain family member 1)
707. Lactoylglutathione lyase (EC 4.4.1.5) (Aldoketomutase) (Glyoxalase I) (Glx I) (Ketone-aldehyde mutase) (Methylglyoxalase) (S-D-lactoylglutathione methylglyoxal lyase)
708. Lamin-B receptor (Integral nuclear envelope inner membrane protein) (LMN2R)
709. Lamin-B1
710. Lamina-associated polypeptide 2, isoform alpha (Thymopoietin isoform alpha) (TP alpha) (Thymopoietin-related peptide isoform alpha) (TPRP isoform alpha) [Cleaved into: Thymopoietin (TP) (Splenin); Thymopentin (TP5)]
711. Laminin subunit beta-1
712. Leucine-rich repeat-containing protein 59 (Ribosome-binding protein p34) (p34)
713. Lipocalin-1 (Tear lipocalin) (Tlc) (Tear prealbumin) (TP) (Von Ebner gland protein) (VEG protein)
714. Loricrin
715. Macrophage migration inhibitory factor (MIF) (EC 5.3.2.1) (Glycosylation-inhibiting factor) (GIF) (L-dopachrome isomerase) (L-dopachromet automerase) (EC 5.3.3.12) (Phenylpyruvate tautomerase)
716. Malate dehydrogenase, cytoplasmic
717. Malate dehydrogenase, mitochondrial (EC 1.1.1.37)
718. Matrin-3
719. Matrix-remodeling-associated protein 5 (Adhesion protein with leucine-rich repeats and immunoglobulin domains related to perlecan) (Adlican)
720. Microtubule-associated protein
721. Moesin (Membrane-organizing extension spike protein)
722. Mov10, Moloney leukemia virus 10, homolog (Mouse), isoform CRA_a (Putative helicase MOV-10)
723. Multifunctional protein ADE2 (Fragment)
724. Multifunctional protein ADE2 (Phosphoribosylaminoimidazole carboxylase, phosphoribosylaminoimidazole succinocarboxamide synthetase, isoform CRA_b)
725. Myosin-9 (Cellular myosin heavy chain, type A) (Myosin heavy chain 9) (Myosin heavy chain, non-muscle IIa) (Non-muscle myosin heavy chain A) (NMMHC-A) (Non-muscle myosin heavy chain IIa) (NMMHC II-a) (NMMHC-IIA)
726. N-fatty-acyl-amino acid synthase/hydrolase PM20D1 (EC 3.5.1.-) (EC 4.3.-.-) (Peptidase M20 domain-containing protein 1)
727. NADH dehydrogenase [ubiquinone] 1 alpha subcomplex assembly factor 4 (Hormone-regulated proliferation-associated protein of 20 kDa)
728. NADH dehydrogenase [ubiquinone] iron-sulfur protein 2, mitochondrial (EC 1.6.5.3) (EC 1.6.99.3) (Complex I-49 kD) (CI-49 kD) (NADH-ubiquinone oxidoreductase 49 kDa subunit)
729. NADH dehydrogenase [ubiquinone] iron-sulfur protein 3, mitochondrial (EC 1.6.5.3) (EC 1.6.99.3) (Complex I-30 kD) (CI-30 kD) (NADH-ubiquinone oxidoreductase 30 kDa subunit)
730. Neuroblast differentiation-associated protein AHNAK (Desmoyokin)
731. NHP2-like protein 1
732. Non-histone chromosomal protein HMG-14
733. Non-POU domain-containing octamer-binding protein (NonO protein) (54 kDa nuclear RNA- and DNA-binding protein) (55 kDa nuclear protein) (DNA-binding p52/p100 complex, 52 kDa subunit) (NMT55) (p54(nrb)) (p54nrb)
734. Nuclear autoantigenic sperm protein (Fragment)
735. Nuclear migration protein nudC (Nuclear distribution protein C homolog)
736. Nuclear pore complex protein Nup214 (214 kDa nucleoporin) (Nucleoporin Nup214) (Protein CAN)
737. Nuclease-sensitive element-binding protein 1 (CCAAT-binding transcription factor I subunit A) (CBF-A) (DNA-binding protein B) (DBPB) (Enhancer factor I subunitA) (EFI-A) (Y-box transcription factor) (Y-box-binding protein 1) (YB-1)
738. Nucleolar and coiled-body phosphoprotein 1 (140 kDa nucleolar phosphoprotein) (Nopp140) (Hepatitis C virus NS5A-transactivated protein 13) (HCV NS5A-transactivated protein 13) (Nucleolar 130 kDa protein) (Nucleolar phosphoprotein p130)
739. Nucleolar GTP-binding protein 1
740. Nucleolar protein 56 (Nucleolar protein 5A)
741. Nucleolar RNA helicase 2 (EC 3.6.4.13) (DEAD box protein 21) (Gu-alpha) (Nucleolar RNA helicase Gu) (Nucleolar RNA helicase II) (RH II/Gu)
742. Nucleolin (Protein C23)
743. Nucleophosmin (NPM) (Nucleolar phosphoprotein B23) (Nucleolar protein NO38) (Numatrin)
744. Nucleoprotein TPR (Megator) (NPC-associated intranuclear protein) (Translocated promoter region protein)
745. Nucleoside diphosphate kinase A (NDK A) (NDP kinase A) (EC 2.7.4.6) (Granzyme A-activated DNase) (GAAD) (Metastasis inhibition factor nm23) (NM23-H1) (Tumor metastatic process-associated protein)
746. Nucleoside diphosphate kinase B (NDK B) (NDP kinase B) (EC 2.7.4.6) (C-myc purine-binding transcription factor PUF) (Histidine protein kinase NDKB) (EC 2.7.13.3) (nm23-H2)
747. PAI-1 mRNA-binding protein variant (cDNA, FLJ92551, *Homo sapiens* PAI-1 mRNA-binding protein (PAI-RBP1), mRNA)
748. Peptidyl-prolyl cis-trans isomerase B (PPIase B) (EC 5.2.1.8) (CYP-S1) (Cyclophilin B) (Rotamase B) (S-cyclophilin) (SCYLP)
749. Peptidyl-prolyl cis-trans isomerase FKBP3 (PPIase FKBP3) (EC 5.2.1.8) (25 kDa FK506-bindingprotein) (25 kDa FKBP) (FKBP-25) (FK506-bindingprotein 3) (FKBP-3) (Immunophilin FKBP25) (Rapamycin-selective 25 kDa immunophilin) (Rotamase)

-continued

750. Peptidyl-prolyl cis-trans isomerase FKBP4 (PPIase FKBP4) (EC 5.2.1.8) (51 kDa FK506-binding protein) (FKBP51) (52 kDa FK506-binding protein) (52 kDa FKBP) (FKBP-52) (59 kDa immunophilin) (p59) (FK506-binding protein 4) (FKBP-4) (FKBP59) (HSP-binding immunophilin) (HBI) (Immunophilin FKBP52) (Rotamase) [Cleaved into: Peptidyl-prolyl cis-trans isomerase FKBP4, N-terminally processed]
751. Peptidyl-prolyl cis-trans isomerase G (Fragment)
752. Peroxiredoxin-1 (EC 1.11.1.15) (Natural killer cell-enhancing factor A) (NKEF-A) (Proliferation-associated gene protein) (PAG) (Thioredoxin peroxidase 2) (Thioredoxin-dependent peroxide reductase 2)
753. Peroxiredoxin-6 (EC 1.11.1.15) (1-Cys peroxiredoxin) (1-Cys PRX) (24 kDa protein) (Acidic calcium-independent phospholipase A2) (aiPLA2) (EC 3.1.1.-) (Antioxidant protein 2) (Liver 2D page spot 40) (Non-selenium glutathione peroxidase) (NSGPx) (EC 1.11.1.9) (Red blood cells page spot 12)
754. Pinin (140 kDa nuclear and cell adhesion-related phosphoprotein) (Desmosome-associated protein) (Domain-rich serine protein) (DRS protein) (DRSP) (Melanoma metastasis clone A protein) (Nuclear protein SDK3) (SR-like protein)
755. Plakophilin-1 (Band 6 protein) (B6P)
756. Plectin (PCN) (PLTN) (Hemidesmosomal protein 1) (HD1) (Plectin-1)
757. Poly [ADP-ribose] polymerase 1 (PARP-1) (EC 2.4.2.30) (ADP-ribosyltransferase diphtheria toxin-like 1) (ARTD1) (NAD(+) ADP-ribosyltransferase 1) (ADPRT1) (Poly[ADP-ribose] synthase 1)
758. Poly(rC)-binding protein 1 (Alpha-CP1) (Heterogeneous nuclear ribonucleoprotein E1) (hnRNP E1) (Nucleic acid-binding protein SUB2.3)
759. Polyadenylate-binding protein (PABP)
760. Polyadenylate-binding protein 1 (PABP-1) (Poly(A)-binding protein 1)
761. Polyadenylate-binding protein 2 (PABP-2) (Poly(A)-binding protein 2) (Nuclear poly(A)-binding protein 1) (Poly(A)-binding protein II) (PABII) (Polyadenylate-binding nuclear protein 1)
762. Polymerase delta-interacting protein 3 (46 kDa DNA polymerase delta interaction protein) (p46) (S6K1 Aly/REF-like target) (SKAR)
763. Polypyrimidine tract binding protein 1, isoform CRA_b (Polypyrimidine tract-binding protein 1)
764. Polypyrimidine tract-binding protein 1 (PTB) (57 kDa RNA-binding protein PPTB-1) (Heterogeneous nuclear ribonucleoprotein I) (hnRNP I)
765. Pre-mRNA-processing factor 19 (EC 2.3.2.27) (Nuclear matrix protein 200) (PRP19/PSO4 homolog) (hPso4) (RING-type E3 ubiquitin transferase PRP19) (Senescence evasion factor)
766. Pre-mRNA-processing factor 19 (Fragment)
767. Prefoldin subunit 2 (cDNA, FLJ96845, *Homo sapiens* prefoldin 2 (PFDN2), mRNA)
768. Prelamin-A/C (Cleaved into: Lamin-A/C (70 kDa lamin) (Renal carcinoma antigen NY-REN-32))
769. Probable ATP-dependent RNA helicase DDX17 (EC 3.6.4.13) (DEAD box protein 17) (DEAD box protein p72) (DEAD box protein p82) (RNA-dependent helicase p72)
770. Probable ATP-dependent RNA helicase DDX5 (EC 3.6.4.13) (DEAD box protein 5) (RNA helicase p68)
771. Probable ATP-dependent RNA helicase DDX6 (EC 3.6.4.13) (ATP-dependent RNA helicase p54) (DEAD box protein 6) (Oncogene RCK)
772. Profilin-1 (Epididymis tissue protein Li 184a) (Profilin I)
773. Prohibitin-2
774. Prolactin-inducible protein (Gross cystic disease fluid protein 15) (GCDFP-15) (Prolactin-induced protein) (Secretory actin-binding protein) (SABP) (gp17)
775. Proliferating cell nuclear antigen (PCNA) (Cyclin)
776. Proliferation-associated protein 2G4 (Cell cycle protein p38-2G4 homolog) (hG4-1) (ErbB3-binding protein 1)
777. Prostaglandin E synthase 3 (EC 5.3.99.3) (Cytosolic prostaglandin E2 synthase) (cPGES) (Hsp90 co-chaperone) (Progesterone receptor complex p23) (Telomerase-binding protein p23)
778. Proteasome endopeptidase complex (EC 3.4.25.1)
779. Proteasome subunit alpha type-3 (EC 3.4.25.1) (Macropain subunit C8) (Multicatalytic endopeptidase complex subunit C8) (Proteasome component C8)
780. Proteasome subunit alpha type-4 (EC 3.4.25.1) (Macropain subunit C9) (Multicatalytic endopeptidase complex subunit C9) (Proteasome component C9) (Proteasome subunit L)
781. Proteasome subunit alpha type-5 (EC 3.4.25.1) (Macropain zeta chain) (Multicatalytic endopeptidase complex zeta chain) (Proteasome zeta chain)
782. Proteasome subunit alpha type-6 (EC 3.4.25.1) (27 kDa prosomal protein) (PROS-27) (p27K) (Macropain iota chain) (Multicatalytic endopeptidase complex iota chain) (Proteasome iota chain)
783. Proteasome subunit alpha type-7 (EC 3.4.25.1) (Proteasome subunit RC6-1) (Proteasome subunit XAPC7)
784. Proteasome subunit beta type-1 (EC 3.4.25.1) (Macropain subunit C5) (Multicatalytic endopeptidase complex subunit C5) (Proteasome component C5) (Proteasome gamma chain)
785. Proteasome subunit beta type-2 (EC 3.4.25.1) (Macropain subunit C7-I) (Multicatalytic endopeptidase complex subunit C7-I) (Proteasome component C7-I)
786. Proteasome subunit beta type-6 (EC 3.4.25.1) (Macropain delta chain) (Multicatalytic endopeptidase complex delta chain) (Proteasome delta chain) (Proteasome subunit Y)
787. Protein arginine N-methyltransferase 1
788. Protein disulfide-isomerase A3 (EC 5.3.4.1) (58 kDa glucose-regulated protein) (58 kDa microsomal protein) (p58) (Disulfide isomerase ER-60) (Endoplasmic reticulum resident protein 57) (ER protein 57) (ERp57) (Endoplasmic reticulum resident protein 60) (ER protein 60) (ERp60)
789. Protein disulfide-isomerase A4 (EC 5.3.4.1) (Endoplasmic reticulum resident protein 70) (ER protein 70) (ERp70) (Endoplasmic reticulum resident protein 72) (ER protein 72) (ERp-72) (ERp72)
790. Protein DJ-1 (DJ-1) (Oncogene DJ1) (Parkinson disease protein 7) (Parkinsonism-associated deglycase) (Protein deglycase DJ-1) (EC 3.1.2.-) (EC 3.5.1.124)
791. Protein ERGIC-53 (ER-Golgi intermediate compartment 53 kDa protein) (Gp58) (Intracellular mannose-specific lectin MR60) (Lectin mannose-binding 1)
792. Protein LYRIC
793. Protein mago nashi homolog 2
794. Protein POF1B (Premature ovarian failure protein 1B)
795. Protein RCC2 (RCC1-like protein TD-60) (Telophase disk protein of 60 kDa)
796. Protein S100-A11 (Calgizzarin) (Metastatic lymph node gene 70 protein) (MLN 70) (Protein S100-C) (S100 calcium-binding protein A11) [Cleaved into: Protein S100-A11, N-terminally processed]
797. Protein S100-A14 (S100 calcium-binding protein Al4) (S114)
798. Protein S100-A16 (Aging-associated gene 13 protein) (Protein S100-F) (S100 calcium-binding protein A16)

-continued

799. Protein S100-A2 (CAN19) (Protein S-100L) (S100 calcium-binding protein A2)
800. Protein S100-A7 (Psoriasin) (S100 calcium-binding protein A7)
801. Protein S100-A8 (Calgranulin-A) (Calprotectin L1L subunit) (Cystic fibrosis antigen) (CFAG) (Leukocyte L1 complex light chain) (Migration inhibitory factor-related protein 8) (MRP-8) (p8) (S100 calcium-binding protein A8) (Urinary stone protein band A) [Cleaved into: Protein S100-A8, N-terminally processed]
802. Protein S100-A9 (Calgranulin-B) (Calprotectin L1H subunit) (Leukocyte L1 complex heavy chain) (Migration inhibitory factor-related protein 14) (MRP-14) (p14) (S100 calcium-binding protein A9)
803. Protein SET (HLA-DR-associated protein II) (Inhibitor of granzyme A-activated DNase) (IGAAD) (PHAPII) (Phosphatase 2A inhibitor I2PP2A) (I-2PP2A) (Template-activatingfactor I) (TAF-I)
804. Protein Shroom3 (Shroom-related protein) (hShrmL)
805. Protein SON (Bax antagonist selected in saccharomyces 1) (BASS1) (Negative regulatory element-binding protein) (NRE-binding protein) (Protein DBP-5) (SON3)
806. Protein SREK1IP1 (SFRS12-interacting protein 1) (SREK1-interacting protein 1) (Splicing regulatory protein of 18 kDa) (p18SRP)
807. Protein-glutamine gamma-glutamyltransferase E (EC 2.3.2.13) (Transglutaminase E) (TG(E)) (TGE) (TGase E) (Transglutaminase-3) (TGase-3) [Cleaved into: Protein-glutamine gamma-glutamyltransferase E 50 kDa catalytic chain; Protein-glutamine gamma-glutamyltransferase E 27 kDa non-catalytic chain]
808. Protein-glutamine gamma-glutamyltransferase K (EC 2.3.2.13) (Epidermal TGase) (Transglutaminase K) (TG(K)) (TGK) (TGase K) (Transglutaminase-1) (TGase-1)
809. Putative heat shock protein HSP 90-beta 4
810. Putative RNA-binding protein Luc7-like 2
811. Putative RRN3-like protein RRN3P2 (RNA polymerase I transcription factor homolog pseudogene 2)
812. Pyruvate kinase PKM (EC 2.7.1.40) (Cytosolic thyroid hormone-binding protein) (CTHBP) (Opa-interacting protein 3) (OIP-3) (Pyruvate kinase 2/3) (Pyruvate kinase muscle isozyme) (Thyroid hormone-binding protein 1) (THBP1) (Tumor M2-PK) (p58)
813. Ran-specific GTPase-activating protein (Ran-binding protein 1) (RanBP1)
814. Ras GTPase-activating protein-binding protein 1 (G3BP-1) (EC 3.6.4.12) (EC 3.6.4.13) (ATP-dependent DNA helicase VIII) (hDH VIII) (GAP SH3 domain-binding protein 1)
815. Ras GTPase-activating-like protein IQGAP1 (p195)
816. Ras-related protein Rab-10
817. Ras-related protein Rab-7a
818. Regulator of chromosome condensation (Fragment)
819. Regulator of nonsense transcripts 1 (EC 3.6.4.-) (ATP-dependent helicase RENT1) (Nonsense mRNA reducing factor 1) (NORF1) (Up-frameshift suppressor 1 homolog) (hUpf1)
820. Retinitis pigmentosa 9 protein (Pim-1-associated protein) (PAP-1)
821. Retroviral-like aspartic protease 1 (EC 3.4.23.-) (Skin-specific retroviral-like aspartic protease) (SASPase) (Skin aspartic protease) (TPA-inducible aspartic proteinase-like protein) (TAPS)
822. Rho GDP-dissociation inhibitor 1 (Rho GDI 1) (Rho-GDI alpha)
823. Ribonuclease 7 (RNase 7) (EC 3.1.27.-) (Skin-derived antimicrobial protein 2) (SAP-2)
824. Ribonuclease inhibitor (Placental ribonuclease inhibitor) (Placental RNase inhibitor) (Ribonuclease/angiogenin inhibitor 1) (RAI)
825. Ribosomal biogenesis protein LAS1L (Protein LAS1 homolog)
826. Ribosomal protein L15
827. Ribosomal protein L5 (Ribosomal protein L5, isoform CRA_c) (cDNA, FLJ95579, Homo sapiens ribosomal protein L5 (RPL5), mRNA)
828. Ribosomal protein S23, isoform CRA_a (cDNA FLJ77921, highly similar to Homo sapiens ribosomal protein S23 (RPS23), mRNA) (cDNA, FLJ92033, Homo sapiens ribosomal protein S23 (RPS23), mRNA)
829. RNA-binding motif protein, X chromosome (Glycoprotein p43) (Heterogeneous nuclear ribonucleoprotein G) (hnRNP G) (Cleaved into: RNA-binding motif protein, X chromosome, N-terminally processed)
830. RNA-binding protein 14 (Paraspeckle protein 2) (PSP2) (RRM-containing coactivator activator/modulator) (Synaptotagmin-interacting protein) (SYT-interacting protein)
831. RNA-binding protein 8A (Binder of OVCA1-1) (BOV-1) (RNA-binding motif protein 8A) (RNA-binding protein Y14) (Ribonucleoprotein RBM8A)
832. RNA-binding protein EWS
833. Rootletin (Fragment)
834. rRNA 2'-O-methyltransferase fibrillarin (EC 2.1.1.-) (34 kDa nucleolar scleroderma antigen) (Histone-glutamine methyltransferase)
835. rRNA/tRNA 2'-O-methyltransferase fibrillarin-like protein 1 (EC 2.1.1.-) (Protein-glutamine methyltransferase)
836. RuvB-like 1 (EC 3.6.4.12) (49 kDa TATA box-binding protein-interacting protein) (49 kDa TBP-interacting protein) (54 kDa erythrocyte cytosolic protein) (ECP-54) (INO80 complex subunit H) (Nuclear matrix protein 238) (NMP 238) (Pontin 52) (TIP49a) (TIP60-associated protein 54-alpha) (TAP54-alpha)
837. RuvB-like 2 (EC 3.6.4.12) (48 kDa TATA box-binding protein-interacting protein) (48 kDa TBP-interacting protein) (51 kDa erythrocyte cytosolic protein) (ECP-51) (INO80 complex subunit J) (Repressing pontin 52) (Reptin52) (TIP49b) (TIP60-associated protein 54-beta) (TAP54-beta)
838. RuvB-like helicase (EC 3.6.4.12)
839. S-formylglutathione hydrolase (FGH) (EC 3.1.2.12) (Esterase D) (Methylumbelliferyl-acetate deacetylase) (EC 3.1.1.56)
840. SAP domain-containing ribonucleoprotein (Cytokine-induced protein of 29 kDa) (Nuclear protein Hcc-1) (Proliferation-associated cytokine-inducible protein CIP29)
841. Septin-2
842. Septin-7
843. Serine-tRNA ligase, cytoplasmic (EC 6.1.1.11) (Seryl-tRNA synthetase) (SerRS) (Seryl-tRNA(Ser/Sec) synthetase)
844. Serine/arginine repetitive matrix protein 2 (300 kDa nuclear matrix antigen) (Serine/arginine-rich splicing factor-related nuclear matrix protein of 300 kDa) (SR-related nuclear matrix protein of 300 kDa) (Ser/Arg-related nuclear matrix protein of 300 kDa) (Splicing coactivator subunit SRm300) (Tax-responsive enhancer element-binding protein 803) (TaxREB803)
845. Serine/arginine-rich splicing factor 1 (Alternative-splicing factor 1) (ASF-1) (Splicing factor, arginine/serine-rich 1) (pre-mRNA-splicing factor SF2, P33 subunit)
846. Serine/arginine-rich splicing factor 10 (40 kDa SR-repressor protein) (SRrp40) (FUS-interacting serine-arginine-rich protein 1) (Splicing factor SRp38) (Splicing factor, arginine/serine-rich 13A) (TLS-associated protein with Ser-Arg repeats) (TASR) (TLS-associated protein with SR repeats) (TLS-associated serine-arginine protein) (TLS-associated SR protein)
847. Serine/arginine-rich splicing factor 11 (Arginine-rich 54 kDa nuclear protein) (p54) (Splicing factor, arginine/serine-rich 11)
848. Serine/arginine-rich splicing factor 6 (Pre-mRNA-splicing factor SRP55) (Splicing factor, arginine/serine-rich 6)
849. Serine/threonine-protein phosphatase (EC 3.1.3.16) (Fragment)
850. Serpin B3 (Protein T4-A) (Squamous cell carcinoma antigen 1) (SCCA-1)

-continued

851. Serpin B4 (Leupin) (Peptidase inhibitor 11) (PI-11) (Squamous cell carcinoma antigen 2) (SCCA-2)
852. SH2 domain-containing protein 3A (Novel SH2-containing protein 1)
853. Signal recognition particle 14 kDa protein (SRP14) (18 kDa Alu RNA-binding protein)
854. Single-stranded DNA-binding protein
855. Skin-specific protein 32
856. Small nuclear ribonucleoprotein E (snRNP-E) (Sm protein E) (Sm-E) (SmE)
857. Small nuclear ribonucleoprotein Sm D1 (Sm-D1) (Sm-D autoantigen) (snRNP core protein D1)
858. Small nuclear ribonucleoprotein Sm D2 (Sm-D2) (snRNP core protein D2)
859. Small proline-rich protein 2E (SPR-2E) (Small proline-rich protein II) (SPR-II)
860. Spindlin-4
861. Splicing factor 3B subunit 1 (Pre-mRNA-splicing factor SF3b 155 kDa subunit) (SF3b155) (Spliceosome-associated protein 155) (SAP 155)
862. Splicing factor 3B subunit 2 (Fragment)
863. Splicing factor arginine/serine-rich 3 (Splicing factor, arginine/serine-rich 3, isoform CRA_d) (cDNA, FLJ92926, Homo sapiens splicing factor, arginine/serine-rich 3 (SFRS3), mRNA)
864. Splicing factor U2AF 35 kDa subunit (U2 auxiliary factor 35 kDa subunit) (U2 small nuclear RNA auxiliary factor 1) (U2 snRNP auxiliary factor small subunit)
865. Splicing factor U2AF 65 kDa subunit (U2 auxiliary factor 65 kDa subunit) (hU2AF(65)) (hU2AF65) (U2 snRNP auxiliary factor large subunit)
866. Splicing factor, proline- and glutamine-rich (100 kDa DNA-pairing protein) (hPOMp100) (DNA-binding p52/p100 complex, 100 kDa subunit) (Polypyrimidine tract-binding protein-associated-splicing factor) (PSF) (PTB-associated-splicing factor)
867. Src substrate cortactin (Amplaxin) (Oncogene EMS1)
868. Stathmin
869. Stress-70 protein, mitochondrial (75 kDa glucose-regulated protein) (GRP-75) (Heat shock 70 kDa protein 9) (Mortalin) (MOT) (Peptide-binding protein 74) (PBP74)
870. Stress-induced-phosphoprotein 1 (STI1) (Hsc70/Hsp90-organizing protein) (Hop) (Renal carcinoma antigen NY-REN-11) (Transformation-sensitive protein IEF SSP 3521)
871. Striatin-3 (Cell cycle autoantigen SG2NA) (S/G2 antigen)
872. Synaptosomal-associated protein 29 (SNAP-29) (Soluble 29 kDa NSF attachment protein) (Vesicle-membrane fusion protein SNAP-29)
873. T-complex protein 1 subunit alpha (TCP-1-alpha) (CCT-alpha)
874. T-complex protein 1 subunit beta (TCP-1-beta) (CCT-beta)
875. T-complex protein 1 subunit eta (TCP-1-eta) (CCT-eta) (HIV-1 Nef-interacting protein) [Cleaved into: T-complex protein 1 subunit eta, N-terminally processed]
876. T-complex protein 1 subunit theta (TCP-1-theta) (CCT-theta) (Renal carcinoma antigen NY-REN-15)
877. T-complex protein 1 subunit zeta (TCP-1-zeta) (Acute morphine dependence-related protein 2) (CCT-zeta-1) (HTR3) (Tcp20)
878. Talin-1
879. Tetratricopeptide repeat protein 1 (TPR repeat protein 1)
880. Thioredoxin-like protein 1 (32 kDa thioredoxin-related protein)
881. THO complex subunit 4
882. Thymidine phosphorylase (Fragment)
883. Thyroid hormone receptor-associated protein 3 (Thyroid hormone receptor-associated protein complex 150 kDa component) (Trap150)
884. Transaldolase (EC 2.2.1.2)
885. Transcription intermediary factor 1-beta (TIF1-beta) (E3 SUMO-protein ligase TRIM28) (EC 2.3.2.27) (KRAB-associated protein 1) (KAP-1) (KRAB-interacting protein 1) (KRIP-1) (Nuclear corepressor KAP-1) (RING finger protein 96) (RING-type E3 ubiquitin transferase TIF1-beta) (Tripartite motif-containing protein 28)
886. Transitional endoplasmic reticulum ATPase (TER ATPase) (EC 3.6.4.6) (15S Mg(2+)-ATPase p97 subunit) (Valosin-containing protein) (VCP)
887. Transketolase (EC 2.2.1.1)
888. Trifunctional purine biosynthetic protein adenosine-3 [Includes: Phosphoribosylamine--glycine ligase (EC 6.3.4.13) (Glycinamide ribonucleotide synthetase) (GARS) (Phosphoribosylglycinamide synthetase); Phosphoribosylformylglycinamidine cyclo-ligase (EC 6.3.3.1) (AIR synthase) (AIRS) (Phosphoribosyl-aminoimidazole synthetase); Phosphoribosylglycinamide formyltransferase (EC 2.1.2.2) (5'-phosphoribosylglycinamide transformylase) (GAR transformylase) (CART)]
889. Tropomyosin alpha-3 chain (Gamma-tropomyosin) (Tropomyosin-3) (Tropomyosin-5) (hTM5)
890. Trypsin-1
891. Tubulin alpha chain
892. Tubulin alpha-1A chain (Alpha-tubulin 3) (Tubulin B-alpha-1) (Tubulin alpha-3 chain) [Cleaved into: Detyrosinated tubulin alpha-1A chain]
893. Tubulin alpha-1B chain (Alpha-tubulin ubiquitous) (Tubulin K-alpha-1) (Tubulin alpha-ubiquitous chain) [Cleaved into: Detyrosinated tubulin alpha-1B chain]
894. Tubulin beta chain (Tubulin beta-5 chain)
895. Tubulin beta-2A chain (Tubulin beta class IIa)
896. Tubulin beta-4B chain (Tubulin beta-2 chain) (Tubulin beta-2C chain)
897. Tudor domain-containing protein 5
898. Tyrosine-tRNA ligase, cytoplasmic (EC 6.1.1.1) (Tyrosyl-tRNA synthetase) (TyrRS) [Cleaved into: Tyrosine-tRNA ligase, cytoplasmic, N-terminally processed]
899. U1 small nuclear ribonucleoprotein 70 kDa (U1 snRNP 70 kDa) (U1-70K) (snRNP70)
900. U1 small nuclear ribonucleoprotein A (U1 snRNP A) (U1-A) (U1A)
901. U2 small nuclear ribonucleoprotein A' (U2 snRNP A')
902. Ubiquitin-associated protein 2-like (Protein NICE-4)
903. Ubiquitin-conjugating enzyme E2 D3
904. Ubiquitin-conjugating enzyme E2 L3 (EC 2.3.2.23) (E2 ubiquitin-conjugating enzyme L3) (L-UBC) (UbcH7) (Ubiquitin carrier protein L3) (Ubiquitin-conjugating enzyme E2-F1) (Ubiquitin-protein ligase L3)
905. V-type proton ATPase subunit G 1 (V-ATPase subunit G 1) (V-ATPase 13 kDa subunit 1) (Vacuolar proton pump subunit G 1) (Vacuolar proton pump subunit M16)
906. Vasodilator-stimulated phosphoprotein (VASP)
907. Vesicle-associated membrane protein-associated protein A (VAMP-A) (VAMP-associated protein A) (VAP-A) (33 kDa VAMP-associated protein) (VAP-33)

908. Vimentin
909. Vinculin (Metavinculin) (MV)
910. Voltage-dependent anion-selective channel protein 2 (Fragment)
911. Voltage-dependent anion-selective channel protein 2 (VDAC-2) (hVDAC2) (Outer mitochondrial membrane protein porin 2)
912. Y-box-binding protein 3 (Cold shock domain-containing protein A) (DNA-binding protein A) (Single-strand DNA-binding protein NF-GMB)
913. Zinc finger CCCH domain-containing protein 11A (Fragment)
914. Zinc-alpha-2-glycoprotein (Zn-alpha-2-GP) (Zn-alpha-2-glycoprotein)

Table 7 Shows Data for Peptide Identification by MS for 10 Day Dimerized Washout Sample 1. >Reverse >sp|A6NN14|ZN729_HUMAN Zinc finger protein 729 OS = *Homo sapiens* GN = ZNF729 PE = 2 SV = 3
2. >Reverse >sp|P0C5W0|PNM6B_HUMAN Paraneoplastic antigen-like protein 6B OS = *Homo sapiens* GN = PNMA6B PE = 2 SV = 1
3. >Reverse >sp|P20929|NEBU_HUMAN Nebulin OS = *Homo sapiens* GN = NEB PE = 1 SV = 4
4. >Reverse >sp|P98088|MUC5A_HUMAN Mucin-5AC (Fragments) OS = *Homo sapiens* GN = MUC5AC PE = 1 SV = 3
5. >Reverse >sp|Q6AHZ1|Z518A_HUMAN Zinc finger protein 518A OS = *Homo sapiens* GN = ZNF518A PE = 1 SV = 2
6. >Reverse >sp|Q86XI2|CNDG2_HUMAN Condensin-2 complex subunit G2 OS = *Homo sapiens* GN = NCAPG2 PE = 1 SV = 1
7. >Reverse >sp|Q96J65|MRP9_HUMAN Multidrug resistance-associated protein 9 OS = *Homo sapiens* GN = ABCC12 PE = 1 SV = 2
8. >Reverse >sp|Q9NPC3|CIP1_HUMAN E3 ubiquitin-protein ligase CCNB1IP1 OS = *Homo sapiens* GN = CCNB1IP1 PE = 1 SV = 1
9. >Reverse >sp|Q9NR99|MXRA5_HUMAN Matrix-remodeling-associated protein 5 OS = *Homo sapiens* GN = MXRA5 PE = 2 SV = 3
10. >Reverse >tr|B0S7Q4|B0S7Q4_HUMAN Chromosome 6 open reading frame 136 (Fragment) OS = *Homo sapiens* GN = C6orf136 PE = 4 SV = 1
11. >Reverse >tr|B4DL02|B4DL02_HUMAN cDNA FLJ56101, highly similar to SHC-transforming protein 1 OS = *Homo sapiens* PE = 2 SV = 1
12. >Reverse >tr|C9JCL9|C9JCL9_HUMAN Uncharacterized protein OS = *Homo sapiens* GN = THOC5 PE = 4 SV = 1
13. >Reverse >tr|C9JRL1|C9JRL1_HUMAN Uncharacterized protein OS = *Homo sapiens* GN = STOX1 PE = 4 SV = 1
14. >Reverse >tr|E7ESM5|E7ESM5_HUMAN Uncharacterized protein OS = *Homo sapiens* GN = MYBPC1 PE = 4 SV = 2
15. >Reverse >tr|E7EW81|E7EW81_HUMAN Uncharacterized protein OS = *Homo sapiens* GN = ZRANB3 PE = 4 SV = 1
16. >Reverse >tr|E9PCV0|E9PCV0_HUMAN Uncharacterized protein OS = *Homo sapiens* GN = GUSB PE = 4 SV = 1
17. >Reverse >tr|E9PPD3|E9PPD3_HUMAN Uncharacterized protein OS = *Homo sapiens* GN = TTN PE = 4 SV = 1
18. >Reverse >tr|F5GYI1|F5GYI1_HUMAN Uncharacterized protein OS = *Homo sapiens* GN = VNN3 PE = 4 SV = 1
19. >Reverse >tr|F5GYQ5|F5GYQ5_HUMAN Uncharacterized protein OS = *Homo sapiens* GN = RNASEH2B PE = 4 SV = 1
20. >Reverse >tr|F5H0C0|F5H0C0_HUMAN Uncharacterized protein OS = *Homo sapiens* PE = 4 SV = 1
21. >sp|B2RPK0|HGB1A_HUMAN Putative high mobility group protein B1-like 1 OS = *Homo sapiens* GN = HMGB1P1 PE = 5 SV = 1
22. >sp|J7RUA5|CAS9_STAAU CRISPR-associated endonuclease Cas9 OS = *Staphylococcus aureus* GN = cas9 PE = 1 SV = 1
23. >sp|O00299|CLIC1_HUMAN Chloride intracellular channel protein 1 OS = *Homo sapiens* GN = CLIC1 PE = 1 SV = 4
24. >sp|O00471|EXOC5_HUMAN Exocyst complex component 5 OS = *Homo sapiens* GN = EXOC5 PE = 1 SV = 1
25. >sp|O00571|DDX3X_HUMAN ATP-dependent RNA helicase DDX3X OS = *Homo sapiens* GN = DDX3X PE = 1 SV = 3
26. >sp|O00712|NFIB_HUMAN Nuclear factor 1 B-type OS = *Homo sapiens* GN = NFIB PE = 1 SV = 2
27. >sp|O15078|CE290_HUMAN Centrosomal protein of 290 kDa OS = *Homo sapiens* GN = CEP290 PE = 1 SV = 2
28. >sp|O43684|BUB3_HUMAN Mitotic checkpoint protein BUB3 OS = *Homo sapiens* GN = BUB3 PE = 1 SV = 1
29. >sp|O60506|HNRPQ_HUMAN Heterogeneous nuclear ribonucleoprotein Q OS = *Homo sapiens* GN = SYNCRIP PE = 1 SV = 2
30. >sp|O60869|EDF1_HUMAN Endothelial differentiation-related factor 1 OS = *Homo sapiens* GN = EDF1 PE = 1 SV = 1
31. >sp|O75306|NDUS2_HUMAN NADH dehydrogenase [ubiquinone] iron-sulfur protein 2, mitochondrial OS = *Homo sapiens* GN = NDUFS2 PE = 1 SV = 2
32. >sp|O75494|SRS10_HUMAN Serine/arginine-rich splicing factor 10 OS = *Homo sapiens* GN = SRSF10 PE = 1 SV = 1
33. >sp|P00540|MOS_HUMAN Proto-oncogene serine/threonine-protein kinase mos OS = *Homo sapiens* GN = MOS PE = 1 SV = 1
34. >sp|P01857|IGHG1_HUMAN Ig gamma-1 chain C region OS = *Homo sapiens* GN = IGHG1 PE = 1 SV = 1
35. >sp|P02533|K1C14_HUMAN Keratin, type I cytoskeletal 14 OS = *Homo sapiens* GN = KRT14 PE = 1 SV = 4
36. >sp|P02538|K2C6A_HUMAN Keratin, type II cytoskeletal 6A OS = *Homo sapiens* GN = KRT6A PE = 1 SV = 3
37. >sp|P04075|ALDOA_HUMAN Fructose-bisphosphate aldolase A OS = *Homo sapiens* GN = ALDOA PE = 1 SV = 2
38. >sp|P04083|ANXA1_HUMAN Annexin A1 OS = *Homo sapiens* GN = ANXA1 PE = 1 SV = 2
39. >sp|P04183|KITH_HUMAN Thymidine kinase, cytosolic OS = *Homo sapiens* GN = TK1 PE = 1 SV = 2
40. >sp|P04259|K2C6B_HUMAN Keratin, type II cytoskeletal 6B OS = *Homo sapiens* GN = KRT6B PE = 1 SV = 5
41. >sp|P04264|K2C1_HUMAN Keratin, type II cytoskeletal 1 OS = *Homo sapiens* GN = KRT1 PE = 1 SV = 6
42. >sp|P05387|RLA2_HUMAN 60S acidic ribosomal protein P2 OS = *Homo sapiens* GN = RPLP2 PE = 1 SV = 1
43. >sp|P05783|K1C18_HUMAN Keratin, type I cytoskeletal 18 OS = *Homo sapiens* GN = KRT18 PE = 1 SV = 2
44. >sp|P06493|CDK1_HUMAN Cyclin-dependent kinase 1 OS = *Homo sapiens* GN = CDK1 PE = 1 SV = 3
45. >sp|P06733|ENOA_HUMAN Alpha-enolase OS = *Homo sapiens* GN = ENO1 PE = 1 SV = 2
46. >sp|P06748|NPM_HUMAN Nucleophosmin OS = *Homo sapiens* GN = NPM1 PE = 1 SV = 2
47. >sp|P06753-2|TPM3_HUMAN Isoform 2 of Tropomyosin alpha-3 chain OS = *Homo sapiens* GN = TPM3
48. >sp|P06899|H2B1J_HUMAN Histone H2B type 1-J OS = *Homo sapiens* GN = HIST1H2BJ PE = 1 SV = 3
49. >sp|P07195|LDHB_HUMAN L-lactate dehydrogenase B chain OS = *Homo sapiens* GN = LDHB PE = 1 SV = 2
50. >sp|P07355|ANXA2_HUMAN Annexin A2 OS = *Homo sapiens* GN = ANXA2 PE = 1 SV = 2
51. >sp|P07437|TBB5_HUMAN Tubulin beta chain OS = *Homo sapiens* GN = TUBB PE = 1 SV = 2
52. >sp|P07737|PROF1_HUMAN Profilin-1 OS = *Homo sapiens* GN = PFN1 PE = 1 SV = 2
53. >sp|P07900|HS90A_HUMAN Heat shock protein HSP 90-alpha OS = *Homo sapiens* GN = HSP90AA1 PE = 1 SV = 5
54. >sp|P07910|HNRPC_HUMAN Heterogeneous nuclear ribonucleoproteins C1/C2 OS = *Homo sapiens* GN = HNRNPC PE = 1 SV = 4
55. >sp|P08238|HS90B_HUMAN Heat shock protein HSP 90-beta OS = *Homo sapiens* GN = HSP90AB1 PE = 1 SV = 4
56. >sp|P08670|VIME_HUMAN Vimentin OS = *Homo sapiens* GN = VIM PE = 1 SV = 4
57. >sp|P08779|K1C16_HUMAN Keratin, type I cytoskeletal 16 OS = *Homo sapiens* GN = KRT16 PE = 1 SV = 4
58. >sp|P09382|LEG1_HUMAN Galectin-1 OS = *Homo sapiens* GN = LGALS1 PE = 1 SV = 2
59. >sp|P09651|ROA_HUMAN Heterogeneous nuclear ribonucleoprotein A1 OS = *Homo sapiens* GN = HNRNPA1 PE = 1 SV = 5
60. >sp|P09874|PARP1_HUMAN Poly [ADP-ribose] polymerase 1 OS = *Homo sapiens* GN = PARP1 PE = 1 SV = 4
61. >sp|P10606|COX5B_HUMAN Cytochrome c oxidase subunit 5B, mitochondrial OS = *Homo sapiens* GN = COX5B PE = 1 SV = 2

| | |
|---|---|
| 62. | >sp\|P10809\|CH60_HUMAN 60 kDa heat shock protein, mitochondrial OS = *Homo sapiens* GN = HSPD1 PE = 1 SV = 2 |
| 63. | >sp\|P13010\|XRCC5_HUMAN X-ray repair cross-complementing protein 5 OS = *Homo sapiens* GN = XRCC5 PE = 1 SV = 3 |
| 64. | >sp\|P13489\|RINI_HUMAN Ribonuclease inhibitor OS = *Homo sapiens* GN = RNH1 PE = 1 SV = 2 |
| 65. | >sp\|P13639\|EF2_HUMAN Elongation factor 2 OS = *Homo sapiens* GN = EEF2 PE = 1 SV = 4 |
| 66. | >sp\|P13645\|K1C10_HUMAN Keratin, type I cytoskeletal 10 OS = *Homo sapiens* GN = KRT10 PE = 1 SV = 6 |
| 67. | >sp\|P13647\|K2C5_HUMAN Keratin, type II cytoskeletal 5 OS = *Homo sapiens* GN = KRT5 PE = 1 SV = 3 |
| 68. | >sp\|P14866\|HNRPL_HUMAN Heterogeneous nuclear ribonucleoprotein L OS = *Homo sapiens* GN = HNRNPL PE = 1 SV = 2 |
| 69. | >sp\|P14868\|SYDC_HUMAN Aspartyl-tRNA synthetase, cytoplasmic OS = *Homo sapiens* GN = DARS PE = 1 SV = 2 |
| 70. | >sp\|P14923\|PLAK_HUMAN Junction plakoglobin OS = *Homo sapiens* GN = JUP PE = 1 SV = 3 |
| 71. | >sp\|P15531\|NDKA_HUMAN Nucleoside diphosphate kinase A OS = *Homo sapiens* GN = NME1 PE = 1 SV = 1 |
| 72. | >sp\|P15880\|RS2_HUMAN 40S ribosomal protein S2 OS = *Homo sapiens* GN = RPS2 PE = 1 SV = 2 |
| 73. | >sp\|P15924\|DESP_HUMAN Desmoplakin OS = *Homo sapiens* GN = DSP PE = 1 SV = 3 |
| 74. | >sp\|P16401\|H15_HUMAN Histone H1.5 OS = *Homo sapiens* GN = HIST1H1B PE = 1 SV = 3 |
| 75. | >sp\|P16989\|DBPA_HUMAN DNA-binding protein A OS = *Homo sapiens* GN = CSDA PE = 1 SV = 4 |
| 76. | >sp\|P17066\|HSP76_HUMAN Heat shock 70 kDa protein 6 OS = *Homo sapiens* GN = HSPA6 PE = 1 SV = 2 |
| 77. | >sp\|P17096-2\|HMGA1_HUMAN Isoform HMG-Y of High mobility group protein HMG-I/HMG-Y OS = *Homo sapiens* GN = HMGA1 |
| 78. | >sp\|P17987\|TCPA_HUMAN T-complex protein 1 subunit alpha OS = *Homo sapiens* GN = TCP1 PE = 1 SV = 1 |
| 79. | >sp\|P18077\|RL35A_HUMAN 60S ribosomal protein L35a OS = *Homo sapiens* GN = RPL35A PE = 1 SV = 2 |
| 80. | >sp\|P18621\|RL17_HUMAN 60S ribosomal protein L17 OS = *Homo sapiens* GN = RPL17 PE = 1 SV = 3 |
| 81. | >sp\|P19338\|NUCL_HUMAN Nucleolin OS = *Homo sapiens* GN = NCL PE = 1 SV = 3 |
| 82. | >sp\|P20671\|H2A1D_HUMAN Histone H2A type 1-D OS = *Homo sapiens* GN = HIST1H2AD PE = 1 SV = 2 |
| 83. | >sp\|P22626\|ROA2_HUMAN Heterogeneous nuclear ribonucleoproteins A2/B1 OS = *Homo sapiens* GN = HNRNPA2B1 PE = 1 SV = 2 |
| 84. | >sp\|P23246\|SFPQ_HUMAN Splicing factor, proline- and glutamine-rich OS = *Homo sapiens* GN = SFPQ PE = 1 SV = 2 |
| 85. | >sp\|P23396\|RS3_HUMAN 40S ribosomal protein S3 OS = *Homo sapiens* GN = RPS3 PE = 1 SV = 2 |
| 86. | >sp\|P25311\|ZA2G_HUMAN Zinc-alpha-2-glycoprotein OS = *Homo sapiens* GN = AZGP1 PE = 1 SV = 2 |
| 87. | >sp\|P25398\|RS12_HUMAN 40S ribosomal protein S12 OS = *Homo sapiens* GN = RPS12 PE = 1 SV = 3 |
| 88. | >sp\|P25705\|ATPA_HUMAN ATP synthase subunit alpha, mitochondrial OS = *Homo sapiens* GN = ATP5A1 PE = 1 SV = 1 |
| 89. | >sp\|P26038\|MOES_HUMAN Moesin OS = *Homo sapiens* GN = MSN PE = 1 SV = 3 |
| 90. | >sp\|P26368\|U2AF2_HUMAN Splicing factor U2AF 65 kDa subunit OS = *Homo sapiens* GN = U2AF2 PE = 1 SV = 4 |
| 91. | >sp\|P28072\|PSB6_HUMAN Proteasome subunit beta type-6 OS = *Homo sapiens* GN = PSMB6 PE = 1 SV = 4 |
| 92. | >sp\|P30050\|RL12_HUMAN 60S ribosomal protein L12 OS = *Homo sapiens* GN = RPL12 PE = 1 SV = 1 |
| 93. | >sp\|P31946\|1433B_HUMAN 14-3-3 protein beta/alpha OS = *Homo sapiens* GN = YWHAB PE = 1 SV = 3 |
| 94. | >sp\|P31947\|1433S_HUMAN 14-3-3 protein sigma OS = *Homo sapiens* GN = SFN PE = 1 SV = 1 |
| 95. | >sp\|P34932\|HSP74_HUMAN Heat shock 70 kDa protein 4 OS = *Homo sapiens* GN = HSPA4 PE = 1 SV = 4 |
| 96. | >sp\|P35268\|RL22_HUMAN 60S ribosomal protein L22 OS = *Homo sapiens* GN = RPL22 PE = 1 SV = 2 |
| 97. | >sp\|P35527\|K1C9_HUMAN Keratin, type I cytoskeletal 9 OS = *Homo sapiens* GN = KRT9 PE = 1 SV = 3 |
| 98. | >sp\|P35908\|K22E_HUMAN Keratin, type II cytoskeletal 2 epidermal OS = *Homo sapiens* GN = KRT2 PE = 1 SV = 2 |
| 99. | >sp\|P38159\|HNRPG_HUMAN Heterogeneous nuclear ribonucleoprotein G OS = *Homo sapiens* GN = RBMX PE = 1 SV = 3 |
| 100. | >sp\|P38646\|GRP75_HUMAN Stress-70 protein, mitochondrial OS = *Homo sapiens* GN = HSPA9 PE = 1 SV = 2 |
| 101. | >sp\|P38919\|IF4A3_HUMAN Eukaryotic initiation factor 4A-III OS = *Homo sapiens* GN = EIF4A3 PE = 1 SV = 4 |
| 102. | >sp\|P40227\|TCPZ_HUMAN T-complex protein 1 subunit zeta OS = *Homo sapiens* GN = CCT6A PE = 1 SV = 3 |
| 103. | >sp\|P40429\|RL13A_HUMAN 60S ribosomal protein L13a OS = *Homo sapiens* GN = RPL13A PE = 1 SV = 2 |
| 104. | >sp\|P40926\|MDHM_HUMAN Malate dehydrogenase, mitochondrial OS = *Homo sapiens* GN = MDH2 PE = 1 SV = 3 |
| 105. | >sp\|P41250\|SYG_HUMAN Glycyl-tRNA synthetase OS = *Homo sapiens* GN = GARS PE = 1 SV = 3 |
| 106. | >sp\|P42229\|STA5A_HUMAN Signal transducer and activator of transcription 5A OS = *Homo sapiens* GN = STAT5A PE = 1 SV = 1 |
| 107. | >sp\|P42677\|RS27_HUMAN 40S ribosomal protein S27 OS = *Homo sapiens* GN = RPS27 PE = 1 SV = 3 |
| 108. | >sp\|P42766\|RL35_HUMAN 60S ribosomal protein L35 OS = *Homo sapiens* GN = RPL35 PE = 1 SV = 2 |
| 109. | >sp\|P45880\|VDAC2_HUMAN Voltage-dependent anion-selective channel protein 2 OS = *Homo sapiens* GN = VDAC2 PE = 1 SV = 2 |
| 110. | >sp\|P46778\|RL21_HUMAN 60S ribosomal protein L21 OS = *Homo sapiens* GN = RPL21 PE = 1 SV = 2 |
| 111. | >sp\|P46782\|RS5_HUMAN 40S ribosomal protein S5 OS = *Homo sapiens* GN = RPS5 PE = 1 SV = 4 |
| 112. | >sp\|P46783\|RS10_HUMAN 40S ribosomal protein S10 OS = *Homo sapiens* GN = RPS10 PE = 1 SV = 1 |
| 113. | >sp\|P47914\|RL29_HUMAN 60S ribosomal protein L29 OS = *Homo sapiens* GN = RPL29 PE = 1 SV = 2 |
| 114. | >sp\|P49207\|RL34_HUMAN 60S ribosomal protein L34 OS = *Homo sapiens* GN = RPL34 PE = 1 SV = 3 |
| 115. | >sp\|P49327\|FAS_HUMAN Fatty acid synthase OS = *Homo sapiens* GN = FASN PE = 1 SV = 3 |
| 116. | >sp\|P49411\|EFTU_HUMAN Elongation factor Tu, mitochondrial OS = *Homo sapiens* GN = TUFM PE = 1 SV = 2 |
| 117. | >sp\|P49591\|SYSC_HUMAN Seryl-tRNA synthetase, cytoplasmic OS = *Homo sapiens* GN = SARS PE = 1 SV = 3 |
| 118. | >sp\|P50990\|TCPQ_HUMAN T-complex protein 1 subunit theta OS = *Homo sapiens* GN = CCT8 PE = 1 SV = 4 |
| 119. | >sp\|P51858\|HDGF_HUMAN Hepatoma-derived growth factor OS = *Homo sapiens* GN = HDGF PE = 1 SV = 1 |
| 120. | >sp\|P52272\|HNRPM_HUMAN Heterogeneous nuclear ribonucleoprotein M OS = *Homo sapiens* GN = HNRNPM PE = 1 SV = 3 |
| 121. | >sp\|P52597\|HNRPF_HUMAN Heterogeneous nuclear ribonucleoprotein F OS = *Homo sapiens* GN = HNRNPF PE = 1 SV = 3 |
| 122. | >sp\|P55072\|TERA_HUMAN Transitional endoplasmic reticulum ATPase OS = *Homo sapiens* GN = VCP PE = 1 SV = 4 |
| 123. | >sp\|P60842\|IF4A1_HUMAN Eukaryotic initiation factor 4A-I OS = *Homo sapiens* GN = EIF4A1 PE = 1 SV = 1 |
| 124. | >sp\|P61353\|RL27_HUMAN 60S ribosomal protein L27 OS = *Homo sapiens* GN = RPL27 PE = 1 SV = 2 |
| 125. | >sp\|P61981\|1433G_HUMAN 14-3-3 protein gamma OS = *Homo sapiens* GN = YWHAG PE = 1 SV = 2 |
| 126. | >sp\|P62241\|RS8_HUMAN 40S ribosomal protein S8 OS = *Homo sapiens* GN = RPS8 PE = 1 SV = 2 |
| 127. | >sp\|P62249\|RS16_HUMAN 40S ribosomal protein S16 OS = *Homo sapiens* GN = RPS16 PE = 1 SV = 2 |
| 128. | >sp\|P62263\|RS14_HUMAN 40S ribosomal protein S14 OS = *Homo sapiens* GN = RPS14 PE = 1 SV = 3 |
| 129. | >sp\|P62269\|RS18_HUMAN 40S ribosomal protein S18 OS = *Homo sapiens* GN = RPS18 PE = 1 SV = 3 |
| 130. | >sp\|P62280\|RS11_HUMAN 40S ribosomal protein S11 OS = *Homo sapiens* GN = RPS11 PE = 1 SV = 3 |
| 131. | >sp\|P62314\|SMD1_HUMAN Small nuclear ribonucleoprotein Sm D1 OS = *Homo sapiens* GN = SNRPD1 PE = 1 SV = 1 |
| 132. | >sp\|P62424\|RL7A_HUMAN 60S ribosomal protein L7a OS = *Homo sapiens* GN = RPL7A PE = 1 SV = 2 |
| 133. | >sp\|P62829\|RL23_HUMAN 60S ribosomal protein L23 OS = *Homo sapiens* GN = RPL23 PE = 1 SV = 1 |
| 134. | >sp\|P62841\|RS15_HUMAN 40S ribosomal protein S15 OS = *Homo sapiens* GN = RPS15 PE = 1 SV = 2 |
| 135. | >sp\|P62851\|RS25_HUMAN 40S ribosomal protein S25 OS = *Homo sapiens* GN = RPS25 PE = 1 SV = 1 |
| 136. | >sp\|P62854\|RS26_HUMAN 40S ribosomal protein S26 OS = *Homo sapiens* GN = RPS26 PE = 1 SV = 3 |
| 137. | >sp\|P62888\|RL30_HUMAN 60S ribosomal protein L30 OS = *Homo sapiens* GN = RPL30 PE = 1 SV = 2 |
| 138. | >sp\|P62906\|RL10A_HUMAN 60S ribosomal protein L10a OS = *Homo sapiens* GN = RPL10A PE = 1 SV = 2 |
| 139. | >sp\|P62913\|RL11_HUMAN 60S ribosomal protein L11 OS = *Homo sapiens* GN = RPL11 PE = 1 SV = 2 |
| 140. | >sp\|P63220\|RS21_HUMAN 40S ribosomal protein S21 OS = *Homo sapiens* GN = RPS21 PE = 1 SV = 1 |

-continued

141. >sp|P63241|IF5A1_HUMAN Eukaryotic translation initiation factor 5A-1 OS = *Homo sapiens* GN = EIF5A PE = 1 SV = 2
142. >sp|P68036|UB2L3_HUMAN Ubiquitin-conjugating enzyme E2 L3 OS = *Homo sapiens* GN = UBE2L3 PE = 1 SV = 1
143. >sp|P68104|EF1A1_HUMAN Elongation factor 1-alpha 1 OS = *Homo sapiens* GN = EEF1A1 PE = 1 SV = 1
144. >sp|P68371|TBB2C_HUMAN Tubulin beta-2C chain OS = *Homo sapiens* GN = TUBB2C PE = 1 SV = 1
145. >sp|P68431|H31_HUMAN Histone H3.1 OS = *Homo sapiens* GN = HIST1H3A PE = 1 SV = 2
146. >sp|P78371|TCPB_HUMAN T-complex protein 1 subunit beta OS = *Homo sapiens* GN = CCT2 PE = 1 SV = 4
147. >sp|P84098|RL19_HUMAN 60S ribosomal protein L19 OS = *Homo sapiens* GN = RPL19 PE = 1 SV = 1
148. >sp|Q00610|CLH1_HUMAN Clathrin heavy chain 1 OS = *Homo sapiens* GN = CLTC PE = 1 SV = 5
149. >sp|Q00839|HNRPU_HUMAN Heterogeneous nuclear ribonucleoprotein U OS = *Homo sapiens* GN = HNRNPU PE = 1 SV = 6
150. >sp|Q02543|RL18A_HUMAN 60S ribosomal protein L18a OS = *Homo sapiens* GN = RPL18A PE = 1 SV = 2
151. >sp|Q02878|RL6_HUMAN 60S ribosomal protein L6 OS = *Homo sapiens* GN = RPL6 PE = 1 SV = 3
152. >sp|Q06830|PRDX1_HUMAN Peroxiredoxin-1 OS = *Homo sapiens* GN = PRDX1 PE = 1 SV = 1
153. >sp|Q07955|SRSF1_HUMAN Serine/arginine-rich splicing factor 1 OS = *Homo sapiens* GN = SRSF1 PE = 1 SV = 2
154. >sp|Q08211|DHX9_HUMAN ATP-dependent RNA helicase A OS = *Homo sapiens* GN = DHX9 PE = 1 SV = 4
155. >sp|Q08378|GOGA3_HUMAN Golgin subfamily A member 3 OS = *Homo sapiens* GN = GOLGA3 PE = 1 SV = 2
156. >sp|Q08554|DSC1_HUMAN Desmocollin-1 OS = *Homo sapiens* GN = DSC1 PE = 1 SV = 2
157. >sp|Q12905|ILF2_HUMAN Interleukin enhancer-binding factor 2 OS = *Homo sapiens* GN = ILF2 PE = 1 SV = 2
158. >sp|Q13151|ROA0_HUMAN Heterogeneous nuclear ribonucleoprotein A0 OS = *Homo sapiens* GN = HNRNPA0 PE = 1 SV = 1
159. >sp|Q13242|SRSF9_HUMAN Serine/arginine-rich splicing factor 9 OS = *Homo sapiens* GN = SRSF9 PE = 1 SV = 1
160. >sp|Q13263|TIF1B_HUMAN Transcription intermediary factor 1-beta OS = *Homo sapiens* GN = TRIM28 PE = 1 SV = 5
161. >sp|Q13347|EIF3I_HUMAN Eukaryotic translation initiation factor 3 subunit I OS = *Homo sapiens* GN = EIF3I PE = 1 SV = 1
162. >sp|Q13838|DX39B_HUMAN Spliceosome RNA helicase DDX39B OS = *Homo sapiens* GN = DDX39B PE = 1 SV = 1
163. >sp|Q14103-3|HNRPD_HUMAN Isoform 3 of Heterogeneous nuclear ribonucleoprotein D0 OS = *Homo sapiens* GN = HNRNPD
164. >sp|Q14669|TRIPC_HUMAN Probable E3 ubiquitin-protein ligase TRIP12 OS = *Homo sapiens* GN = TRIP12 PE = 1 SV = 1
165. >sp|Q14978|NOLC1_HUMAN Nucleolar and coiled-body phosphoprotein 1 OS = *Homo sapiens* GN = NOLC1 PE = 1 SV = 2
166. >sp|Q15056|IF4H_HUMAN Eukaryotic translation initiation factor 4H OS = *Homo sapiens* GN = EIF4H PE = 1 SV = 5
167. >sp|Q15181|IPYR_HUMAN Inorganic pyrophosphatase OS = *Homo sapiens* GN = PPA1 PE = 1 SV = 2
168. >sp|Q15233|NONO_HUMAN Non-POU domain-containing octamer-binding protein OS = *Homo sapiens* GN = NONO PE = 1 SV = 4
169. >sp|Q15365|PCBP1_HUMAN Poly(rC)-binding protein 1 OS = *Homo sapiens* GN = PCBP1 PE = 1 SV = 2
170. >sp|Q15428|SF3A2_HUMAN Splicing factor 3A subunit 2 OS = *Homo sapiens* GN = SF3A2 PE = 1 SV = 2
171. >sp|Q16658|FSCN1_HUMAN Fascin OS = *Homo sapiens* GN = FSCN1 PE = 1 SV = 3
172. >sp|Q5D862|FILA2_HUMAN Filaggrin-2 OS = *Homo sapiens* GN = FLG2 PE = 1 SV = 1
173. >sp|Q86YZ3|HORN_HUMAN Hornerin OS = *Homo sapiens* GN = HRNR PE = 1 SV = 2
174. >sp|Q8IYV9|IZUM1_HUMAN Izumo sperm-egg fusion protein 1 OS = *Homo sapiens* GN = IZUMO1 PE = 1 SV = 2
175. >sp|Q8N1N4|K2C78_HUMAN Keratin, type II cytoskeletal 78 OS = *Homo sapiens* GN = KRT78 PE = 1 SV = 2
176. >sp|Q8NAT2|TDRD5_HUMAN Tudor domain-containing protein 5 OS = *Homo sapiens* GN = TDRD5 PE = 1 SV = 3
177. >sp|Q8NEZ4|MLL3_HUMAN Histone-lysine N-methyltransferase MLL3 OS = *Homo sapiens* GN = MLL3 PE = 1 SV = 3
178. >sp|Q8TF72|SHRM3_HUMAN Protein Shroom3 OS = *Homo sapiens* GN = SHROOM3 PE = 1 SV = 2
179. >sp|Q92688|AN32B_HUMAN Acidic leucine-rich nuclear phosphoprotein 32 family member B OS = *Homo sapiens* GN = ANP32B PE = 1 SV = 1
180. >sp|Q92841|DDX17_HUMAN Probable ATP-dependent RNA helicase DDX17 OS = *Homo sapiens* GN = DDX17 PE = 1 SV = 1
181. >sp|Q96MK3|FA20A_HUMAN Protein FAM20A OS = *Homo sapiens* GN = FAM20A PE = 2 SV = 4
182. >sp|Q96PK6|RBM14_HUMAN RNA-binding protein 14 OS = *Homo sapiens* GN = RBM14 PE = 1 SV = 2
183. >sp|Q99623|PHB2_HUMAN Prohibitin-2 OS = *Homo sapiens* GN = PHB2 PE = 1 SV = 2
184. >sp|Q99832|TCPH_HUMAN T-complex protein 1 subunit eta OS = *Homo sapiens* GN = CCT7 PE = 1 SV = 2
185. >sp|Q99ZW2|CAS9_STRP1 CRISPR-associated endonuclease Cas9/Csn1 OS = *Streptococcus pyogenes* serotype M1 GN = cas9 PE = 1 SV = 1
186. >sp|Q9BWD1|THIC_HUMAN Acetyl-CoA acetyltransferase, cytosolic OS = *Homo sapiens* GN = ACAT2 PE = 1 SV = 2
187. >sp|Q9NQ75|CASS4_HUMAN Cas scaffolding protein family member 4 OS = *Homo sapiens* GN = CASS4 PE = 1 SV = 2
188. >sp|Q9NR30|DDX21_HUMAN Nucleolar RNA helicase 2 OS = *Homo sapiens* GN = DDX21 PE = 1 SV = 5
189. >sp|Q9NX58|LYAR_HUMAN Cell growth-regulating nucleolar protein OS = *Homo sapiens* GN = LYAR PE = 1 SV = 2
190. >sp|Q9NZI8|IF2B1_HUMAN Insulin-like growth factor 2 mRNA-binding protein 1 OS = *Homo sapiens* GN = IGF2BP1 PE = 1 SV = 2
191. >sp|Q9P0L0|VAPA_HUMAN Vesicle-associated membrane protein-associated protein A OS = *Homo sapiens* GN = VAPA PE = 1 SV = 3
192. >sp|Q9UBQ5|EIF3K_HUMAN Eukaryotic translation initiation factor 3 subunit K OS = *Homo sapiens* GN = EIF3K PE = 1 SV = 1
193. >sp|Q9UQ80|PA2G4_HUMAN Proliferation-associated protein 2G4 OS = *Homo sapiens* GN = PA2G4 PE = 1 SV = 3
194. >sp|Q9Y266|NUDC_HUMAN Nuclear migration protein nudC OS = *Homo sapiens* GN = NUDC PE = 1 SV = 1
195. >sp|Q9Y2W1|TR150_HUMAN Thyroid hormone receptor-associated protein 3 OS = *Homo sapiens* GN = THRAP3 PE = 1 SV = 2
196. >sp|Q9Y4G6|TLN2_HUMAN Talin-2 OS = *Homo sapiens* GN = TLN2 PE = 1 SV = 4
197. >tr|A2A2D0|A2A2D0_HUMAN Stathmin (Fragment) OS = *Homo sapiens* GN = STMN1 PE = 3 SV = 1
198. >tr|A2A3R6|A2A3R6_HUMAN 40S ribosomal protein S6 OS = *Homo sapiens* GN = RPS6 PE = 2 SV = 1
199. >tr|A2BF75|A2BF75_HUMAN ATP-binding cassette sub-family F (GCN20) member 1 OS = *Homo sapiens* GN = ABCF1 PE = 2 SV = 1
200. >tr|A2RUM7|A2RUM7_HUMAN Ribosomal protein L5 OS = *Homo sapiens* GN = RPL5 PE = 2 SV = 1
201. >tr|A3KPC7|A3KPC7_HUMAN Histone H2A OS = *Homo sapiens* GN = HIST1H2AH PE = 2 SV = 1
202. >tr|A3R0T8|A3R0T8_HUMAN Histone 1, H1e OS = *Homo sapiens* GN = HIST1H1E PE = 2 SV = 1
203. >tr|A4D0Z6|A4D0Z6_HUMAN Inosine-5'-monophosphate dehydrogenase OS = *Homo sapiens* GN = IMPDH1 PE = 3 SV = 1
204. >tr|A4D177|A4D177_HUMAN Chromobox homolog 3 (HP1 gamma homolog *Drosophila*) OS = *Homo sapiens* GN = CBX3 PE = 4 SV = 1
205. >tr|A4D1N4|A4D1N4_HUMAN Coiled-coil-helix-coiled-coil-helix domain containing 3 OS = *Homo sapiens* GN = CHCHD3 PE = 4 SV = 1
206. >tr|A4D1U3|A4D1U3_HUMAN Single-stranded DNA binding protein 1 OS = *Homo sapiens* GN = SSBP1 PE = 2 SV = 1
207. >tr|A5JHP3|A5JHP3_HUMAN Dermcidin isoform 2 OS = *Homo sapiens* GN = DCD PE = 2 SV = 1
208. >tr|A6NBZ8|A6NBZ8_HUMAN Uncharacterized protein OS = *Homo sapiens* GN = ALB PE = 4 SV = 2
209. >tr|A6NDY9|A6NDY9_HUMAN Filamin A OS = *Homo sapiens* GN = FLNA PE = 2 SV = 4
210. >tr|A6NE05|A6NE05_HUMAN Uncharacterized protein OS = *Homo sapiens* GN = RPL26 PE = 3 SV = 1
211. >tr|A6NE09|A6NE09_HUMAN Uncharacterized protein OS = *Homo sapiens* PE = 3 SV = 1
212. >tr|A6NE14|A6NE14_HUMAN Uncharacterized protein OS = *Homo sapiens* GN = CCT3 PE = 2 SV = 1
213. >tr|A6NEL0|A6NEL0_HUMAN Uncharacterized protein OS = *Homo sapiens* GN = HMGN1 PE = 4 SV = 1
214. >tr|A6NFX8|A6NFX8_HUMAN Uncharacterized protein OS = *Homo sapiens* GN = NUDT5 PE = 3 SV = 1
215. >tr|A6NGV1|A6NGV1_HUMAN Uncharacterized protein OS = *Homo sapiens* GN = SET PE = 2 SV = 2
216. >tr|A6NHK2|A6NHK2_HUMAN Uncharacterized protein OS = *Homo sapiens* GN = SNRPE PE = 4 SV = 1
217. >tr|A6NJA2|A6NJA2_HUMAN Ubiquitin carboxyl-terminal hydrolase OS = *Homo sapiens* GN = USP14 PE = 3 SV = 1

-continued

| | |
|---|---|
| 218. | >tr\|A6NKB1\|A6NKB1_HUMAN Uncharacterized protein OS = *Homo sapiens* GN = TTN PE = 4 SV = 4 |
| 219. | >tr\|A6NL76\|A6NL76_HUMAN Uncharacterized protein OS = *Homo sapiens* GN = ACTA1 PE = 3 SV = 2 |
| 220. | >tr\|A8K220\|A8K220_HUMAN Peptidyl-prolyl cis-trans isomerase OS = *Homo sapiens* GN = PPIA PE = 1 SV = 1 |
| 221. | >tr\|A8K3M3\|A8K3M3_HUMAN Protein tyrosine phosphatase, non-receptor type 1, isoform CRA_c OS = *Homo sapiens* GN = PTPN1 PE = 2 SV = 1 |
| 222. | >tr\|A8K3Z8\|A8K3Z8_HUMAN RAN, member RAS oncogene family, isoform CRA_b OS = *Homo sapiens* GN = RAN PE = 1 SV = 1 |
| 223. | >tr\|A8K4C8\|A8K4C8_HUMAN 60S ribosomal protein L13 OS = *Homo sapiens* GN = RPL13 PE = 2 SV = 1 |
| 224. | >tr\|A8K4I2\|A8K4I2_HUMAN Histone 1, H1c OS = *Homo sapiens* GN = HIST1H1C PE = 2 SV = 1 |
| 225. | >tr\|A8K517\|A8K517_HUMAN Ribosomal protein S23, isoform CRA_a OS = *Homo sapiens* GN = RPS23 PE = 2 SV = 1 |
| 226. | >tr\|A8K5I0\|A8K5I0_HUMAN Heat shock 70 kDa protein 1A OS = *Homo sapiens* GN = HSPA1A PE = 2 SV = 1 |
| 227. | >tr\|A8MUD9\|A8MUD9_HUMAN Uncharacterized protein OS = *Homo sapiens* GN = RPL7 PE = 3 SV = 1 |
| 228. | >tr\|A8MUS3\|A8MUS3_HUMAN Ribosomal protein L23a, isoform CRA_a OS = *Homo sapiens* GN = RPL23A PE = 3 SV = 1 |
| 229. | >tr\|A8MV89\|A8MV89_HUMAN Uncharacterized protein OS = *Homo sapiens* GN = SPECC1 PE = 4 SV = 1 |
| 230. | >tr\|A8MWD3\|A8MWD3_HUMAN Uncharacterized protein OS = *Homo sapiens* GN = EIF3D PE = 2 SV = 2 |
| 231. | >tr\|A8MX94\|A8MX94_HUMAN Uncharacterized protein OS = *Homo sapiens* GN = GSTP1 PE = 4 SV = 1 |
| 232. | >tr\|A8MXP9\|A8MXP9_HUMAN Uncharacterized protein OS = *Homo sapiens* GN = MATR3 PE = 4 SV = 1 |
| 233. | >tr\|A8MYV2\|A8MYV2_HUMAN LUC7-like (*S. cerevisiae*) OS = *Homo sapiens* GN = LUC7L PE = 4 SV = 1 |
| 234. | >tr\|A9C4C1\|A9C4C1_HUMAN Ribosomal protein S9 OS = *Homo sapiens* GN = RPS9 PE = 3 SV = 1 |
| 235. | >tr\|B0QYK0\|B0QYK0_HUMAN Ewing sarcoma breakpoint region 1 OS = *Homo sapiens* GN = EWSR1 PE = 4 SV = 1 |
| 236. | >tr\|B0V043\|B0V043_HUMAN Valyl-tRNA synthetase OS = *Homo sapiens* GN = VARS PE = 3 SV = 1 |
| 237. | >tr\|B0ZBD0\|B0ZBD0_HUMAN 40S ribosomal protein S19 OS = *Homo sapiens* GN = RPS19 PE = 2 SV = 1 |
| 238. | >tr\|B1AHC8\|B1AHC8_HUMAN X-ray repair complementing defective repair in Chinese hamster cells 6 (Ku autoantigen, 70 kDa) OS = *Homo sapiens* GN = XRCC6 PE = 2 SV = 1 |
| 239. | >tr\|B1AHD1\|B1AHD1_HUMAN NHP2 non-histone chromosome protein 2-like 1 (*S. cerevisiae*) OS = *Homo sapiens* GN = NHP2L1 PE = 4 SV = 1 |
| 240. | >tr\|B1ALW1\|B1ALW1_HUMAN Thioredoxin OS = *Homo sapiens* GN = TXN PE = 4 SV = 1 |
| 241. | >tr\|B1ALY5\|B1ALY5_HUMAN ROD1 regulator of differentiation 1 (*S. pombe*) OS = *Homo sapiens* GN = ROD1 PE = 2 SV = 1 |
| 242. | >tr\|B1ANK7\|B1ANK7_HUMAN Fumarate hydratase OS = *Homo sapiens* GN = FH PE = 2 SV = 1 |
| 243. | >tr\|B1ANR0\|B1ANR0_HUMAN Poly(A) binding protein, cytoplasmic 4 (Inducible form) OS = *Homo sapiens* GN = PABPC4 PE = 4 SV = 1 |
| 244. | >tr\|B1B0M1\|B1B0M1_HUMAN GRIP1 associated protein 1 OS = *Homo sapiens* GN = GRIPAP1 PE = 4 SV = 1 |
| 245. | >tr\|B2R491\|B2R491_HUMAN Ribosomal protein S4, X-linked, isoform CRA_c OS = *Homo sapiens* GN = RPS4X PE = 2 SV = 1 |
| 246. | >tr\|B2R4P8\|B2R4P8_HUMAN HCG2016482, isoform CRA_b OS = *Homo sapiens* GN = hCG_2016482 PE = 2 SV = 1 |
| 247. | >tr\|B2R4R0\|B2R4R0_HUMAN Histone H4 OS = *Homo sapiens* GN = HIST1H4J PE = 3 SV = 1 |
| 248. | >tr\|B2R4S9\|B2R4S9_HUMAN Histone H2B OS = *Homo sapiens* GN = HIST1H2BC PE = 2 SV = 1 |
| 249. | >tr\|B2R4W8\|B2R4W8_HUMAN HCG1994130, isoform CRA_a OS = *Homo sapiens* GN = hCG_1994130 PE = 2 SV = 1 |
| 250. | >tr\|B2R6F3\|B2R6F3_HUMAN Splicing factor arginine/serine-rich 3 OS = *Homo sapiens* GN = SFRS3 PE = 2 SV = 1 |
| 251. | >tr\|B2RDF2\|B2RDF2_HUMAN Pescadillo homolog 1 OS = *Homo sapiens* GN = PES1 PE = 2 SV = 1 |
| 252. | >tr\|B2RDW1\|B2RDW1_HUMAN Ribosomal protein S27a, isoform CRA_c OS = *Homo sapiens* GN = RPS27A PE = 2 SV = 1 |
| 253. | >tr\|B2REA7\|B2REA7_HUMAN Ribosomal protein L36a OS = *Homo sapiens* GN = RPL36A PE = 3 SV = 1 |
| 254. | >tr\|B2RP62\|B2RP62_HUMAN HCG2027369, isoform CRA_a OS = *Homo sapiens* GN = KIF21B PE = 2 SV = 1 |
| 255. | >tr\|B3KPZ8\|B3KPZ8_HUMAN cDNA FLJ32530 fis, clone SMINT2000185, highly similar to TRANSKETOLASE (EC 2.2.1.1) OS = *Homo sapiens* PE = 2 SV = 1 |
| 256. | >tr\|B3KQ59\|B3KQ59_HUMAN RuvB-like 2 (*E. coli*), isoform CRA_a OS = *Homo sapiens* GN = RUVBL2 PE = 2 SV = 1 |
| 257. | >tr\|B3KS98\|B3KS98_HUMAN Eukaryotic translation initiation factor 3, subunit 3 gamma, 40 kDa, isoform CRA_b OS = *Homo sapiens* GN = EIF3S3 PE = 2 SV = 1 |
| 258. | >tr\|B3KTE3\|B3KTE3_HUMAN cDNA FLJ38125 fis, clone D60ST2000127, moderately similar to RAS-RELATED PROTEIN RAB-8B OS = *Homo sapiens* PE = 4 SV = 1 |
| 259. | >tr\|B3KX15\|B3KX15_HUMAN cDNA FLJ44468 fis, clone UTERU2026025, moderately similar to SPLICING FACTOR, ARGININE/SERINE-RICH 2 OS = *Homo sapiens* PE = 2 SV = 1 |
| 260. | >tr\|B4DDB6\|B4DDB6_HUMAN Heterogeneous nuclear ribonucleoprotein A3, isoform CRA_a OS = *Homo sapiens* GN = HNRPA3 PE = 2 SV = 1 |
| 261. | >tr\|B4DEP9\|B4DEP9_HUMAN cDNA FLJ57954, highly similar to 60S ribosomal protein L28 OS = *Homo sapiens* PE = 2 SV = 1 |
| 262. | >tr\|B4DF70\|B4DF70_HUMAN cDNA FLJ60461, highly similar to Peroxiredoxin-2 (EC 1.11.1.15) OS = *Homo sapiens* PE = 2 SV = 1 |
| 263. | >tr\|B4DIW5\|B4DIW5_HUMAN cDNA FLJ55515, highly similar to Breast cancer anti-estrogen resistanceprotein 1 OS = *Homo sapiens* PE = 2 SV = 1 |
| 264. | >tr\|B4DJI4\|B4DJI4_HUMAN cDNA FLJ58065, highly similar to LIM and SH3 domain protein 1 OS = *Homo sapiens* PE = 2 SV = 1 |
| 265. | >tr\|B4DJP7\|B4DJP7_HUMAN cDNA FLJ51872, highly similar to Small nuclear ribonucleoprotein Sm D3 OS = *Homo sapiens* PE = 4 SV = 1 |
| 266. | >tr\|B4DL87\|B4DL87_HUMAN Uncharacterized protein OS = *Homo sapiens* GN = HSPB1 PE = 2 SV = 1 |
| 267. | >tr\|B4DLP4\|B4DLP4_HUMAN Ribosomal protein L15 OS = *Homo sapiens* PE = 2 SV = 1 |
| 268. | >tr\|B4DR70\|B4DR70_HUMAN cDNA FLJ58049, highly similar to RNA-binding protein FUS OS = *Homo sapiens* PE = 2 SV = 1 |
| 269. | >tr\|B4DT31\|B4DT31_HUMAN Uncharacterized protein OS = *Homo sapiens* GN = FUBP1 PE = 2 SV = 1 |
| 270. | >tr\|B4DTG2\|B4DTG2_HUMAN cDNA FLJ56389, highly similar to Elongation factor 1-gamma OS = *Homo sapiens* PE = 2 SV = 1 |
| 271. | >tr\|B4DUQ1\|B4DUQ1_HUMAN cDNA FLJ54552, highly similar to Heterogeneous nuclear ribonucleoprotein K OS = *Homo sapiens* PE = 2 SV = 1 |
| 272. | >tr\|B4DW28\|B4DW28_HUMAN cDNA FLJ58953, highly similar to 40S ribosomal protein S20 OS = *Homo sapiens* PE = 2 SV = 1 |
| 273. | >tr\|B4DYD8\|B4DYD8_HUMAN cDNA FLJ52362, highly similar to T-complex protein 1 subunit epsilon OS = *Homo sapiens* PE = 2 SV = 1 |
| 274. | >tr\|B4E335\|B4E335_HUMAN cDNA FLJ52842, highly similar to Actin, cytoplasmic 1 OS = *Homo sapiens* PE = 2 SV = 1 |
| 275. | >tr\|B5MCP9\|B5MCP9_HUMAN Uncharacterized protein OS = *Homo sapiens* GN = RPS7 PE = 4 SV = 1 |
| 276. | >tr\|B7Z4C8\|B7Z4C8_HUMAN Uncharacterized protein OS = *Homo sapiens* GN = RPL31 PE = 2 SV = 1 |
| 277. | >tr\|B8ZZL8\|B8ZZL8_HUMAN Heat shock 10 kDa protein 1 (Chaperonin 10), isoform CRA_b OS = *Homo sapiens* GN = HSPE1 PE = 3 SV = 1 |
| 278. | >tr\|C9J296\|C9J296_HUMAN Uncharacterized protein OS = *Homo sapiens* GN = LAMB1 PE = 4 SV = 1 |
| 279. | >tr\|C9J4C3\|C9J4C3_HUMAN DNA topoisomerase 2 OS = *Homo sapiens* GN = TOP2A PE = 3 SV = 1 |
| 280. | >tr\|C9J673\|C9J673_HUMAN Uncharacterized protein OS = *Homo sapiens* GN = XPO1 PE = 4 SV = 1 |
| 281. | >tr\|C9J7T6\|C9J7T6_HUMAN Uncharacterized protein OS = *Homo sapiens* GN = RPL10 PE = 4 SV = 1 |
| 282. | >tr\|C9JBL2\|C9JBL2_HUMAN Uncharacterized protein OS = *Homo sapiens* GN = RPL32 PE = 4 SV = 1 |
| 283. | >tr\|C9JGT8\|C9JGT8_HUMAN Uncharacterized protein OS = *Homo sapiens* GN = AP2M1 PE = 4 SV = 1 |
| 284. | >tr\|C9JHR8\|C9JHR8_HUMAN Uncharacterized protein OS = *Homo sapiens* GN = CD163 PE = 4 SV = 1 |

-continued

| | |
|---|---|
| 285. | >tr\|C9JI87\|C9JI87_HUMAN Uncharacterized protein OS = *Homo sapiens* GN = VDAC1 PE = 4 SV = 1 |
| 286. | >tr\|C9JV77\|C9JV77_HUMAN Uncharacterized protein OS = *Homo sapiens* GN = AHSG PE = 4 SV = 1 |
| 287. | >tr\|C9JXG8\|C9JXG8_HUMAN Uncharacterized protein OS = *Homo sapiens* GN = RANBP1 PE = 4 SV = 2 |
| 288. | >tr\|D0PNI1\|D0PNI1_HUMAN Tyrosine 3-monooxygenase/tryptophan 5-monooxygenase activation protein zeta polypeptide OS = *Homo sapiens* GN = YWHAZ PE = 3 SV = 1 |
| 289. | >tr\|D1MGQ2\|D1MGQ2_HUMAN Alpha-2 globin chain OS = *Homo sapiens* GN = HBA2 PE = 3 SV = 1 |
| 290. | >tr\|D6R9B9\|D6R9B9_HUMAN Uncharacterized protein OS = *Homo sapiens* GN = FRYL PE = 4 SV = 1 |
| 291. | >tr\|D6R9K7\|D6R9K7_HUMAN Uncharacterized protein OS = *Homo sapiens* GN = RBM4 PE = 4 SV = 1 |
| 292. | >tr\|D6R9P3\|D6R9P3_HUMAN Uncharacterized protein OS = *Homo sapiens* GN = HNRNPAB PE = 4 SV = 1 |
| 293. | >tr\|D6RAC2\|D6RAC2_HUMAN Uncharacterized protein OS = *Homo sapiens* GN = GNB2L1 PE = 4 SV = 1 |
| 294. | >tr\|D6RAQ3\|D6RAQ3_HUMAN Uncharacterized protein OS = *Homo sapiens* GN = LMNA PE = 3 SV = 1 |
| 295. | >tr\|D6RAT0\|D6RAT0_HUMAN Uncharacterized protein OS = *Homo sapiens* GN = RPS3A PE = 3 SV = 1 |
| 296. | >tr\|D6RDG3\|D6RDG3_HUMAN Uncharacterized protein OS = *Homo sapiens* GN = BTF3 PE = 4 SV = 1 |
| 297. | >tr\|E5RJR5\|E5RJR5_HUMAN Uncharacterized protein OS = *Homo sapiens* GN = SKP1 PE = 4 SV = 1 |
| 298. | >tr\|E7DVW5\|E7DVW5_HUMAN Fatty acid binding protein 5 (Psoriasis-associated) OS = *Homo sapiens* GN = FABP5 PE = 3 SV = 1 |
| 299. | >tr\|E7EME9\|E7EME9_HUMAN Uncharacterized protein OS = *Homo sapiens* GN = EIF3B PE = 3 SV = 1 |
| 300. | >tr\|E7EMI4\|E7EMI4_HUMAN Uncharacterized protein OS = *Homo sapiens* GN = SART3 PE = 4 SV = 1 |
| 301. | >tr\|E7EMN0\|E7EMN0_HUMAN Uncharacterized protein OS = *Homo sapiens* GN = EPRS PE = 3 SV = 1 |
| 302. | >tr\|E7EMU2\|E7EMU2_HUMAN Uncharacterized protein OS = *Homo sapiens* GN = HMGA1 PE = 4 SV = 1 |
| 303. | >tr\|E7ENK9\|E7ENK9_HUMAN Uncharacterized protein OS = *Homo sapiens* GN = CSE1L PE = 4 SV = 1 |
| 304. | >tr\|E7ENY9\|E7ENY9_HUMAN Adenylyl cyclase-associated protein OS = *Homo sapiens* GN = CAP1 PE = 3 SV = 2 |
| 305. | >tr\|E7EP12\|E7EP12_HUMAN Uncharacterized protein OS = *Homo sapiens* GN = TTLL5 PE = 4 SV = 2 |
| 306. | >tr\|E7EP96\|E7EP96_HUMAN Uncharacterized protein OS = *Homo sapiens* GN = KHSRP PE = 4 SV = 1 |
| 307. | >tr\|E7EPB3\|E7EPB3_HUMAN Uncharacterized protein OS = *Homo sapiens* GN = RPL14 PE = 4 SV = 1 |
| 308. | >tr\|E7EQD1\|E7EQD1_HUMAN Uncharacterized protein OS = *Homo sapiens* GN = TRA2B PE = 4 SV = 1 |
| 309. | >tr\|E7EQR4\|E7EQR4_HUMAN Uncharacterized protein OS = *Homo sapiens* GN = EZR PE = 4 SV = 2 |
| 310. | >tr\|E7EQV3\|E7EQV3_HUMAN Uncharacterized protein OS = *Homo sapiens* GN = PABPC1 PE = 4 SV = 1 |
| 311. | >tr\|E7EQZ3\|E7EQZ3_HUMAN Uncharacterized protein OS = *Homo sapiens* GN = GSPT1 PE = 4 SV = 1 |
| 312. | >tr\|E7ERE4\|E7ERE4_HUMAN Uncharacterized protein OS = *Homo sapiens* GN = HNRNPR PE = 4 SV = 1 |
| 313. | >tr\|E7ERN5\|E7ERN5_HUMAN Uncharacterized protein OS = *Homo sapiens* GN = SLCO2B1 PE = 4 SV = 1 |
| 314. | >tr\|E7ESM6\|E7ESM6_HUMAN Uncharacterized protein OS = *Homo sapiens* GN = SND1 PE = 4 SV = 2 |
| 315. | >tr\|E7ETA0\|E7ETA0_HUMAN Uncharacterized protein OS = *Homo sapiens* GN = YBX1 PE = 4 SV = 1 |
| 316. | >tr\|E7ETK8\|E7ETK8_HUMAN Uncharacterized protein OS = *Homo sapiens* GN = AARS PE = 3 SV = 1 |
| 317. | >tr\|E7ETL9\|E7ETL9_HUMAN Uncharacterized protein OS = *Homo sapiens* GN = DDX5 PE = 3 SV = 1 |
| 318. | >tr\|E7ETM1\|E7ETM1_HUMAN Uncharacterized protein OS = *Homo sapiens* GN = KNDC1 PE = 4 SV = 1 |
| 319. | >tr\|E7ETR0\|E7ETR0_HUMAN Uncharacterized protein OS = *Homo sapiens* GN = RUVBL1 PE = 4 SV = 1 |
| 320. | >tr\|E7EUT4\|E7EUT4_HUMAN Glyceraldehyde-3-phosphate dehydrogenase OS = *Homo sapiens* GN = GAPDH PE = 3 SV = 1 |
| 321. | >tr\|E7EUY0\|E7EUY0_HUMAN Uncharacterized protein OS = *Homo sapiens* GN = PRKDC PE = 4 SV = 1 |
| 322. | >tr\|E7EW92\|E7EW92_HUMAN Ribosomal protein L18 OS = *Homo sapiens* GN = RPL18 PE = 3 SV = 2 |
| 323. | >tr\|E7EWF1\|E7EWF1_HUMAN Uncharacterized protein OS = *Homo sapiens* GN = RPL4 PE = 4 SV = 1 |
| 324. | >tr\|E9KL30\|E9KL30_HUMAN Proteasome subunit beta type OS = *Homo sapiens* PE = 2 SV = 1 |
| 325. | >tr\|E9PAU2\|E9PAU2_HUMAN Uncharacterized protein OS = *Homo sapiens* GN = RAVER1 PE = 4 SV = 1 |
| 326. | >tr\|E9PBS1\|E9PBS1_HUMAN Uncharacterized protein OS = *Homo sapiens* GN = PAICS PE = 4 SV = 1 |
| 327. | >tr\|E9PCY7\|E9PCY7_HUMAN Uncharacterized protein OS = *Homo sapiens* GN = HNRNPH1 PE = 4 SV = 1 |
| 328. | >tr\|E9PDG5\|E9PDG5_HUMAN Uncharacterized protein OS = *Homo sapiens* GN = LARP4 PE = 4 SV = 1 |
| 329. | >tr\|E9PDU1\|E9PDU1_HUMAN Uncharacterized protein OS = *Homo sapiens* GN = KARS PE = 3 SV = 2 |
| 330. | >tr\|E9PE52\|E9PE52_HUMAN Uncharacterized protein OS = *Homo sapiens* GN = RSL1D1 PE = 4 SV = 1 |
| 331. | >tr\|E9PEK6\|E9PEK6_HUMAN Uncharacterized protein OS = *Homo sapiens* GN = CAPRIN1 PE = 4 SV = 2 |
| 332. | >tr\|E9PFS0\|E9PFS0_HUMAN Uncharacterized protein OS = *Homo sapiens* GN = PRPF40A PE = 4 SV = 1 |
| 333. | >tr\|E9PFU1\|E9PFU1_HUMAN Uncharacterized protein OS = *Homo sapiens* GN = PDCD6IP PE = 4 SV = 1 |
| 334. | >tr\|E9PH51\|E9PH51_HUMAN L-lactate dehydrogenase OS = *Homo sapiens* GN = LDHA PE = 3 SV = 2 |
| 335. | >tr\|E9PIZ1\|E9PIZ1_HUMAN Uncharacterized protein OS = *Homo sapiens* GN = EEF1D PE = 4 SV = 1 |
| 336. | >tr\|E9PIZ3\|E9PIZ3_HUMAN Uncharacterized protein OS = *Homo sapiens* GN = RPL8 PE = 4 SV = 1 |
| 337. | >tr\|E9PJ04\|E9PJ04_HUMAN Uncharacterized protein OS = *Homo sapiens* GN = SF3B2 PE = 4 SV = 1 |
| 338. | >tr\|E9PJ81\|E9PJ81_HUMAN Uncharacterized protein OS = *Homo sapiens* GN = UBXN1 PE = 4 SV = 1 |
| 339. | >tr\|E9PK25\|E9PK25_HUMAN Uncharacterized protein OS = *Homo sapiens* GN = CFL1 PE = 4 SV = 1 |
| 340. | >tr\|E9PKE3\|E9PKE3_HUMAN Uncharacterized protein OS = *Homo sapiens* GN = HSPA8 PE = 3 SV = 1 |
| 341. | >tr\|E9PP73\|E9PP73_HUMAN Uncharacterized protein OS = *Homo sapiens* GN = COPB1 PE = 4 SV = 1 |
| 342. | >tr\|E9PRH9\|E9PRH9_HUMAN Uncharacterized protein OS = *Homo sapiens* GN = NASP PE = 4 SV = 1 |
| 343. | >tr\|F2Z3A5\|F2Z3A5_HUMAN Uncharacterized protein OS = *Homo sapiens* GN = RPL3 PE = 4 SV = 1 |
| 344. | >tr\|F2Z3D0\|F2Z3D0_HUMAN Uncharacterized protein OS = *Homo sapiens* GN = SUMO2 PE = 4 SV = 1 |
| 345. | >tr\|F5GY56\|F5GY56_HUMAN Uncharacterized protein OS = *Homo sapiens* GN = PRPF19 PE = 4 SV = 1 |
| 346. | >tr\|F5GZ16\|F5GZ16_HUMAN Uncharacterized protein OS = *Homo sapiens* GN = PSMD2 PE = 4 SV = 1 |
| 347. | >tr\|F5H0F5\|F5H0F5_HUMAN Uncharacterized protein OS = *Homo sapiens* GN = ZC3H15 PE = 4 SV = 1 |
| 348. | >tr\|F5H0T1\|F5H0T1_HUMAN Uncharacterized protein OS = *Homo sapiens* GN = STIP1 PE = 4 SV = 1 |
| 349. | >tr\|F5H119\|F5H119_HUMAN Uncharacterized protein OS = *Homo sapiens* GN = PDIA3 PE = 4 SV = 1 |
| 350. | >tr\|F5H1C6\|F5H1C6_HUMAN Uncharacterized protein OS = *Homo sapiens* GN = FERMT3 PE = 4 SV = 1 |
| 351. | >tr\|F5H5D3\|F5H5D3_HUMAN Uncharacterized protein OS = *Homo sapiens* GN = TUBA1C PE = 4 SV = 1 |
| 352. | >tr\|F5H5W3\|F5H5W3_HUMAN Uncharacterized protein OS = *Homo sapiens* GN = CCT4 PE = 4 SV = 1 |
| 353. | >tr\|F5H656\|F5H656_HUMAN Uncharacterized protein OS = *Homo sapiens* GN = PSPC1 PE = 4 SV = 1 |
| 354. | >tr\|F5H6K0\|F5H6K0_HUMAN Uncharacterized protein OS = *Homo sapiens* GN = DHX15 PE = 4 SV = 1 |
| 355. | >tr\|F5H737\|F5H737_HUMAN Uncharacterized protein OS = *Homo sapiens* GN = AHCY PE = 4 SV = 1 |
| 356. | >tr\|Q5TEC6\|Q5TEC6_HUMAN Histone H3 OS = *Homo sapiens* GN = HIST2H3PS2 PE = 3 SV = 1 |
| 357. | >tr\|Q5VU21\|Q5VU21_HUMAN PAI-1 mRNA-binding protein variant OS = *Homo sapiens* GN = SERBP1 PE = 2 SV = 1 |
| 358. | >tr\|Q86X94\|Q86X94_HUMAN TAF15 RNA polymerase II, TATA box binding protein (TBP)-associated factor, 68 kDa OS = *Homo sapiens* GN = TAF15 PE = 2 SV = 2 |
| 359. | 10 kDa heat shock protein, mitochondrial (Heat shock 10 kDa protein 1 (Chaperonin 10), isoform CRA_b) |
| 360. | 10 kDa heat shock protein, mitochondrial (Hsp10) (10 kDa chaperonin) (Chaperonin 10) (CPN10) (Early-pregnancy factor) (EPF) |

-continued 361. 14-3-3 protein beta/alpha (Protein 1054) (Protein kinase C inhibitor protein 1) (KCIP-1) [Cleaved into: 14-3-3 protein beta/alpha, N-terminally processed]
362. 14-3-3 protein epsilon (14-3-3E)
363. 14-3-3 protein eta (Protein AS1)
364. 14-3-3 protein gamma (Protein kinase C inhibitor protein 1) (KCIP-1) [Cleaved into: 14-3-3 protein gamma, N-terminally processed]
365. 14-3-3 protein sigma (Epithelial cell marker protein 1) (Stratifin)
366. 14-3-3 protein theta (14-3-3 protein T-cell) (14-3-3 protein tau) (Protein HS1)
367. 14-3-3 protein theta (Fragment)
368. 2-oxoglutarate dehydrogenase, mitochondrial (Fragment)
369. 2',5'-phosphodiesterase 12 (2'-PDE) (2-PDE) (EC 3.1.4.-) (Mitochondrial deadenylase) (EC 3.1.13.4)
370. 26S protease regulatory subunit 10B (26S proteasome AAA-ATPase subunit RPT4) (Proteasome 26S subunit ATPase 6) (Proteasome subunit p42)
371. 26S protease regulatory subunit 4 (P26s4) (26S proteasome AAA-ATPase subunit RPT2) (Proteasome 26S subunit ATPase 1)
372. 26S protease regulatory subunit 6A
373. 26S protease regulatory subunit 7 (26S proteasome AAA-ATPase subunit RPT1) (Proteasome 26S subunit ATPase 2) (Protein MSS1)
374. 26S protease regulatory subunit 8 (26S proteasome AAA-ATPase subunit RPT6) (Proteasome 26S subunit ATPase 5) (Proteasome subunit p45) (Thyroid hormone receptor-interacting protein 1) (TRIP1) (p45/SUG)
375. 26S proteasome non-ATPase regulatory subunit 1 (26S proteasome regulatory subunit RPN2) (26S proteasome regulatory subunit S1) (26S proteasome subunit p112)
376. 26S proteasome non-ATPase regulatory subunit 11 (26S proteasome regulatory subunit RPN6) (26S proteasome regulatory subunit S9) (26S proteasome regulatory subunit p44.5)
377. 26S proteasome non-ATPase regulatory subunit 13 (26S proteasome regulatory subunit RPN9) (26S proteasome regulatory subunit S11) (26S proteasome regulatory subunit p40.5)
378. 26S proteasome non-ATPase regulatory subunit 14 (EC 3.4.19.-) (26S proteasome regulatory subunit RPN11) (26S proteasome-associated PAD1 homolog 1)
379. 26S proteasome non-ATPase regulatory subunit 3
380. 26S proteasome non-ATPase regulatory subunit 4 (26S proteasome regulatory subunit RPN10) (26S proteasome regulatory subunit S5A) (Antisecretory factor 1) (AF) (ASF) (Multiubiquitin chain-binding protein)
381. 26S proteasome non-ATPase regulatory subunit 7 (26S proteasome regulatory subunit RPN8) (26S proteasome regulatory subunit S12) (Mov34 protein homolog) (Proteasome subunit p40)
382. 26S proteasome non-ATPase regulatory subunit 8 (26S proteasome regulatory subunit RPN12) (26S proteasome regulatory subunit S14) (p31)
383. 28 kDa heat- and acid-stable phosphoprotein (PDGF-associated protein) (PAP) (PDGFA-associated protein 1) (PAP1)
384. 28S ribosomal protein S11, mitochondrial (MRP-S11) (S11mt) (Mitochondrial small ribosomal subunit protein uS11m) (Cervical cancer proto-oncogene 2 protein) (HCC-2)
385. 28S ribosomal protein S16, mitochondrial
386. 28S ribosomal protein S17, mitochondrial (Fragment)
387. 28S ribosomal protein S22, mitochondrial (MRP-S22) (S22mt) (Mitochondrial small ribosomal subunit protein mS22)
388. 28S ribosomal protein S36, mitochondrial (MRP-S36) (S36mt)
389. 28S ribosomal protein S5, mitochondrial (MRP-S5) (S5mt) (Mitochondrial small ribosomal subunit protein uS5m)
390. 28S ribosomal protein S7, mitochondrial (MRP-S7) (S7mt) (Mitochondrial small ribosomal subunit protein uS7m) (bMRP-27a) (bMRP27a)
391. 28S ribosomal protein S9, mitochondrial (MRP-S9) (S9mt) (Mitochondrial small ribosomal subunit protein uS9m)
392. 3'(2'),5'-bisphosphate nucleotidase 1
393. 39S ribosomal protein L12, mitochondrial (L12mt) (MRP-L12) (5c5-2) (Mitochondrial large ribosomal subunit protein bL12m)
394. 39S ribosomal protein L14, mitochondrial (L14mt) (MRP-L14) (39S ribosomal protein L32, mitochondrial) (L32mt) (MRP-L32) (Mitochondrial large ribosomal subunit protein uL14m)
395. 39S ribosomal protein L15, mitochondrial (L15mt) (MRP-L15) (Mitochondrial large ribosomal subunit protein uL15m)
396. 39S ribosomal protein L17, mitochondrial (Fragment)
397. 39S ribosomal protein L19, mitochondrial (L19mt) (MRP-L19) (39S ribosomal protein L15, mitochondrial) (L15mt) (MRP-L15) (Mitochondrial large ribosomal subunit protein bL19m)
398. 39S ribosomal protein L27, mitochondrial (L27mt) (MRP-L27) (Mitochondrial large ribosomal subunit protein bL27m)
399. 39S ribosomal protein L35, mitochondrial
400. 39S ribosomal protein L39, mitochondrial (Fragment)
401. 39S ribosomal protein L43, mitochondrial
402. 39S ribosomal protein L45, mitochondrial (L45mt) (MRP-L45) (Mitochondrial large ribosomal subunit protein mL45)
403. 40S ribosomal protein S10 (Small ribosomal subunit protein eS10)
404. 40S ribosomal protein S11 (Small ribosomal subunit protein uS17)
405. 40S ribosomal protein S12 (Small ribosomal subunit protein eS12)
406. 40S ribosomal protein S13 (Small ribosomal subunit protein uS15)
407. 40S ribosomal protein S14 (Small ribosomal subunit protein uS11)
408. 40S ribosomal protein S15 (RIG protein) (Small ribosomal subunit protein uS19)
409. 40S ribosomal protein S16 (Small ribosomal subunit protein uS9)
410. 40S ribosomal protein S17 (Small ribosomal subunit protein eS17)
411. 40S ribosomal protein S18 (Ke-3) (Ke3) (Small ribosomal subunit protein uS13)
412. 40S ribosomal protein S19 (Ribosomal protein S19, isoform CRA_a) (cDNA, FLJ92047, *Homo sapiens* ribosomal protein S19 (RPS19), mRNA)
413. 40S ribosomal protein S2 (40S ribosomal protein S4) (Protein LLRep3) (Small ribosomal subunit protein uS5)
414. 40S ribosomal protein S21 (Small ribosomal subunit protein eS21)
415. 40S ribosomal protein S25 (Small ribosomal subunit protein eS25)
416. 40S ribosomal protein S26 (Small ribosomal subunit protein eS26)
417. 40S ribosomal protein S27
418. 40S ribosomal protein S27 (Metallopan-stimulin 1) (MPS-1) (Small ribosomal subunit protein eS27)
419. 40S ribosomal protein S27-like (Small ribosomal subunit protein eS27-like)
420. 40S ribosomal protein S29 (Small ribosomal subunit protein uS14)
421. 40S ribosomal protein S3 (EC 4.2.99.18) (Small ribosomal subunit protein uS3)
422. 40S ribosomal protein S30

-continued

| | |
|---|---|
| 423. | 40S ribosomal protein S3a (Small ribosomal subunit protein eS1) (v-fos transformation effector protein) (Fte-1) |
| 424. | 40S ribosomal protein S4 |
| 425. | 40S ribosomal protein S5 (Small ribosomal subunit protein uS7) [Cleaved into: 40S ribosomal protein S5, N-terminally processed] |
| 426. | 40S ribosomal protein S6 |
| 427. | 40S ribosomal protein S7 (Small ribosomal subunit protein eS7) |
| 428. | 40S ribosomal protein S8 (Small ribosomal subunit protein eS8) |
| 429. | 40S ribosomal protein SA (Fragment) |
| 430. | 5'-3' exoribonuclease 2 (EC 3.1.13.-) (DHM1-like protein) (DHP protein) |
| 431. | 55 kDa erythrocyte membrane protein (Fragment) |
| 432. | 55 kDa erythrocyte membrane protein (p55) (Membrane protein, palmitoylated 1) |
| 433. | 60 kDa heat shock protein, mitochondrial (EC 3.6.4.9) (60 kDa chaperonin) (Chaperonin 60) (CPN60) (Heat shock protein 60) (HSP-60) (Hsp60) (HuCHA60) (Mitochondrial matrix protein P1) (P60 lymphocyte protein) |
| 434. | 60 kDa SS-A/Ro ribonucleoprotein (60 kDa Ro protein) (60 kDa ribonucleoprotein Ro) (RoRNP) (Ro 60 kDa autoantigen) (Sjoegren syndrome antigen A2) (Sjoegren syndrome type A antigen) (SS-A) (TROVE domain family member 2) |
| 435. | 60S acidic ribosomal protein P0 (60S ribosomal protein L10E) (Large ribosomal subunit protein uL10) |
| 436. | 60S acidic ribosomal protein P2 (Large ribosomal subunit protein P2) (Renal carcinoma antigen NY-REN-44) |
| 437. | 60S ribosomal export protein NMD3 (Fragment) |
| 438. | 60S ribosomal protein L10 (Laminin receptor homolog) (Large ribosomal subunit protein uL16) (Protein QM) (Tumor suppressor QM) |
| 439. | 60S ribosomal protein L10a (CSA-19) (Large ribosomal subunit protein uL1) (Neural precursor cell expressed developmentally down-regulated protein 6) (NEDD-6) |
| 440. | 60S ribosomal protein L11 (CLL-associated antigen KW-12) (Large ribosomal subunit protein uL5) |
| 441. | 60S ribosomal protein L12 (Large ribosomal subunit protein uL11) |
| 442. | 60S ribosomal protein L13 |
| 443. | 60S ribosomal protein L13a (23 kDa highly basic protein) (Large ribosomal subunit protein uL13) |
| 444. | 60S ribosomal protein L14 |
| 445. | 60S ribosomal protein L14 (CAG-ISL 7) (Large ribosomal subunit protein eL14) |
| 446. | 60S ribosomal protein L15 (Large ribosomal subunit protein eL15) |
| 447. | 60S ribosomal protein L17 (60S ribosomal protein L23) (Large ribosomal subunit protein uL22) (PD-1) |
| 448. | 60S ribosomal protein L18 (Large ribosomal subunit protein eL18) |
| 449. | 60S ribosomal protein L18a (Large ribosomal subunit protein eL20) |
| 450. | 60S ribosomal protein L19 (Large ribosomal subunit protein eL19) |
| 451. | 60S ribosomal protein L21 (Large ribosomal subunit protein eL21) |
| 452. | 60S ribosomal protein L22 (EBER-associated protein) (EAP) (Epstein-Barr virus small RNA-associated protein) (Heparin-binding protein HBp15) (Large ribosomal subunit protein eL22) |
| 453. | 60S ribosomal protein L23 (60S ribosomal protein L17) (Large ribosomal subunit protein uL14) |
| 454. | 60S ribosomal protein L23a (Ribosomal protein L23a, isoform CRA_a) |
| 455. | 60S ribosomal protein L24 (60S ribosomal protein L30) (Large ribosomal subunit protein eL24) |
| 456. | 60S ribosomal protein L24 (Ribosomal protein L24, isoform CRA_e) |
| 457. | 60S ribosomal protein L26 (Large ribosomal subunit protein uL24) |
| 458. | 60S ribosomal protein L27 (Large ribosomal subunit protein eL27) |
| 459. | 60S ribosomal protein L27a |
| 460. | 60S ribosomal protein L27a (Large ribosomal subunit protein uL15) |
| 461. | 60S ribosomal protein L29 (Cell surface heparin-binding protein HIP) (Large ribosomal subunit protein eL29) |
| 462. | 60S ribosomal protein L3 (HIV-1 TAR RNA-binding protein B) (TARBP-B) (Large ribosomal subunit protein uL3) |
| 463. | 60S ribosomal protein L30 (Fragment) |
| 464. | 60S ribosomal protein L31 (cDNA FLJ57527, highly similar to 60S ribosomal protein L31) |
| 465. | 60S ribosomal protein L31 (Large ribosomal subunit protein eL31) |
| 466. | 60S ribosomal protein L34 (Large ribosomal subunit protein eL34) |
| 467. | 60S ribosomal protein L35 (Large ribosomal subunit protein uL29) |
| 468. | 60S ribosomal protein L35a (Cell growth-inhibiting gene 33 protein) (Large ribosomal subunit protein eL33) |
| 469. | 60S ribosomal protein L35a (Fragment) |
| 470. | 60S ribosomal protein L36 (Large ribosomal subunit protein eL36) |
| 471. | 60S ribosomal protein L36a (60S ribosomal protein L44) (Cell growth-inhibiting gene 15 protein) (Cell migration-inducing gene 6 protein) (Large ribosomal subunit protein eL42) |
| 472. | 60S ribosomal protein L37 (G1.16) (Large ribosomal subunit protein eL37) |
| 473. | 60S ribosomal protein L37a (Large ribosomal subunit protein eL43) |
| 474. | 60S ribosomal protein L37a (Ribosomal protein L37a, isoform CRA_c) |
| 475. | 60S ribosomal protein L38 (Large ribosomal subunit protein eL38) |
| 476. | 60S ribosomal protein L39 (Large ribosomal subunit protein eL39) |
| 477. | 60S ribosomal protein L4 (60S ribosomal protein L1) (Large ribosomal subunit protein uL4) |
| 478. | 60S ribosomal protein L6 (Large ribosomal subunit protein eL6) (Neoplasm-related protein C140) (Tax-responsive enhancer element-binding protein 107) (TaxREB107) |
| 479. | 60S ribosomal protein L7 (Large ribosomal subunit protein uL30) |
| 480. | 60S ribosomal protein L7-like 1 (Large ribosomal subunit protein uL30-like 1) |
| 481. | 60S ribosomal protein L7a (Large ribosomal subunit protein eL8) (PLA-X polypeptide) (Surfeit locus protein 3) |
| 482. | 60S ribosomal protein L8 (Large ribosomal subunit protein uL2) |
| 483. | 60S ribosomal protein L9 (Large ribosomal subunit protein uL6) |
| 484. | 78 kDa glucose-regulated protein (GRP-78) (Endoplasmic reticulum lumenal Ca(2+)-binding protein grp78) (Heat shock 70 kDa protein 5) (Immunoglobulin heavy chain-binding protein) (BiP) |
| 485. | AarF domain containing kinase 2 (AarF domain containing kinase 2, isoform CRA_a) |
| 486. | ABC50 protein (ATP-binding cassette, sub-family F (GCN20), member 1) (ATP-binding cassette, sub-family F (GCN20), member 1, isoform CRA_a) |
| 487. | Acetyl-CoA acetyltransferase, cytosolic (EC 2.3.1.9) (Acetyl-CoA transferase-like protein) (Cytosolic acetoacetyl-CoA thiolase) |
| 488. | Acetyl-CoA acetyltransferase, mitochondrial (EC 2.3.1.9) (Acetoacetyl-CoA thiolase) (T2) |
| 489. | Acetyl-Coenzyme A carboxylase alpha (HCG30204, isoform CRA_b) |
| 490. | Acetyltransferase component of pyruvate dehydrogenase complex (EC 2.3.1.12) |
| 491. | Acidic leucine-rich nuclear phosphoprotein 32 family member B (Acidic protein rich in leucines) (Putative HLA-DR-associated protein I-2) (PHAPI2) (Silver-stainable protein SSP29) |

-continued

| | |
|---|---|
| 492. | Acidic leucine-rich nuclear phosphoprotein 32 family member E (Fragment) |
| 493. | Aconitate hydratase, mitochondrial |
| 494. | Actin related protein 2/3 complex, subunit 1B, 41 kDa (Actin related protein 2/3 complex, subunit 1B, 41 kDa, isoform CRA_a) (cDNA, FLJ95695, Homo sapiens actin related protein 2/3 complex, subunit 1B, 41 kDa(ARPC1B), mRNA) |
| 495. | Actin-like protein 6A (53 kDa BRG1-associated factor A) (Actin-related protein Baf53a) (ArpNbeta) (BRG1-associated factor 53A) (BAF53A) (INO80 complex subunit K) |
| 496. | Actin-related protein 2 (Actin-like protein 2) |
| 497. | Actin-related protein 2/3 complex subunit 2 (Arp2/3 complex 34 kDa subunit) (p34-ARC) |
| 498. | Actin-related protein 2/3 complex subunit 3 (Arp2/3 complex 21 kDa subunit) (p21-ARC) |
| 499. | Actin-related protein 2/3 complex subunit 5 (Arp2/3 complex 16 kDa subunit) (p16-ARC) |
| 500. | Actin-related protein 3 (Actin-like protein 3) |
| 501. | Actin, alpha cardiac muscle 1 (Alpha-cardiac actin) |
| 502. | Actin, cytoplasmic 1 (Beta-actin) [Cleaved into: Actin, cytoplasmic 1, N-terminally processed] |
| 503. | Activated RNA polymerase II transcriptional coactivator p15 (Positive cofactor 4) (PC4) (SUB1 homolog) (p14) |
| 504. | Acyl-protein thioesterase 1 (Fragment) |
| 505. | Adenine phosphoribosyltransferase (APRT) (EC 2.4.2.7) |
| 506. | Adenosylhomocysteinase (AdoHcyase) (EC 3.3.1.1) (S-adenosyl-L-homocysteine hydrolase) |
| 507. | Adenylate kinase 2, mitochondrial (AK 2) (EC 2.7.4.3) (ATP-AMP transphosphorylase 2) (ATP:AMP phosphotransferase) (Adenylate monophosphate kinase) [Cleaved into: Adenylate kinase 2, mitochondrial, N-terminally processed] |
| 508. | Adenylosuccinate lyase (ADSL) (ASL) (EC 4.3.2.2) (Adenylosuccinase) (ASase) |
| 509. | Adenylosuccinate synthetase isozyme 2 (AMPSase 2) (AdSS 2) (EC 6.3.4.4) (Adenylosuccinate synthetase, acidic isozyme) (Adenylosuccinate synthetase, liver isozyme) (L-type adenylosuccinate synthetase) (IMP--aspartate ligase 2) |
| 510. | Adenylyl cyclase-associated protein 1 (CAP 1) |
| 511. | ADP-ribosylation factor 4 |
| 512. | ADP-ribosylation factor 5 (ADP-ribosylation factor 5, isoform CRA_a) (cDNA, FLJ92389, Homo sapiens ADP-ribosylation factor 5 (ARF5), mRNA) |
| 513. | ADP-sugar pyrophosphatase |
| 514. | ADP/ATP translocase 2 (ADP, ATP carrier protein 2) (ADP, ATP carrier protein, fibroblast isoform) (Adenine nucleotide translocator 2) (ANT 2) (Solute carrier family 25 member 5) [Cleaved into: ADP/ATP translocase 2, N-terminally processed] |
| 515. | AH receptor-interacting protein (AIP) (Aryl-hydrocarbon receptor-interacting protein) (HBV X-associated protein 2) (XAP-2) (Immunophilin homolog ARA9) |
| 516. | Alanine--tRNA ligase, cytoplasmic (EC 6.1.1.7) (Alanyl-tRNA synthetase) (AlaRS) (Renal carcinoma antigen NY-REN-42) |
| 517. | Alcohol dehydrogenase [NADP(+)] (EC 1.1.1.2) (Aldehyde reductase) (Aldo-keto reductase family 1 member A1) |
| 518. | Alcohol dehydrogenase class-3 (EC 1.1.1.1) (Alcohol dehydrogenase 5) (Alcohol dehydrogenase class chi chain) (Alcohol dehydrogenase class-III) (Glutathione-dependent formaldehyde dehydrogenase) (FALDH) (FDH) (GSH-FDH) (EC 1.1.1.-) (S-(hydroxymethyl)glutathione dehydrogenase) (EC 1.1.1.284) |
| 519. | Aldo-keto reductase family 1 member C1 (EC 1.1.1.-) (20-alpha-hydroxysteroid dehydrogenase) (20-alpha-HSD) (EC 1.1.1.149) (Chlordecone reductase homolog HAKRC) (Dihydrodiol dehydrogenase 1/2) (DD1/DD2) (High-affinity hepatic bile acid-binding protein) (HBAB) (Indanol dehydrogenase) (EC 1.1.1.112) (Trans-1,2-dihydrobenzene-1,2-diol dehydrogenase) (EC 1.3.1.20) |
| 520. | Aldo-keto reductase family 1 member C2 (cDNA FLJ52680, highly similar to Aldo-keto reductase family 1 member C2 (EC 1.-.-.-)) |
| 521. | Aldo-keto reductase family 1 member C3 (EC 1.-.-.-) (17-beta-hydroxysteroid dehydrogenase type 5) (17-beta-HSD 5) (3-alpha-HSD type II, brain) (3-alpha-hydroxysteroid dehydrogenase type 2) (3-alpha-HSD type 2) (EC 1.1.1.357) (Chlordecone reductase homolog HAKRb) (Dihydrodiol dehydrogenase 3) (DD-3) (DD3) (Dihydrodiol dehydrogenase type I) (HA1753) (Indanol dehydrogenase) (EC 1.1.1.112) (Prostaglandin F synthase) (PGFS) (EC 1.1.1.188) (Testosterone 17-beta-dehydrogenase 5) (EC 1.1.1.239) (EC 1.1.1.64) (Trans-1,2-dihydrobenzene-1,2-diol dehydrogenase) (EC 1.3.1.20) |
| 522. | Alpha-2 globin chain (Delta globin) (HCG1745306, isoform CRA_b) |
| 523. | Alpha-2-HS-glycoprotein |
| 524. | Alpha-2-macroglobulin (Alpha-2-M) (C3 and PZP-like alpha-2-macroglobulin domain-containing protein 5) |
| 525. | Alpha-actinin-4 (Non-muscle alpha-actinin 4) |
| 526. | Alpha-endosulfine |
| 527. | Alpha-enolase (EC 4.2.1.11) (2-phospho-D-glycerate hydro-lyase) (C-myc promoter-binding protein) (Enolase 1) (MBP-1) (MPB-1) (Non-neural enolase) (NNE) (Phosphopyruvate hydratase) (Plasminogen-binding protein) |
| 528. | Alpha-soluble NSF attachment protein (SNAP-alpha) (N-ethylmaleimide-sensitive factor attachment protein alpha) |
| 529. | Amidophosphoribosyltransferase (ATase) (EC 2.4.2.14) (Glutamine phosphoribosylpyrophosphate amidotransferase) |
| 530. | Aminoacyl tRNA synthase complex-interacting multifunctional protein 1 (Multisynthase complex auxiliary component p43) [Cleaved into: Endothelial monocyte-activating polypeptide 2 (EMAP-2) (Endothelial monocyte-activating polypeptide II) (EMAP-II) (Small inducible cytokine subfamily E member 1)] |
| 531. | Aminoacyl tRNA synthase complex-interacting multifunctional protein 2 |
| 532. | Aminoacyl tRNA synthase complex-interacting multifunctional protein 2 (Multisynthase complex auxiliary component p38) (Protein JTV-1) |
| 533. | Anamorsin (Cytokine-induced apoptosis inhibitor 1) (Fe—S cluster assembly protein DRE2 homolog) |
| 534. | Anaphase-promoting complex subunit 7 (APC7) (Cyclosome subunit 7) |
| 535. | Annexin A1 (Annexin I) (Annexin-1) (Calpactin II) (Calpactin-2) (Chromobindin-9) (Lipocortin I) (Phospholipase A2 inhibitory protein) (p35) |
| 536. | Annexin A2 (Annexin II) (Annexin-2) (Calpactin I heavy chain) (Calpactin-1 heavy chain) (Chromobindin-8) (Lipocortin II) (Placental anticoagulant protein IV) (PAP-IV) (Protein I) (p36) |
| 537. | Annexin A7 (Annexin VII) (Annexin-7) (Synexin) |
| 538. | AP-2 complex subunit alpha-1 (100 kDa coated vesicle protein A) (Adaptor protein complex AP-2 subunit alpha-1) (Adaptor-related protein complex 2 subunit alpha-1) (Alpha-adaptin A) (Alpha1-adaptin) (Clathrin assembly protein complex 2 alpha-A large chain) (Plasma membrane adaptor HA2/AP2 adaptin alpha A subunit) |
| 539. | AP-2 complex subunit beta (AP105B) (Adaptor protein complex AP-2 subunit beta) (Adaptor-related protein complex 2 subunit beta) (Beta-2-adaptin) (Beta-adaptin) (Clathrin assembly protein complex 2 beta large chain) (Plasma membrane adaptor HA2/AP2 adaptin beta subunit) |
| 540. | AP-2 complex subunit mu |
| 541. | AP-2 complex subunit mu (Fragment) |
| 542. | AP-3 complex subunit mu-1 (AP-3 adaptor complex mu3A subunit) (Adaptor-related protein complex 3 subunit mu-1) (Mu-adaptin 3A) (Mu3A-adaptin) |
| 543. | Apoptosis-inducing factor 1, mitochondrial (EC 1.1.1.-) (Programmed cell death protein 8) |
| 544. | Apoptotic chromatin condensation inducer in the nucleus |

-continued

545. Arachidonate 12-lipoxygenase, 12R-type (12R-LOX) (12R-lipoxygenase) (EC 1.13.11.-) (Epidermis-type lipoxygenase 12)
546. Arginase-1 (EC 3.5.3.1) (Liver-type arginase) (Type I arginase)
547. Arginine-tRNA ligase, cytoplasmic (EC 6.1.1.19) (Arginyl-tRNA synthetase) (ArgRS)
548. Asparagine--tRNA ligase, cytoplasmic (EC 6.1.1.22) (Asparaginyl-tRNA synthetase) (AsnRS)
549. Aspartate aminotransferase, cytoplasmic (cAspAT) (EC 2.6.1.1) (EC 2.6.1.3) (Cysteine aminotransferase, cytoplasmic) (Cysteine transaminase, cytoplasmic) (cCAT) (Glutamate oxaloacetate transaminase 1) (Transaminase A)
550. Aspartate--tRNA ligase, cytoplasmic (EC 6.1.1.12) (Aspartyl-tRNA synthetase) (AspRS) (Cell proliferation-inducing gene 40 protein)
551. Aspartyl aminopeptidase (Aspartyl aminopeptidase, isoform CRA_c)
552. ATP synthase F(0) complex subunit B1, mitochondrial (ATP synthase proton-transporting mitochondrial F(0) complex subunit B1) (ATP synthase subunit b) (ATPase subunit b)
553. ATP synthase subunit alpha, mitochondrial
554. ATP synthase subunit beta, mitochondrial (EC 3.6.3.14)
555. ATP synthase subunit d, mitochondrial
556. ATP synthase subunit d, mitochondrial (ATPase subunit d)
557. ATP synthase subunit delta, mitochondrial (F-ATPase delta subunit)
558. ATP synthase subunit e, mitochondrial (ATPase subunit e) [Cleaved into: ATP synthase subunit e, mitochondrial, N-terminally processed]
559. ATP synthase subunit gamma, mitochondrial (F-ATPase gamma subunit)
560. ATP synthase subunit O, mitochondrial (Oligomycin sensitivity conferral protein) (OSCP)
561. ATP-binding cassette sub-family E member 1
562. ATP-binding cassette sub-family E member 1 (2'-5'-oligoadenylate-binding protein) (HuHP68) (RNase L inhibitor) (Ribonuclease 4 inhibitor) (RNS4I)
563. ATP-binding cassette sub-family F member 2 (Fragment)
564. ATP-dependent 6-phosphofructokinase, platelet type (cDNA FLJ40373 fis, clone TESTI2035003, highly similar to 6-phosphofructokinase type C (EC 2.7.1.11))
565. ATP-dependent RNA helicase A (RHA) (EC 3.6.4.13) (DEAH box protein 9) (Leukophysin) (LKP) (Nuclear DNA helicase II) (NDH II)
566. ATP-dependent RNA helicase DDX1 (DEAD (Asp-Clu-Ala-Asp) box polypeptide 1, isoform CRA_d) (DEAD box polypeptide 1) (cDNA, FLJ94573, *Homo sapiens* DEAD (Asp-Glu-Ala-Asp) box polypeptide 1 (DDX1), mRNA)
567. ATP-dependent RNA helicase DDX18 (EC 3.6.4.13) (DEAD box protein 18) (Myc-regulated DEAD box protein) (MrDb)
568. ATP-dependent RNA helicase DDX24
569. ATP-dependent RNA helicase DDX39A (EC 3.6.4.13) (DEAD box protein 39) (Nuclear RNA helicase URH49)
570. ATP-dependent RNA helicase DDX3X (EC 3.6.4.13) (DEAD box protein 3, X-chromosomal) (DEAD box, X isoform) (Helicase-like protein 2) (HLP2)
571. ATP-dependent RNA helicase DDX54 (EC 3.6.4.13) (ATP-dependent RNA helicase DP97) (DEAD box RNA helicase 97 kDa) (DEAD box protein 54)
572. ATP-dependent RNA helicase DHX29 (EC 3.6.4.13) (DEAH box protein 29) (Nucleic acid helicase DDXx)
573. BAG family molecular chaperone regulator 2 (BAG-2) (Bcl-2-associated athanogene 2)
574. BAG family molecular chaperone regulator 3 (Fragment)
575. Barrier-to-autointegration factor (Breakpoint cluster region protein 1) [Cleaved into: Barrier-to-autointegration factor, N-terminally processed]
576. Basic leucine zipper and W2 domain-containing protein 2
577. Bcl-2-associated transcription factor 1 (Btf)
578. Bcl-2-associated transcription factor 1 (Fragment)
579. Beta-adrenergic receptor kinase 2 (Beta-ARK-2) (EC 2.7.11.15) (G-protein-coupled receptor kinase 3)
580. Beta-centractin (Actin-related protein 1B) (ARP1B)
581. Bifunctional coenzyme A synthase (CoA synthase) (NBP) (POV-2) [Includes: Phosphopantetheine adenylyltransferase (EC 2.7.7.3) (Dephospho-CoA pyrophosphorylase) (Pantetheine-phosphate adenylyltransferase) (PPAT); Dephospho-CoA kinase (DPCK) (EC 2.7.1.24) (Dephosphocoenzyme A kinase) (DPCOAK)]
582. Bifunctional glutamate/proline--tRNA ligase (Bifunctional aminoacyl-tRNA synthetase) (Cell proliferation-inducing gene 32 protein) (Glutamatyl-prolyl-tRNA synthetase) [Includes: Glutamate--tRNA ligase (EC 6.1.1.17) (Glutamyl-tRNA synthetase) (GluRS); Proline--tRNA ligase (EC 6.1.1.15) (Prolyl-tRNA synthetase)]
583. Bifunctional purine biosynthesis protein PURH [Cleaved into: Bifunctional purine biosynthesis protein PURH, N-terminally processed] [Includes: Phosphoribosylaminoimidazolecarboxamide formyltransferase (EC 2.1.2.3) (5-aminoimidazole-4-carboxamide ribonucleotide formyltransferase) (AICAR transformylase); IMP cyclohydrolase (EC 3.5.4.10) (ATIC) (IMP synthase) (Inosinicase)]
584. Biliverdin reductase A (BVR A) (EC 1.3.1.24) (Biliverdin-IX alpha-reductase)
585. BolA-like protein 2
586. BRO1 domain-containing protein BROX (BRO1 domain- and CAAX motif-containing protein)
587. Bystin
588. C-1-tetrahydrofolate synthase, cytoplasmic
589. C-Jun-amino-terminal kinase-interacting protein 4 (JIP-4) (JNK-interacting protein 4) (Cancer/testis antigen 89) (CT89) (Human lung cancer oncogene 6 protein) (HLC-6) (JNK-associated leucine-zipper protein) (JLP) (Mitogen-activated protein kinase 8-interacting protein 4) (Proliferation-inducing protein 6) (Protein highly expressed in testis) (PHET) (Sperm surface protein) (Sperm-associated antigen 9) (Sperm-specific protein) (Sunday driver 1)
590. C-terminal-binding protein 1 (Fragment)
591. C-type lysozyme (Lysozyme) (EC 3.2.1.17) (Lysozyme (Renal amyloidosis), isoform CRA_a) (Lysozyme F1) (cDNA, FLJ92040, *Homo sapiens* lysozyme (renal amyloidosis) (LYZ), mRNA
592. CAD protein [Includes: Glutamine-dependent carbamoyl-phosphate synthase (EC 6.3.5.5); Aspartate carbamoyltransferase (EC 2.1.3.2); Dihydroorotase (EC 3.5.2.3)]
593. Calcium homeostasis endoplasmic reticulum protein (ERPROT 213-21) (SR-related CTD-associated factor 6)
594. Calmodulin 1 (Phosphorylase kinase, delta), isoform CRA_a (Calmodulin 3 (Phosphorylase kinase, delta), isoform CRA_b) (Epididymis secretory protein Li 72) (cDNA FLJ61744, highly similar to Calmodulin)
595. Calpain small subunit 1 (CSS1) (Calcium-activated neutral proteinase small subunit) (CANP small subunit) (Calcium-dependent protease small subunit) (CDPS) (Calcium-dependent protease small subunit 1) (Calpain regulatory subunit)
596. Calpain-1 catalytic subunit (Fragment)
597. Calreticulin (CRP55) (Calregulin) (Endoplasmic reticulum resident protein 60) (ERp60) (HACBP) (grp60)
598. cAMP-specific 3',5'-cyclic phosphodiesterase 4D (EC 3.1.4.53) (DPDE3) (PDE43)
599. Cancer/testis antigen family 45 member A2 (Cancer/testis antigen 45-2) (Cancer/testis antigen 45A2)
600. Capping protein (Actin filament) muscle Z-line, beta, isoform CRA_a (F-actin-capping protein subunit beta)

-continued

| | |
|---|---|
| 601. | Caprin-1 (Cell cycle-associated protein 1) (Cytoplasmic activation- and proliferation-associated protein 1) (GPI-anchored membrane protein 1) (GPI-anchored protein p137) (GPI-p137) (p137GPI) (Membrane component chromosome 11 surface marker 1) (RNA granule protein 105) |
| 602. | Carboxymethylenebutenolidase homolog (EC 3.1.-.-) |
| 603. | Cas scaffolding protein family member 4 (HEF-like protein) (HEF1-EFS-p130Cas-like protein) (HEPL) |
| 604. | Caspase 14, apoptosis-related cysteine peptidase (Caspase-14) (cDNA, FLJ94644, Homo sapiens caspase 14, apoptosis-related cysteine protease(CASP14), mRNA) |
| 605. | Catalase (EC 1.11.1.6) |
| 606. | Catechol O-methyltransferase (EC 2.1.1.6) |
| 607. | Cathepsin D (EC 3.4.23.5) [Cleaved into: Cathepsin D light chain; Cathepsin D heavy chain] |
| 608. | CD2-associated protein (Adapter protein CMS) (Cas ligand with multiple SH3 domains) |
| 609. | cDNA FLJ46199 fis, clone TESTI4007965, highly similar to AP-1 complex subunit gamma-1 |
| 610. | cDNA FLJ46898 fis, clone UTERU3022168, highly similar to Protein FAM62A |
| 611. | cDNA FLJ52068, highly similar to Microtubule-associated protein RP/EB family member 1 |
| 612. | cDNA FLJ52123, highly similar to Platelet-activating factor acetylhydrolase IB alpha subunit |
| 613. | cDNA FLJ52148, highly similar to Apoptosis inhibitor 5 |
| 614. | cDNA FLJ52842, highly similar to Actin, cytoplasmic 1 |
| 615. | cDNA FLJ53160, highly similar to Zyxin |
| 616. | cDNA FLJ53425, highly similar to Far upstream element-binding protein 1 |
| 617. | cDNA FLJ53699, moderately similar to 4F2 cell-surface antigen heavy chain |
| 618. | cDNA FLJ54453, highly similar to Glutaminyl-tRNA synthetase (EC 6.1.1.18) |
| 619. | cDNA FLJ54552, highly similar to Heterogeneous nuclear ribonucleoprotein K |
| 620. | cDNA FLJ56153, highly similar to Homo sapiens transforming growth factor beta regulator 4 (TBRG4), transcript variant 1, mRNA |
| 621. | cDNA FLJ56531, highly similar to UV excision repair protein RAD23 homolog B |
| 622. | cDNA FLJ57893, highly similar to Parafibromin |
| 623. | cDNA FLJ58049, highly similar to RNA-binding protein FUS |
| 624. | cDNA FLJ58787, highly similar to Cleavage stimulation factor 64 kDa subunit |
| 625. | cDNA FLJ59430, highly similar to Protein disulfide-isomerase (EC 5.3.4.1) |
| 626. | cDNA FLJ59571, highly similar to Eukaryotic translation initiation factor 4gamma 2 |
| 627. | cDNA FLJ60058, highly similar to Myosin light chain 1, slow-twitch muscle A isoform |
| 628. | cDNA FLJ60165, highly similar to Translation initiation factor eIF-2B subunit delta |
| 629. | cDNA FLJ60461, highly similar to Peroxiredoxin-2 (EC 1.11.1.15) |
| 630. | cDNA FLJ60857, highly similar to Polymerase delta-interacting protein 3 |
| 631. | cDNA FLJ61021, highly similar to Far upstream element-binding protein 1 |
| 632. | cDNA, FLJ92557, highly similar to Homo sapiens thioredoxin reductase 1 (TXNRD1), mRNA |
| 633. | CDW11/WDR57 (WD repeat domain 57 (U5 snRNP specific), isoform CRA_a) (cDNA FLJ90035 fis, clone HEMBA1001878, highly similar to WD repeat protein 57) |
| 634. | CDW3/SMU1 (Smu-1 suppressor of mec-8 and unc-52 homolog (C. elegans), isoform CRA_a) |
| 635. | Cell cycle and apoptosis regulator protein 2 (Cell division cycle and apoptosis regulator protein 2) (DBIRD complex subunit KIAA1967) (Deleted in breast cancer gene 1 protein) (DBC-1) (DBC.1) (NET35) (p30 DBC) |
| 636. | Cell cycle and apoptosis regulator protein 2 (Fragment) |
| 637. | Cell growth-regulating nucleolar protein |
| 638. | Ceramide-1-phosphate transfer protein (CPTP) (Glycolipid transfer protein domain-containing protein 1) (GLTP domain-containing protein 1) |
| 639. | Chloride intracellular channel protein 1 (Chloride channel ABP) (Nuclear chloride ion channel 27) (NCC27) (Regulatory nuclear chloride ion channel protein) (hRNCC) |
| 640. | Chromatin target of PRMT1 protein |
| 641. | Chromatin target of PRMT1 protein (Friend of PRMT1 protein) (Small arginine- and glycine-rich protein) (SRAG) |
| 642. | Chromobox homolog 3 (HP1 gamma homolog Drosophila) (Chromobox homolog 3 (HP1 gamma homolog Drosophila), isoform CRA_a) (Coiled-coil domain containing 32, isoform CRA_c) |
| 643. | Chromodomain-helicase-DNA-binding protein 4 |
| 644. | Citrate synthase, mitochondrial (EC 2.3.3.1) (Citrate (Si)-synthase) |
| 645. | Clathrin heavy chain 1 (Clathrin heavy chain on chromosome 17) (CLH-17) |
| 646. | CLE7 (Chromosome 14 open reading frame 166, isoform CRA_a) (Lcrp369) (cDNA, FLJ92278) |
| 647. | Cleavage and polyadenylation specificity factor subunit 5 (Cleavage and polyadenylation specificity factor 25 kDa subunit) (CFIm25) (CPSF 25 kDa subunit) (Nucleoside diphosphate-linked moiety X motif 21) (Nudix motif 21) (Pre-mRNA cleavage factor Im 25 kDa subunit) |
| 648. | Cleavage and polyadenylation-specificity factor subunit 7 (Fragment) |
| 649. | Coatomer subunit alpha (Alpha-coat protein) (Alpha-COP) (HEP-COP) (HEPCOP) [Cleaved into: Xenin (Xenopsin-related peptide); Proxenin] |
| 650. | Coatomer subunit beta (Beta-coat protein) (Beta-COP) |
| 651. | Coatomer subunit delta |
| 652. | Coatomer subunit gamma-2 (Gamma-2-coat protein) (Gamma-2-COP) |
| 653. | Coatomer subunit zeta-1 (Zeta-1-coat protein) (Zeta-1 COP) |
| 654. | Cofilin-1 |
| 655. | Coiled-coil domain-containing protein 124 |
| 656. | Coiled-coil domain-containing protein 86 (Cytokine-induced protein with coiled-coil domain) |
| 657. | Coilin (p80-coilin) |
| 658. | Cold-inducible RNA-binding protein (A18 hnRNP) (Glycine-rich RNA-binding protein CIRP) |
| 659. | COMM domain-containing protein 8 |
| 660. | Complement component 1 Q subcomponent-binding protein, mitochondrial (ASF/SF2-associated protein p32) (Glycoprotein gC1qBP) (C1qBP) (Hyaluronan-binding protein 1) (Mitochondrial matrix protein p32) (gC1q-R protein) (p33) |
| 661. | Complex III assembly factor LYRM7 (LYR motif-containing protein 7) |
| 662. | Condensin complex subunit 3 (Chromosome-associated protein G) (Condensin subunit CAP-G) (hCAP-G) (Melanoma antigen NY-MEL-3) (Non-SMC condensin I complex subunit G) (XCAP-G homolog) |
| 663. | COP9 signalosome complex subunit 2 (SGN2) (Signalosome subunit 2) (Alien homolog) (JAB1-containing signalosome subunit 2) (Thyroid receptor-interacting protein 15) (TR-interacting protein 15) (TRIP-15) |
| 664. | COP9 signalosome complex subunit 5 (SGN5) (Signalosome subunit 5) (EC 3.4.-.-) (Jun activation domain-binding protein 1) |
| 665. | Copine-1 (HCG38213, isoform CRA_b) |

-continued

666. Copine-3 (Copine III)
667. Core histone macro-H2A.1 (Histone macroH2A1) (mH2A1) (Histone H2A.y) (H2A/y) (Medulloblastoma antigen MU-MB-50.205)
668. Corneodesmosin
669. Cornifin-B (14.9 kDa pancornulin) (Small proline-rich protein IB) (SPR-IB)
670. Coronin-1B (Coronin-2)
671. Creatine kinase B-type (EC 2.7.3.2) (B-CK) (Creatine kinase B chain)
672. CRISPR-associated endonuclease Cas9 (EC 3.1.-.-) (SaCas9)
673. CRISPR-associated endonuclease Cas9/Csn1 (EC 3.1.-.-) (SpCas9) (SpyCas9)
674. Crk-like protein
675. CUGBP Elav-like family member 1 (CELF-1) (50 kDa nuclear polyadenylated RNA-binding protein) (Bruno-like protein 2) (CUG triplet repeat RNA-binding protein 1) (CUG-BP1) (CUG-BP- and ETR-3-like factor 1) (Deadenylation factor CUG-BP) (Embryo deadenylation element-binding protein homolog) (EDEN-BP homolog) (RNA-binding protein BRUNOL-2)
676. Cullin-3 (CUL-3)
677. Cullin-5 (CUL-5) (Vasopressin-activated calcium-mobilizing receptor 1) (VACM-1)
678. Cullin-associated NEDD8-dissociated protein 1 (Cullin-associated and neddylation-dissociated protein 1) (TBP-interacting protein of 120 kDa A) (TBP-interacting protein 120A) (p120 CAND1)
679. Cyclin-dependent kinase 1 (CDK1) (EC 2.7.11.22) (EC 2.7.11.23) (Cell division control protein 2 homolog) (Cell division protein kinase 1) (p34 protein kinase)
680. Cyclin-dependent kinase 2
681. Cyclin-dependent kinase 9 (EC 2.7.11.22) (EC 2.7.11.23) (C-2K) (Cell division cycle 2-like protein kinase 4) (Cell division protein kinase 9) (Serine/threonine-protein kinase PITALRE) (Tat-associated kinase complex catalytic subunit)
682. Cystatin-B (CPI-B) (Liver thiol proteinase inhibitor) (Stefin-B)
683. Cystatin-S (Cystatin-4) (Cystatin-SA-III) (Salivary acidic protein 1)
684. Cysteine and histidine-rich domain-containing protein 1
685. Cysteine and histidine-rich domain-containing protein 1 (CHORD domain-containing protein 1) (CHORD-containing protein 1) (CHP-1) (Protein morgana)
686. Cysteine dioxygenase type 1 (EC 1.13.11.20) (Cysteine dioxygenase type I) (CDO) (CDO-I)
687. Cysteinyl-tRNA synthetase, isoform CRA_b (cDNA FLJ38994 fis, clone NT2RI2009259, highly similar to Cysteinyl-tRNA synthetase (EC 6.1.1.16))
688. Cytochrome b-c1 complex subunit 1, mitochondrial (Complex III subunit 1) (Core protein I) (Ubiquinol-cytochrome-c reductase complex core protein 1)
689. Cytochrome b-c1 complex subunit 2, mitochondrial (Complex III subunit 2) (Core protein II) (Ubiquinol-cytochrome-c reductase complex core protein 2)
690. Cytochrome b-c1 complex subunit 7 (cDNA FLJ52271, moderately similar to Ubiquinol-cytochrome c reductase complex 14 kDa protein (EC 1.10.2.2))
691. Cytochrome c (Fragment)
692. Cytochrome c oxidase subunit 2 (Cytochrome c oxidase polypeptide II)
693. Cytochrome c oxidase subunit 4 isoform 1, mitochondrial (Cytochrome c oxidase polypeptide IV) (Cytochrome c oxidase subunit IV isoform 1) (COX IV-1)
694. Cytochrome c oxidase subunit 5A, mitochondrial (Cytochrome c oxidase polypeptide Va)
695. Cytochrome c oxidase subunit 5B, mitochondrial (Cytochrome c oxidase polypeptide Vb)
696. Cytochrome c oxidase subunit 6B1 (Cytochrome c oxidase subunit VIb isoform 1) (COX VIb-1)
697. Cytochrome c1, heme protein, mitochondrial (Complex III subunit 4) (Complex III subunit IV) (Cytochrome b-c1 complex subunit 4) (Ubiquinol-cytochrome-c reductase complex cytochrome c1 subunit) (Cytochrome c-1)
698. Cytohesin-4 (Fragment)
699. Cytoplasmic dynein 1 heavy chain 1 (Cytoplasmic dynein heavy chain 1) (Dynein heavy chain, cytosolic)
700. Cytoplasmic dynein 1 light intermediate chain 1 (LIC1) (Dynein light chain A) (DLC-A) (Dynein light intermediate chain 1, cytosolic)
701. Cytoskeleton-associated protein 5 (Colonic and hepatic tumor overexpressed gene protein) (Ch-TOG)
702. Cytosol aminopeptidase (EC 3.4.11.1) (Leucine aminopeptidase 3) (LAP-3) (Leucyl aminopeptidase) (Peptidase S) (Proline aminopeptidase) (EC 3.4.11.5) (Prolyl aminopeptidase)
703. Cytosolic acyl coenzyme A thioester hydrolase (EC 3.1.2.2) (Acyl-CoA thioesterase 7) (Brain acyl-CoA hydrolase) (BACH) (CTE-IIa) (CTE-II) (Long chain acyl-CoA thioester hydrolase)
704. D-3-phosphoglycerate dehydrogenase (3-PGDH) (EC 1.1.1.95) (2-oxoglutarate reductase) (EC 1.1.1.399) (Malate dehydrogenase) (EC 1.1.1.37)
705. DAZ-associated protein 1 (Deleted in azoospermia-associated protein 1)
706. Delta-l-pyrroline-5-carboxylate synthase (P5CS) (Aldehyde dehydrogenase family 18 member A1) [Includes: Glutamate 5-kinase (GK) (EC 2.7.2.11) (Gamma-glutamyl kinase); Gamma-glutamyl phosphate reductase (GPR) (EC 1.2.1.41) (Glutamate-5-semialdehyde dehydrogenase) (Glutamyl-gamma-semialdehyde dehydrogenase)]
707. Density-regulated protein (DRP) (Protein DRP1) (Smooth muscle cell-associated protein 3) (SMAP-3)
708. Deoxynucleotidyltransferase terminal-interacting protein 2 (Estrogen receptor-binding protein) (LPTS-interacting protein 2) (LPTS-RP2) (Terminal deoxynucleotidyltransferase-interacting factor 2) (TdIF2) (TdT-interacting factor 2)
709. Deoxyuridine 5'-triphosphate nucleotidohydrolase, mitochondrial (dUTPase) (EC 3.6.1.23) (dUTP pyrophosphatase)
710. Desmocollin-1 (Cadherin family member 1) (Desmosomal glycoprotein 2/3) (DG2/DG3)
711. Desmocollin-3 (Cadherin family member 3) (Desmocollin-4) (HT-CP)
712. Desmoglein-1 (Cadherin family member 4) (Desmosomal glycoprotein 1) (DG1) (DGI) (Pemphigus foliaceus antigen)
713. Desmoplakin (DP) (250/210 kDa paraneoplastic pemphigus antigen)
714. Developmentally-regulated GTP-binding protein 1 (DRG-1) (Neural precursor cell expressed developmentally down-regulated protein 3) (NEDD-3)
715. Diablo homolog mitochondrial (Fragment)
716. Dihydrofolate reductase (EC 1.5.1.3) (cDNA, FLJ93028, *Homo sapiens* dihydrofolate reductase (DHFR), mRNA)
717. Dihydrolipoyllysine-residue succinyltransferase component of 2-oxoglutarate dehydrogenase complex, mitochondrial (EC 2.3.1.61) (2-oxoglutarate dehydrogenase complex component E2) (OGDC-E2) (Dihydrolipoamide succinyltransferase component of 2-oxoglutarate dehydrogenase complex) (E2K)
718. Diphosphoinositol polyphosphate phosphohydrolase 2 (DIPP-2) (EC 3.6.1.52) (Diadenosine 5',5'''-P1,P6-hexaphosphate hydrolase 2) (EC 3.6.1.-) (Nucleoside diphosphate-linked moiety X motif 4) (Nudix motif 4)
719. Diphosphomevalonate decarboxylase (EC 4.1.1.33) (Mevalonate (diphospho)decarboxylase) (MDDase) (Mevalonate pyrophosphate decarboxylase)
720. DNA damage-binding protein 1

-continued

721. DNA damage-binding protein 1 (DDB p127 subunit) (DNA damage-binding protein a) (DDBa) (Damage-specific DNA-binding protein 1) (HBV X-associated protein 1) (XAP-1) (UV-damaged DNA-binding factor) (UV-damaged DNA-binding protein 1) (UV-DDB 1) (XPE-binding factor) (XPE-BF) (Xeroderma pigmentosum group E-complementing protein) (XPCe)
722. DNA helicase (EC 3.6.4.12)
723. DNA mismatch repair protein
724. DNA mismatch repair protein Msh6 (hMSH6) (G/T mismatch-binding protein) (GTBP) (GTMBP) (MutS protein homolog 6) (MutS-alpha 160 kDa subunit) (p160)
725. DNA polymerase epsilon subunit 3 (EC 2.7.7.7) (Arsenic-transactivated protein) (AsTP) (Chromatin accessibility complex 17 kDa protein) (CHRAC-17) (HuCHRAC17) (DNA polymerase II subunit 3) (DNA polymerase epsilon subunit p17)
726. DNA repair protein RAD50 (hRAD50) (EC 3.6.-.-)
727. DNA replication licensing factor MCM6 (EC 3.6.4.12) (p105MCM)
728. DNA replication licensing factor MCM7 (EC 3.6.4.12) (CDC47 homolog) (P1.1-MCM3)
729. DNA topoisomerase (EC 5.99.1.2)
730. DNA topoisomerase 1 (EC 5.99.1.2) (DNA topoisomerase I)
731. DNA topoisomerase 2 (EC 5.99.1.3) (Fragment)
732. DNA-(apurinic or apyrimidinic site) lyase (EC 3.1.-.-) (EC 4.2.99.18) (APEX nuclease) (APEN) (Apurinic-apyrimidinic endonuclease 1) (AP endonuclease 1) (APE-1) (REF-1) (Redox factor-1) [Cleaved into: DNA-(apurinic or apyrimidinic site) lyase, mitochondrial]
733. DNA-dependent protein kinase catalytic subunit (DNA-PK catalytic subunit) (DNA-PKcs) (EC 2.7.11.1) (DNPK1) (p460)
734. DNA-directed RNA polymerase I subunit RPA34 (A34.5) (Antisense to ERCC-1 protein) (ASE-1) (CD3-epsilon-associated protein) (CAST) (CD3E-associated protein) (RNA polymerase I-associated factor PAF49)
735. DNA-directed RNA polymerase subunit beta (EC 2.7.7.6)
736. DNA-directed RNA polymerase subunit RPABC1
737. DNA-directed RNA polymerases I and III subunit RPAC1
738. DNA-directed RNA polymerases I and III subunit RPAC2 (RNA polymerases I and III subunit AC2) (AC19) (DNA-directed RNA polymerase I subunit D) (RNA polymerase I 16 kDa subunit) (RPA16) (RPC16) (hRPA19)
739. DnaJ homolog subfamily A member 1 (DnaJ protein homolog 2) (HSDJ) (Heat shock 40 kDa protein 4) (Heat shock protein J2) (HSJ-2) (Human DnaJ protein 2) (hDj-2)
740. DnaJ homolog subfamily B member 1 (DnaJ protein homolog 1) (Heat shock 40 kDa protein 1) (HSP40) (Heat shock protein 40) (Human DnaJ protein 1) (hDj-1)
741. DnaJ homolog subfamily C member 11 (Fragment)
742. DnaJ homolog subfamily C member 2 (M-phase phosphoprotein 11) (Zuotin-related factor 1) [Cleaved into: DnaJ homolog subfamily C member 2, N-terminally processed]
743. DnaJ homolog subfamily C member 21 (DnaJ homolog subfamily A member 5) (Protein GS3)
744. DnaJ homolog subfamily C member 8 (Splicing protein spf31)
745. Dolichyl-diphosphooligosaccharide--protein glycosyltransferase 48 kDa subunit (DDOST 48 kDa subunit) (Oligosaccharyl transferase 48 kDa subunit)
746. Dolichyl-diphosphooligosaccharide--protein glycosyltransferase subunit 1 (Dolichyl-diphosphooligosaccharide--protein glycosyltransferase 67 kDa subunit) (Ribophorin I) (RPN-I) (Ribophorin-1)
747. Dolichyl-diphosphooligosaccharide--protein glycosyltransferase subunit 1 (EC 2.4.99.18) (Dolichyl-diphosphooligosaccharide--protein glycosyltransferase 67 kDa subunit) (Ribophorin I) (RPN-I) (Ribophorin-1)
748. Dolichyl-diphosphooligosaccharide--protein glycosyltransferase subunit STT3A (Oligosaccharyl transferase subunit STT3A) (STT3-A) (EC 2.4.99.18) (B5) (Integral membrane protein 1) (Transmembrane protein TMC)
749. Double-stranded RNA-binding protein Staufen homolog 1
750. Double-stranded RNA-binding protein Staufen homolog 1 (Fragment)
751. Double-stranded RNA-binding protein Staufen homolog 2
752. Double-stranded RNA-binding protein Staufen homolog 2 (Fragment)
753. Dynactin 2 (P50), isoform CRA_b (cDNA FLJ31120 fis, clone IMR322000730, highly similar to Dynactin subunit 2) (cDNA FLJ77785)
754. Dynamin 1-like, isoform CRA_f
755. Dynamin-1 (EC 3.6.5.5)
756. Dynein heavy chain 9, axonemal
757. Dynein light chain 1, cytoplasmic (8 kDa dynein light chain) (DLC8) (Dynein light chain LC8-type 1) (Protein inhibitor of neuronal nitric oxide synthase) (PIN)
758. E3 SUMO-protein ligase RanBP2 (EC 6.3.2.-) (358 kDa nucleoporin) (Nuclear pore complex protein Nup358) (Nucleoporin Nup358) (Ran-binding protein 2) (RanBP2) (p270)
759. E3 ubiquitin-protein ligase CHIP (EC 2.3.2.27) (Antigen NY-CO-7) (CLL-associated antigen KW-8) (Carboxy terminus of Hsp70-interacting protein) (RING-type E3 ubiquitin transferase CHIP) (STIP1 homology and U box-containing protein 1)
760. E3 ubiquitin-protein ligase RBX1 (EC 6.3.2.-) (Protein ZYP) (RING finger protein 75) (RING-box protein 1) (Rbx1) (Regulator of cullins 1) [Cleaved into: E3 ubiquitin-protein ligase RBX1, N-terminally processed]
761. E3 ubiquitin-protein ligase UBR4 (EC 2.3.2.27) (600 kDa retinoblastoma protein-associated factor) (N-recognin-4) (RING-type E3 ubiquitin transferase UBR4) (Retinoblastoma-associated factor of 600 kDa) (RBAF600) (p600) (Zinc finger UBR1-type protein 1)
762. EBNA1 binding protein 2 (EBNA1 binding protein 2 variant) (EBNA1 binding protein 2, isoform CRA_a) (EBNA1BP2 protein)
763. Echinoderm microtubule-associated protein-like 4
764. EEF1E1-BLOC1S5 readthrough (NMD candidate) (HCG2043275)
765. EF-hand domain-containing protein D2 (Swiprosin-1)
766. EH-domain containing 1, isoform CRA_b (cDNA FLJ40523 fis, clone TESTI2046872, highly similar to EH-domain-containing protein 1) (cDNA, FLJ92624, highly similar to *Homo sapiens* EH-domain containing 1 (EHD1), mRNA)
767. eIF-2-alpha kinase activator GCN1 (GCN1 eIF-2-alpha kinase activator homolog) (GCN1-like protein 1) (General control of amino-acid synthesis 1-like protein 1) (Translational activator GCN1) (HsGCN1)
768. Electron transfer flavoprotein subunit alpha, mitochondrial (Alpha-ETF)
769. Electron transfer flavoprotein subunit beta (Beta-ETF)
770. Elongation factor 1-alpha 1 (EF-1-alpha-1) (Elongation factor Tu) (EF-Tu) (Eukaryotic elongation factor 1 A-1) (eEF1A-1) (Leukocyte receptor cluster member 7)
771. Elongation factor 1-beta (EF-1-beta)
772. Elongation factor 1-delta
773. Elongation factor 1-delta (Fragment)
774. Elongation factor 2 (EF-2)
775. Elongation factor G, mitochondrial
776. Elongation factor Tu, mitochondrial (EF-Tu) (P43)
777. Emerin

| | |
|---|---|
| 778. | Endoplasmic reticulum resident protein 29 (ERp29) (Endoplasmic reticulum resident protein 28) (ERp28) (Endoplasmic reticulum resident protein 31) (ERp31) |
| 779. | Endoplasmin (94 kDa glucose-regulated protein) (GRP-94) (Heat shock protein 90 kDa beta member 1) (Tumor rejection antigen 1) (gp96 homolog) |
| 780. | Endothelial differentiation-related factor 1 (EDF-1) (Multiprotein-bridging factor 1) (MBF1) |
| 781. | Enhancer of mRNA-decapping protein 4 (Autoantigen Ge-1) (Autoantigen RCD-8) (Human enhancer of decapping large subunit) (Hedls) |
| 782. | Enhancer of rudimentary homolog |
| 783. | Enoyl-CoA delta isomerase 1, mitochondrial (EC 5.3.3.8) (3,2-trans-enoyl-CoA isomerase) (Delta(3),Delta(2)-enoyl-CoA isomerase) (D3,D2-enoyl-CoA isomerase) (Dodecenoyl-CoA isomerase) |
| 784. | Epidermal growth factor receptor substrate 15-like 1 (Eps15-related protein) (Eps15R) |
| 785. | Epididymis luminal protein 112 (Ribosomal protein S27a, isoform CRA_c) (cDNA, FLJ96793, Homo sapiens ribosomal protein S27a (RPS27A), mRNA) |
| 786. | Epididymis luminal protein 4 (Epididymis secretory protein Li 3) (Epididymis secretory protein Li 93) (Tyrosine 3-monooxygenase/tryptophan 5-monooxygenase activation protein zeta polypeptide) (Tyrosine 3-monooxygenase/tryptophan 5-monooxygenase activation protein, zeta polypeptide, isoform CRA_a) |
| 787. | Epididymis secretory protein Li 103 (Heat shock 70 kDa protein 1A) (Heat shock 70 kDa protein 1B) (cDNA FLJ75127, highly similar to Homo sapiens heat shock 70 kDa protein 1A, mRNA) |
| 788. | Epididymis secretory protein Li 34 (Phosphatidylethanolamine binding protein 1, isoform CRA_a) (Phosphatidylethanolamine-binding protein 1) |
| 789. | Epididymis tissue sperm binding protein Li 14m |
| 790. | Epididymis tissue sperm binding protein Li 18mP (Glutamate dehydrogenase 1, isoform CRA_d) |
| 791. | Epididymis tissue sperm binding protein Li 3a |
| 792. | ER membrane protein complex subunit 1 |
| 793. | ES1 protein homolog mitochondrial (Protein GT335) (Protein KNP-1) |
| 794. | Eukaryotic initiation factor 4A-I (eIF-4A-I) (eIF4A-I) (EC 3.6.4.13) (ATP-dependent RNA helicase eIF4A-1) |
| 795. | Eukaryotic initiation factor 4A-II |
| 796. | Eukaryotic initiation factor 4A-III (eIF-4A-III) (eIF4A-III) (EC 3.6.4.13) (ATP-dependent RNA helicase DDX48) (ATP-dependent RNA helicase eIF4A-3) (DEAD box protein 48) (Eukaryotic initiation factor 4A-like NUK-34) (Eukaryotic translation initiation factor 4A isoform 3) (Nuclear matrix protein 265) (NMP 265) (hNMP 265) [Cleaved into: Eukaryotic initiation factor 4A-III, N-terminally processed] |
| 797. | Eukaryotic peptide chain release factor subunit 1 (cDNA FLJ56175, highly similar to Eukaryotic peptide chain release factor subunit1) |
| 798. | Eukaryotic peptide chain release factor subunit 1 (Eukaryotic release factor 1) (eRF1) (Protein C11) (TB3-1) |
| 799. | Eukaryotic translation elongation factor 1 epsilon-1 (Aminoacyl tRNA synthetase complex-interacting multifunctional protein 3) (Elongation factor p18) (Multisynthase complex auxiliary component p18) |
| 800. | Eukaryotic translation initiation factor 1A, X-chromosomal (eIF-1Aχ isoform) (Eukaryotic translation initiation factor 4C) (eIF-4C) |
| 801. | Eukaryotic translation initiation factor 1A, Y-chromosomal |
| 802. | Eukaryotic translation initiation factor 1b (eIF1b) (Protein translation factor SUI1 homolog GC20) |
| 803. | Eukaryotic translation initiation factor 2 subunit 1 (Eukaryotic translation initiation factor 2 subunit alpha) (eIF-2-alpha) (eIF-2A) (eIF-2alpha) |
| 804. | Eukaryotic translation initiation factor 2 subunit 2 (Eukaryotic translation initiation factor 2 subunit beta) (eIF-2-beta) |
| 805. | Eukaryotic translation initiation factor 2 subunit 3 (Eukaryotic translation initiation factor 2 subunit gamma X) (eIF-2-gamma X) (eIF-2gX) |
| 806. | Eukaryotic translation initiation factor 3 subunit A (eIF3a) (Eukaryotic translation initiation factor 3 subunit 10) (eIF-3-theta) (eIF3 p167) (eIF3 p180) (eIF3 p185) |
| 807. | Eukaryotic translation initiation factor 3 subunit C (eIF3c) (Eukaryotic translation initiation factor 3 subunit 8) (eIF3 p110) |
| 808. | Eukaryotic translation initiation factor 3 subunit C-like protein |
| 809. | Eukaryotic translation initiation factor 3 subunit E (eIF3e) (Eukaryotic translation initiation factor 3 subunit 6) (eIF-3 p48) |
| 810. | Eukaryotic translation initiation factor 3 subunit E (eIF3e) (Eukaryotic translation initiation factor 3 subunit 6) (Viral integration site protein INT-6 homolog) (eIF-3 p48) |
| 811. | Eukaryotic translation initiation factor 3 subunit F (eIF3f) (Eukaryotic translation initiation factor 3 subunit 5) (eIF-3-epsilon) (eIF3 p47) |
| 812. | Eukaryotic translation initiation factor 3 subunit G (eIF3g) (Eukaryotic translation initiation factor 3 RNA-binding subunit) (eIF-3 RNA-binding subunit) (Eukaryotic translation initiation factor 3 subunit 4) (eIF-3-delta) (eIF3 p42) (eIF3 p44) |
| 813. | Eukaryotic translation initiation factor 3 subunit H (eIF3h) (Eukaryotic translation initiation factor 3 subunit 3) (eIF-3 gamma) (eIF3 p40 subunit) |
| 814. | Eukaryotic translation initiation factor 3 subunit I (eIF3i) (Eukaryotic translation initiation factor 3 subunit 2) (TGF-beta receptor-interacting protein 1) (TRIP-1) (eIF-3-beta) (eIF3 p36) |
| 815. | Eukaryotic translation initiation factor 3 subunit K (eIF3k) (Eukaryotic translation initiation factor 3 subunit 12) (Muscle-specific gene M9 protein) (PLAC-24) (eIF-3 p25) (eIF-3 p28) |
| 816. | Eukaryotic translation initiation factor 3 subunit L (eIF3l) (Eukaryotic translation initiation factor 3 subunit 6-interacting protein) (Eukaryotic translation initiation factor 3 subunit E-interacting protein) |
| 817. | Eukaryotic translation initiation factor 3 subunit M (Fragment) |
| 818. | Eukaryotic translation initiation factor 4H (eIF-4H) (Williams-Beuren syndrome chromosomal region 1 protein) |
| 819. | Eukaryotic translation initiation factor 5 (eIF-5) |
| 820. | Eukaryotic translation initiation factor 5A (eIF-5A) (Fragment) |
| 821. | Eukaryotic translation initiation factor 5A-1 (eIF-5A-1) (eIF-5A1) (Eukaryotic initiation factor 5A isoform 1) (eIF-5A) (Rev-binding factor) (eIF-4D) |
| 822. | Eukaryotic translation initiation factor 5B (eIF-5B) (EC 3.6.5.3) (Translation initiation factor IF-2) |
| 823. | Eukaryotic translation initiation factor 6 (eIF-6) (B(2)GCN homolog) (B4 integrin interactor) (CAB) (p27(BBP)) |
| 824. | Eukaryotic translation initiation factor 6 (Fragment) |
| 825. | Exocyst complex component 8 (Exocyst complex 84 kDa subunit) |
| 826. | Exosome complex component CSL4 |
| 827. | Exosome complex component RRP40 (Exosome components) (Ribosomal RNA-processing protein 40) (p10) |
| 828. | Exosome complex component RRP41 |
| 829. | Exosome complex component RRP45 (Exosome component 9, isoform CRA_f) |
| 830. | Exosome complex component RRP46 (Chronic myelogenous leukemia tumor antigen 28) (Exosome component 5) (Ribosomal RNA-processing protein 46) (p12B) |

-continued

| | |
|---|---|
| 831. | Exosome complex exonuclease RRP44 (EC 3.1.13.-) (EC 3.1.26.-) (Protein DIS3 homolog) (Ribosomal RNA-processing protein 44) |
| 832. | Exosome component 10 (EC 3.1.13.-) (Autoantigen PM/Scl 2) (P100 polymyositis-scleroderma overlap syndrome-associated autoantigen) (Polymyositis/scleroderma autoantigen 100 kDa) (PM/Scl-100) (Polymyositis/scleroderma autoantigen 2) |
| 833. | Exportin-1 (Exp1) (Chromosome region maintenance 1 protein homolog) |
| 834. | Exportin-2 (Exp2) (Cellular apoptosis susceptibility protein) (Chromosome segregation 1-like protein) (Importin-alpha re-exporter) |
| 835. | Exportin-7 |
| 836. | Exportin-T (Exportin(tRNA)) (tRNA exportin) |
| 837. | Ezrin (Cytovillin) (Villin-2) (p81) |
| 838. | F-actin-capping protein subunit alpha-1 (CapZ alpha-1) |
| 839. | F-actin-capping protein subunit beta (CapZ beta) |
| 840. | F-box only protein 50 (NCC receptor protein 1 homolog) (NCCRP-1) (Non-specific cytotoxic cell receptor protein 1 homolog) |
| 841. | FACT complex subunit SPT16 (Chromatin-specific transcription elongation factor 140 kDa subunit) (FACT 140 kDa subunit) (FACTp140) (Facilitates chromatin transcription complex subunit SPT16) (hSPT16) |
| 842. | FACT complex subunit SSRP1 (Chromatin-specific transcription elongation factor 80 kDa subunit) (Facilitates chromatin transcription complex 80 kDa subunit) (FACT 80 kDa subunit) (FACTp80) (Facilitates chromatin transcription complex subunit SSRP1) (Recombination signal sequence recognition protein 1) (Structure-specific recognition protein 1) (hSSRP1) (T160) |
| 843. | Far upstream element-binding protein 2 (FUSE-binding protein 2) (KH type-splicing regulatory protein) (KSRP) (p75) |
| 844. | FARSLA protein (Phenylalanine-tRNA synthetase-like, alpha subunit, isoform CRA_b) (cDNA FLJ34774 fis, clone NT2NE2003309, highly similar to Phenylalanyl-tRNA synthetase alpha chain (EC 6.1.1.20)) |
| 845. | Fascin (55 kDa actin-bundling protein) (Singed-like protein) (p55) |
| 846. | Fatty acid binding protein 5 (Psoriasis-associated) |
| 847. | Fatty acid synthase (EC 2.3.1.85) [Includes: [Acyl-carrier-protein] S-acetyltransferase (EC 2.3.1.38); [Acyl-carrier-protein] S-malonyltransferase (EC 2.3.1.39); 3-oxoacyl-[acyl-carrier-protein] synthase (EC 2.3.1.41); 3-oxoacyl-[acyl-carrier-protein] reductase (EC 1.1.1.100); 3-hydroxyacyl-[acyl-carrier-protein] dehydratase (EC 4.2.1.59); Enoyl-[acyl-carrier-protein] reductase (EC 1.3.1.39); Oleoyl-[acyl-carrier-protein] hydrolase (EC 3.1.2.14)] |
| 848. | Fermitin family homolog 3 (Kindlin-3) (MIG2-like protein) (Unc-112-related protein 2) |
| 849. | Ferric-chelate reductase 1 (EC 1.-.-.-) (Stromal cell-derived receptor 2) (SDR-2) |
| 850. | Ferritin heavy chain (Ferritin H subunit) (EC 1.16.3.1) (Cell proliferation-inducing gene 15 protein) [Cleaved into: Ferritin heavy chain, N-terminally processed] |
| 851. | Ferrochelatase, mitochondrial (EC 4.99.1.1) (Heme synthase) (Protoheme ferro-lyase) |
| 852. | Filaggrin |
| 853. | Filaggrin-2 (FLG-2) (Intermediate filament-associated and psoriasis-susceptibility protein) (Ifapsoriasin) |
| 854. | Filamin A |
| 855. | Filamin-C (FLN-C) (FLNc) (ABP-280-like protein) (ABP-L) (Actin-binding-like protein) (Filamin-2) (Gamma-filamin) |
| 856. | Flap endonuclease 1 (FEN-1) (EC 3.1.-.-) (DNase IV) (Flap structure-specific endonuclease 1) (Maturation factor 1) (MFI) (hFEN-1) |
| 857. | Flavin reductase (NADPH) (FR) (EC 1.5.1.30) (Biliverdin reductase B) (BVR-B) (EC 1.3.1.24) (Biliverdin-IX beta-reductase) (Green heme-binding protein) (GHBP) (NADPH-dependent diaphorase) (NADPH-flavin reductase) (FLR) |
| 858. | Flotillin-1 |
| 859. | Four and a half LIM domains protein 3 (FHL-3) (Skeletal muscle LIM-protein 2) (SLIM-2) |
| 860. | Fragile X mental retardation syndrome-related protein 1 (cDNA FLJ58644, highly similar to Fragile X mental retardation syndrome-related protein 1) |
| 861. | Fructose-bisphosphate aldolase A (EC 4.1.2.13) (Lung cancer antigen NY-LU-1) (Muscle-type aldolase) |
| 862. | Fructose-bisphosphate aldolase C (EC 4.1.2.13) (Brain-type aldolase) |
| 863. | G antigen 12B/C/D/E (GAGE-12B) (GAGE-12C) (GAGE-12D) (GAGE-12E) |
| 864. | G2/mitotic-specific cyclin-B1 (Fragment) |
| 865. | Galectin-1 (Gal-1) (14 kDa laminin-binding protein) (HLBP14) (14 kDa lectin) (Beta-galactoside-binding lectin L-14-I) (Galaptin) (HBL) (HPL) (Lactose-binding lectin 1) (Lectin galactoside-binding soluble 1) (Putative MAPK-activating protein PM12) (S-Lac lectin 1) |
| 866. | Galectin-7 (Gal-7) (HKL-14) (PI7) (p53-induced gene 1 protein) |
| 867. | Gamma-glutamylcyclotransferase (EC 2.3.2.4) (Cytochrome c-releasing factor 21) |
| 868. | Gasdermin-A (Gasdermin-1) |
| 869. | Gem-associated protein 4 (Gemin-4) (Component of gems 4) (p97) |
| 870. | Gem-associated protein 5 (Gemin5) |
| 871. | General transcription factor II-I (GTFII-I) (TFII-I) (Bruton tyrosine kinase-associated protein 135) (BAP-135) (BTK-associated protein 135) (SRF-Phox1-interacting protein) (SPIN) (Williams-Beuren syndrome chromosomal region 6 protein) |
| 872. | General vesicular transport factor p115 (Protein USO1 homolog) (Transcytosis-associated protein) (TAP) (Vesicle-docking protein) |
| 873. | Globin B1 (Hemoglobin, gamma A) |
| 874. | Globin B2 (Hemoglobin, gamma G) |
| 875. | Globin B3 (Hemoglobin, epsilon 1) |
| 876. | Glucose-6-phosphate 1-dehydrogenase (G6PD) (EC 1.1.1.49) |
| 877. | Glucose-6-phosphate isomerase (GPI) (EC 5.3.1.9) (Autocrine motility factor) (AMF) (Neuroleukin) (NLK) (Phosphoglucose isomerase) (PGI) (Phosphohexose isomerase) (PHI) (Sperm antigen 36) (SA-36) |
| 878. | Glutamine-fructose-6-phosphate aminotransferase [isomerizing] 1 (EC 2.6.1.16) (D-fructose-6-phosphate amidotransferase 1) (Glutamine:fructose-6-phosphate amidotransferase 1) (GFAT 1) (GFAT1) (Hexosephosphate aminotransferase 1) |
| 879. | Glutamine--tRNA ligase (EC 6.1.1.18) (Glutaminyl-tRNA synthetase) (GlnRS) |
| 880. | Glutaredoxin-3 (PKC-interacting cousin of thioredoxin) (PICOT) (PKC-theta-interacting protein) (PKCq-interacting protein) (Thioredoxin-like protein 2) |
| 881. | Glutathione reductase, mitochondrial (GR) (GRase) (EC 1.8.1.7) |
| 882. | Glutathione S-transferase omega-1 (GSTO-1) (EC 2.5.1.18) (Glutathione S-transferase omega 1-1) (GSTO 1-1) (Glutathione-dependent dehydroascorbate reductase) (EC 1.8.5.1) (Monomethylarsonic acid reductase) (MMA(V) reductase) (EC 1.20.4.2) (S-(Phenacyl)glutathione reductase) (SPG-R) |
| 883. | Glutathione S-transferase P (EC 2.5.1.18) (GST class-pi) (GSTP1-1) |
| 884. | Glyceraldehyde-3-phosphate dehydrogenase (GAPDH) (EC 1.2.1.12) (Peptidyl-cysteine S-nitrosylase GAPDH) (EC 2.6.99.-) |
| 885. | Glycine--tRNA ligase (EC 6.1.1.17) (EC 6.1.1.14) (Diadenosine tetraphosphate synthetase) (AP-4-A synthetase) (Glycyl-tRNA synthetase) (GlyRS) |
| 886. | Glycogen debranching enzyme (Glycogen debrancher) [Includes: 4-alpha-glucanotransferase (EC 2.4.1.25) (Oligo-1,4-1,4-glucantransferase); Amylo-alpha-1,6-glucosidase (Amylo-1,6-glucosidase) (EC 3.2.1.33) (Dextrin 6-alpha-D-glucosidase)] |

-continued

887. Glycylpeptide N-tetradecanoyltransferase 1 (EC 2.3.1.97) (Myristoyl-CoA:protein N-myristoyltransferase 1) (NMT 1) (Type I N-myristoyltransferase) (Peptide N-myristoyltransferase 1)
888. Growth factor receptor-bound protein 2 (Growth factor receptor-bound protein 2, isoform CRA_a) (cDNA, FLJ96637, *Homo sapiens* growth factor receptor-bound protein 2 (GRB2), mRNA)
889. GrpE protein homolog
890. GTP-binding protein SAR1b (Fragment)
891. GTPase Era, mitochondrial (H-ERA) (hERA) (Conserved ERA-like GTPase) (CEGA) (ERA-W) (ERA-like protein 1)
892. Guanine nucleotide-binding protein G(I)/G(S)/G(T) subunit beta-2
893. Guanine nucleotide-binding protein G(k) subunit alpha (G(i) alpha-3)
894. Guanine nucleotide-binding protein G(s) subunit alpha isoforms short (Fragment)
895. Guanine nucleotide-binding protein subunit alpha-12 (G alpha-12) (G-protein subunit alpha-12)
896. Guanine nucleotide-binding protein-like 3 (E2-induced gene 3 protein) (Novel nucleolar protein 47) (NNP47) (Nucleolar GTP-binding protein 3) (Nucleostemin)
897. H/ACA ribonucleoprotein complex subunit 1 (Nucleolar protein family A member 1) (snoRNP protein GAR1)
898. H/ACA ribonucleoprotein complex subunit 3 (Nucleolar protein 10) (Nucleolar protein family A member 3) (snoRNP protein NOP10)
899. HCG1994130, isoform CRA_a (cDNA FLJ30359 fis, clone BRACE2007760, highly similar to 40S RIBOSOMAL PROTEIN S15A) (cDNA, FLJ92249, *Homo sapiens* ribosomal protein S15a (RPS15A), mRNA)
900. HCG2033702, isoform CRA_a (Suppressor of SWI4 1 homolog)
901. HCG26477 (Ribosomal protein S28, isoform CRA_a) (cDNA, FLJ92192, *Homo sapiens* ribosomal protein S28 (RPS28), mRNA)
902. HCTP4 (TPX2, microtubule-associated, homolog (*Xenopus laevis*), isoform CRA_b) (cDNA, FLJ92922)
903. Heatshock 70 kDa protein 14 (HSP70-like protein 1) (Heat shock protein HSP60)
904. Heat shock 70 kDa protein 4 (HSP70RY) (Heat shock 70-related protein APG-2)
905. Heat shock 70 kDa protein 6 (Heat shock 70 kDa protein B')
906. Heat shock cognate 71 kDa protein (Fragment)
907. Heat shock cognate 71 kDa protein (Heat shock 70 kDa protein 8) (Lipopolysaccharide-associated protein 1) (LAP-1) (LPS-associated protein 1)
908. Heat shock protein beta-1 (HspB1) (28 kDa heat shock protein) (Estrogen-regulated 24 kDa protein) (Heat shock 27 kDa protein) (HSP 27) (Stress-responsive protein 27) (SRP27)
909. Heat shock protein HSP 90-alpha (Heat shock 86 kDa) (HSP 86) (HSP86) (Lipopolysaccharide-associated protein 2) (LAP-2) (LPS-associated protein 2) (Renal carcinoma antigen NY-REN-38)
910. Heat shock protein HSP 90-beta (HSP 90) (Heat shock 84 kDa) (HSP 84) (HSP84)
911. Helicase-like transcription factor (EC 2.3.2.27) (EC 3.6.4.-) (DNA-binding protein/plasminogen activator inhibitor 1 regulator) (HIP116) (RING finger protein 80) (RING-type E3 ubiquitin transferase HLTF) (SWI/SNF-related matrix-associated actin-dependent regulator of chromatin subfamily A member 3) (Sucrose nonfermenting protein 2 -like 3)
912. Hemogen (Erythroid differentiation-associated gene protein) (EDAG-1) (Hemopoietic gene protein) (Negative differentiation regulator protein)
913. Hemoglobin subunit gamma-1 (Gamma-1-globin) (Hb F Agamma) (Hemoglobin gamma-1 chain) (Hemoglobin gamma-A chain)
914. Hemoglobin subunit zeta (HBAZ) (Hemoglobin zeta chain) (Zeta-globin)
915. Hepatoma-derived growth factor (HDGF) (High mobility group protein 1-like 2) (HMG-1L2)
916. Heterochromatin protein 1-binding protein 3 (Fragment)
917. Heterogeneous nuclear ribonucleoprotein A/B
918. Heterogeneous nuclear ribonucleoprotein A0 (hnRNP A0)
919. Heterogeneous nuclear ribonucleoprotein A1 (hnRNP A1) (Helix-destabilizing protein) (Single-strand RNA-binding protein) (hnRNP core protein A1) [Cleaved into: Heterogeneous nuclear ribonucleoprotein A1, N-terminally processed]
920. Heterogeneous nuclear ribonucleoprotein A3, isoform CRA_a (cDNA FLJ52659, highly similar to Heterogeneous nuclear ribonucleoprotein A3) (cDNA, FLJ79333, highly similar to Heterogeneous nuclear ribonucleoprotein A3)
921. Heterogeneous nuclear ribonucleoprotein D-like (hnRNP D-like) (hnRNP DL) (AU-rich element RNA-binding factor) (JKT41-binding protein) (Protein laAUF1)
922. Heterogeneous nuclear ribonucleoprotein F (hnRNP F) (Nucleolin-like protein mcs94-1) [Cleaved into: Heterogeneous nuclear ribonucleoprotein F, N-terminally processed]
923. Heterogeneous nuclear ribonucleoprotein H
924. Heterogeneous nuclear ribonucleoprotein H2 (hnRNP H2) (FTP-3) (Heterogeneous nuclear ribonucleoprotein H') (hnRNP H') [Cleaved into: Heterogeneous nuclear ribonucleoprotein H2, N-terminally processed]
925. Heterogeneous nuclear ribonucleoprotein H3 (hnRNP H3) (Heterogeneous nuclear ribonucleoprotein 2H9) (hnRNP 2H9)
926. Heterogeneous nuclear ribonucleoprotein L (hnRNP L)
927. Heterogeneous nuclear ribonucleoprotein M (hnRNP M)
928. Heterogeneous nuclear ribonucleoprotein Q (hnRNP Q) (Glycine- and tyrosine-rich RNA-binding protein) (GRY-RBP) (NS1-associated protein 1) (Synaptotagmin-binding cytoplasmic RNA-interacting protein)
929. Heterogeneous nuclear ribonucleoprotein U (hnRNP U) (Scaffold attachment factor A) (SAF-A) (p120) (pp120)
930. Heterogeneous nuclear ribonucleoprotein U-like protein 1 (Adenovirus early region 1B-associated protein 5) (E1B-55 kDa-associated protein 5) (E1B-AP5)
931. Heterogeneous nuclear ribonucleoprotein U-like protein 2 (Scaffold-attachment factor A2) (SAF-A2)
932. Heterogeneous nuclear ribonucleoproteins A2/B1 (hnRNP A2/B1)
933. Heterogeneous nuclear ribonucleoproteins C1/C2 (hnRNP C1/C2)
934. High mobility group nucleosome-binding domain-containing protein 3 (Thyroid receptor-interacting protein 7) (TR-interacting protein 7) (TRIP-7)
935. High mobility group protein B2 (Fragment)
936. High mobility group protein B2 (High mobility group protein 2) (HMG-2)
937. High mobility group protein B3 (Fragment)
938. High mobility group protein HMG-I/HMG-Y (HMG-I(Y)) (High mobility group AT-hook protein 1) (High mobility group protein A1) (High mobility group protein R)
939. Histidine triad nucleotide-binding protein 1 (EC 3.-.-.-) (Adenosine 5'-monophosphoramidase) (Protein kinase C inhibitor 1) (Protein kinase C-interacting protein 1) (PKCI-1)
940. Histidine triad nucleotide-binding protein 2, mitochondrial (HINT-2) (EC 3.-.-.-) (HINT-3) (HIT-17 kDa) (PKCI-1-related HIT protein)
941. Histone 1, H1e (Histone H1e)
942. Histone acetyltransferase type B catalytic subunit (EC 2.3.1.48) (Histone acetyltransferase 1)
943. Histone deacetylase 1 (HD1) (EC 3.5.1.98)
944. Histone H1.5 (Histone H1a) (Histone H1b) (Histone H1s-3)

-continued

945. Histone H1x
946. Histone H2A
947. Histone H2A type 1-C (Histone H2A/l)
948. Histone H2A.Z (H2A/z)
949. Histone H2B
950. Histone H2B type 1-J (Histone H2B.1) (Histone H2B.r) (H2B/r)
951. Histone H2B type 1-K (H2B K) (HIRA-interacting protein 1)
952. Histone H2B type 1-L (Histone H2B.c) (H2B/c)
953. Histone H2B type 1-O (Histone H2B.2) (Histone H2B.n) (H2B/n)
954. Histone H3
955. Histone H3.1 (Histone H3/a) (Histone H3/b) (Histone H3/c) (Histone H3/d) (Histone H3/f) (Histone H3/h) (Histone H3/i) (Histone H3/j) (Histone H3/k) (Histone H3/l)
956. Histone H3.2 (Histone H3/m) (Histone H3/o)
957. Histone H4
958. Histone-arginine methyltransferase CARM1 (EC 2.1.1.319) (Coactivator-associated arginine methyltransferase 1) (Protein arginine N-methyltransferase 4)
959. Histone-binding protein RBBP4 (Chromatin assembly factor 1 subunit C) (CAF-1 subunit C) (Chromatin assembly factor I p48 subunit) (CAF-1 48 kDa subunit) (CAF-I p48) (Nucleosome-remodeling factor subunit RBAP48) (Retinoblastoma-binding protein 4) (RBBP-4) (Retinoblastoma-binding protein p48)
960. Histone-binding protein RBBP7
961. Hornerin
962. Host cell factor 1
963. Hsc70-interacting protein (Hip) (Aging-associated protein 2) (Progesterone receptor-associated p48 protein) (Protein FAM10A1) (Putative tumor suppressor ST13) (Renal carcinoma antigen NY-REN-33) (Suppression of tumorigenicity 13 protein)
964. Hsp90 co-chaperone Cdc37 (Hsp90 chaperone protein kinase-targeting subunit) (p50Cdc37) [Cleaved into: Hsp90 co-chaperone Cdc37, N-terminally processed]
965. Hydroxyacyl-coenzyme A dehydrogenase, mitochondrial
966. Hypermethylated in cancer 2 protein (Hic-2) (HIC1-related gene on chromosome 22 protein) (Hic-3) (Zinc finger and BTB domain-containing protein 30)
967. Immunoglobulin heavy constant alpha 1 (Ig alpha-1 chain C region) (Ig alpha-1 chain C region BUR) (Ig alpha-1 chain C region TRO)
968. Immunoglobulin heavy constant gamma 1 (Ig gamma-1 chain C region) (Ig gamma-1 chain C region EU) (Ig gamma-1 chain C region KOL) (Ig gamma-1 chain C region NIE)
969. Immunoglobulin kappa constant (Ig kappa chain C region) (Ig kappa chain C region AG) (Ig kappa chain C region CUM) (Ig kappa chain C region EU) (Ig kappa chain C region OU) (Ig kappa chain C region ROY) (Ig kappa chain C region TI)
970. Importin subunit alpha-1 (Karyopherin subunit alpha-2) (RAG cohort protein 1) (SRP1-alpha)
971. Importin subunit alpha-4 (Importin alpha Q2) (Qip2) (Karyopherin subunit alpha-3) (SRP1-gamma)
972. Importin subunit beta-1 (Importin-90) (Karyopherin subunit beta-1) (Nuclear factor p97) (Pore targeting complex 97 kDa subunit) (PTAC97)
973. Importin-11
974. Importin-11 (Fragment)
975. Importin-4 (Imp4) (Importin-4b) (Imp4b) (Ran-binding protein 4) (RanBP4)
976. Importin-5 (Imp5) (Importin subunit beta-3) (Karyopherin beta-3) (Ran-binding protein 5) (RanBP5)
977. Importin-7 (Imp7) (Ran-binding protein 7) (RanBP7)
978. Importin-8 (Imp8) (Ran-binding protein 8) (RanBP8)
979. Inorganic pyrophosphatase (EC 3.6.1.1) (Pyrophosphate phospho-hydrolase) (PPase)
980. Inosine-5'-monophosphate dehydrogenase 2 (IMP dehydrogenase 2) (IMPD 2) (IMPDH 2) (EC 1.1.1.205) (IMPDH-II)
981. Inositol-3-phosphate synthase 1 (IPS 1) (EC 5.5.1.4) (Myo-inositol 1-phosphate synthase) (MI-1-P synthase) (MIP synthase) (hIPS) (Myo-inositol 1-phosphate synthase A1) (hINO1)
982. Insulin-like growth factor 2 mRNA-binding protein 1 (IGF2 mRNA-binding protein 1) (IMP-1) (IMP1) (Coding region determinant-binding protein) (CRD-BP) (IGF-II mRNA-binding protein 1) (VICKZ family member 1) (Zipcode-binding protein 1) (ZBP-1)
983. Insulin-like growth factor 2 mRNA-binding protein 2 (IGF2 mRNA-binding protein 2) (IMP-2) (Hepatocellular carcinoma autoantigen p62) (IGF-II mRNA-binding protein 2) (VICKZ family member 2)
984. Insulin-like growth factor 2 mRNA-binding protein 3 (IGF2 mRNA-binding protein 3) (IMP-3) (IGF-II mRNA-binding protein 3) (KH domain-containing protein overexpressed in cancer) (hKOC) (VICKZ family member 3)
985. Integrin-linked kinase-associated serine/threonine phosphatase 2C (Fragment)
986. Interferon-induced transmembrane protein 2
987. Interferon-inducible double-stranded RNA-dependent protein kinase activator A (Fragment)
988. Interleukin enhancer-binding factor 2 (Nuclear factor of activated T-cells 45 kDa)
989. Interleukin enhancer-binding factor 3 (Double-stranded RNA-binding protein 76) (DRBP76) (M-phase phosphoprotein 4) (MPP4) (Nuclear factor associated with dsRNA) (NFAR) (Nuclear factor of activated T-cells 90 kDa) (NF-AT-90) (Translational control protein 80) (TCP80)
990. Intron-binding protein aquarius (Intron-binding protein of 160 kDa) (IBP160)
991. Isocitrate dehydrogenase [NADP], mitochondrial (IDH) (EC 1.1.1.42) (ICD-M) (IDP) (NADP(+)-specific ICDH) (Oxalosuccinate decarboxylase)
992. Isoleucine--tRNA ligase, cytoplasmic (EC 6.1.1.5) (Isoleucyl-tRNA synthetase) (IRS) (IleRS)
993. Isoleucine--tRNA ligase, mitochondrial (EC 6.1.1.5) (Isoleucyl-tRNA synthetase) (IleRS)
994. Junction plakoglobin (Catenin gamma) (Desmoplakin III) (Desmoplakin-3)
995. Katanin p60 ATPase-containing subunit A-like 2 (Katanin p60 subunit A-like 2) (EC 3.6.4.3) (p60 katanin-like 2)
996. Keratin, type I cytoskeletal 10 (Cytokeratin-10) (CK-10) (Keratin-10) (K10)
997. Keratin, type I cytoskeletal 14 (Cytokeratin-14) (CK-14) (Keratin-14) (K14)
998. Keratin, type I cytoskeletal 17
999. Keratin, type I cytoskeletal 18 (Cell proliferation-inducing gene 46 protein) (Cytokeratin-18) (CK-18) (Keratin-18) (K18)
1000. Keratin, type I cytoskeletal 19 (Cytokeratin-19) (CK-19) (Keratin-19) (K19)
1001. Keratin, type I cytoskeletal 9 (Cytokeratin-9) (CK-9) (Keratin-9) (K9)
1002. Keratin, type II cytoskeletal 1 (67 kDa cytokeratin) (Cytokeratin-1) (CK-1) (Hair alpha protein) (Keratin-1) (K1) (Type-II keratin Kb1)
1003. Keratin, type II cytoskeletal 2 epidermal (Cytokeratin-2e) (CK-2e) (Epithelial keratin-2e) (Keratin-2 epidermis) (Keratin-2e) (K2e) (Type-II keratin Kb2)
1004. Keratin, type II cytoskeletal 5 (58 kDa cytokeratin) (Cytokeratin-5) (CK-5) (Keratin-5) (K5) (Type-II keratin Kb5)

-continued

1005. Keratin, type II cytoskeletal 8 (Cytokeratin-8) (CK-8) (Keratin-8) (K8) (Type-II keratin Kb8)
1006. KH domain-containing RNA-binding, signal transduction-associated protein 1 (GAP-associated tyrosine phosphoprotein p62) (Src-associated in mitosis 68 kDa protein) (Sam68) (p21 Ras GTPase-activating protein-associated p62) (p68)
1007. Kinesin-like protein
1008. Kinesin-like protein KIF2C (Kinesin-like protein 6) (Mitotic centromere-associated kinesin) (MCAK)
1009. Kinetochore protein Spc25 (hSpc25)
1010. L-lactate dehydrogenase A chain (LDH-A) (EC 1.1.1.27) (Cell proliferation-inducing gene 19 protein) (LDH muscle subunit) (LDH-M) (Renal carcinoma antigen NY-REN-59)
1011. L-lactate dehydrogenase B chain (LDH-B) (EC 1.1.1.27) (LDH heart subunit) (LDH-H) (Renal carcinoma antigen NY-REN-46)
1012. L-xylulose reductase (XR) (EC 1.1.1.10) (Carbonyl reductase II) (Dicarbonyl/L-xylulose reductase) (Kidney dicarbonyl reductase) (kiDCR) (Short chain dehydrogenase/reductase family 20C member 1) (Sperm surface protein P34H)
1013. La-related protein 1 (La ribonucleoprotein domain family member 1)
1014. Lactoylglutathione lyase (EC 4.4.1.5) (Aldoketomutase) (Glyoxalase I) (Glx I) (Ketone-aldehyde mutase) (Methylglyoxalase) (S-D-lactoylglutathione methylglyoxal lyase)
1015. Lamin-B receptor (Integral nuclear envelope inner membrane protein) (LMN2R)
1016. Lamin-B1
1017. Lamin-B2
1018. Lamina-associated polypeptide 2, isoform alpha (Thymopoietin isoform alpha) (TP alpha) (Thymopoietin-related peptide isoform alpha) (TPRP isoform alpha) [Cleaved into: Thymopoietin (TP) (Splenin); Thymopentin (TP5)]
1019. Lamina-associated polypeptide 2, isoforms beta/gamma (Thymopoietin, isoforms beta/gamma) (TP beta/gamma) (Thymopoietin-related peptide isoforms beta/gamma) (TPRP isoforms beta/gamma) [Cleaved into: Thymopoietin (TP) (Splenin); Thymopentin (TP5)]
1020. Large subunit GTPase 1 homolog (hLsg1) (EC 3.6.1.-)
1021. Leucine--tRNA ligase, cytoplasmic (EC 6.1.1.4) (Leucyl-tRNA synthetase) (LeuRS)
1022. Leucine-rich PPR-motif containing (Mitochondrial leucine-rich PPR motif-containing protein)
1023. Leucine-rich repeat flightless-interacting protein 1 (LRR FLII-interacting protein 1) (GC-binding factor 2) (TAR RNA-interacting protein)
1024. Leucine-rich repeat-containing protein 47
1025. Leucine-rich repeat-containing protein 59 (Ribosome-binding protein p34) (p34)
1026. Leukocyte elastase inhibitor (LEI) (Monocyte/neutrophil elastase inhibitor) (EI) (M/NEI) (Peptidase inhibitor 2) (PI-2) (Serpin B1)
1027. Lipocalin-1 (Tearlipocalin) (Tlc) (Tear prealbumin) (TP) (Von Ebner gland protein) (VEG protein)
1028. Lon protease homolog mitochondrial (EC 3.4.21.-) (Lon protease-like protein) (LONP) (Mitochondrial ATP-dependent protease Lon) (Serine protease 15)
1029. Loricrin
1030. Low molecular weight phosphotyrosine protein phosphatase (LMW-PTP) (LMW-PTPase) (EC 3.1.3.48) (Adipocyte acid phosphatase) (Low molecular weight cytosolic acid phosphatase) (EC 3.1.3.2) (Red cell acid phosphatase 1)
1031. Luc7-like protein 3 (Fragment)
1032. Lysine--tRNA ligase (EC 6.1.1.6) (Lysyl-tRNA synthetase) (LysRS)
1033. Lysine-specific histone demethylase 1A (EC 1.-.-.-) (BRAF35-HDAC complex protein BHC110) (Flavin-containing amine oxidase domain-containing protein 2)
1034. Macrophage migration inhibitory factor (MIF) (EC 5.3.2.1) (Glycosylation-inhibiting factor) (GIF) (L-dopachrome isomerase) (L-dopachrome tautomerase) (EC 5.3.3.12) (Phenylpyruvate tautomerase)
1035. Malate dehydrogenase (EC 1.1.1.37) (Fragment)
1036. Malate dehydrogenase, cytoplasmic
1037. Malate dehydrogenase, mitochondrial (EC 1.1.1.37)
1038. Malignant T-cell-amplified sequence 1 (MCT-1) (Multiple copies T-cell malignancies)
1039. Matrin-3
1040. MAU2 chromatid cohesion factor homolog (MAU-2) (Cohesin loading complex subunit SCC4 homolog)
1041. Melanoma-associated antigen B2 (Cancer/testis antigen 3.2) (CT3.2) (DSS-AHC critical interval MAGE superfamily 6) (DAM6) (MAGE XP-2 antigen) (MAGE-B2 antigen)
1042. Metastasis-associated protein MTA2 (Metastasis-associated 1-like 1) (MTA1-L1 protein) (p53 target protein in deacetylase complex)
1043. Methionine adenosyltransferase 2 subunit beta
1044. Methionine aminopeptidase 2 (MAP 2) (MetAP 2) (EC 3.4.11.18) (Initiation factor 2-associated 67 kDa glycoprotein) (p67) (p67eIF2) (Peptidase M)
1045. Methionine--tRNA ligase, cytoplasmic (EC 6.1.1.10) (Methionyl-tRNA synthetase) (MetRS)
1046. Methylcrotonoyl-CoA carboxylase beta chain, mitochondrial (MCCase subunit beta) (EC 6.4.1.4) (3-methylcrotonyl-CoA carboxylase 2) (3-methylcrotonyl-CoA carboxylase non-biotin-containing subunit) (3-methylcrotonyl-CoA:carbon dioxide ligase subunit beta)
1047. MICOS complex subunit
1048. MICOS complex subunit MIC60 (Mitofilin)
1049. Microtubule-associated protein
1050. Mitochondrial carrier homolog 2 (Fragment)
1051. Mitochondrial import inner membrane translocase subunit TIM50
1052. Mitochondrial import receptor subunit TOM40 homolog (Protein Haymaker) (Translocase of outer membrane 40 kDa subunit homolog) (p38.5)
1053. Mitochondrial import receptor subunit TOM70 (Mitochondrial precursor proteins import receptor) (Translocase of outer membrane 70 kDa subunit) (Translocase of outer mitochondrial membrane protein 70)
1054. Mitochondrial Rho GTPase 2 (MIRO-2) (hMiro-2) (EC 3.6.5.-) (Ras homolog gene family member T2)
1055. Mitochondrial transcription factor A (Transcription factor A, mitochondrial, isoform CRA_c)
1056. Mitogen-activated protein kinase 1 (MAP kinase 1) (MAPK 1) (EC 2.7.11.24) (ERT1) (Extracellular signal-regulated kinase 2) (ERK-2) (MAP kinase isoform p42) (p42-MAPK) (Mitogen-activated protein kinase 2) (MAP kinase 2) (MAPK 2)
1057. Mitogen-activated protein kinase 15 (MAP kinase 15) (MAPK 15) (EC 2.7.11.24) (Extracellular signal-regulated kinase 7) (ERK-7) (Extracellular signal-regulated kinase 8) (ERK-8)
1058. Mitotic checkpoint protein BUB3
1059. MKI67 FHA domain-interacting nucleolar phosphoprotein (Nucleolar phosphoprotein Nopp34) (Nucleolar protein interacting with the FHA domain of pKI-67) (hNIFK)
1060. Moesin (Membrane-organizing extension spike protein)
1061. Monocarboxylate transporter 1 (MCT 1) (Solute carrier family 16 member 1)
1062. Mov10, Moloney leukemia virus 10, homolog (Mouse), isoform CRA_a (Putative helicase MOV-10)

1063. mRNA turnover protein 4 homolog (Ribosome assembly factor MRTO4)
1064. Multifunctional methyltransferase subunit TRM112-like protein
1065. Multifunctional protein ADE2 (Fragment)
1066. Multifunctional protein ADE2 [Includes: Phosphoribosylaminoimidazole-succinocarboxamide synthase (EC 6.3.2.6) (SAICAR synthetase); Phosphoribosylaminoimidazole carboxylase (EC 4.1.1.21) (AIR carboxylase) (AIRC)]
1067. Muscleblind-like 2 (*Drosophila*), isoform CRA_a (cDNA FLJ76890, highly similar to *Homo sapiens* muscleblind-like 2 (*Drosophila*) (MBNL2), transcript variant 3, mRNA) (cDNA, FLJ79493, highly similar to *Homo sapiens* muscleblind-like 2 (*Drosophila*) (MBNL2), transcript variant 3, mRNA)
1068. Myb-binding protein 1A
1069. Myeloid-derived growth factor (MYDGF) (Interleukin-25) (IL-25) (Stromal cell-derived growth factor SF20)
1070. Myosin light chain 4 (Myosin light chain 1, embryonic muscle/atrial isoform) (Myosin light chain alkali GT-1 isoform)
1071. Myosin-10 (Cellular myosin heavy chain, type B) (Myosin heavy chain 10) (Myosin heavy chain, non-muscle IIb) (Non-muscle myosin heavy chain B) (NMMHC-B) (Non-muscle myosin heavy chain IIb) (NMMHC II-b) (NMMHC-IIB)
1072. Myosin-9 (Cellular myosin heavy chain, type A) (Myosin heavy chain 9) (Myosin heavy chain, non-muscle IIa) (Non-muscle myosin heavy chain A) (NMMHC-A) (Non-muscle myosin heavy chain IIa) (NMMHCII-a) (NMMHC-IIA)
1073. Myotrophin (Protein V-1)
1074. N-acylneuraminate cytidylyltransferase (Fragment)
1075. N-alpha-acetyltransferase 15, NatA auxiliary subunit (Gastric cancer antigen Ga19) (N-terminal acetyltransferase) (NMDA receptor-regulated protein 1) (Protein tubedown-1) (Tbdn100)
1076. N-alpha-acetyltransferase 50
1077. NAD(P) transhydrogenase, mitochondrial
1078. NAD(P)H dehydrogenase [quinone] 1 (cDNA FLJ50573, highly similar to *Homo sapiens* NAD(P)H dehydrogenase, quinone 1 (NQO1), transcript variant 3, mRNA)
1079. NADH dehydrogenase (Ubiquinone) 1 beta subcomplex, 10, 22 kDa, isoform CRA_b (cDNA FLJ78612, highly similar to *Homo sapiens* NADH dehydrogenase (ubiquinone) 1 beta subcomplex, 10, 22 kDa (NDUFB10), mRNA) (cDNA, FLJ92003, *Homo sapiens* NADH dehydrogenase (ubiquinone) 1 beta subcomplex, 10,22 kDa (NDUFB10), mRNA)
1080. NADH dehydrogenase [ubiquinone] 1 alpha subcomplex subunit 5 (Complex I subunit B13) (CI-13kD-B) (CI-13kD-B) (NADH-ubiquinone oxidoreductase 13 kDa-B subunit)
1081. NADH dehydrogenase [ubiquinone] 1 alpha subcomplex subunit 6 (Complex I-B14) (CI-B14) (LYR motif-containing protein 6) (NADH-ubiquinone oxidoreductase B14 subunit)
1082. NADH dehydrogenase [ubiquinone] 1 alpha subcomplex subunit 9, mitochondrial (Complex I-39kD) (CI-39kD) (NADH-ubiquinone oxidoreductase 39 kDa subunit)
1083. NADH dehydrogenase [ubiquinone] 1 beta subcomplex subunit 11, mitochondrial (Complex I-ESSS) (CI-ESSS) (NADH-ubiquinone oxidoreductase ESSS subunit) (Neuronal protein 17.3) (Np17.3) (p17.3)
1084. NADH dehydrogenase [ubiquinone] iron-sulfur protein 2, mitochondrial (EC 1.6.5.3) (EC 1.6.99.3) (Complex I-49kD) (CI-49kD) (NADH-ubiquinone oxidoreductase 49 kDa subunit)
1085. NADH dehydrogenase [ubiquinone] iron-sulfur protein 3, mitochondrial (EC 1.6.5.3) (EC 1.6.99.3) (Complex I-30kD) (CI-30kD) (NADH-ubiquinone oxidoreductase 30 kDa subunit)
1086. NADPH-cytochrome P450 reductase
1087. Nascent polypeptide-associated complex subunit alpha, muscle-specific form (Alpha-NAC, muscle-specific form) (skNAC)
1088. NEDD8-conjugating enzyme Ubc12 (EC 6.3.2.-) (NEDD8 carrier protein) (NEDD8 protein ligase) (Ubiquitin-conjugating enzyme E2 M)
1089. NEDD8-MDP1 readthrough (Fragment)
1090. Neuroguidin (Centromere accumulated nuclear protein 1) (CANu1) (EIF4E-binding protein)
1091. Neutral alpha-glucosidase AB (EC 3.2.1.84) (Alpha-glucosidase 2) (Glucosidase II subunit alpha)
1092. Neutral amino acid transporter B(0) (ATB(0)) (Baboon M7 virus receptor) (RD114/simian type D retrovirus receptor) (Sodium-dependent neutral amino acid transporter type 2) (Solute carrier family 1 member 5)
1093. NF-kappaB repressing factor (NF-kappaB repressing factor, isoform CRA_b)
1094. NHP2-like protein 1
1095. Nicalin (Nicastrin-like protein)
1096. Nodal modulator 2 (pM5 protein 2)
1097. Non-histone chromosomal protein HMG-14
1098. Non-histone chromosomal protein HMG-17 (High mobility group nucleosome-binding domain-containing protein 2)
1099. Non-POU domain-containing octamer-binding protein (NonO protein) (54 kDa nuclear RNA- and DNA-binding protein) (55 kDa nuclear protein) (DNA-binding p52/p100 complex, 52 kDa subunit) (NMT55) (p54(nrb)) (p54nrb)
1100. Nuclear autoantigenic sperm protein (NASP)
1101. Nuclear cap-binding protein subunit 1 (80 kDa nuclear cap-binding protein) (CBP80) (NCBP 80 kDa subunit)
1102. Nuclear fragile X mental retardation protein interacting protein 2 (Nuclear fragile X mental retardation protein interacting protein 2, isoform CRA_a) (cDNA FLJ75095, highly similar to *Homo sapiens* 82-kD FMRP Interacting Protein (182-FIP), mRNA)
1103. Nuclear migration protein nudC (Nuclear distribution protein C homolog)
1104. Nuclear mitotic apparatus protein 1 (NuMA protein) (Nuclear matrix protein-22) (NMP-22) (SP-H antigen)
1105. Nuclear pore complex protein Nup153 (153 kDa nucleoporin) (Nucleoporin Nup153)
1106. Nuclear pore complex protein Nup205 (205 kDa nucleoporin) (Nucleoporin Nup205)
1107. Nuclear pore complex protein Nup214 (214 kDa nucleoporin) (Nucleoporin Nup214) (Protein CAN)
1108. Nuclear pore complex protein Nup88 (88 kDa nucleoporin) (Nucleoporin Nup88)
1109. Nuclear pore complex protein Nup93 (93 kDa nucleoporin) (Nucleoporin Nup93)
1110. Nuclear pore glycoprotein p62 (62 kDa nucleoporin) (Nucleoporin Nup62)
1111. Nuclear pore membrane glycoprotein 210 (Nuclear pore protein gp210) (Nuclear envelope pore membrane protein POM 210) (POM210) (Nucleoporin Nup210) (Pore membrane protein of 210 kDa)
1112. Nuclear protein localization protein 4 homolog (Protein NPL4)
1113. Nuclear transport factor 2 (NTF-2) (Placental protein 15) (PP15)
1114. Nuclease-sensitive element-binding protein 1 (CCAAT-binding transcription factor I subunit A) (CBF-A) (DNA-binding protein B) (DBPB) (Enhancer factor I subunit A) (EFI-A) (Y-box transcription factor) (Y-box-binding protein 1) (YB-1)
1115. Nucleolar and coiled-body phosphoprotein 1 (140 kDa nucleolar phosphoprotein) (Nopp140) (Hepatitis C virus NS5A-transactivated protein 13) (HCV NS5A-transactivated protein 13) (Nucleolar 130 kDa protein) (Nucleolar phosphoprotein p130)
1116. Nucleolar complex protein 2 homolog (Protein NOC2 homolog) (NOC2-like protein) (Novel INHAT repressor)
1117. Nucleolar complex protein 4 homolog (Fragment)
1118. Nucleolar GTP-binding protein 1
1119. Nucleolar protein 16 (HBV pre-S2 trans-regulated protein 3)

-continued

1120. Nucleolar protein 56 (Nucleolar protein 5A)
1121. Nucleolar protein 58 (Nucleolar protein 5)
1122. Nucleolar protein 7 (Nucleolar protein of 27 kDa)
1123. Nucleolar RNA helicase 2 (EC 3.6.4.13) (DEAD box protein 21) (Gu-alpha) (Nucleolar RNA helicase Gu) (Nucleolar RNA helicase II) (RH II/Gu)
1124. Nucleolin (Protein C23)
1125. Nucleophosmin (NPM) (Nucleolar phosphoprotein B23) (Nucleolar protein NO38) (Numatrin)
1126. Nucleoplasmin-3
1127. Nucleoporin Nup43 (Nup107-160 subcomplex subunit Nup43) (p42)
1128. Nucleoporin SEH1 (Nup107-160 subcomplex subunit SEH1) (SEC13-like protein)
1129. Nucleoprotein TPR (Megator) (NPC-associated intranuclear protein) (Translocated promoter region protein)
1130. Nucleoside diphosphate kinase A (NDK A) (NDP kinase A) (EC 2.7.4.6) (Granzyme A-activated DNase) (GAAD) (Metastasis inhibition factor nm23) (NM23-H1) (Tumor metastatic process-associated protein)
1131. Nucleoside diphosphate kinase B (NDK B) (NDP kinase B) (EC 2.7.4.6) (C-myc purine-binding transcription factor PUF) (Histidine protein kinase NDKB) (EC 2.7.13.3) (nm23-H2)
1132. Nucleosome assembly protein 1-like 4 (Fragment)
1133. Ornithine aminotransferase, mitochondrial (EC 2.6.1.13) (Ornithine delta-aminotransferase) (Ornithine--oxo-acid aminotransferase) [Cleaved into: Ornithine aminotransferase, hepatic form; Ornithine aminotransferase, renal form]
1134. OTU domain-containing protein 6B (EC 3.4.19.12) (DUBA-5)
1135. Oxysterol-binding protein 1
1136. p21-activated protein kinase-interacting protein 1 (PAK/PLC-interacting protein 1) (hPIP1) (PAK1-interacting protein 1) (WD repeat-containing protein 84)
1137. PAI-1 mRNA-binding protein variant (cDNA, FLJ92551, Homo sapiens PAI-1 mRNA-binding protein (PAI-RBP1), mRNA)
1138. PC4 and SFRS1-interacting protein (CLL-associated antigen KW-7) (Dense fine speckles 70 kDa protein) (DFS 70) (Lens epithelium-derived growth factor) (Transcriptional coactivator p75/p52)
1139. PDZ and LIM domain protein 1 (C-terminal LIM domain protein 1) (Elfin) (LIM domain protein CLP-36)
1140. PDZ and LIM domain protein 7 (Fragment)
1141. Peptidyl-prolyl cis-trans isomerase (PPIase) (EC 5.2.1.8) (Fragment)
1142. Peptidyl-prolyl cis-trans isomerase B (PPIase B) (EC 5.2.1.8) (CYP-S1) (Cyclophilin B) (Rotamase B) (S-cyclophilin) (SCYLP)
1143. Peptidyl-prolyl cis-trans isomerase D (Testicular tissue protein Li 147)
1144. Peptidyl-prolyl cis-trans isomerase F, mitochondrial (PPIase F) (EC 5.2.1.8) (Cyclophilin D) (CyP-D) (CypD) (Cyclophilin F) (Mitochondrial cyclophilin) (CyP-M) (Rotamase F)
1145. Peptidyl-prolyl cis-trans isomerase FKBP3 (PPIase FKBP3) (EC 5.2.1.8) (25 kDa FK506-binding protein) (25 kDa FKBP) (FKBP-25) (FK506-binding protein 3) (FKBP-3) (Immunophilin FKBP25) (Rapamycin-selective 25 kDa immunophilin) (Rotamase)
1146. Peptidyl-prolyl cis-trans isomerase FKBP4 (PPIase FKBP4) (EC 5.2.1.8) (51 kDa FK506-binding protein) (FKBP51) (52 kDa FK506-binding protein) (52 kDa FKBP) (FKBP-52) (59 kDa immunophilin) (p59) (FK506-binding protein 4) (FKBP-4) (FKBP59) (HSP-binding immunophilin) (HBI) (Immunophilin FKBP52) (Rotamase) [Cleaved into: Peptidyl-prolyl cis-trans isomerase FKBP4, N-terminally processed]
1147. Peptidyl-prolyl cis-trans isomerase FKBP8 (PPIase FKBP8) (EC 5.2.1.8) (38 kDa FK506-binding protein) (38 kDa FKBP) (FKBP-38) (hFKBP38) (FK506-binding protein 8) (FKBP-8) (FKBPR38) (Rotamase)
1148. Peptidyl-prolyl cis-trans isomerase G
1149. Peptidyl-prolyl cis-trans isomerase G (PPIase G) (Peptidyl-prolyl isomerase G) (EC 5.2.1.8) (CASP10) (Clk-associating RS-cyclophilin) (CARS-Cyp) (CARS-cyclophilin) (SR-cyclophilin) (SR-cyp) (SRcyp) (Cyclophilin G) (Rotamase G)
1150. Peptidyl-prolyl cis-trans isomerase NIMA-interacting 4 (EC 5.2.1.8) (Parvulin-14) (Par14) (hPar14) (Parvulin-17) (Par17) (hPar17) (Peptidyl-prolyl cis-trans isomerase Pin4) (PPIase Pin4) (Peptidyl-prolyl cis/trans isomerase EPVH) (hEPVH) (Rotamase Pin4)
1151. Peptidyl-prolyl cis-trans isomerase-like 1 (PPIase) (EC 5.2.1.8) (Rotamase PPIL1)
1152. Peptidyl-tRNA hydrolase 2, mitochondrial (PTH 2) (EC 3.1.1.29) (Bcl-2 inhibitor of transcription 1)
1153. Peptidylprolyl isomerase (EC 5.2.1.8) (Fragment)
1154. Perilipin-3 (47 kDa mannose 6-phosphate receptor-binding protein) (47 kDa MPR-binding protein) (Cargo selection protein TIP47) (Mannose-6-phosphate receptor-binding protein 1) (Placental protein 17) (PP17)
1155. Peroxiredoxin-1 (EC 1.11.1.15) (Natural killer cell-enhancing factor A) (NKEF-A) (Proliferation-associated gene protein) (PAG) (Thioredoxin peroxidase 2) (Thioredoxin-dependent peroxide reductase 2)
1156. Peroxiredoxin-2 (EC 1.11.1.15) (Natural killer cell-enhancing factor B) (NKEF-B) (PRP) (Thiol-specific antioxidant protein) (TSA) (Thioredoxin peroxidase 1) (Thioredoxin-dependent peroxide reductase 1)
1157. Peroxiredoxin-4 (EC 1.11.1.15) (Antioxidant enzyme AOE372) (AOE37-2) (Peroxiredoxin IV) (Prx-IV) (Thioredoxin peroxidase AO372) (Thioredoxin-dependent peroxide reductase AO372)
1158. Peroxiredoxin-6 (EC 1.11.1.15) (1-Cys peroxiredoxin) (1-Cys PRX) (24 kDa protein) (Acidic calcium-independent phospholipase A2) (aiPLA2) (EC 3.1.1.-) (Antioxidant protein 2) (Liver 2D page spot 40) (Non-selenium glutathione peroxidase) (NSGPx) (EC 1.11.1.9) (Red blood cells page spot 12)
1159. Peroxisomal multifunctional enzyme type 2
1160. Peroxisomal multifunctional enzyme type 2 (MFE-2) (17-beta-hydroxysteroid dehydrogenase 4) (17-beta-HSD 4) (D-bifunctional protein) (DBP) (Multifunctional protein 2) (MPF-2) (Short chain dehydrogenase/reductase family 8C member 1) [Cleaved into: (3R)-hydroxyacyl-CoA dehydrogenase (EC 1.1.1.n12); Enoyl-CoA hydratase 2 (EC 4.2.1.107) (EC 4.2.1.119) (3-alpha,7-alpha,12-alpha-trihydroxy-5-beta-cholest-24-enoyl-CoA hydratase)]
1161. Pescadillo homolog
1162. PEST proteolytic signal-containing nuclear protein (PCNP) (PEST-containing nuclear protein)
1163. PHD finger-like domain-containing protein 5A (PHD finger-like domain protein 5A) (Splicing factor 3B-associated 14 kDa protein) (SF3b14b)
1164. Phenylalanine--tRNA ligase beta subunit (EC 6.1.1.20) (Phenylalanyl-tRNA synthetase beta subunit) (PheRS)
1165. Phosphate carrier protein, mitochondrial (Phosphate transport protein) (PTP) (Solute carrier family 25 member 3)
1166. Phosphatidylinositide phosphatase SAC1
1167. Pinin (140 kDa nuclear and cell adhesion-related phosphoprotein) (Desmosome-associated protein) (Domain-rich serine protein) (DRS protein) (DRSP) (Melanoma metastasis clone A protein) (Nuclear protein SDK3) (SR-like protein)
1168. Plakophilin-1 (Band 6 protein) (B6P)
1169. Platelet-activating factor acetylhydrolase IB subunit alpha (Lissencephaly-1 protein) (LIS-1) (PAF acetylhydrolase 45 kDa subunit) (PAF-AH 45 kDa subunit) (PAF-AH alpha) (PAFAH alpha)
1170. Platelet-activating factor acetylhydrolase IB subunit gamma (EC 3.1.1.47) (PAF acetylhydrolase 29 kDa subunit) (PAF-AH 29 kDa subunit) (PAF-AH subunit gamma) (PAFAH subunit gamma)
1171. Plectin (PCN) (PLTN) (Hemidesmosomal protein 1) (HD1) (Plectin-1)

| | |
|---|---|
| 1172. | Poly [ADP-ribose] polymerase 1 (PARP-1) (EC 2.4.2.30) (ADP-ribosyltransferase diphtheria toxin-like 1) (ARTD1) (NAD(+) ADP-ribosyltransferase 1) (ADPRT1) (Poly[ADP-ribose] synthase 1) |
| 1173. | Poly(rC)-binding protein 1 (Alpha-CP1) (Heterogeneous nuclear ribonucleoprotein E1) (hnRNP E1) (Nucleic acid-binding protein SUB2.3) |
| 1174. | Poly(U)-binding-splicing factor PUF60 (60 kDa poly(U)-binding-splicing factor) (FUSE-binding protein-interacting repressor) (FBP-interacting repressor) (Ro-binding protein 1) (RoBP1) (Siah-binding protein 1) (Siah-BP1) |
| 1175. | Polyadenylate-binding protein (PABP) |
| 1176. | Polyadenylate-binding protein 1 (PABP-1) (Poly(A)-binding protein 1) |
| 1177. | Polyadenylate-binding protein 2 (PABP-2) (Poly(A)-binding protein 2) (Nuclear poly(A)-binding protein 1) (Poly(A)-binding protein II) (PABII) (Polyadenylate-binding nuclear protein 1) |
| 1178. | Polypyrimidine tract-binding protein 1 (PTB) (57 kDa RNA-binding protein PPTB-1) (Heterogeneous nuclear ribonucleoprotein I) (hnRNP I) |
| 1179. | Polyribonucleotide nucleotidyltransferase 1, mitochondrial (EC 2.7.7.8) (3'-5' RNA exonuclease OLD35) (PNPase old-35) (Polynucleotide phosphorylase 1) (PNPase 1) (Polynucleotide phosphorylase-like protein) |
| 1180. | Porphobilinogen deaminase |
| 1181. | Porphobilinogen deaminase (Fragment) |
| 1182. | Pre-mRNA-processing factor 19 (EC 2.3.2.27) (Nuclear matrix protein 200) (PRP19/PSO4 homolog) (hPso4) (RING-type E3 ubiquitin transferase PRP19) (Senescence evasion factor) |
| 1183. | Pre-mRNA-processing factor 6 (Androgen receptor N-terminal domain-transactivating protein 1) (ANT-1) (PRP6 homolog) (U5 snRNP-associated 102 kDa protein) (U5-102 kDa protein) |
| 1184. | Pre-mRNA-processing-splicing factor 8 (220 kDa U5 snRNP-specific protein) (PRP8 homolog) (Splicing factor Prp8) (p220) |
| 1185. | pre-rRNA processing protein FTSJ3 (EC 2.1.1.-) (2'-O-ribose RNA methyltransferase SPB1 homolog) (Protein ftsJ homolog 3) (Putative rRNA methyltransferase 3) |
| 1186. | Pre-rRNA-processing protein TSR1 homolog |
| 1187. | Prefoldin subunit 2 (cDNA, FLJ96845, *Homo sapiens* prefoldin 2 (PFDN2), mRNA) |
| 1188. | Prefoldin subunit 5 (C-Myc-binding protein Mm-1) (Myc modulator 1) |
| 1189. | Prefoldin subunit 6 |
| 1190. | Prefoldin subunit 6 (Protein Ke2) |
| 1191. | Prelamin-A/C [Cleaved into: Lamin-A/C (70 kDa lamin) (Renal carcinoma antigen NY-REN-32)] |
| 1192. | Probable 28S rRNA (cytosine(4447)-C(5))-methyltransferase (EC 2.1.1.-) (Nucleolar protein 1) (Nucleolar protein 2 homolog) (Proliferating-cell nucleolar antigen p120) (Proliferation-associated nucleolar protein p120) |
| 1193. | Probable ATP-dependent RNA helicase DDX17 (EC 3.6.4.13) (DEAD box protein 17) (DEAD box protein p72) (DEAD box protein p82) (RNA-dependent helicase p72) |
| 1194. | Probable ATP-dependent RNA helicase DDX17 (EC 3.6.4.13) (DEAD box protein 17) (DEAD box protein p72) (RNA-dependent helicase p72) |
| 1195. | Probable ATP-dependent RNA helicase DDX27 (EC 3.6.4.13) (DEAD box protein 27) |
| 1196. | Probable ATP-dependent RNA helicase DDX46 (EC 3.6.4.13) (DEAD box protein 46) (PRP5 homolog) |
| 1197. | Probable ATP-dependent RNA helicase DDX49 (EC 3.6.4.13) (DEAD box protein 49) |
| 1198. | Probable ATP-dependent RNA helicase DDX5 (EC 3.6.4.13) (DEAD box protein 5) (RNA helicase p68) |
| 1199. | Probable ATP-dependent RNA helicase DDX6 (EC 3.6.4.13) (ATP-dependent RNA helicase p54) (DEAD box protein 6) (Oncogene RCK) |
| 1200. | Probable ATP-dependent RNA helicase DHX37 (EC 3.6.4.13) (DEAH box protein 37) |
| 1201. | Probable cytosolic iron-sulfur protein assembly protein CIAO1 (WD repeat-containing protein 39) |
| 1202. | Probable dimethyladenosine transferase (EC 2.1.1.183) (DIM1 dimethyladenosine transferase 1 homolog) (DIM1 dimethyladenosine transferase 1-like) (Probable 18S rRNA (adenine(1779)-N(6)/adenine(1780)-N(6))-dimethyltransferase) (Probable 18S rRNA dimethylase) (Probable S-adenosylmethionine-6-N',N'-adenosyl(rRNA) dimethyltransferase) |
| 1203. | Probable ubiquitin carboxyl-terminal hydrolase FAF-X (EC 3.4.19.12) (Deubiquitinating enzyme FAF-X) (Fat facets in mammals) (hFAM) (Fat facets protein-related, X-linked) (Ubiquitin thioesterase FAF-X) (Ubiquitin-specific protease 9, X chromosome) (Ubiquitin-specific-processing protease FAF-X) |
| 1204. | Profilin-1 (Epididymis tissue protein Li 184a) (Profilin I) |
| 1205. | Programmed cell death 6-interacting protein (PDCD6-interacting protein) (ALG-2-interacting protein 1) (ALG-2-interacting protein X) (Hp95) |
| 1206. | Programmed cell death protein 10 (Fragment) |
| 1207. | Programmed cell death protein 5 (TF-1 cell apoptosis-related protein 19) (Protein TFAR19) |
| 1208. | Programmed cell death protein 6 (Apoptosis-linked gene 2 protein homolog) (ALG-2) |
| 1209. | Programmed cell death protein 6 (Apoptosis-linked gene 2 protein) (Probable calcium-binding protein ALG-2) |
| 1210. | Prohibitin-2 |
| 1211. | Prohibitin, isoform CRA_a (cDNA FLJ78511, highly similar to *Homo sapiens* prohibitin (PHB), mRNA) (cDNA, FLJ93035, *Homo sapiens* prohibitin (PHB), mRNA) |
| 1212. | Prolactin-inducible protein (Gross cystic disease fluid protein 15) (GCDFP-15) (Prolactin-induced protein) (Secretory actin-binding protein) (SABP) (gp17) |
| 1213. | Proliferating cell nuclear antigen (PCNA) (Cyclin) |
| 1214. | Proliferation-associated protein 2G4 (Cell cycle protein p38-2G4 homolog) (hG4-1) (ErbB3-binding protein 1) |
| 1215. | Prostaglandin E synthase 3 (EC 5.3.99.3) (Cytosolic prostaglandin E2 synthase) (cPGES) (Hsp90 co-chaperone) (Progesterone receptor complex p23) (Telomerase-binding protein p23) |
| 1216. | Proteasome (Prosome, macropain) 26S subunit, ATPase, 4, isoform CRA_b (cDNA FLJ78505, highly similar to *Homo sapiens* proteasome (prosome, macropain) 26S subunit, ATPase, 4 (PSMC4), transcript variant 1, mRNA) (cDNA, FLJ93682, *Homo sapiens* proteasome (prosome, macropain) 26S subunit ATPase, 4(PSMC4), transcript variant 1, mRNA) |
| 1217. | Proteasome activator complex subunit 3 (11S regulator complex subunit gamma) (REG-gamma) (Activator of multicatalytic protease subunit 3) (Ki nuclear autoantigen) (Proteasome activator 28 subunit gamma) (PA28g) (PA28gamma) |
| 1218. | Proteasome assembly chaperone 1 (PAC-1) (Chromosome 21 leucine-rich protein) (C21-LRP) (Down syndrome critical region protein 2) |
| 1219. | Proteasome endopeptidase complex (EC 3.4.25.1) |
| 1220. | Proteasome subunit alpha type-1 (EC 3.4.25.1) (30 kDa prosomal protein) (PROS-30) (Macropain subunit C2) (Multicatalytic endopeptidase complex subunit C2) (Proteasome component C2) (Proteasome nu chain) |
| 1221. | Proteasome subunit alpha type-2 (EC 3.4.25.1) (Macropain subunit C3) (Multicatalytic endopeptidase complex subunit C3) (Proteasome component C3) |
| 1222. | Proteasome subunit alpha type-3 (EC 3.4.25.1) (Macropain subunit C8) (Multicatalytic endopeptidase complex subunit C8) (Proteasome component C8) |

-continued

1223. Proteasome subunit alpha type-4 (EC 3.4.25.1) (Macropain subunit C9) (Multicatalytic endopeptidase complex subunit C9) (Proteasome component C9) (Proteasome subunit L)
1224. Proteasome subunit alpha type-5 (EC 3.4.25.1) (Macropain zeta chain) (Multicatalytic endopeptidase complex zeta chain) (Proteasome zeta chain)
1225. Proteasome subunit alpha type-6 (EC 3.4.25.1) (27 kDa prosomal protein) (PROS-27) (p27K) (Macropain iota chain) (Multicatalytic endopeptidase complex iota chain) (Proteasome iota chain)
1226. Proteasome subunit alpha type-7 (EC 3.4.25.1) (Proteasome subunit RC6-1) (Proteasome subunit XAPC7)
1227. Proteasome subunit beta type (EC 3.4.25.1)
1228. Proteasome subunit beta type-1 (EC 3.4.25.1) (Macropain subunit C5) (Multicatalytic endopeptidase complex subunit C5) (Proteasome component C5) (Proteasome gamma chain)
1229. Proteasome subunit beta type-2 (EC 3.4.25.1) (Macropain subunit C7-I) (Multicatalytic endopeptidase complex subunit C7-I) (Proteasome component C7-I)
1230. Proteasome subunit beta type-3 (EC 3.4.25.1) (Proteasome chain 13) (Proteasome component C10-II) (Proteasome theta chain)
1231. Proteasome subunit beta type-4 (EC 3.4.25.1) (26 kDa prosomal protein) (HsBPROS26) (PROS-26) (Macropain beta chain) (Multicatalytic endopeptidase complex beta chain) (Proteasome beta chain) (Proteasome chain 3) (HsN3)
1232. Proteasome subunit beta type-5 (EC 3.4.25.1) (Macropain epsilon chain) (Multicatalytic endopeptidase complex epsilon chain) (Proteasome chain 6) (Proteasome epsilon chain) (Proteasome subunit MB1) (Proteasome subunit X)
1233. Proteasome subunit beta type-6 (EC 3.4.25.1) (Macropain delta chain) (Multicatalytic endopeptidase complex delta chain) (Proteasome delta chain) (Proteasome subunit Y)
1234. Proteasome-associated protein ECM29 homolog (Ecm29)
1235. Protein arginine N-methyltransferase 1
1236. Protein CDV3 homolog
1237. Protein CutA
1238. Protein DEK
1239. Protein DEK (cDNA FLJ53031, highly similar to Protein DEK)
1240. Protein disulfide-isomerase A3 (EC 5.3.4.1) (58 kDa glucose-regulated protein) (58 kDa microsomal protein) (p58) (Disulfide isomerase ER-60) (Endoplasmic reticulum resident protein 57) (ER protein 57) (ERp57) (Endoplasmic reticulum resident protein 60) (ER protein 60) (ERp60)
1241. Protein disulfide-isomerase A4 (EC 5.3.4.1) (Endoplasmic reticulum resident protein 70) (ER protein 70) (ERp70) (Endoplasmic reticulum resident protein 72) (ER protein 72) (ERp-72) (ERp72)
1242. Protein DJ-1 (DJ-1) (Oncogene DJ1) (Parkinson disease protein 7) (Parkinsonism-associated deglycase) (Protein deglycase DJ-1) (EC 3.1.2.-) (EC 3.5.1.124)
1243. Protein ERGIC-53 (ER-Golgi intermediate compartment 53 kDa protein) (Gp58) (Intracellular mannose-specific lectin MR60) (Lectin mannose-binding 1)
1244. Protein FAM50A (Fragment)
1245. Protein FRG1 (FSHD region gene 1 protein)
1246. Protein kinase C, alpha
1247. Protein kinase, cAMP-dependent, regulatory, type I, alpha (Tissue specific extinguisher 1), isoform CRA_a (cDNA FLJ40261 fis, clone TESTI2025609, highly similar to cAMP-dependent protein kinase type I-alpha regulatory subunit) (cDNA, FLJ92612, *Homo sapiens* protein kinase, cAMP-dependent, regulatory, type I, alpha (tissue specific extinguisher 1) (PRKAR1A), mRNA)
1248. Protein LTV1 homolog
1249. Protein LYRIC
1250. Protein mago nashi homolog 2
1251. Protein MAK16 homolog (NNP78) (Protein RBM13)
1252. Protein NipSnap homolog 3A (NipSnap3A) (Protein NipSnap homolog 4) (NipSnap4) (Target for Salmonella secreted protein C) (TassC)
1253. Protein pelota homolog (EC 3.1.-.-)
1254. Protein phosphatase 1 regulatory subunit 7
1255. Protein phosphatase 1F (EC 3.1.3.16) (Ca(2+)/calmodulin-dependent protein kinase phosphatase) (CaM-kinase phosphatase) (CaMKPase) (Partner of PIX 2) (Protein fem-2 homolog) (hFem-2)
1256. Protein phosphatase 2 (Formerly 2A), regulatory subunit A (PR 65), alpha isoform (Testicular secretory protein Li 1) (cDNA FLJ78455, highly similar to *Homo sapiens* protein phosphatase 2 (formerly 2A), regulatory subunit A (PR 65), alpha isoform (PPP2R1A), mRNA) (cDNA, FLJ96799, *Homo sapiens* protein phosphatase 2 (formerly 2A), regulatory subunit A (PR 65), alpha isoform (PPP2R1A), mRNA)
1257. Protein POF1B (Premature ovarian failure protein 1B)
1258. Protein quaking (Fragment)
1259. Protein quaking (Hqk) (HqkI)
1260. Protein RCC2 (RCC1-like protein TD-60) (Telophase disk protein of 60 kDa)
1261. Protein Red (Cytokine IK) (IK factor) (Protein RER)
1262. Protein RRP5 homolog (NF-kappa-B-binding protein) (NFBP) (Programmed cell death protein 11)
1263. Protein RTF2 homolog (Fragment)
1264. Protein S100-A11 (Calgizzarin) (Metastatic lymph node gene 70 protein) (MLN 70) (Protein S100-C) (S100 calcium-binding protein A11) [Cleaved into: Protein S100-A11, N-terminally processed]
1265. Protein S100-A16 (Aging-associated gene 13 protein) (Protein S100-F) (S100 calcium-binding protein A16)
1266. Protein S100-A8 (Calgranulin-A) (Calprotectin L1L subunit) (Cystic fibrosis antigen) (CFAG) (Leukocyte L1 complex light chain) (Migration inhibitory factor-related protein 8) (MRP-8) (p8) (S100 calcium-binding protein A8) (Urinary stone protein band A) [Cleaved into: Protein S100-A8, N-terminally processed]
1267. Protein S100-A9 (Calgranulin-B) (Calprotectin L1H subunit) (Leukocyte L1 complex heavy chain) (Migration inhibitory factor-related protein 14) (MRP-14) (p14) (S100 calcium-binding protein A9)
1268. Protein SET (HLA-DR-associated protein II) (Inhibitor of granzyme A-activated DNase) (IGAAD) (PHAPII) (Phosphatase 2A inhibitor I2PP2A) (I-2PP2A) (Template-activating factor I) (TAF-I)
1269. Protein Shroom3 (Shroom-related protein) (hShrmL)
1270. Protein SON (Bax antagonist selected in *saccharomyces* 1) (BASS1) (Negative regulatory element-binding protein) (NRE-binding protein) (Protein DBP-5) (SON3)
1271. Protein SSX2 (Cancer/testis antigen 5.2) (CT5.2) (Synovial sarcoma, X breakpoint 2) (Tumor antigen HOM-MEL-40)
1272. Protein strawberry notch homolog 1 (Monocyte protein 3) (MOP-3)
1273. Protein transport protein Sec31A (ABP125) (ABP130) (SEC31-like protein 1) (SEC31-related protein A) (Web1-like protein)

| | |
|---|---|
| 1274. | Protein-glutamine gamma-glutamyltransferase E (EC 2.3.2.13) (Transglutaminase E) (TG(E)) (TGE) (TGase E) (Transglutaminase-3) (TGase-3) [Cleaved into: Protein-glutamine gamma-glutamyltransferase E 50 kDa catalytic chain; Protein-glutamine gamma-glutamyltransferase E 27 kDa non-catalytic chain] |
| 1275. | Protein-L-isoaspartate(D-aspartate) O-methyltransferase (Fragment) |
| 1276. | Prothymosin alpha |
| 1277. | Protocadherin Fat 3 |
| 1278. | Pseudouridylate synthase 7 homolog (EC 5.4.99.-) |
| 1279. | Pumilio homolog 3 (HBV X-transactivated gene 5 protein) (HBV XAg-transactivated protein 5) (Minor histocompatibility antigen HA-8) (HLA-HA8) |
| 1280. | Purine nucleoside phosphorylase (PNP) (EC 2.4.2.1) (Inosine phosphorylase) (Inosine-guanosine phosphorylase) |
| 1281. | Puromycin-sensitive aminopeptidase |
| 1282. | Putative heat shock protein HSP 90-beta 2 (Heat shock protein 90-beta b) (Heat shock protein 90Bb) |
| 1283. | Putative heat shock protein HSP 90-beta 4 |
| 1284. | Putative nucleoside diphosphate kinase (NDK) (NDP kinase) (EC 2.7.4.6) |
| 1285. | Putative Polycomb group protein ASXL3 (Additional sex combs-like protein 3) |
| 1286. | Putative RNA-binding protein Luc7-like 2 |
| 1287. | Putative RRN3-like protein RRN3P2 (RNA polymerase I transcription factor homolog pseudogene 2) |
| 1288. | Putative small nuclear ribonucleoprotein G-like protein 15 |
| 1289. | Pyrroline-5-carboxylate reductase 2 (P5C reductase 2) (P5CR 2) (EC 1.5.1.2) |
| 1290. | Pyruvate kinase PKM (EC 2.7.1.40) (Cytosolic thyroid hormone-binding protein) (CTHBP) (Opa-interacting protein 3) (OIP-3) (Pyruvate kinase 2/3) (Pyruvate kinase muscle isozyme) (Thyroid hormone-binding protein 1) (THBP1) (Tumor M2-PK) (p58) |
| 1291. | RAB27A, member RAS oncogene family (RAB27A, member RAS oncogene family, isoform CRA_a) (cDNA, FLJ93274, Homo sapiens RAB27A, member RAS oncogene family (RAB27A), mRNA) |
| 1292. | Ragulator complex protein LAMTOR1 |
| 1293. | Ran GTPase-activating protein 1 (RanGAP1) |
| 1294. | Ran-specific GTPase-activating protein (Ran-binding protein 1) (RanBP1) |
| 1295. | RAP1A, member of RAS oncogene family (Ras-related protein Rap-1A) (cDNA FLJ75985, highly similar to Homo sapiens RAP1A, member of RAS oncogene family (RAP1A), transcript variant 2, mRNA) |
| 1296. | Ras GTPase-activating protein-binding protein 1 (G3BP-1) (EC 3.6.4.12) (EC 3.6.4.13) (ATP-dependent DNA helicase VIII) (hDH VIII) (GAP SH3 domain-binding protein 1) |
| 1297. | Ras GTPase-activating protein-binding protein 2 (G3BP-2) (GAP SH3 domain-binding protein 2) |
| 1298. | Ras GTPase-activating-like protein IQGAP1 (p195) |
| 1299. | Ras GTPase-activating-like protein IQGAP2 (Fragment) |
| 1300. | Ras-related C3 botulinum toxin substrate 1 (Rho family, small GTP binding protein Rac1) (Ras-related C3 botulinum toxin substrate 1 (Rho family, small GTP binding protein Rac1), isoform CRA_e) (cDNA FLJ77333, highly similar to Homo sapiens ras-related C3 botulinum toxin substrate 1 (rho family, small GTP binding protein Rac1) (RAC1), transcript variant Rac1b, mRNA) |
| 1301. | Ras-related protein Rab-10 |
| 1302. | Ras-related protein Rab-1A (YPT1-related protein) |
| 1303. | Ras-related protein Rab-35 (Fragment) |
| 1304. | Ras-related protein Rab-5C (L1880) (RAB5L) |
| 1305. | Ras-related protein Rab-7a (Fragment) |
| 1306. | Regulator of chromosome condensation (Fragment) |
| 1307. | Regulator of nonsense transcripts 1 (EC 3.6.4.-) (ATP-dependent helicase RENT1) (Nonsense mRNA reducing factor 1) (NORF1) (Up-frameshift suppressor 1 homolog) (hUpf1) |
| 1308. | Replication factor C subunit 2 (Activator 1 40 kDa subunit) (A1 40 kDa subunit) (Activator 1 subunit 2) (Replication factor C 40 kDa subunit) (RF-C 40 kDa subunit) (RFC40) |
| 1309. | Replication factor C subunit 3 (Activator 1 38 kDa subunit) (A1 38 kDa subunit) (Activator 1 subunit 3) (Replication factor C 38 kDa subunit) (RF-C 38 kDa subunit) (RFC38) |
| 1310. | Replication factor C subunit 4 |
| 1311. | Replication protein A 32 kDa subunit (RP-A p32) (Replication factor A protein 2) (RF-A protein 2) (Replication protein A 34 kDa subunit) (RP-A p34) |
| 1312. | Replication protein A 70 kDa DNA-binding subunit (RP-A p70) (Replication factor A protein 1) (RF-A protein 1) (Single-stranded DNA-binding protein) [Cleaved into: Replication protein A 70 kDa DNA-binding subunit N-terminally processed] |
| 1313. | Replication protein A3, 14 kDa (Replication protein A3, 14 kDa, isoform CRA_b) (cDNA, FLJ92105, Homo sapiens replication protein A3, 14 kDa (RPA3), mRNA) |
| 1314. | Rho GDP-dissociation inhibitor 1 (Rho GDI 1) (Rho-GDI alpha) |
| 1315. | Rho guanine nucleotide exchange factor 1 (115 kDa guanine nucleotide exchange factor) (p115-RhoGEF) (p115RhoGEF) (Sub1.5) |
| 1316. | Rho guanine nucleotide exchange factor 2 |
| 1317. | Rho-related GTP-binding protein RhoC (Fragment) |
| 1318. | Rho-related GTP-binding protein RhoG |
| 1319. | Ribonuclease inhibitor (Placental ribonuclease inhibitor) (Placental RNase inhibitor) (Ribonuclease/angiogenin inhibitor 1) (RAI) |
| 1320. | Ribonucleoprotein PTB-binding 1 |
| 1321. | Ribonucleoside-diphosphate reductase subunit M2 (Fragment) |
| 1322. | Ribose-phosphate pyrophosphokinase 2 (EC 2.7.6.1) (PPRibP) (Phosphoribosyl pyrophosphate synthase II) (PRS-II) |
| 1323. | Ribosomal biogenesis protein LAS1L (Protein LAS1 homolog) |
| 1324. | Ribosomal L1 domain-containing protein 1 (CATX-11) (Cellular senescence-inhibited gene protein) (Protein PBK1) |
| 1325. | Ribosomal protein L5 (Ribosomal protein L5, isoform CRA_c) (cDNA, FLJ95579, Homo sapiens ribosomal protein L5 (RPL5), mRNA) |
| 1326. | Ribosomal protein S23, isoform CRA_a (cDNA FLJ77921, highly similar to Homo sapiens ribosomal protein S23 (RPS23), mRNA) (cDNA, FLJ92033, Homo sapiens ribosomal protein S23 (RPS23), mRNA) |
| 1327. | Ribosomal RNA processing protein 1 homolog A (Novel nuclear protein 1) (NNP-1) (Nucleolar protein Nop52) (RRP1-like protein) |
| 1328. | Ribosomal RNA-processing protein 8 |
| 1329. | Ribosome biogenesis protein BOP1 (Block of proliferation 1 protein) |
| 1330. | Ribosome biogenesis protein BRX1 homolog (Brix domain-containing protein 2) |
| 1331. | Ribosome biogenesis protein NSA2 homolog (Hairy cell leukemia protein 1) (TGF-beta-inducible nuclear protein 1) |
| 1332. | Ribosome biogenesis regulatory protein homolog |
| 1333. | Ribosome maturation protein SBDS (Shwachman-Bodian-Diamond syndrome protein) |
| 1334. | Ribosome production factor 2 homolog (Brix domain-containing protein 1) (Ribosome biogenesis protein RPF2 homolog) |

1335. RNA 3'-terminal phosphate cyclase (RNA cyclase) (RNA-3'-phosphate cyclase) (EC 6.5.1.4) (RNA terminal phosphate cyclase domain-containing protein 1) (RTC domain-containing protein 1)
1336. RNA binding protein S1 (RNA binding protein S1, serine-rich domain, isoform CRA_a)
1337. RNA-binding motif protein, X chromosome (Glycoprotein p43) (Heterogeneous nuclear ribonucleoprotein G) (hnRNP G) [Cleaved into: RNA-binding motif protein, X chromosome, N-terminally processed]
1338. RNA-binding protein 12 (RNA-binding motif protein 12) (SH3/WW domain anchor protein in the nucleus) (SWAN)
1339. RNA-binding protein 12B
1340. RNA-binding protein 14 (Paraspeckle protein 2) (PSP2) (RNA-binding motif protein 14) (RRM-containing coactivator activator/modulator) (Synaptotagmin-interacting protein) (SYT-interacting protein)
1341. RNA-binding protein 25 (Arg/Glu/Asp-rich protein of 120 kDa) (RED120) (Protein S164) (RNA-binding motif protein 25) (RNA-binding region-containing protein 7)
1342. RNA-binding protein 25 (Fragment)
1343. RNA-binding protein 28 (RNA-binding motif protein 28)
1344. RNA-binding protein 3 (RNA-binding motif protein 3) (RNPL)
1345. RNA-binding protein 4
1346. RNA-binding protein 4 (Fragment)
1347. RNA-binding protein 42 (RNA-binding motif protein 42)
1348. RNA-binding protein 8A (Binder of OVCA1-1) (BOV-1) (RNA-binding motif protein 8A) (RNA-binding protein Y14) (Ribonucleoprotein RBM8A)
1349. RNA-binding protein EWS
1350. RNA-binding protein NOB1 (Phosphorylation regulatory protein HP-10) (Protein ART-4)
1351. RNA-binding protein PNO1
1352. RNA-binding protein Raly (Fragment)
1353. Rootletin (Fragment)
1354. rRNA 2'-O-methyltransferase fibrillarin (EC 2.1.1.-) (34 kDa nucleolar scleroderma antigen) (Histone-glutamine methyltransferase)
1355. rRNA adenine N(6)-methyltransferase (EC 2.1.1.-)
1356. rRNA/tRNA 2'-O-methyltransferase fibrillarin-like protein 1 (EC 2.1.1.-) (Protein-glutamine methyltransferase)
1357. RRP15-like protein (Ribosomal RNA-processing protein 15)
1358. RuvB-like 1 (EC 3.6.4.12) (49 kDa TATA box-binding protein-interacting protein) (49 kDa TBP-interacting protein) (54 kDa erythrocyte cytosolic protein) (ECP-54) (INO80 complex subunit H) (Nuclear matrix protein 238) (NMP 238) (Pontin 52) (TIP49a) (TIP60-associated protein 54-alpha) (TAP54-alpha)
1359. RuvB-like 2 (EC 3.6.4.12) (48 kDa TATA box-binding protein-interacting protein) (48 kDa TBP-interacting protein) (51 kDa erythrocyte cytosolic protein) (ECP-51) (INO80 complex subunit J) (Repressing pontin 52) (Reptin52) (TIP49b) (TIP60-associated protein 54-beta) (TAP54-beta)
1360. S-adenosylmethionine synthase isoform type-2 (AdoMet synthase 2) (EC 2.5.1.6) (Methionine adenosyltransferase 2) (MAT 2) (Methionine adenosyltransferase II) (MAT-II)
1361. S-formylglutathione hydrolase (FGH) (EC 3.1.2.12) (Esterase D) (Methylumbelliferyl-acetate deacetylase) (EC 3.1.1.56)
1362. S-phase kinase-associated protein 1
1363. SAP domain-containing ribonucleoprotein (Cytokine-induced protein of 29 kDa) (Nuclear protein Hcc-1) (Proliferation-associated cytokine-inducible protein CIP29)
1364. SAR1 gene homolog A (S. cerevisiae), isoform CRA_a (Small GTP-binding protein)
1365. Secretory carrier-associated membrane protein 3 (Secretory carrier membrane protein 3)
1366. Selenoprotein H (SelH)
1367. Septin-11
1368. Septin-11 (Fragment)
1369. Septin-2
1370. Septin-7
1371. Septin-9 (MLL septin-like fusion protein MSF-A) (MLL septin-like fusion protein) (Ovarian/Breast septin) (Ov/Br septin) (Septin D1)
1372. Serine hydroxymethyltransferase (EC 2.1.2.1)
1373. Serine--tRNA ligase, cytoplasmic (EC 6.1.1.11) (Seryl-tRNA synthetase) (SerRS) (Seryl-tRNA(Ser/Sec) synthetase)
1374. Serine/arginine repetitive matrix protein 1
1375. Serine/arginine repetitive matrix protein 2 (300 kDa nuclear matrix antigen) (Serine/arginine-rich splicing factor-related nuclear matrix protein of 300 kDa) (SR-related nuclear matrix protein of 300 kDa) (Ser/Arg-related nuclear matrix protein of 300 kDa) (Splicing coactivator subunit SRm300) (Tax-responsive enhancer element-binding protein 803) (TaxREB803)
1376. Serine/arginine-rich splicing factor 1 (Alternative-splicing factor 1) (ASF-1) (Splicing factor, arginine/serine-rich 1) (pre-mRNA-splicing factor SF2, P33 subunit)
1377. Serine/arginine-rich splicing factor 10 (40 kDa SR-repressor protein) (SRrp40) (FUS-interacting serine-arginine-rich protein 1) (Splicing factor SRp38) (Splicing factor, arginine/serine-rich 13A) (TLS-associated protein with Ser-Arg repeats) (TASR) (TLS-associated protein with SR repeats) (TLS-associated serine-arginine protein) (TLS-associated SR protein)
1378. Serine/arginine-rich splicing factor 11 (Arginine-rich 54 kDa nuclear protein) (p54) (Splicing factor, arginine/serine-rich 11)
1379. Serine/arginine-rich splicing factor 2 (Protein PR264) (Splicing component 35 kDa) (Splicing factor SC35) (SC-35) (Splicing factor, arginine/serine-rich 2)
1380. Serine/arginine-rich splicing factor 5 (Delayed-early protein HRS) (Pre-mRNA-splicing factor SRP40) (Splicing factor, arginine/serine-rich 5)
1381. Serine/arginine-rich splicing factor 6 (Pre-mRNA-splicing factor SRP55) (Splicing factor, arginine/serine-rich 6)
1382. Serine/arginine-rich splicing factor 9 (Pre-mRNA-splicing factor SRp30C) (Splicing factor, arginine/serine-rich 9)
1383. Serine/threonine-protein kinase 26 (cDNA FLJ54528, highly similar to Serine/threonine-protein kinase MST4 (EC 2.7.11.1)) (cDNA, FLJ79036, highly similar to Serine/threonine-protein kinase MST4 (EC 2.7.11.1))
1384. Serine/threonine-protein kinase PAK 2 (EC 2.7.11.1) (Gamma-PAK) (PAK65) (S6/H4 kinase) (p21-activated kinase 2) (PAK-2) (p58) [Cleaved into: PAK-2p27 (p27); PAK-2p34 (p34) (C-t-PAK2)]
1385. Serine/threonine-protein kinase PLK1 (EC 2.7.11.21) (Polo-like kinase 1) (PLK-1) (Serine/threonine-protein kinase 13) (STPK13)
1386. Serine/threonine-protein kinase VRK1 (EC 2.7.11.1) (Vaccinia-related kinase 1)
1387. Serine/threonine-protein phosphatase (EC 3.1.3.16)
1388. Serine/threonine-protein phosphatase 2A 56 kDa regulatory subunit delta isoform
1389. Serine/threonine-protein phosphatase 6 catalytic subunit (PP6C) (EC 3.1.3.16) [Cleaved into: Serine/threonine-protein phosphatase 6 catalytic subunit N-terminally processed]
1390. Serine/threonine-protein phosphatase PP1-alpha catalytic subunit (PP-1A) (EC 3.1.3.16)
1391. Serine/threonine-protein phosphatase PP1-beta catalytic subunit (PP-1B) (PPP1CD) (EC 3.1.3.16) (EC 3.1.3.53)

1392. Serine/threonine-protein phosphatase PP1-gamma catalytic subunit (PP-1G) (EC 3.1.3.16) (Protein phosphatase 1C catalytic subunit)
1393. Serpin B4 (Fragment)
1394. Serpin B6 (Cytoplasmic antiproteinase) (CAP) (Peptidase inhibitor 6) (PI-6) (Placental thrombin inhibitor)
1395. Serpin H1 (Fragment)
1396. Serrate RNA effector molecule homolog (Arsenite-resistance protein 2)
1397. Serum deprivation-response protein (Cavin-2) (PS-p68) (Phosphatidylserine-binding protein)
1398. SH3 domain GRB2-like 1 (SH3-domain GRB2-like 1) (SH3-domain GRB2-like 1, isoform CRA_b) (SH3GL1 protein) (cDNA, FLJ96508, *Homo sapiens* SH3-domain GRB2-like 1 (SH3GL1), mRNA)
1399. Sialic acid synthase (N-acetylneuraminate synthase) (EC 2.5.1.56) (N-acetylneuraminate-9-phosphate synthase) (EC 2.5.1.57) (N-acetylneuraminic acid phosphate synthase) (N-acetylneuraminic acid synthase)
1400. Sideroflexin-1 (Tricarboxylate carrier protein) (TCC)
1401. Signal peptidase complex catalytic subunit SEC11A (EC 3.4.21.89) (Endopeptidase SP18) (Microsomal signal peptidase 18 kDa subunit) (SPase 18 kDa subunit) (SEC11 homolog A) (SEC11-like protein 1) (SPC18)
1402. Signal recognition particle 14 kDa protein (SRP14) (18 kDa Alu RNA-binding protein)
1403. Signal recognition particle 19 kDa protein (SRP19)
1404. Signal recognition particle receptor beta subunit (Signal recognition particle receptor, B subunit isoform CRA_b)
1405. Signal recognition particle subunit SRP72 (SRP72) (Signal recognition particle 72 kDa protein)
1406. Signal transducer and activator of transcription 3 (Acute-phase response factor)
1407. Signal transducer and activator of transcription 5A
1408. Single-stranded DNA-binding protein
1409. Sister chromatid cohesion protein PDS5 homolog A (Cell proliferation-inducing gene 54 protein) (Sister chromatid cohesion protein 112) (SCC-112)
1410. Sjoegren syndrome/scleroderma autoantigen 1 (Autoantigen p27)
1411. Skin-specific protein 32
1412. Small nuclear ribonucleoprotein E (snRNP-E) (Sm protein E) (Sm-E) (SmE)
1413. Small nuclear ribonucleoprotein F (snRNP-F) (Sm protein F) (Sm-F) (SmF)
1414. Small nuclear ribonucleoprotein Sm D1 (Sm-D1) (Sm-D autoantigen) (snRNP core protein D1)
1415. Small nuclear ribonucleoprotein Sm D2 (Sm-D2) (snRNP core protein D2)
1416. Small ubiquitin-related modifier 1
1417. Small ubiquitin-related modifier 3
1418. SMARCD2 protein (SWI/SNF-related matrix-associated actin-dependent regulator of chromatin subfamily D member 2)
1419. SNARE protein Ykt6 (SNARE protein Ykt6, isoform CRA_a) (cDNA, FLJ93006, *Homo sapiens* SNARE protein Ykt6 (YKT6), mRNA)
1420. SNW domain-containing protein 1 (Nuclear protein SkiP) (Nuclear receptor coactivator NCoA-62) (Ski-interacting protein)
1421. Sodium/potassium-transporting ATPase subunit beta-3 (Fragment)
1422. Sorbitol dehydrogenase (EC 1.1.1.14) (L-iditol 2-dehydrogenase)
1423. Sorting and assembly machinery component 50 homolog (Transformation-related gene 3 protein) (TRG-3)
1424. Sorting nexin-3 (Protein SDP3)
1425. Spectrin alpha chain, erythrocytic 1 (Erythroid alpha-spectrin)
1426. Spectrin beta chain
1427. Spermatid perinuclear RNA-binding protein
1428. Spermidine synthase (SPDSY) (EC 2.5.1.16) (Putrescine aminopropyltransferase)
1429. Spermine synthase (SPMSY) (EC 2.5.1.22) (Spermidine aminopropyltransferase)
1430. Spliceosome RNA helicase DDX39B (EC 3.6.4.13) (56 kDa U2AF65-associated protein) (ATP-dependent RNA helicase p47) (DEAD box protein UAP56) (HLA-B-associated transcript 1 protein)
1431. Spliceosome-associated protein CWC15 homolog
1432. Splicing factor 3A subunit 1 (SF3a120) (Spliceosome-associated protein 114) (SAP 114)
1433. Splicing factor 3B subunit 1 (Pre-mRNA-splicing factor SF3b 155 kDa subunit) (SF3b155) (Spliceosome-associated protein 155) (SAP 155)
1434. Splicing factor 3B subunit 2 (Pre-mRNA-splicing factor SF3b 145 kDa subunit) (SF3b145) (SF3b150) (Spliceosome-associated protein 145) (SAP 145)
1435. Splicing factor 3B subunit 3 (Pre-mRNA-splicing factor SF3b 130 kDa subunit) (SF3b130) (STAF130) (Spliceosome-associated protein 130) (SAP 130)
1436. Splicing factor 3B subunit 4 (Pre-mRNA-splicing factor SF3b 49 kDa subunit) (SF3b50) (Spliceosome-associated protein 49) (SAP 49)
1437. Splicing factor arginine/serine-rich 3 (Splicing factor, arginine/serine-rich 3, isoform CRA_d) (cDNA, FLJ92926, *Homo sapiens* splicing factor, arginine/serine-rich 3 (SFRS3), mRNA)
1438. Splicing factor U2AF 35 kDa subunit (U2 auxiliary factor 35 kDa subunit) (U2 small nuclear RNA auxiliary factor 1) (U2 snRNP auxiliary factor small subunit)
1439. Splicing factor U2AF 65 kDa subunit (U2 auxiliary factor 65 kDa subunit) (hU2AF(65)) (hU2AF65) (U2 snRNP auxiliary factor large subunit)
1440. Splicing factor, proline- and glutamine-rich (100 kDa DNA-pairing protein) (hPOMp100) (DNA-binding p52/p100 complex, 100 kDa subunit) (Polypyrimidine tract-binding protein-associated-splicing factor) (PSF) (PTB-associated-splicing factor)
1441. SRA stem-loop-interacting RNA-binding protein, mitochondrial
1442. Src substrate cortactin (Amplaxin) (Oncogene EMS1)
1443. Stathmin
1444. Stathmin (Fragment)
1445. Stathmin (Leukemia-associated phosphoprotein p18) (Metablastin) (Oncoprotein 18) (Op18) (Phosphoprotein p19) (pp19) (Prosolin) (Protein Pr22) (pp17)
1446. Stress-70 protein, mitochondrial (75 kDa glucose-regulated protein) (GRP-75) (Heat shock 70 kDa protein 9) (Mortalin) (MOT) (Peptide-binding protein 74) (PBP74)
1447. Stress-induced-phosphoprotein 1 (STI1) (Hsc70/Hsp90-organizing protein) (Hop) (Renal carcinoma antigen NY-REN-11) (Transformation-sensitive protein IEF SSP 3521)
1448. Striatin-3 (Cell cycle autoantigen SG2NA) (S/G2 antigen)
1449. Stromal interaction molecule 1
1450. Structural maintenance of chromosomes flexible hinge domain-containing protein 1 (SMC hinge domain-containing protein 1)
1451. Structural maintenance of chromosomes protein
1452. Structural maintenance of chromosomes protein 2 (SMC protein 2) (SMC-2) (Chromosome-associated protein E) (hCAP-E) (XCAP-E homolog)

-continued

1453. Structural maintenance of chromosomes protein 3 (SMC protein 3) (SMC-3) (Basement membrane-associated chondroitin proteoglycan) (Bamacan) (Chondroitin sulfate proteoglycan 6) (Chromosome-associated polypeptide) (hCAP)
1454. Succinate dehydrogenase [ubiquinone] flavoprotein subunit, mitochondrial (EC 1.3.5.1)
1455. Succinate dehydrogenase [ubiquinone] iron-sulfur subunit mitochondrial (EC 1.3.5.1) (Iron-sulfur subunit of complex II) (Ip)
1456. SUMO-activating enzyme subunit 2 (EC 6.3.2.-) (Anthracycline-associated resistance ARX) (Ubiquitin-like 1-activating enzyme E1B) (Ubiquitin-like modifier-activating enzyme 2)
1457. SUMO-conjugating enzyme (EC 2.3.2.-)
1458. Surfeit locus protein 6
1459. Survival of motor neuron-related-splicing factor 30 (30 kDa splicing factor SMNrp) (SMN-related protein) (Survival motor neuron domain-containing protein 1)
1460. SWI/SNF related, matrix associated, actin dependent regulator of chromatin, subfamily a, member 4 (SWI/SNF related, matrix associated, actin dependent regulator of chromatin, subfamily a, member 4, isoform CRA_a) (cDNA FLJ77531, highly similar to *Homo sapiens* SWI/SNF related, matrix associated, actin dependent regulator of chromatin, subfamily a, member 4 (SMARCA4), mRNA)
1461. Synapse-associated protein 1
1462. Synaptosomal-associated protein 29 (Fragment)
1463. Synaptosomal-associated protein 29 (SNAP-29) (Soluble 29 kDa NSF attachment protein) (Vesicle-membrane fusion protein SNAP-29)
1464. Syntaxin-18 (Fragment)
1465. T-complex protein 1 subunit alpha (TCP-1-alpha) (CCT-alpha)
1466. T-complex protein 1 subunit beta (TCP-1-beta) (CCT-beta)
1467. T-complex protein 1 subunit delta (TCP-1-delta) (CCT-delta) (Stimulator of TAR RNA-binding)
1468. T-complex protein 1 subunit epsilon (cDNA, FLJ79275, highly similar to T-complex protein 1 subunit epsilon)
1469. T-complex protein 1 subunit epsilon (TCP-1-epsilon) (CCT-epsilon)
1470. T-complex protein 1 subunit eta (TCP-1-eta) (CCT-eta) (HIV-1 Nef-interacting protein) [Cleaved into: T-complex protein 1 subunit eta, N-terminally processed]
1471. T-complex protein 1 subunit theta (TCP-1-theta) (CCT-theta) (Renal carcinoma antigen NY-REN-15)
1472. T-complex protein 1 subunit zeta (TCP-1-zeta) (Acute morphine dependence-related protein 2) (CCT-zeta-1) (HTR3) (Tcp20)
1473. Talin-1
1474. TAR DNA-binding protein 43
1475. TAR DNA-binding protein 43 (TDP-43)
1476. Testis derived transcript (3 LIM domains) (Testis derived transcript (3 LIM domains), isoform CRA_d)
1477. Tetratricopeptide repeat protein 4 (TPR repeat protein 4)
1478. Thioredoxin (Trx) (ATL-derived factor) (ADF) (Surface-associated sulphydryl protein) (SASP)
1479. Thioredoxin domain-containing protein 17 (14 kDa thioredoxin-related protein) (TRP14) (Protein 42-9-9) (Thioredoxin-like protein 5)
1480. Thioredoxin domain-containing protein 9 (Fragment)
1481. Thioredoxin-like protein 1 (32 kDa thioredoxin-related protein)
1482. THO complex subunit 4
1483. Threonine--tRNA ligase, cytoplasmic (EC 6.1.1.3) (Threonyl-tRNA synthetase) (ThrRS)
1484. THUMP domain-containing protein 3
1485. Thymidine kinase, cytosolic (EC 2.7.1.21)
1486. Thymidylate synthase (TS) (TSase) (EC 2.1.1.45)
1487. Thymocyte nuclear protein 1 (Thymocyte protein Thy28)
1488. Thyroid hormone receptor-associated protein 3 (Thyroid hormone receptor-associated protein complex 150 kDa component) (Trap150)
1489. Thyroid receptor-interacting protein 6 (TR-interacting protein 6) (TRIP-6) (Opa-interacting protein 1) (OIP-1) (Zyxin-related protein 1) (ZRP-1)
1490. Torsin-1A-interacting protein 1 (Lamin-associated protein 1B) (LAP1B)
1491. TRAF-type zinc finger domain-containing protein 1 (Protein FLN29)
1492. Transaldolase (EC 2.2.1.2)
1493. Transcription and mRNA export factor ENY2 (Enhancer of yellow 2 transcription factor homolog)
1494. Transcription elongation factor A protein 1 (Transcription elongation factor S-II protein 1) (Transcription elongation factor TFIIS.o)
1495. Transcription elongation regulator 1 (TATA box-binding protein-associated factor 2S) (Transcription factor CA150)
1496. Transcription factor BTF3 (Fragment)
1497. Transcription factor BTF3 (Nascent polypeptide-associated complex subunit beta) (NAC-beta) (RNA polymerase B transcription factor 3)
1498. Transcription intermediary factor 1-beta (TIF1-beta) (E3 SUMO-protein ligase TRIM28) (EC 2.3.2.27) (KRAB-associated protein 1) (KAP-1) (KRAB-interacting protein 1) (KRIP-1) (Nuclear corepressor KAP-1) (RING finger protein 96) (RING-type E3 ubiquitin transferase TIF1-beta) (Tripartite motif-containing protein 28)
1499. Transcription termination factor 2 (EC 3.6.4.-) (Lodestar homolog) (RNA polymerase II termination factor) (Transcription release factor 2) (F2) (HuF2)
1500. Transcriptional activator protein Pur-alpha (Purine-rich single-stranded DNA-binding protein alpha)
1501. Transcriptional activator protein Pur-beta (Purine-rich element-binding protein B)
1502. Transducin beta-like protein 2
1503. Transducin beta-like protein 3 (WD repeat-containing protein SAZD)
1504. Transferrin receptor protein 1 (TR) (TfR) (TfR1) (Trfr) (T9) (p90) (CD antigen CD71) [Cleaved into: Transferrin receptor protein 1, serum form (sTfR)]
1505. Transitional endoplasmic reticulum ATPase (TER ATPase) (EC 3.6.4.6) (15S Mg(2+)-ATPase p97 subunit) (Valosin-containing protein) (VCP)
1506. Translation initiation factor eIF-2B subunit beta (S20I15) (S20III15) (eIF-2B GDP-GTP exchange factor subunit beta)
1507. Translation initiation factor eIF-2B subunit delta
1508. Translation initiation factor eIF-2B subunit gamma (eIF-2B GDP-GTP exchange factor subunit gamma)
1509. Translationally-controlled tumor protein (Fragment)
1510. Translin
1511. Translin, isoform CRA_b (cDNA FLJ34596 fis, clone KIDNE2009191, highly similar to TRANSLIN)
1512. Translocon-associated protein subunit delta (TRAP-delta) (Signal sequence receptor subunit delta) (SSR-delta)
1513. Transmembrane emp24 domain-containing protein 9 (GMP25) (Glycoprotein 25L2) (p24 family protein alpha-2) (p24alpha2) (p25)

| | |
|---|---|
| 1514. | Transmembrane protein 33 (Protein DB83) (SHINC-3) |
| 1515. | Transportin-1 (Importin beta-2) (Karyopherin beta-2) (M9 region interaction protein) (MIP) |
| 1516. | Treacle protein |
| 1517. | Tricarboxylate transport protein, mitochondrial (Citrate transport protein) (CTP) (Solute carrier family 25 member 1) (Tricarboxylate carrier protein) |
| 1518. | Trifunctional enzyme subunit beta, mitochondrial |
| 1519. | Trifunctional purine biosynthetic protein adenosine-3 [Includes: Phosphoribosylamine--glycine ligase (EC 6.3.4.13) (Glycinamide ribonucleotide synthetase) (GARS) (Phosphoribosylglycinamide synthetase); Phosphoribosylformylglycinamidine cyclo-ligase (EC 6.3.3.1) (AIR synthase) (AIRS) (Phosphoribosyl-aminoimidazole synthetase); Phosphoribosylglycinamide formyltransferase (EC 2.1.2.2) (5'-phosphoribosylglycinamide transformylase) (GAR transformylase) (GART)] |
| 1520. | tRNA-splicing ligase RtcB homolog (EC 6.5.1.3) |
| 1521. | Tropomodulin-1 (Erythrocyte tropomodulin) (E-Tmod) |
| 1522. | Tropomyosin alpha-3 chain (Gamma-tropomyosin) (Tropomyosin-3) (Tropomyosin-5) (hTM5) |
| 1523. | Trypsin-1 |
| 1524. | Tryptophan--tRNA ligase, cytoplasmic (EC 6.1.1.2) (Interferon-induced protein 53) (IFP53) (Tryptophanyl-tRNA synthetase) (TrpRS) (hWRS) [Cleaved into: T1-TrpRS; T2-TrpRS] |
| 1525. | Tubulin alpha chain |
| 1526. | Tubulin alpha chain-like 3 |
| 1527. | Tubulin alpha-1A chain (Alpha-tubulin 3) (Tubulin B-alpha-1) (Tubulin alpha-3 chain) [Cleaved into: Detyrosinated tubulin alpha-1A chain] |
| 1528. | Tubulin alpha-1B chain (Alpha-tubulin ubiquitous) (Tubulin K-alpha-1) (Tubulin alpha-ubiquitous chain) [Cleaved into: Detyrosinated tubulin alpha-1B chain] |
| 1529. | Tubulin beta chain (Tubulin beta-5 chain) |
| 1530. | Tubulin beta-2A chain (Tubulin beta class IIa) |
| 1531. | Tubulin beta-4B chain (Tubulin beta-2 chain) (Tubulin beta-2C chain) |
| 1532. | Tubulin beta-8 chain (Tubulin beta 8 class VIII) |
| 1533. | Tubulin gamma-1 chain (1) (Gamma-tubulin complex component 1) (GCP-1) |
| 1534. | Tubulin-specific chaperone A |
| 1535. | Tumor susceptibility gene 101 protein |
| 1536. | Tyrosine--tRNA ligase, cytoplasmic (EC 6.1.1.1) (Tyrosyl-tRNA synthetase) (TyrRS) [Cleaved into: Tyrosine--tRNA ligase, cytoplasmic, N-terminally processed] |
| 1537. | Tyrosine-protein kinase (EC 2.7.10.2) |
| 1538. | Tyrosine-protein kinase BAZ1B (EC 2.7.10.2) (Bromodomain adjacent to zinc finger domain protein 1B) (Williams syndrome transcription factor) (Williams-Beuren syndrome chromosomal region 10 protein) (Williams-Beuren syndrome chromosomal region 9 protein) (hWALp2) |
| 1539. | Tyrosine-protein kinase BTK (EC 2.7.10.2) (Agammaglobulinemia tyrosine kinase) (ATK) (B-cell progenitor kinase) (BPK) (Bruton tyrosine kinase) |
| 1540. | U1 small nuclear ribonucleoprotein 70 kDa (U1 snRNP 70 kDa) (U1-70K) (snRNP70) |
| 1541. | U1 small nuclear ribonucleoprotein A (U1 snRNP A) (U1-A) (U1A) |
| 1542. | U1 small nuclear ribonucleoprotein C (U1 snRNP C) (U1-C) (U1C) |
| 1543. | U2 small nuclear ribonucleoprotein A' (U2 snRNP A') |
| 1544. | U2 small nuclear ribonucleoprotein B" (U2 snRNP B") |
| 1545. | U2 snRNP-associated SURP motif-containing protein |
| 1546. | U3 small nucleolar RNA-associated protein 18 homolog (WD repeat-containing protein 50) |
| 1547. | U5 small nuclear ribonucleoprotein 200 kDa helicase (EC 3.6.4.13) (Activating signal cointegrator 1 complex subunit 3-like 1) (BRR2 homolog) (U5 snRNP-specific 200 kDa protein) (U5-200KD) |
| 1548. | U6 snRNA-associated Sm-like protein LSm4 (Glycine-rich protein) (GRP) |
| 1549. | Ubiquilin-4 (Ataxin-1 interacting ubiquitin-like protein) (A1Up) (Ataxin-1 ubiquitin-like-interacting protein A1U) (Connexin43-interacting protein of 75 kDa) (CIP75) |
| 1550. | Ubiquitin carboxyl-terminal hydrolase 10 (EC 3.4.19.12) (Deubiquitinating enzyme 10) (Ubiquitin thioesterase 10) (Ubiquitin-specific-processing protease 10) |
| 1551. | Ubiquitin carboxyl-terminal hydrolase 14 |
| 1552. | Ubiquitin carboxyl-terminal hydrolase 4 (EC 3.4.19.12) (Deubiquitinating enzyme 4) (Ubiquitin thioesterase 4) (Ubiquitin-specific-processing protease 4) (Ubiquitous nuclear protein homolog) |
| 1553. | Ubiquitin thioesterase OTU1 (EC 3.4.19.12) (DUBA-8) (HIV-1-induced protease 7) (HIN-7) (HsHIN7) (OTU domain-containing protein 2) |
| 1554. | Ubiquitin thioesterase OTUB1 |
| 1555. | Ubiquitin-60S ribosomal protein L40 (CEP52) (Ubiquitin A-52 residue ribosomal protein fusion product 1) [Cleaved into: Ubiquitin; 60S ribosomal protein L40 (Large ribosomal subunit protein eL40)] |
| 1556. | Ubiquitin-associated domain-containing protein 1 (UBA domain-containing protein 1) (E3 ubiquitin-protein ligase subunit KPC2) (Glialblastoma cell differentiation-related protein 1) (Kip1 ubiquitination-promoting complex protein 2) |
| 1557. | Ubiquitin-associated protein 2-like (Protein NICE-4) |
| 1558. | Ubiquitin-conjugating enzyme E2 D3 |
| 1559. | Ubiquitin-conjugating enzyme E2 L3 (EC 2.3.2.23) (E2 ubiquitin-conjugating enzyme L3) (L-UBC) (UbcH7) (Ubiquitin carrier protein L3) (Ubiquitin-conjugating enzyme E2-F1) (Ubiquitin-protein ligase L3) |
| 1560. | Ubiquitin-conjugating enzyme E2 S (EC 2.3.2.23) (E2 ubiquitin-conjugating enzyme S) (E2-EPF) (Ubiquitin carrier protein S) (Ubiquitin-conjugating enzyme E2-24 kDa) (Ubiquitin-conjugating enzyme E2-EPF5) (Ubiquitin-protein ligase S) |
| 1561. | Ubiquitin-conjugating enzyme E2 variant 2 (Ubiquitin-conjugating enzyme E2 variant 2, isoform CRA_b) (cDNA, FLJ93989, *Homo sapiens* ubiquitin-conjugating enzyme E2 variant 2 (UBE2V2), mRNA |
| 1562. | Ubiquitin-like modifier-activating enzyme 1 (EC 6.2.1.45) (Protein A1S9) (Ubiquitin-activating enzyme E1) |
| 1563. | Ubiquitin-like modifier-activating enzyme 6 (Ubiquitin-activating enzyme 6) (EC 6.2.1.45) (Monocyte protein 4) (MOP-4) (Ubiquitin-activating enzyme E1-like protein 2) (E1-L2) |
| 1564. | UMP-CMP kinase (EC 2.7.4.14) (Deoxycytidylate kinase) (CK) (dCMP kinase) (Nucleoside-diphosphate kinase) (EC 2.7.4.6) (Uridine monophosphate/cytidine monophosphate kinase) (UMP/CMP kinase) (UMP/CMPK) |
| 1565. | Uncharacterized protein |
| 1566. | Uncharacterized protein C9orf78 (Hepatocellular carcinoma-associated antigen 59) |
| 1567. | Uncharacterized protein KIAA1614 |
| 1568. | Unconventional myosin-XVIIIa (Molecule associated with JAK3 N-terminus) (MAJN) (Myosin containing a PDZ domain) (Surfactant protein receptor SP-R210) (SP-R210) |

-continued

1569. Upstream-binding protein 1 (Transcription factor LBP-1)
1570. Uroporphyrinogen decarboxylase (UPD) (URO-D) (EC 4.1.1.37)
1571. V-type proton ATPase catalytic subunit A (V-ATPase subunit A) (EC 3.6.3.14) (V-ATPase 69 kDa subunit) (Vacuolar ATPase isoform VA68) (Vacuolar proton pump subunit alpha)
1572. V-type proton ATPase subunit B, brain isoform (V-ATPase subunit B 2) (Endomembrane proton pump 58 kDa subunit) (HO57) (Vacuolar proton pump subunit B 2)
1573. V-type proton ATPase subunit d 1
1574. Vacuolar protein sorting-associated protein 35 (hVPS35) (Maternal-embryonic 3) (Vesicle protein sorting 35)
1575. Vacuolar protein sorting-associated protein 4A (EC 3.6.4.6) (Protein SKD2) (VPS4-1) (hVPS4)
1576. Vasodilator-stimulated phosphoprotein (VASP)
1577. Very-long-chain enoyl-CoA reductase (EC 1.3.1.93) (Synaptic glycoprotein SC2) (Trans-2,3-enoyl-CoA reductase) (TER)
1578. Vesicle-associated membrane protein-associated protein A (VAMP-A) (VAMP-associated protein A) (VAP-A) (33 kDa VAMP-associated protein) (VAP-33)
1579. Vesicle-associated membrane protein-associated protein B/C
1580. Vesicle-trafficking protein SEC22b (ER-Golgi SNARE of 24 kDa) (ERS-24) (ERS24) (SEC22 vesicle-trafficking protein homolog B) (SEC22 vesicle-trafficking protein-like 1)
1581. Vigilin (High density lipoprotein-binding protein) (HDL-binding protein)
1582. Vimentin
1583. Vinculin (Metavinculin) (MV)
1584. Voltage-dependent anion-selective channel protein 1 (Fragment)
1585. Voltage-dependent anion-selective channel protein 1 (VDAC-1) (hVDAC1) (Outer mitochondrial membrane protein porin 1) (Plasmalemmal porin) (Porin 31HL) (Porin 31HM)
1586. Voltage-dependent anion-selective channel protein 2 (VDAC-2) (hVDAC2) (Outer mitochondrial membrane protein porin 2)
1587. WD repeat and HMG-box DNA-binding protein 1 (Acidic nucleoplasmic DNA-binding protein 1) (And-1)
1588. WD repeat-containing protein 36 (T-cell activation WD repeat-containing protein) (TA-WDRP)
1589. WD repeat-containing protein 43 (Fragment)
1590. WD repeat-containing protein 5 (BMP2-induced 3-kb gene protein)
1591. WD repeat-containing protein 55
1592. WD repeat-containing protein 74
1593. WD repeat-containing protein 82 (Protein TMEM113) (Swd2)
1594. X-ray repair cross-complementing protein 5 (EC 3.6.4.-) (86 kDa subunit of Ku antigen) (ATP-dependent DNA helicase 2 subunit 2) (ATP-dependent DNA helicase II 80 kDa subunit) (CTC box-binding factor 85 kDa subunit) (CTC85) (CTCBF) (DNA repair protein XRCC5) (Ku80) (Ku86) (Lupus Ku autoantigen protein p86) (Nuclear factor IV) (Thyroid-lupus autoantigen) (TLAA) (X-ray repair complementing defective repair in Chinese hamster cells 5 (double-strand-break rejoining))
1595. X-ray repair cross-complementing protein 6
1596. Y-box-binding protein 3 (Cold shock domain-containing protein A) (DNA-binding protein A) (Single-strand DNA-binding protein NF-GMB)
1597. YTH domain-containing family protein 3
1598. Zinc finger CCCH domain-containing protein 11A
1599. Zinc finger CCCH-type antiviral protein 1
1600. Zinc finger homeobox protein 3 (AT motif-binding factor 1) (AT-binding transcription factor 1) (Alpha-fetoprotein enhancer-binding protein) (Zinc finger homeodomain protein 3) (ZFH-3)
1601. Zinc finger protein 622 (Zinc finger-like protein 9)
1602. Zinc finger protein 706
1603. Zinc finger protein ZPR1 (Zinc finger protein 259)
1604. Zinc finger Ran-binding domain-containing protein 2 (Zinc finger protein 265) (Zinc finger, splicing)
1605. Zinc-alpha-2-glycoprotein (Zn-alpha-2-GP) (Zn-alpha-2-glycoprotein)

Table 8 Shows Data for Peptide Identification by MS for 10 Day Control Washout Sample 1. >sp|A4UGR9|XIRP2_HUMAN Xin actin0binding repeat0containing protein 2 OS = *Homo sapiens* GN = XIRP2 PE = 1 SV = 2
2. >sp|A6NKH3|RL37L_HUMAN Putative 60S ribosomal protein L37a0like OS = *Homo sapiens* GN = RPL37L PE = 5 SV = 2
3. >sp|B1APH4|ZN487_HUMAN Putative zinc finger protein 487 OS = *Homo sapiens* GN = ZNF487P PE = 5 SV = 3
4. >sp|B2RPK0|HGB1A_HUMAN Putative high mobility group protein B10like 1 OS = *Homo sapiens* GN = HMGB1P1 PE = 5 SV = 1
5. >sp|O00151|PDLI1_HUMAN PDZ and LIM domain protein 1 OS = *Homo sapiens* GN = PDLIM1 PE = 1 SV = 4
6. >sp|O00712|NFIB_HUMAN Nuclear factor 1 B0type OS = *Homo sapiens* GN = NFIB PE = 1 SV = 2
7. >sp|O15446|RPA34_HUMAN DNA0directed RNA polymerase I subunit RPA34 OS = *Homo sapiens* GN = CD3EAP PE = 1 SV = 1
8. >sp|O75306|NDUS2_HUMAN NADH dehydrogenase [ubiquinone] iron0sulfur protein 2, mitochondrial OS = Homo sapiens GN = NDUFS2 PE = 1 SV = 2
9. >sp|P01857|IGHG1_HUMAN Ig gamma01 chain C region OS = *Homo sapiens* GN = IGHG1 PE = 1 SV = 1
10. >sp|P02533|K1C14_HUMAN Keratin, type I cytoskeletal 14 OS = *Homo sapiens* GN = KRT14 PE = 1 SV = 4
11. >sp|P04075|ALDOA_HUMAN Fructose0bisphosphate aldolase A OS = *Homo sapiens* GN = ALDOA PE = 1 SV = 2
12. >sp|P04264|K2C1_HUMAN Keratin, type II cytoskeletal 1 OS = *Homo sapiens* GN = KRT1 PE = 1 SV = 6
13. >sp|P04350|TBB4_HUMAN Tubulin beta04 chain OS = *Homo sapiens* GN = TUBB4 PE = 1 SV = 2
14. >sp|P05387|RLA2_HUMAN 60S acidic ribosomal protein P2 OS = *Homo sapiens* GN = RPLP2 PE = 1 SV = 1
15. >sp|P06576|ATPB_HUMAN ATP synthase subunit beta, mitochondrial OS = *Homo sapiens* GN = ATP5B PE = 1 SV = 3
16. >sp|P06733|ENOA_HUMAN Alpha0enolase OS = *Homo sapiens* GN = ENO1 PE = 1 SV = 2
17. >sp|P06748|NPM_HUMAN Nucleophosmin OS = *Homo sapiens* GN = NPM1 PE = 1 SV = 2
18. >sp|P06899|H2B1J_HUMAN Histone H2B type 10J OS = *Homo sapiens* GN = HIST1H2BJ PE = 1 SV = 3
19. >sp|P07437|TBB5_HUMAN Tubulin beta chain OS = *Homo sapiens* GN = TUBB PE = 1 SV = 2
20. >sp|P07737|PROF1_HUMAN Profilin01 OS = *Homo sapiens* GN = PFN1 PE = 1 SV = 2
21. >sp|P07900|HS90A_HUMAN Heat shock protein HSP 900alpha OS = *Homo sapiens* GN = HSP90AA1 PE = 1 SV = 5
22. >sp|P07910|HNRPC_HUMAN Heterogeneous nuclear ribonucleoproteins C1/C2 OS = *Homo sapiens* GN = HNRNPC PE = 1 SV = 4
23. >sp|P08238|HS90B_HUMAN Heat shock protein HSP 900beta OS = *Homo sapiens* GN = HSP90AB1 PE = 1 SV = 4
24. >sp|P08708|RS17_HUMAN 40S ribosomal protein S17 OS = *Homo sapiens* GN = RPS17 PE = 1 SV = 2

-continued

| | |
|---|---|
| 25. | >sp\|P08779\|K1C16_HUMAN Keratin, type I cytoskeletal 16 OS = *Homo sapiens* GN = KRT16 PE = 1 SV = 4 |
| 26. | >sp\|P09651\|ROA1_HUMAN Heterogeneous nuclear ribonucleoprotein A1 OS = *Homo sapiens* GN = HNRNPA1 PE = 1 SV = 5 |
| 27. | >sp\|P09651○2\|ROA1_HUMAN Isoform A10A of Heterogeneous nuclear ribonucleoprotein A1 OS = *Homo sapiens* GN = HNRNPA1 |
| 28. | >sp\|P0CW18\|PRS56_HUMAN Putative serine protease 56 OS = *Homo sapiens* GN = PRSS56 PE = 5 SV = 1 |
| 29. | >sp\|P13639\|EF2_HUMAN Elongation factor 2 OS = *Homo sapiens* GN = EEF2 PE = 1 SV = 4 |
| 30. | >sp\|P13645\|K1C10_HUMAN Keratin, type I cytoskeletal 10 OS = *Homo sapiens* GN = KRT10 PE = 1 SV = 6 |
| 31. | >sp\|P13647\|K2C5_HUMAN Keratin, type II cytoskeletal 5 OS = *Homo sapiens* GN = KRT5 PE = 1 SV = 3 |
| 32. | >sp\|P14174\|MIF_HUMAN Macrophage migration inhibitory factor OS = *Homo sapiens* GN = MIF PE = 1 SV = 4 |
| 33. | >sp\|P16402\|H13_HUMAN Histone H1.3 OS = *Homo sapiens* GN = HIST1H1D PE = 1 SV = 2 |
| 34. | >sp\|P17066\|HSP76_HUMAN Heat shock 70 kDa protein 6 OS = *Homo sapiens* GN = HSPA6 PE = 1 SV = 2 |
| 35. | >sp\|P22626\|ROA2_HUMAN Heterogeneous nuclear ribonucleoproteins A2/B1 OS = *Homo sapiens* GN = HNRNPA2B1 PE = 1 SV = 2 |
| 36. | >sp\|P23246\|SFPQ_HUMAN Splicing factor, proline0 and glutamine0rich OS = *Homo sapiens* GN = SFPQ PE = 1 SV = 2 |
| 37. | >sp\|P26038\|MOES_HUMAN Moesin OS = *Homo sapiens* GN = MSN PE = 1 SV = 3 |
| 38. | >sp\|P26599\|PTBP1_HUMAN Polypyrimidine tract0binding protein 1 OS = *Homo sapiens* GN = PTBP1 PE = 1 SV = 1 |
| 39. | >sp\|P35268\|RL22_HUMAN 60S ribosomal protein L22 OS = *Homo sapiens* GN = RPL22 PE = 1 SV = 2 |
| 40. | >sp\|P35527\|K1C9_HUMAN Keratin, type I cytoskeletal 9 OS = *Homo sapiens* GN = KRT9 PE = 1 SV = 3 |
| 41. | >sp\|P35908\|K22E_HUMAN Keratin, type II cytoskeletal 2 epidermal OS = *Homo sapiens* GN = KRT2 PE = 1 SV = 2 |
| 42. | >sp\|P38159\|HNRPG_HUMAN Heterogeneous nuclear ribonucleoprotein G OS = *Homo sapiens* GN = RBMX PE = 1 SV = 3 |
| 43. | >sp\|P38646\|GRP75_HUMAN Stress070 protein, mitochondrial OS = *Homo sapiens* GN = HSPA9 PE = 1 SV = 2 |
| 44. | >sp\|P46782\|RS5_HUMAN 40S ribosomal protein S5 OS = *Homo sapiens* GN = RPS5 PE = 1 SV = 4 |
| 45. | >sp\|P47914\|RL29_HUMAN 60S ribosomal protein L29 OS = *Homo sapiens* GN = RPL29 PE = 1 SV = 2 |
| 46. | >sp\|P49207\|RL34_HUMAN 60S ribosomal protein L34 OS = *Homo sapiens* GN = RPL34 PE = 1 SV = 3 |
| 47. | >sp\|P51685\|CCR8_HUMAN C0C chemokine receptor type 8 OS = *Homo sapiens* GN = CCR8 PE = 1 SV = 1 |
| 48. | >sp\|P52292\|IMA2_HUMAN Importin subunit alpha02 OS = *Homo sapiens* GN = KPNA2 PE = 1 SV = 1 |
| 49. | >sp\|P52597\|HNRPF_HUMAN Heterogeneous nuclear ribonucleoprotein F OS = *Homo sapiens* GN = HNRNPF PE = 1 SV = 3 |
| 50. | >sp\|P60709\|ACTB_HUMAN Actin, cytoplasmic 1 OS = *Homo sapiens* GN = ACTB PE = 1 SV = 1 |
| 51. | >sp\|P60842\|IF4A1_HUMAN Eukaryotic initiation factor 4A0I OS = *Homo sapiens* GN = EIF4A1 PE = 1 SV = 1 |
| 52. | >sp\|P61353\|RL27_HUMAN 60S ribosomal protein L27 OS = *Homo sapiens* GN = RPL27 PE = 1 SV = 2 |
| 53. | >sp\|P62166\|NCS1_HUMAN Neuronal calcium sensor 1 OS = *Homo sapiens* GN = NCS1 PE = 1 SV = 2 |
| 54. | >sp\|P62263\|RS14_HUMAN 40S ribosomal protein S14 OS = *Homo sapiens* GN = RPS14 PE = 1 SV = 3 |
| 55. | >sp\|P62269\|RS18_HUMAN 40S ribosomal protein S18 OS = *Homo sapiens* GN = RPS18 PE = 1 SV = 3 |
| 56. | >sp\|P62280\|RS11_HUMAN 40S ribosomal protein S11 OS = *Homo sapiens* GN = RPS11 PE = 1 SV = 3 |
| 57. | >sp\|P62424\|RL7A_HUMAN 60S ribosomal protein L7a OS = *Homo sapiens* GN = RPL7A PE = 1 SV = 2 |
| 58. | >sp\|P62829\|RL23_HUMAN 60S ribosomal protein L23 OS = *Homo sapiens* GN = RPL23 PE = 1 SV = 1 |
| 59. | >sp\|P62851\|RS25_HUMAN 40S ribosomal protein S25 OS = *Homo sapiens* GN = RPS25 PE = 1 SV = 1 |
| 60. | >sp\|P63173\|RL38_HUMAN 60S ribosomal protein L38 OS = *Homo sapiens* GN = RPL38 PE = 1 SV = 2 |
| 61. | >sp\|P63220\|RS21_HUMAN 40S ribosomal protein S21 OS = *Homo sapiens* GN = RPS21 PE = 1 SV = 1 |
| 62. | >sp\|P68104\|EF1A1_HUMAN Elongation factor 10alpha 1 OS = *Homo sapiens* GN = EEF1A1 PE = 1 SV = 1 |
| 63. | >sp\|P68363\|TBA1B_HUMAN Tubulin alpha01B chain OS = *Homo sapiens* GN = TUBA1B PE = 1 SV = 1 |
| 64. | >sp\|Q02878\|RL6_HUMAN 60S ribosomal protein L6 OS = *Homo sapiens* GN = RPL6 PE = 1 SV = 3 |
| 65. | >sp\|Q06830\|PRDX1_HUMAN Peroxiredoxin01 OS = *Homo sapiens* GN = PRDX1 PE = 1 SV = 1 |
| 66. | >sp\|Q07955\|SRSF1_HUMAN Serine/arginine0rich splicing factor 1 OS = *Homo sapiens* GN = SRSF1 PE = 1 SV = 2 |
| 67. | >sp\|Q08211\|DHX9_HUMAN ATP0dependent RNA helicase A OS = *Homo sapiens* GN = DHX9 PE = 1 SV = 4 |
| 68. | >sp\|Q08499○12\|PDE4D_HUMAN Isoform 12 of cAMP0specific 3',5'0cyclic phosphodiesterase 4D OS = *Homo sapiens* GN = PDE4D |
| 69. | >sp\|Q12905\|ILF2_HUMAN Interleukin enhancer0binding factor 2 OS = *Homo sapiens* GN = ILF2 PE = 1 SV = 2 |
| 70. | >sp\|Q12906\|ILF3_HUMAN Interleukin enhancer0binding factor 3 OS = *Homo sapiens* GN = ILF3 PE = 1 SV = 3 |
| 71. | >sp\|Q13263\|TIF1B_HUMAN Transcription intermediary factor 10beta OS = *Homo sapiens* GN = TRIM28 PE = 1 SV = 5 |
| 72. | >sp\|Q14669\|TRIPC_HUMAN Probable E3 ubiquitin0protein ligase TRIP12 OS = *Homo sapiens* GN = TRIP12 PE = 1 SV = 1 |
| 73. | >sp\|Q15233\|NONO_HUMAN Non0POU domain0containing octamer0binding protein OS = *Homo sapiens* GN = NONO PE = 1 SV = 4 |
| 74. | >sp\|Q69YZ2\|T200B_HUMAN Transmembrane protein 200B OS = *Homo sapiens* GN = TMEM200B PE = 2 SV = 1 |
| 75. | >sp\|Q7Z6W7\|DNJB7_HUMAN DnaJ homolog subfamily B member 7 OS = *Homo sapiens* GN = DNAJB7 PE = 2 SV = 2 |
| 76. | >sp\|Q86YZ3\|HORN_HUMAN Hornerin OS = *Homo sapiens* GN = HRNR PE = 1 SV = 2 |
| 77. | >sp\|Q8N9V7\|CC077_HUMAN Uncharacterized protein C3orf77 OS = *Homo sapiens* GN = C3orf77 PE = 2 SV = 3 |
| 78. | >sp\|Q8TF72\|SHRM3_HUMAN Protein Shroom3 OS = *Homo sapiens* GN = SHROOM3 PE = 1 SV = 2 |
| 79. | >sp\|Q92841○4\|DDX17_HUMAN Isoform 4 of Probable ATP0dependent RNA helicase DDX17 OS = *Homo sapiens* GN = DDX17 |
| 80. | >sp\|Q92945\|FUBP2_HUMAN Far upstream element0binding protein 2 OS = *Homo sapiens* GN = KHSRP PE = 1 SV = 4 |
| 81. | >sp\|Q96EP5\|DAZP1_HUMAN DAZ0associated protein 1 OS = *Homo sapiens* GN = DAZAP1 PE = 1 SV = 1 |
| 82. | >sp\|Q96MK3\|FA20A_HUMAN Protein FAM20A OS = *Homo sapiens* GN = FAM20A PE = 2 SV = 4 |
| 83. | >sp\|Q96PK6\|RBM14_HUMAN RNA0binding protein 14 OS = *Homo sapiens* GN = RBM14 PE = 1 SV = 2 |
| 84. | >sp\|Q96T51\|RUFY1_HUMAN RUN and FYVE domain0containing protein 1 OS = *Homo sapiens* GN = RUFY1 PE = 1 SV = 2 |
| 85. | >sp\|Q99ZW2\|CAS9_STRP1 CRISPR0associated endonuclease Cas9/Csn1 OS = Streptococcus pyogenes serotype M1 GN = cas9 PE = 1 SV = 1 |
| 86. | >sp\|Q9BV35\|SCMC3_HUMAN Calcium0binding mitochondrial carrier protein SCaMC03 OS = *Homo sapiens* GN = SLC25A23 PE = 1 SV = 2 |
| 87. | >sp\|Q9H4B6\|SAV1_HUMAN Protein salvador homolog 1 OS = *Homo sapiens* GN = SAV1 PE = 1 SV = 2 |
| 88. | >sp\|Q9NQ75\|CASS4_HUMAN Cas scaffolding protein family member 4 OS = *Homo sapiens* GN = CASS4 PE = 1 SV = 2 |
| 89. | >sp\|Q9NR30\|DDX21_HUMAN Nucleolar RNA helicase 2 OS = *Homo sapiens* GN = DDX21 PE = 1 SV = 5 |
| 90. | >sp\|Q9UHR6\|ZNHI2_HUMAN Zinc finger HIT domain0containing protein 2 OS = *Homo sapiens* GN = ZNHIT2 PE = 1 SV = 1 |
| 91. | >sp\|Q9UQ80\|PA2G4_HUMAN Proliferation0associated protein 2G4 OS = *Homo sapiens* GN = PA2G4 PE = 1 SV = 3 |
| 92. | >sp\|Q9Y266\|NUDC_HUMAN Nuclear migration protein nudC OS = *Homo sapiens* GN = NUDC PE = 1 SV = 1 |
| 93. | >tr\|A0AV56\|A0AV56_HUMAN SAFB protein OS = *Homo sapiens* GN = SAFB PE = 2 SV = 1 |
| 94. | >tr\|A3KPC7\|A3KPC7_HUMAN Histone H2A OS = *Homo sapiens* GN = HIST1H2AH PE = 2 SV = 1 |
| 95. | >tr\|A3R0T8\|A3R0T8_HUMAN Histone 1, H1e OS = *Homo sapiens* GN = HIST1H1E PE = 2 SV = 1 |
| 96. | >tr\|A4D1U3\|A4D1U3_HUMAN Single0stranded DNA binding protein 1 OS = *Homo sapiens* GN = SSBP1 PE = 2 SV = 1 |
| 97. | >tr\|A6NCD2\|A6NCD2_HUMAN Uncharacterized protein OS = *Homo sapiens* GN = CCT6A PE = 3 SV = 1 |
| 98. | >tr\|A6NE05\|A6NE05_HUMAN Uncharacterized protein OS = *Homo sapiens* GN = RPL26 PE = 3 SV = 1 |
| 99. | >tr\|A6NE09\|A6NE09_HUMAN Uncharacterized protein OS = *Homo sapiens* PE = 3 SV = 1 |
| 100. | >tr\|A6NIT8\|A6NIT8_HUMAN Uncharacterized protein OS = *Homo sapiens* GN = HNRNPL PE = 2 SV = 1 |
| 101. | >tr\|A6PWM2\|A6PWM2_HUMAN Cysteine0rich with EGF0like domains 2 (Fragment) OS = *Homo sapiens* GN = CRELD2 PE = 4 SV = 1 |

-continued

| | |
|---|---|
| 102. | >tr\|A8K220\|A8K220_HUMAN Peptidyl0prolyl cis0trans isomerase OS = *Homo sapiens* GN = PPIA PE = 1 SV = 1 |
| 103. | >tr\|A8K3Z8\|A8K3Z8_HUMAN RAN, member RAS oncogene family, isoform CRA_b OS = *Homo sapiens* GN = RAN PE = 1 SV = 1 |
| 104. | >tr\|A8K4C8\|A8K4C8_HUMAN 60S ribosomal protein L13 OS = *Homo sapiens* GN = RPL13 PE = 2 SV = 1 |
| 105. | >tr\|A8K4I2\|A8K4I2_HUMAN Histone 1, H1c OS = *Homo sapiens* GN = HIST1H1C PE = 2 SV = 1 |
| 106. | >tr\|A8K5I0\|A8K5I0_HUMAN Heat shock 70 kDa protein 1A OS = *Homo sapiens* GN = HSPA1A PE = 2 SV = 1 |
| 107. | >tr\|A8K7X6\|A8K7X6_HUMAN Poly(RC) binding protein 2, isoform CRA_b OS = *Homo sapiens* GN = PCBP2 PE = 2 SV = 1 |
| 108. | >tr\|A8MU27\|A8MU27_HUMAN Uncharacterized protein OS = *Homo sapiens* GN = SUMO3 PE = 4 SV = 1 |
| 109. | >tr\|A8MUB1\|A8MUB1_HUMAN Tubulin, alpha 1 (Testis specific), isoform CRA_a OS = *Homo sapiens* GN = TUBA4A PE = 2 SV = 1 |
| 110. | >tr\|A8MUD9\|A8MUD9_HUMAN Uncharacterized protein OS = *Homo sapiens* GN = RPL7 PE = 3 SV = 1 |
| 111. | >tr\|A8MV89\|A8MV89_HUMAN Uncharacterized protein OS = *Homo sapiens* GN = SPECC1 PE = 4 SV = 1 |
| 112. | >tr\|A8MWN8\|A8MWN8_HUMAN Uncharacterized protein OS = *Homo sapiens* GN = DLGAP1 PE = 2 SV = 1 |
| 113. | >tr\|A8MX84\|A8MX84_HUMAN Uncharacterized protein OS = *Homo sapiens* GN = SHMT1 PE = 3 SV = 1 |
| 114. | >tr\|A8MXP9\|A8MXP9_HUMAN Uncharacterized protein OS = *Homo sapiens* GN = MATR3 PE = 4 SV = 1 |
| 115. | >tr\|B0QYK0\|B0QYK0_HUMAN Ewing sarcoma breakpoint region 1 OS = *Homo sapiens* GN = EWSR1 PE = 4 SV = 1 |
| 116. | >tr\|B0YJC4\|B0YJC4_HUMAN Vimentin variant 3 OS = *Homo sapiens* GN = VIM PE = 3 SV = 1 |
| 117. | >tr\|B0ZBD0\|B0ZBD0_HUMAN 40S ribosomal protein S19 OS = *Homo sapiens* GN = RPS19 PE = 2 SV = 1 |
| 118. | >tr\|B1ALY2\|B1ALY2_HUMAN ROD1 regulator of differentiation 1 (S. pombe) (Fragment) OS = *Homo sapiens* GN = ROD1 PE = 4 SV = 1 |
| 119. | >tr\|B2R4P8\|B2R4P8_HUMAN HCG2016482, isoform CRA_b OS = *Homo sapiens* GN = hCG_2016482 PE = 2 SV = 1 |
| 120. | >tr\|B2R4P9\|B2R4P9_HUMAN Histone H3 OS = *Homo sapiens* GN = H3F3A PE = 2 SV = 1 |
| 121. | >tr\|B2R4R0\|B2R4R0_HUMAN Histone H4 OS = *Homo sapiens* GN = HIST1H4J PE = 3 SV = 1 |
| 122. | >tr\|B2R4S9\|B2R4S9_HUMAN Histone H2B OS = *Homo sapiens* GN = HIST1H2BC PE = 2 SV = 1 |
| 123. | >tr\|B2R6F3\|B2R6F3_HUMAN Splicing factor arginine/serine0rich 3 OS = *Homo sapiens* GN = SFRS3 PE = 2 SV = 1 |
| 124. | >tr\|B2RDW1\|B2RDW1_HUMAN Ribosomal protein S27a, isoform CRA_c OS = *Homo sapiens* GN = RPS27A PE = 2 SV = 1 |
| 125. | >tr\|B3KUP2\|B3KUP2_HUMAN RAN binding protein 1, isoform CRA_f OS = *Homo sapiens* GN = RANBP1 PE = 2 SV = 1 |
| 126. | >tr\|B3KVR1\|B3KVR1_HUMAN cDNA FLJ41124 fis, clone BRACE2014850, highly similar to Small nuclear ribonucleoprotein0associated protein N OS = *Homo sapiens* PE = 2 SV = 1 |
| 127. | >tr\|B3KX15\|B3KX15_HUMAN cDNA FLJ44468 fis, clone UTERU2026025, moderately similar to SPLICING FACTOR, ARGININE/SERINE0RICH 2 OS = *Homo sapiens* PE = 2 SV = 1 |
| 128. | >tr\|B4DE78\|B4DE78_HUMAN cDNA FLJ52141, highly similar to 140303 protein gamma OS = *Homo sapiens* PE = 2 SV = 1 |
| 129. | >tr\|B4DEP9\|B4DEP9_HUMAN cDNA FLJ57954, highly similar to 60S ribosomal protein L28 OS = *Homo sapiens* PE = 2 SV = 1 |
| 130. | >tr\|B4DF70\|B4DF70_HUMAN cDNA FLJ60461, highly similar to Peroxiredoxin02 (EC 1.11.1.15) OS = *Homo sapiens* PE = 2 SV = 1 |
| 131. | >tr\|B4DIW5\|B4DIW5_HUMAN cDNA FLJ55515, highly similar to Breast cancer anti0estrogen resistanceprotein 1 OS = Homo sapiens PE = 2 SV = 1 |
| 132. | >tr\|B4DLP4\|B4DLP4_HUMAN Ribosomal protein L15 OS = *Homo sapiens* PE = 2 SV = 1 |
| 133. | >tr\|B4DLR3\|B4DLR3_HUMAN cDNA FLJ54020, highly similar to Heterogeneous nuclear ribonucleoprotein U OS = Homo sapiens PE = 2 SV = 1 |
| 134. | >tr\|B4DM94\|B4DM94_HUMAN cDNA FLJ51502, highly similar to 60S ribosomal protein L18a OS = *Homo sapiens* PE = 2 SV = 1 |
| 135. | >tr\|B4DTG2\|B4DTG2_HUMAN cDNA FLJ56389, highly similar to Elongation factor 10gamma OS = *Homo sapiens* PE = 2 SV = 1 |
| 136. | >tr\|B4DTU0\|B4DTU0_HUMAN cDNA FLJ59249, highly similar to CD166 antigen OS = *Homo sapiens* PE = 2 SV = 1 |
| 137. | >tr\|B4DUQ1\|B4DUQ1_HUMAN cDNA FLJ54552, highly similar to Heterogeneous nuclear ribonucleoprotein K OS = Homo sapiens PE = 2 SV = 1 |
| 138. | >tr\|B4DVB8\|B4DVB8_HUMAN cDNA FLJ60076, highly similar to ELAV0like protein 1 OS = *Homo sapiens* PE = 2 SV = 1 |
| 139. | >tr\|B4DWC6\|B4DWC6_HUMAN cDNA FLJ52787, highly similar to Guanine nucleotide0binding protein subunitbeta 20like 1 OS = *Homo sapiens* PE = 2 SV = 1 |
| 140. | >tr\|B4DZX6\|B4DZX6_HUMAN cDNA FLJ54769, moderately similar to Ankyrin repeat and SOCS box protein 3 (ASB03) OS = Homo sapiens PE = 2 SV = 1 |
| 141. | >tr\|B4E102\|B4E102_HUMAN cDNA FLJ57766, moderately similar to Eukaryotic initiation factor 4A0I (EC 3.6.1.0) OS = Homo sapiens PE = 2 SV = 1 |
| 142. | >tr\|B4E335\|B4E335_HUMAN cDNA FLJ52842, highly similar to Actin, cytoplasmic 1 OS = *Homo sapiens* PE = 2 SV = 1 |
| 143. | >tr\|B5MCW2\|B5MCW2_HUMAN Uncharacterized protein OS = *Homo sapiens* GN = RPL3 PE = 3 SV = 1 |
| 144. | >tr\|B8ZZC9\|B8ZZC9_HUMAN Uncharacterized protein OS = *Homo sapiens* GN = CCT7 PE = 3 SV = 1 |
| 145. | >tr\|B8ZZL8\|B8ZZL8_HUMAN Heat shock 10 kDa protein 1 (Chaperonin 10), isoform CRA_b OS = *Homo sapiens* GN = HSPE1 PE = 3 SV = 1 |
| 146. | >tr\|C9J296\|C9J296_HUMAN Uncharacterized protein OS = *Homo sapiens* GN = LAMB1 PE = 4 SV = 1 |
| 147. | >tr\|C9J4W5\|C9J4W5_HUMAN Uncharacterized protein OS = *Homo sapiens* GN = EIF5A2 PE = 4 SV = 1 |
| 148. | >tr\|C9JA77\|C9JA77_HUMAN Uncharacterized protein OS = *Homo sapiens* GN = KRT13 PE = 4 SV = 1 |
| 149. | >tr\|C9JMU5\|C9JMU5_HUMAN Uncharacterized protein OS = *Homo sapiens* GN = DDX17 PE = 3 SV = 1 |
| 150. | >tr\|C9JNW5\|C9JNW5_HUMAN Ribosomal protein L24, isoform CRA_e OS = *Homo sapiens* GN = RPL24 PE = 4 SV = 1 |
| 151. | >tr\|D6R9B6\|D6R9B6_HUMAN Ribosomal protein S3A, isoform CRA_e OS = *Homo sapiens* GN = RPS3A PE = 4 SV = 1 |
| 152. | >tr\|D6R9P3\|D6R9P3_HUMAN Uncharacterized protein OS = *Homo sapiens* GN = HNRNPAB PE = 4 SV = 1 |
| 153. | >tr\|D6R9T0\|D6R9T0_HUMAN Uncharacterized protein OS = *Homo sapiens* GN = HNRNPH1 PE = 4 SV = 1 |
| 154. | >tr\|E5RGW4\|E5RGW4_HUMAN Uncharacterized protein OS = *Homo sapiens* GN = NPM1 PE = 4 SV = 1 |
| 155. | >tr\|E5RH77\|E5RH77_HUMAN Uncharacterized protein OS = *Homo sapiens* GN = RPS14 PE = 4 SV = 1 |
| 156. | >tr\|E5RIT9\|E5RIT9_HUMAN Uncharacterized protein OS = *Homo sapiens* GN = C2orf81 PE = 4 SV = 1 |
| 157. | >tr\|E7EMU2\|E7EMU2_HUMAN Uncharacterized protein OS = *Homo sapiens* GN = HMGA1 PE = 4 SV = 1 |
| 158. | >tr\|E7EP12\|E7EP12_HUMAN Uncharacterized protein OS = *Homo sapiens* GN = TTLL5 PE = 4 SV = 2 |
| 159. | >tr\|E7EPB3\|E7EPB3_HUMAN Uncharacterized protein OS = *Homo sapiens* GN = RPL14 PE = 4 SV = 1 |
| 160. | >tr\|E7EPW1\|E7EPW1_HUMAN Uncharacterized protein OS = *Homo sapiens* GN = GAPDH PE = 3 SV = 1 |
| 161. | >tr\|E7EQ64\|E7EQ64_HUMAN Uncharacterized protein OS = *Homo sapiens* GN = PRSS1 PE = 3 SV = 1 |
| 162. | >tr\|E7EQV3\|E7EQV3_HUMAN Uncharacterized protein OS = *Homo sapiens* GN = PABPC1 PE = 4 SV = 1 |
| 163. | >tr\|E7EQV7\|E7EQV7_HUMAN Uncharacterized protein OS = *Homo sapiens* GN = KRT6C PE = 3 SV = 2 |
| 164. | >tr\|E7ERL0\|E7ERL0_HUMAN Uncharacterized protein OS = *Homo sapiens* GN = NME1 PE = 3 SV = 1 |
| 165. | >tr\|E7ETA0\|E7ETA0_HUMAN Uncharacterized protein OS = *Homo sapiens* GN = YBX1 PE = 4 SV = 1 |
| 166. | >tr\|E7ETL9\|E7ETL9_HUMAN Uncharacterized protein OS = *Homo sapiens* GN = DDX5 PE = 3 SV = 1 |
| 167. | >tr\|E7ETM1\|E7ETM1_HUMAN Uncharacterized protein OS = *Homo sapiens* GN = KNDC1 PE = 4 SV = 1 |
| 168. | >tr\|E7EU23\|E7EU23_HUMAN Uncharacterized protein OS = *Homo sapiens* GN = GDI2 PE = 4 SV = 1 |
| 169. | >tr\|E7EU87\|E7EU87_HUMAN Uncharacterized protein OS = *Homo sapiens* GN = KRT5 PE = 3 SV = 1 |
| 170. | >tr\|E7EUT4\|E7EUT4_HUMAN Glyceraldehyde030phosphate dehydrogenase OS = *Homo sapiens* GN = GAPDH PE = 3 SV = 1 |
| 171. | >tr\|E7EW01\|E7EW01_HUMAN Uncharacterized protein OS = *Homo sapiens* GN = RPL8 PE = 4 SV = 1 |

-continued

| | |
|---|---|
| 172. | >tr\|E7EWF1\|E7EWF1_HUMAN Uncharacterized protein OS = *Homo sapiens* GN = RPL4 PE = 4 SV = 1 |
| 173. | >tr\|E7EX81\|E7EX81_HUMAN Uncharacterized protein OS = *Homo sapiens* GN = NCL PE = 4 SV = 1 |
| 174. | >tr\|E9KL35\|E9KL35_HUMAN Epididymis tissue sperm binding protein Li 3a OS = *Homo sapiens* PE = 2 SV = 1 |
| 175. | >tr\|E9KL39\|E9KL39_HUMAN Epididymis tissue sperm binding protein Li 7e OS = *Homo sapiens* PE = 2 SV = 1 |
| 176. | >tr\|E9PBS1\|E9PBS1_HUMAN Uncharacterized protein OS = *Homo sapiens* GN = PAICS PE = 4 SV = 1 |
| 177. | >tr\|E9PDB2\|E9PDB2_HUMAN Uncharacterized protein OS = *Homo sapiens* GN = MDH2 PE = 4 SV = 1 |
| 178. | >tr\|E9PFH8\|E9PFH8_HUMAN Uncharacterized protein OS = *Homo sapiens* GN = SSB PE = 4 SV = 1 |
| 179. | >tr\|E9PFU1\|E9PFU1_HUMAN Uncharacterized protein OS = *Homo sapiens* GN = PDCD6IP PE = 4 SV = 1 |
| 180. | >tr\|E9PK25\|E9PK25_HUMAN Uncharacterized protein OS = *Homo sapiens* GN = CFL1 PE = 4 SV = 1 |
| 181. | >tr\|E9PKE3\|E9PKE3_HUMAN Uncharacterized protein OS = *Homo sapiens* GN = HSPA8 PE = 3 SV = 1 |
| 182. | >tr\|E9PL09\|E9PL09_HUMAN Uncharacterized protein OS = *Homo sapiens* GN = RPS3 PE = 3 SV = 1 |
| 183. | >tr\|E9PM36\|E9PM36_HUMAN Uncharacterized protein OS = *Homo sapiens* GN = RPS2 PE = 3 SV = 1 |
| 184. | >tr\|E9PS50\|E9PS50_HUMAN Uncharacterized protein OS = *Homo sapiens* GN = RPS13 PE = 4 SV = 1 |
| 185. | >tr\|F2Z388\|F2Z388_HUMAN Uncharacterized protein OS = *Homo sapiens* GN = RPL35 PE = 4 SV = 1 |
| 186. | >tr\|F5GWE6\|F5GWE6_HUMAN Uncharacterized protein OS = *Homo sapiens* GN = CPSF7 PE = 4 SV = 1 |
| 187. | >tr\|F5GWQ7\|F5GWQ7_HUMAN Uncharacterized protein OS = *Homo sapiens* GN = TAF15 PE = 4 SV = 1 |
| 188. | >tr\|F5GXA5\|F5GXA5_HUMAN Uncharacterized protein OS = *Homo sapiens* GN = DHX9 PE = 4 SV = 1 |
| 189. | >tr\|F5GXQ0\|F5GXQ0_HUMAN Uncharacterized protein OS = *Homo sapiens* GN = BROX PE = 4 SV = 1 |
| 190. | >tr\|F5GYZ3\|F5GYZ3_HUMAN Uncharacterized protein OS = *Homo sapiens* GN = NONO PE = 4 SV = 1 |
| 191. | >tr\|F5H5W3\|F5H5W3_HUMAN Uncharacterized protein OS = *Homo sapiens* GN = CCT4 PE = 4 SV = 1 |
| 192. | >tr\|F5H7Z1\|F5H7Z1_HUMAN Uncharacterized protein OS = *Homo sapiens* GN = HNRNPM PE = 4 SV = 1 |
| 193. | >tr\|F5H897\|F5H897_HUMAN Uncharacterized protein OS = *Homo sapiens* GN = TRAP1 PE = 4 SV = 1 |
| 194. | >tr\|Q8NE73\|Q8NE73_HUMAN ENTPD4 protein OS = *Homo sapiens* GN = ENTPD4 PE = 2 SV = 1 |
| 195. | 140303 protein beta/alpha (Protein 1054) (Protein kinase C inhibitor protein 1) (KCIP01) [Cleaved into: 140303 protein beta/alpha, N0terminally processed] |
| 196. | 140303 protein epsilon (140303E) |
| 197. | 140303 protein gamma (Protein kinase C inhibitor protein 1) (KCIP01) [Cleaved into: 140303 protein gamma, N0terminally processed] |
| 198. | 140303 protein sigma (Epithelial cell marker protein 1) (Stratifin) |
| 199. | 140303 protein theta (140303 protein T0cell) (140303 protein tau) (Protein HS1) |
| 200. | 40S ribosomal protein S10 (Small ribosomal subunit protein eS10) |
| 201. | 40S ribosomal protein S11 (Small ribosomal subunit protein uS17) |
| 202. | 40S ribosomal protein S12 (Small ribosomal subunit protein eS12) |
| 203. | 40S ribosomal protein S13 (Small ribosomal subunit protein uS15) |
| 204. | 40S ribosomal protein S14 |
| 205. | 40S ribosomal protein S15 (RIG protein) (Small ribosomal subunit protein uS19) |
| 206. | 40S ribosomal protein S16 (Small ribosomal subunit protein uS9) |
| 207. | 40S ribosomal protein S17 (Small ribosomal subunit protein eS17) |
| 208. | 40S ribosomal protein S18 (Ke03) (Ke3) (Small ribosomal subunit protein uS13) |
| 209. | 40S ribosomal protein S19 (Ribosomal protein S19, isoform CRA_a) (cDNA, FLJ92047, *Homo sapiens* ribosomal protein S19 (RPS19), mRNA) |
| 210. | 40S ribosomal protein S2 (40S ribosomal protein S4) (Protein LLRep3) (Small ribosomal subunit protein uS5) |
| 211. | 40S ribosomal protein S25 (Small ribosomal subunit protein eS25) |
| 212. | 40S ribosomal protein S26 (Small ribosomal subunit protein eS26) |
| 213. | 40S ribosomal protein S27 |
| 214. | 40S ribosomal protein S27 (Metallopan0stimulin 1) (MPS01) (Small ribosomal subunit protein eS27) |
| 215. | 40S ribosomal protein S3 |
| 216. | 40S ribosomal protein S3 (EC 4.2.99.18) (Small ribosomal subunit protein uS3) |
| 217. | 40S ribosomal protein S30 |
| 218. | 40S ribosomal protein S3a (Small ribosomal subunit protein eS1) (v0fos transformation effector protein) (Fte01) |
| 219. | 40S ribosomal protein S4 |
| 220. | 40S ribosomal protein S5 (Small ribosomal subunit protein uS7) [Cleaved into: 40S ribosomal protein S5, N0terminally processed] |
| 221. | 40S ribosomal protein S6 |
| 222. | 40S ribosomal protein S7 |
| 223. | 40S ribosomal protein S8 (Small ribosomal subunit protein eS8) |
| 224. | 60 kDa heat shock protein, mitochondrial (EC 3.6.4.9) (60 kDa chaperonin) (Chaperonin 60) (CPN60) (Heat shock protein 60) (HSP060) (Hsp60) (HuCHA60) (Mitochondrial matrix protein P1) (P60 lymphocyte protein) |
| 225. | 60S acidic ribosomal protein P0 (60S ribosomal protein L10E) (Large ribosomal subunit protein uL10) |
| 226. | 60S acidic ribosomal protein P2 (Large ribosomal subunit protein P2) (Renal carcinoma antigen NY0REN044) |
| 227. | 60S ribosomal protein L10a (CSA019) (Large ribosomal subunit protein uL1) (Neural precursor cell expressed developmentally down0regulated protein 6) (NEDD06) |
| 228. | 60S ribosomal protein L11 (CLL0associated antigen KW012) (Large ribosomal subunit protein uL5) |
| 229. | 60S ribosomal protein L12 (Large ribosomal subunit protein uL11) |
| 230. | 60S ribosomal protein L13 |
| 231. | 60S ribosomal protein L13a (23 kDa highly basic protein) (Large ribosomal subunit protein uL13) |
| 232. | 60S ribosomal protein L14 |
| 233. | 60S ribosomal protein L15 (Large ribosomal subunit protein eL15) |
| 234. | 60S ribosomal protein L17 (60S ribosomal protein L23) (Large ribosomal subunit protein uL22) (PD01) |
| 235. | 60S ribosomal protein L18 (Large ribosomal subunit protein eL18) |
| 236. | 60S ribosomal protein L18a (Large ribosomal subunit protein eL20) |
| 237. | 60S ribosomal protein L19 (Large ribosomal subunit protein eL19) |
| 238. | 60S ribosomal protein L21 (Large ribosomal subunit protein eL21) |
| 239. | 60S ribosomal protein L22 (EBER0associated protein) (EAP) (Epstein0Barr virus small RNA0associated protein) (Heparin0binding protein HBp15) (Large ribosomal subunit protein eL22) |
| 240. | 60S ribosomal protein L23 |
| 241. | 60S ribosomal protein L23a (Ribosomal protein L23a, isoform CRA_a) |
| 242. | 60S ribosomal protein L24 (Ribosomal protein L24, isoform CRA_e) |
| 243. | 60S ribosomal protein L27 (Large ribosomal subunit protein eL27) |
| 244. | 60S ribosomal protein L27a |

-continued 245. 60S ribosomal protein L29 (Cell surface heparin0binding protein HIP) (Large ribosomal subunit protein eL29)
246. 60S ribosomal protein L30 (Fragment)
247. 60S ribosomal protein L31 (cDNA FLJ57527, highly similar to 60S ribosomal protein L31)
248. 60S ribosomal protein L34 (Large ribosomal subunit protein eL34)
249. 60S ribosomal protein L35
250. 60S ribosomal protein L36 (Large ribosomal subunit protein eL36)
251. 60S ribosomal protein L38 (Large ribosomal subunit protein eL38)
252. 60S ribosomal protein L6 (Large ribosomal subunit protein eL6) (Neoplasm0related protein C140) (Tax0responsive enhancer element0binding protein 107) (TaxREB107)
253. 60S ribosomal protein L7 (Large ribosomal subunit protein uL30)
254. 60S ribosomal protein L7a (Large ribosomal subunit protein eL8) (PLA0X polypeptide) (Surfeit locus protein 3)
255. 60S ribosomal protein L9 (Fragment)
256. 78 kDa glucose0regulated protein (GRP078) (Endoplasmic reticulum lumenal Ca(2+)0binding protein grp78) (Heat shock 70 kDa protein 5) (Immunoglobulin heavy chain0binding protein) (BiP)
257. AarF domain containing kinase 2 (AarF domain containing kinase 2, isoform CRA_a)
258. Acid ceramidase
259. Actin, alpha 2, smooth muscle, aorta (Actin, alpha 2, smooth muscle, aorta, isoform CRA_a)
260. Actin0related protein 2/3 complex subunit 3 (Arp2/3 complex 21 kDa subunit) (p210ARC)
261. Activated RNA polymerase II transcriptional coactivator p15 (Positive cofactor 4) (PC4) (SUB1 homolog) (p14)
262. Adenosylhomocysteinase (AdoHcyase) (EC 3.3.1.1) (S0adenosyl0L0homocysteine hydrolase)
263. Aldo0keto reductase family 1 member C2 (cDNA FLJ52680, highly similar to Aldo0keto reductase family 1 member C2 (EC 1.0.0.0))
264. Alpha020macroglobulin0like protein 1 (C3 and PZP0like alpha020macroglobulin domain0containing protein 9)
265. Alpha0actinin04 (Non0muscle alpha0actinin 4)
266. Alpha0enolase (EC 4.2.1.11) (20phospho0D0glycerate hydro0lyase) (C0myc promoter0binding protein) (Enolase 1) (MBP01) (MPB01) (Non0neural enolase) (NNE) (Phosphopyruvate hydratase) (Plasminogen0binding protein)
267. Ankyrin repeat domain0containing protein 20A4
268. Annexin A1 (Annexin I) (Annexin01) (Calpactin II) (Calpactin02) (Chromobindin09) (Lipocortin I) (Phospholipase A2 inhibitory protein) (p35)
269. Annexin A2 (Annexin II) (Annexin02) (Calpactin I heavy chain) (Calpactin01 heavy chain) (Chromobindin08) (Lipocortin II) (Placental anticoagulant protein IV) (PAP0IV) (Protein I) (p36)
270. Annexin A7 (Annexin VII) (Annexin07) (Synexin)
271. Apoptotic chromatin condensation inducer in the nucleus
272. Arachidonate 120lipoxygenase, 12R0type (12R0L0X) (12R0lipoxygenase) (EC 1.13.11.0) (Epidermis0type lipoxygenase 12)
273. Arginase01 (EC 3.5.3.1) (Liver0type arginase) (Type I arginase)
274. Arginine and glutamate0rich protein 1
275. ATP synthase subunit alpha, mitochondrial
276. ATP0dependent RNA helicase DDX39A (EC 3.6.4.13) (DEAD box protein 39) (Nuclear RNA helicase URH49)
277. ATP0dependent RNA helicase DDX3X (EC 3.6.4.13) (DEAD box protein 3, X0chromosomal) (DEAD box, X isoform) (Helicase0like protein 2) (HLP2)
278. Bifunctional glutamate/proline00tRNA ligase (Bifunctional aminoacyl0tRNA synthetase) (Cell proliferation0inducing gene 32 protein) (Glutamatyl0prolyl0tRNA synthetase) [Includes: Glutamate00tRNA ligase (EC 6.1.1.17) (Glutamyl0tRNA synthetase) (GluRS); Proline00tRNA ligase (EC 6.1.1.15) (Prolyl0tRNA synthetase)]
279. C0type lysozyme (Lysozyme) (EC 3.2.1.17) (Lysozyme (Renal amyloidosis), isoform CRA_a) (Lysozyme F1) (cDNA, FLJ92040, Homo sapiens lysozyme (renal amyloidosis) (LYZ), mRNA)
280. Calmodulin0like protein 3 (CaM0like protein) (CLP) (Calmodulin0related protein NB01)
281. Calmodulin0like protein 5 (Calmodulin0like skin protein)
282. Calpain small subunit 1 (CSS1) (Calcium0activated neutral proteinase small subunit) (CANP small subunit) (Calcium0dependent protease small subunit) (CDPS) (Calcium0dependent protease small subunit 1) (Calpain regulatory subunit)
283. Calpain01 catalytic subunit (Fragment)
284. cAMP0specific 3',5'0cyclic phosphodiesterase 4D (EC 3.1.4.53) (DPDE3) (PDE43)
285. Carboxypeptidase A4 (Carboxypeptidase A4, isoform CRA_a) (cDNA FLJ75086, highly similar to Homo sapiens carboxypeptidase A4, mRNA)
286. Cas scaffolding protein family member 4 (HEF0like protein) (HEF10EFS0p130Cas0like protein) (HEPL)
287. Caspase 14, apoptosis0related cysteine peptidase (Caspase014) (cDNA, FLJ94644, Homo sapiens caspase 14, apoptosis0related cysteine protease(CASP14), mRNA)
288. Catalase (EC 1.11.1.6)
289. Cathepsin D (EC 3.4.23.5) [Cleaved into: Cathepsin D light chain; Cathepsin D heavy chain]
290. cDNA FLJ32530 fis, clone SMINT2000185, highly similar to TRANSKETOLASE (EC 2.2.1.1)
291. cDNA FLJ51502, highly similar to 60S ribosomal protein L18a
292. cDNA FLJ51535, highly similar to Phosphatidylethanolamine0binding protein 1
293. cDNA FLJ52842, highly similar to Actin, cytoplasmic 1
294. cDNA FLJ53122, highly similar to ATP0dependent RNA helicase DDX3Y (EC 3.6.1.0)
295. cDNA FLJ53160, highly similar to Zyxin
296. cDNA FLJ53425, highly similar to Far upstream element0binding protein 1
297. cDNA FLJ54020, highly similar to Heterogeneous nuclear ribonucleoprotein U
298. cDNA FLJ54020, highly similar to Heterogeneous nuclear ribonucleoprotein U
299. cDNA FLJ54552, highly similar to Heterogeneous nuclear ribonucleoprotein K
300. cDNA FLJ58049, highly similar to RNA0binding protein FUS
301. cDNA FLJ60058, highly similar to Myosin light chain 1, slow0twitch muscle A isoform
302. cDNA FLJ60461, highly similar to Peroxiredoxin02 (EC 1.11.1.15)
303. Chloride intracellular channel protein 1 (Chloride channel ABP) (Nuclear chloride ion channel 27) (NCC27) (Regulatory nuclear chloride ion channel protein) (hRNCC)
304. Chromatin target of PRMT1 protein (Friend of PRMT1 protein) (Small arginine0 and glycine0rich protein) (SRAG)
305. Chromobox homolog 3 (HP1 gamma homolog Drosophila) (Chromobox homolog 3 (HP1 gamma homolog Drosophila), isoform CRA_a) (Coiled0coil domain containing 32, isoform CRA_c)
306. Clathrin heavy chain 1 (Clathrin heavy chain on chromosome 17) (CLH017)
307. Cofilin01
308. Copine03 (Copine III)
309. Corneodesmosin

| | |
|---|---|
| 310. | Cornifin0B (14.9 kDa pancornulin) (Small proline0rich protein IB) (SPR0IB) |
| 311. | CRISPR0associated endonuclease Cas9/Csn1 (EC 3.1.0.0) (SpCas9) (SpyCas9) |
| 312. | Cyclin0dependent kinase 1 (Fragment) |
| 313. | Cystatin0A |
| 314. | Cystatin0A (Cystatin0AS) (Stefin0A) [Cleaved into: Cystatin0A, N0terminally processed] |
| 315. | Cystatin0M (Cystatin06) (Cystatin0E) |
| 316. | Desmocollin01 (Cadherin family member 1) (Desmosomal glycoprotein 2/3) (DG2/DG3) |
| 317. | Desmocollin03 (Cadherin family member 3) (Desmocollin04) (HT0CP) |
| 318. | Desmoglein01 (Cadherin family member 4) (Desmosomal glycoprotein 1) (DG1) (DGI) (Pemphigus foliaceus antigen) |
| 319. | Desmoplakin (DP) (250/210 kDa paraneoplastic pemphigus antigen) |
| 320. | DNA topoisomerase (EC 5.99.1.2) |
| 321. | DNA topoisomerase 1 (EC 5.99.1.2) (DNA topoisomerase I) |
| 322. | DnaJ homolog subfamily A member 1 (DnaJ protein homolog 2) (HSDJ) (Heat shock 40 kDa protein 4) (Heat shock protein J2) (HSJ02) (Human DnaJ protein 2) (hDj02) |
| 323. | Doublesex0 and mab030related transcription factor A1 |
| 324. | Elongation factor 10alpha 1 (EF010alpha01) (Elongation factor Tu) (EFOTu) (Eukaryotic elongation factor 1 A01) (eEF1A01) (Leukocyte receptor cluster member 7) |
| 325. | Elongation factor 10beta (EF010beta) |
| 326. | Elongation factor 10delta (Fragment) |
| 327. | Elongation factor 2 (EF02) |
| 328. | Elongation factor Tu, mitochondrial (EFOTu) (P43) |
| 329. | Enhancer of rudimentary homolog |
| 330. | Envoplakin (210 kDa cornified envelope precursor protein) (210 kDa paraneoplastic pemphigus antigen) (p210) |
| 331. | Epididymis luminal protein 112 (Ribosomal protein S27a, isoform CRA_c) (cDNA, FLJ96793, *Homo sapiens* ribosomal protein S27a (RPS27A), mRNA) |
| 332. | Epididymis luminal protein 4 (Epididymis secretory protein Li 3) (Epididymis secretory protein Li 93) (Tyrosine 30monooxygenase/tryptophan 50monooxygenase activation protein zeta polypeptide) (Tyrosine 30monooxygenase/tryptophan 50monooxygenase activation protein, zeta polypeptide, isoform CRA_a) |
| 333. | Epididymis secretory protein Li 103 (Heat shock 70 kDa protein 1A) (Heat shock 70 kDa protein 1B) (cDNA FLJ75127, highly similar to *Homo sapiens* heat shock 70 kDa protein 1A, mRNA) |
| 334. | Eukaryotic initiation factor 4A0I (eIF04A0I) (eIF4A0I) (EC 3.6.4.13) (ATP0dependent RNA helicase eIF4A01) |
| 335. | Eukaryotic initiation factor 4A0III (eIF04A0III) (eIF4A0III) (EC 3.6.4.13) (ATP0dependent RNA helicase DDX48) (ATP0dependent RNA helicase eIF4A03) (DEAD box protein 48) (Eukaryotic initiation factor 4A0like NUK034) (Eukaryotic translation initiation factor 4A isoform 3) (Nuclear matrix protein 265) (NMP 265) (hNMP 265) [Cleaved into: Eukaryotic initiation factor 4A0III, N0terminally processed] |
| 336. | Eukaryotic translation initiation factor 1A, Y0chromosomal |
| 337. | Eukaryotic translation initiation factor 2 subunit 2 (Eukaryotic translation initiation factor 2 subunit beta) (eIF020beta) |
| 338. | Eukaryotic translation initiation factor 3 subunit E (eIF3e) (Eukaryotic translation initiation factor 3 subunit 6) (eIF03 p48) |
| 339. | Eukaryotic translation initiation factor 3 subunit G (eIF3g) (Eukaryotic translation initiation factor 3 RNA0binding subunit) (eIF03 RNA0binding subunit) (Eukaryotic translation initiation factor 3 subunit 4) (eIF030delta) (eIF3 p42) (eIF3 p44) |
| 340. | Eukaryotic translation initiation factor 3 subunit I (eIF3i) (Eukaryotic translation initiation factor 3 subunit 2) (TGF0beta receptor0interacting protein 1) (TRIP01) (eIF030beta) (eIF3 p36) |
| 341. | Eukaryotic translation initiation factor 5A01 (eIF05A01) (eIF5A1) (Eukaryotic initiation factor 5A isoform 1) (eIF05A) (Rev0binding factor) (eIF04D) |
| 342. | Eukaryotic translation initiation factor 5B (eIF05B) (EC 3.6.5.3) (Translation initiation factor IF02) |
| 343. | Extracellular glycoprotein lacritin |
| 344. | Extracellular matrix protein 1 (Secretory component p85) |
| 345. | F0box only protein 50 (NCC receptor protein 1 homolog) (NCCRP01) (Non0specific cytotoxic cell receptor protein 1 homolog) |
| 346. | Far upstream element0binding protein 2 (FUSE0binding protein 2) (KH type0splicing regulatory protein) (KSRP) (p75) |
| 347. | Fascin (55 kDa actin0bundling protein) (Singed0like protein) (p55) |
| 348. | Fatty acid binding protein 5 (Psoriasis0associated) |
| 349. | Fatty acid synthase (EC 2.3.1.85) [Includes: [Acyl0carrier0protein] S0acetyltransferase (EC 2.3.1.38); [Acyl0carrier0protein] S0malonyltransferase (EC 2.3.1.39); 30oxoacyl0[acyl0carrier0protein] synthase (EC 2.3.1.41); 30oxoacyl0[acyl0carrier0protein] reductase (EC 1.1.1.100); 30hydroxyacyl0[acyl0carrier0protein] dehydratase (EC 4.2.1.59); Enoyl0[acyl0carrier0protein] reductase (EC 1.3.1.39); Oleoyl0[acyl0carrier0protein] hydrolase (EC 3.1.2.14)] |
| 350. | Ferric0chelate reductase 1 (EC 1.0.0.0) (Stromal cell0derived receptor 2) (SDR02) |
| 351. | Filaggrin |
| 352. | Filaggrin02 (FLG02) (Intermediate filament0associated and psoriasis0susceptibility protein) (Ifapsoriasin) |
| 353. | Filamin A |
| 354. | Fragile X mental retardation syndrome0related protein 2 |
| 355. | Fructose0bisphosphate aldolase A (EC 4.1.2.13) (Lung cancer antigen NY0LU01) (Muscle0type aldolase) |
| 356. | Galectin03 (Gal03) (35 kDa lectin) (Carbohydrate0binding protein 35) (CBP 35) (Galactose0specific lectin 3) (Galactoside0binding protein) (GALBP) (IgE0binding protein) (L031) (Laminin0binding protein) (Lectin L029) (Mac02 antigen) |
| 357. | Galectin07 (Gal07) (HKL014) (PI7) (p530induced gene 1 protein) |
| 358. | Gamma0glutamylcyclotransferase |
| 359. | Gamma0tubulin complex component 6 |
| 360. | Gasdermin0A (Gasdermin01) |
| 361. | Glutaredoxin01 (Thioltransferase01) (TTase01) |
| 362. | Glutathione S0transferase P |
| 363. | Glutathione S0transferase P (EC 2.5.1.18) (GST class0pi) (GSTP101) |
| 364. | Glyceraldehyde030phosphate dehydrogenase (GAPDH) (EC 1.2.1.12) (Peptidyl0cysteine S0nitrosylase GAPDH) (EC 2.6.99.0) |
| 365. | Golgin subfamily A member 3 (Golgi complex0associated protein of 170 kDa) (GCP170) (Golgin0160) |
| 366. | HCG1994130, isoform CRA_a (cDNA FLJ30359 fis, clone BRACE2007760, highly similar to 40S RIBOSOMAL PROTEIN S15A) (cDNA, FLJ92249, *Homo sapiens* ribosomal protein S15a (RPS15A), mRNA) |
| 367. | Heat shock 70 kDa protein 6 (Heat shock 70 kDa protein B') |
| 368. | Heat shock cognate 71 kDa protein (Fragment) |
| 369. | Heat shock cognate 71 kDa protein (Heat shock 70 kDa protein 8) (Lipopolysaccharide0associated protein 1) (LAP01) (LPS0associated protein 1) |

-continued

| | |
|---|---|
| 370. | Heat shock protein beta01 (HspB1) (28 kDa heat shock protein) (Estrogen0regulated 24 kDa protein) (Heat shock 27 kDa protein) (HSP 27) (Stress0responsive protein 27) (SRP27) |
| 371. | Heat shock protein HSP 900alpha (Heat shock 86 kDa) (HSP 86) (HSP86) (Lipopolysaccharide0associated protein 2) (LAP02) (LPS0associated protein 2) (Renal carcinoma antigen NY0REN038) |
| 372. | Heat shock protein HSP 900beta (HSP 90) (Heat shock 84 kDa) (HSP 84) (HSP84) |
| 373. | Heterogeneous nuclear ribonucleoprotein A0 (hnRNP A0) |
| 374. | Heterogeneous nuclear ribonucleoprotein A1 (hnRNP A1) (Helix0destabilizing protein) (Single0strand RNA0binding protein) (hnRNP core protein A1) [Cleaved into: Heterogeneous nuclear ribonucleoprotein A1, N0terminally processed] |
| 375. | Heterogeneous nuclear ribonucleoprotein A3, isoform CRA_a (cDNA FLJ52659, highly similar to Heterogeneous nuclear ribonucleoprotein A3) (cDNA, FLJ79333, highly similar to Heterogeneous nuclear ribonucleoprotein A3) |
| 376. | Heterogeneous nuclear ribonucleoprotein D0like (hnRNP D0like) (hnRNP DL) (AU0rich element RNA0binding factor) (JKT410binding protein) (Protein laAUF1) |
| 377. | Heterogeneous nuclear ribonucleoprotein F (hnRNP F) (Nucleolin0like protein mcs9401) [Cleaved into: Heterogeneous nuclear ribonucleoprotein F, N0terminally processed] |
| 378. | Heterogeneous nuclear ribonucleoprotein H |
| 379. | Heterogeneous nuclear ribonucleoprotein H (Fragment) |
| 380. | Heterogeneous nuclear ribonucleoprotein H3 (hnRNP H3) (Heterogeneous nuclear ribonucleoprotein 2H9) (hnRNP 2H9) |
| 381. | Heterogeneous nuclear ribonucleoprotein L (hnRNP L) |
| 382. | Heterogeneous nuclear ribonucleoprotein M (hnRNP M) |
| 383. | Heterogeneous nuclear ribonucleoprotein Q (hnRNP Q) (Glycine0 and tyrosine0rich RNA0binding protein) (GRY0RBP) (NS10associated protein 1) (Synaptotagmin0binding cytoplasmic RNA0interacting protein) |
| 384. | Heterogeneous nuclear ribonucleoproteins A2/B1 (hnRNP A2/B1) |
| 385. | Heterogeneous nuclear ribonucleoproteins C1/C2 (hnRNP C1/C2) |
| 386. | Histone 1, H1e (Histone H1e) |
| 387. | Histone deacetylase complex subunit SAP18 (18 kDa Sin30associated polypeptide) (2H0R0202) (Cell growth0inhibiting gene 38 protein) (Sin30associated polypeptide p18) |
| 388. | Histone H1.5 (Histone H1a) (Histone H1b) (Histone H1s03) |
| 389. | Histone H2A |
| 390. | Histone H2B |
| 391. | Histone H2B type 10J (Histone H2B.1) (Histone H2B.r) (H2B/r) |
| 392. | Histone H2B type 100 (Histone H2B.2) (Histone H2B.n) (H2B/n) |
| 393. | Histone H3 |
| 394. | Histone H4 |
| 395. | Histone0binding protein RBBP7 |
| 396. | Hornerin |
| 397. | Hsp90 co0chaperone Cdc37 (Hsp90 chaperone protein kinase0targeting subunit) (p50Cdc37) [Cleaved into: Hsp90 co0chaperone Cdc37, N0terminally processed] |
| 398. | Hydroperoxide isomerase ALOXE3 (EC 5.4.4.7) (Epidermis0type lipoxygenase 3) (Epidermal L0X03) (e0L0X03) (eL0X03) (Hydroperoxy icosatetraenoate dehydratase) (EC 4.2.1.152) |
| 399. | Immunoglobulin heavy constant alpha 1 (Ig alpha01 chain C region) (Ig alpha01 chain C region BUR) (Ig alpha01 chain C region TRO) |
| 400. | Immunoglobulin heavy constant gamma 1 (Ig gamma01 chain C region) (Ig gamma01 chain C region EU) (Ig gamma01 chain C region KOL) (Ig gamma01 chain C region NIE) |
| 401. | Immunoglobulin J chain (Fragment) |
| 402. | Immunoglobulin kappa constant (Ig kappa chain C region) (Ig kappa chain C region AG) (Ig kappa chain C region CUM) (Ig kappa chain C region EU) (Ig kappa chain C region OU) (Ig kappa chain C region ROY) (Ig kappa chain C region TI) |
| 403. | Importin subunit beta01 (Importin090) (Karyopherin subunit beta01) (Nuclear factor p97) (Pore targeting complex 97 kDa subunit) (PTAC97) |
| 404. | Inorganic pyrophosphatase (EC 3.6.1.1) (Pyrophosphate phospho0hydrolase) (PPase) |
| 405. | Insulin0degrading enzyme (EC 3.4.24.56) (Abeta0degrading protease) (Insulin protease) (Insulinase) (Insulysin) |
| 406. | Insulin0like growth factor 2 mRNA0binding protein 1 (IGF2 mRNA0binding protein 1) (IMP01) (IMP1) (Coding region determinant0binding protein) (CRD0BP) (IGF0II mRNA0binding protein 1) (VICKZ family member 1) (Zipcode0binding protein 1) (ZBP01) |
| 407. | Interleukin enhancer0binding factor 2 (Nuclear factor of activated T0cells 45 kDa) |
| 408. | Involucrin |
| 409. | Isoleucine00tRNA ligase, cytoplasmic (EC 6.1.1.5) (Isoleucyl0tRNA synthetase) (IRS) (IleRS) |
| 410. | Junction plakoglobin (Catenin gamma) (Desmoplakin III) (Desmoplakin3) |
| 411. | Katanin p60 ATPase0containing subunit A0like 2 (Katanin p60 subunit A0like 2) (EC 3.6.4.3) (p60 katanin0like 2) |
| 412. | Keratin, type I cytoskeletal 17 |
| 413. | L0lactate dehydrogenase (EC 1.1.1.27) |
| 414. | L0lactate dehydrogenase B chain (LDH0B) (EC 1.1.1.27) (LDH heart subunit) (LDH0H) (Renal carcinoma antigen NY0REN046) |
| 415. | Late cornified envelope protein 2B (Late envelope protein 10) (Skin0specific protein Xp5) (Small proline0rich0like epidermal differentiation complex protein 1B) |
| 416. | Leucine0rich repeat0containing protein 59 (Ribosome0binding protein p34) (p34) |
| 417. | Lipocalin01 (Tear lipocalin) (Tlc) (Tear prealbumin) (TP) (Von Ebner gland protein) (VEG protein) |
| 418. | Loricrin |
| 419. | LUC70like (S. cerevisiae) (LUC70like (S. cerevisiae), isoform CRA_f) (Putative RNA0binding protein Luc70like 1) |
| 420. | Malate dehydrogenase (EC 1.1.1.37) (Fragment) |
| 421. | Matrin03 |
| 422. | Microtubule0associated protein 4 (Fragment) |
| 423. | Moesin (Membrane0organizing extension spike protein) |
| 424. | Mov10, Moloney leukemia virus 10, homolog (Mouse), isoform CRA_a (Putative helicase MOV010) |
| 425. | Multifunctional protein ADE2 (Fragment) |
| 426. | Multifunctional protein ADE2 [Includes: Phosphoribosylaminoimidazole0succinocarboxamide synthase (EC 6.3.2.6) (SAICAR synthetase); Phosphoribosylaminoimidazole carboxylase (EC 4.1.1.21) (AIR carboxylase) (AIRC)] |
| 427. | Myosin light chain 1/3, skeletal muscle isoform (MLC1/MLC3) (MLC1F/MLC3F) (Myosin light chain alkali 1/2) (Myosin light chain A1/A2) |
| 428. | Myosin regulatory light chain 2, skeletal muscle isoform (Fast skeletal myosin light chain 2) (MLC2B) |

| | |
|---|---|
| 429. | Myosin01 (Myosin heavy chain 1) (Myosin heavy chain 2x) (MyHC02x) (Myosin heavy chain IIx/d) (MyHC0IIx/d) (Myosin heavy chain, skeletal muscle, adult 1) |
| 430. | Myosin02 (Myosin heavy chain 2) (Myosin heavy chain 2a) (MyHC02a) (Myosin heavy chain IIa) (MyHC0IIa) (Myosin heavy chain, skeletal muscle, adult 2) |
| 431. | Myosin03 (Muscle embryonic myosin heavy chain) (Myosin heavy chain 3) (Myosin heavy chain, fast skeletal muscle, embryonic) (SMHCE) |
| 432. | Myosin04 (Myosin heavy chain 2b) (MyHC02b) (Myosin heavy chain 4) (Myosin heavy chain IIb) (MyHC0IIb) (Myosin heavy chain, skeletal muscle, fetal) |
| 433. | Myosin09 (Cellular myosin heavy chain, type A) (Myosin heavy chain 9) (Myosin heavy chain, non0muscle IIa) (Non0muscle myosin heavy chain A) (NMMHC0A) (Non0muscle myosin heavy chain IIa) (NMMHCII0a) (NMMHC0IIA) |
| 434. | NADH dehydrogenase [ubiquinone] 1 alpha subcomplex assembly factor 4 (Hormone0regulated proliferation0associated protein of 20 kDa) |
| 435. | NADH dehydrogenase [ubiquinone] iron0sulfur protein 2, mitochondrial (EC 1.6.5.3) (EC 1.6.99.3) (Complex I049kD) (CI049kD) (NADH0ubiquinone oxidoreductase 49 kDa subunit) |
| 436. | NADH dehydrogenase [ubiquinone] iron0sulfur protein 3, mitochondrial (EC 1.6.5.3) (EC 1.6.99.3) (Complex I030kD) (CI030kD) (NADH0ubiquinone oxidoreductase 30 kDa subunit) |
| 437. | Neuroblast differentiation0associated protein AHNAK (Desmoyokin) |
| 438. | NF0kappa0B0activating protein |
| 439. | Non0POU domain0containing octamer0binding protein (NonO protein) (54 kDa nuclear RNA0 and DNA0binding protein) (55 kDa nuclear protein) (DNA0binding p52/p100 complex, 52 kDa subunit) (NMT55) (p54(nrb)) (p54nrb) |
| 440. | Nuclear migration protein nudC (Nuclear distribution protein C homolog) |
| 441. | Nuclear pore complex protein Nup214 (214 kDa nucleoporin) (NucleoporinNup214) (Protein CAN) |
| 442. | Nuclease0sensitive element0binding protein 1 (CCAAT0binding transcription factor I subunit A) (CBF0A) (DNA0binding protein B) (DBPB) (Enhancer factor I subunit A) (EFI0A) (Y0box transcription factor) (Y0box0binding protein 1) (YB01) |
| 443. | Nucleolar RNA helicase 2 (EC 3.6.4.13) (DEAD box protein 21) (Gu0alpha) (Nucleolar RNA helicase Gu) (Nucleolar RNA helicase II) (RH II/Gu) |
| 444. | Nucleolin (Protein C23) |
| 445. | Nucleophosmin (NPM) (Nucleolar phosphoprotein B23) (Nucleolar protein NO38) (Numatrin) |
| 446. | Nucleoside diphosphate kinase A |
| 447. | Nucleoside diphosphate kinase A (NDK A) (NDP kinase A) (EC 2.7.4.6) (Granzyme A0activated DNase) (GAAD) (Metastasis inhibition factor nm23) (NM230H1) (Tumor metastatic process0associated protein) |
| 448. | p53 apoptosis effector related to PMP022 (Keratinocyte0associated protein 1) (KCP01) (P530induced protein PIGPC1) (Transmembrane protein THW) |
| 449. | PAI01 mRNA0binding protein variant (cDNA, FLJ92551, *Homo sapiens* PAI01 mRNA0binding protein (PAI0RBP1), mRNA) |
| 450. | Peptidyl0prolyl cis0trans isomerase FKBP4 (PPIase FKBP4) (EC 5.2.1.8) (51 kDa FK5060binding protein) (FKBP51) (52 kDa FK5060binding protein) (52 kDa FKBP) (FKBP052) (59 kDa immunophilin) (p59) (FK5060binding protein 4) (FKBP04) (FKBP59) (HSP0binding immunophilin) (HBI) (Immunophilin FKBP52) (Rotamase) [Cleaved into: Peptidyl0prolyl cis0trans isomerase FKBP4, N0terminally processed] |
| 451. | Peroxiredoxin01 (EC 1.11.1.15) (Natural killer cell0enhancing factor A) (NKEF0A) (Proliferation0associated gene protein) (PAG) (Thioredoxin peroxidase 2) (Thioredoxin0dependent peroxide reductase 2) |
| 452. | Peroxiredoxin06 (EC 1.11.1.15) (10Cys peroxiredoxin) (10Cys PRX) (24 kDa protein) (Acidic calcium0independent phospholipase A2) (aiPLA2) (EC 3.1.1.0) (Antioxidant protein 2) (Liver 2D page spot 40) (Non0selenium glutathione peroxidase) (NSGPx) (EC 1.11.1.9) (Red blood cells page spot 12) |
| 453. | Pinin (140 kDa nuclear and cell adhesion0related phosphoprotein) (Desmosome0associated protein) (Domain0rich serine protein) (DRS protein) (DRSP) (Melanoma metastasis clone A protein) (Nuclear protein SDK3) (SR0like protein) |
| 454. | Plakophilin01 (Band 6 protein) (B6P) |
| 455. | Plectin (PCN) (PLTN) (Hemidesmosomal protein 1) (HD1) (Plectin01) |
| 456. | Poly [ADP0ribose] polymerase 1 (PARP01) (EC 2.4.2.30) (ADP0ribosyltransferase diphtheria toxin0like 1) (ARTD1) (NAD(+) ADP0ribosyltransferase 1) (ADPRT1) (Poly[ADP0ribose] synthase 1) |
| 457. | Poly(rC)0binding protein 1 (Alpha0CP1) (Heterogeneous nuclear ribonucleoprotein E1) (hnRNP E1) (Nucleic acid0binding protein SUB2.3) |
| 458. | Polyadenylate0binding protein 1 (PABP01) (Poly(A)0binding protein 1) |
| 459. | Polymerase delta0interacting protein 3 (46 kDa DNA polymerase delta interaction protein) (p46) (S6K1 Aly/REF0like target) (SKAR) |
| 460. | Polymeric immunoglobulin receptor (PIgR) (Poly0Ig receptor) (Hepatocellular carcinoma0associated protein TB6) [Cleaved into: Secretory component] |
| 461. | Polypyrimidine tract0binding protein 1 (PTB) (57 kDa RNA0binding protein PPTB01) (Heterogeneous nuclear ribonucleoprotein I) (hnRNP I) |
| 462. | Prelamin0A/C [Cleaved into: Lamin0A/C (70 kDa lamin) (Renal carcinoma antigen NY0REN032)] |
| 463. | Probable ATP0dependent RNA helicase DDX17 (EC 3.6.4.13) (DEAD box protein 17) (DEAD box protein p72) (DEAD box protein p82) (RNA0dependent helicase p72) |
| 464. | Probable ATP0dependent RNA helicase DDX5 (EC 3.6.4.13) (DEAD box protein 5) (RNA helicase p68) |
| 465. | Profilin01 (Epididymis tissue protein Li 184a) (Profilin I) |
| 466. | Prohibitin02 |
| 467. | Prolactin0inducible protein (Gross cystic disease fluid protein 15) (GCDFP015) (Prolactin0induced protein) (Secretory actin0binding protein) (SABP) (gp17) |
| 468. | Proliferation0associated protein 2G4 (Cell cycle protein p3802G4 homolog) (hG401) (ErbB30binding protein 1) |
| 469. | Prostaglandin E synthase 3 (EC 5.3.99.3) (Cytosolic prostaglandin E2 synthase) (cPGES) (Hsp90 co0chaperone) (Progesterone receptor complex p23) (Telomerase0binding protein p23) |
| 470. | Proteasome endopeptidase complex (EC 3.4.25.1) |
| 471. | Proteasome subunit alpha type03 (EC 3.4.25.1) (Macropain subunit C8) (Multicatalytic endopeptidase complex subunit C8) (Proteasome component C8) |
| 472. | Proteasome subunit alpha type04 (EC 3.4.25.1) (Macropain subunit C9) (Multicatalytic endopeptidase complex subunit C9) (Proteasome component C9) (Proteasome subunit L) |
| 473. | Proteasome subunit alpha type05 (EC 3.4.25.1) (Macropain zeta chain) (Multicatalytic endopeptidase complex zeta chain) (Proteasome zeta chain) |
| 474. | Proteasome subunit alpha type06 (EC 3.4.25.1) (27 kDa prosomal protein) (PROS027) (p27K) (Macropain iota chain) (Multicatalytic endopeptidase complex iota chain) (Proteasome iota chain) |
| 475. | Proteasome subunit beta type (EC 3.4.25.1) |

| | |
|---|---|
| 476. | Proteasome subunit beta type04 (EC 3.4.25.1) (26 kDa prosomal protein) (HsBPROS26) (PROS026) (Macropain beta chain) (Multicatalytic endopeptidase complex beta chain) (Proteasome beta chain) (Proteasome chain 3) (HsN3) |
| 477. | Proteasome subunit beta type06 (EC 3.4.25.1) (Macropain delta chain) (Multicatalytic endopeptidase complex delta chain) (Proteasome delta chain) (Proteasome subunit Y) |
| 478. | Protein ABHD12B (EC 3.0.0.0) (Abhydrolase domain0containing protein 12B) (Alpha/beta hydrolase domain0containing protein 12B) |
| 479. | Protein DJ01 (DJ01) (Oncogene DJ1) (Parkinson disease protein 7) (Parkinsonism0associated deglycase) (Protein deglycase DJ01) (EC 3.1.2.0) (EC 3.5.1.124) |
| 480. | Protein mago nashi homolog |
| 481. | Protein mago nashi homolog 2 |
| 482. | Protein POF1B (Premature ovarian failure protein 1B) |
| 483. | Protein rogdi homolog |
| 484. | Protein S1000A11 (Calgizzarin) (Metastatic lymph node gene 70 protein) (MLN 70) (Protein S1000C) (S100 calcium0binding protein A11) [Cleaved into: Protein S1000A11, N0terminally processed] |
| 485. | Protein S1000A14 (S100 calcium0binding protein A14) (S114) |
| 486. | Protein S1000A16 (Aging0associated gene 13 protein) (Protein S1000F) (S100 calcium0binding protein A16) |
| 487. | Protein S1000A2 (CAN19) (Protein S0100L) (S100 calcium0binding protein A2) |
| 488. | Protein S1000A7 (Psoriasin) (S100 calcium0binding protein A7) |
| 489. | Protein S1000A8 (Calgranulin0A) (Calprotectin L1L subunit) (Cystic fibrosis antigen) (CFAG) (Leukocyte L1 complex light chain) (Migration inhibitory factor0related protein 8) (MRP08) (p8) (S100 calcium0binding protein A8) (Urinary stone protein band A) [Cleaved into: Protein S1000A8, N0terminally processed] |
| 490. | Protein S1000A9 (Calgranulin0B) (Calprotectin L1H subunit) (Leukocyte L1 complex heavy chain) (Migration inhibitory factor0related protein 14) (MRP014) (p14) (S100 calcium0binding protein A9) |
| 491. | Protein Shroom3 (Shroom0related protein) (hShrmL) |
| 492. | Protein SOGA1 (SOGA family member 1) (Suppressor of glucose by autophagy) (Suppressor of glucose, autophagy0associated protein 1) [Cleaved into: N0terminal form; C0terminal 80 kDa form (800 kDa SOGA fragment)] |
| 493. | Protein SREK1IP1 (SFRS120interacting protein 1) (SREK10interacting protein 1) (Splicing regulatory protein of 18 kDa) (p18SRP) |
| 494. | Protein0glutamine gamma0glutamyltransferase E (EC 2.3.2.13) (Transglutaminase E) (TG(E)) (TGE) (TGase E) (Transglutaminase03) (TGase03) [Cleaved into: Protein0glutamine gamma0glutamyltransferase E 50 kDa catalytic chain; Protein0glutamine gamma0glutamyltransferase E 27 kDa non0catalytic chain] |
| 495. | Protein0glutamine gamma0glutamyltransferase K (EC 2.3.2.13) (Epidermal TGase) (Transglutaminase K) (TG(K)) (TGK) (TGase K) (Transglutaminase01) (TGase01) |
| 496. | Putative heat shock protein HSP 900beta 2 (Heat shock protein 900beta b) (Heat shock protein 90Bb) |
| 497. | Putative RRN30like protein RRN3P2 (RNA polymerase I transcription factor homolog pseudogene 2) |
| 498. | Pyruvate dehydrogenase E1 component subunit alpha, somatic form, mitochondrial |
| 499. | Pyruvate kinase PKM (EC 2.7.1.40) (Cytosolic thyroid hormone0binding protein) (CTHBP) (Opa0interacting protein 3) (OIP03) (Pyruvate kinase 2/3) (Pyruvate kinase muscle isozyme) (Thyroid hormone0binding protein 1) (THBP1) (Tumor M20PK) (p58) |
| 500. | RAB30, member RAS oncogene family, isoform CRA_a (cDNA FLJ78283, highly similar to *Homo sapiens* RAB30, member RAS oncogene family (RAB30), mRNA) (cDNA, FLJ92634, *Homo sapiens* RAB30, member RAS oncogene family (RAB30), mRNA) |
| 501. | Ran0specific GTPase0activating protein (Ran0binding protein 1) (RanBP1) |
| 502. | Ras GTPase0activating protein0binding protein 1 (Fragment) |
| 503. | Ras0related protein Rab010 |
| 504. | Receptor of0activated protein C kinase 1 |
| 505. | Regulator of nonsense transcripts 1 (EC 3.6.4.0) (ATP0dependent helicase RENT1) (Nonsense mRNA reducing factor 1) (NORF1) (Up0frameshift suppressor 1 homolog) (hUpf1) |
| 506. | Ribonuclease inhibitor (Placental ribonuclease inhibitor) (Placental RNase inhibitor) (Ribonuclease/angiogenin inhibitor 1) (RAI) |
| 507. | Ribosomal protein L5 (Ribosomal protein L5, isoform CRA_c) (cDNA, FLJ95579, *Homo sapiens* ribosomal protein L5 (RPL5), mRNA) |
| 508. | RNA0binding motif protein, X chromosome (Glycoprotein p43) (Heterogeneous nuclear ribonucleoprotein G) (hnRNP G) [Cleaved into: RNA0binding motif protein, X chromosome, N0terminally processed] |
| 509. | RNA0binding protein 14 (Paraspeckle protein 2) (PSP2) (RNA0binding motif protein 14) (RRM0containing coactivator activator/modulator) (Synaptotagmin0interacting protein) (SYT0interacting protein) |
| 510. | RNA0binding protein 8A (Binder of OVCA101) (BOV01) (RNA0binding motif protein 8A) (RNA0binding protein Y14) (Ribonucleoprotein RBM8A) |
| 511. | RNA0binding protein EWS |
| 512. | RuvB0like 1 (EC 3.6.4.12) (49 kDa TATA box0binding protein0interacting protein) (49 kDa TBP0interacting protein) (54 kDa erythrocyte cytosolic protein) (ECP054) (INO80 complex subunit H) (Nuclear matrix protein 238) (NMP 238) (Pontin 52) (TIP49a) (TIP600associated protein 540alpha) (TAP540alpha) |
| 513. | RuvB0like helicase (EC 3.6.4.12) |
| 514. | SAP domain0containing ribonucleoprotein (Cytokine0induced protein of 29 kDa) (Nuclear protein Hcc01) (Proliferation0associated cytokine0inducible protein CIP29) |
| 515. | Secretoglobin family 1D member 1 (Lipophilin0A) |
| 516. | Serine/arginine0rich splicing factor 1 (Alternative0splicing factor 1) (ASF01) (Splicing factor, arginine/serine0rich 1) (pre0mRNA0splicing factor SF2, P33 subunit) |
| 517. | Serine/arginine0rich splicing factor 11 (Arginine0rich 54 kDa nuclear protein) (p54) (Splicing factor, arginine/serine0rich 11) |
| 518. | Serine/arginine0rich splicing factor 2 (Protein PR264) (Splicing component, 35 kDa) (Splicing factor SC35) (SC035) (Splicing factor, arginine/serine0rich 2) |
| 519. | Serine/arginine0rich splicing factor 5 (Delayed0early protein HRS) (Pre0mRNA0splicing factor SRP40) (Splicing factor, arginine/serine0rich 5) |
| 520. | Serine/arginine0rich splicing factor 6 (Pre0mRNA0splicing factor SRP55) (Splicing factor, arginine/serine0rich 6) |
| 521. | Serpin A12 (OL064) (Visceral adipose tissue0derived serine protease inhibitor) (Vaspin) (Visceral adipose0specific serpin) |
| 522. | Serpin B3 (Protein T40A) (Squamous cell carcinoma antigen 1) (SCCA01) |
| 523. | Serpin B4 (Leupin) (Peptidase inhibitor 11) (PI011) (Squamous cell carcinoma antigen 2) (SCCA02) |
| 524. | Serpin B5 (Fragment) |
| 525. | Serpin B5 (Maspin) (Peptidase inhibitor 5) (PI05) |
| 526. | SH2 domain0containing protein 3A (Novel SH20containing protein 1) |
| 527. | Signal recognition particle 14 kDa protein (SRP14) (18 kDa Alu RNA0binding protein) |
| 528. | Skin0specific protein 32 |
| 529. | Small nuclear ribonucleoprotein E (snRNP0E) (Sm protein E) (Sm0E) (SmE) |
| 530. | Small nuclear ribonucleoprotein Sm D1 (Sm0D1) (Sm0D autoantigen) (snRNP core protein D1) |

-continued

531. Small nuclear ribonucleoprotein Sm D2 (SmOD2) (snRNP core protein D2)
532. Small proline0rich protein 2A (SPR02A) (201)
533. Small proline0rich protein 2D (SPR02D) (Small proline0rich protein II) (SPR0II)
534. Small proline0rich protein 2E (SPR02E) (Small proline0rich protein II) (SPR0II)
535. Small proline0rich protein 2G (SPR02G)
536. Small ubiquitin0related modifier 3
537. Spindlin04
538. Splicing factor arginine/serine0rich 3 (Splicing factor, arginine/serine0rich 3, isoform CRA_d) (cDNA, FLJ92926, Homo sapiens splicing factor, arginine/serine0rich 3 (SFRS3), mRNA)
539. Splicing factor U2AF 35 kDa subunit (U2 auxiliary factor 35 kDa subunit) (U2 small nuclear RNA auxiliary factor 1) (U2 snRNP auxiliary factor small subunit)
540. Splicing factor U2AF 65 kDa subunit (U2 auxiliary factor 65 kDa subunit) (hU2AF(65)) (hU2AF65) (U2 snRNP auxiliary factor large subunit)
541. Splicing factor, proline0 and glutamine0rich (100 kDa DNA0pairing protein) (hPOMp100) (DNA0binding p52/p100 complex, 100 kDa subunit) (Polypyrimidine tract0binding protein0associated0splicing factor) (PSF) (PTB0associated0splicing factor)
542. Src substrate cortactin (Amplaxin) (Oncogene EMS1)
543. Stathmin
544. Stress070 protein, mitochondrial (75 kDa glucose0regulated protein) (GRP075) (Heat shock 70 kDa protein 9) (Mortalin) (MOT) (Peptide0binding protein 74) (PBP74)
545. Stress0induced0phosphoprotein 1 (STI1) (Hsc70/Hsp900organizing protein) (Hop) (Renal carcinoma antigen NY0REN011) (Transformation0sensitive protein IEF SSP 3521)
546. Striatin03 (Cell cycle autoantigen SG2NA) (S/G2 antigen)
547. Synaptic functional regulator FMR1
548. Synemin
549. T0complex protein 1 subunit alpha (TCP010alpha) (CCT0alpha)
550. T0complex protein 1 subunit theta (TCP010theta) (CCT0theta) (Renal carcinoma antigen NY0REN015)
551. T0complex protein 1 subunit zeta (TCP010zeta) (Acute morphine dependence0related protein 2) (CCT0zeta01) (HTR3) (Tcp20)
552. Talin01
553. TAR DNA0binding protein 43
554. Thioredoxin domain0containing protein 17 (14 kDa thioredoxin0related protein) (TRP14) (Protein 420909) (Thioredoxin0like protein 5)
555. Thioredoxin0like protein 1 (32 kDa thioredoxin0related protein)
556. THO complex subunit 4
557. Transaldolase (EC 2.2.1.2)
558. Transitional endoplasmic reticulum ATPase (TER ATPase) (EC 3.6.4.6) (15S Mg(2+)0ATPase p97 subunit) (Valosin0containing protein) (VCP)
559. Transketolase (EC 2.2.1.1)
560. Trifunctional purine biosynthetic protein adenosine03 [Includes: Phosphoribosylamine00glycine ligase (EC 6.3.4.13) (Glycinamide ribonucleotide synthetase) (GARS) (Phosphoribosylglycinamide synthetase); Phosphoribosylformylglycinamidine cyclo0ligase (EC 6.3.3.1) (AIR synthase) (AIRS) (Phosphoribosyl0aminoimidazole synthetase); Phosphoribosylglycinamide formyltransferase (EC 2.1.2.2) (5'0phosphoribosylglycinamide transformylase) (GAR transformylase) (GART)]
561. Tropomyosin alpha03 chain (Gamma0tropomyosin) (Tropomyosin03) (Tropomyosin05) (hTM5)
562. Trypsin01
563. Tubulin alpha chain
564. Tubulin alpha chain0like 3
565. Tubulin alpha01B chain (Alpha0tubulin ubiquitous) (Tubulin K0alpha01) (Tubulin alpha0ubiquitous chain) [Cleaved into: Detyrosinated tubulin alpha01B chain]
566. Tubulin beta chain
567. Tubulin beta chain (Tubulin beta05 chain)
568. Tubulin beta04B chain (Tubulin beta02 chain) (Tubulin beta02C chain)
569. Tyrosine00tRNA ligase, cytoplasmic (EC 6.1.1.1) (Tyrosyl0tRNA synthetase) (TyrRS) [Cleaved into: Tyrosine00tRNA ligase, cytoplasmic, N0terminally processed]
570. Ubiquitin0conjugating enzyme E2 D3
571. Ubiquitin0conjugating enzyme E2 L3 (EC 2.3.2.23) (E2 ubiquitin0conjugating enzyme L3) (L0UBC) (UbcH7) (Ubiquitin carrier protein L3) (Ubiquitin0conjugating enzyme E20F1) (Ubiquitin0protein ligase L3)
572. Uncharacterized protein C19orf47
573. Uncharacterized protein KIAA1109 (Fragile site0associated protein)
574. Vasodilator0stimulated phosphoprotein (VASP)
575. Vesicle0associated membrane protein0associated protein A (VAMP0A) (VAMP0associated protein A) (VAP0A) (33 kDa VAMP0associated protein) (VAP033)
576. Vimentin
577. Vinculin (Metavinculin) (MV)
578. Voltage0dependent anion0selective channel protein 2 (VDAC02) (hVDAC2) (Outer mitochondrial membrane protein porin 2)
579. X0ray repair cross0complementing protein 5 (EC 3.6.4.0) (86 kDa subunit of Ku antigen) (ATP0dependent DNA helicase 2 subunit 2) (ATP0dependent DNA helicase II 80 kDa subunit) (CTC box0binding factor 85 kDa subunit) (CTC85) (CTCBF) (DNA repair protein XRCC5) (Ku80) (Ku86) (Lupus Ku autoantigen protein p86) (Nuclear factor IV) (Thyroid0lupus autoantigen) (TLAA) (X0ray repair complementing defective repair in Chinese hamster cells 5 (double0strand0break rejoining))
580. Zinc finger MYM0type protein 3
581. Zinc0alpha020glycoprotein (Zn0alpha020GP) (Zn0alpha020glycoprotein)

FIG. 19C shows MS/ChIP data of dimerized CLOuD9 cells after 72 hour and 7 day treatment demonstrate differential enrichment of novel proteins at the induced looping loci after 7 days. Proteins that persist after dimerizer washout are highlighted in bold.

Figure 19D:
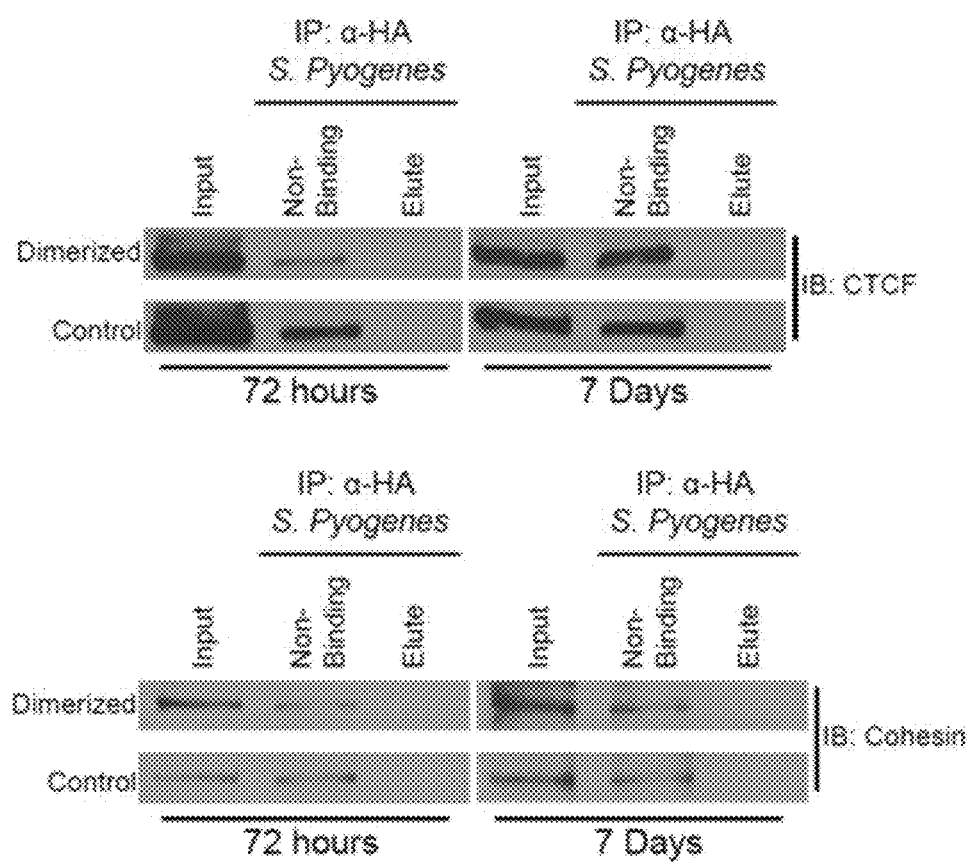
FIG. 19D shows validation of MS/ChIP data by co-immunoprecipitation.

FIG. 19D shows validation of MS/ChIP by co-immunoprecipitation shows no evidence of cohesin and CTCF in association with CLOuD9 constructs before or after loop stabilization.

To determine what might underlie the preservation of chromatin conformation with long-term induced dimerization, mass spectrometry analysis was performed following double chromatin immunoprecipitation (MS/ChIP) on dimerized CLOuD9 cells with durations of 72 hours and 7 days. As shown in FIG. 19C, after 72 hours of induced looping, the CLOuD9 associated dCas9 proteins, a small number of RNA helicases, and members of the heterogeneous nuclear ribonucleoprotein machinery are preferentially enriched in the dimerized samples, though none of these proteins persisted at the induced contact site following ligand washout. However, longer duration chromatin loop formation was accompanied by recruitment of additional RNA helicases and heterogeneous nuclear ribonucleoproteins to the contact region that remained at the site of induced contact even after 7 days of ligand washout (FIG. 19C), implying a functional role for these proteins in maintaining the early stages of novel chromatin contacts. Notably absent from the MS analyses are the traditional regulators of chromatin architecture, CCCTC-binding factor (CTCF) and cohesin (FIG. 19D), perhaps suggesting a novel regulatory mechanism of stabilizing genome topology.

Figure 4B:
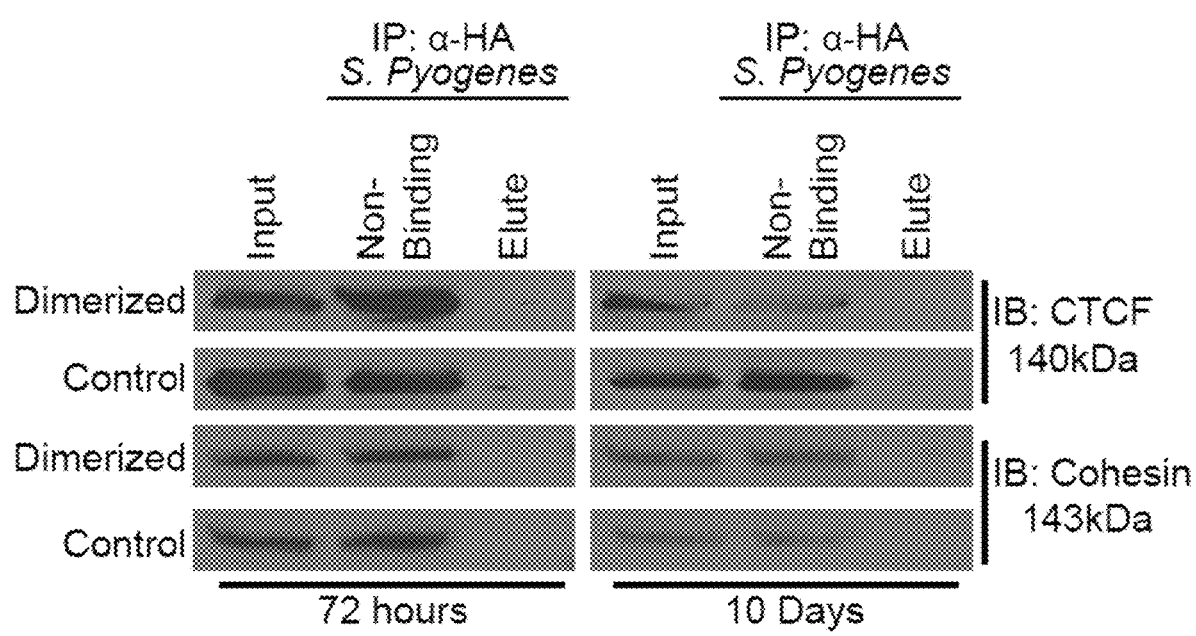
FIG. 4B shows immunoprecipitation of CLOuD9 complexes demonstrates that CTCF and cohesin were not found to be localized to the induced loops.
Figure 12:
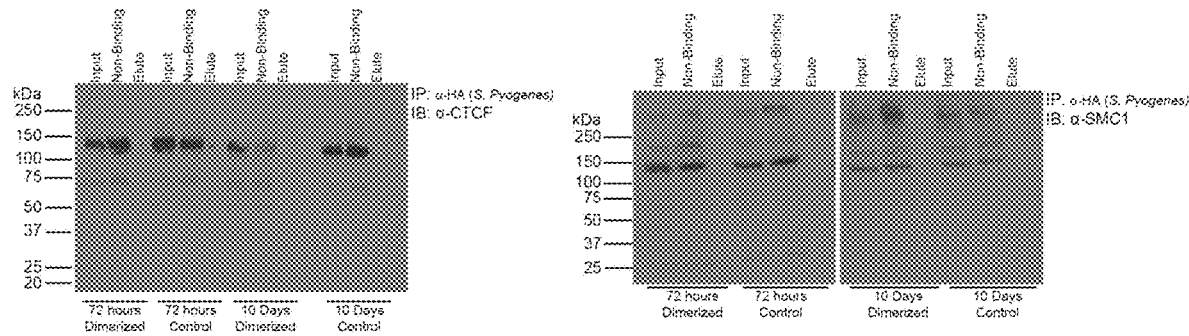
FIG. 12 shows uncropped images of immunoblots in FIG. 4B.

FIG. 12 shows uncropped images of immunoblots in FIG. 4B. Immunoprecipitation of CLOuD9 complexes demonstrates that CTCF and cohesin were not found to be localized to the induced loops.

Figure 13:
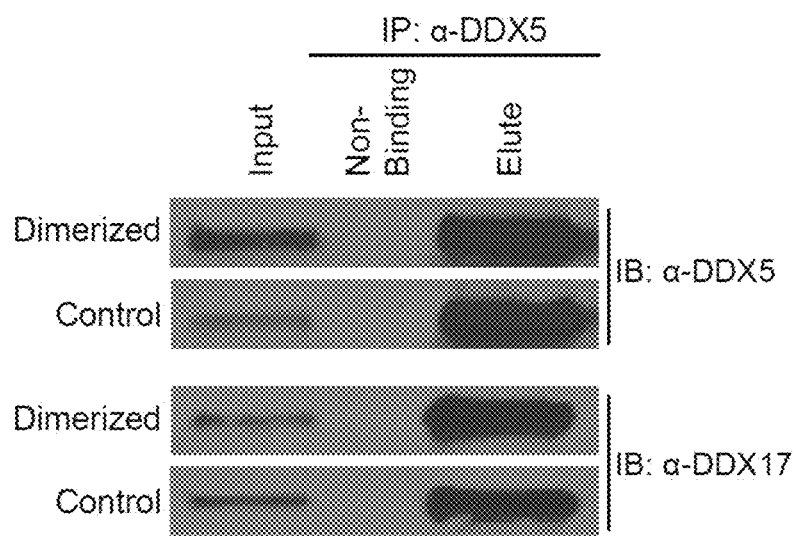
FIG. 13 shows RNA helicases DDX5 and DDX17 co-associate.
Figure 14:
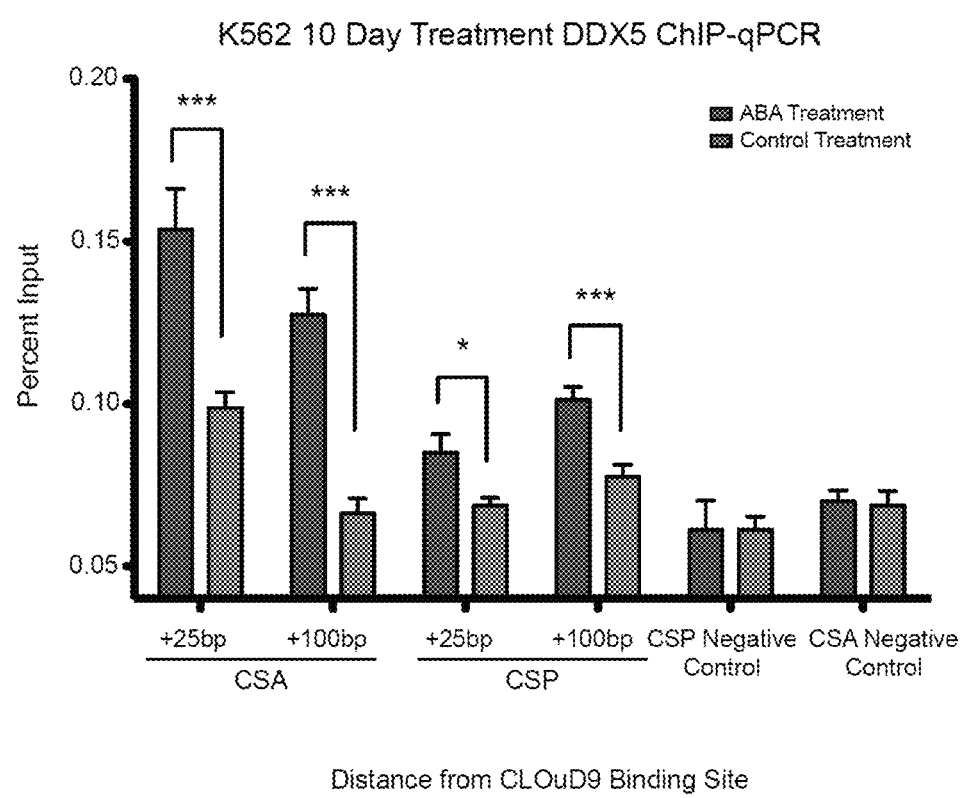
FIG. 14 shows RNA helicases DDX5 and DDX17 localize to CLOuD9 target regions.

Recruitment of the most robust RNA helicases in the MS/ChIP samples, DDX5 and DDX17, which co-immunoprecipitated (FIG. 13), was confirmed by ChIP-qPCR (FIG. 14).

FIG. 13 shows RNA helicases DDX5 and DDX17 co-associate. Co-immunoprecipitations demonstrating DDX17 associates with DDX5 in K562 cells regardless of treatment condition.

FIG. 14 shows RNA helicases DDX5 and DDX17 localize to CLOuD9 target regions. Chromatin immunoprecipitation and quantitative PCR of CLOuD9 constructs demonstrates their localization to regions of chromatin immediately adjacent to CLOuD9 target sites. *p<0.05, t=2.662, df=14; ***p<0.0001, left to right t=4.1, df=14, t=6.659, df=14; t=4.392, df=14. All error bars indicate SD.

To test the possible involvement of these RNA helicases in the long-term maintenance of de novo chromatin contacts, shRNA mediated knockdown of both DDX5 and DDX17 (FIG. 4C and FIG. 15) was performed.

Figure 4C:
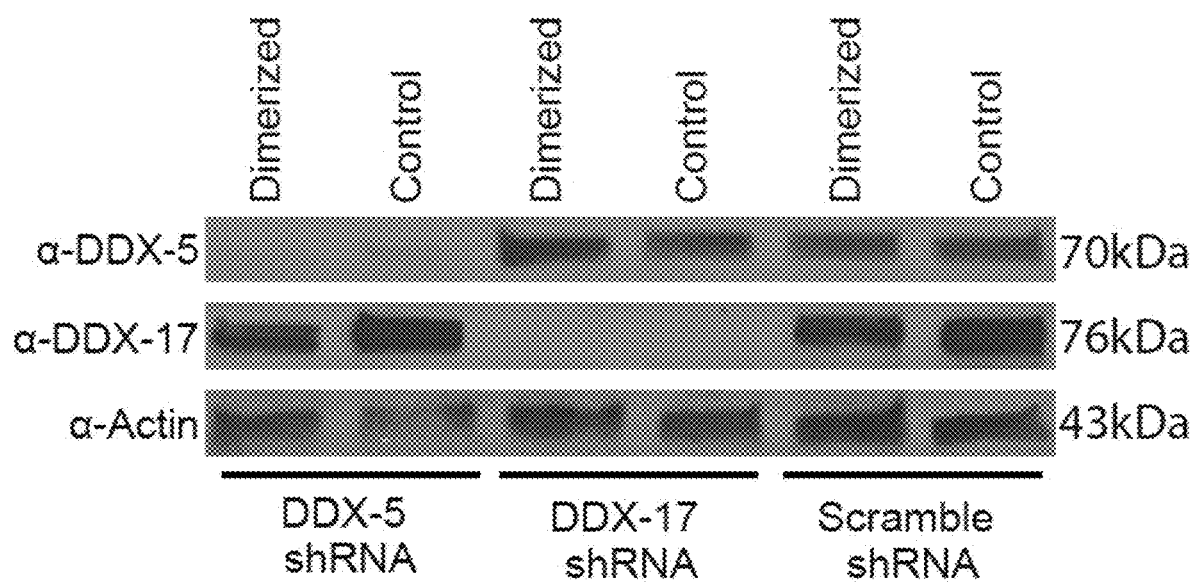
FIG. 4C shows shRNA knockdown of DDX5 and DDX17 in K562 cells containing CLOuD9 constructs.
Figure 15:
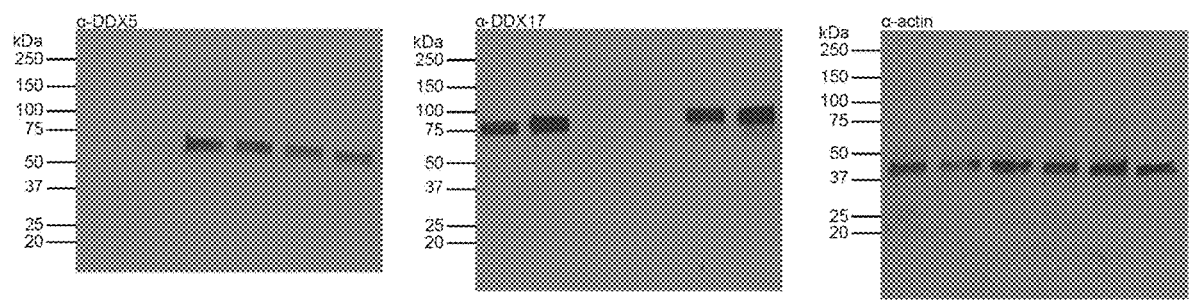
FIG. 15 shows uncropped images of immunoblots in FIG. 4C.

FIG. 15 shows uncropped images of immunoblots in FIG. 4C. shRNA knockdown of DDX5 and DDX17 in K562 cells containing CLOuD9 constructs.

Stable knockdowns were made only of either protein individually, as simultaneous knockdown of both proteins resulted in cell death. Interestingly, while knockdown of either protein had no impact on loop formation or gene expression following 72 hours or 10 days of ABA-mediated β-globin/LCR dimerization (FIG. 4D-FIG. 4F, FIG. 16 and FIG. 17), long-term dimerization followed by ligand washout no longer resulted in sustained chromatin looping, and β-globin expression following ligand washout returned to baseline levels (FIG. 4E, FIG. 4F, and FIG. 17).

Figure 4D:
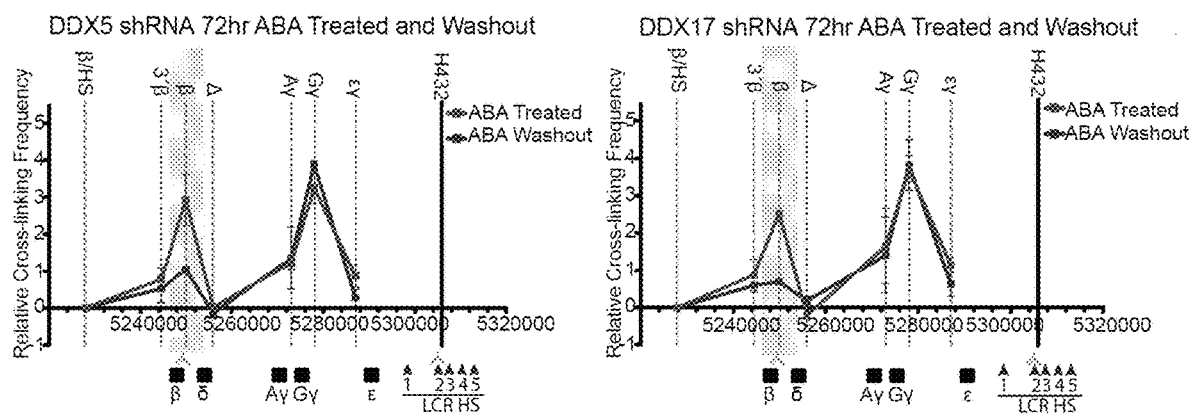
FIG. 4D shows effect of DDX5 and DDX17 knockdown at 72 hr.
Figure 4E:
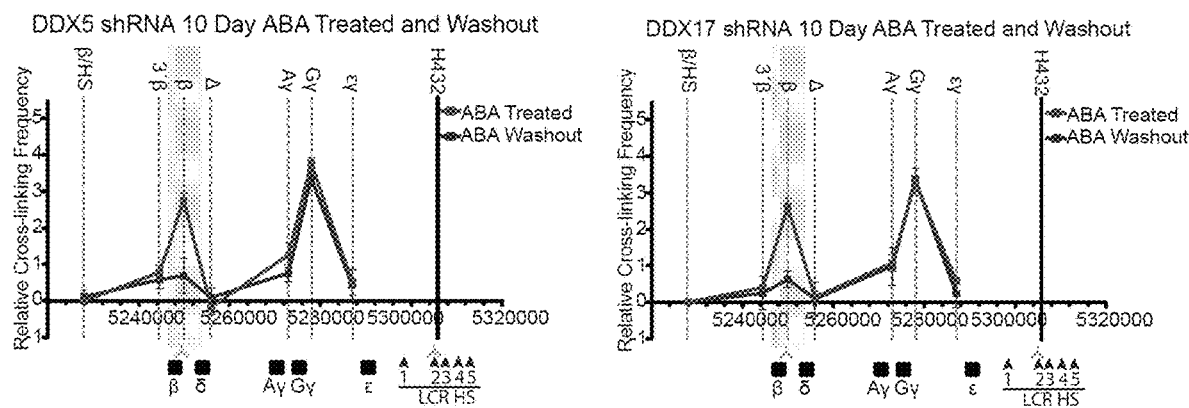
FIG. 4E shows effect of DDX5 and DDX17 knockdown at 10 days.

In FIG. 4D and FIG. 4E, 3C demonstrates that while DDX5 and DDX17 knockdown do not affect induction of β-globin/LCR contacts, the induced chromatin loops are no longer stabilized following 10 days of dimerization and subsequent washout. 3C values were normalized to tubulin, and interaction frequencies between the anchor fragment and the fragment encompassing the β/HS fragment were set to zero. Error bars indicate SD. n=3.

Figure 4F:
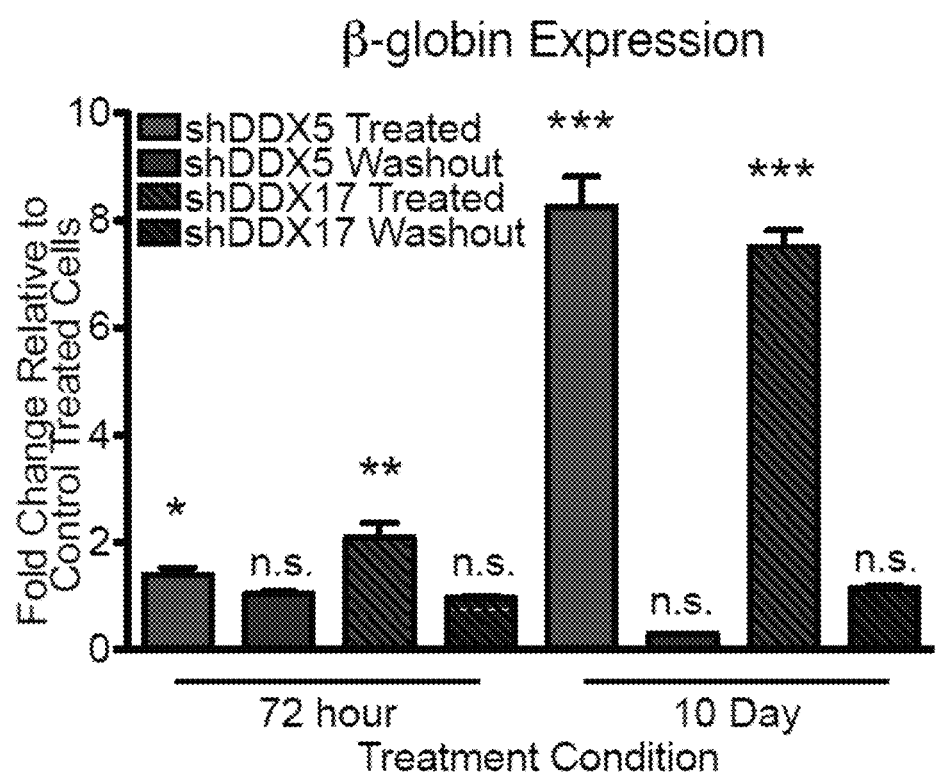
FIG. 4F shows restoration of endogenous β-globin expression following short and long-term dimerization and subsequent ligand washout in DDX5 and DDX17 knockdown cells.

FIG. 4F shows endogenous β-globin expression is restored following short and long-term dimerization and subsequent ligand washout in DDX5 and DDX17 knockdown cells. Significance given relative to control treated cells. *p<0.05, t=2.538, df=6; p<0.001, t=3.791, df=6; *p<0.0001, shDDX5 t=12.6, df=6, shDDX17 t=19.35, df=6; n.s. non-significant. All error bars indicate SD.

Figure 16:
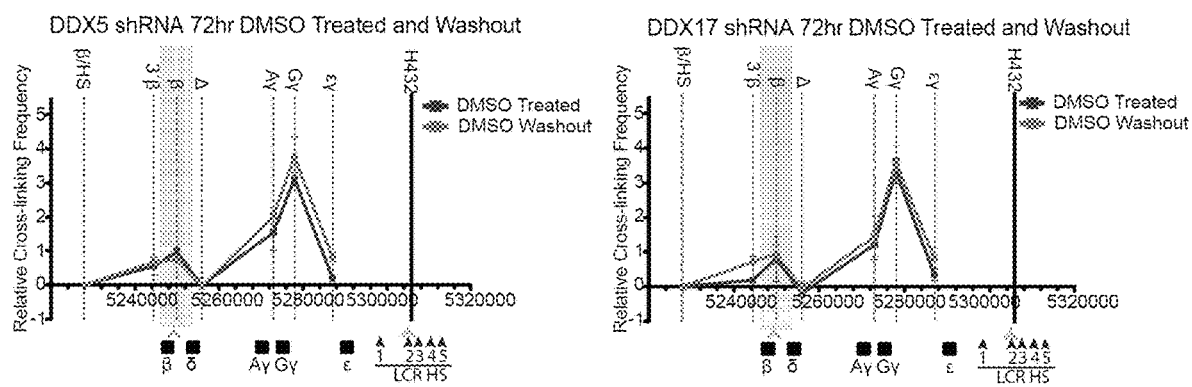
FIG. 16 shows control treatment of DDX5 and DDX17 knockdown CLOuD9 cells induces no changes in chromatin contacts.
Figure 17:
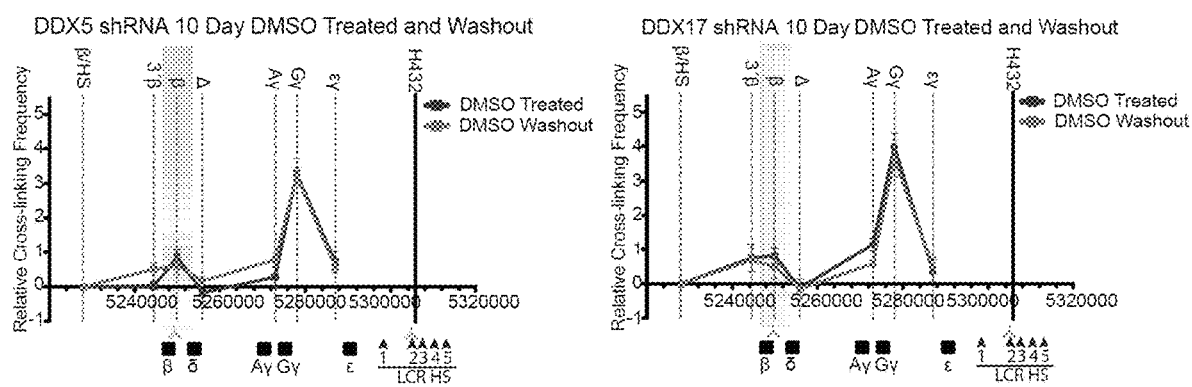
FIG. 17 shows long-term control treatment of DDX5 and DDX17 knockdown CLOuD9 cells induces no changes in chromatin contacts.

FIG. 16 shows control treatment of DDX5 and DDX17 knockdown CLOuD9 cells induces no changes in chromatin contacts. Treatment with DMSO, a control agent, for 72 hours induces no changes in endogenous chromatin conformation by 3C in DDX5 or DDX17 knockdown K562 cells. 3C values were normalized to tubulin, and interaction frequencies between the anchor fragment and the fragment encompassing the β/HS fragment were set to zero. Error bars indicate SD. n=3.

FIG. 17 shows long-term control treatment of DDX5 and DDX17 knockdown CLOuD9 cells induces no changes in chromatin contacts. Treatment with DMSO, a control agent, for 10 days induces no changes in endogenous chromatin conformation by 3C in DDX5 or DDX17 knockdown K562 cells. 3C values were normalized to tubulin, and interaction frequencies between the anchor fragment and the fragment encompassing the β/HS fragment were set to zero. Error bars indicate SD. n=3.

In some embodiments, one or more compositions comprising the CLOuD9 system are provided. In some embodiments, the compositions are formulated in the form of one or more pharmaceutical formulations.

In some embodiments, the composition and formulations are provided in liquid, solid, or semi-solid dosage form. Non-limiting examples include capsule, tablet, an ovule, suppository, an insert, a wafer, a chewable tablet, a buccal tablet, a sub-lingual tablet, a quick-dissolve tablet, an effervescent tablet, a granule, a pellet, a bead, a pill, a sachet, sprinkle, film, ointment, a cream, a gel, a dry syrup, a reconstitutable solid, a suspension, an emulsion, a lozenge, a troche, an implant, a powder, a triturate, a platelet, or a strip. Compositions and formulations for oral administration can be any dosage form that is suitable for oral ingestion, for example, liquid compositions and formulations such as elixir, suspension, syrup, emulsion, ampoule, etc., solid compositions and formulations such as gel, gum, drop, powder, granule, pill, sugar-coated tablet, film-coated tablet, capsule, package agent, etc. Also contemplated are sustained-release compositions and formulations such as gel-coated compositions and formulations, multi-coated compositions and formulations, localized release compositions and formulations.

In some embodiments, the compositions and formulations can be formulated for immediate release, pulsatile release, controlled release, extended release, modified release, delayed release, targeted release, or targeted delayed release.

In some embodiments, the compositions and formulations provided herein comprise active ingredients, inactive ingredients, excipients, additives, and/or pharmaceutically acceptable carriers. Examples of additives include natural polymer compounds, inorganic salts, binders, lubricants, disintegrants, surfactants, thickeners, coating agents, pH adjusters, antioxidants, flavoring agents, preservatives, and colorants among others. Examples of other pharmaceutically acceptable carriers include liquid carriers such as water, alcohol, emulsion, and solid carriers such as gel, powder, etc.

A pharmaceutically acceptable carrier may include one or more solvents, buffers, solutions, dispersion media, coatings, antibacterial and antifungal agents, isotonic and absorption delaying agents and the like acceptable for use in formulating pharmaceuticals, such as compositions and formulations suitable for administration to humans. Standard pharmaceutical formulation techniques and ingredients can be used, such as those disclosed in Remington's The Science and Practice of Pharmacy, 21st Ed., Lippincott Williams & Wilkins (2005), which is hereby incorporated by reference in its entirety. The compositions and formulations may comprise appropriate salts and buffers to render deliver vehicles stable and allow for uptake by target cells. Aqueous compositions and formulations comprise an effective amount of the delivery vehicle comprising the CLOuD9 system (e.g. liposomes, nanoparticles, or other complexes), dissolved or dispersed in a pharmaceutically acceptable carrier or aqueous medium. Other excipients include water soluble polymer, water insoluble polymers, hydrophobic materials, hydrophilic materials, waxes, disintegrants, superdisintegrants, diluents, binders, etc.

In some embodiments, compositions and formulations for intravenous administration comprise excipient and pharmaceutically acceptable carries including one or more of sodium chloride, dextrose, and sterile water. Compositions and formulations can comprise aqueous isotonic sterile injection solutions, which can comprise one or more of antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

In some embodiments, the compositions and formulations are administered by intravenous infusion. The compositions and formulations can be presented in unit-dose or multi-dose sealed containers, such as ampules and/or vials. Injection solutions and suspensions can be prepared from sterile powders, granules, and/or tablets. In some embodiments, the compositions and formulations to be administered can be formulated as pharmaceutical formulations for delivery via one or more of the routes provided herein.

The route of administration of the compositions and formulations herein can be determined by one of ordinary skill in the art based on the circumstances and need. Several non-limiting routes of administrations are possible including parenteral, subcutaneous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, intralesional, bolus, vaginal, rectal, buccal, sublingual, intranasal, or transdermal.

In some embodiments, the compositions and formulations provided herein are used to prevent and/or treat one or more diseases, including but not limited to: cancer, hematopoietic diseases, congenital diseases, Huntington's disease, etc. In some embodiments, the compositions and formulations provided herein are used in methods to prevent and/or treat one or more diseases in a subject.

As used herein, the term "subject" or "patient" refers to any vertebrate including, without limitation, humans and other primates (e.g., chimpanzees and other apes and monkey species), farm animals (e.g., cattle, sheep, pigs, goats and horses), domestic mammals (e.g., dogs and cats), laboratory animals (e.g., rodents such as mice, rats, and guinea pigs), and birds (e.g., domestic, wild and game birds such as chickens, turkeys and other gallinaceous birds, ducks, geese, etc.). In some embodiments, the subject is a mammal. In some embodiments, the subject is a human. In some embodiments, the subject is a male or a female.

In some embodiments, the compositions and formulations disclosed herein can be provided in the form of a kit. For example, all of the components of CLOuD9 technology can be packaged into an all-in-one type kit for technical applications. For example, an all-in-one kit comprising the CLOuD9 technology can be similar to kits that are already available for CRISPR from, for example, ThermoFisher.

EXAMPLES

The following Examples are non-limiting and other variants contemplated by one of ordinary skill in the art are included within the scope of this disclosure.

Example 1—Cell Culture

Wild type K562 cells, a gift from Dr. Ravindra Majeti, were cultured in RPMI 1640 media (Life Technologies, 11875-119) with addition of 10% FBS and 1% penicillin/streptomycin. Cells were maintained in 25 $cm^2$ canted neck flasks, and were adjusted to a density of 400,000 cells/mL daily.

Following transduction with CLOuD9 constructs, cells were maintained in media supplemented with 2 μg/mL puromycin and 100 μg/mL hygromycin.

Wild type 293T cells, a gift from Dr. Howard Chang, were cultured in DMEM media (Life Technologies, 11995-065) with addition of 10% FBS and 1% penicillin/streptomycin. Cells were maintained in 10 $cm^2$ plates and passaged when confluent. Following transduction with CLOuD9 constructs, cells were maintained in media supplemented with 1 μg/ml puromycin and 25 μg/ml hygromycin.

Example 2—Development of CLOuD9 Plasmids

Briefly, for CSA, beginning with lentiCRISPR v2 (Addgene plasmid #52961), the gRNA and Cas-9 sequences were replaced with *S. aureus* nuclease deficient Cas-9 and compatible gRNA sequence. The reversibly dimerizeable ABI1 domain was then added to the modified Cas-9 sequences. Briefly, for CSP, beginning with lentiCRISPR v2 (Addgene plasmid #52961), the gRNA and Cas-9 sequences were replaced with *S. pyogenes* nuclease deficient Cas-9 and compatible gRNA sequence. The reversibly dimerizeable PYL1 domain was then added to the modified Cas-9 sequences. The gRNA sequences utilized for location-specific targeting are in Table 9.

TABLE 9

List of Primer Sequences for gRNAs, qRT-PCR, 3C, and ChIP qPCR gRNA Sequences

| Name | Sequence 5'-3' | CLOuD9 Construct |
|---|---|---|
| HBB Promoter Pair 1 | TAGTCTGGGTATACTTAGAGG (SEQ ID NO: 1) | CSA |
| LCR Pair 1 | CTAGAGTGATGACTCCTATC (SEQ ID NO: 2) | CSP |
| HBB Promoter Pair 2 | AAGTTGATGCACTAAAAGTGG (SEQ ID NO: 3) | CSA |
| LCR Pair 2 | AATATGTCACATTCTGTCTC (SEQ ID NO: 4) | CSP |
| Oct4 Promoter | CTTATGGCTGTTGATGCATTG (SEQ ID NO: 5) | CSA |
| Oct4 Distal 5'Enhancer | CTCTTTGGATCGCGTCACTC (SEQ ID NO: 6) | CSP | qPCR Primers

| Primer | Forward 5'-3' | Reverse 5'-3' |
|---|---|---|
| β-globin | TGGGCAACCCTAAGGTGAAG (SEQ ID NO: 7) | GTGAGCCAGGCCATCACTA AA (SEQ ID NO: 8) |
| Oct4 | TGTACTCCTCGGTCCCTTTC (SEQ ID NO: 9) | TCCAGGTTTTCTTTCCCTA GC (SEQ ID NO: 10) |
| GapDH | ACCACAGTCCATGCCATCACT (SEQ ID NO: 11) | CCATCACGCCACAGTTTCC (SEQ ID NO: 12) |

3C Primers
β-globin

| Name | Primer Sequence 5'-3' |
|---|---|
| 3C B/HS | TCTTAGAAAGCCTTTACAATTTCCTTTATC (SEQ ID NO: 13) |
| 3C 3 Beta | AGCTTAGTGATACTTGTGGGCCA (SEQ ID NO: 14) |
| 3C Beta | GCTCGGCACATGTCCCATCCAG (SEQ ID NO: 15) |
| 3C Delta | AAAAAATGTGGAATTAGACCCAGGAATG (SEQ ID NO: 16) |
| 3C 5 Delta | GGGTGTGTATTTGTCTGCCA (SEQ ID NO: 17) |
| 3C G/A | AATTTGAAGATACAGCTTGCCTCCGATAAG (SEQ ID NO: 18) |
| 3C Gg | GGGTTCATCTTTATTGTCTCCT (SEQ ID NO: 19) |
| 3C E/G | CCACCCCGATAAAGATTTTCTCCATCA (SEQ ID NO: 20) |
| 3C H5432 | CCAAATGGGTGACTGTAGGGTTGAGA (SEQ ID NO: 21) |
| 3' HS1 | ATTCCCGTTTTTATGAAATCAACTTT (SEQ ID NO: 22) |
| 3' 3'H51 | CTCATAGATTTCTCAATGGCCAAA (SEQ ID NO: 23) |

Oct4

| Name | Primer Sequence 5'-3' |
|---|---|
| PromoterF1 | TGTGCCTTCAGGGGCCAGTC (SEQ ID NO: 24) |
| PromoterF2 | AGTCACCCTCTCAGCTCCTCA (SEQ ID NO: 25) |
| PromoterR1 | TGGGGTGAAATTTGGCAGGCT (SEQ ID NO: 26) |
| PromoterR2 | AGGCTGGGCAGATGGTGCCA (SEQ ID NO: 27) |
| 5'EnhF1 | CAAAGTCACACTGCACCCGCT (SEQ ID NO: 28) |
| 5'EnhF2 | ATGTGGCTCCCTCCCATGTAC (SEQ ID NO: 29) |

TABLE 9-continued

List of Primer Sequences for gRNAs, qRT-PCR, 3C, and ChIP qPCR

| | |
|---|---|
| 5'EnhR1 | CACTGGCAAGGATTATCTCATG (SEQ ID NO: 30) |
| 5'EnhR2 | TGTGTCCAGTTGCCAAATGAGG (SEQ ID NO: 31) |
| DistalEnhF1 | CAGGGCACACACACTTTTGCAG (SEQ ID NO: 32) |
| DistalEnhF2 | GTATCCAAAAACCCAAGCCAGGTC (SEQ ID NO: 33) |
| DistalEnhR1 | TAGCAGGCCCCCAAGGAGGA (SEQ ID NO: 34) |
| DistalEnhR2 | ACTGGGAAGGAACTGGCACT (SEQ ID NO: 35) |
| 3'EnhF1 | TGCCATTACCATCCCACGGT (SEQ ID NO: 36) |
| 3'EnhF2 | CTAGGGGAGAAGCCCGGGTTG (SEQ ID NO: 37) |
| 3'EnhR1 | TGGTCCCCACTTCCCCAGGTG (SEQ ID NO: 38) |
| 3'EnhR2 | GCGGGAACAGGCAGGCTCT (SEQ ID NO: 39) |

ChIP qPCR Primers

| Name | Primer Sequence 5' - 3' |
|---|---|
| HBB 7F1 | CAACAAGGTGCCAAGTCTTTT (SEQ ID NO: 40) |
| HBB 7R1 | ACATCACCTGGATGGGACAT (SEQ ID NO: 41) |
| HBB 13F1 | GAATGGCCCTAGTCTGGGTA (SEQ ID NO: 42) |
| HBB 13R1 | TGCTGCTTTTGAAACAAATGA (SEQ ID NO: 43) |
| HBB 10F1 | CCTATGGCAAAAATGGTGCT (SEQ ID NO: 44) |
| HBB 10R1 | CATGCAGTAAACAACCGAACA (SEQ ID NO: 45) |
| C5 1F2 | TTTGCCATCTGCCCTGTAAG (SEQ ID NO: 46) |
| C5 1R2 | AGTCATGCTGAGGCTTAGGG (SEQ ID NO: 47) |
| C5 6F1 | TCAGCTCTGCCTTTCTCCTC (SEQ ID NO: 48) |
| C5 6R1 | GCAGACCTTAACTGGCATCC (SEQ ID NO: 49) |
| C5 8F1 | CAGTTGCATGCTACCTTAAAGA (SEQ ID NO: 50) |
| C5 8R1 | AAGCTGAATCTGCTGCCAAC (SEQ ID NO: 51) |
| DistalHBBF | GCCGTAAAACATGGAAGGAA (SEQ ID NO: 52) |
| DistalHBBR | CCCATTTGCTTATCCTGCAT (SEQ ID NO: 53) |
| 3'HBBF | TTCCAGAATCTAGCATCTACCTACC (SEQ ID NO: 54) |
| 3'HBBR | TGCTTCTGGCTCTGCAGTTA (SEQ ID NO: 55) |
| HBBF | GCAAGAAAGCGAGCTTAGTGA (SEQ ID NO: 56) |
| HBBR | CAAAGAATTCACCCCACCAG (SEQ ID NO: 57) |
| 5'HBBF | CCTCACCACCAACTTCATCC (SEQ ID NO: 58) |
| 5'HBBR | GCAACCTCAAACAGACACCA (SEQ ID NO: 59) |
| Proximal PromF | TAGATGGCTCTGCCCTGACT (SEQ ID NO: 60) |
| Proximal PromR | CACTTAGACCTCACCCTGTGG (SEQ ID NO: 61) |
| Distal PromF | TGGGGTAATCAGTGGTGTCA (SEQ ID NO: 62) |
| Distal PromR | TTTTGTTCCCCCAGACACTC (SEQ ID NO: 63) |
| Positive Control1F | ACCCTTCAGCAGTTCCACAC (SEQ ID NO: 64) |
| Positive Control1R | ACCCTTCAGCAGTTCCACAC (SEQ ID NO: 65) |
| Positive Control2F | TGGTATTTTATTCTGAAACACAGAGG (SEQID NO: 66) |

TABLE 9-continued

List of Primer Sequences for gRNAs, qRT-PCR, 3C, and ChIP qPCR

| | |
|---|---|
| Positive Control2R | GCTTCGGTGTTCAGTGGATT (SEQ ID NO: 67) |
| Negative ControlF | CCCAAATGAGATTATGCCACTG (SEQ ID NO: 68) |
| Negative ControlR | CTATGTTTGTGTTGCAGAGCCC (SEQ ID NO: 69) |

Example 3—Lentivirus Production

Lentivirus was produced using sequence verified packaging constructs pRSV-Rev (Addgene plasmid #12253), pMD2.G (Addgene plasmid #12259), and pMDLg/pRRE (Addgene plasmid #12251). Briefly, 750,000 293T cells/well were seeded into a 6-well plate. Twenty-four hours after seeding, media was changed to fresh antibiotic free DMEM (Life Technologies, 11995-065) with 10% FBS. Plasmids were transfected into 293T cells using Lipofectamine 2000 following manufacturer's protocol (Thermo-Fisher Scientific 11668). After 12 hours, media was changed to viral production media (RPMI 1640 for K562 cells, DMEM for 293T cells, both with 10% FBS). Forty-eight hours later, viral production media was collected and spun down at low speed to remove any cell debris. Virus was then used immediately for transduction or frozen at −80 C for future use.

Example 4—Lentivirus Transduction

K562 cells were transduced through addition of 250 µl of each viral construct of interest to a 15 mL conical tube containing 80,000 cells. Total volume of media in each conical was brought to 1 mL with antibiotic free RPMI 1640+10% FBS, and polybrene was added to each tube to a final concentration of 4 µg/mL. Cells were then spun at 800×g for 30 minutes at room temperature, resuspended briefly by pipetting without removing the viral supernatant, and moved to cell culture plates. Twenty-four hours later, cells were spun down at 300×g for 5 minutes at room temperature, viral supernatant was aspirated, and cells were resuspended and re-plated in RPMI 1640+10% FBS+1% penicillin/streptomycin overnight. On the following day, puromycin (2 µg per mL) and hygromycin (100 µg per mL) were added to the culture medium to select for transduced cells.

293T cells were transduced through addition of 250 µL each viral construct of interest to one well of a 6-well plate. Total volume of media was brought to 2 mL with antibiotic free DMEM+10% FBS, and polybrene was added to a final concentration of 2 µg per mL. Twenty-four hours later, viral supernatant was aspirated, and media was changed to DMEM+10% FBS+1% penicillin/streptomycin overnight.

On the following day, puromycin (1 µg per mL) and hygromycin (25 µg per mL) were added to the culture medium to select for transduced cells.

For both cell lines, cells were kept in selection media for at least one-week prior to use in any downstream experiments, and were maintained in selection media for the duration of all experiments.

Example 5—Cell Dimerization and Washout

For dimerization treatment of CLOuD9 transduced cells, 1 mM Abscisic Acid (or an equivalent volume of DMSO for controls) was added to the culture medium. Abscisic acid was used within 6 months of date of receipt, and was kept cold, protected from light throughout use. Media was changed and fresh abscisic acid or DMSO was added daily.

For washout/reversal of dimerization, cells that had been subjected to dimerization were spun down, washed once in PBS, and resuspended in fresh culture medium without dimerization agent.

Example 6—Immunoprecipitation and Co-Immunoprecipitations

Cells dimerized as described above were collected and spun down prior to crosslinking with 1% formaldehyde at room temperature for 10 minutes followed by glycine quenching. Cells were lysed in 0.1 M Tris pH 7.5, 10 mM potassium acetate, 15 mM magnesium acetate, 1% NP-40 and spun to isolate nuclei, then nuclei were lysed using 0.1 M Tris pH 8, 1% SDS, 10 mM EDTA. Nuclei were sonicated briefly to solubilize material, and SDS was quenched with dilution buffer containing 0.01% SDS, 1.1% Triton X-100, 1.2 mM EDTA, 16.7 mM Tris pH 7.5, and 167 mM NaCl. Protein complexes were immunoprecipitated overnight using the antibodies against HA (Cell Signaling 3724), Flag (Sigma F1804), or DDX5 (Bethyl A300-523A), all at 1:50, and were washed three times with 100 mM Tris pH 9, 100 mM LiCl, 1% NP-40, and 1% sodium deoxycholate. Complexes were eluted by vortexing twice with 1% SDS, 15 mM NaHCO$_3$ for 15 minutes each time. Elutes were run on SDS-page gels and probed with antibodies against the HA tag (Cell Signaling 3724), Flag tag (Sigma F1804), CTCF (Cell Signaling 2899), SMC1 (Bethyl A300-055A), or DDX17 (Bethyl A300-509A) as indicated, all at 1:1000.

Example 7—RNA Extraction and Quantitative PCR

Total RNA was isolated using TRIzol® (Life Technologies 15596-018) and RNeasy Kit (QIAGEN 74106) according to the manufacturer's protocol. cDNA was made with Superscript VILO (Life Technologies 11754-050). All primers utilized were previously reported[10], but are also summarized in Table 9. qPCR analyses were performed using SYBR Green I MasterMix (Roche 4707516001) on the Light Cycler 48011 (Roche).

Example 8—Statistical Analysis of Gene Expression Changes

Statistical analysis was performed using GraphPad Prism 5 for MacOS X. For every sample, two sets of duplicates were averaged for each of three biological replicates to obtain a final n of three for all statistical analyses. Two-tailed student's T tests were performed on ABA and control treated samples. Error bars represent the standard deviation.

Example 9—Chromosome Conformation Capture Assay (3C)

3C assays of the β-globin locus were performed as previously described[10], with the following modifications.

Cells were crosslinked with 1% formaldehyde at room temperature for 10 minutes followed by glycine quenching, cell lysis, EcoRI digestion, and T4 ligation. 3C ligation products were quantified in two sets of duplicates for each of three biological replicates by quantitative SYBR Green real-time PCR using SYBR Green I MasterMix (Roche 4707516001) on the Light Cycler 48011 (Roche).

The HS432 fragment was used as the anchor fragment for all experiments at the globin loci. Samples were normalized to 3C signals from the tubulin locus. To eliminate variability between samples, interaction frequencies between the anchor fragment and the fragment encompassing the β/HS fragment were set to zero. Primer sequences are listed in Table 9.

3C assays of the Oct4 locus were also performed as previously described[13], with the following modifications. Cells were crosslinked with 1% formaldehyde at room temperature for 10 minutes followed by glycine quenching, cell lysis, MboI digestion, and T4 ligation. 3C ligation products were quantified in two sets of duplicates for each of three biological replicates by PCR amplification and Image J quantification of amplicon intensity. Primer sequences are listed in Table 9.

Example 10—Mass Spectrometry Chromatin Immunoprecipitation

Immunoprecipitations were performed as described above. Briefly, cells were crosslinked with 1% formaldehyde at room temperature for 10 minutes followed by glycine quenching, cell lysis, nuclei isolation and lysis, and brief sonication. Protein complexes were immunoprecipitated overnight using an anti-HA antibody (Cell Signaling 3724), and were washed and eluted as described above. Elutes were used directly for mass spectrometry experiments without further dilution.

Example 11—CLOuD9 Mass Spectrometry Sample Preparation

Samples were reduced and alkylated by diluting 2× the sample's volume with exchange buffer containing 8 M urea (Acros Organics, New Jersey) and 100 mM ammonium bicarbonate (Sigma-Aldrich, St. Louis Mo.). Dithioteitol (DTT; Sigma-Aldrich, St. Louis Mo.) was added to a final concentration of 10 mM DTT. Samples were incubated at room temperature for 1.5 hours.

Iodoacetamide (Acros Organics, New Jersey) was added in 1.5-fold molar excess of DTT followed by another incubation for 1 hour at room temperature in the dark. Samples were buffer exchanged using a Filtered Aided Sample Preparation (FASP) method[12]. First, samples were transferred into a Microcon Ultrafiltration 10 kDa filter (ED Millipore, Billerica Mass., Cat #MRCPRT010) and centrifuged at 14,000 g for 30 minutes. 200 μL of exchange buffer was added and the 30 minute centrifugation and addition of exchange buffer was repeated three times. Next, 200 μL of digestion buffer (50 mM ammonium bicarbonate) was added to the Microcon filter followed by centrifugation at 14,000 g for 25 minutes and repeated three additional times. Samples were digested with 6 μg of trypsin (Promega, Sunnyvale, Calif.) at 37° C. with shaking at 900 rpm for 18 hours. After digestion, samples were centrifuged at 14,000 g for 15 minutes to collect tryptic peptides. Peptides were dried using a Speed-Vac (Labconco, Kansas City, Mo.). Samples were further desalted by C18 Zip-Tips (EMD Millipore, Darmstadt, Germany, Cat #ZTC18S096).

Example 12—LC/MS Analysis

Tryptic peptides were loaded onto a C18 nanospray column (50 mm length, 2 um particle size, Thermo Fisher Scientific, San Jose, Calif.) and separated by reversed-phase chromatography using a nanoEasy nLC-1200 (Thermo Fisher Scientific, San Jose, Calif.). Eluted peptides were analyzed subject to online LC-MS analysis using a Q Exactive mass spectrometer (Thermo Fisher Scientific, San Jose, Calif.).

Mobile phase A consisted of 0.1% formic acid in water and the LC was pumped at 250 nL/min. Mobile phase B (0.1% formic acid in acetonitrile) was run at 2% for the first 5 minutes, slowly ramped up to 20% in 150 minutes, and rapidly increased to 95% in 40 minutes. The top 15 most abundant ions per MS1 scan were selected for higher energy collision induced dissociation (27 eV) in a data-dependent fashion. MS1 resolution was set at 70,000, AGC target was set to 3e6, and the m/z scan range was set from m/z=375-1500. MS2 resolution was set at 17,500 and AGC target at 2e5. Dynamic exclusion was enabled for 30 seconds.

Example 13—CLOuD9 ChIP-qPCR

Conventional ChIP-qPCR was performed. Briefly, cells were crosslinked with 1% formaldehyde at room temperature for 10 minutes followed by glycine quenching, cell lysis, nuclei isolation and lysis, and sonication to obtain 150-200 bp DNA fragments. Complexes were immunoprecipitated overnight using 10 μg of anti-HA tag (Cell Signaling 3724), anti-Flag tag (Sigma F1804), anti-H3K4me3 (AbCam ab8580), anti-RNA Pol-II (Active Motif 61083), or anti-DDX5 (Bethyl A300-523A). Real-time qPCR of purified DNA was performed using SYBR Green I MasterMix (Roche 4707516001) on the Light Cycler 48011 (Roche). qPCR primers are provided in Table 9.

Example 14—shRNA Knockdown of DDX5 and DDX17

MISSION shRNA bacterial stocks (TRCN0000272488, TRCN0000287046) were obtained from Sigma Aldrich, and prepared as recommended by manufacturer. shRNA plasmids were isolated using a Qiagen Miniprep kit (Qiagen 27106) and lentiviral constructs were produced and delivered to K562 cells as described above. Efficient knockdown was validated by Western Blot.

Example 15—Protein Extraction and Western Blot Analysis

Cellular extracts were prepared using lysis buffer containing 50 mM Tris HCL (pH 7.5), 250 mM NaCl, 1% NP-40, 0.5% Na-deoxycholate, 0.1% SDS, and EDTA free protease inhibitor (Roche 11873580001). Extracts were run on a 4-12% Tris-Glycine gel (BioRad) and transferred onto PVDF membranes. Blots were blocked in 5% milk PBS-T for 1 hour at room temperature followed by overnight incubation at 4° C. with primary antibodies at 1:1000 (anti-HA Tag, Cell Signaling 3724S; anti-Flag Tag, Sigma F1804; anti-DDX5, Bethyl A300-523A; anti-DDX17, Bethyl A300-509A). HRP-conjugated secondary antibodies were used at 1:10,000 (anti-rabbit HRP, Santa Cruz sc-2030) or 1:1000 (anti-mouse HRP, Cell Signaling 7076S).

Example 16—ChIP-seq Sample Acquisition and Analysis

K562 and HEK293 ChIP-Seq data were obtained from Encode (ENCSR000AKU, ENCSR000APE, ENCSR000FCJ) and GEO (GSM1479215). Alignment was performed using Bowtie, and duplicates were removed using samtools. The filtered files were converted to bigwig format for visualization using genomeCoverageBed from Bedtools, as well as bedGraphToBigWig. The bigwig files were normalized using bamCoverage.

CONCLUSION AND PERSPECTIVES

In summary, the CLOuD9 technology, a new, broadly applicable tool for the precise manipulation of three-dimensional chromatin structure is disclosed herein. Using this tool, it is demonstrated herein that chromatin looping alone is sufficient to alter gene expression in the proper biological context. In addition, a novel mechanism for stable formation of de novo chromatin contacts independent of cohesin and CTCF, through the RNA helicases DDX5 and DDX17 is identified herein. Whether these or other RNA helicases are broadly involved in maintaining de novo chromatin contacts will be an important area of future study.

Without being bound by any theory, the findings reported here indicate that CLOuD9 can be utilized to elucidate more precisely how chromatin structure regulates gene expression and enhance the understanding of the role of large-scale chromatin organization in the control of transcriptional dynamics. This will be particularly important in contexts such as cancer and congenital disorders, where disruptions of genomic organization by chromosomal rearrangements markedly affect gene expression[15-18]. Understanding how chromatin restructuring may be harnessed in these contexts to regulate gene expression for therapeutic benefit will be of significant importance in future studies. Taken together, future work with CLOuD9 technology will undoubtedly shed greater light on the hierarchy and dynamics of chromatin domains that facilitate chromatin restructuring, as well as how both de novo and sustained loops can be harnessed and reorganized to alter transcriptional programs in development and disease.

In some embodiments, a CRISPR-dCas9 based technology, CLOuD9, for the targeted, selective, and reversible manipulation of 3D chromatin structure is disclosed. In some embodiments, CLOuD9 can be utilized in a variety of chromatin contexts and states. In some embodiments, by altering chromatin contacts, in the proper biological context CLOuD9 can alter gene expression.

In some embodiments, significant benefits of CLOuD9 technology include, without limitations, ease of utilization at multiple genomic locations, application to additional genomic loci, applicability to any genomic locus where that can be targeted by CRISPR gRNAs, ease of use by one of ordinary skill in the art (e.g., a scientist) as no special biological techniques are required to use this technology, and many constructs similar to those disclosed herein (e.g., plasmids) are commercially available through ThermoFisher, Origene, Addgene, and SBI. It will be understood by one of ordinary skill in the art that other forms of constructs are within the scope of this disclosure (e.g., RNA-based constructs, adenoviral vectors, etc.). In some embodiments, the technology is to be applicable to virtually any gene, in any disease related to altered gene expression where there is not an underlying gene sequence mutation.

In some embodiments, applications of CLOuD9 technology include, without limitation, validation of observations made through 3C based technologies about chromatin structure in different biological contexts, induction or repression of gene expression at will through juxtaposition of critical regulatory elements over long genomic distances, previously impossible study of chromatin interactions across the genome to more fully elucidate their biological functions, and maintenance of cell state in the absence of exogenous factor additions.

In some embodiments, this technology is primarily marketable for life science, biotech and pharmaceutical research applications. In some embodiments, the customer base is bioscientists in both industry and academia. In some embodiments, geneticists, epigeneticists, developmental biologists, and stem cell biologists can particularly benefit from this product.

Although this disclosure is in the context of certain embodiments and examples, those skilled in the art will understand that the present disclosure extends beyond the specifically disclosed embodiments to other alternative embodiments and/or uses of the embodiments and obvious modifications and equivalents thereof. In addition, while several variations of the embodiments have been shown and described in detail, other modifications, which are within the scope of this disclosure, will be readily apparent to those of skill in the art based upon this disclosure. It is also contemplated that various combinations or sub-combinations of the specific features and aspects of the embodiments may be made and still fall within the scope of the disclosure. It should be understood that various features and aspects of the disclosed embodiments can be combined with, or substituted for, one another in order to form varying modes or embodiments of the disclosure. Thus, it is intended that the scope of the present disclosure herein disclosed should not be limited by the particular disclosed embodiments described above.

As used herein, the section headings are for organizational purposes only and are not to be construed as limiting the described subject matter in any way. All literature and similar materials cited in this application, including but not limited to, patents, patent applications, articles, books, treatises, and internet web pages are expressly incorporated by reference in their entirety for any purpose. When definitions of terms in incorporated references appear to differ from the definitions provided in the present teachings, the definition provided in the present teachings shall control. It will be appreciated that there is an implied "about" prior to the temperatures, concentrations, times, etc. discussed in the present teachings, such that slight and insubstantial deviations are within the scope of the present teachings herein.

In this application, the use of the singular includes the plural unless specifically stated otherwise. Also, the use of "comprise", "comprises", "comprising", "contain", "contains", "containing", "include", "includes", and "including" are not intended to be limiting.

As used in this specification and claims, the singular forms "a," "an" and "the" include plural references unless the content clearly dictates otherwise.

REFERENCES

All references cited in this disclosure are incorporated herein by reference in their entireties.

1. Krivega, I. & Dean, A. Chromatin looping as a target for altering erythroid gene expression. *Ann. N.Y. Acad. Sci.* 1368, 31-39 (2016).
2. Matharu, N. & Ahituv, N. Minor loops in major folds: Enhancer-promoter looping, chromatin restructuring, and their association with transcriptional regulation and disease. *PLoS Genet.* 11, e1005640 (2015).
3. Dekker, J., Martí-Renom, M. A. & Mirny, L. A. Exploring the three-dimensional organization of genomes: interpreting chromatin interaction data. *Nature Publishing Group.* 14, 390-403 (2013).
4. Kim, A. & Dean, A. Chromatin loop formation in the β-globin locus and its role in globin gene transcription. *Mol Cells.* 34, 1-5 (2012).
5. Stadhouders, R. et al. Transcription regulation by distal enhancers. *Transcription.* doi:10.4161/trns.20720 (2012).
6. van Steensel, B. & Dekker, J. Genomics tools for unraveling chromosome architecture. *Nat. Biotechnol.* 28, 1089-1095 (2010).
7. Petrascheck, M. et al. DNA looping induced by a transcriptional enhancer in vivo. *Nucleic Acids Res.* 33, 3743-3750 (2005).
8. Ameres, S. L. et al. Inducible DNA-loop formation blocks transcriptional activation by an SV40 enhancer. *EMBO J.* 24, 358-367 (2005).
9. Deng, W. et al. Controlling Long-Range Genomic Interactions at a Native Locus by Targeted Tethering of a Looping Factor. *Cell.* 149, 1233-1244 (2012).
10. Deng, W. et al. Reactivation of developmentally silenced globin genes by forced chromatin looping. *Cell.* 158, 849-860 (2014).
11. Liang, F.-S., Ho, W. Q. & Crabtree, G. R. Engineering the ABA plant stress pathway for regulation of induced proximity. *Science Signaling.* 4, rs2-rs2 (2011).
12. Theunissen, T. W., et al. Systematic identification of culture conditions for induction and maintenance of naive human pluripotency. *Cell Stem Cell.* 15, 471-487 (2014).
13. Zhang, H. et al. Intrachromosomal looping is required for activation of endogenous pluripotency genes during reprogramming. *Cell Stem Cell.* 13, 30-35 (2013).
14. Mokry, M. et al. Integrated genome-wide analysis of transcription factor occupancy, RNA polymerase II binding and steady state RNA levels identify differentially regulated functional gene classes. *Nucleic Acids Res.* 40, 148-158 (2012).
15. Drier, Y. et al. An oncogenic MYB feedback loop drives alternate cell fates in adenoid cystic carcinoma. *Nat Genet.* 48, 265-272 (2016).
16. Ryan, R. J. H. et al. Detection of enhancer-associated rearrangements reveals mechanisms of oncogene dysregulation in B-cell lymphoma. *Cancer Discov.* 5, 1058-1071 (2015).
17. Montavon, T. et al. A regulatory archipelago controls Hox genes transcription in digits. *Cell.* 147, 1132-1145 (2011).
18. Lupianez, D. G. et al. Disruptions of topological chromatin domains cause pathogenic rewiring of gene-enhancer interactions. *Cell.* 161, 1012-1025 (2015).

What is claimed is:

1. A system for juxtaposing a first chromosomal locus and a second chromosomal locus, the system comprising:
   a first nucleic acid construct encoding a first fusion protein and a first guide RNA, wherein the first fusion protein comprises a dCas9 from a first species, a first dimerization protein, and a first tag; and
   a second nucleic acid construct encoding a second fusion protein and a second guide RNA, wherein the second fusion protein comprises a dCas9 from a second different species, a second dimerization protein, and a second tag,
   wherein the first fusion protein is directed to the first chromosomal locus by the first guide RNA, and the second fusion protein is directed to the second chromosomal locus by the second guide RNA, and
   wherein the first fusion protein and the second fusion protein are configured to dimerize, thereby juxtaposing the first chromosomal locus and the second chromosomal locus.

2. The system of claim 1, wherein the first nucleic acid construct and the second nucleic acid construct are DNA-based.

3. The system of claim 1, wherein the first nucleic acid construct and the second nucleic acid construct are RNA-based.

4. The system of claim 1, wherein the first guide RNA and the second guide RNA are about 5 to about 100 nucleotides.

5. The system of claim 1, wherein the first species and second different species are selected from the group consisting of *S. pyogenes, S. aureus, N. meningitides, S. thermophiles, T. denticola, S. pasteurianus, N. cinerea, C. lari, P. lavamentivorans, C. diphtheria*, and any bacterial species utilizing the CRISPR-Cas9 bacterial adaptive immune system.

6. The system of claim 1, wherein the first fusion protein and the second fusion protein are configured to dimerize via a reversible chemical induced proximity system.

7. The system of claim 6, wherein the reversible chemical induced proximity system comprises the first dimerization protein and second dimerization protein, wherein the first dimerization protein and the second dimerization protein are configured to be brought into proximity in the presence of a dimerizing agent, thereby allowing the first fusion protein and the second fusion protein to dimerize.

8. The system of claim 1, wherein the first dimerization protein and the second dimerization protein are selected from the group consisting of plant ABA signaling pathway, gibberellin-induced dimerization system, rapalog-induced dimerization system, RNA-mediated protein recruitment dimerization system, and derivatives thereof.

9. The system of claim 1, wherein the first dimerization protein is ABI1 and the second dimerization protein is PYL1 of the plant ABA signaling pathway.

10. The system of claim 1, wherein the first dimerization protein is PYL1 and the second dimerization protein is ABI1 of the plant ABA signaling pathway.

11. The system of claim 7, wherein the dimerizing agent is ABA.

12. A method to alter an expression of at least one gene at a first chromosomal locus by juxtaposing the first chromosomal locus and a second chromosomal locus, the method comprising:
   providing the system of claim 1;
   directing the first fusion protein to the first chromosomal locus by the first guide RNA, and
   directing the second fusion protein to the second chromosomal locus by the second guide RNA, and
   dimerizing the first fusion protein and the second fusion protein to juxtapose the first chromosomal locus and the second chromosomal locus,
   thereby altering an expression of at least one gene at a first chromosomal locus.

13. The method of claim 12, wherein the expression of at least one gene at the second chromosomal locus is altered by juxtaposing the first chromosomal locus and the second chromosomal locus.

14. The method of claim 12, wherein the second chromosomal locus comprises one or more regulatory elements that alter the expression of the at least one gene at the first chromosomal locus.

15. The method of claim 13, wherein the first chromosomal locus comprises one or more regulatory elements that alter the expression of the at least one gene at the second chromosomal locus.

16. The method of claim 12, wherein the first species and second different species are selected from the group consisting of *S. pyogenes, S. aureus, N. meningitides, S. thermophiles, T. denticola, S. pasteurianus, N. cinerea, C. lari, P. lavamentivorans, C. diphtheria*, and any bacterial species utilizing the CRISPR-Cas9 bacterial adaptive immune system.

17. The method of claim 12, wherein the first fusion protein and the second fusion protein dimerize via a reversible chemical induced proximity system.

18. The method of claim 17, wherein the reversible chemical induced proximity system comprises the first dimerization protein and second dimerization protein, wherein the first dimerization protein and the second dimerization protein are brought into proximity in the presence of a dimerizing agent, thereby allowing the first fusion protein and the second fusion protein to dimerize.

19. The method of claim 12, wherein the first dimerization protein and the second dimerization protein are selected from the group consisting of plant ABA signaling pathway, gibberellin-induced dimerization system, rapalog-induced dimerization system, RNA-mediated protein recruitment dimerization system, and derivatives thereof.

20. The method of claim 12, wherein the first dimerization protein is ABI1 and the second dimerization protein is PYL1 of the plant ABA signaling pathway.

21. The method of claim 12, wherein the first dimerization protein is ABI1 and the second dimerization protein is PYL1 of the plant ABA signaling pathway.

22. The method of claim 18, wherein the dimerizing agent is ABA.

23. A system for juxtaposing a first chromosomal locus and a second chromosomal locus, the system comprising:
   a first fusion protein and a first guide RNA, wherein the first fusion protein comprises a dCas9 from a first species, a first dimerization protein, and a first tag; and
   a second fusion protein and a second guide RNA, wherein the second fusion protein comprises a dCas9 from a second different species, a second dimerization protein, and a second tag,
   wherein the first fusion protein is directed to the first chromosomal locus by the first guide RNA, and the second fusion protein is directed to the second chromosomal locus by the second guide RNA, and
   wherein the first fusion protein and the second fusion protein are configured to dimerize, thereby juxtaposing the first chromosomal locus and the second chromosomal locus.

* * * * *

SEQUENCE LISTING

<160> NUMBER OF SEQ ID NOS: 69

<210> SEQ ID NO 1
<211> LENGTH: 21
<212> TYPE: DNA
<213> ORGANISM: Artificial
<220> FEATURE:
<223> OTHER INFORMATION: Synthetic

<400> SEQUENCE: 1
tagtctgggt atacttagag g            21

<210> SEQ ID NO 2
<211> LENGTH: 20
<212> TYPE: DNA
<213> ORGANISM: Artificial
<220> FEATURE:
<223> OTHER INFORMATION: Synthetic

<400> SEQUENCE: 2
ctagagtgat gactcctatc            20

<210> SEQ ID NO 3
<211> LENGTH: 21
<212> TYPE: DNA
<213> ORGANISM: Artificial
<220> FEATURE:
<223> OTHER INFORMATION: Synthetic

<400> SEQUENCE: 3
aagttgatgc actaaaagtg g            21

<210> SEQ ID NO 4
<211> LENGTH: 20
<212> TYPE: DNA

```
<213> ORGANISM: Artificial
<220> FEATURE:
<223> OTHER INFORMATION: Synthetic

<400> SEQUENCE: 4
aatatgtcac attctgtctc                                                20

<210> SEQ ID NO 5
<211> LENGTH: 21
<212> TYPE: DNA
<213> ORGANISM: Artificial
<220> FEATURE:
<223> OTHER INFORMATION: Synthetic

<400> SEQUENCE: 5
cttatggctg ttgatgcatt g                                              21

<210> SEQ ID NO 6
<211> LENGTH: 20
<212> TYPE: DNA
<213> ORGANISM: Artificial
<220> FEATURE:
<223> OTHER INFORMATION: Synthetic

<400> SEQUENCE: 6
ctctttggat cgcgtcactc                                                20

<210> SEQ ID NO 7
<211> LENGTH: 20
<212> TYPE: DNA
<213> ORGANISM: Artificial
<220> FEATURE:
<223> OTHER INFORMATION: Synthetic

<400> SEQUENCE: 7
tgggcaaccc taaggtgaag                                                20

<210> SEQ ID NO 8
<211> LENGTH: 21
<212> TYPE: DNA
<213> ORGANISM: Artificial
<220> FEATURE:
<223> OTHER INFORMATION: Synthetic

<400> SEQUENCE: 8
gtgagccagg ccatcactaa a                                              21

<210> SEQ ID NO 9
<211> LENGTH: 20
<212> TYPE: DNA
<213> ORGANISM: Artificial
<220> FEATURE:
<223> OTHER INFORMATION: Synthetic

<400> SEQUENCE: 9
tgtactcctc ggtcccttttc                                               20

<210> SEQ ID NO 10
<211> LENGTH: 21
<212> TYPE: DNA
<213> ORGANISM: Artificial
<220> FEATURE:
<223> OTHER INFORMATION: Synthetic

<400> SEQUENCE: 10
tccaggtttt ctttccctag c                                              21
```

<210> SEQ ID NO 11
<211> LENGTH: 21
<212> TYPE: DNA
<213> ORGANISM: Artificial
<220> FEATURE:
<223> OTHER INFORMATION: Synthetic

<400> SEQUENCE: 11
accacagtcc atgccatcac t                                              21

<210> SEQ ID NO 12
<211> LENGTH: 19
<212> TYPE: DNA
<213> ORGANISM: Artificial
<220> FEATURE:
<223> OTHER INFORMATION: Synthetic

<400> SEQUENCE: 12
ccatcacgcc acagtttcc                                                 19

<210> SEQ ID NO 13
<211> LENGTH: 30
<212> TYPE: DNA
<213> ORGANISM: Artificial
<220> FEATURE:
<223> OTHER INFORMATION: Synthetic

<400> SEQUENCE: 13
tcttagaaag cctttacaat ttcctttatc                                     30

<210> SEQ ID NO 14
<211> LENGTH: 23
<212> TYPE: DNA
<213> ORGANISM: Artificial
<220> FEATURE:
<223> OTHER INFORMATION: Synthetic

<400> SEQUENCE: 14
agcttagtga tacttgtggg cca                                            23

<210> SEQ ID NO 15
<211> LENGTH: 22
<212> TYPE: DNA
<213> ORGANISM: Artificial
<220> FEATURE:
<223> OTHER INFORMATION: Synthetic

<400> SEQUENCE: 15
gctcggcaca tgtcccatcc ag                                             22

<210> SEQ ID NO 16
<211> LENGTH: 28
<212> TYPE: DNA
<213> ORGANISM: Artificial
<220> FEATURE:
<223> OTHER INFORMATION: Synthetic

<400> SEQUENCE: 16
aaaaaatgtg gaattagacc caggaatg                                       28

<210> SEQ ID NO 17
<211> LENGTH: 20
<212> TYPE: DNA
<213> ORGANISM: Artificial
<220> FEATURE:

<223> OTHER INFORMATION: Synthetic

<400> SEQUENCE: 17
gggtgtgtat ttgtctgcca                                         20

<210> SEQ ID NO 18
<211> LENGTH: 30
<212> TYPE: DNA
<213> ORGANISM: Artificial
<220> FEATURE:
<223> OTHER INFORMATION: Synthetic

<400> SEQUENCE: 18
aatttgaaga tacagcttgc ctccgataag                              30

<210> SEQ ID NO 19
<211> LENGTH: 22
<212> TYPE: DNA
<213> ORGANISM: Artificial
<220> FEATURE:
<223> OTHER INFORMATION: Synthetic

<400> SEQUENCE: 19
gggttcatct ttattgtctc ct                                      22

<210> SEQ ID NO 20
<211> LENGTH: 28
<212> TYPE: DNA
<213> ORGANISM: Artificial
<220> FEATURE:
<223> OTHER INFORMATION: Synthetic

<400> SEQUENCE: 20
ccaccccgat aaagattttt ctccatca                                28

<210> SEQ ID NO 21
<211> LENGTH: 26
<212> TYPE: DNA
<213> ORGANISM: Artificial
<220> FEATURE:
<223> OTHER INFORMATION: Synthetic

<400> SEQUENCE: 21
ccaaatgggt gactgtaggg ttgaga                                  26

<210> SEQ ID NO 22
<211> LENGTH: 26
<212> TYPE: DNA
<213> ORGANISM: Artificial
<220> FEATURE:
<223> OTHER INFORMATION: Synthetic

<400> SEQUENCE: 22
attcccgttt ttatgaaatc aacttt                                  26

<210> SEQ ID NO 23
<211> LENGTH: 24
<212> TYPE: DNA
<213> ORGANISM: Artificial
<220> FEATURE:
<223> OTHER INFORMATION: Synthetic

<400> SEQUENCE: 23
ctcatagatt tctcaatggc caaa                                    24

```
<210> SEQ ID NO 24
<211> LENGTH: 20
<212> TYPE: DNA
<213> ORGANISM: Artificial
<220> FEATURE:
<223> OTHER INFORMATION: Synthetic

<400> SEQUENCE: 24
tgtgccttca ggggccagtc                                                   20

<210> SEQ ID NO 25
<211> LENGTH: 21
<212> TYPE: DNA
<213> ORGANISM: Artificial
<220> FEATURE:
<223> OTHER INFORMATION: Synthetic

<400> SEQUENCE: 25
agtcaccctc tcagctcctc a                                                 21

<210> SEQ ID NO 26
<211> LENGTH: 21
<212> TYPE: DNA
<213> ORGANISM: Artificial
<220> FEATURE:
<223> OTHER INFORMATION: Synthetic

<400> SEQUENCE: 26
tggggtgaaa tttggcaggc t                                                 21

<210> SEQ ID NO 27
<211> LENGTH: 20
<212> TYPE: DNA
<213> ORGANISM: Artificial
<220> FEATURE:
<223> OTHER INFORMATION: Synthetic

<400> SEQUENCE: 27
aggctgggca gatggtgcca                                                   20

<210> SEQ ID NO 28
<211> LENGTH: 21
<212> TYPE: DNA
<213> ORGANISM: Artificial
<220> FEATURE:
<223> OTHER INFORMATION: Synthetic

<400> SEQUENCE: 28
caaagtcaca ctgcacccgc t                                                 21

<210> SEQ ID NO 29
<211> LENGTH: 21
<212> TYPE: DNA
<213> ORGANISM: Artificial
<220> FEATURE:
<223> OTHER INFORMATION: Synthetic

<400> SEQUENCE: 29
atgtggctcc ctcccatgta c                                                 21

<210> SEQ ID NO 30
<211> LENGTH: 22
<212> TYPE: DNA
<213> ORGANISM: Artificial
<220> FEATURE:
<223> OTHER INFORMATION: Synthetic
```

```
<400> SEQUENCE: 30
cactggcaag gattatctca tg                                            22

<210> SEQ ID NO 31
<211> LENGTH: 22
<212> TYPE: DNA
<213> ORGANISM: Artificial
<220> FEATURE:
<223> OTHER INFORMATION: Synthetic

<400> SEQUENCE: 31
tgtgtccagt tgccaaatga gg                                            22

<210> SEQ ID NO 32
<211> LENGTH: 22
<212> TYPE: DNA
<213> ORGANISM: Artificial
<220> FEATURE:
<223> OTHER INFORMATION: Synthetic

<400> SEQUENCE: 32
cagggcacac acactttgc ag                                             22

<210> SEQ ID NO 33
<211> LENGTH: 24
<212> TYPE: DNA
<213> ORGANISM: Artificial
<220> FEATURE:
<223> OTHER INFORMATION: Synthetic

<400> SEQUENCE: 33
gtatccaaaa acccaagcca ggtc                                          24

<210> SEQ ID NO 34
<211> LENGTH: 20
<212> TYPE: DNA
<213> ORGANISM: Artificial
<220> FEATURE:
<223> OTHER INFORMATION: Synthetic

<400> SEQUENCE: 34
tagcaggccc ccaaggagga                                               20

<210> SEQ ID NO 35
<211> LENGTH: 20
<212> TYPE: DNA
<213> ORGANISM: Artificial
<220> FEATURE:
<223> OTHER INFORMATION: Synthetic

<400> SEQUENCE: 35
actgggaagg aactggcact                                               20

<210> SEQ ID NO 36
<211> LENGTH: 20
<212> TYPE: DNA
<213> ORGANISM: Artificial
<220> FEATURE:
<223> OTHER INFORMATION: Synthetic

<400> SEQUENCE: 36
tgccattacc atcccacggt                                               20

<210> SEQ ID NO 37
<211> LENGTH: 21
```

```
<212> TYPE: DNA
<213> ORGANISM: Artificial
<220> FEATURE:
<223> OTHER INFORMATION: Synthetic

<400> SEQUENCE: 37 ctagggaga  agcccgggtt  g                                              21

<210> SEQ ID NO 38
<211> LENGTH: 21
<212> TYPE: DNA
<213> ORGANISM: Artificial
<220> FEATURE:
<223> OTHER INFORMATION: Synthetic

<400> SEQUENCE: 38
tggtccccac  ttccccaggt  g                                             21

<210> SEQ ID NO 39
<211> LENGTH: 19
<212> TYPE: DNA
<213> ORGANISM: Artificial
<220> FEATURE:
<223> OTHER INFORMATION: Synthetic

<400> SEQUENCE: 39
gcgggaacag  gcaggctct                                                 19

<210> SEQ ID NO 40
<211> LENGTH: 21
<212> TYPE: DNA
<213> ORGANISM: Artificial
<220> FEATURE:
<223> OTHER INFORMATION: Synthetic

<400> SEQUENCE: 40
caacaaggtg  ccaagtcttt  t                                             21

<210> SEQ ID NO 41
<211> LENGTH: 20
<212> TYPE: DNA
<213> ORGANISM: Artificial
<220> FEATURE:
<223> OTHER INFORMATION: Synthetic

<400> SEQUENCE: 41
acatcacctg  gatgggacat                                                20

<210> SEQ ID NO 42
<211> LENGTH: 20
<212> TYPE: DNA
<213> ORGANISM: Artificial
<220> FEATURE:
<223> OTHER INFORMATION: Synthetic

<400> SEQUENCE: 42
gaatggccct  agtctgggta                                                20

<210> SEQ ID NO 43
<211> LENGTH: 21
<212> TYPE: DNA
<213> ORGANISM: Artificial
<220> FEATURE:
<223> OTHER INFORMATION: Synthetic

<400> SEQUENCE: 43
```

```
tgctgcttttt gaaacaaatg a                                                    21

<210> SEQ ID NO 44
<211> LENGTH: 20
<212> TYPE: DNA
<213> ORGANISM: Artificial
<220> FEATURE:
<223> OTHER INFORMATION: Synthetic

<400> SEQUENCE: 44
cctatggcaa aaatggtgct                                                       20

<210> SEQ ID NO 45
<211> LENGTH: 21
<212> TYPE: DNA
<213> ORGANISM: Artificial
<220> FEATURE:
<223> OTHER INFORMATION: Synthetic

<400> SEQUENCE: 45
catgcagtaa acaaccgaac a                                                     21

<210> SEQ ID NO 46
<211> LENGTH: 20
<212> TYPE: DNA
<213> ORGANISM: Artificial
<220> FEATURE:
<223> OTHER INFORMATION: Synthetic

<400> SEQUENCE: 46
tttgccatct gccctgtaag                                                       20

<210> SEQ ID NO 47
<211> LENGTH: 20
<212> TYPE: DNA
<213> ORGANISM: Artificial
<220> FEATURE:
<223> OTHER INFORMATION: Synthetic

<400> SEQUENCE: 47
agtcatgctg aggcttaggg                                                       20

<210> SEQ ID NO 48
<211> LENGTH: 20
<212> TYPE: DNA
<213> ORGANISM: Artificial
<220> FEATURE:
<223> OTHER INFORMATION: Synthetic

<400> SEQUENCE: 48
tcagctctgc ctttctcctc                                                       20

<210> SEQ ID NO 49
<211> LENGTH: 20
<212> TYPE: DNA
<213> ORGANISM: Artificial
<220> FEATURE:
<223> OTHER INFORMATION: Synthetic

<400> SEQUENCE: 49
gcagacctta actggcatcc                                                       20

<210> SEQ ID NO 50
<211> LENGTH: 22
<212> TYPE: DNA
<213> ORGANISM: Artificial
```

<220> FEATURE:
<223> OTHER INFORMATION: Synthetic

<400> SEQUENCE: 50
cagttgcatg ctaccttaaa ga                                      22

<210> SEQ ID NO 51
<211> LENGTH: 20
<212> TYPE: DNA
<213> ORGANISM: Artificial
<220> FEATURE:
<223> OTHER INFORMATION: Synthetic

<400> SEQUENCE: 51
aagctgaatc tgctgccaac                                         20

<210> SEQ ID NO 52
<211> LENGTH: 20
<212> TYPE: DNA
<213> ORGANISM: Artificial
<220> FEATURE:
<223> OTHER INFORMATION: Synthetic

<400> SEQUENCE: 52
gccgtaaaac atggaaggaa                                         20

<210> SEQ ID NO 53
<211> LENGTH: 20
<212> TYPE: DNA
<213> ORGANISM: Artificial
<220> FEATURE:
<223> OTHER INFORMATION: Synthetic

<400> SEQUENCE: 53
cccatttgct tatcctgcat                                         20

<210> SEQ ID NO 54
<211> LENGTH: 25
<212> TYPE: DNA
<213> ORGANISM: Artificial
<220> FEATURE:
<223> OTHER INFORMATION: Synthetic

<400> SEQUENCE: 54
ttccagaatc tagcatctac ctacc                                   25

<210> SEQ ID NO 55
<211> LENGTH: 20
<212> TYPE: DNA
<213> ORGANISM: Artificial
<220> FEATURE:
<223> OTHER INFORMATION: Synthetic

<400> SEQUENCE: 55
tgcttctggc tctgcagtta                                         20

<210> SEQ ID NO 56
<211> LENGTH: 21
<212> TYPE: DNA
<213> ORGANISM: Artificial
<220> FEATURE:
<223> OTHER INFORMATION: Synthetic

<400> SEQUENCE: 56
gcaagaaagc gagcttagtg a                                       21

```
<210> SEQ ID NO 57
<211> LENGTH: 20
<212> TYPE: DNA
<213> ORGANISM: Artificial
<220> FEATURE:
<223> OTHER INFORMATION: Synthetic

<400> SEQUENCE: 57
caaagaattc accccaccag                                               20

<210> SEQ ID NO 58
<211> LENGTH: 20
<212> TYPE: DNA
<213> ORGANISM: Artificial
<220> FEATURE:
<223> OTHER INFORMATION: Synthetic

<400> SEQUENCE: 58
cctcaccacc aacttcatcc                                               20

<210> SEQ ID NO 59
<211> LENGTH: 20
<212> TYPE: DNA
<213> ORGANISM: Artificial
<220> FEATURE:
<223> OTHER INFORMATION: Synthetic

<400> SEQUENCE: 59
gcaacctcaa acagacacca                                               20

<210> SEQ ID NO 60
<211> LENGTH: 20
<212> TYPE: DNA
<213> ORGANISM: Artificial
<220> FEATURE:
<223> OTHER INFORMATION: Synthetic

<400> SEQUENCE: 60
tagatggctc tgccctgact                                               20

<210> SEQ ID NO 61
<211> LENGTH: 21
<212> TYPE: DNA
<213> ORGANISM: Artificial
<220> FEATURE:
<223> OTHER INFORMATION: Synthetic

<400> SEQUENCE: 61
cacttagacc tcaccctgtg g                                             21

<210> SEQ ID NO 62
<211> LENGTH: 20
<212> TYPE: DNA
<213> ORGANISM: Artificial
<220> FEATURE:
<223> OTHER INFORMATION: Synthetic

<400> SEQUENCE: 62
tggggtaatc agtggtgtca                                               20

<210> SEQ ID NO 63
<211> LENGTH: 20
<212> TYPE: DNA
<213> ORGANISM: Artificial
<220> FEATURE:
<223> OTHER INFORMATION: Synthetic
```

```
<400> SEQUENCE: 63
ttttgttccc ccagacactc                                                    20

<210> SEQ ID NO 64
<211> LENGTH: 20
<212> TYPE: DNA
<213> ORGANISM: Artificial
<220> FEATURE:
<223> OTHER INFORMATION: Synthetic

<400> SEQUENCE: 64
acccttcagc agttccacac                                                    20

<210> SEQ ID NO 65
<211> LENGTH: 20
<212> TYPE: DNA
<213> ORGANISM: Artificial
<220> FEATURE:
<223> OTHER INFORMATION: Synthetic

<400> SEQUENCE: 65
acccttcagc agttccacac                                                    20

<210> SEQ ID NO 66
<211> LENGTH: 26
<212> TYPE: DNA
<213> ORGANISM: Artificial
<220> FEATURE:
<223> OTHER INFORMATION: Synthetic

<400> SEQUENCE: 66
tggtatttta ttctgaaaca cagagg                                             26

<210> SEQ ID NO 67
<211> LENGTH: 20
<212> TYPE: DNA
<213> ORGANISM: Artificial
<220> FEATURE:
<223> OTHER INFORMATION: Synthetic

<400> SEQUENCE: 67
gcttcggtgt tcagtggatt                                                    20

<210> SEQ ID NO 68
<211> LENGTH: 22
<212> TYPE: DNA
<213> ORGANISM: Artificial
<220> FEATURE:
<223> OTHER INFORMATION: Synthetic

<400> SEQUENCE: 68
cccaaatgag attatgccac tg                                                 22

<210> SEQ ID NO 69
<211> LENGTH: 22
<212> TYPE: DNA
<213> ORGANISM: Artificial
<220> FEATURE:
<223> OTHER INFORMATION: Synthetic

<400> SEQUENCE: 69
ctatgtttgt gttgcagagc cc                                                 22
```